US012721814B2

(12) United States Patent
Beri

(10) Patent No.: US 12,721,814 B2
(45) Date of Patent: Sep. 1, 2026

(54) METHOD AND COMPOSITION FOR AN IMPROVED BIOAVAILABILITY DELIVERY SYSTEM

(71) Applicant: Americana Pharma LLC, Houston, TX (US)

(72) Inventor: Aman Beri, Buena Park, CA (US)

(73) Assignee: AMERICANA PHARMA LLC, Houston, TX (US)

( * ) Notice: Subject to any disclaimer, the term of this patent is extended or adjusted under 35 U.S.C. 154(b) by 0 days.

(21) Appl. No.: 19/391,914

(22) Filed: Nov. 17, 2025

(65) Prior Publication Data

US 2026/0157968 A1 Jun. 11, 2026

Related U.S. Application Data

(63) Continuation-in-part of application No. 19/366,427, filed on Oct. 22, 2025, and a continuation-in-part of application No. 18/976,941, filed on Dec. 11, 2024, now Pat. No. 12,472,188.

(51) Int. Cl.

| | |
|---|---|
| *A61K 9/14* | (2006.01) |
| *A61K 31/045* | (2006.01) |
| *A61K 31/198* | (2006.01) |
| *A61K 31/5685* | (2006.01) |
| *A61K 36/258* | (2006.01) |
| *A61K 36/81* | (2006.01) |
| *A61K 47/24* | (2006.01) |
| *A61K 47/40* | (2006.01) |

(52) U.S. Cl.
CPC ............ *A61K 9/146* (2013.01); *A61K 31/045* (2013.01); *A61K 31/198* (2013.01); *A61K 31/5685* (2013.01); *A61K 36/258* (2013.01); *A61K 36/81* (2013.01); *A61K 47/24* (2013.01); *A61K 47/40* (2013.01)

(58) Field of Classification Search
None
See application file for complete search history.

(56) References Cited

FOREIGN PATENT DOCUMENTS

| | | | | |
|---|---|---|---|---|
| RU | 2087152 C1 * | 8/1997 | | |
| WO | WO-2022217103 A1 * | 10/2022 | ......... | A61K 36/3482 |

OTHER PUBLICATIONS

Technology Scientific, Biopolymer Technologies Green and Smart, Published Jul. 16, 2024, Retrieved from Internet <https://web.archive.org/web/20240716115747/https://technologyscientific.com/en/micronization-what-does-it-do-for-supplements/> (Year: 2024).*

AnabolicMinds.com, Anabolics, Published Apr. 3, 2021, Retrieved from Internet <https://anabolicminds.com/community/threads/regarding-4-dhea-what-is-the-best-bang-for-your-buck.322319/> (Year: 2021).*

Translation of Vorob'ev et al. RU2087152C1, Published Aug. 20, 1997. Machine translation by Espacenet. Retrieved from https://worldwide.espacenet.com/patent/search/family/020170526/publication/RU2087152C1?q=RU2087152C1 (Year: 1997).*

* cited by examiner

*Primary Examiner* — Ali Soroush
*Assistant Examiner* — Afua Bamfoaa Boateng
(74) *Attorney, Agent, or Firm* — Trojan Law Offices, P.C.

(57) ABSTRACT

A polarity-specific, multi-route delivery system for dietary supplement bioactives with each active pre-mapped to an optimized carrier tailored for oral, transdermal, or topical delivery. A unified formulation stability framework incorporates antioxidants, photoprotectants, oxygen scavengers, and nitrogen-flushed packaging, ensuring integrity under ICH Q1A(R2) conditions. The system supports modular formulations combining esterified DHEA analogs with adaptogens, minerals, amino acids, polyphenols, fatty acids, and vitamins, including coordinated oral-dermal or oral-transdermal regimens. Embodiments demonstrate enhanced nutrient bioavailability, reduced dosing frequency, and multi-phasic nutritional support for anabolic, metabolic, cognitive, cardiovascular, and healthy aging outcomes.

20 Claims, 105 Drawing Sheets

Figure 2: Chemical structure of Ashwagandhanolide and Withanamides A–I

*FIG. 2*

Orientin

2-(3,4-dihydroxyphenyl)-5,7-dihydroxy-8-[(2S,3R,4R,5S,6R)-3,4,5-trihydroxy-6-(hydroxymethyl)oxan-2-yl]chromen-4-one

Vicenin-2

5,7-Dihydroxy-2-(4-hydroxyphenyl)-6,8-bis[(2S,3R,4R,5S,6R)-3,4,5-trihydroxy-6-(hydroxymethyl)oxan-2-yl]chromen-4-one

Ursolic acid

Carvacrol

2-methyl-5-(propan-2-yl)phenol

*Chemical Structure of Ginkgolide B.*

Ginkgolides

| Name | $R^1$ | $R^2$ | $R^3$ |
|---|---|---|---|
| Ginkgolide A | OH | H | H |
| Ginkgolide B | OH | OH | H |
| Ginkgolide C | OH | OH | OH |
| Ginkgolide J | OH | H | OH |
| Ginkgolide M | H | OH | OH |

*Chemical structure of chelated minerals*

*FIG. 17*

*trans*-resveratrol
(3,5,4′-trihydroxy-*trans*-stilbene)

*trans-resveatrol*-3-O-β-glucoside
(*trans*-piceid)

Valine Isoleucine Leucine Phenylalanine

Methionine Lysine Threonine Tryptophan

Vitamin $K_1$

Vitamin $K_2$

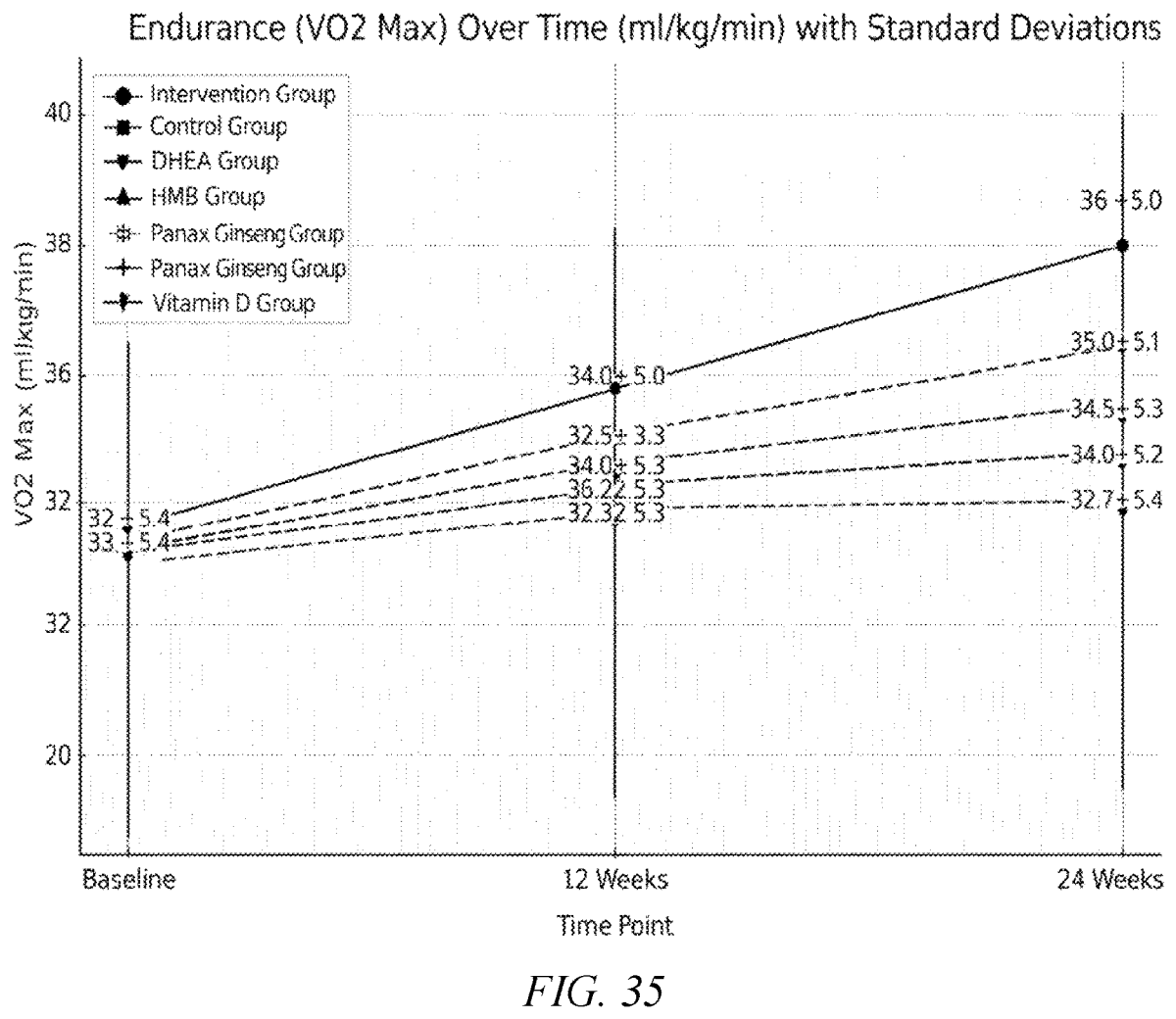

Endurance (VO2 Max) Over Time (ml/kg/min) with Standard Deviations

Intervention Group
Control Group
DHEA Group
HMB Group
Panax Ginseng Group
Panax Ginseng Group
Vitamin D Group VO2 Max (ml/kg/min)

40
38
36
32
32
20

32 ± 5.4
33.1 ± 5.4
34.0 ± 5.0
32.5 ± 3.3
34.0 ± 5.3
36.22 5.3
32.32 5.3
36 ± 5.0
35.0 ± 5.1
34.5 ± 5.3
34.0 ± 5.2
32.7 ± 5.4

Baseline
12 Weeks
24 Weeks

Time Point

FIG. 35

α-HBCD β-HBCD γ-HBCD

*FIG. 42*

1-DHEA Enanthate

4-DHEA Enanthate

5-DHEA Enanthate

19 Nor-DHEA Enanthate

Epiandrosterone undecanoate

R-DHEA

SUPER R-DHEA (Reduced R-DHEA)
3a-enanthoxy-5a-androstan-17-one

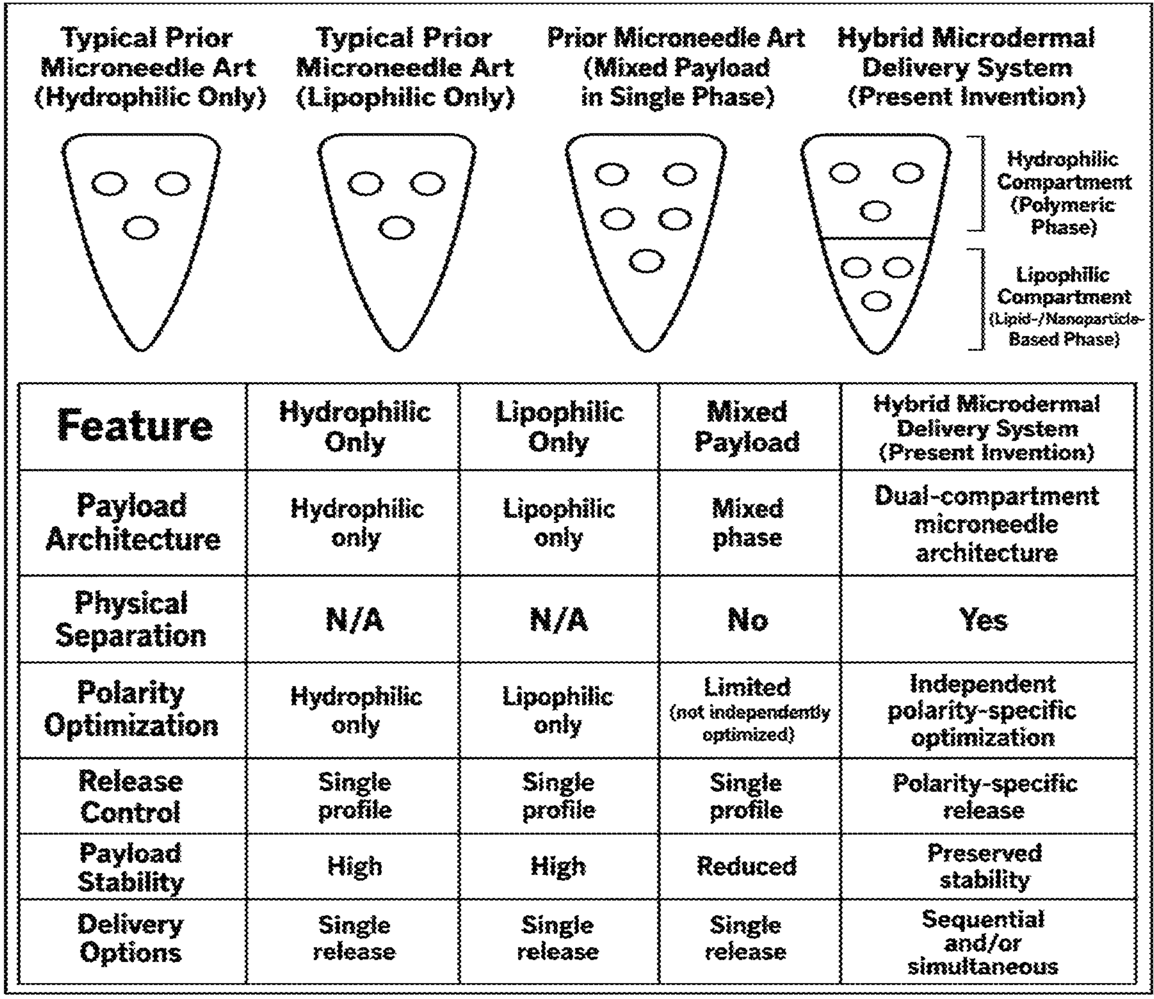

| Feature | Hydrophilic Only | Lipophilic Only | Mixed Payload | Hybrid Microdermal Delivery System (Present Invention) |
|---|---|---|---|---|
| Payload Architecture | Hydrophilic only | Lipophilic only | Mixed phase | Dual-compartment microneedle architecture |
| Physical Separation | N/A | N/A | No | Yes |
| Polarity Optimization | Hydrophilic only | Lipophilic only | Limited (not independently optimized) | Independent polarity-specific optimization |
| Release Control | Single profile | Single profile | Single profile | Polarity-specific release |
| Payload Stability | High | High | Reduced | Preserved stability |
| Delivery Options | Single release | Single release | Single release | Sequential and/or simultaneous |

*FIG. 51*

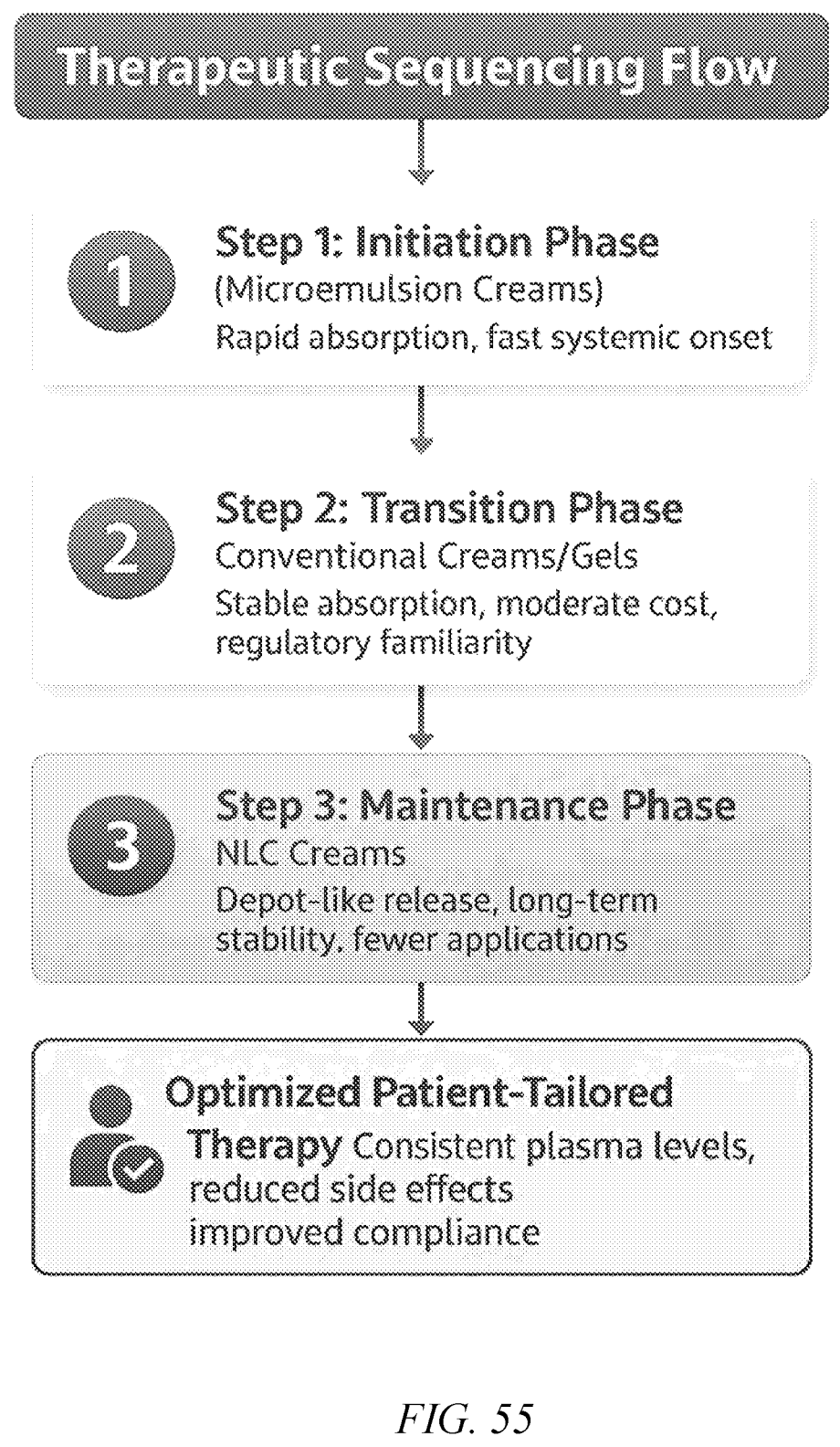

Therapeutic Sequencing Flow

1 Step 1: Initiation Phase
(Microemulsion Creams)
Rapid absorption, fast systemic onset 2 Step 2: Transition Phase
Conventional Creams/Gels
Stable absorption, moderate cost, regulatory familiarity 3 Step 3: Maintenance Phase
NLC Creams
Depot-like release, long-term stability, fewer applications Optimized Patient-Tailored Therapy Consistent plasma levels, reduced side effects improved compliance

FIG. 55

*Figure: Study 1A – Secondary PK Endpoints (Nicotinamide)*

* Sterol derivative group included, in certain embodiments, 4-DHEA enanthate.

METHOD AND COMPOSITION FOR AN IMPROVED BIOAVAILABILITY DELIVERY SYSTEM

CROSS-REFERENCE TO RELATED APPLICATIONS

This application is a continuation-in-part of U.S. patent application Ser. No. 19/366,427, filed on Oct. 22, 2025, entitled "A Method and Composition for an Improved Bioavailability Delivery System," and a continuation-in-part of U.S. patent application Ser. No. 18/976,941, filed on Dec. 11, 2024, entitled "A Method and Composition for an Improved Bioavailability Delivery System," the contents of both of which are incorporated by reference herein in their entireties.

FIELD OF THE INVENTION

The present invention relates to the bioavailability of dietary supplements. More specifically, the present invention relates to a modified composition and method of use of adaptogens, modified stilbenoid complexes, non-esterified omega fatty acids (NEFAs), essential amino acids (EAAs) and β-hydroxy-β-methylbutyrate-free (HMB-free) acid, water-soluble vitamins (B and C), fat-soluble vitamins (D, E, K, and A), L-arginine, creatine, green tea extracts, and chelated forms of minerals with dehydroepiandrosterone (DHEA) derivatives.

The invention represents a novel approach to utilizing a multi-bioavailability system based on the nature of the constituents, and reduces supplements dosage while increasing active ingredients efficacy and bioavailability by providing a targeted delivery system promoting nutritional effects for muscular hypertrophy, physical performance, stamina improvement, muscle strength, and bone mineral density. The delivery system supports anti-aging, weight loss, libido and sexual function improvement, hormonal regulation, anti-inflammation, muscle preservation, cognitive function enhancement, reproductive health, and cardiovascular endurance.

BACKGROUND

In order to optimize their health, individuals frequently turn to a variety of dietary supplements. However, many commonly used supplements, including DHEA derivatives, HMB Free Acids, NEFAs, L-arginine, creatine, chelated minerals, essential amino acids, trans-resveratrol, green tea extract, and adaptogens such as ashwagandha (*Withania somnifera*), *Rhodiola rosea*, and stilbenoids, as well as water-soluble and fat-soluble vitamins, face significant challenges related to poor bioavailability and low efficacy when taken individually. This disclosure discusses the limitations of these supplements and introduces an innovative bioavailability delivery system designed to enhance absorption, efficacy, and nutritional effects of these supplements, particularly when the supplements are combined to achieve synergistic benefits.

The following supplement limitations and toxicities are related to poor bioavailability and high dosages:

DHEA derivatives: DHEA is commonly used for its anti-aging and hormonal balance benefits, but suffers from poor bioavailability due to rapid liver metabolism, limiting its systemic effects. High doses of DHEA can cause hormonal imbalances, acne, liver toxicity, and mood swings. While DHEA supplementation can improve bone density, its systemic benefits are limited. A minimal effect on body composition has also been noted, underscoring the need for more bioavailable DHEA formulations.

NEFAs: Omega-3s are essential for cardiovascular and neurological health, but exhibit poor absorption, unless taken with fat, which limits their efficacy. High doses of omega-3 NEFAs can lead to gastrointestinal discomfort, increased bleeding risk, and have a fishy aftertaste. Omega-3 fatty acid absorption improved significantly when taken with dietary fat, and including emulsifiers when taken can further enhance bioavailability.

L-arginine: L-arginine presents bioavailability challenges due to gastrointestinal degradation, which results in limited absorption. High doses of L-arginine can cause gastrointestinal issues such as bloating and diarrhea, and have been shown to exacerbate asthma symptoms. While L-arginine improves endothelial function, its low bioavailability hinders its effectiveness. Additionally, L-citrulline, a precursor to L-arginine, has been shown to offer a more sustained benefit.

EAAs: EAAs are vital for muscle recovery, but their rapid metabolism limits their effectiveness. Overconsumption can lead to digestive issues and increased ammonia levels. EAA supplementation has been found to improve muscle protein synthesis when paired with insulin, and the timing of EAA ingestion plays a critical role in maximizing its anabolic effects.

HMB free acids: HMB (β-hydroxy β-methylbutyrate) is effective for muscle preservation, but its absorption can be inconsistent, with high doses leading to gastrointestinal discomfort. HMB supplementation significantly improves muscle mass and strength in resistance training, although absorption variability remained an issue. Combining HMB with other agents like creatine can help mitigate some of the bioavailability challenges.

Trans-resveratrol: Resveratrol is known for its antioxidant properties, but its rapid metabolism and elimination limit its bioavailability. High doses can cause gastrointestinal discomfort and headaches. Resveratrol is also rapidly metabolized, limiting its systemic effects. Additionally, combining resveratrol with absorption-enhancing agents like piperine improves its effectiveness.

Adaptogens: Adaptogens, such as ashwagandha (*Withania somnifera*), *Rhodiola rosea*, and holy basil), are valued for their stress-reducing properties but have poor bioavailability due to low solubility and absorption issues. Large doses can lead to gastrointestinal upset and drowsiness. Although ashwagandha has stress-relieving effects, bioavailability remains a limiting factor, and improved delivery systems are needed to enhance adaptogen efficacy.

Water-soluble vitamins: B vitamins are quickly excreted in urine, limiting their sustained bioavailability. And high doses, particularly of B6, can lead to nerve damage and gastrointestinal issues. B vitamin supplementation improves energy metabolism but requires frequent intake for any sustained benefit. Additionally, the bioavailability of these vitamins can be enhanced when paired with whole food sources.

Fat-soluble vitamins: Fat-soluble vitamins such as A, D, E, and K require dietary fat for optimal absorption, and excessive intake can lead to toxicity. For example, Vitamin A can cause liver damage, while high doses of vitamin D may result in hypercalcemia. Vitamin D absorption is improved when paired with dietary fat, and vitamins E and K show similar results when administered with fats.

The limited bioavailability of these supplements can reduce their efficacy, and high doses may lead to adverse effects, including gastrointestinal distress, organ damage, and hormonal imbalances. Innovative multi bioavailability delivery systems that enhance absorption and efficacy are crucial to maximizing the nutritional potential of these supplements.

For these reasons there is a need to enhance the nutritional effects of supplements using multiple-bioavailability delivery systems to overcome poor bioavailability, and combining supplements for enhanced efficacy. These and other objects of the invention are more fully described in the following specification and drawings.

SUMMARY

In accordance with a first embodiment of the invention, a method of use and a composition of constituents and their modifications is disclosed, including adaptogens, modified stilbenoids complex, NEFAs, EAAs, HMB free acid, water-soluble vitamins (B and C), fat-soluble vitamins (D, E, K, and A), L-arginine, creatine, green tea extracts, and chelated form of minerals with DHEA derivatives. This represents a novel approach to utilizing a multi-bioavailability system, based on the nature of the constituents, aims to reduce dosage while increasing supplements efficacy and bioavailability by providing a targeted delivery system to promote nutritional effects for muscular hypertrophy, physical performance, improvement of stamina, muscle strength, and bone mineral density, supports anti-aging, weight loss, improvement of libido and sexual function, hormonal regulation, anti-inflammation, muscle preservation, cognitive function enhancement, reproductive health, and cardiovascular endurance.

The following more detailed description of various preferred embodiments the present invention provides a significant advance in current methods of use and compositions of constituents.

A first embodiment daily wellness capsule to support overall wellness, stress adaptation, muscle hypertrophy, enhancing physical performance and increasing bone mineral density, with multiple bioavailability delivery system (Micronizing, Phytosome, Micronized-cyclodextrin complex) is disclosed.

Formulation includes preparing a supplement with micronized DHEA derivatives, specifically 4-androstene-3b-ol-one propionate, mixed with cyclodextrin, alongside a separate blend containing micronized ergocalciferol or cholecalciferol, ashwagandha or *ginseng*, free fatty acids, HMB free acid, and a phytosome delivery system. The first step in the process is micronizing the DHEA derivatives, ensuring that the compound is in a dry and free-flowing powder form. Jet milling or ball milling is employed to reduce the particle size to less than 10 microns. Quality control measures, including sieve analysis, microscopy, and stability testing, are then used to ensure that the desired particle size is achieved and that no chemical degradation has occurred.

Cyclodextrin is micronized similarly, with the dry, free-flowing powder being reduced to a fine form through jet or cryogenic milling, the latter using liquid nitrogen for finer milling. Quality control involves particle size analysis and functionality testing to confirm that the cyclodextrin retains its capacity to form inclusion complexes. The micronization of ergocalciferol or cholecalciferol follows, ensuring the vitamins are processed into fine particles to enhance absorption, and ball milling can also be used if mechanical methods are feasible. Quality control tests ensure the vitamins remain stable and within the desired particle size range.

Ashwagandha or *ginseng* herbs are dried and powdered before undergoing micronization through jet or ball milling, preserving the active compounds. For free fatty acids, essential amino acids, and HMB-free acid, the same techniques are applied, with rigorous particle size and consistency testing to ensure uniformity.

Phytosome complexes are prepared by dissolving phospholipids in a solvent and adding the active ingredients, such as ashwagandha or *ginseng*, to form the complex. After drying the complex via rotary evaporation, jet milling may be applied if further size reduction is needed. Quality control involves testing encapsulation efficiency through HPLC and verifying particle size and morphology using microscopy.

The mixing procedure involves blending the micronized DHEA derivative with HPBCD cyclodextrin using a high-shear mixer. After ensuring both substances are of the same particle size, they are blended for 10-15 minutes at moderate speed to avoid heat buildup. The separate blend, including micronized ergocalciferol or cholecalciferol, ashwagandha or *ginseng*, free fatty acids, HMB free acid, and the phytosome complex, is mixed in a similar manner, with testing for uniformity and consistency throughout the process.

The following weight calculations are intended for 10,000 capsules, with a recommended dosage per capsule of 25 mg micronized DHEA derivative (4-Androstene-3b-ol-one Propionate), 50 mg micronized HPBCD cyclodextrin, 10 mg micronized ergocalciferol or cholecalciferol, 100 mg micronized ashwagandha or *ginseng,* 50 mg free fatty acids, 500 mg micronized HMB free acid, and 50 mg phytosome complex.

In such an arrangement, the total weight for 10,000 capsules is 250 mg micronized DHEA derivative, 500 g micronized HPBCD Cyclodextrin, 100 g micronized ergocalciferol or cholecalciferol, 1 kg micronized ashwagandha or *ginseng,* 500 g free fatty acids, 5 kg micronized HMB free acid, and 500 g phytosome complex. The sum of each ingredient per capsule results in a total weight per capsule of 785 mg.

Regarding microcrystalline cellulose (filler), assuming microcrystalline cellulose makes up 25% of the total capsule weight, the weight of microcrystalline cellulose per capsule is 196.25 mg. Thus, the total weight for 10,000 capsules is 1.96 kg. Regarding the magnesium stearate (anti-caking agent) calculation, assuming magnesium stearate makes up 2% of the total capsule weight, the weight of magnesium stearate per capsule is 15.7 mg. Thus, the total weight for 10,000 capsules is 157 grams.

In preferred embodiments, the capsule type is 00 or 000 capsules, depending on the total volume of the powder blend. Regarding the filling process, a capsule filling machine is used to ensure uniform filling to achieve consistent dosage per capsule. Excipients are preferably included, such as fillers (e.g., microcrystalline cellulose), binders (e.g., hypromellose), and anti-caking agents (e.g., magnesium stearate) if necessary to facilitate the encapsulation process.

Quality control procedures ensure the accuracy of the micronized powders and capsules. Particle size analysis is performed using laser diffraction or sieve analysis, and uniformity testing checks for consistent distribution across the blend. The filled capsules undergo content uniformity tests, dissolution testing, and stability studies to ensure that they release the active ingredients properly and remain stable over time. Encapsulation efficiency and particle size are tested within the phytosome complex to confirm its compatibility with other ingredients.

A second embodiment daily wellness capsule for anti-aging, muscle preservation, improved metabolic function, anti-inflammation, and hormone regulation is disclosed. A supplement is prepared with micronized DHEA derivative (androst-S-ene-3β,7β, 17β-triol) mixed with cyclodextrin, and a separate blend of micronized vitamin B6, NEFAs, HMB free acids and a phytosomes with Siberian *ginseng*, a multiple bioavailability technology to increase bioavailability and increase supplements' efficacy. All ingredients are micronized, including phytosome, NEFAs, and a cyclodextrin complex.

Androst-5-ene-3β,7β,17β-triol at 25 mg offers several benefits, including modulating inflammation through androgen receptors, preserving muscle mass, influencing metabolism and body composition, indirectly impacting immune function through hormonal balance, supporting muscle and bone health for anti-aging, and regulating testosterone metabolism and activity. Siberian *ginseng* (eleuthero) extract at 25 mg reduces inflammation through adaptogenic compounds, supports health and recovery, enhances energy and adrenal function, boosts immune response, helps manage stress for anti-aging, and supports adrenal health and hormonal balance.

Omega-3 Fatty Acids at 25 mg reduce systemic inflammation and oxidative stress, support muscle health, improve lipid profiles and insulin sensitivity, enhance immune response, support cardiovascular and cognitive health for anti-aging, and balance hormone levels while reducing inflammation. Vitamin B6 at 25 mg reduces inflammation, is vital for amino acid metabolism and protein synthesis, supports neurotransmitter production and metabolism, enhances immune responses, supports skin and nerve health for anti-aging, and aids in hormone synthesis and balance.

Trans-resveratrol at 25 mg is a potent antioxidant with anti-inflammatory properties, may influence muscle function and recovery, improves insulin sensitivity and metabolic health, enhances immune response, activates longevity pathways for anti-aging, and influences estrogen receptors. HMB free acids at 25 mg reduce muscle inflammation and damage, support muscle mass and strength, help maintain muscle mass and metabolic health, support immune function and reduce muscle breakdown, contribute to muscle preservation and overall vitality for anti-aging, and may influence muscle-related hormone levels.

The preparation details involve the micronization process, aimed at increasing the surface area and enhancing the bioavailability of the ingredients, using equipment such as a jet mill or ball mill to achieve particle sizes less than 10 micrometers for each ingredient. The phytosome application improves absorption and bioavailability for herbal extracts like Siberian *ginseng* by combining the extract with phospholipids, such as lecithin, to form a phytosome complex, with the same method applicable to other herbal extracts if needed. Cyclodextrin complexation increases the solubility and stability of Androst-5-ene-3β,7β,17β-triol by mixing the micronized compound with cyclodextrins, such as β-cyclodextrin, in a 1:1 ratio to form an inclusion complex.

The formulation consists of micronized ingredients, including Androst-5-ene-3β,7β,17β-triol complexed with cyclodextrin, Siberian *ginseng* extract phytosome-encapsulated, and, where possible, micronized Omega-3 fatty acids, Vitamin B6, Trans-Resveratrol, and HMB Free Acids. The micronized ingredients are blended thoroughly to ensure uniform distribution, with excipients incorporated as needed. Finally, the blend is encapsulated into size 0 or 00 capsules, depending on the final blend volume.

Regarding weight and quantity calculations, the total capsules in a batch are 10,000, with 50 capsules per bottle, and a total bottle count of 200. The capsule content (per capsule) is as follows: Androst-5-ene-3β,7β,17β-triol (25 mg), Siberian *ginseng* extract (25 mg), omega-3 fatty acids (25 mg), vitamin B6 (25 mg), trans-resveratrol (25 mg), and HMB free acids (25 mg). The active total ingredient quantities per batch are as follows: Androst-5-ene-38,76,176-triol (250 g), Siberian *ginseng* extract (250 g), omega-3 fatty acids (250 g), vitamin B6 (250 g), trans-resveratrol (250 g), and HMB free acids (250 g).

Regarding excipient requirements, a microcrystalline cellulose (filler) is provided of approximately 2000 grams (200 mg per capsule, adjust for bulk density and blending efficiency), a hypromellose (binder) is provided of approximately 500 grams (50 mg per capsule), a croscarmellose sodium (disintegrant) is provided of approximately 200 grams (20 mg per capsule), a magnesium stearate (lubricant) is provided of approximately 100 grams (10 mg per capsule), and capsules (size 0 or 00), with a quantity dependent on the final blend volume and capsule size.

The quality and testing guidelines for the production process begin with raw material testing, where the identity of the ingredients is confirmed using HPLC or mass spectrometry. Purity is ensured by verifying that the ingredients are free from contaminants, including heavy metals, pesticides, and microbial impurities, while potency testing is conducted to confirm the concentrations of active ingredients. During micronization and complexation testing, particle size analysis confirms that particles are less than 10 micrometers, and the stability and solubility of phytosome and cyclodextrin complexes are verified.

In the formulation testing phase, blend uniformity is checked to ensure an even distribution of active ingredients, and content uniformity testing confirms that each capsule contains the correct amount of active ingredients. Final product testing involves verifying the capsule fill weight to ensure consistency, conducting disintegration and dissolution testing to confirm that the capsules release the ingredients as required, and microbiological testing to detect any microbial contamination. Stability testing ensures the product remains effective and stable over time.

For labeling and documentation, compliance with regulatory requirements is verified, including accurate ingredient lists, dosage instructions, and safety warnings. Detailed records of the formulation, manufacturing processes, and quality testing are maintained to ensure traceability and adherence to guidelines.

BRIEF DESCRIPTION OF THE FIGURES

FIG. 1 illustrates the chemical structure of HMB free acid.

FIG. 2 illustrates the chemical structure of ashwagandhanolide.

FIG. 6 illustrates the chemical structure of ginsenoside.

FIG. 7 illustrates the chemical structure of ginsenoside RB1.

FIG. 8 illustrates the chemical structure of ginsenoside RB2.

FIG. 9 illustrates the chemical structure of ginsenoside RC.

FIG. 14 illustrates the chemical structure of an eleutherococcus of Siberian *ginseng*.

FIG. 15 illustrates the chemical structure of cordycepin.

FIG. 16 illustrates the chemical structure of 20-hydroxyecdysone of *Rhaponticum carthamoides*.

FIG. 17 illustrates the chemical structures of chelated minerals generally, and the structure of magnesium glycinate.

FIG. 20 illustrates the chemical structures of trans-resveratrol and trans-resveratrol glucoside.

FIG. 21 illustrates the chemical structure of green tea extract.

FIG. 22 illustrates the chemical structures for the EAAs valine, isoleucine, leucine, phenylalanine, methionine, lysine, threonine, and tryptophan are shown FIG. 23 illustrates the chemical structure for L-arginine.

FIG. 28 illustrates the chemical structures of vitamin D in its most significant forms, $D_2$ (ergocalciferol) and $D_3$ (cholecalciferol).

FIG. 29 illustrates vitamin A in its two main types: preformed vitamin A (retinol) and provitamin A carotenoids.

FIG. 30 illustrates the chemical structure of creatine.

FIG. 35 illustrates a percentage change in $VO_2$ max (endurance) from baseline to 24 weeks.

FIG. 42 illustrates the chemical formulas for α-HBCD, β-HBCD, and γ-HBCD.

FIG. 51 illustrates compartmentalization of hydrophilic and lipophilic compounds within microneedle patches.

FIG. 55 illustrates the therapeutic treatment sequencing strategy.

FIG. 117 illustrates sensory and consumer acceptability attributes at baseline and Week 8 for Oral and Topical formulations.

FIG. 118 illustrates safety and tolerability outcomes at baseline and Week 8 for Study 6. Skin irritation scores increased minimally from 0.2 to 0.3 (+0.1).

FIG. 119 illustrates percentage change (A Change %) in cardiometabolic and hormonal outcomes from baseline to Week 12 for Active versus Placebo groups.

FIG. 120 illustrates baseline and Week 12 values for skin irritation (0-3 scale) and serum calcium (mg/dL) in Study 7.

FIG. 121 illustrates potency retention (%) of Vitamin D3 and 1-DHEA Enanthate after simulated light exposure, comparing UV-blocking versus transparent packaging.

FIG. 122A illustrates muscle mass changes in outcome measures across different groups at three and six months.

FIG. 122B illustrates strength changes in outcome measures across different groups at three and six months.

FIG. 122C illustrates endurance changes in outcome measures across different groups at three and six months.

FIG. 122D illustrates IIEF changes in outcome measures across different groups at three and six months.

DESCRIPTION

Figure 3:
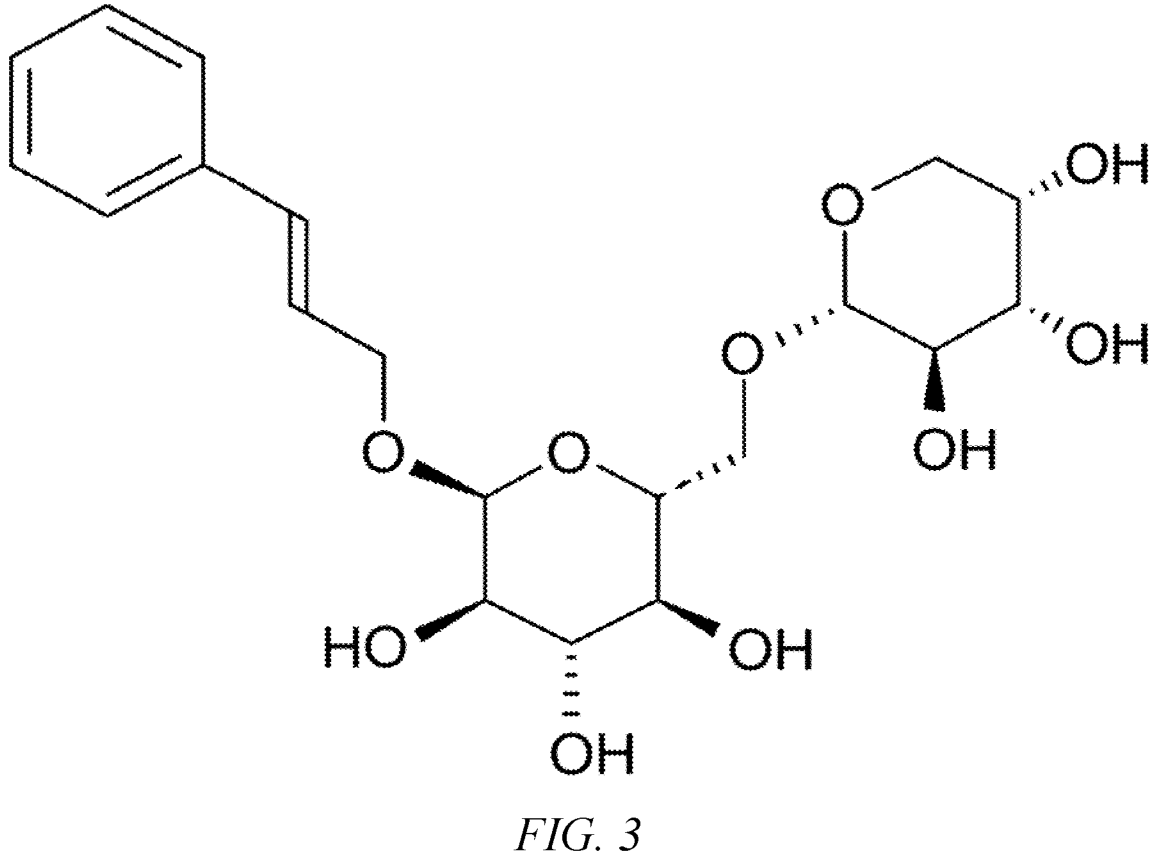
FIG. 3 illustrates the chemical structure of *Rhodiola rosea* extract.

The present invention is described more fully hereinafter, but not all embodiments are shown. While the invention has been described with reference to exemplary embodiments, it will be understood by those skilled in the art that various changes may be made, and equivalents may be substituted for elements thereof without departing from the scope of the disclosure. In addition, many modifications may be made to adapt a particular structure or material to the teachings of the disclosure without departing from the essential scope thereof.

The drawings accompanying the application are for illustrative purposes only. They are not intended to limit the embodiments of the present application. Additionally, the drawings are not drawn to scale. Common elements between different figures may retain the same numerical designation.

The following methods can significantly enhance the absorption, permeability, and nutritional efficacy of these compounds: (1) Micronization to reduce the particle size of supplements, increasing their surface area and improving solubility and absorption. This technique is particularly beneficial for poorly soluble compounds like omega-3 fatty acids and *Panax ginseng*. (2) Phytosome technology is used to form phytosomes, complexes formed by combining phytochemicals with phospholipids, enhancing the bioavailability of plant-derived compounds. This significantly improves the absorption of *ginseng, Ginkgo biloba*, green tea extract, ashwagandha, resveratrol and other herbal extracts. (3) Cyclodextrin complexation, which involves using cyclodextrins, cyclic oligosaccharides that can encapsulate hydrophobic compounds, enhancing their solubility and stability. This approach can improve the bioavailability of vitamins and fatty acids. (4) Including NEFAs, which can serve as an effective delivery system by enhancing solubility and absorption of lipophilic supplements, facilitating transport across cell membranes. NEFAs encapsulate supplements by forming micelles that improve stability and bioavailability. Additionally, NEFAs can target specific tissues, allowing localized nutrients release and action, since they are readily metabolized by cells, thereby reducing dosages and minimizing side effects while improving nutritional efficacy.

By pairing or combining supplements strategically, their nutritional effects can be amplified. For example, pairing DHEA derivatives with adaptogens like *Panax ginseng* can promote hormonal balance and enhance stress resilience. Combining essential amino acids with HMB can improve muscle preservation and recovery. Incorporating L-arginine with other performance-enhancing supplements can further support cardiovascular health and boost nitric oxide production. Combining omega-3 fatty acids with antioxidants like trans-resveratrol may enhance cardiovascular protection and anti-inflammatory effects. In various embodiments of the present invention, the following supplements are combined:

(1) Adaptogens, such as *Panax ginseng, Rhodiola rosea, Ginkgo biloba* to promote hormonal balance and resilience to stress. (2) Non-esterified omega-3 fatty acids that support cardiovascular and cognitive health, especially when paired with antioxidants. (3) Essential amino acids such as leucine, isoleucine, valine enhance muscle recovery and growth when combined with HMB and L-arginine. (4) HMB free acid enhances muscle recovery and works synergistically with essential amino acids for better muscle preservation. (5) L-arginine supports nitric oxide production and cardiovascular health, and enhances the effects of exercise when paired with essential amino acids and omega-3 fatty acids. (6) Creatine improves athletic performance and muscle mass, and works effectively with essential amino acids and HMB to support muscle recovery and energy production. (7) Water-soluble vitamins, such as B-complex vitamins and Vitamin C support energy metabolism and antioxidant protection, complementing amino acids and fatty acids. (8) Fat-Soluble Vitamins, such as Vitamins A, D, E, K are critical for various bodily functions; their absorption may be enhanced when taken with fats from omega-3s. (9) Selective DHEA derivatives support hormonal health and may improve the effects of adaptogens in regulating stress responses. (10) Trans-Resveratrol, including various other stilbenoid derivatives used for antioxidant support can enhance the cardiovascular benefits of L-arginine and omega-3s, offering additional protection against oxidative stress. (11) Green Tea Extract for additional antioxidant and anti-inflammatory effects works synergistically with trans-resveratrol and omega-3 fatty acids for enhanced overall health benefits. (12) Chelated minerals such as chelated zinc and magnesium improve bioavailability and absorption, supporting a variety of physiological functions. By combining these supplements, individuals may achieve enhanced health benefits, improved overall efficacy, and a more comprehensive approach to increase their nutritional effects and bioavailability.

A novel approach to multi-bioavailability bioavailability systems utilizes the inherent properties of the above constituents to enhance nutritional effects while minimizing required dosages. By formulating a synergistic combination of selected adaptogens, essential fatty acids, amino acids, and DHEA derivatives, targeted outcomes can be achieved. Muscle preservation is facilitated through the combination of HMB and essential amino acids, while anti-aging effects are supported by DHEA and adaptogens. Anti-inflammatory benefits arise from the incorporation of omega-3 fatty acids and antioxidants, specifically vitamins E and K. Additionally, sexual function and hormonal balance are addressed through the use of DHEA derivatives in conjunction with zinc and magnesium.

Various embodiments of the invention encompass a composition of constituents and their modifications, including adaptogens, modified stilbenoids complex, non-esterified omega fatty acids, essential amino acids, and HMB in its free acid form, both water-soluble vitamins such as B and C, and fat-soluble vitamins like A, D, E, and K, alongside L-arginine, creatine, green tea extracts, and chelated forms of minerals combined with DHEA derivatives enhances the nutritional effects of DHEA-based supplements. These constituent supplements and their nutritional effects are discussed in more detail as follows.

Figure 1:
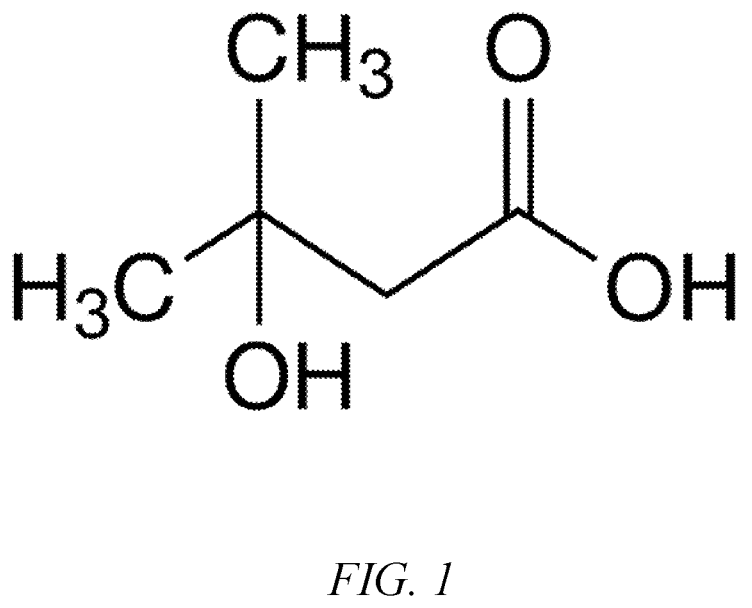

Referring to FIG. 1, the chemical structure of HMB free acid is shown. HMB Free Acid (beta-hydroxy beta-methylbutyrate) is a metabolite of the branched-chain amino acid leucine, widely studied for its potential benefits in muscle health, recovery, and hypertrophy. Sarcopenia, characterized by the progressive loss of muscle mass and strength with age, significantly impacts the elderly population. This condition contributes to increased frailty, falls, and a decreased quality of life (1, 2). As conventional interventions such as resistance exercise and adequate protein intake may be challenging for many older adults, there is growing interest in supplements that can support muscle health. β-Hydroxy-β-Methylbutyrate (HMB), a metabolite of leucine, has emerged as a potential supplement to improve muscle strength and mass in the elderly. This meta-analysis aims to evaluate the efficacy of HMB in enhancing muscle strength among older adults based on current research studies and clinical trials.

HMB free acid influences muscle protein metabolism through several mechanisms. It stimulates the mTOR pathway, enhancing protein synthesis and muscle hypertrophy, which is crucial since aging often leads to reduced mTOR signaling and decreased muscle protein synthesis. Additionally, HMB inhibits the ubiquitin-proteasome pathway, reducing muscle protein breakdown, which is particularly relevant for counteracting muscle wasting and maintaining muscle mass.

Research indicates that HMB supplementation positively affects muscle strength and mass, especially in populations experiencing muscle loss. Clinical trials involving older adults demonstrate significant improvements in muscle strength and physical function, with randomized controlled trials reporting gains in muscle strength, gait speed, and increased muscle mass among elderly individuals taking HMB. Meta-analyses have consolidated these findings, showing modest but significant improvements in muscle strength and physical function among HMB users compared to placebo groups.

HMB free acid supplementation has been studied in various clinical contexts. It shows potential in mitigating sarcopenia by improving muscle mass and strength, particularly in older adults with limited capacity for physical exercise. In patients recovering from critical illness or major surgery, HMB supports muscle preservation and function, aiding quicker recovery and reducing complications. For older adults with inadequate protein intake or malnutrition, HMB can be a valuable adjunct to dietary interventions, helping to preserve muscle mass and strength. The recommended dosage for HMB supplementation is 3 grams per day, particularly in contexts of muscle preservation and strength enhancement.

Recent studies reinforce the beneficial effects of HMB supplementation in the elderly population. Evidence from various randomized controlled trials indicates that HMB leads to improvements in muscle strength, function, and overall physical performance. For instance, significant improvements in muscle strength and physical function have been shown in older adults who supplemented with HMB compared to a placebo group.

Possible side effects include gastrointestinal issues like stomach cramps, nausea, or diarrhea. Allergic reactions are rare but can occur in sensitive individuals. Some evidence suggests altered blood lipids, and HMB may interact with certain medications affecting liver metabolism. Uncommon effects, such as muscle cramps or mood changes, have also been reported. The typical dosage of HMB free acid ranges from 1.5 to 3 grams per day, with most studies using 3 grams daily, split into two or three doses for optimal effects. HMB can be taken before or after workouts, with benefits noted from both timing strategies. Ongoing research continues to explore optimal dosing, long-term effects, and potential synergistic effects when combined with exercise or other nutritional supplements.

β-Hydroxy-β-Methylbutyrate (HMB) free acid is an effective supplement for improving muscle strength and function in the elderly. Its ability to enhance muscle protein synthesis and reduce muscle breakdown makes it a valuable intervention, especially for those with sarcopenia, critical illness, or nutritional deficiencies. Ongoing research aims to refine recommendations regarding dosing, duration, and combination therapies to maximize HMB's benefits for older adults.

Adaptogens and their Derivatives

Adaptogens are natural substances, often derived from herbs and fungi, that help the body resist stressors of various kinds, promoting homeostasis. They are believed to enhance the body's ability to adapt to physical, mental, and environmental stressors. Adaptogens play a vital role in supporting the body's response to stress while maintaining balance across various physiological systems. They assist in regulating the adrenal glands, which produce hormones such as cortisol, thereby enhancing resilience against stressors benefits of adaptogens are manifold. They provide stress relief by alleviating both the physiological and psychological impacts of stress, promoting a sense of calm. Adaptogens also help reduce anxiety symptoms and improve overall mood. Certain varieties enhance physical performance by boosting stamina, endurance, and recovery in athletes. Additionally, they possess anti-inflammatory effects that may reduce inflammation and support immune function. Adaptogens are effective in regulating hormonal fluctuations, particularly during stressful periods, and some can enhance cognitive function by improving mental clarity, focus, and memory.

Adaptogens and their derivatives play a significant role in managing stress and enhancing overall health. These compounds are known to modulate the body's stress response, reduce inflammation, improve circulation, and provide antioxidant protection. Research has demonstrated the efficacy of several adaptogens, including Ashwagandha, *Ginseng*, and *Rhodiola rosea*, in promoting cardiovascular health. For instance, studies indicate that Ashwagandha can significantly lower cortisol levels and reduce stress-related hypertension. A randomized controlled trial published in 2019 showed that participants taking Ashwagandha experienced a marked reduction in blood pressure compared to the placebo group.

Similarly, *Ginseng* has been associated with improved lipid profiles; a meta-analysis from 2016 highlighted its ability to reduce total cholesterol and triglyceride levels, thereby enhancing cardiovascular function. *Rhodiola rosea* also contributes to cardiovascular health. Studies found that *Rhodiola* supplementation resulted in improved blood flow and reduced heart rate during stressful conditions, supporting its role as an adaptogen. Overall, the collective evidence underscores the benefits of these adaptogens in enhancing cardiovascular function, highlighting their potential as natural interventions for managing stress and promoting heart health.

Figure 2:
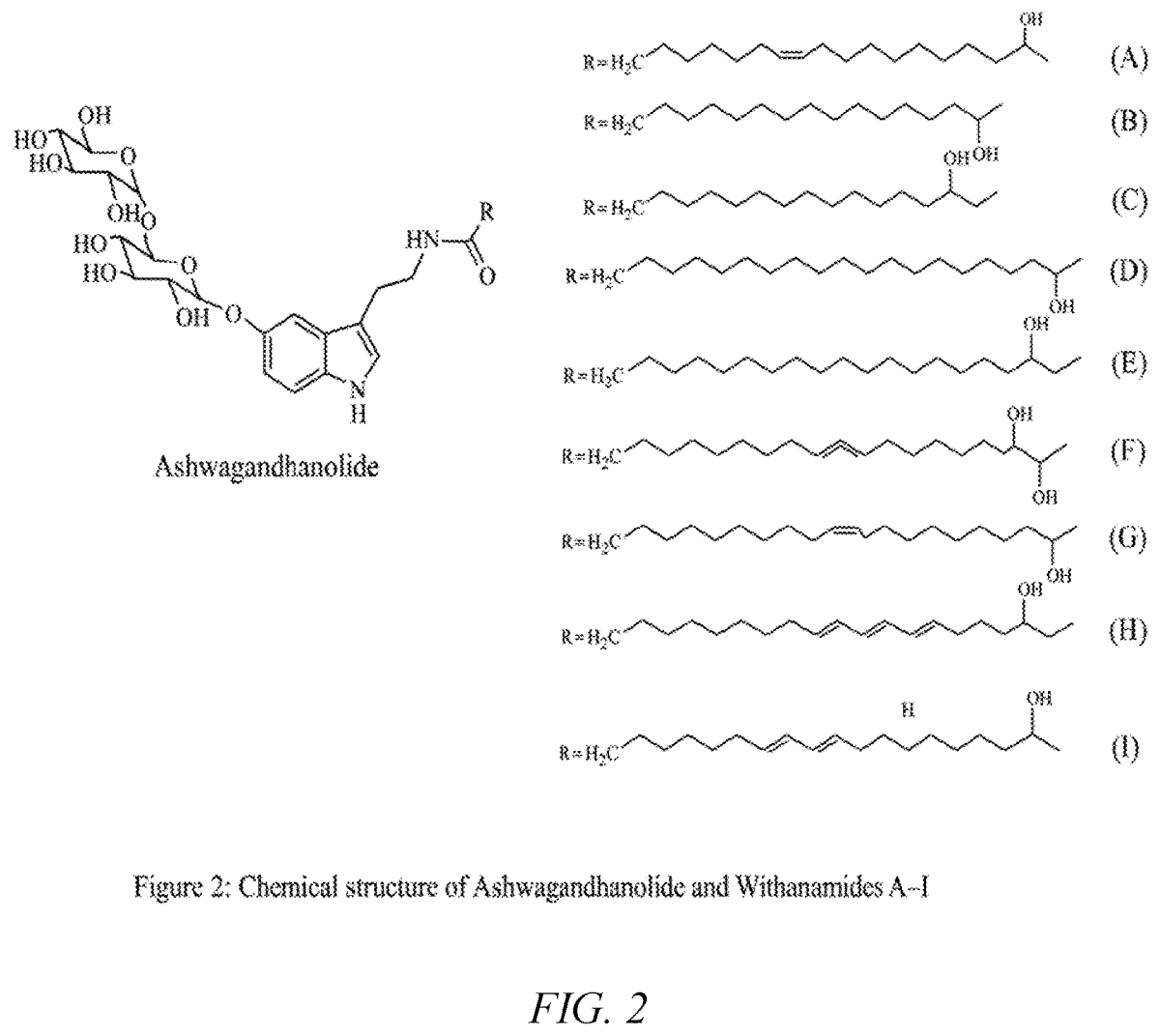

Referring to FIG. 2, the chemical structure of ashwagandhanolide is shown. Widthania *somnifera*, known as ashwagandha, or Indian *Ginseng*, is known for its ability to reduce stress and anxiety, improve sleep quality, and enhance overall vitality. It has also been shown to support cognitive function and physical performance. It is often used to combat chronic stress and fatigue, support adrenal function, and improve mood. Ashwagandhanolide, derived from the ashwagandha plant, has several derivatives that have been studied for their potential pharmacological effects.

Some notable derivatives and their characteristics include: Acetylated ashwagandhanolide, a derivative with an acetyl group added, which may enhance its bioavailability and efficacy, methoxy-ashwagandhanolide, wherein the addition of methoxy groups can modify its interaction with biological targets, potentially affecting its activity, hydroxy-ashwagandhanolide, wherein hydroxylation can enhance the compound's solubility and may increase its antioxidant properties, silylated ashwagandhanolide, which may enhance stability and facilitate the extraction of the active compound, glycosylated ashwagandhanolide, wherein glycosylation improves water solubility and may enhance the compound's bioactivity, fluorinated ashwagandhanolide, wherein introducing fluorine atoms can influence the compound's pharmacokinetics and receptor binding affinity, and phosphorylated ashwagandhanolide, wherein phosphorylation can modify its signaling pathways and increase its potential nutritional applications. These derivatives (from A-I) can be synthesized through various chemical modifications and may exhibit different pharmacological activities compared to the parent compound.

Referring to FIG. 3, the chemical structure of *Rhodiola rosea* extract is shown. *Rhodiola Rosea* enhances physical endurance, reduces fatigue, and improves mental clarity. It is also used to alleviate symptoms of depression and anxiety. It is known to improve resilience to stress, enhance cognitive function, and increase energy levels.

Figure 4:
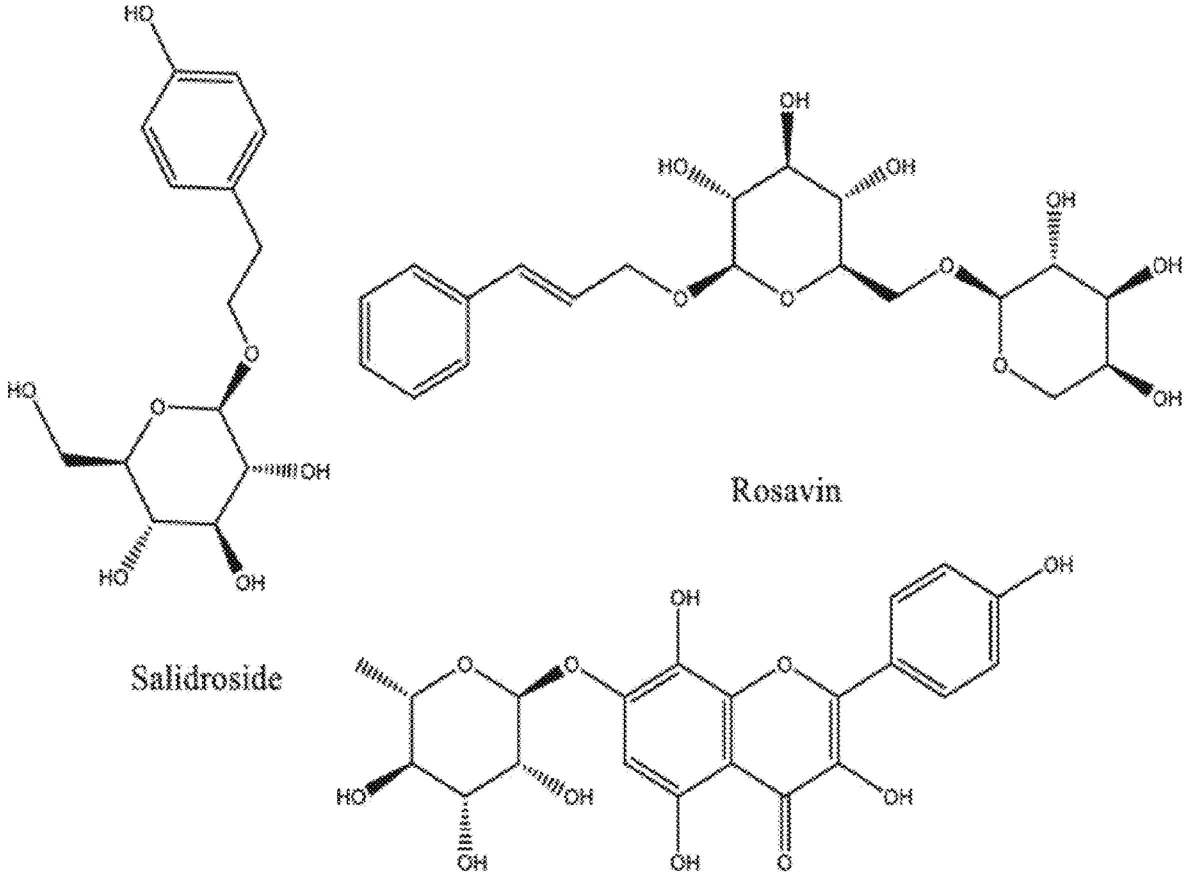
FIG. 4 illustrates the chemical structures of rosavin, salidroside, and rhodionin.

Referring to FIG. 4, the chemical structures of rosavin, salidroside, and rhodlonin are shown. Rosavin is a key bioactive compound found in *Rhodiola rosea*, contributing significantly to its adaptogenic properties. Research indicates that rosavin plays a vital role in stress reduction, cognitive enhancement, fatigue alleviation, mood improvement, and antioxidant activity. One of the primary benefits of rosavin is its ability to reduce stress by lowering cortisol levels and modulating the body's stress response. This makes it particularly effective for individuals facing high stress. Additionally, rosavin has been shown to improve cognitive functions such as memory and concentration, especially under stressful conditions. It also alleviates both physical and mental fatigue, helping to combat feelings of exhaustion. Furthermore, rosavin may improve mood by reducing symptoms of anxiety and depression, which are common in stressful situations. Its antioxidant properties enable it to neutralize free radicals, thus protecting cells from oxidative damage.

The mechanism of action for rosavin involves its influence on the hypothalamic-pituitary-adrenal (HPA) axis, which is crucial in regulating stress hormone production. By enhancing neurotransmitter levels, such as serotonin and dopamine, rosavin activates neuroprotective pathways that promote mental clarity and resilience. Research supports the nutritional effects of rosavin, indicating that its supplementation can enhance mental performance, alleviate fatigue, and improve mood. This makes rosavin particularly beneficial for individuals experiencing high levels of stress or cognitive decline. Overall, rosavin is recognized for its multifaceted benefits, making it a valuable compound in managing stress and enhancing cognitive function, especially in challenging conditions.

Salidroside is a notable compound found in *Rhodiola rosea*, renowned for its protective effects on the nervous system. It offers several key benefits that contribute to both mental and physical well-being. First, salidroside exhibits strong neuroprotective properties, safeguarding neurons from damage induced by oxidative stress. This protective action is essential for maintaining cognitive health and preventing neurodegenerative diseases. Additionally, salidroside enhances cognitive improvement by facilitating learning and memory processes. This makes it particularly valuable for individuals seeking to boost their mental performance.

Salidroside has been linked to antidepressant effects, with potential to alleviate symptoms of depression and anxiety. This attribute positions it as a beneficial option for those dealing with mood disorders. Finally, salidroside possesses anti-inflammatory properties, which help reduce inflammation in various tissues throughout the body. By mitigating inflammation, it supports overall health and enhances both brain function and emotional resilience. Salidroside's neuroprotective, cognitive-enhancing, antidepressant, and anti-inflammatory benefits highlight its significance as a natural agent for promoting mental health and overall well-being.

Salidroside activates the SIRT1 pathway, which promotes cellular stress resistance and enhances mitochondrial function. It also modulates levels of neurotransmitters, contributing to mood regulation. Clinical studies suggest that salidroside can improve cognitive function and mood, reduce anxiety, and provide neuroprotective effects, making it a promising adjunct for mental health conditions.

Rhodionin is a lesser-known compound found in *Rhodiola rosea*, contributing to the plant's overall health benefits. It is recognized for its anti-fatigue effects, helping to reduce both physical and mental fatigue. Additionally, rhodionin may enhance cognitive support by improving focus and mental clarity, while also exhibiting adaptogenic effects that aid the body in adapting to stress. The mechanism of action of rhodionin is believed to parallel that of other compounds in *Rhodiola*, such as rosavin and salidroside. It is thought to modulate neurotransmitter levels and enhance the body's stress response, promoting resilience and mental clarity. While specific studies on rhodionin are limited, its adaptogenic and anti-fatigue properties suggest potential benefits for enhancing physical performance and cognitive function, especially under stressful conditions.

Rosavin, salidroside, and rhodionin are bioactive compounds in *Rhodiola rosea* that offer various health benefits, particularly in stress management, cognitive enhancement, and fatigue reduction. Their mechanisms primarily involve modulating the HPA axis, enhancing neurotransmitter levels, and exerting antioxidant and anti-inflammatory effects. Collectively, they contribute to the nutritional potential of *Rhodiola rosea*, making it valuable in the management of stress-related conditions, cognitive decline, and overall well-being.

Figure 5:
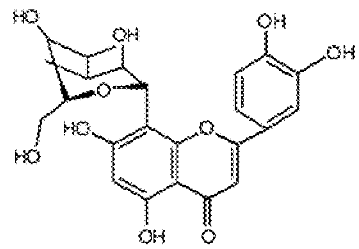
FIG. 5 illustrates the chemical structures of orientin, vicenin-2, ursolic acid, and carvacrol.

Referring to FIG. 5, the chemical structures of the flavonoids orientin and vicenin-2, the triterpenoid ursolic acid, and the monoterpenic phenol carvacrola, from the plant

*Ocimum sanctum* or *Ocimum* tenuiflorum, otherwise known as holy basil. Holy basil supports immune function, reduces inflammation, and helps manage stress. It is also known for its adaptogenic and anti-anxiety properties. It is often used to balance stress hormones, support metabolic function, and improve overall well-being.

The most important antioxidant compounds of basil are caffeic, vanillic, rosmarinic acids, quercetin, rutin, apigenin, chlorogenic, and p-hydroxybenzoic. Essential oils of basil are α-Pinene, β-Pinene, Methyl chavicol, 1,8 cineole, Llinalool, Ocimene, Borneol, Geraneol, B-Caryphyllone, n-Cinnamate and Eugenol.

Figures 6, 7:
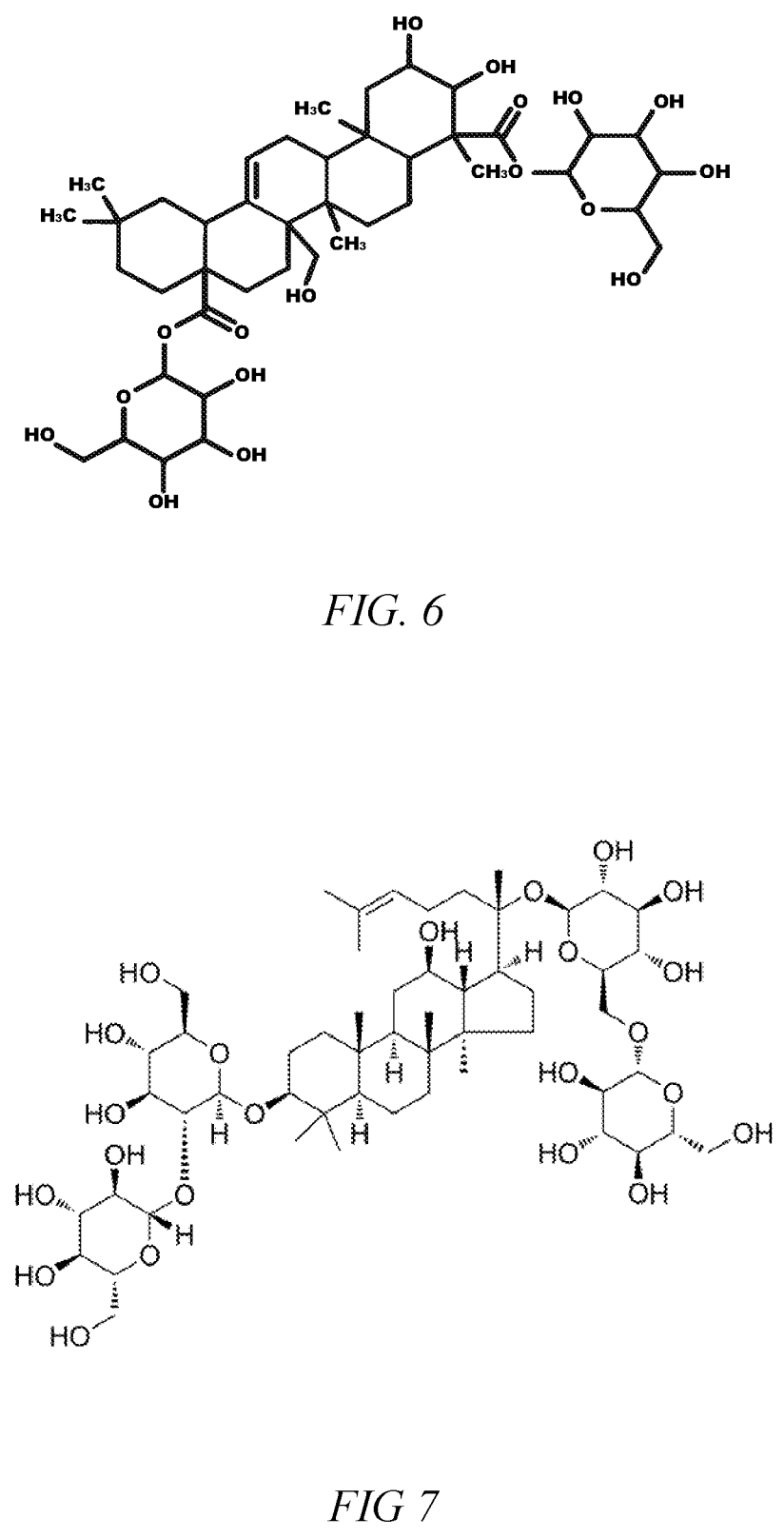

Referring to FIG. 6, the chemical structure of ginsenoside is shown. Ginsenosides are active compounds found in *ginseng*, particularly in the *Panax* genus. *Panax ginseng* enhances mental and physical performance, supports immune health, and reduces fatigue. It has been shown to have anti-inflammatory and antioxidant properties. It is commonly used to improve energy, cognitive function, and stress resilience. Several benefits are associated with specific ginsenosides RB1, RB2, RC, and RD.

Referring to FIG. 7, the chemical structure of ginsenoside RB1 is shown. Ginsenoside RB1 has been shown to enhance cognitive performance and memory. It may improve learning abilities and has neuroprotective effects. Ginsenoside can help reduce fatigue and increase physical endurance, making it beneficial for athletes and those with high physical demands. RB1 may enhance immune function, helping the body resist infections and diseases.

Figures 8, 9:
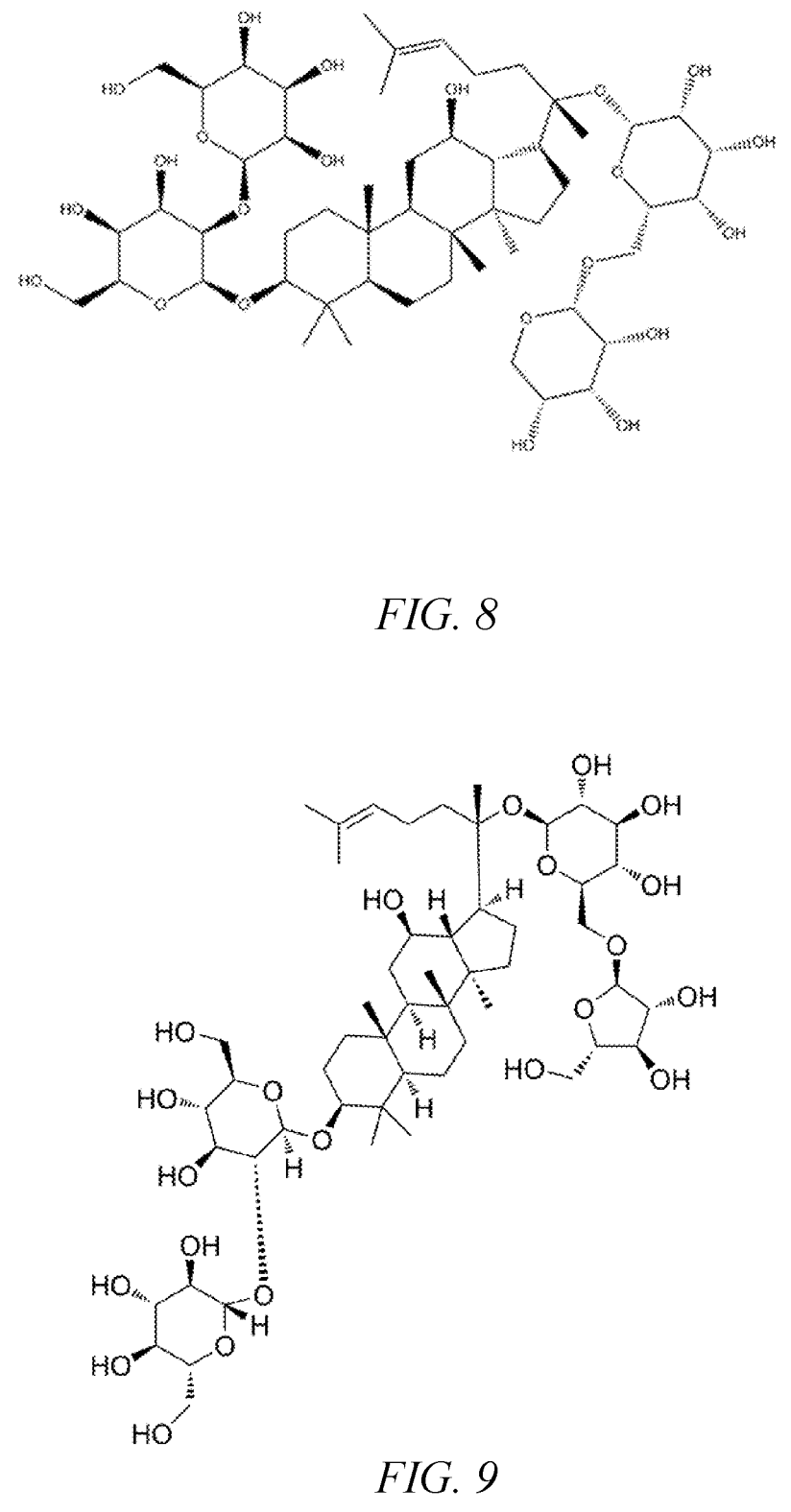

Referring to FIG. 8, the chemical structure of ginsenocide RB2 is shown. Ginsenoside RB2 exhibits strong antioxidant properties, helping to neutralize free radicals and reduce oxidative stress in the body. It may help reduce inflammation, contributing to overall health and potentially alleviating symptoms of chronic inflammatory conditions. Some studies suggest that RB2 can assist in regulating blood sugar levels, which could be beneficial for those with insulin sensitivity or diabetes.

Referring to FIG. 9, the chemical structure of ginsenoside RC is shown. Ginsenoside RC may protect neurons from damage, promoting brain health and potentially aiding in conditions like neurodegenerative diseases. This ginsenoside can help modulate the body's response to stress, promoting relaxation and overall mental well-being. Ginsenoside RC may support heart health by improving circulation and reducing blood pressure.

Figures 10, 11:
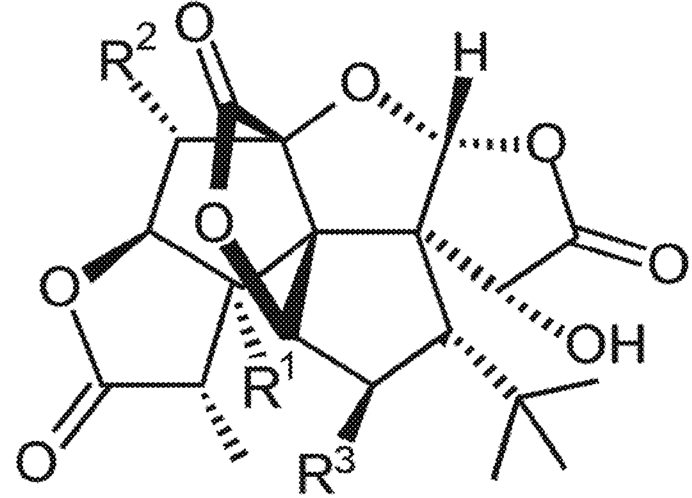
FIG. 10 illustrates the chemical structure of ginsenoside RD.
FIG. 11 illustrates the chemical structure of ginkgolide.

Referring to FIG. 10, the chemical structure of ginsenoside RD is shown. Ginsenoside RD has been investigated for its potential anti-cancer effects, including inhibiting tumor growth and promoting apoptosis in cancer cells. It may help regulate hormone levels, particularly in relation to stress hormones, which can contribute to overall hormonal balance. RD has shown hepatoprotective effects, potentially safeguarding the liver from damage and promoting its health.

These ginsenosides each offer a range of health benefits, particularly in enhancing cognitive function, supporting immune health, reducing inflammation, and providing neuroprotection. They also play roles in stress management and may have anti-cancer properties. Incorporating *ginseng* or ginsenoside supplements may provide these health benefits, though it's always advisable to consult a healthcare professional before starting any new supplement regimen. Ginsenosides often have poor bioavailability when taken orally, as they can be poorly absorbed or metabolized quickly. Research is ongoing to develop delivery systems to improve their bioavailability. The optimal dosage and formulation of ginsenosides for different conditions are still being studied, as *ginseng* products can vary widely in their ginsenoside content.

Ginko *biloba*, also known as *ginkgo*, is a tree species native to China known for its distinctive fan-shaped leaves. It has been used in traditional medicine for centuries. Commonly used to improve memory and cognitive function, especially in older adults. It Contains flavonoids and terpenoids that help protect cells from oxidative stress. It enhances blood flow, potentially benefiting conditions like peripheral artery disease and tinnitus. Several studies find it can help reduce symptoms of anxiety. *Ginkgo* promotes blood vessel dilation, improving blood circulation and neutralizes free radicals, reducing oxidative damage. It can Influence neurotransmitters like serotonin and dopamine, affecting mood and cognition.

Referring to FIG. 11, the chemical structure of ginkgolide is shown. Ginkgolides are biologically active terpenic lactones present in *Ginkgo biloba*. They are diterpenoids with 20-carbon skeletons, which are biosynthesized from geranylgeranyl pyrophosphate.

Figures 12, 13:
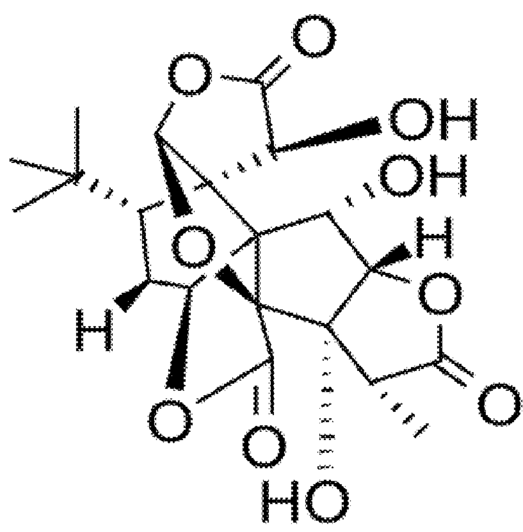
FIG. 12 illustrates the chemical structure of ginkgolide B.
FIG. 13 illustrates the chemical structure of a *Schisandra chinensis* lignan.

Referring to FIG. 12, the chemical structure of ginkgolide B is shown, with reference to ginkgolide A, C, J, and M, having different $R^1$, $R^2$, and $R^3$ groups. Ginkgolide B, specifically, is a diterpenoid trilactone with six five-membered rings. It contains a spiro[4,4]-nonane carbocyclic ring, a tetrahydrofuran ring, and a very specific tert-butyl group at one of the rings (above figure). The class of ginkgolides was first isolated from the tree *Ginkgo biloba* in 1932.

Referring to FIG. 13, the chemical structure of a *Schisandra chinensis* lignan is shown. *Schisandra chinensis* is known for its ability to support liver function, improve endurance, and enhance mental clarity. It also has antioxidant and anti-inflammatory effects. It is often used to boost energy, support detoxification, and enhance overall vitality.

Figures 14, 15:
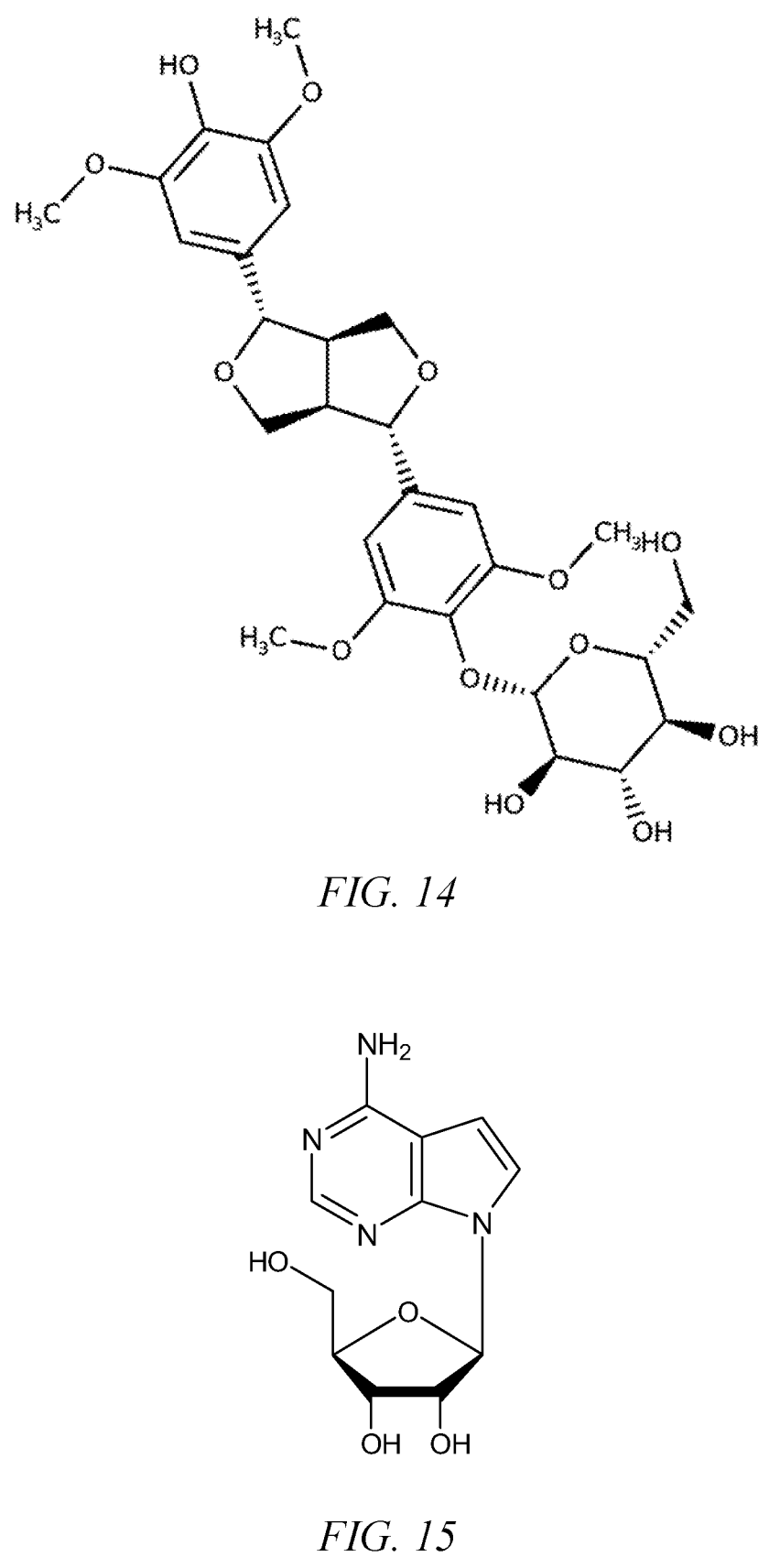

Referring to FIG. 14, the chemical structure of an eleutheroside of Siberian *ginseng* is shown. Eleutherococcus senticosus, also known as Siberian *ginseng*, improves physical endurance, reduces fatigue, and supports the immune system. It is also used to enhance mental performance and resilience, used to increase stamina, support recovery from stress, and improve overall well-being.

Referring to FIG. 15, the chemical structure of cordycepin is shown. *Cordyceps* is a genus of ascomycete fungi that enhances physical performance, supports immune function, and helps manage fatigue. It is also known for its potential anti-aging properties. It is often used by athletes to improve exercise performance and by those seeking to boost energy and stamina.

Figures 16, 17:
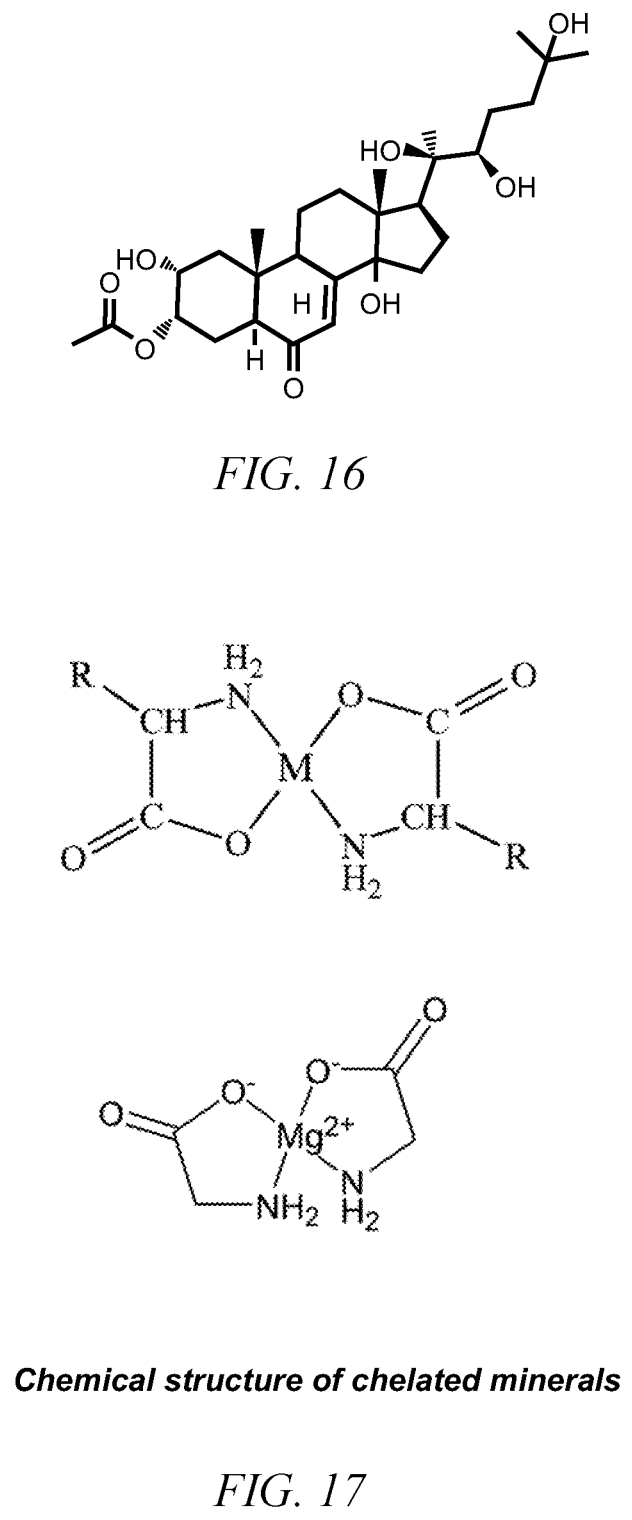

Referring to FIG. 16, the chemical structure of 20-hydroxyecdysone from *Rhaponticum carthamoides* is shown. *Rhaponticum carthamoides*, commonly known as maral root or Siberian *rhaponticum*, is celebrated for its adaptogenic properties and numerous health benefits. For energy and endurance, *Rhaponticum carthamoides* is often used to enhance physical performance and reduce fatigue, particularly among athletes. Research has shown that supplementation with *rhaponticum* led to improved exercise performance and reduced fatigue in trained individuals.

Cognitive enhancement is another benefit of maral root, particularly in individuals suffering from fatigue, supporting its potential to aid memory and concentration. Regarding immune support, research has shown that *Rhaponticum carthamoides* extracts can stimulate immune responses in vitro, suggesting a potential role in strengthening immune health. The plant also appears to aid hormonal balance, especially in regulating stress hormones, such as maintaining balanced cortisol levels during stressful situations. *Rhaponticum carthamoides* is recognized for its anti-inflammatory properties as well. The antioxidant activity of *Rhaponticum carthamoides* is also noteworthy, as it may help combat oxidative stress and lower the risk of chronic diseases.

Adaptogens exert their effects through various biological mechanisms. They help regulate the hypothalamic-pituitary-adrenal (HPA) axis, which is crucial for managing stress responses. By modulating cortisol levels, adaptogens can mitigate the negative consequences of chronic stress. Many adaptogens also influence neurotransmitter systems, increasing levels of serotonin, dopamine, and other mood-regulating compounds, which can lead to improved emotional well-being and reduced anxiety.

Furthermore, adaptogens often exhibit antioxidant properties, protecting cells from oxidative stress and inflammation exacerbated by stress. They enhance immune function by regulating cytokine production and promoting the activity of immune cells, thereby aiding the body's response to stress and pathogens. Some adaptogens also improve mitochondrial function, which boosts energy production and reduces fatigue, particularly beneficial during periods of heightened physical or mental demand.

Adaptogens play a significant role in helping the body adapt to stress and maintain balance. Their diverse benefits stem from complex mechanisms that involve hormonal regulation, neurotransmitter modulation, and antioxidant protection. While many individuals find them helpful for managing stress and enhancing overall well-being, following research studies show effects on stress relief, anxiety, improves mood, inflammation and physical performance.

The Recommended Dietary Allowance (RDA) for adaptogens is not standardized like that for vitamins and minerals, as these herbal supplements can vary significantly in their active constituents and effects. However, general dosage guidelines based on common research and traditional use suggest that for ashwagandha (*Withania somnifera*), a typical dosage is 300 to 600 mg of a standardized extract containing at least 5% withanolides per day. For *Rhodiola rosea*, the recommended dosage ranges from 200 to 600 mg of a standardized extract with at least 3% rosavin and 1% salidroside daily. Holy basil (*Ocimum sanctum*) is generally taken at 300 to 2,000 mg of dried leaf or 300 to 500 mg of extract per day. *Ginseng* (*Panax ginseng*) typically involves a dosage of 200 to 400 mg of a standardized extract with at least 4 to 7% ginsenosides per day. *Schisandra chinensis* is often dosed at 500 to 2,000 mg of dried berries or 100 to 200 mg of extract daily. For *cordyceps sinensis*, the usual dosage is 1,000 to 3,000 mg of a standardized extract per day. It is important to consider that dosages may vary based on individual health conditions, age, and specific health goals.

While adaptogens are generally considered safe for most individuals, they can cause adverse effects in some cases, particularly if taken inappropriately or in high doses. Ashwagandha (*Withania somnifera*) may lead to gastrointestinal upset, including nausea and diarrhea, as well as drowsiness or sedation. It can also affect hormonal levels, potentially increasing thyroid hormone, and some individuals may experience allergic reactions. *Rhodiola Rosea* might result in insomnia, particularly if taken in high doses or late in the day, along with irritability, dry mouth, and nausea. Holy Basil (*Ocimum sanctum*) has been associated with gastrointestinal issues such as nausea and diarrhea, as well as low blood sugar (hypoglycemia). It may also interact with anticoagulant medications. *Ginseng* (*Panax ginseng*) can cause insomnia or sleep disturbances, headaches, and upset stomach. It may lead to changes in blood pressure, either raising or lowering it, and can affect hormonal levels by influencing estrogen. *Schisandra chinensis* may result in gastrointestinal discomfort, including diarrhea and heartburn, and in some cases, allergic reactions. *Cordyceps Sinensis* can also cause gastrointestinal issues such as diarrhea and upset stomach, and may lead to allergic reactions. There is a possibility of interactions with immunosuppressive drugs. It is important to note that many adaptogens have not been studied extensively in pregnant or breastfeeding women, so caution is advised in these populations. Adaptogens can also interact with various medications, particularly those for diabetes, blood pressure, and anticoagulants.

Chelated Minerals

Referring to FIG. 17, the general chemical structure of chelated minerals and the chemical structure of magnesium glycinate are shown. Chelated minerals are minerals that have been chemically bound to another molecule, typically an amino acid, to enhance their absorption and bioavailability in the body. This chelation process creates a more stable compound that the body recognizes and absorbs more effectively than non-chelated forms of the mineral. Chelated minerals involve covalent or coordinate bonds with organic molecules, while salts are formed through ionic bonds between positively and negatively charged ions. Chelated minerals are not considered salts because their chemical structure and behavior differ from ionic salts. Chelated minerals are more readily absorbed by the digestive system compared to non-chelated forms. This is because the body more easily identifies and absorbs chelated compounds, especially when the chelate involves amino acids or organic molecules. Some examples of chelated minerals include magnesium glycinate, zinc gluconate, and calcium citrate. Chelated minerals are generally gentler on the stomach and intestines, causing less gastrointestinal discomfort (such as bloating or constipation) compared to non-chelated forms like calcium carbonate or magnesium oxide.

Chelation enhances the stability of the mineral, preventing it from reacting with other compounds in the digestive tract. This can prevent the formation of insoluble complexes that reduce the mineral's absorption. The chelation process helps minerals remain soluble in the low pH environment of the stomach, allowing for better absorption even in individuals with impaired digestion or those who take antacids. Chelated minerals are absorbed differently than their non-chelated counterparts, often through amino acid transport pathways rather than mineral-specific pathways. This can reduce competition between minerals like calcium, magnesium, and iron, leading to more efficient absorption of each.

Because of the higher bioavailability of chelated minerals, lower doses are often required to achieve the same physiological benefits as non-chelated minerals. This is advantageous for individuals who have difficulty absorbing or tolerating larger doses of minerals. Chelated minerals are absorbed more effectively in the intestines due to their stable structure. The chelation protects the minerals from interactions with dietary components that can inhibit absorption (e.g., phytates, oxalates). Once absorbed, these minerals can be more readily transported to tissues where they exert their effects.

Calcium (e.g., calcium citrate, calcium glycinate): Used for bone health and muscle function. Magnesium (e.g., magnesium glycinate, magnesium malate): Important for muscle relaxation, nerve function, and cardiovascular health. Zinc (e.g., zinc picolinate, zinc gluconate): Essential for immune function, wound healing, and protein synthesis. Iron (e.g., iron bisglycinate) is Important for red blood cell production and oxygen transport. Copper (e.g., copper gluconate), supports immune function, red blood cell formation, and collagen synthesis.

Chelated calcium and magnesium are often recommended for improving bone density and preventing conditions like osteoporosis. Chelated magnesium, especially magnesium glycinate, is known for its calming effects on muscles and its ability to relieve cramps and spasms. Chelated zinc and copper support immune function, with better absorption leading to greater efficacy in supplementing diets low in these minerals. Minerals like magnesium, when chelated, help regulate heart rhythm and blood pressure.

Chelated minerals are commonly used in dietary supplements, particularly for individuals with malabsorption issues, those taking medications that impair mineral absorption, or those with increased mineral needs, such as athletes or pregnant women. The bioavailability of chelated minerals is generally higher compared to non-chelated forms due to improved absorption rates. Zinc bioavailability can range from 30-50% for chelated forms, compared to 20-25% for non-chelated. Magnesium, Chelated forms like magnesium glycinate are often better absorbed than magnesium oxide.

The Recommended Dietary Allowance (RDA) for minerals varies according to age, gender, and life stage. For zinc, the RDA is 11 mg for adult men and 8 mg for adult women. Magnesium requirements range from 400 to 420 mg for men and 310 to 320 mg for women. The RDA for iron is 8 mg for men and 18 mg for women. Recommended dosages for chelated minerals can differ based on individual needs; for zinc chelate, a typical dosage is 15 to 30 mg per day. Magnesium chelate is usually taken at 200 to 400 mg per day, while iron chelate may be dosed at 18 to 30 mg per day for those with iron deficiency.

Chelated minerals can have several potential adverse effects. Gastrointestinal issues are common, with some individuals experiencing discomfort such as nausea, diarrhea, or constipation, particularly when taking high doses or sensitive forms of minerals. Over-supplementation may lead to mineral imbalances; for example, excessive zinc can hinder copper absorption, while too much magnesium can disrupt calcium levels. Although rare, allergic reactions to specific chelating agents or minerals can occur, presenting symptoms like rash, itching, or respiratory difficulties.

High doses of certain chelated minerals, especially magnesium, may strain kidney function, particularly in those with existing kidney conditions. Additionally, chelated minerals can interact with medications, potentially affecting their absorption and effectiveness. This includes interference with antibiotics and medications for thyroid disorders. Inappropriate or excessive intake can lead to toxicity, notably with minerals such as iron, where high levels may cause oxidative damage to tissues. Lastly, there is a risk of bioaccumulation of some minerals in the body if taken over extended periods, which could result in long-term adverse effects.

Optimal dosages of minerals like calcium, magnesium, and zinc in combination with vitamins have synergistic effects on bone density and metabolic health. Calcium and magnesium play a role in maximizing bone density and preventing osteoporosis. Zinc is important in enhancing immune function, and is an effective supplement alongside vitamin C. Magnesium interacts with various nutrients for improved cardiovascular and metabolic health. Chelation also enhances mineral absorption and bioavailability. Iron supplement dosages, when paired with vitamin C and other minerals, improves absorption as well.

Other research has shown that minerals in combination with DHEA or DHEA derivatives have beneficial effects. The bioavailability of various chelated minerals is enhanced compared to non-chelated forms. Zinc is critical to immune function, and its deficiency can impair immune responses. And chelated zinc forms enhance bioavailability and support better immune health. Chelated forms of magnesium can improve absorption and efficacy in promoting bone health. Chelation also enhances iron bioavailability. A comprehensive review of the health benefits and mechanisms of action of chelated minerals. Combining DHEA with essential minerals has shown clinically supported synergistic benefits across various physiological functions. Zinc, crucial for testosterone synthesis and immune modulation, enhances DHEA's anabolic effects, as evidenced by studies linking zinc supplementation with improved hormonal balance and muscle strength. Magnesium, known to modulate the hypothalamic-pituitary-adrenal (HPA) axis, complements DHEA's stress-relieving effects, supported by clinical trials demonstrating magnesium's efficacy in reducing cortisol levels and improving mood. Selenium, a potent antioxidant, boosts DHEA's anti-inflammatory properties, as shown in studies where selenium supplementation reduced oxidative stress markers. Calcium and DHEA together improve bone density, particularly in postmenopausal women, as highlighted in research on osteoporosis prevention. Chromium enhances metabolic health by improving insulin sensitivity, aligning with findings that DHEA and chromium together reduce markers of metabolic syndrome. Additionally, potassium supports DHEA's cardiovascular benefits by maintaining blood pressure, while iron optimizes red blood cell production, complementing DHEA's role in oxygen transport. These clinically supported interactions make mineral and DHEA combinations effective for improving hormone regulation, metabolic function, and overall health.

Non-Esterified Omega-3 Fatty Acids (NEFAS)

Figure 18:
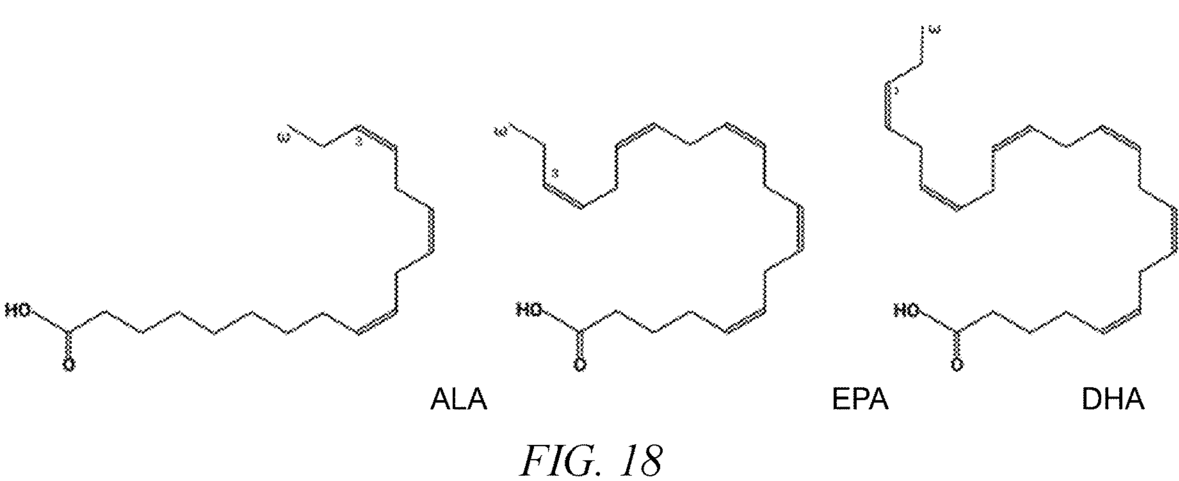
FIG. 18 illustrates the chemical structures of alpha-linolenic acid, eicosapentaenoic acid, and docosahexaenoic acid.

Referring to FIG. 18, the chemical structures of three NEFAs, alpha-linolenic acid (ALA), eicosapentaenoic acid (EPA), and docosahexaenoic acid (DHA) are shown. NEFAs can serve as an effective bioavailability delivery system due to their unique properties. NEFAs enhance the solubility and absorption of lipophilic supplements, facilitating their transport across cell membranes. By forming micelles, NEFAs can encapsulate supplements, improving their stability and bioavailability. Additionally, NEFAs can target specific tissues, as they are readily metabolized by cells, allowing for localized nutrients release and action. This delivery method can reduce the necessary dosage and minimize side effects while improving nutritional efficacy. Overall, NEFAs represent a promising approach for enhancing bioavailability delivery in various nutritional applications.

NEFAs, also known as free fatty acids (FFAs), are fatty acids not bound to glycerol or other molecules, circulating in the blood and released from adipose tissue or ingested through diet. Various types of NEFAs have distinct effects on health. Recent research highlights the benefits of omega-3 fatty acids. NEFAs play a role in reducing triglyceride levels, inflammation, and improving endothelial function, and positively affect cognitive health, particularly in reducing cognitive decline and supporting brain function. NEFAs may also influence hormones like cortisol and testosterone, suggesting a potential to modulate hormonal balance and improve markers related to stress and inflammation.

DHEA and omega-3 PUFAs (particularly EPA and DHA) are highlighted for their complementary roles in modulating brain function and mental health. Omega-3s act through anti-inflammatory pathways, reducing neuroinflammation by lowering pro-inflammatory cytokines and promoting the production of specialized pro-resolving mediators like resolvins. They also enhance synaptic plasticity, regulate neurotransmitters such as serotonin and dopamine, and influence the hypothalamic-pituitary-adrenal (HPA) axis, which is crucial for stress response. DHEA, a neurosteroid, similarly regulates the HPA axis by counteracting cortisol's effects, reduces oxidative stress, and promotes neuroprotection and neurogenesis. The study suggests that omega-3 supplementation may enhance DHEA production, with both contributing to improved mood and cognitive function through their combined neuroprotective, anti-inflammatory, and synaptic-enhancing mechanisms, offering potential antidepressant effects.

The combination of DHEA and NEFAs may have synergistic effects on inflammatory markers and hormonal balance. Combining NEFAs and DHEA may also yield synergistic benefits for cardiovascular health, cognitive function, and metabolic regulation. Additional studies demonstrate that free fatty acids increase androgen precursors in vivo.

The study investigates how elevated free fatty acids (FFAs) affect androgen metabolism, particularly in adrenal androgen precursors such as dehydroepiandrosterone (DHEA). The research demonstrates that increased FFAs, induced via lipid and heparin infusions, lead to a rise in circulating androgen precursors. This effect is independent of insulin sensitivity, which remained unchanged during the short-term elevation of FFAs. The findings highlight a potential mechanism where metabolic states with elevated FFAs, such as obesity or insulin resistance, may contribute to androgen excess, which is observed in conditions like polycystic ovary syndrome (PCOS).

Stilbenoids

Figure 19:
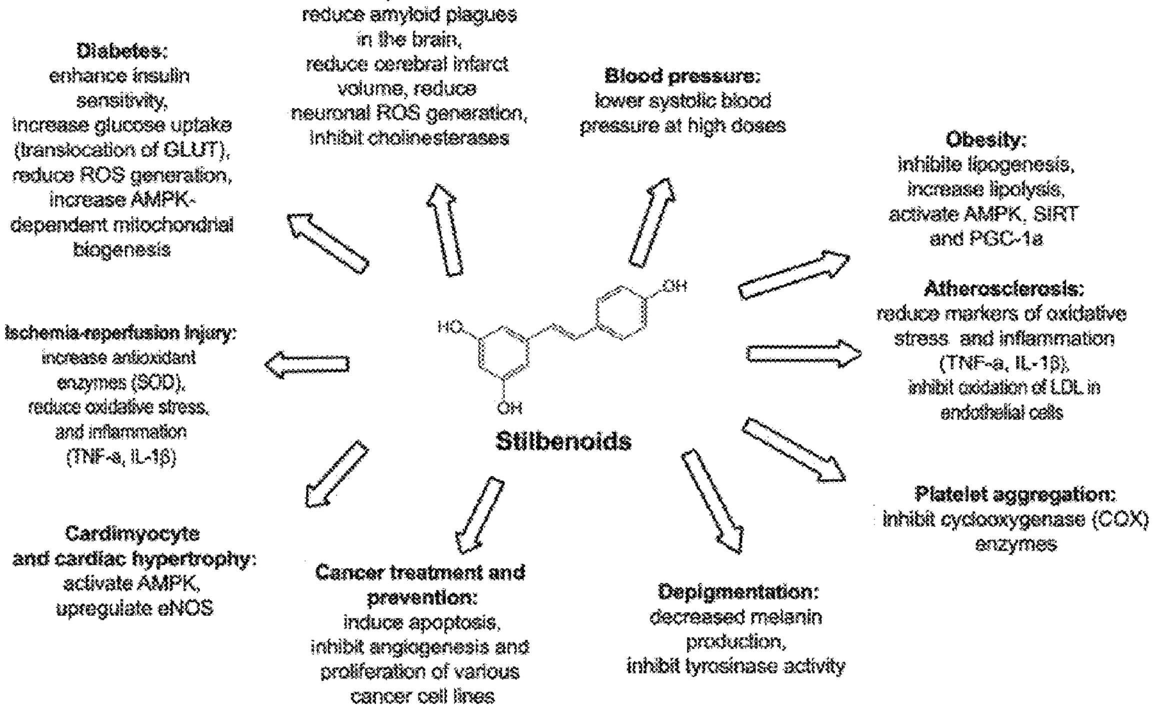
FIG. 19 illustrates the general chemical structure of a stilbenoid and its various uses.

Referring to FIG. 19, the general chemical structure of stilbenoids and various uses are shown. Stilbenoids are a class of natural compounds that are derived from stilbene, primarily known for their potential health benefits. The most well-known stilbenoid is resveratrol, but there are several others, each with unique properties. Here's an overview of the key stilbenoids, their benefits, mechanisms of action, nutritional effects, and other relevant information.

Common dosages for stilbenoids typically range from 100 mg to 500 mg per day, with higher doses used in clinical settings. Stilbenoids are recognized for their antioxidant, anti-inflammatory, cardioprotective, and potential neuroprotective effects. For example, stilbenoids play a role in reducing oxidative stress and inflammation. The mechanism of action involves the activation of sirtuins (SIRT1), which are crucial for cellular longevity and metabolism. These compounds also interact with various signaling pathways, such as AMPK and NF-kB, enhancing their protective effects.

Stilbenoids may improve cardiovascular health, reduce cancer risk, and support cognitive function. Generally, stilbenoids are well-tolerated, but some individuals may experience gastrointestinal upset. They can also interact with blood thinners, warranting caution for those undergoing anticoagulant therapy. Pterostilbene is commonly dosed around 50 mg to 150 mg per day and is recognized for supporting brain health, metabolic health, and exhibiting antioxidant properties. Research indicates that pterostilbene may offer similar benefits to resveratrol but with improved bioavailability. The mechanism of action for pterostilbene includes the activation of SIRT1 and a positive influence on lipid metabolism. Research demonstrates that pterostilbene affects lipid profiles, indicating its potential for cardiovascular health. It may aid in managing cholesterol levels and show anti-cancer properties. Pterostilbene supplementation has been shown to improve cholesterol levels and cardiovascular markers.

Trans-stilbene is not well-studied in humans, and specific dosage recommendations are limited. While there are potential antioxidant effects, more research is necessary to fully understand its benefits. Hopeaphenol has limited human studies, and typical doses have not been established. Known for antioxidant and anti-inflammatory properties, hopeaphenol shows potential in cancer therapy. Its mechanism of action involves modulating oxidative stress pathways, but specific details require further investigation. The nutritional effects are acknowledged, particularly regarding cancer prevention, but more research is necessary to validate these claims. Adverse effects remain poorly documented due to a lack of extensive research.

Stilbenoids generally exhibit antioxidant activity, reducing oxidative stress and inflammation, and are linked to improved cardiovascular health, as supported by various studies. For instance, stilbenoids positively influence heart health by enhancing endothelial function and lipid profiles. They may also provide neuroprotection against neurodegenerative diseases and exhibit metabolic benefits that support weight management and glucose metabolism. While generally regarded as safe, stilbenoids can cause mild gastrointestinal upset and may interact with medications, particularly anticoagulants. Long-term safety data, especially concerning high doses, are limited.

Trans-Resveratrol

Figures 20, 21:
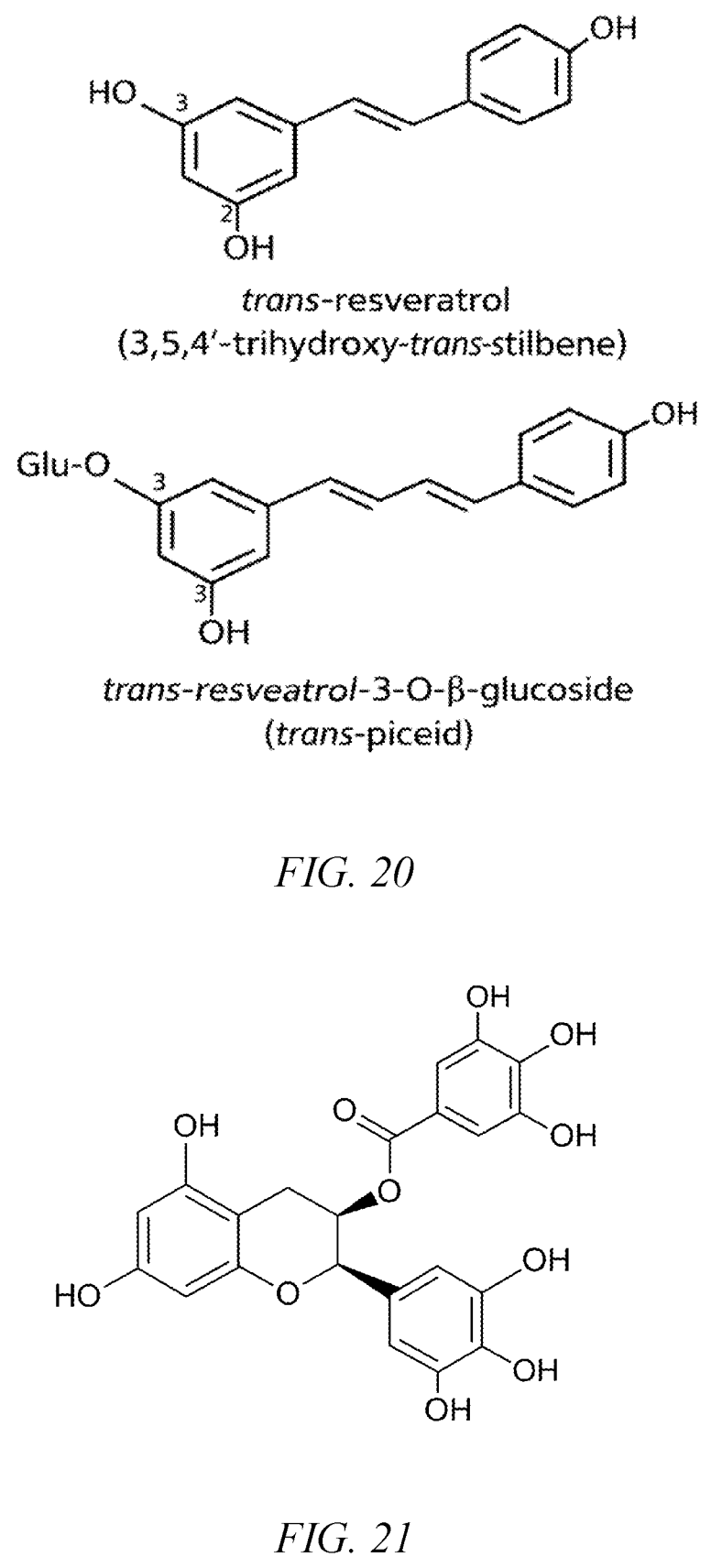

Referring to FIG. 20, the chemical structures of trans-resveratrol and trans-resveratrol glucoside are shown. Trans-resveratrol is a natural polyphenolic compound found in various plants, particularly in the skin of red grapes, berries, peanuts, and certain medicinal herbs. It is often praised for its antioxidant properties and potential health benefits.

Trans-resveratrol may improve cardiovascular health by enhancing endothelial function and reducing inflammation, with studies indicating associations with lower blood pressure and improved cholesterol levels. For instance, trans-resveratrol supplementation significantly improves endothelial function and reduced arterial stiffness in subjects with cardiovascular risk factors.

Trans-resveratrol also exhibits strong antioxidant effects by neutralizing free radicals, potentially reducing oxidative stress in the body. Trans-resveratrol scavenges free radicals, thereby enhancing the body's antioxidant defense systems.

In terms of anti-inflammatory properties, trans-resveratrol may inhibit inflammatory pathways and cytokine production, which can help manage chronic inflammatory conditions. Trans-resveratrol significantly reduces levels of pro-inflammatory cytokines, suggesting its utility in treating conditions like arthritis and metabolic syndrome. Trans-resveratrol also shows promise in providing neuroprotective effects against neurodegenerative diseases like Alzheimer's and Parkinson's disease by reducing oxidative damage and inflammation.

Regarding anti-aging effects, trans-resveratrol is thought to activate sirtuins, specifically sirtuin 1 (SIRT1), which are proteins involved in regulating cellular health. This activation may contribute to longevity and improved metabolic health. Preliminary studies suggest potential cancer prevention properties of trans-resveratrol, particularly through the inhibition of cancer cell proliferation and induction of apoptosis. The mechanisms of action for trans-resveratrol include its antioxidant activity, where it scavenges free radicals and enhances antioxidant defense systems, and sirtuin activation, influencing longevity and metabolism.

Additionally, trans-resveratrol modulates the NF-κB signaling pathway, which plays a critical role in inflammation and immune response. Trans-resveratrol enhances nitric oxide production, promoting vascular health and improving blood flow.

Trans-resveratrol has nutritional effects in managing cardiovascular disease, as evidence suggests it can help control risk factors associated with heart disease. Furthermore, it may aid in managing chronic inflammatory diseases and has potential as a nutritional agent in neurodegenerative diseases, although further research is needed for clinical application. Ongoing studies are exploring its role in cancer prevention and treatment, with promising preclinical results.

Generally considered safe, trans-resveratrol, when taken in appropriate doses (typically up to 1,000 mg per day), is well-tolerated. However, some individuals may experience gastrointestinal issues such as nausea, diarrhea, or stomach upset, particularly at higher doses. Additionally, trans-resveratrol can interact with anticoagulant medications, increasing bleeding risk, and caution is advised for individuals on blood thinners. There is potential for estrogenic activity, so those with hormone-sensitive conditions should consult a healthcare provider.

Referring again to FIG. 20, trans-resveratrol glycoside is a compound formed when trans-resveratrol is attached to a sugar molecule, enhancing its stability and altering its absorption and metabolism compared to free trans-resveratrol. This compound is primarily sourced from plants, particularly grape skins and berries. Glycosylation can improve its solubility and stability, but it may also influence the effectiveness of its health benefits. Like trans-resveratrol, trans-resveratrol glycoside may exhibit antioxidant, anti-inflammatory, and cardioprotective properties, although research specifically focused on glycosides is still evolving. Both trans-resveratrol and its glycoside modification present a variety of potential health benefits, particularly in cardiovascular health, antioxidant protection, and anti-inflammatory effects. While generally considered safe at recommended doses, individuals should consult healthcare professionals before starting supplementation, especially if they have underlying health conditions or are taking medications. Ongoing research will further elucidate their nutritional potential and mechanisms of action.

Studies indicate glycosylation of resveratrol enhances its pharmacokinetic properties, by affecting bioavailability and metabolic pathways. A comparative study of the antioxidant activity of resveratrol and its glycosides indicates varied efficacy of the antioxidant properties of trans-resveratrol compared to its glycoside forms. Other related research found cardiovascular benefits, an effect of pterostilbene on metabolic syndrome. Overall, trans-resveratrol and its glycoside modification show promise for a range of health benefits, particularly in cardiovascular and metabolic health.

Green Tea Extract

Referring to FIG. 21, the chemical structure of green tea extract is shown. Green tea extracts, derived from the leaves of *Camellia sinensis*, are rich in bioactive compounds, particularly polyphenols like catechins. These extracts have gained popularity for their health benefits and are commonly used in dietary supplements and functional foods. Green tea extracts play a significant role in promoting overall health due to their antioxidant properties and potential effects on metabolism, cardiovascular health, and weight management. They are often utilized for their ability to support wellness and prevent various health issues.

Green tea extracts are high in catechins, particularly epigallocatechin gallate (EGCG), which help combat oxidative stress and reduce free radical damage. Some studies suggest that green tea extracts can enhance fat oxidation and improve metabolic rate, making them useful for weight management and fat loss. Regular consumption of green tea extracts may lower cholesterol levels, reduce blood pressure, and improve overall heart health. Green tea extracts may help improve insulin sensitivity and lower blood sugar levels, which can be beneficial for individuals with diabetes. The anti-inflammatory properties of catechins can help reduce inflammation in the body, potentially lowering the risk of chronic diseases. Some research indicates that green tea extracts may support brain health and improve cognitive function, possibly reducing the risk of neurodegenerative diseases.

Green tea extracts exert their effects primarily through catechins that neutralize free radicals and reduce oxidative stress, protecting cells and tissues from damage. Green tea extracts can enhance thermogenesis (the body's production of heat) and fat oxidation, leading to increased energy expenditure. EGCG and other catechins inhibit certain enzymes, such as lipase and amylase, which can reduce the absorption of fats and carbohydrates. Green tea extracts can also influence hormone levels related to appetite and metabolism, such as increasing levels of norepinephrine, which aids in fat burning. The compounds in green tea can inhibit inflammatory pathways, reducing the production of pro-inflammatory cytokines and promoting a balanced inflammatory response.

The appropriate dosage of green tea extract can vary depending on the specific formulation and intended use. For standardized extracts containing 50-90% catechins, a common dosage ranges from 250 mg to 500 mg per day. Many supplements emphasize epigallocatechin gallate (EGCG), with recommended dosages typically between 100 mg and 400 mg of EGCG per day. For liquid green tea extracts, it's important to follow the manufacturer's recommendations, as these can differ significantly. Drinking 3 to 5 cups of brewed green tea daily generally provides beneficial amounts of catechins, usually yielding between 240 mg and 320 mg.

Dosages may need adjustment based on individual health status, tolerance, and specific health goals. It's also worth noting that green tea extracts can contain caffeine, so individuals sensitive to caffeine should monitor their intake accordingly. Studies have shown various health-related aspects of green tea, including its potential benefits for weight loss, cardiovascular health, and cancer prevention, weight loss and maintenance through increased fat oxidation, protection against neurodegenerative diseases, improvement in insulin sensitivity and blood glucose management, resistance to certain cancers, and antioxidant properties among other benefits. These studies collectively underscore the wide-ranging nutritional effects associated with green tea extract, particularly concerning cardiovascular health, weight management, neuroprotection, metabolic health, cancer prevention, and general wellness.

Essential Amino Acids (EAAs)

Figures 22, 23:
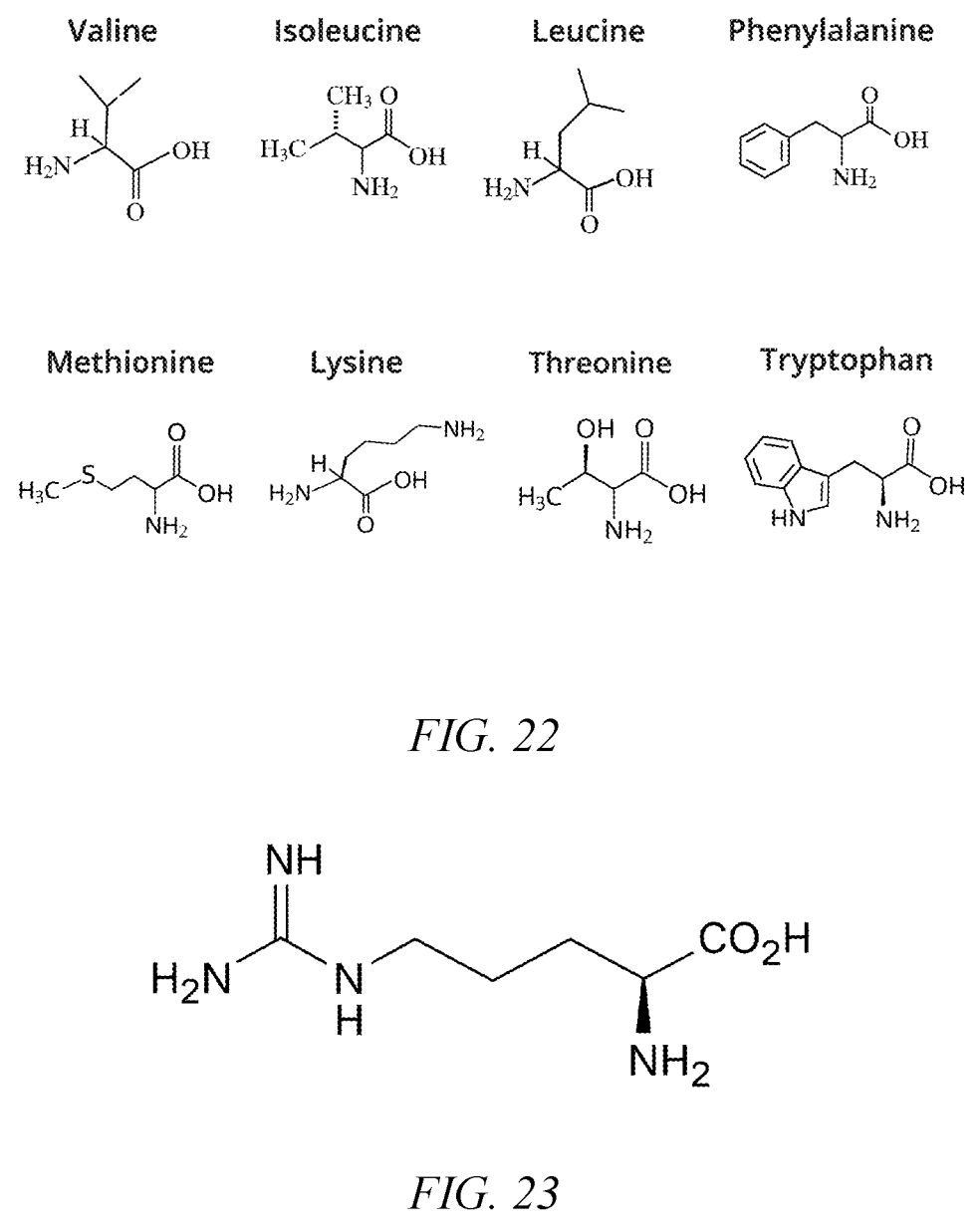

Referring to FIG. 22, the chemical structures for the EAAs valine, isoleucine, leucine, phenylalanine, methionine, lysine, threonine, and tryptophan are shown. These are amino acids that the body cannot synthesize and must be obtained from dietary sources. There are nine EAAs: Leucine, Isoleucine, Valine, Lysine, Methionine, Threonine, Tryptophan, Phenylalanine, Histidine.

There are several forms of EAAs available for supplementation, each with its own dosage recommendations. EAA powders are concentrated forms that can be mixed with water or other liquids, typically flavored for taste. The recommended dosage for EAA powders is 10-15 grams per serving, commonly taken post-workout or during workouts. EAA capsules and tablets provide a convenient and portable option, with a dosage of 5-10 grams per serving, taken with water for ease of use. Liquid EAAs are ready-to-drink formulations that also deliver 10-15 grams per serving, often consumed around workout times. EAA blends, which may include additional ingredients like electrolytes or carbohydrates to enhance performance and recovery, usually recommend a dosage of 10-20 grams per serving, depending on the specific formulation.

The benefits of EAAs are significant. They are crucial for muscle protein synthesis, especially leucine, which plays a key role in stimulating this process to support muscle repair and growth. Research has shown the importance of leucine in protein metabolism. EAAs also improve recovery, with EAA supplementation reducing muscle soreness and promote faster recovery after intense exercise. Additionally, EAAs can enhance endurance by serving as an energy source during prolonged exercise. Furthermore, they support muscle retention during caloric restriction or weight loss by promoting protein synthesis. EAAs also influence hormonal regulation, including the secretion of insulin, which is critical for nutrient uptake and metabolism.

While EAAs are generally safe for most individuals, they may cause some adverse effects, including digestive issues such as nausea, diarrhea, or stomach cramps. Excessive intake can disrupt the balance of amino acids in the body, potentially leading to kidney strain, especially in individuals with pre-existing kidney conditions. There is also a risk of potential allergic reactions to specific EAA supplements, although these are rare. Lastly, EAAs might interact with certain medications, affecting their efficacy. Overall, EAAs are essential for various physiological processes, particularly in muscle health and recovery, and their diverse forms make them accessible for supplementation.

L-Arginine

Referring to FIG. 23 the chemical structure for L-arginine is shown. L-arginine is a semi-essential amino acid that plays a crucial role in various physiological processes in the body, particularly in the production of nitric oxide (NO). It is a precursor to nitric oxide, which aids in dilating blood vessels, thus improving blood flow and circulation. This enhancement in blood flow contributes to cardiovascular health by potentially lowering blood pressure and improving endothelial function. Additionally, L-arginine can enhance exercise performance by improving oxygen and nutrient delivery to muscles during physical activity. It may also promote wound healing through increased collagen synthesis and improved blood flow to injured areas. Furthermore, L-arginine supports immune function by promoting the proliferation of immune cells and is commonly used as a treatment for erectile dysfunction due to its role in enhancing blood flow.

For general health, a typical dosage of L-arginine ranges from 2 to 6 grams per day, often divided into doses, while higher dosages of 5 to 10 grams per day may be used for specific conditions like erectile dysfunction or cardiovascular health. L-arginine is frequently taken before exercise or in divided doses throughout the day.

The mechanism of action for L-arginine includes its conversion to nitric oxide by nitric oxide synthase, leading to vasodilation and increased blood flow. It serves as a building block for protein synthesis, supports muscle growth and repair, stimulates the release of growth hormone and insulin, and plays a role in the urea cycle to help remove excess ammonia from the body.

Nutritional ally, L-arginine supplementation has shown promise in managing cardiovascular disorders such as hypertension and atherosclerosis. It may enhance exercise performance and recovery by improving blood flow and nutrient delivery. L-arginine is also used in clinical settings to aid recovery from surgery and injury and is commonly recommended for men experiencing erectile dysfunction.

While L-arginine is generally safe, it can have adverse effects. Common gastrointestinal issues include nausea, diarrhea, and abdominal pain. Some individuals may experience allergic reactions, such as rash or swelling. Due to its vasodilatory effects, L-arginine may cause hypotension in some individuals. It can also interact with medications for hypertension or erectile dysfunction, enhancing their effects. Those with asthma or herpes virus infections should consult a healthcare provider before use, as L-arginine may exacerbate these conditions.

Recent research highlights L-arginine's benefits, including improvement in cardiovascular health by enhancing endothelial function and reducing blood pressure, enhancing exercise performance and recovery, improving erectile function in men with erectile dysfunction, benefiting patients with coronary artery disease and vascular function, and enhancing wound healing processes, highlighting its potential clinical applications.

L-arginine is a versatile amino acid with various health benefits, particularly for cardiovascular health, exercise performance, and wound healing. While generally safe, potential side effects and interactions warrant consideration, and consultation with a healthcare provider is recommended before starting supplementation.

Water Soluble Vitamins

Figures 24, 25:
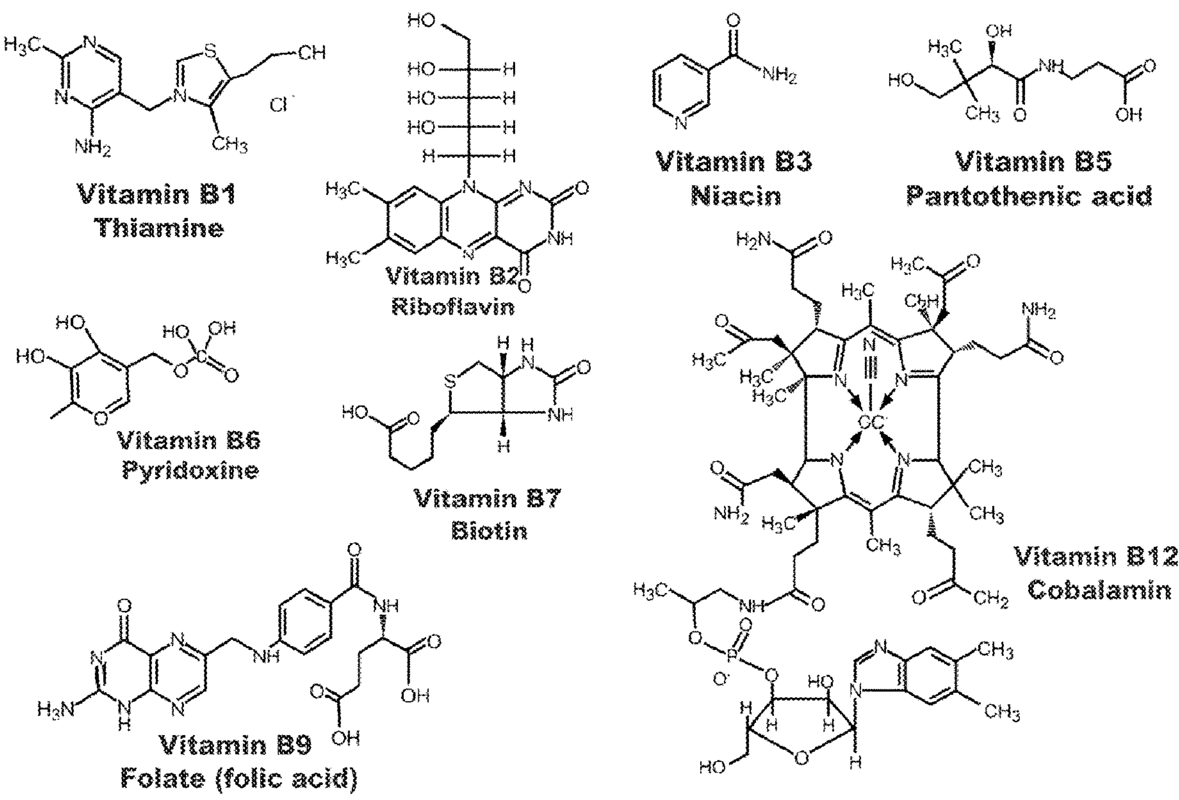
FIG. 24 illustrates the chemical structures of Vitamin B1, B2, B3, B4, B5, B6, B7, B9, and B12.
FIG. 25 illustrates the chemical structure of vitamin C (ascorbic acid).

Referring to FIG. 24, the chemical structures of Vitamin B1, B2, B3, B4, B5, B6, B7, B9, and B12 are shown. Vitamin B refers to a group of water-soluble vitamins that play essential roles in cellular metabolism, energy production, and various bodily functions. The B vitamins include B1 (Thiamine), B2 (Riboflavin), B3 (Niacin), B5 (Pantothenic Acid), B6 (Pyridoxine), B7 (Biotin), B9 (Folate), and B12 (Cobalamin).

Vitamin B comprises various forms, each with distinct health benefits. Vitamin B1, or thiamine, supports energy metabolism, nerve function, and carbohydrate utilization, with a recommended dosage of 1.1 mg for women and 1.2 mg for men daily. It converts carbohydrates into energy through glycolysis and the Krebs cycle, and may help prevent Wernicke-Korsakoff syndrome, a serious brain disorder associated with alcoholism. Generally safe, high doses may cause allergic reactions.

Vitamin B2, known as riboflavin, is important for energy production, skin health, and eye health, with daily dosages of 1.1 mg for women and 1.3 mg for men. It functions as a coenzyme in energy metabolism and antioxidant processes and may reduce the frequency of migraines. Adverse effects are rare, though it may cause bright yellow urine.

Vitamin B3, or niacin, supports cholesterol levels, skin health, and nervous system function, with recommended dosages of 14 mg for women and 16 mg for men daily. It converts food into energy and synthesizes hormones, making it useful for managing hyperlipidemia. High doses can lead to flushing, itching, and gastrointestinal issues.

Vitamin B5, or pantothenic acid, is essential for synthesizing coenzyme A, which is involved in fatty acid metabolism, with a daily dosage of 5 mg. It plays a role in the Krebs cycle and may help manage stress and improve energy levels. Adverse effects are rare but may include diarrhea at very high doses.

Vitamin B6, known as pyridoxine, supports amino acid metabolism, red blood cell production, and immune function, with a dosage of 1.3 mg for adults, higher for those over 50. It acts as a coenzyme in over 100 enzymatic reactions, particularly those involving amino acids, and may assist in managing premenstrual syndrome and depression. High doses can lead to nerve damage and sensory neuropathy.

Vitamin B7, or biotin, is important for hair, skin, and nail health, and aids in carbohydrate and fat metabolism, with a daily dosage of 30 mcg. It serves as a coenzyme for carboxylase enzymes in fatty acid synthesis, potentially improving nail strength and hair health. Adverse effects are rare, and it is generally considered safe.

Vitamin B9, or folate, is crucial for DNA synthesis, red blood cell formation, and fetal development during pregnancy, with dosages of 400 mcg for women and 600 mcg for pregnant women daily. It is involved in one-carbon metabolism and nucleotide synthesis, reducing the risk of neural tube defects during pregnancy, but high doses may mask vitamin B12 deficiency.

Finally, Vitamin B12, known as cobalamin, is essential for nerve function, red blood cell formation, and DNA synthesis, with a recommended dosage of 2.4 mcg daily. It participates in methylation processes and myelin production, potentially improving cognitive function and energy levels in those with deficiency. It is generally safe, though high doses can lead to acne and rosacea in some individuals.

Studies have shown that thiamine assists in liver disease management, and plays a role in preventing Wernicke's encephalopathy. Riboflavin has the potential to reducing migraine frequency by improving mitochondrial energy production. B6 supplementation plays a role in lowering homocysteine levels, but while it reduced homocysteine, it did not significantly lower cardiovascular events. A combination of B6, B12, and folate have been shown to reduce brain atrophy in elderly participants with mild cognitive impairment. Riboflavin supplementation also improved hemoglobin levels in women with riboflavin deficiency anemia. The B6, B12 combination with folate has been shown to slow brain atrophy in elderly individuals with mild cognitive impairment. Niacin plays a role in lipid management and has cardiovascular benefits. Folic acid is effective in reducing neural tube defects in pregnancies.

The B vitamins play vital roles in numerous physiological processes, contributing to energy metabolism, nerve function, and overall health. While generally safe, specific dosages and potential side effects should be considered. Consultation with a healthcare provider is recommended before starting any supplementation.

Referring to FIG. 25, the chemical structure of vitamin C (ascorbic acid) is shown. Vitamin C provides multiple health benefits, including antioxidant protection that neutralizes free radicals, reducing oxidative stress and potentially lowering the risk of chronic diseases. It enhances immune function by supporting various cellular activities within both the innate and adaptive immune systems. Vitamin C is essential for collagen synthesis, which is crucial for skin, cartilage, and connective tissues, and promotes faster wound healing by aiding collagen formation and maintaining skin integrity. Additionally, it increases the absorption of non-heme iron from plant-based foods, helping to prevent anemia, and may support cognitive health while reducing the risk of neurodegenerative diseases due to its antioxidant properties.

The recommended dietary allowance (RDA) for adult men is 90 mg per day and for adult women is 75 mg per day, with increased requirements for pregnant (85 mg) and lactating women (120 mg). The upper limit is set at 2,000 mg per day to avoid potential adverse effects.

Vitamin C functions as an antioxidant by donating electrons to neutralize free radicals, thereby reducing oxidative stress. It serves as a cofactor for enzymes involved in collagen synthesis, neurotransmitter production, and the metabolism of certain amino acids. Furthermore, it influences immune modulation by enhancing the production and function of white blood cells. In terms of nutritional effects, vitamin C is crucial for the prevention and treatment of scurvy, correcting vitamin C deficiency and improving overall health. Some studies suggest that regular supplementation may reduce the duration and severity of colds, while its antioxidant properties may lower the risk of chronic diseases, including cardiovascular diseases and certain cancers, although more research is needed.

Potential adverse effects of vitamin C include gastrointestinal disturbances such as diarrhea, nausea, and abdominal cramps at high doses. Excessive intake may increase the risk of kidney stones, particularly in susceptible individuals, and in those with conditions like hemochromatosis, high vitamin C intake may exacerbate iron overload.

Vitamin C is a crucial nutrient with diverse roles in promoting health through its antioxidant properties, support for collagen synthesis, and enhancement of immune function. Vitamin C enhances immune function and its potential in reducing the severity and duration of respiratory infections. Vitamin C also shows a positive relationship with iron absorption, health benefits including neuroprotective effects, protective effects against UV-induced skin damage, and disease prevention.

Oil Soluble Vitamins (K, E, D, A)

Figures 26, 27:
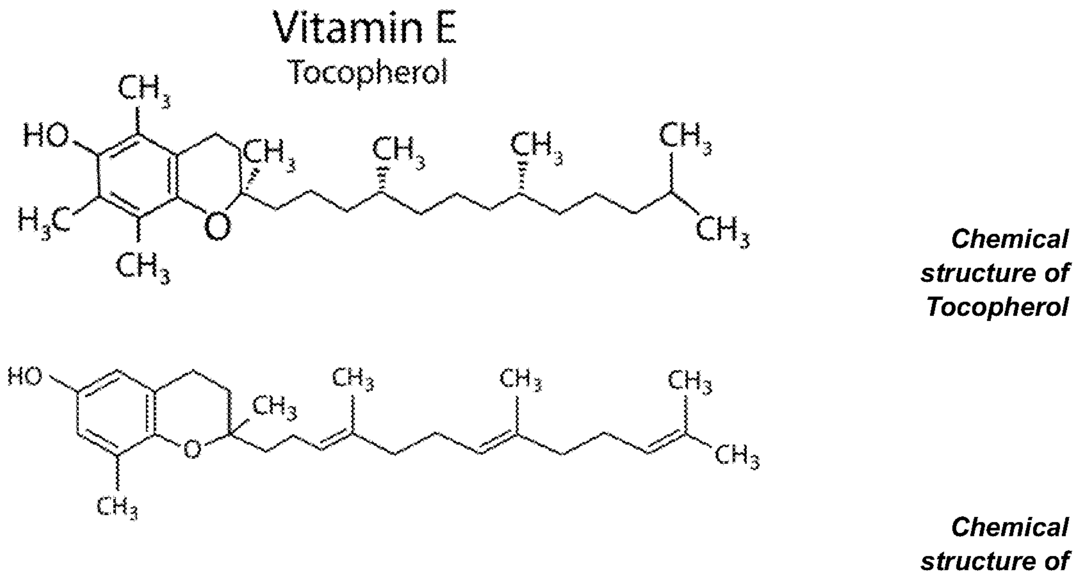
FIG. 26 illustrates the chemical structures of phylloquinone and menaquinone (vitamin K).
FIG. 27 illustrates the chemical structures of tocopherol and tocotrienols (Vitamin E).

Referring to FIG. 26, the chemical structures of phylloquinone and menaquinone (vitamin K) are shown. Vitamin K is a fat-soluble vitamin crucial for various bodily functions, particularly in blood clotting and bone health. There are two main forms of vitamin K: $K_1$ (phylloquinone) and $K_2$ (menaquinone), which further includes several subtypes.

Vitamin $K_1$ is primarily found in green leafy vegetables such as kale, spinach, and broccoli. The recommended dietary allowance (RDA) is about 90 mcg/day for women and 120 mcg/day for men. Vitamin $K_1$ acts as a cofactor for the enzyme that activates clotting factors like prothrombin and proteins involved in bone metabolism, supporting blood coagulation and potentially improving bone density. It is generally safe, but excessive intake from supplements may interfere with anticoagulant medications.

Vitamin $K_2$ is found in fermented foods such as natto and cheese, as well as animal products like egg yolks and liver. There is no established RDA, but typical intake ranges from 90 to 120 mcg/day. Vitamin $K_2$ activates proteins that aid in calcium metabolism, including osteocalcin, which is involved in bone mineralization, and matrix Gla-protein, which prevents vascular calcification. It may enhance bone health, cardiovascular health, and support dental health. Adverse effects are rare, although high doses can interfere with anticoagulant therapy.

Vitamin $K_3$ (Menadione) is a synthetic form not commonly found in foods and is not recommended for supplementation in humans due to potential toxicity. It can be converted into active forms in the body but has a risk of high doses leading to toxicity, liver damage, or hemolytic anemia.

Health benefits of Vitamin K include its essential role in blood clotting by synthesizing clotting factors in the liver, thereby reducing the risk of excessive bleeding. It aids in bone health by regulating calcium in bones and the bloodstream, potentially reducing the risk of fractures and osteoporosis. Additionally, it may help prevent arterial calcification, supporting overall cardiovascular health, and some studies suggest a role in maintaining healthy teeth and gums.

Recent research studies have reviewed the impact of vitamin $K_1$ supplementation on bone mineral density, showing promising benefits. Menaquinone-7 improves bone mineral density and reduces bone loss in postmenopausal women, and higher vitamin K intake is associated with a lower risk of cardiovascular diseases. Vitamin $K_2$ plays a role in preventing arterial calcification and supporting cardiovascular health, in bone health, and shows potential as a preventive strategy against osteoporosis.

Vitamin K is generally safe when obtained from food sources, but caution is advised with supplements, particularly for individuals on anticoagulant therapy, as excessive supplementation can increase the risk of clotting. Rare allergic reactions may occur in sensitive individuals. Vitamin K plays a vital role in several physiological processes, particularly blood clotting and bone health. Monitoring dosage and consulting with a healthcare provider, especially for those on medications, is recommended, as recent research continues to uncover its nutritional potential in various health areas.

Referring to FIG. 27, the chemical structures of tocopherol and tocotrienols (Vitamin E) are shown. Vitamin E is a fat-soluble antioxidant that plays a crucial role in protecting cells from oxidative damage. It consists of various forms, with tocopherols and tocotrienols being the most studied.

Forms of Vitamin E include tocopherols, which comprise types Alpha (α), Beta (β), Gamma (γ), and Delta (δ) tocopherols. They are primarily found in vegetable oils, such as sunflower and safflower, nuts, seeds, and green leafy vegetables. The recommended dietary allowance (RDA) for adults is 15 mg (22.4 IU) of alpha-tocopherol per day. Tocopherols act as primary lipid-soluble antioxidants, protecting cell membranes from oxidative stress by neutralizing free radicals. They may help reduce the risk of chronic diseases, support immune function, and promote skin health. Generally safe, high doses (over 1,000 mg/day) can lead to increased bleeding risk, particularly in individuals on anticoagulants.

Tocotrienols are another form of vitamin E, consisting of Alpha (α), Beta (β), Gamma (γ), and Delta (δ) tocotrienols. They are found in certain grains, such as rice bran and barley, palm oil, and some nuts. There is no established RDA, but typical supplemental doses range from 50 to 400 mg per day. Tocotrienols also act as antioxidants but may have additional roles in reducing cholesterol and promoting brain health. They are potentially beneficial for cardiovascular health, cancer prevention, and neuroprotection, and are generally well tolerated, although high doses may cause gastrointestinal discomfort.

Marine-derived tocopherols are sourced from marine organisms, including fish, algae, and certain types of seaweed. Common sources include fish oils from salmon or mackerel, algae, and phytoplankton, with algal oil gaining popularity as a plant-based source of tocopherols. These tocopherols primarily exist in four forms: alpha (α), beta (β), gamma (γ), and delta (δ), with alpha-tocopherol being the most biologically active form in humans. They help neutralize free radicals, may improve cardiovascular health by lowering cholesterol levels and reducing inflammation, and are often used in cosmetics for their protective effects against UV damage and skin aging. Marine-derived tocopherols may be more easily absorbed by the body compared to those from terrestrial sources, enhancing their efficacy.

Key characteristics of tocotrienols include their chemical structure, which differs from tocopherols due to the saturation of the isoprenoid side chain, contributing to their unique biological activity. Health benefits include potent antioxidant properties that combat oxidative stress and reduce cellular damage. Tocotrienols may help lower cholesterol levels, reduce arterial stiffness, and improve overall heart health. They possess anti-inflammatory properties, potentially benefiting various chronic conditions, and preliminary studies suggest they may inhibit cancer cell growth and promote apoptosis in certain cancer types. Emerging evidence indicates that tocotrienols may support brain health and protect against neurodegenerative diseases, and like tocopherols, they contribute to skin protection and may improve skin conditions.

Notable research on tocotrienols reviews tocotrienols' cardiovascular benefits, focusing on their effects on cholesterol levels and blood pressure. Tocotrienols play a role in inhibiting cancer cell proliferation and inducing apoptosis. Tocotrienols' neuroprotective mechanisms have the potential for preventing neurodegenerative diseases. Tocotrienols also have anti-inflammatory effects and benefit skin health, including protective effects against UV damage. Tocotrienols have the potential to help manage diabetes and its complications, and recent research studies have analyzed the impact of vitamin E on cognitive function, showing potential benefits for memory and cognitive decline in older adults. Tocotrienols have the potential to manage cholesterol levels and reduce cardiovascular risks. The antioxidant mechanisms of vitamin E enhance food preservation and nutrition. Vitamin E supplementation can enhance immune response in older adults, and may reduce the risk of developing age-related macular degeneration.

Adverse effects of vitamin E include that it is generally safe and well-tolerated from food sources. However, caution is advised with supplements, as high doses can lead to adverse effects such as increased risk of bleeding, particularly in individuals taking anticoagulants, gastrointestinal issues at high doses, and potential interactions with certain medications. Vitamin E is an essential nutrient with significant health benefits, particularly in antioxidant protection and promoting overall health. While it is generally safe, individuals considering supplementation should consult with a healthcare provider, especially those on medications or with existing health conditions. Ongoing research continues to reveal its potential nutritional effects across various health domains.

Vitamin D is a fat-soluble vitamin essential for bone and skeletal muscle health. It can be obtained from dietary sources such as fortified foods (e.g., bread and milk), fatty fish, mushrooms, and supplements, as well as synthesized in the skin upon exposure to ultraviolet B (UVB) rays. After ingestion or synthesis, vitamin D undergoes two hydroxylation reactions to become biologically active 1.25-dihydroxyvitamin D [1.25(OH)D]. The first hydroxylation occurs in the liver, where vitamin D is converted to 25-hydroxyvitamin D [25(OH)D] by vitamin D-25-hydroxylase. The second hydroxylation is carried out by CYP27B1-encoded 1α-hydroxylase (CYP27B1) in the kidneys, producing 1.25(OH) D, with additional CYP27B1 activity found in macrophages, monocytes, and muscle fibers. The active form, 1.25(OH) D, acts as a transcription factor by binding to the vitamin D receptor (VDR) and forming a heterodimer with the retinoid X receptor (RXR) to regulate gene expression through vitamin D response elements (VDREs).

Serum 25(OH)D levels, which indicate vitamin D exposure and absorption and have a long half-life, are used to assess vitamin D status. Levels below 30 nmol/L (12 ng/ml) are indicative of vitamin D deficiency, while levels between 30 and 50 nmol/L (12-20 ng/ml) are considered insufficient. Adequate levels for bone health are generally defined as greater than 50 nmol/L (20 ng/ml). However, full suppression of parathyroid hormone occurs at around 100 nmol/L (40 ng/ml), suggesting that optimal vitamin D levels might be higher than those necessary to prevent deficiency. This lack of consensus on vitamin D cut points complicates comparisons in skeletal muscle research.

Regions with limited sunlight exposure, such as those above 43°N latitude, have higher rates of vitamin D deficiency. For instance, residents of Erie, Pennsylvania are more prone to deficiency compared to those in Bradenton, Florida. Individuals with darker skin tones and higher body fat percentages also have a higher risk of deficiency. Vitamin D plays a crucial role in calcium absorption in the intestines, maintaining blood calcium levels, and bone mineralization. Severe deficiency leads to rickets in children and osteomalacia in adults, conditions marked by weakened bones. Inadequate vitamin D is associated with decreased bone density, fractures, muscle weakness, osteopenia, and osteoporosis.

Vitamin D status has been linked to muscle strength across various age groups. In older adults, plasma 25(OH)D levels below 25 nmol/L are associated with reduced grip strength. In younger adults, higher baseline 25(OH)D levels correlate with improved strength recovery following intense resistance exercise. Despite variations in supplementation methodologies, including dosing and participant characteristics, evidence supports that correcting vitamin D deficiencies through supplementation enhances muscle strength. A meta-analysis conducted in 2015, focusing primarily on younger individuals with 25(OH)D levels below 25 nmol/L, demonstrated that weekly vitamin D supplementation ranging from 4,000 to 60,000 IU significantly improved both upper and lower body strength.

Vitamin D is not only crucial for maintaining muscle strength but also plays a significant role in muscle regeneration. Muscle damage, characterized by disrupted muscle fiber architecture, compromised contractile proteins, and mitochondrial dysfunction, requires effective regeneration processes. This regeneration involves restoring mitochondrial function and activating satellite cells (SCs), the resident skeletal muscle stem cells. Research shows that VDR expression increases markedly following muscle injury, particularly in central nuclei and SCs in animal models. Mechanistic studies have shed light on how vitamin D impacts injured muscle. Both in vitro and in vivo rodent studies indicate that vitamin D reduces reactive oxygen species (ROS) production, enhances antioxidant capacity, and mitigates oxidative stress-factors that contribute to muscle damage. Additionally, VDR knockdown leads to decreased mitochondrial oxidative capacity and ATP production, highlighting vitamin D's role in mitochondrial oxidative phosphorylation, a key driver of muscle regeneration. Vitamin D's influence on mitochondrial health may also affect SC activity and self-renewal, further impacting muscle regeneration. However, optimal timing, form, and dosage of vitamin D for muscle regeneration remain undetermined. Further research is needed to explore the mechanistic actions of 1.25(OH)D on mitochondria and SCs and to determine how these actions affect muscle injury recovery in vivo. Standardizing vitamin D sufficiency cut points, studying the efficacy of vitamin D administration over time, and comparing different vitamin D analogs are essential for clarifying its role in muscle regeneration.

Vitamin D is crucial for muscle and bone health, with emerging evidence supporting its role in muscle damage and regeneration. Understanding the optimal levels and mechanisms through which vitamin D aids muscle repair and strength recovery is vital for developing effective treatments and interventions. Further research will help to elucidate the full potential of vitamin D in enhancing muscle regeneration following injury.

Skeletal muscle exhibits remarkable plasticity, enabling it to adapt and regenerate robustly in response to various forms of stress and damage. Muscle damage can arise from multiple stimuli, including crush injuries, ischemia-reperfusion injuries, and resistance exercise. Rodent models offer reproducible and controlled environments for studying these injuries. Among human models, unaccustomed resistance exercise, particularly involving high-load eccentric contractions, is a well-studied cause of muscle damage.

Vitamin D deficiency adversely affects mitochondrial function, leading to decreased ATP production, increased reactive oxygen species (ROS) production, oxidative damage, muscle atrophy, and impaired muscle function. These symptoms may exacerbate typical muscle damage outcomes. During muscle regeneration, activated vitamin D [1.25(OH)D] increases vitamin D receptor (VDR) abundance in satellite cells (SCs) and central myonuclei. This upregulation of VDR is accompanied by inhibition of SC proliferation, stimulation of differentiation, and increased mitochondrial biogenesis and fusion, which mitigate oxidative stress and enhance regenerative capacity.

Although 25(OH)D functions as a biomarker of exposure, the extent to which 25(OH)D levels also serve as a biomarker of effect on the body (i.e., relating to health status or outcomes) is not clear. Researchers have not definitively identified serum concentrations of 25(OH)D associated with deficiency (e.g., rickets), adequacy for bone health, and overall health. After reviewing data on vitamin D needs, an expert committee of the Food and Nutrition Board (FNB) at the National Academies of Sciences, Engineering, and Medicine (NASEM) concluded that people are at risk of vitamin D deficiency at serum 25(OH)D concentrations less than 30 nmol/L (12 ng/ml; see Table 1 for definitions of deficiency and inadequacy). Some people are potentially at risk of inadequacy at 30 to 50 nmol/L (12-20 ng/ml). Levels of 50 nmol/L (20 ng/mL) or more are sufficient for most people. The FNB committee also noted that serum concentrations greater than 125 nmol/L (50 ng/mL) can be associated with adverse effects (See Table 1 below). The Endocrine Society has not identified 25(OH)D concentrations associated with vitamin D sufficiency, insufficiency, and deficiency and does not recommend routine testing of 25(OH)D concentrations in healthy individuals.

TABLE 1

Serum 25-Hydroxyvitamin D [25(OH)D] Concentrations and Health

| nmol/L* | ng/mL* | Health status |
|---|---|---|
| <30 | <12 | Associated with vitamin D deficiency, which can lead to rickets in infants and children and osteomalacia in adults |
| 30 to <50 | 12 to <20 | Generally considered inadequate for bone and overall health in healthy individuals |
| ≥50 | ≥20 | Generally considered adequate for bone and overall health in healthy individuals |
| >125 | >50 | Linked to potential adverse effects, particularly at >150 nmol/L (>60 ng/mL) |

*Serum concentrations of 25(OH)D are reported in both nanomoles per liter (nmol/L) and nanograms per milliliter (ng/mL). One nmol/L = 0.4 ng/mL, and 1 ng/mL = 2.5 nmol/L.

Optimal serum concentrations of 25(OH)D for bone and general health have not been established because they are likely to vary by stage of life, by race and ethnicity, and with each physiological measure used. In addition, although 25(OH)D levels rise in response to increased vitamin D intake, the relationship is nonlinear. The amount of increase varies, for example, by baseline serum levels and duration of supplementation.

Intake recommendations for vitamin D and other nutrients are provided in the Dietary Reference Intakes (DRIs) developed by expert committees of NASEM. DRI is the general term for a set of reference values used for planning and assessing nutrient intakes of healthy people.

These values, which vary by age and sex, include the following:

- Recommended Dietary Allowance (RDA): Average daily level of intake sufficient to meet the nutrient requirements of nearly all (97%-98%) healthy individuals; often used to plan nutritionally adequate diets for individuals;
- Adequate Intake (AI): Intake at this level is assumed to ensure nutritional adequacy; established when evidence is insufficient to develop an RDA;
- Estimated Average Requirement (EAR): Average daily level of intake estimated to meet the requirements of 50% of healthy individuals; usually used to assess the nutrient intakes of groups of people and to plan nutritionally adequate diets for them; can also be used to assess the nutrient intakes of individuals; and
- Tolerable Upper Intake Level (UL): Maximum daily intake unlikely to cause adverse health effects.

An FNB committee established RDAs for vitamin D to indicate daily intakes sufficient to maintain bone health and normal calcium metabolism in healthy people. RDAs for vitamin D are listed in both micrograms (meg) and International Units (IU); 1 mcg vitamin D is equal to 40 IU (Table 2). Even though sunlight is a major source of vitamin D for some people, the FNB based the vitamin D RDAs on the assumption that people receive minimal sun exposure [1]. For infants, the FNB committee developed AIs based on the amount of vitamin D that maintains serum 25(OH)D levels above 20 ng/ml (50 nmol/L) and supports bone development.

Table 2 shows recommended dietary allowances (RDAs) for vitamin D.

TABLE 2

Vitamin D recommended daily allowances

| Age | Male | Female | Pregnancy | Lactation |
|---|---|---|---|---|
| 0-12 months* | 10 mcg (400 IU) | 10 mcg (400 IU) | | |
| 1-13 years | 15 mcg (600 IU) | 15 mcg (600 IU) | | |
| 14-18 years | 15 mcg (600 IU) | 15 mcg (600 IU) | 15 mcg (600 IU) | 15 mcg (600 IU) |
| 19-50 years | 15 mcg (600 IU) | 15 mcg (600 IU) | 15 mcg (600 IU) | 15 mcg (600 IU) |
| 51-70 years | 15 mcg (600 IU) | 15 mcg (600 IU) | | |

Various countries and professional organizations have established differing guidelines for vitamin D intake due to several factors. These variations stem from an incomplete understanding of vitamin D's biology and clinical implications, different objectives for the guidelines (such as public health recommendations versus clinical practice), and the reliance on observational studies alongside randomized clinical trials in some cases. For instance, the UK Scientific Advisory Committee on Nutrition advises a daily intake of 10 mcg (400 IU) for individuals aged 4 and older. Meanwhile, the Endocrine Society recommends routine vitamin D supplementation for children and teens aged 1 to 18, pregnant individuals, adults with pre-diabetes, and those aged 75 and older, but does not suggest supplementation for healthy adults aged 19 to 74. The Endocrine Society does not specify doses, but emphasizes that everyone should meet the recommended dietary allowance (RDA).

Vitamin D plays a role in muscle damage and regeneration mechanisms. Severe muscle damage disrupts muscle fiber integrity, impairing muscle structure and function. Indicators of muscle fiber damage include Z-disc streaming and a smeared appearance of sarcomeres, reflecting ultrastructural damage. This damage extends to contractile proteins, leading to necrotic zones where muscle regeneration begins. These necrotic zones attract neutrophils and macrophages, which play a critical role in cellular damage and regeneration. Increased cellular turnover and muscle fiber biogenesis in these regions contribute to muscle tissue regeneration.

Muscle fiber damage is characterized by the preservation of the basement membrane, allowing for regeneration rather than de novo fiber formation. This regenerative capacity is due to the presence of satellite cells (SCs), which are located on the periphery of muscle fibers between the basal lamina and sarcolemma. SCs are essential for muscle regeneration after severe injury, and are marked by the expression of Pax7. Following muscle damage, SCs undergo asymmetric division to produce a "sister" cell that returns to quiescence and a "daughter" cell that differentiates, integrates into the muscle tissue, and contributes its nucleus.

Recent studies emphasize the role of vitamin D signaling in muscle regeneration, particularly highlighting the expression of the Vitamin D Receptor (VDR). In both mature and aged mice, VDR protein expression is closely linked to serum 25(OH)D levels, underscoring the connection between vitamin D status and muscle health. Under normal conditions, VDR and the enzyme CYP27B1, which activates vitamin D, are minimally expressed in skeletal muscle. This was demonstrated in both C2C12 myoblasts and mouse muscle through immunocytochemistry and immunoblotting techniques. Following muscle injury, there is a significant upregulation of VDR and CYP27B1. VDR is highly expressed in regenerating muscle fibers, colocalizing with central myonuclei. Moreover, VDR colocalizes with Pax7 in satellite cells, which are essential for muscle regeneration. Further evidence of vitamin D's role in muscle repair comes from findings that Pax7 and VDR expression increase following high-intensity exercise, highlighting the importance of vitamin D in the recovery process. These studies collectively underscore the role of vitamin D in muscle regeneration, especially in response to injury and exercise.

Muscle regeneration efficiency declines with age due to various multifactorial changes. Muscle mass peaks in the third decade of life, and noticeable declines begin in the fifth decade. Age-related muscle atrophy is primarily driven by imbalances in muscle protein synthesis and degradation. Mitochondrial dysfunction and excessive reactive oxygen species (ROS) production further contribute to muscle loss, with these issues being linked to impaired mitochondrial fusion, fission, mitophagy, and biogenesis.

Aging also reduces the satellite cell (SC) pool and SC activity, which are essential for muscle regeneration. Additionally, this reduction in SC activity leads to decreased regenerative capacity and increased fibrosis, possibly due to the transition of SCs to a fibrogenic phenotype. Interestingly, in mice, VDR expression increases with age, suggesting a role for vitamin D in supporting muscle regeneration during aging. In contrast, human studies show that VDR expression decreases with age. Notably, in older women, VDR expression correlates with circulating 25(OH)D levels following vitamin D supplementation.

Elevated VDR expression in aged mouse muscle is associated with central nucleation, which indicates muscle fiber recovery from damage. Understanding the factors that impair muscle regeneration with age, and the potential role of vitamin D signaling, may provide new nutritional supplement strategies to enhance muscle regeneration throughout life.

Vitamin D is also implicated in mitochondrial health. Vitamin D deficiency, defined by serum 25(OH)D levels below 50 nmol/L, has been consistently linked to muscle atrophy and reduced muscle strength across several clinical studies. In particular, research shows that individuals with low Vitamin D levels experience diminished muscle function and higher risks of falls, especially in older populations. Similarly, studies have shown the association between Vitamin D insufficiency and muscle weakness in both healthy individuals and patients with chronic conditions.

Recent research also emphasizes the importance of Vitamin D in mitochondrial function. Deficiency in Vitamin D has been associated with impaired mitochondrial health, but supplementation in deficient individuals has been linked to improvements in mitochondrial density and function. Animal studies support these findings, showing that Vitamin D supplementation improves mitochondrial parameters such as density and bioenergetic capacity. These findings highlight Vitamin D's essential role not only in muscle protein synthesis but also in promoting overall mitochondrial health, offering promising nutritional avenues for addressing muscle weakness and atrophy in Vitamin D-deficient populations.

Vitamin D's impact on mitochondrial health is gaining attention, particularly regarding its role in skeletal muscle atrophy. Overexpression of the vitamin D receptor (VDR) in rat skeletal muscle has been shown to increase muscle hypertrophy, primarily through enhanced anabolic signaling, ribosomal biogenesis, and protein synthesis. Although the effects of VDR overexpression on mitochondrial dynamics are not yet fully understood, vitamin D is known to regulate oxidative capacity through the binding of 1.25(OH)D to the VDR in skeletal muscle. In studies with VDR-knockdown C2C12 myoblasts, mitochondrial ATP production was significantly reduced, highlighting the critical role of 1.25 (OH)D signaling in maintaining ATP availability. This reduction in ATP production could adversely affect muscle regeneration, as mitochondrial capacity is essential for this process.

Interestingly, reductions in ATP generation following VDR knockdown occurred without significant changes in several mitochondrial machinery components, including electron transport system (ETS) subunits I-V, citrate synthase, and cytochrome c oxidase. Similarly, in vivo experiments with vitamin D-deficient mice revealed reduced maximum oxidative capacity without alterations in ETS protein expression. These findings suggest that 1.25(OH)D regulation of oxidative capacity might not solely depend on mitochondrial density or ETS protein abundance.

Further investigations have shown that VDR knockdown in C2C12 myotubes leads to increased levels of optic atrophy 1 (OPA1), a marker associated with mitochondrial fusion, which results in larger mitochondria and potentially greater oxidative capacity. However, increased OPA1 expression was also observed in response to vitamin D supplementation in both vitamin D-deficient mice with statin-induced myopathy and human skeletal muscle cells treated with 1.25(OH) D. The reason behind the increased OPA1 expression under both conditions remains unclear. Moreover, while 1.25(OH)D administration increased the oxygen consumption rate in human skeletal muscle cells, neither 25(OH)D nor vitamin D3 had this effect. These contrasting results underscore the need for further research to clarify the impact of VDR expression and various vitamin D analogs on mitochondrial dynamics.

Vitamin D plays a role in ROS production and antioxidant systems. Vitamin D deficiency may contribute to muscle atrophy through excessive mitochondrial ROS production. Although ROS are crucial for muscle signaling after injury, excessive ROS that overwhelm antioxidant defenses can damage muscle tissue. Vitamin D deficiency has been linked to increased lipid and protein oxidation in skeletal muscle. It also alters antioxidant enzyme activities, with some studies showing increased superoxide dismutase (SOD) activity in humans with chronic lower back pain, while other studies report decreased SOD activity in deficient rats. Despite these differences, studies agree that vitamin D deficiency increases muscle glutathione peroxidase (GPx) activity. Vitamin D supplementation has been associated with normalization of SOD and GPx activities in both human and animal models.

Studies indicate that vitamin D analogs can protect skeletal muscle and cells from oxidative stress. In vitro studies have shown that 1.25(OH)D reduces ROS production, lipid and protein oxidation, protein ubiquitination, muscle proteolysis, intracellular damage, and gene markers for atrophy, while increasing SOD activity and markers of mitochondrial biogenesis. However, data on the protective effects of vitamin D analogs in vivo are limited. One study involving patients with chronic lower back pain found that vitamin D3 supplementation reduced Cu/Zn SOD and GPx activity in paraspinal muscle, with corresponding decreases in protein and lipid peroxidation. These findings underscore the importance of vitamin D for maintaining redox balance and promoting muscle mitochondrial health during oxidative stress. Vitamin D's role in maintaining mitochondrial health and mitigating muscle atrophy is multifaceted, involving regulation of oxidative capacity, mitochondrial dynamics, and antioxidant defenses.

Studies also indicate Vitamin D plays a role in satellite cell mitochondrial function. Mitochondrial oxidative capacity is vital for skeletal muscle regeneration following injury. Mitochondria not only supply energy for protein synthesis but also play a crucial role in regulating satellite cell (SC) activity. Quiescent SCs have fewer mitochondria and lower oxidative capacity compared to activated, differentiating SCs, making mitochondrial function a key factor in SC activation. This difference in oxidative capacity has been observed in vivo; for example, endurance-trained mice exhibit reduced mitochondrial respiration in SCs, which correlates with a higher proportion of SCs expressing self-renewal markers. Beyond metabolic reprogramming, other mitochondrial processes are critical for SC function. For instance, effective mitophagy, the process of removing damaged mitochondria, is essential for normal SC activity. In Parkin null mice, which lack the E3 ubiquitin ligase Parkin crucial for mitophagy, SC proliferation increased while differentiation was impaired after muscle injury with cardiotoxin. This resulted in delayed muscle fiber repair and smaller muscle fibers during regeneration.

Vitamin D influences SC mitochondrial function. Mitochondrial production of reactive oxygen species (ROS) also affects SC activity, as ROS can stimulate symmetric cell division and subsequent terminal differentiation. Notably, a study on human skeletal muscle myoblasts showed that vitamin D treatment inhibited myoblast proliferation while increasing differentiation and mitochondrial oxygen consumption rate. This suggests that vitamin D may help maintain SC quiescence while enhancing mitochondrial activity to support differentiation and myotube formation. However, the specific changes in mitochondrial density or ROS production that contribute to increased oxygen consumption and altered SC activity remain unclear. Further research is needed to fully understand how vitamin D signaling affects mitochondrial function and SC regulation.

Vitamin D analogs play a role in mitigating skeletal muscle injury. The potential for vitamin D to aid in muscle regeneration after injury is supported by studies showing improved cellular turnover and muscle function with vitamin D3 administration following crush injury in rats. Immediate post-injury treatment with vitamin D3 increased proliferation of interstitial cells and decreased necrotic cell presence, suggesting enhanced activity of muscle repair-related cells like macrophages and fibrogenic cells. However, vitamin D3 did not significantly alter Pax7+SC abundance or muscle morphology through 42 days post-injury. Despite this, vitamin D3-treated rats exhibited better peak tetanic torque compared to controls, indicating improved muscle function.

In contrast, delayed administration of 1.25(OH)D (the active form of vitamin D) 4 days after muscle injury did not yield regenerative benefits. Both physiological and supraphysiological doses of 1.25(OH)D increased VDR protein expression but did not produce larger muscle fibers 8 days post-injury. Moreover, supraphysiological doses led to impaired SC differentiation and de novo myogenesis, resulting in smaller muscle fibers and excessive fibrosis. These studies highlight the importance of timing, dose, and delivery method for optimizing muscle regeneration with vitamin D analogs. Research indicates that supplementation with vitamin D3 in young men with marginally insufficient vitamin D status improved knee extensor torque following exercise-induced muscle damage. This suggests that vitamin D3 can enhance muscle regeneration and function in individuals with insufficient vitamin D levels. Given the high prevalence of vitamin D deficiency among athletes and the general population, these findings are particularly relevant.

Figures 28, 29:
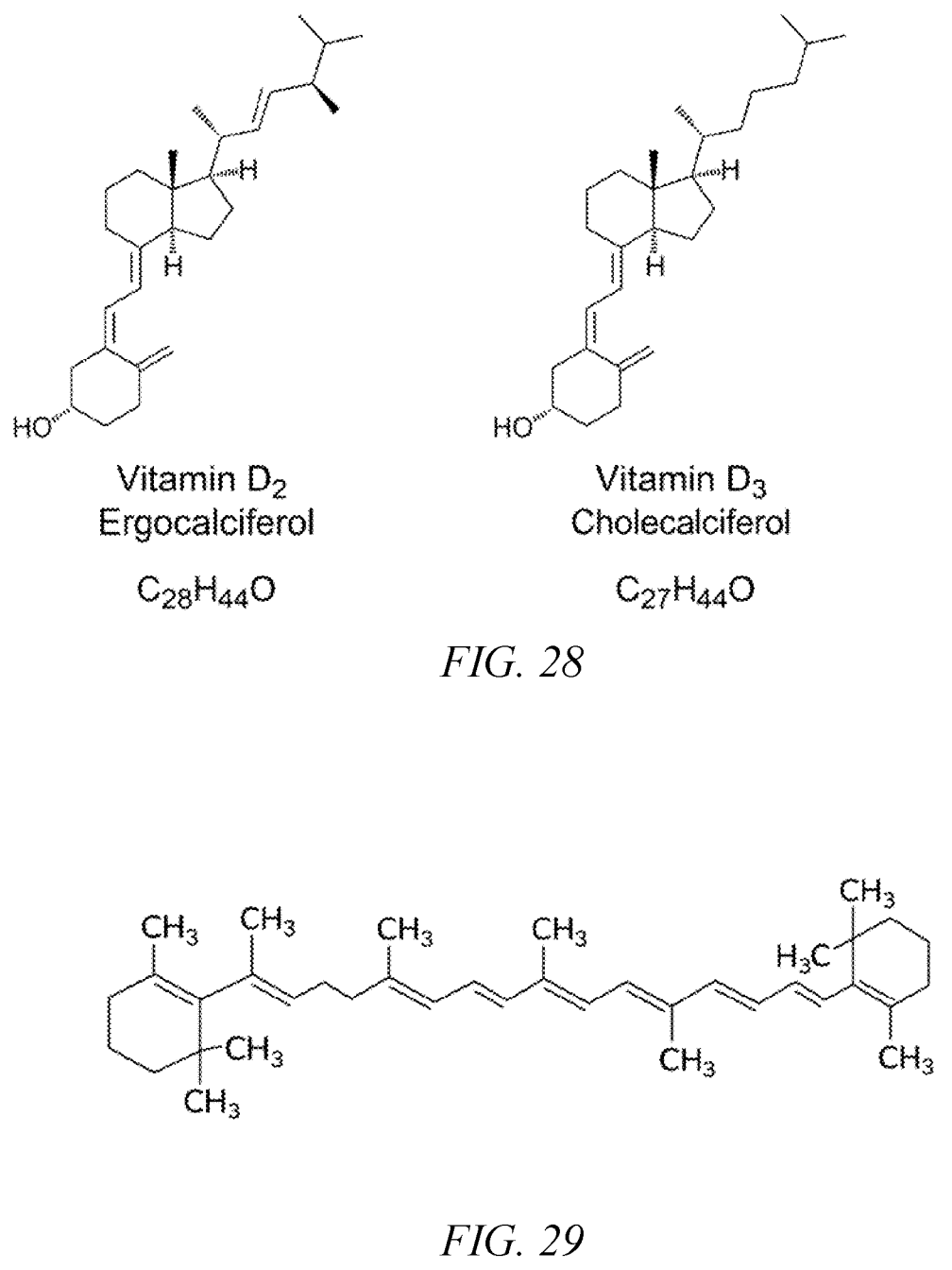

Referring to FIG. 28, vitamin D is shown in its most significant forms, $D_2$ (ergocalciferol) and $D_3$ (cholecalciferol). Vitamin D is a fat-soluble vitamin essential for several bodily functions, including calcium and phosphate metabolism, immune function, and muscle health. Vitamin $D_2$ is found in some fungi and yeast and is often used in fortified foods and supplements. Its bioavailability is generally less effective at raising blood levels of vitamin D compared to $D_3$. Vitamin $D_3$ is synthesized in the skin upon exposure to sunlight and is also found in animal-based foods like fatty fish, liver, and egg yolks. Its bioavailability is more effective than $D_2$ at raising and maintaining serum levels of vitamin D. Calcidiol (25-hydroxyvitamin D) is the main circulating form of vitamin D in the body and is often measured in blood tests to assess vitamin D status. Calcitriol (1.25-dihydroxyvitamin D) is the active form of vitamin D, produced from calcidiol, and it regulates calcium and phosphate metabolism.

The benefits of Vitamin D include its essential role in bone health, as it is critical for calcium absorption and bone mineralization, helping to prevent osteoporosis and fractures. It supports muscle function; deficiency is linked to muscle weakness and increased fall risk in older adults. Vitamin D plays a role in modulating immune responses, potentially reducing the risk of infections and autoimmune diseases. It may help regulate blood pressure and cardiovascular function; some studies suggest a link between low vitamin D levels and heart disease. Additionally, low levels of vitamin D have been associated with mood disorders, including depression.

Referring to FIG. 29, vitamin A can be categorized into two main types: preformed vitamin A (retinol) and provitamin A carotenoids. Preformed vitamin A is found in animal products such as liver, fish, and dairy, where it is readily utilized by the body. In contrast, provitamin A carotenoids, such as beta-carotene, are sourced from plant-based foods like carrots, sweet potatoes, and spinach, and the body converts these into retinol.

The role of vitamin A is essential for various physiological processes, including vision, immune function, and cellular communication. It plays a critical part in maintaining healthy skin and mucous membranes. Among its numerous benefits, vitamin A is crucial for vision as it is necessary for the formation of rhodopsin, a pigment in the retina that aids night vision. It also supports immune function by maintaining the integrity of mucosal surfaces and enhancing immune cell function. Additionally, vitamin A promotes skin health by facilitating cell production and repair, making it beneficial for conditions such as acne. Its derivatives, known as retinoids, are recognized for their anti-aging properties, helping to reduce fine lines, wrinkles, and improve overall skin texture. Moreover, vitamin A is important for reproductive health, particularly in fetal development.

The mechanisms by which vitamin A exerts its effects include gene regulation through binding to nuclear receptors (retinoic acid receptors), which helps regulate gene expression involved in cell differentiation and proliferation. Carotenoids also possess antioxidant properties that neutralize free radicals, protecting cells from oxidative damage. Additionally, vitamin A is involved in the visual cycle, converting light into electrical signals in the retina.

In terms of anti-aging benefits, vitamin A, especially in its retinoid form, is widely utilized in skincare for its ability to promote cell turnover, reduce the appearance of fine lines and wrinkles, and improve skin texture and tone by stimulating collagen production.

The recommended dietary allowance (RDA) for vitamin A varies: for adults, it is generally between 700 and 900 mcg RAE (Retinol Activity Equivalents) per day. Pregnant women are advised to consume 770 mcg RAE daily, while lactating women should aim for 1,300 mcg RAE. Higher doses may be prescribed for specific conditions but should only be taken under medical supervision.

While vitamin A is essential, excessive intake can lead to toxicity, known as hypervitaminosis A. Symptoms of this condition may include nausea, vomiting, dizziness, blurred vision, liver damage, and increased risk of bone fractures. In summary, vitamin A is vital for numerous bodily functions, including vision, immune support, and skin health. It offers significant benefits, particularly in anti-aging, but adherence to recommended dosages is crucial to avoid adverse effects.

Creatine

Figure 30:
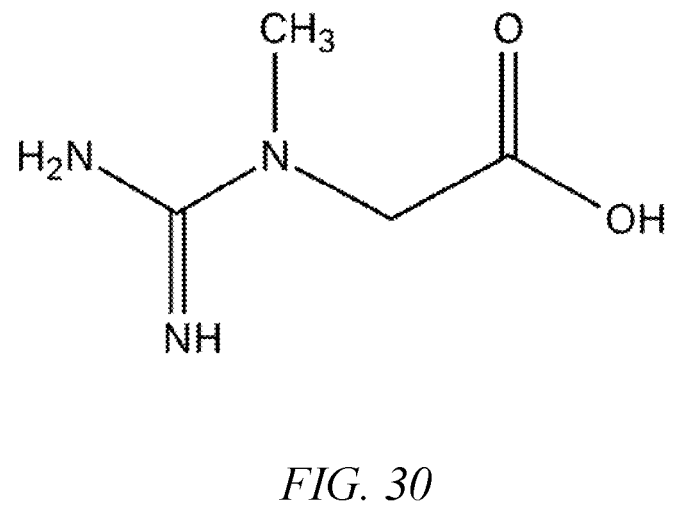

Referring to FIG. 30, the chemical structure of creatine is shown. Benefits of creatine include enhanced athletic performance, as it improves strength, power, and performance in high-intensity exercise and sports. It supports muscle mass increase, aiding in muscle hypertrophy and recovery, making it popular among bodybuilders and athletes. Creatine improves recovery by reducing muscle cell damage and inflammation following intense exercise. It may provide cognitive benefits, enhancing cognitive function and reducing mental fatigue, particularly in tasks requiring quick thinking and concentration. Additionally, creatine shows neuroprotective effects, potentially beneficial in neurological disorders like Parkinson's and Huntington's disease.

The mechanism of action for creatine involves ATP regeneration, as it enhances the rephosphorylation of adenosine triphosphate (ATP), the primary energy carrier in cells, particularly during short bursts of intense activity. It increases phosphocreatine stores in muscles, allowing for quicker energy production. Creatine also influences cellular signaling pathways that promote muscle growth and adaptation to stress, such as the mTOR pathway. Furthermore, it has a hydration effect, increasing water content in muscle cells, which may contribute to increased muscle size and performance. Nutritional effects of creatine include aiding in the management of muscle disorders, such as muscular dystrophy. It shows potential benefits in chronic fatigue syndrome by reducing fatigue and enhancing quality of life. Some studies suggest that creatine may support bone health and density through enhanced muscle strength.

There is no official recommended daily allowance (RDA) for creatine, but common supplementation protocols include a loading phase of 20 grams per day, divided into four doses for 5-7 days, followed by a maintenance phase of 3-5 grams per day.

Adverse effects of creatine are generally mild, with some users experiencing stomach cramps, diarrhea, or nausea. It can cause weight gain due to increased water retention in muscles. There are potential concerns for individuals with pre-existing kidney conditions; however, studies generally show that creatine is safe for healthy individuals.

Research indicates creatine has a positive effect on performance in competitive sports, provides cognitive benefits, and promotes muscle health in older adults. Creatine is a well-researched supplement known for its significant benefits in athletic performance, muscle growth, and potential cognitive effects. While generally safe, users should adhere to recommended dosages and be aware of possible side effects.

DHEA Derivatives

DHEA is commonly used as a dietary supplement. DHEA (dehydroepiandrosterone) is a hormone produced by the adrenal glands and serves as a precursor to both androgens (like testosterone) and estrogens (like estrogen). Its derivatives and metabolites can have various effects on the body. Some key DHEA derivatives and related compounds include:

DHEA-S(dehydroepiandrosterone sulfate) is a sulfated form of DHEA that is more stable in the bloodstream and is often measured in blood tests to assess adrenal function and hormone levels. Androstenedione is a direct precursor to testosterone and estrogen, functioning as an androgenic steroid and playing a role in the production of sex hormones. Testosterone is a primary male sex hormone and anabolic steroid derived from DHEA through intermediate steps, crucial for the development of male reproductive tissues and the promotion of secondary sexual characteristics. Estrogens are derived from DHEA, including estrone (E1) and estradiol (E2), which regulate the menstrual cycle and reproductive system in females. DHEA-3 (dehydroepiandrosterone 3β-sulfate) is another sulfate ester of DHEA, involved in similar physiological processes. 7-Keto-DHEA is a derivative of DHEA that is not converted into estrogens or androgens and is often marketed as a supplement for weight loss and metabolic support, though its efficacy and safety are subjects of ongoing research. DHEA-P (dehydroepiandrosterone propionate) is a less common derivative used primarily in research contexts. Each of these applications of DHEA derivatives is supported to varying degrees by scientific research, with effectiveness depending on the specific derivative, dosage, and individual health conditions. Further research is often needed to fully understand the scope of benefits and mechanisms involved.

DHEA (dehydroepiandrosterone) derivatives have a broad range of benefits, particularly in areas such as muscle hypertrophy, anti-aging, hormonal balance, and cancer-related muscle preservation. The research also covers their effects on various cell lines, inflammatory responses, and bioavailability enhancement strategies. Muscle hypertrophy benefits from DHEA derivatives, which can promote muscle growth by influencing anabolic pathways and muscle protein synthesis. Recent research indicates improvement in muscle strength and physical performance with DHEA supplementation, muscle mass and strength improvements in older men using DHEA, and that DHEA supplementation increases lean body mass and decreases fat mass.

In terms of anti-aging benefits, DHEA derivatives may help mitigate age-related declines in muscle mass, bone density, and overall vitality. DHEA has been shown to improve bone density and body composition in the elderly, and can help reduce age-related physical decline.

Regarding sexual hormonal balance, DHEA derivatives act as precursors to estrogen and testosterone, aiding in hormonal balance and sexual health. DHEA affects sexual hormones and function, and plays a role in hormone replacement therapy and sexual dysfunction. In the context of muscle preservation in cancer, DHEA derivatives may help preserve muscle mass and counteract cachexia in cancer patients, including avoiding or mitigating muscle wasting, and influence cell proliferation. DHEA has also shown anti-inflammatory properties that can benefit chronic inflammatory conditions, and has been used supplementally by pre- and post-menopausal women.

DHEA derivatives face solubility and bioavailability challenges, primarily due to their low water solubility. Enhancement strategies include micronization, which improves solubility and absorption, and cyclodextrin complexes, which enhance solubility and bioavailability through encapsulation. Additionally, combining DHEA with β-hydroxy β-methylbutyrate free acid (HMB-FA) can improve efficacy. Micronization and cyclodextrin encapsulation have been shown to improve the bioavailability of DHEA.

DHEA Enanthate is a longer-acting ester of dehydroepiandrosterone (DHEA), designed for nutritional use to enhance hormone levels in the body. Its extended release allows for less frequent dosing compared to other forms, making it a convenient option for hormone replacement therapies. DHEA Enanthate is often administered via intramuscular injection, providing a sustained release of DHEA into the bloodstream.

Research has shown that DHEA Enanthate can effectively increase serum DHEA levels, leading to various potential benefits. For instance, studies have indicated its role in improving muscle mass, strength, and physical performance, particularly in older adults. Research on DHEA and its effects on hormone levels and sexual function have demonstrated the positive impacts of DHEA derivatives, including enanthate, on sexual health and hormonal balance, and the benefits of DHEA in promoting muscle strength and mass.

DHEA Enanthate has also been explored for its anti-aging effects, with some studies suggesting it may help mitigate declines in bone density and muscle mass associated with aging. Research on the effect of DHEA supplementation on bone density and body composition in older adults has shown improvements in bone density through DHEA supplementation.

In the context of sexual hormonal balance, DHEA enanthate functions as a precursor to both estrogen and testosterone, thus supporting overall hormonal regulation. Testosterone and DHEA are used to address in sexual dysfunction in hormone replacement therapies. While DHEA enanthate has shown promise in various nutritional applications, further research is necessary to fully understand its long-term effects, optimal dosing strategies, and potential side effects. As with other DHEA derivatives, individual responses can vary significantly based on health conditions and baseline hormone levels.

Dehydroepiandrosterone DHEA supplementation is effective in women with adrenal insufficiency and chronically treated with exogenous glucocorticoids, postmenopausal women with low bone mineral density and/or osteoporosis, premenopausal women with sexual disorders and low libido, and in women with vulvovaginal atrophy due to menopause or genitourinary syndrome of menopause. Currently available clinical trials also suggest that DHEA supplementation is probably effective in postmenopausal women with hypoactive sexual disorders, infertile women with diminished ovarian reserve, women suffering from depression and anxiety, and women with obesity and insulin resistance.

Unfortunately, DHEA is rapidly metabolized by liver enzymes referred to as sulfotransferases. Sulfotransferases rapidly convert the much of the supplementary DHEA into DHEA sulfate, which is quickly excreted from the body and is not effective as an anti-aging, muscle-building or fat reduction compound. In addition, DHEA sulfate does not restore the balance of the adrenal steroids discussed above. As a result, frequent and larger doses of DHEA must be taken. DHEA is also metabolized in the body to one of several compounds including, for example, etiocholanolone (5-beta-androstan-3-alpha-ol-17-one), beta etiocholanolone (5-beta-androstan-3-beta-ol-17-one), androsterone (5-alpha-androstan-3-alpha-ol-17-one), epiandrosterone (5-alpha-androstan-3-beta-ol-17-one), 7-keto-DHEA, 7-alpha-hydroxy-DHEA, 7-beta-hydroxy-DHEA, androstenedione, estrone and estradiol.

Taking large doses of DHEA (dehydroepiandrosterone) to overcome its poor bioavailability can be problematic and may not necessarily lead to better outcomes. High doses of DHEA can lead to a range of side effects, including acne, hair loss, mood changes, and more serious issues like hormonal imbalances. Excessive DHEA can disrupt the normal balance of sex hormones in the body, leading to symptoms related to both androgens and estrogens. These increased doses of DHEA can result in increased conversion to estrone and estradiol, with resulting negative side effects for males including growth of male breast tissue, known as gynecomastia.

DHEA serves as a precursor to both androgens (such as testosterone) and estrogens (such as estrone). High doses can lead to elevated levels of these hormones, potentially causing issues like increased risk of prostate issues in men and breast tenderness or irregular menstrual cycles in women.

DHEA is poorly absorbed when taken orally. This is partly due to its lipophilic nature (fat-loving) and also because of first-pass metabolism in the liver, which can significantly reduce the amount of DHEA that enters the bloodstream. The stomach and intestines can break down DHEA before it has a chance to be absorbed. This is compounded by its poor solubility in water, which affects its dissolution and absorption in the gastrointestinal tract.

There is great individual variability in the metabolism of oral DHEA. The DHEA metabolites estrone and estradiol can result in negative estrogenic side effects for males including growth of male breast tissue, known as gynecomastia.

Nutritional Effects of Individual Supplements

A variety of individual supplements provide nutritional effects in combination with DHEA. These include:

β-Hydroxy-β-Methylbutyrate (HMB) free acid: HMB benefits include muscle preservation, recovery enhancement, and reduction of muscle damage. The mechanism involves its role in muscle protein synthesis and recovery processes.

Adaptogens and their modified constituents: Adaptogens reduce fatigue, enhance cognitive function, and improve sexual function. The mechanism suggests that ginsenosides in *ginseng* possess adaptogenic properties that modulate hormone levels while enhancing performance.

Vitamin D: Vitamin D supports bone health, muscle function, and hormonal balance. The mechanism involves enhancing calcium absorption and influencing testosterone levels.

Essential Amino Acids (EAAs): EAAs promote muscle protein synthesis and enhance recovery. They are directly involved in muscle repair and growth processes.

Creatine: Creatine increases strength, enhances high-intensity performance, and promotes muscle recovery. Its mechanism centers on enhancing ATP production during exercise.

Non-Esterified Omega-3 Fatty Acids (Free Acids): These fatty acids reduce inflammation, support cardiovascular health, and may improve muscle recovery. Their mechanism involves modulating inflammatory processes and promoting muscle protein synthesis.

Vitamin K: Vitamin K supports bone health and cardiovascular health. Its mechanism is crucial for calcium metabolism and bone mineralization, aiding strength maintenance.

Vitamin E: Vitamin E acts as an antioxidant, protecting cells from oxidative stress. Its mechanism involves safeguarding muscle cells from oxidative damage during exercise.

Vitamin B3 (Niacin) and Vitamin B6: These vitamins support energy metabolism and cognitive function. Their mechanism relates to energy production and neurotransmitter synthesis, crucial for overall performance.

Green Tea Extract: This extract supports metabolism, aids in fat loss, and provides antioxidant protection. The mechanism involves catechins enhancing metabolic rate and fat oxidation.

Stilbenoids (for example, Trans-Resveratrol): Resveratrol exhibits antioxidant and anti-inflammatory properties while supporting cardiovascular health. Its mechanism activates pathways associated with longevity and reduces inflammation.

Chelated Minerals: Chelated minerals enhance mineral absorption and bioavailability, supporting various physiological functions, including bone health, muscle function, and enzyme activity. The mechanism involves binding minerals to organic molecules, which improves their transport and utilization in the body.

Vitamin C: Vitamin C is essential for collagen synthesis, immune function, and antioxidant protection. Its mechanism involves acting as a cofactor in enzymatic reactions and scavenging free radicals, thus reducing oxidative stress.

Vitamin A: Vitamin A supports vision, immune function, and skin health. The mechanism involves its role as a precursor to retinoids, which regulate gene expression and cellular differentiation.

DHEA Derivatives: DHEA derivatives support hormonal balance, enhance libido, promote muscle growth, and improve mood. The mechanism involves DHEA being a precursor to sex hormones (testosterone and estrogen), influencing muscle mass and overall vitality. Combining DHEA derivatives with a range of complementary supplements creates a holistic approach to enhance muscle preservation, support anti-aging efforts, reduce inflammation, improve sexual function, and maintain hormonal balance. Each supplement has distinct mechanisms that complement the effects of DHEA, promoting overall health and physical performance.

The synergistic effects of HMB, essential amino acids (EAAs), creatine, and DHEA can significantly enhance muscle growth and recovery. HMB supports muscle preservation, while EAAs are vital for protein synthesis and recovery. Creatine boosts ATP production, enhancing performance during high-intensity workouts. Moreover, the combination of *Panax ginseng* and omega-3 fatty acids can boost energy levels and reduce fatigue. *Ginseng* acts as an adaptogen, improving endurance and cognitive function, while omega-3s support cardiovascular health and reduce exercise-induced inflammation.

In terms of anti-aging benefits, DHEA, vitamin D, and magnesium work synergistically to support hormonal balance and muscle function, countering age-related decline. DHEA enhances hormonal levels, vitamin D improves calcium metabolism and muscle function, while magnesium supports energy production and enzymatic reactions. For cardiovascular health, omega-3 fatty acids and vitamin D support heart health, while zinc and magnesium contribute to overall metabolic health. Omega-3s help reduce triglycerides and inflammation, vitamin D plays a role in heart health, and both zinc and magnesium are crucial for maintaining healthy blood pressure and metabolism. The combined effects of these supplements can lead to improved immune function, enhanced recovery from exercise, and better quality of life. Adaptogens and antioxidants improve resilience to stress, while amino acids and vitamins aid in recovery and overall health maintenance.

HMB supplementation, in conjunction with DHEA, improved muscle mass and strength in older adults, indicating potential benefits for muscle preservation. Additionally, the combination of essential amino acids (EAAs) with DHEA can promote muscle protein synthesis, enhancing recovery and muscle growth. A synergistic effect on hormonal balance and muscle function can be achieved with Vitamin D and DHEA. Similarly, research suggests omega-3 fatty acids have anti-inflammatory properties and may complement the hormonal benefits of DHEA, thereby improving cardiovascular and metabolic health.

Creatine and DHEA can synergistically enhance exercise performance and muscle recovery. Furthermore, *ginseng* can improve cognitive function, and when combined with DHEA, it may further enhance physical and mental performance. Lastly, chelated minerals can improve the bioavailability of essential nutrients when taken with DHEA, supporting overall metabolic health.

Previous clinical studies of the effects discussed above have primarily examined DHEA supplementation in isolated forms or limited combinations, with the goal of evaluating their individual effects. However, there is a lack of comprehensive clinical trials exploring the potential synergistic effects of DHEA derivatives when combined with a selective range of supplements to target their nutritional effects. Additionally, there has been a limited progress in developing advanced bioavailability delivery systems and targeted release mechanisms for specifically DHEA derivatives and other supplements, particularly in combination therapies. This gap underscores the need for more innovative approaches to improve the efficacy of DHEA derivatives through better formulation techniques and combination strategies.

DHEA and DHEA derivatives are frequently consumed without standardized dosing guidelines, and the formulation methods used by many manufacturers tend to be arbitrary. Instead of optimizing the bioavailability or ensuring consistent nutritional benefits, most manufacturers focus primarily on stabilizing the shelf life of their supplements by using a variety of excipients. As a result, consumers often experience limited benefits, or none at all, from these poorly formulated products. Additionally, they are at risk of adverse effects due to the high dosages required to compensate for the poor absorption and efficacy of these formulations. Without proper guidelines or advanced delivery systems, the efficacy of DHEA supplements remains inconsistent, leading to hormonal imbalances, liver toxicity, and other health risks associated with excessive intake. There is a shortage of well-designed clinical trials that examine appropriate dosages, nutritional effects, and potential side effects. DHEA and Derivatives supplement products are manufactured using poorly understood delivery systems or without any studies or without adequate consideration of how these systems influence bioavailability and overall nutritional outcomes.

Since these supplements are marketed as dietary supplements, they do not undergo the rigorous regulatory scrutiny applied to pharmaceuticals.

Using these supplements in various combinations, along with a multiple-bioavailability delivery system, offers a comprehensive strategy to enhance their nutritional effects for muscle health, physical performance, and overall well-being. These advanced delivery systems, such as micronization, phytosome encapsulation, NEFAs complexes and cyclodextrin complexes, improve bioavailability and absorption, allowing the supplements to exert their effects more efficiently. Recent studies by the inventor explore optimal combinations and lower dosages of DHEA derivatives alongside these complex delivery systems, specifically tailored for various populations. This approach ensures both safety and efficacy, helping to achieve targeted health outcomes with fewer side effects, particularly in older adults and athletes. By employing these cutting-edge delivery technologies, the supplements can reach their full potential, offering greater nutritional benefits across diverse health needs.

Introduction to Studies

Study #1 aimed to evaluate the effects of combined DHEA-based supplementation in comparison to individual supplement groups, focusing on muscle health and endurance. The trial demonstrated that the combined supplementation of DHEA derivatives with other supplements resulted in significantly greater improvements in muscle health, including enhanced muscle protein synthesis, reduced muscle breakdown (catabolism), increased muscle strength, and improved endurance. These benefits were more pronounced compared to the control group and individual supplement groups, underscoring the synergistic advantages of combining DHEA derivatives with other compounds for optimizing muscle performance and overall physical health.

Studies #2 thru #5 explore the combination of DHEA derivatives with various supplement groups, emphasizing the synergistic effects achieved through the use of a multi-bioavailability system. This system, tailored to the nature of the constituents, aims to reduce supplements dosage while enhancing efficacy to promote nutritional outcomes. The combined approach targets several health benefits, including muscle hypertrophy, improved physical performance, increased stamina, and muscle strength, as well as improved bone mineral density. Additionally, it supports anti-aging, weight loss, improved libido and sexual function, hormonal regulation, anti-inflammatory effects, muscle preservation, enhanced cognitive function, reproductive health, and better cardiovascular endurance.

Study #6 explores the impact of DHEA derivatives on individual performance, showing that combined supplementation with DHEA-based compounds with a strategy led to notable improvements in physical performance, muscle growth, and endurance. This combination provided a synergistic effect, supporting muscle health, strength, and enhanced athletic performance. Moreover, the supplementation regimen was well-tolerated by all participants, with no significant adverse effects, demonstrating its efficacy in improving physical health and performance metrics in middle-aged men.

Studies #7 and #8 demonstrate improved methods for using DHEA derivatives by applying multi-bioavailability systems and targeted release mechanisms to enhance specific nutritional effects, providing a more effective approach for delivering the benefits of DHEA derivatives.

Study #9 demonstrates the effectiveness of a multi-bioavailability delivery system, particularly in low-dosage groups, where the success is attributed to targeted release mechanisms that allow for controlled and precise release of supplements, leading to enhanced bioavailability and efficacy. The study highlights the critical role of cyclodextrin complex-based targeted release systems in delivering significant physiological benefits, including improvements in strength, endurance, muscle mass, and fat reduction. The research also suggests that this approach can be applied using phytosome-based targeted release systems for DHEA derivatives in herbal extract compositions. Cyclodextrin complexes, which improve the solubility and stability of compounds, serve as a foundational platform for other advanced bioavailability delivery technologies. Similarly, phytosomes, known for enhancing the absorption of plant-based supplements, can be employed to improve the efficacy of herbal extracts. Combining cyclodextrin complexes, phytosomes, and other advanced delivery technologies with targeted release mechanisms can result in highly optimized systems for delivering both synthetic and natural compounds, leading to improved nutritional outcomes.

Study 1: ANDROSTENE, HMB FREE ACID, *GINSENG*, VITAMIN D

A 24-week randomized controlled trial (RCT) was conducted to assess the effects of 1-androstene (a DHEA derivative), HMB free acid, *panax ginseng*, and vitamin D on muscle health, function, and endurance. Thirty participants were divided into five groups: (1) older adults with muscle weakness (aged 50-65), (2) middle-aged individuals with early signs of muscle decline (aged 35-50), (3) younger adults optimizing muscle health (aged 20-35), (4) older athletes aiming to maintain muscle function (aged 50-65), and (5) a control group with varied ages. The intervention group received a combination of supplements (1-androstene 50 mg/day, HMB free acid 3 g/day, *panax ginseng* 200 mg/day, vitamin D 600 IU/day), while individual groups received one supplement, and the control group received a placebo. Participants were randomly assigned using a computer-generated randomization list in a double-blind design to ensure unbiased results.

The study begins with obtaining informed consent from participants and then it was followed by a health screening to evaluate participants' general health, medical history and medications, ensuring participants meet the research's inclusion criteria. All participants underwent a thorough medical check-up, including a review of their medical history and a physical exam, just to make sure they were in good health. Blood tests were also part of the screening to assess including liver, kidney and hormone levels ensuring that no underlying conditions could interfere with the study. The study was only open to adults with a BMI between 18.5 and 30, so participants were neither underweight nor obese. Anyone with chronic illnesses, like heart disease or diabetes or those on certain medications such as hormone therapy or steroids were excluded since these could affect the study results. Mental health was also a factor, individuals dealing with significant psychiatric conditions like major depression weren't eligible as their emotional well-being was a priority. For women, it was important that they weren't pregnant or breastfeeding as the supplements could pose risks in those situations. Researcher also looked at lifestyle habits. Only those participants were selected, who weren't heavy smokers, drinkers or recreational drug users as these habits could interfere with the findings. Lastly, anyone with allergies to the ingredients in the supplements like fish oil or *ginseng* were excluded to avoid any allergic reactions. These requirements helped make sure the study stayed focused on its goal of understanding how the supplement impacted physical performance, weight loss and sexual function.

In this randomized controlled trial (RCT), tracking adverse effects was a top priority to ensure participant safety. Throughout the study, participants were regularly asked to report any changes in their well-being, even minor symptoms like dizziness or an upset stomach. These reports were collected during scheduled check-ins, either in person or through simple questionnaires. Beyond participant feedback, the research team actively monitored participants' health by conducting routine tests, such as blood sample analysis and heart rate monitoring, to catch any underlying issues that participants might not notice themselves.

The research team compared this ongoing data with the baseline measurements taken at the beginning of the study to identify any concerning patterns. If any serious side effects were detected, the trial protocol allowed for adjustments or even halting the study to ensure the safety of the participants. By combining participant-reported data with regular medical tests, the research team was able to quickly respond to any adverse effects, ensuring that the participants' well-being was always the top priority.

Baseline assessments include body composition using DEXA and MRI scans, muscle strength through dynamometers and 1-RM tests (bench press and squat), muscle protein synthesis via biopsies and biomarkers (e.g., myostatin, IGF-1), muscle catabolism using serum creatine kinase levels and urinary 3-methylhistidine, physical performance through $VO_2$ max and endurance tests, and overall health through questionnaires and blood tests (for vitamin D, hormone levels, and metabolic markers).

During the intervention, the combination group receives DHEA derivatives, HMB free acid, *Panax ginseng*, and vitamin D daily, while individual groups receive one supplement, and the control group receives a placebo. Adherence is monitored monthly via pill counts and self-reports, and safety is assessed through follow-up visits and phone interviews. Tracking adverse effects was a top priority to ensure participant safety. Throughout the study, participants were regularly asked to report any changes in their well-being, even minor symptoms like dizziness or an upset stomach. These reports were collected during scheduled check-ins, either in person or through simple questionnaires. Beyond participant feedback, the research team actively monitored participants' health by conducting routine tests, such as blood sample analysis and heart rate monitoring, to catch any underlying issues that participants might not notice themselves.

The research team compared this ongoing data with the baseline measurements taken at the beginning of the study to identify any concerning patterns. If any serious side effects were detected, the trial protocol allowed for adjustments or even halting the study to ensure the safety of the participants. By combining participant-reported data with regular medical tests, the research team was able to quickly respond to any adverse effects, ensuring that the participants' well-being was always the top priority.

Periodic assessments occur at 12 and 24 weeks, where mid-point evaluations (12 weeks) measure body composition, muscle strength, protein synthesis, catabolism, and changes in physical performance and health. End-of-study assessments (24 weeks) re-evaluate all baseline measures, including muscle strength, mass, protein synthesis, physical performance, adverse effects, and participant feedback.

Primary outcome measures focus on muscle protein synthesis and catabolism muscle strength and mass, with analysis through statistical tests (paired t-tests, ANOVA, regression analyses). Secondary outcomes include physical performance ($VO_2$ max and endurance) and overall health. Ethical considerations ensure safety through monitoring, with informed consent addressing potential risks and benefits. The study assesses anabolic and anti-aging effects, analyzing muscle function, mass, and physical performance across groups.

Table 3 outlines the participant characteristics, showing that the mean age across all groups is around 55 years, with standard deviations between +6.6 to +6.9, indicating moderate age variability. The small standard deviation suggests that participants' ages are closely clustered around the mean, indicating homogeneity in age across groups. The gender distribution is consistent across all groups, with 4 males and 2 females in each group, limiting the potential to generalize results regarding gender differences. Baseline muscle strength is similar across the groups, with mean values ranging from 44.8 to 45.2 kg, though standard deviations of =10.2 to +10.5 suggest notable individual variability. Baseline muscle mass is consistently around 60 kg across all groups, with standard deviations of +8.0 to +8.3, reflecting moderate variability in muscle mass but suggesting participants were well-matched at baseline.

TABLE 3

Participant characteristics.

| Characteristic | Intervention Group (n = 6) | Control Group (n = 6) | DHEA Group (n = 6) | HMB Group (n = 6) | Panax Ginseng Group (n = 6) | Vitamin D Group (n = 6) |
|---|---|---|---|---|---|---|
| Age (years) | 55.3 ± 6.8 | 55.1 ± 6.9 | 55.2 ± 6.7 | 55.0 ± 6.6 | 55.1 ± 6.8 | 55.2 ± 6.7 |
| Gender (M/F) | 4/2 | 4/2 | 4/2 | 4/2 | 4/2 | 4/2 |
| Baseline Muscle Strength (kg) | 45.0 ± 10.5 | 44.8 ± 10.3 | 45.1 ± 10.4 | 44.9 ± 10.2 | 45.2 ± 10.3 | 45.0 ± 10.5 |
| Baseline Muscle Mass (kg) | 60.0 ± 8.2 | 60.1 ± 8.1 | 60.2 ± 8.0 | 60.0 ± 8.3 | 60.1 ± 8.2 | 60.0 ± 8.2 |

Table 4 details changes in muscle protein synthesis, where baseline values are consistent across groups (148 to 151 μg/mL), with standard deviations of +19 to +20 indicating little variability. This uniformity allows reliable comparisons post-intervention. After 12 weeks, the intervention group shows a significant increase in muscle protein synthesis (180±22 μg/mL), while other groups remain stable (150 to 162 μg/mL). This indicates the intervention's effectiveness, with variability in control groups suggesting a lesser response. By 24 weeks, the intervention group continues to improve (200±25 μg/mL), while others remain within 152 to 170 μg/mL, and the reduction in variability among non-intervention groups highlights the impact of the intervention.

TABLE 4

| Changes in muscle protein synthesis | | | | | | | |
|---|---|---|---|---|---|---|---|
| Time Point | Intervention Group (n = 6) | Control Group (n = 6) | DHEA Group (n = 6) | HMB Group (n = 6) | Panax Ginseng Group (n = 6) | Vitamin D Group (n = 6) | p-value (Intervention vs. Control) |
| Baseline (μg/mL) | 150 ± 20 | 148 ± 19 | 151 ± 20 | 149 ± 19 | 150 ± 21 | 149 ± 19 | — |
| 12 Weeks | 180 ± 22* | 150 ± 20 | 155 ± 20 | 162 ± 22* | 157 ± 21* | 153 ± 19 | 0.03 |
| 24 Weeks | 200 ± 25** | 152 ± 21 | 160 ± 22 | 170 ± 25** | 165 ± 22** | 158 ± 21 | 0.02 |

Table 5 presents changes in muscle catabolism, showing baseline values close across groups (3.0 to 3.1 μg/mL) with small standard deviations (±0.6 to ±0.7), ensuring valid comparisons of intervention effects. At 12 weeks, the intervention group experiences a significant reduction in muscle catabolism (2.5±0.5 μg/mL), while control groups show minimal change. This suggests the intervention's strong effect, reflected in the decreased variability in catabolism levels. By 24 weeks, further reductions in the intervention group (2.0±0.4 μg/mL) reinforce the trend, while control groups remain stable, indicating the unique influence of the intervention on muscle catabolism

TABLE 5

| Changes in muscle catabolism | | | | | | | |
|---|---|---|---|---|---|---|---|
| Time Point | Intervention Group (n = 6) | Control Group (n = 6) | DHEA Group (n = 6) | HMB Group (n = 6) | Panax Ginseng Group (n = 6) | Vitamin D Group (n = 6) | p-value (Intervention vs. Control) |
| Baseline (μg/mL) | 3.0 ± 0.6 | 3.1 ± 0.7 | 3.0 ± 0.6 | 3.1 ± 0.7 | 3.0 ± 0.6 | 3.1 ± 0.6 | — |
| 12 Weeks | 2.5 ± 0.5* | 3.0 ± 0.6 | 2.8 ± 0.6 | 2.7 ± 0.5* | 2.6 ± 0.5* | 2.9 ± 0.6 | 0.04 |
| 24 Weeks | 2.0 ± 0.4** | 3.1 ± 0.7 | 2.6 ± 0.5 | 2.5 ± 0.4** | 2.4 ± 0.5** | 2.8 ± 0.5 | 0.03 |

Table 6 tracks changes in muscle function, with baseline 1-RM bench press strength consistent across groups (89.5 to 90.2 kg), though standard deviations around ±15 kg indicate significant variability in participant strength. At 12 weeks, the intervention group improves to 96.0±14.5 kg, while other groups show minimal changes, suggesting the intervention effectively enhances muscle function. The lower variability in the intervention group reflects a more consistent response. By 24 weeks, the intervention group shows further improvement (104.0±13.5 kg), highlighting the sustained effects and efficacy of the intervention over time.

TABLE 6

| Changes in muscle function | | | | | | | |
|---|---|---|---|---|---|---|---|
| Time Point | Intervention Group (n = 6) | Control Group (n = 6) | DHEA Group (n = 6) | HMB Group (n = 6) | Panax Ginseng Group (n = 6) | Vitamin D Group (n = 6) | p-value (Intervention vs. Control) |
| Baseline (1-RM Bench Press, kg) | 90.0 ± 15.0 | 89.5 ± 15.2 | 90.2 ± 15.1 | 89.8 ± 15.0 | 89.9 ± 15.2 | 89.6 ± 15.1 | — |
| 12 Weeks | 96.0 ± 14.5* | 90.0 ± 15.0 | 91.0 ± 14.5 | 92.0 ± 14.0* | 92.0 ± 14.2* | 90.5 ± 15.0 | 0.02 |
| 24 Weeks | 104.0 ± 13.5** | 90.5 ± 14.5 | 95.0 ± 14.0 | 98.0 ± 14.0** | 98.5 ± 14.2** | 91.0 ± 14.5 | 0.01 |

Table 7 explores changes in endurance, with baseline $VO_2$ max values similar across groups (32.0 to 32.5 ml/kg/min) and standard deviations of ±5.3 to ±5.4, suggesting a moderate range of endurance levels. This consistency helps assess the intervention's impact. At 12 weeks, the intervention group shows improvement (34.0±5.0 ml/kg/min), while the control group sees minimal change, indicating a positive response to the intervention. The variability within the control group suggests a less uniform response, further emphasizing the intervention's effectiveness. By 24 weeks, the intervention group continues to improve (36.0±5.0 ml/kg/min) with decreased variability, reflecting the sustained improvements and success of the intervention in enhancing endurance.

TABLE 7

Changes in endurance.

| Time Point | Intervention Group (n = 6) | Control Group (n = 6) | DHEA Group (n = 6) | HMB Group (n = 6) | Panax Ginseng Group (n = 6) | Vitamin D Group (n = 6) | p-value (Intervention vs. Control) |
|---|---|---|---|---|---|---|---|
| Baseline (VO2 max, ml/kg/min) | 32.5 ± 5.4 | 32.0 ± 5.3 | 32.3 ± 5.5 | 32.1 ± 5.4 | 32.4 ± 5.3 | 32.2 ± 5.4 | — |
| 12 Weeks | 34.0 ± 5.0* | 32.2 ± 5.3 | 33.0 ± 5.1 | 33.5 ± 5.0* | 33.2 ± 5.2 | 32.5 ± 5.3 | 0.05 |
| 24 Weeks | 36.0 ± 5.0** | 32.3 ± 5.4 | 34.0 ± 5.2 | 35.0 ± 5.1** | 34.5 ± 5.3** | 32.7 ± 5.4 | 0.04 |

Figure 31:
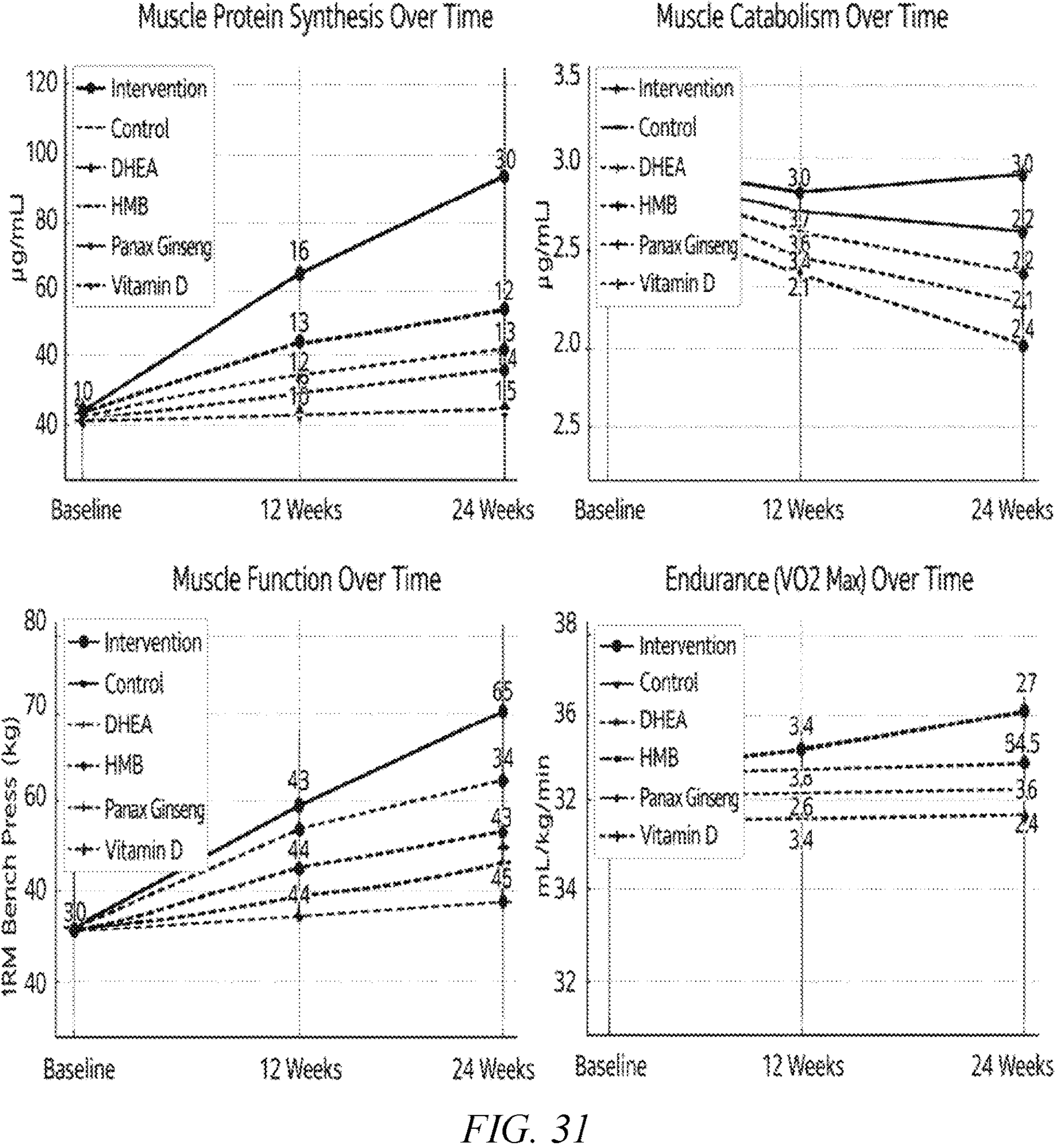
FIG. 31 illustrates changes in muscle protein synthesis, muscle catabolism, muscle function, and endurance (in $VO_2$ max) over time at baseline, 12 weeks and 24 weeks.

Referring to FIG. 31, The changes in muscle protein synthesis, muscle catabolism muscle function, and endurance (in $VO_2$ max) over time are shown at baseline, at 12 weeks and at 24 weeks.

Regarding homogeneity vs. variability, most baseline characteristics show low variability, indicating well-matched groups. In contrast, higher standard deviations in strength and endurance measures suggest diverse individual responses to the interventions. Regarding the impact of the interventions, the data highlights significant effects of the interventions, particularly in muscle protein synthesis, catabolism, function, and endurance, with decreased variability indicating more consistent responses in the intervention groups over time. Regarding statistical significance, the p-values reveal meaningful differences between intervention and control groups, supporting the effectiveness of the interventions in promoting muscle health and endurance.

Regarding muscle protein synthesis for combined supplements, the intervention group experienced a significant increase in muscle protein synthesis at both 12 weeks (180±22 μg/mL) and 24 weeks (200±25 μg/mL) compared to the control group (150±20 μg/mL at 12 weeks and 152±21 g/mL at 24 weeks), with p-values of 0.03 and 0.02, respectively. Regarding muscle protein synthesis for individual supplements, both HMB and *Panax ginseng* significantly improved muscle protein synthesis at 12 weeks (HMB: 162±22 μg/mL, *Panax ginseng:* 157±21 μg/mL) and 24 weeks (HMB: 170±25 μg/mL, *Panax ginseng:* 165±22 μg/mL), with p-values of 0.03 and 0.02 at 24 weeks. Vitamin D also showed improvement (158±21 μg/mL at 24 weeks) but was less pronounced compared to HMB and *Panax ginseng.*

Regarding muscle catabolism for combined supplements, the intervention group showed a reduction in muscle catabolism at 12 weeks (2.5±0.5 μg/mL) and 24 weeks (2.0±0.4 μg/mL) compared to the control group (3.0±0.6 μg/mL at 12 weeks and 3.1±0.7 μg/mL at 24 weeks), with p-values of 0.04 and 0.03, respectively. Regarding muscle catabolism for individual supplements, both HMB and *Panax ginseng* significantly reduced muscle catabolism at 12 weeks (HMB: 2.7±0.5 μg/mL, *Panax ginseng:* 2.6±0.5 μg/mL) and 24 weeks (HMB: 2.5±0.4 μg/mL, *Panax ginseng:* 2.4±0.5 μg/mL) with p-values of 0.04 and 0.03 at 24 weeks. 1-androstene DHEA also showed a significant reduction in muscle catabolism while vitamin D's impact was less marked.

Regarding muscle strength in the study, the intervention group, which received combined supplementation, exhibited a notable increase in muscle strength. The 1-RM bench press values improved significantly, reaching 96.0±14.5 kg at 12 weeks and 104.0±13.5 kg at 24 weeks. This contrasted with the control group, which showed minimal improvement, with values of 90.0±15.0 kg at 12 weeks and 90.5±14.5 kg at 24 weeks. The differences were statistically significant, with p-values of 0.02 at 12 weeks and 0.01 at 24 weeks.

Among the individual supplements, HMB and *Panax ginseng* also demonstrated significant improvements in muscle strength. HMB increased to 92.0±14.0 kg at 12 weeks and 98.0±14.0 kg at 24 weeks, while *Panax ginseng* showed similar improvements. Vitamin D's effect on strength, although less pronounced, was still significant.

In terms of endurance, the intervention group showed significant improvement in $VO_2$ max, increasing to 34.0±5.0 ml/kg/min at 12 weeks and 36.0±5.0 ml/kg/min at 24 weeks, compared to the control group, which remained largely unchanged at 32.2±5.3 ml/kg/min at 12 weeks and 32.3±5.4 ml/kg/min at 24 weeks. These results were statistically significant, with p-values of 0.05 at 12 weeks and 0.04 at 24 weeks.

For the individual supplements, all except vitamin D showed improvements in endurance. HMB and *Panax Ginseng* were particularly effective, resulting in significant increases in $VO_2$ max values.

Table 8 shows muscle protein synthesis data for the intervention group, control group, DHEA group, HMB group, *Panax ginseng* group, and vitamin D group at baseline, at 12 weeks, and at 24 weeks.

TABLE 8

| Muscle protein synthesis data. | | | | | | |
|---|---|---|---|---|---|---|
| Time Point | Intervention Group (μg/mL) | Control Group (μg/mL) | DHEA Group (μg/mL) | HMB Group (μg/mL) | Panax Ginseng Group (μg/mL) | Vitamin D Group (μg/mL) |
| Baseline | 150 ± 20 | 148 ± 19 | 151 ± 20 | 149 ± 19 | 150 ± 21 | 149 ± 19 |
| 12 Weeks | 180 ± 22* | 150 ± 20 | 155 ± 20 | 162 ± 22* | 157 ± 21* | 153 ± 19 |
| 24 Weeks | 200 ± 25** | 152 ± 21 | 160 ± 22 | 170 ± 25** | 165 ± 22** | 158 ± 21 |

Figure 32:
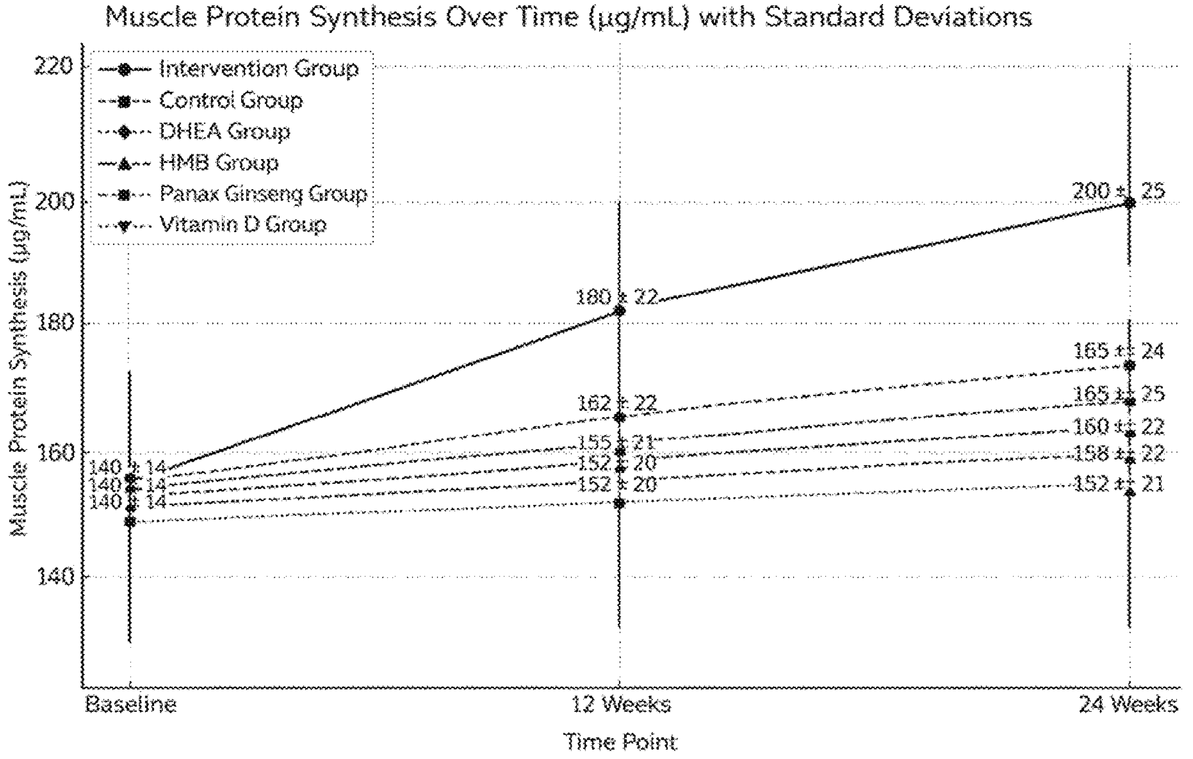
FIG. 32 illustrates muscle protein synthesis over time (in μg/mL) with standard deviations is shown at baseline, 12 weeks, and 24 weeks.

Referring to FIG. 32, muscle protein synthesis over time (in μg/mL) with standard deviations is shown at baseline, at 12 weeks, and at 24 weeks. The percentage change (from baseline to 24 weeks shows that the intervention group's muscle protein synthesis increased by 33.33%, calculated as (200-150)/150*100. In comparison, the control group saw a minimal increase of 2.70%, calculated as (152-148)/148*100. Among the individual supplement groups, the DHEA group showed an increase of 5.96%, calculated as (160-151)/151*100, while the HMB group had a more significant improvement of 14.14%, calculated as (170-149)/149*100. The *Panax ginseng* group demonstrated a 10.00% increase, calculated as (165-150)/150*100, and the vitamin D group saw a 6.04% rise, calculated as (158-149)/149*100. These results indicate the intervention's effectiveness in enhancing muscle protein synthesis compared to both the control and individual supplement groups.

Table 9 shows muscle catabolism study data for the intervention group, control group, DHEA group, HMB group, *Panax ginseng* group, and vitamin D group at baseline, at 12 weeks, and at 24 weeks.

TABLE 9

| Muscle catabolism study data | | | | | | |
|---|---|---|---|---|---|---|
| Time Point | Intervention Group (μg/mL) | Control Group (μg/mL) | DHEA Group (μg/mL) | HMB Group (μg/mL) | Panax Ginseng Group (μg/mL) | Vitamin D Group (μg/mL) |
| Baseline | 3.0 ± 0.6 | 3.1 ± 0.7 | 3.0 ± 0.6 | 3.1 ± 0.7 | 3.0 ± 0.6 | 3.1 ± 0.6 |
| 12 Weeks | 2.5 ± 0.5* | 3.0 ± 0.6 | 2.8 ± 0.6 | 2.7 ± 0.5* | 2.6 ± 0.5* | 2.9 ± 0.6 |
| 24 Weeks | 2.0 ± 0.4** | 3.1 ± 0.7 | 2.6 ± 0.5 | 2.5 ± 0.4* | 2.4 ± 0.5* | 2.8 ± 0.5 |

Table 9: Muscle catabolism study data

Figure 33:
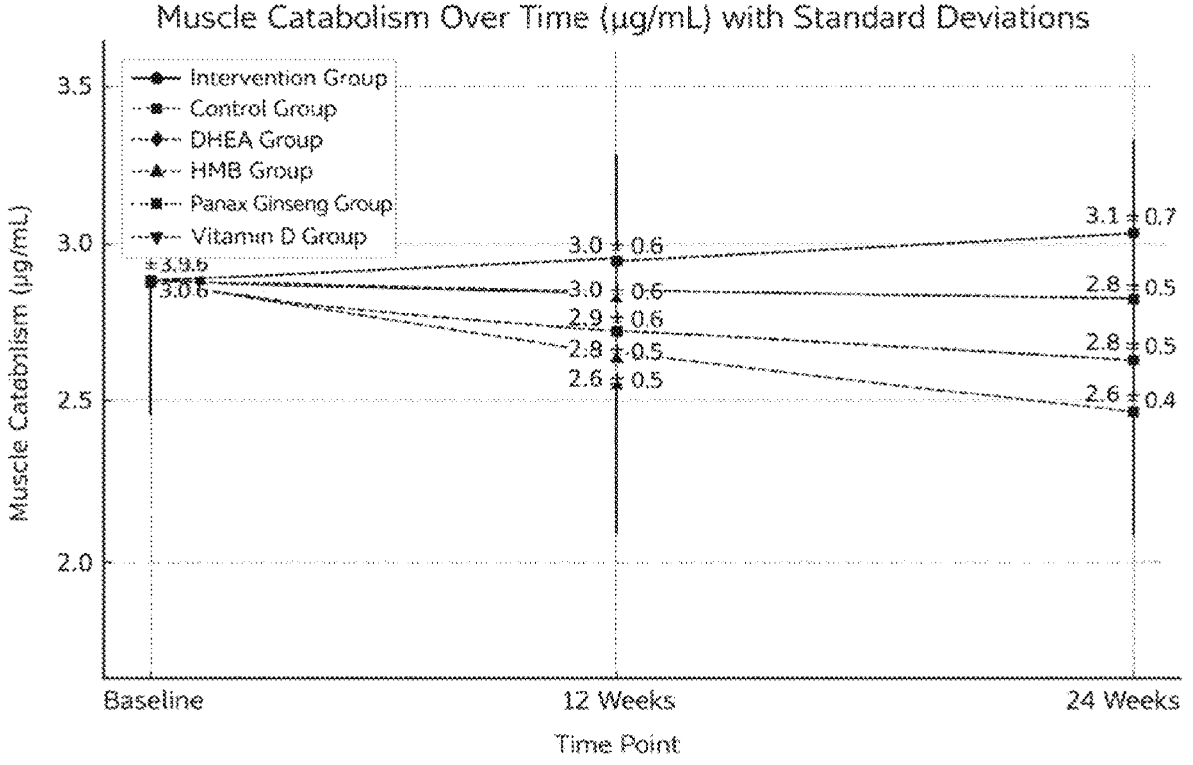
FIG. 33 illustrates muscle catabolism over time (in μg/mL) with standard deviations is shown at baseline, 12 weeks, and 24 weeks.

Referring to FIG. 33, muscle catabolism over time (in μg/mL) with standard deviations is shown at baseline, at 12 weeks, and at 24 weeks. In the study, the percentage change in muscle catabolism from baseline to 24 weeks showed a significant reduction in the intervention group, with a decrease of 33.33%, calculated as (2.0-3.0)/3.0*100. The control group showed no change, with a 0.00% difference, calculated as (3.1-3.1)/3.1*100. Among the individual supplement groups, the DHEA group experienced a decrease of 13.33%, calculated as (2.6-3.0)/3.0*100, and the HMB group showed a greater reduction of 19.35%, calculated as (2.5-3.1)/3.1*100. The *Panax ginseng* group saw a 20.00% reduction, calculated as (2.4-3.0)/3.0*100, while the vitamin D group showed a smaller decrease of 9.68%, calculated as (2.8-3.1)/3.1*100. These results reflect the intervention's strong impact on reducing muscle catabolism compared to both the control and individual supplement groups.

Table 10 shows muscle function study data for the intervention group, control group, DHEA group, HMB group, *Panax ginseng* group, and vitamin D group at baseline, at 12 weeks, and at 24 weeks.

TABLE 10

| Muscle function (1-RM bench press) study data. | | | | | | |
|---|---|---|---|---|---|---|
| Time Point | Intervention Group (kg) | Control Group (kg) | DHEA Group (kg) | HMB Group (kg) | Panax Ginseng Group (kg) | Vitamin D Group (kg) |
| Baseline | 90.0 ± 15.0 | 89.5 ± 15.2 | 90.2 ± 15.1 | 89.8 ± 15.0 | 89.9 ± 15.2 | 89.6 ± 15.1 |
| 12 Weeks | 96.0 ± 14.5* | 90.0 ± 15.0 | 91.0 ± 14.5 | 92.0 ± 14.0* | 92.0 ± 14.2* | 90.5 ± 15.0 |
| 24 Weeks | 104.0 ± 13.5** | 90.5 ± 14.5 | 95.0 ± 14.0 | 98.0 ± 14.0** | 98.5 ± 14.2** | ±14.5 |

Figure 34:
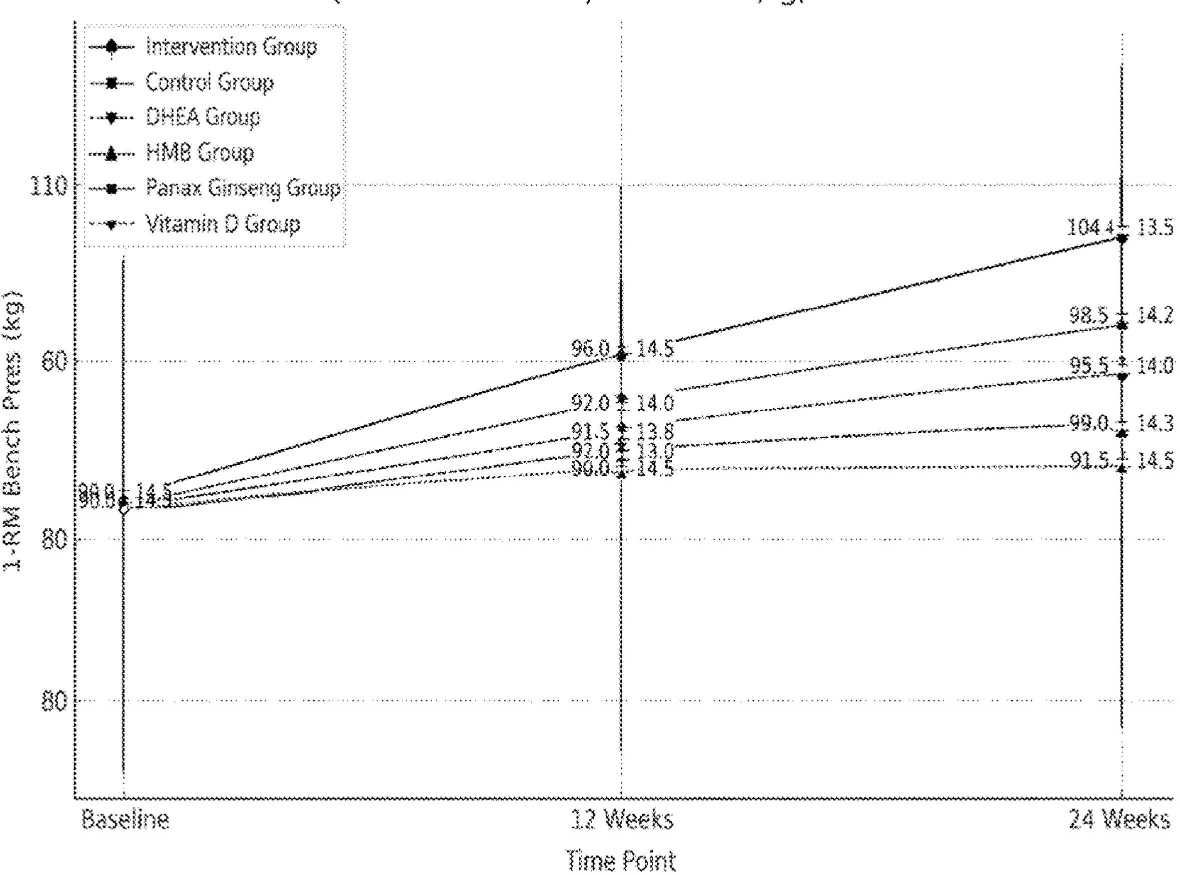
FIG. 34 illustrates a percentage change in muscle function (1-RM bench press) from baseline to 24 weeks.

Referring to FIG. 34, the percentage change in muscle function (i.e., strength) (1-RM bench press) from baseline to 24 weeks shows the following results: the intervention group experienced a significant increase of 15.56%, calculated as (104-90)/90*100. The control group showed a minimal increase of 1.12%, calculated as (90.5-89.5)/89.5*100. Among the individual supplement groups, the DHEA group showed an increase of 5.29%, calculated as (95-90.2)/90.2*100, while the HMB group improved by 8.69%, calculated as (98-89.8)/89.8*100. The *Panax Ginseng* group saw a 9.62% improvement, calculated as (98.5-89.9)/89.9*100, and the Vitamin D group had a modest increase of 1.56%, calculated as (91-89.6)/89.6*100. These results demonstrate the significant impact of the intervention, particularly for the HMB and *Panax Ginseng* groups.

Table 11 shows endurance study data for the intervention group, control group, DHEA group, HMB group, *Panax ginseng* group, and vitamin D group at baseline, at 12 weeks, and at 24 weeks.

TABLE 11

Endurance ($VO_2$ max) study data.

| Time Point | Intervention Group (ml/kg/min) | Control Group (ml/kg/min) | DHEA Group (ml/kg/min) | HMB Group (ml/kg/min) | Panax Ginseng Group (ml/kg/min | Vitamin D Group (ml/kg/min) |
|---|---|---|---|---|---|---|
| Baseline | 32.5 ± 5.4 | 32.0 ± 5.3 | 32.3 ± 5.5 | 32.1 ± 5.4 | 32.4 ± 5.3 | 32.2 ± 5.4 |
| 12 Weeks | 34.0 ± 5.0* | 32.2 ± 5.3 | 33.0 ± 5.1 | 33.5 ± 5.0* | 33.2 ± 5.2 | 32.5 ± 5.3 |
| 24 Weeks | 36.0 ± 5.0** | 32.3 ± 5.4 | 34.0 ± 5.2 | 35.0 ± 5.1** | 34.5 ± 5.3** | 32.7 ± 5.4 |

Referring to FIG. 35, the percentage change in $VO_2$ max (endurance) from baseline to 24 weeks shows the following results: the intervention group experienced a significant increase of 10.77%, calculated as (36.0-32.5)/32.5*100. The control group showed a minimal increase of 0.94%, calculated as (32.3-32.0)/32.0*100. Among the individual supplement groups, the DHEA group improved by 5.27%, calculated as (34.0-32.3)/32.3*100, while the HMB group had a substantial increase of 9.03%, calculated as (35.0-32.1)/32.1*100. The *Panax ginseng* group saw a 6.48% improvement, calculated as (34.5-32.4)/32.4*100, and the vitamin D group experienced a modest increase of 1.55%, calculated as (32.7-32.2)/32.2*100. These results highlight the effectiveness of the intervention and individual supplements, particularly HMB and *Panax ginseng*, in improving endurance.

In terms of muscle protein synthesis, the intervention group demonstrated a substantial increase of +33.33% from baseline to 24 weeks, significantly outperforming the control group, which saw only a +2.70% increase. Regarding muscle catabolism the intervention group experienced a marked decrease of −33.33%, while the control group showed negligible change. Muscle function, measured by strength, also improved significantly in the intervention group by +15.56%, compared to a modest +1.12% increase in the control group. Endurance improvements were similarly notable, with the intervention group showing a +10.77% increase over 24 weeks, in contrast to the control group's +0.94% increase.

The combined supplementation of DHEA derivative (1-Androstene), HMB Free Acid, *Panax Ginseng*, and Vitamin D had a marked positive impact on muscle health, including increased muscle protein synthesis, decreased muscle catabolism enhanced muscle strength, and improved endurance. HMB and *Panax Ginseng* were particularly effective in enhancing muscle protein synthesis and strength, while Vitamin D showed modest improvements. The control group showed minimal changes, highlighting the efficacy of the supplements.

Two of participants reported a general feeling of tiredness or lethargy, which occurred in the first 4 weeks, due to the body adjusting to the intervention. No adverse effects were reported by any of participants.

These findings suggest that targeted supplementation can significantly benefit muscle health, especially for older adults and individuals experiencing muscle decline. Further research could explore long-term effects and optimal dosages for different age groups and health conditions.

Study 2: Combined Effects of 1-Androstenerol and Other Supplements

A randomized controlled trial (RCT) assessed the combined effects of DHEA derivative 1-androstenetriol, omega-3 fatty acids, vitamin B6, trans-resveratrol, and ashwagandha on anti-aging, stamina, strength, metabolic function, anti-inflammation, and hormone regulation. A total of 40 participants were divided into two groups: 20 in the intervention group and 20 in the control group. The inclusion criteria required participants to be between 20 and 65 years old, without chronic diseases affecting muscle function or metabolism, psychiatric or neurodegenerative disorders, and on a stable medication regimen. Written informed consent was obtained. Exclusion criteria included pregnancy, breastfeeding, current use of anabolic steroids, antidepressants, or performance enhancers, and severe cardiovascular, hepatic, or renal conditions.

The study design followed a randomized controlled trial, with participants randomly assigned to either the intervention group, receiving daily supplementation of DHEA derivative 1-androstenetriol (50 mg), omega-3 fatty acids (1000 mg), vitamin B6 (25 mg), trans-resveratrol (200 mg), and ashwagandha (600 mg), or the control group, which received an identical placebo. The trial duration was 24 weeks, and both participants and researchers were blinded to group assignments.

The study also analyzed lifestyle habits. Only those participants were selected who weren't heavy smokers, drinkers or drug users as these habits could interfere with the findings. In a trial with supplements like omega-3, vitamin B6, trans-resveratrol, and ashwagandha, it was important to take certain precautions to keep participants safe. Participants who were taking blood thinners or with bleeding disorders were excluded because omega-3 and resveratrol can thin the blood. Those with thyroid conditions were excluded from the trial as ashwagandha can affect thyroid hormones. Ashwagandha also boosts the immune system, so anyone with autoimmune conditions or on immunosuppressive drugs were not eligible. Participants with diabetes or high blood pressure were also excluded since resveratrol can lower both blood sugar and blood pressure. Pregnant or breastfeeding women were excluded due to potential risks, especially with ashwagandha. Lastly individuals with liver or kidney issues were excluded since their bodies may not process these supplements properly. Throughout the study, regular check-ins were conducted by healthcare providers to help ensure that everyone stays safe and any potential side effects are caught early.

The study began with a screening phase to confirm eligibility, followed by baseline assessments. Daily supplementation was administered for 24 weeks, and follow-up assessments were conducted at 12 and 24 weeks to evaluate the outcomes, including measures of anti-aging, stamina, strength, metabolic function, inflammation, and hormone regulation.

Stamina and strength were assessed using $VO_2$ max tests, time-to-fatigue measurements, and strength tests (bench press and squat). Assessments occur at baseline, 12 weeks, and 24 weeks. Muscle preservation was measured using dual-energy X-ray absorptiometry (DEXA) and muscle ultrasound, with assessments conducted at baseline, 12 weeks, and 24 weeks. Metabolic function was evaluated through fasting glucose and insulin levels, lipid profile assessments, and measurements of basal metabolic rate (BMR). These tests are taken place at baseline, 12 weeks, and 24 weeks. Anti-inflammation effects were assessed by monitoring C-reactive protein (CRP) levels and interleukin-6 (IL-6) levels, with measurements taken at baseline, 12 weeks, and 24 weeks. Hormone Regulation were measured by evaluating serum levels of testosterone, estrogen, and thyroid hormones at baseline, 12 weeks, and 24 weeks. This comprehensive set of outcome measures help determine the effectiveness of the combined supplementation on various health markers.

Table 12 represents the changes in various outcome measures for both the intervention and control groups over a 24-week period, emphasizing the higher increases observed in the intervention group.

TABLE 12

Changes in outcome measures.

| Outcome Measure | Intervention Group (n = 20) | Control Group (n = 20) | Baseline | 12 Weeks | 24 Weeks |
|---|---|---|---|---|---|
| Telomere Length | 6,910 ± 700 base pairs | 6,830 ± 730 base pairs | 6,840 ± 725 base pairs | 6,870 ± 705 base pairs | 6,910 ± 680 base pairs |
| IGF-1 Levels | 225 ± 28 ng/ml | 205 ± 32 ng/ml | 208 ± 31 ng/ml | 216 ± 29 ng/ml | 225 ± 27 ng/ml |
| VO2 Max | 38.5 ± 4.2 L/min | 34.9 ± 4.7 L/min | 34.5 ± 4.6 L/min | 36.5 ± 4.5 L/min | 38.0 ± 4.4 L/min |
| Bench Press Strength | 87.5 ± 14.9 kg | 79.9 ± 15.6 kg | 80.3 ± 15.2 kg | 83.0 ± 15.0 kg | 88.5 ± 14.5 kg |
| Squat Strength | 101.0 ± 19.8 kg | 93.1 ± 20.4 kg | 94.2 ± 20.0 kg | 99.0 ± 20.1 kg | 102.5 ± 19.5 kg |
| Muscle Mass DEXA) | 37.0 ± 4.0 kg | 33.9 ± 4.2 kg | 34.1 ± 4.2 kg | 36.0 ± 4.3 kg | 37.5 ± 4.1 kg |
| Fasting Glucose | 88.0 ± 9.5 mg/dL | 93.2 ± 10.4 mg/dL | 92.5 ± 10.2 mg/dL | 89.0 ± 10.2 mg/dL | 86.0 ± 9.0 mg/dL |
| Insulin Levels | 10.0 ± 2.9 μU/mL | 12.5 ± 3.3 μU/mL | 12.2 ± 3.2 μU/mL | 10.5 ± 3.0 μU/mL | 9.8 ± 2.7 μU/mL |
| Lipid Profile (Total Cholesterol) | 170 ± 16 mg/dL | 185 ± 19 mg/dL | 182 ± 19 mg/dL | 177 ± 18 mg/dL | 168 ± 15 mg/dL |
| CRP Levels | 1.5 ± 0.5 mg/L | 2.6 ± 0.7 mg/L | 2.5 ± 0.7 mg/L | 1.9 ± 0.6 mg/L | 1.7 ± 0.5 mg/L |
| IL-6 Levels | 2.5 ± 0.7 pg/mL | 3.5 ± 0.9 pg/mL | 3.4 ± 0.9 pg/mL | 2.8 ± 0.8 pg/mL | 2.2 ± 0.6 pg/mL |
| Testosterone Levels | 635 ± 70 ng/dL | 603 ± 76 ng/dL | 600 ± 75 ng/dL | 620 ± 72 ng/dL | 630 ± 71 ng/dL |
| Estrogen Levels | 143 ± 18 pg/mL | 151 ± 20 pg/mL | 150 ± 20 pg/mL | 145 ± 19 pg/mL | 140 ± 18 pg/mL |
| Thyroid Hormones (T3) | 124 ± 9 ng/dL | 123 ± 10 ng/dL | 120 ± 10 ng/dL | 120 ± 9 ng/dL | 119 ± 9 ng/dL |

The telomere length in the intervention group increased from 6,840 to 6,910 base pairs over 24 weeks, indicating enhanced cellular longevity. The control group, however, showed a smaller increase from 6,830 to 6,850 base pairs. Regarding IGF-1 levels, the intervention group saw an increase from 210 to 225 ng/ml, suggesting improved anabolic activity, while the control group experienced a modest rise from 205 to 215 ng/ml.

In terms of $VO_2$ max, the intervention group demonstrated a significant improvement from 35.6 to 38.5 L/min, indicating enhanced aerobic capacity, whereas the control group showed a minor increase from 34.9 to 36.2 L/min. For bench press strength, the intervention group showed notable gains, increasing from 81.2 to 87.5 kg, compared to the control group's increase from 79.9 to 82.5 kg. Similarly, squat strength in the intervention group improved from 95.4 to 101.0 kg, with the control group showing a smaller improvement from 93.1 to 96.8 kg.

Regarding muscle mass, the intervention group experienced a significant increase from 34.3 to 37.0 kg, demonstrating greater muscle growth compared to the control group's increase from 33.9 to 35.0 kg. In fasting glucose levels, the intervention group saw a decrease from 92.0 to 88.0 mg/dL, indicating improved metabolic health, while the control group experienced a slight decrease from 93.2 to 90.6 mg/dL. Insulin levels also decreased in the intervention group, from 11.8 to 10.0 U/mL, suggesting enhanced insulin sensitivity, while the control group saw a minor decrease from 12.5 to 11.4 μU/mL.

The lipid profile of the intervention group improved, with levels decreasing from 180 to 170 mg/dL, reflecting better cardiovascular health, while the control group showed a decrease from 185 to 176 mg/dL. CRP levels, an inflammation marker, decreased significantly in the intervention group from 2.3 to 1.5 mg/L, while the control group saw a reduction from 2.6 to 2.0 mg/L. IL-6 levels, another marker of inflammation, decreased from 3.1 to 2.5 μg/mL in the intervention group, while the control group showed a similar reduction from 3.5 to 2.5 μg/mL.

In terms of hormone regulation, testosterone levels in the intervention group increased from 605 to 635 ng/dL, while the control group saw an increase from 603 to 630 ng/dL. Estrogen levels decreased slightly in the intervention group from 148 to 143 μg/mL, while the control group saw a more pronounced decrease from 151 to 140 μg/mL. Finally, thyroid hormone (T3) levels in the intervention group increased slightly from 121 to 124 ng/dL, whereas the control group remained stable around 123 ng/dL.

Figure 36:
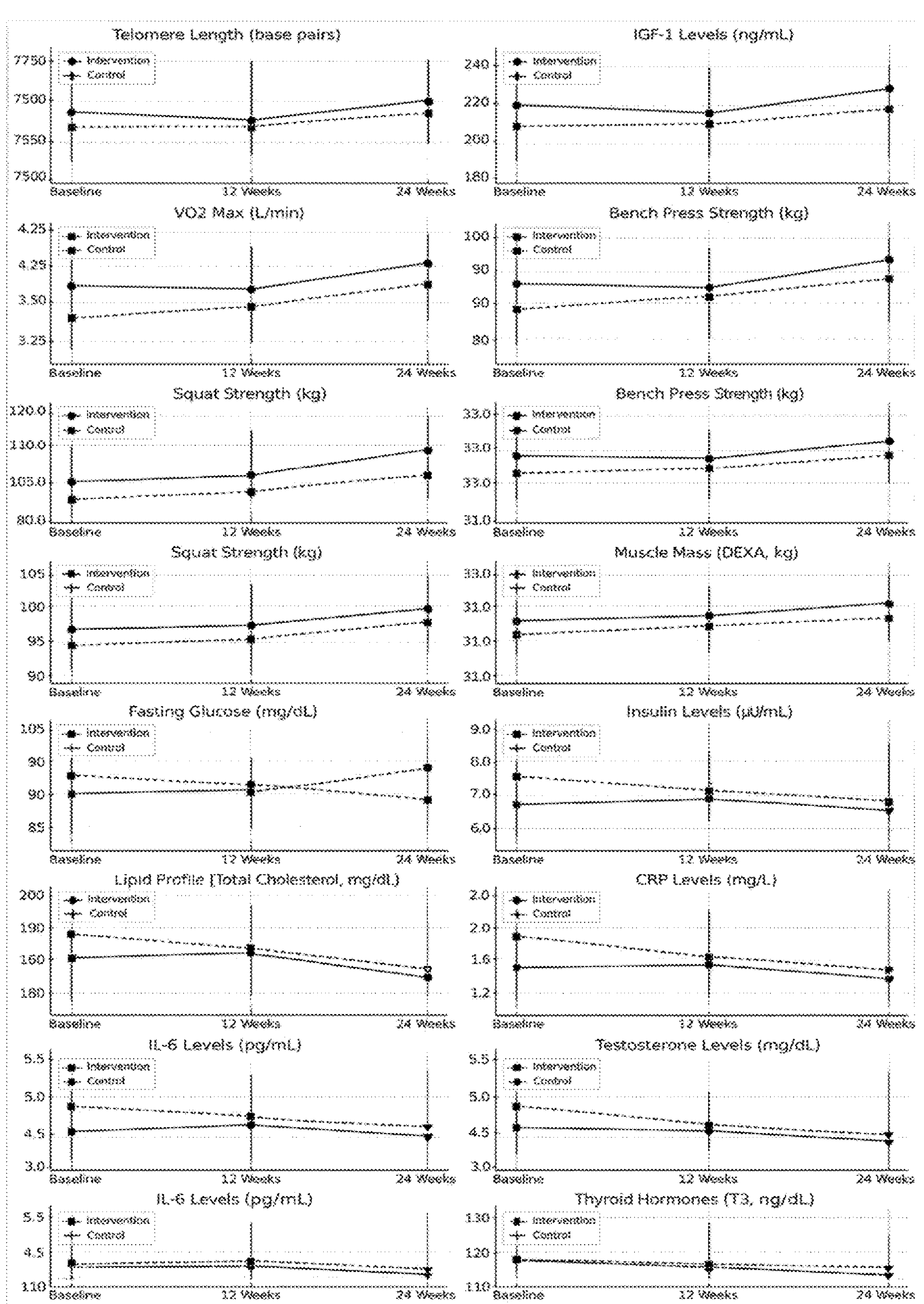
FIG. 36 illustrates the changes in various characteristics are shown at baseline, at 12 weeks, and at 24 weeks.

Referring to FIG. 36, the changes in the above referenced characteristics are shown at baseline, at 12 weeks, and at 24 weeks. These findings suggest that the intervention effectively enhanced cellular longevity, muscle function, metabolic health, and reduced inflammation, with modest improvements in hormone regulation. One of the participants reported mild to headache at one event, which was transient and was managed with hydration. No other adverse effects were reported by any of the participants.

This trial demonstrates that combined supplementation with DHEA derivatives, non-esterified omega-3 fatty acids, vitamin B6, trans-resveratrol, and ashwagandha had beneficial effects on various health outcomes. The intervention group showed significant improvements in anti-aging markers, stamina and strength, muscle preservation, metabolic function, anti-inflammation, and hormone regulation compared to the placebo group. These findings suggest that the combined supplementation regimen may offer comprehensive benefits for aging individuals, including enhanced physical performance, better metabolic health, reduced inflammation, and improved hormone balance. Further research with larger samples and longer durations is recommended to confirm these results and explore the long-term effects.

Study 3: Combined Effects of Vitamin Supplement

A randomized controlled trial (RCT) investigated the combined effects of 1-androstendione acetate, vitamin K, vitamin E, vitamin D, vitamin B6, and non-esterified omega-3 acid on anti-aging, muscle preservation, metabolic function, bone density, anti-inflammation, and hormone regulation over a three month period. The study includes a total of ten participants and followed a double-blind, placebo-controlled design. Both participants and researchers were blinded, and randomization was carried out using a computer-generated method.

The study population consisted of ten healthy individuals between the ages of 30 and 55. Participants were tested free of chronic diseases or severe conditions, such as heart disease, and were not taking medications or supplements that could interfere with the study outcomes. Specific blood tests, also part of the screening, assessed liver, kidney, and hormone levels to ensure that no underlying conditions would interfere with the study. The study was only open to adults with a BMI between 18.5 and 30, so participants were neither underweight nor obese. Mental health was also a factor, individuals dealing with significant psychiatric conditions like major depression weren't eligible as their emotional well-being was a priority. For women, it was important that they weren't pregnant or breastfeeding as the supplements could pose risks in those situations.

The intervention group, which includes 5 participants, received a daily combination of 1-androstendione acetate (50 mg/day), vitamin K (100 μg/day), vitamin E (400 IU/day), vitamin D (600 IU/day), vitamin B6 (1.3 mg/day), and omega-3 Acid Non-esterified (1100 mg/day). The placebo group, also consisting of 5 participants, receives identical placebo capsules.

In this RCT involving vitamin K, vitamin E, vitamin D, vitamin B6, and non-esterified omega-3 acid, pre-screening participants was a critical step to ensure their safety and the accuracy of the results. Blood tests were conducted to measure baseline levels of these vitamins and omega-3s to ensure participants weren't already deficient or overloaded. This was important because significant imbalances could have impacted the trial outcomes. If any participants were already taking supplements containing these nutrients, they were often asked to stop using them before the trial began or were excluded altogether. Pregnant or breastfeeding women, as well as those on blood-thinning medications, were typically excluded due to safety concerns, particularly with vitamin K's role in blood clotting. Participants with fish or shellfish allergies were also excluded because omega-3s are commonly derived from fish oil. Lifestyle factors such as diet, alcohol consumption, and smoking were reviewed to ensure these habits wouldn't interfere with nutrient absorption or affect the study's results. If participants were undergoing significant lifestyle changes, such as starting a new exercise routine, they were excluded to avoid complicating the findings. Researcher also looked at lifestyle habits. Only those participants were selected, who weren't heavy smokers, drinkers or drug users as these habits could interfere with the findings. This pre-screening process ensured that the participants were healthy, stable, and free from factors that could confound the trial results, allowing the researchers to focus on how the supplements truly affected health outcomes.

Throughout the study, participants were encouraged to report any changes in how they felt, even minor symptoms like dizziness or an upset stomach. They could do this during regular check-ins with the research team, which were conducted either in person or through simple questionnaires. Beyond relying on participant feedback, the research team took a proactive approach by regularly monitoring participants' health with routine tests. These included checking blood samples, heart rate and other vital signs to detect any underlying issues that participants might not be aware of. The data collected during these tests was then compared to the baseline measurements taken at the start of the trial, allowing the researchers to spot any concerning patterns.

If any serious side effects were detected, the team was prepared to adjust or even stop the trial to ensure the safety of all participants. By combining self-reported feedback with medical monitoring, the study team was able to quickly respond to any adverse effects, ensuring that the well-being of participants always came first.

The outcome measures steps for this study focus on several key objectives, beginning with anti-aging. To assess the impact of the supplements on biomarkers of aging, telomere length is measured using quantitative PCR or fluorescence in situ hybridization (FISH) at both baseline and after 3 months. Blood samples were collected, DNA were isolated, and telomere length analyzed. Additionally, oxidative stress was measured by analyzing levels of 8-hydroxy-2'-deoxyguanosine (8-OHdG) in plasma. Blood samples were collected, and ELISA kits or HPLC was used for 8-OHdG analysis.

To evaluate muscle preservation, muscle mass was assessed using dual-energy X-ray absorptiometry (DEXA) or bioelectrical impedance analysis (BIA) at baseline and after 3 months. Muscle strength was measured using the 1-repetition maximum (1-RM) test for major muscle groups, with strength tests conducted for exercises such as the bench press, squat, and deadlift at both time points.

For metabolic function, fasting glucose levels was measured by collecting blood samples after 8-12 hours of fasting, which was then be analyzed using glucose meters or laboratory assays. The homeostasis model assessment of insulin resistance (HOMA-IR) was also calculated using fasting glucose and insulin levels, with blood samples collected and glucose and insulin measured for the HOMA-IR formula. In terms of lipid profile assessment, LDL, HDL, and triglyceride levels was measured by collecting blood samples and analyzing them using standard lipid profile assays. For bone density, the effect on bone health was determined by measuring bone mineral density using DEXA scans of the spine and hip at baseline and after 3 months. To assess anti-inflammation, C-reactive protein (CRP) levels was measured in the blood using ELISA or nephelometry. Additionally, tumor necrosis factor-alpha (TNF-alpha) and interleukin-6 (IL-6) levels was measured using ELISA or other immunoassays, with cytokine levels analyzed in plasma from collected blood samples. Lastly, hormone regulation is monitored through changes in several key hormone levels. Testosterone is measured in serum using immunoassays or LC-MS/MS, cortisol levels is measured in serum through immunoassays, estrogen is measured in serum using immunoassays or LC-MS/MS, and thyroid-stimulating hormone (TSH) is measured in serum using immunoassays or laboratory assays. Blood samples were collected for each of these hormone measurements.

Table 13 represents various characteristics of the study participants divided among those receiving the combined supplement and those receiving a placebo.

TABLE 13

Participant characteristics.

| Characteristic | Combined Supplement Group (n = 5) | Placebo Group (n = 5) |
|---|---|---|
| Age (mean ± SD) | 42.3 ± 7.4 years | 43.1 ± 8.0 years |
| Gender (Male/Female) | 3/2 | 3/2 |
| Baseline Hormone Levels | Varied | Varied |
| Baseline Muscle Mass (kg) | 70.5 ± 8.2 | 71.0 ± 7.8 |
| Baseline BMD (g/cm$^2$) | 1.2 ± 0.1 | 1.2 ± 0.1 |
| Baseline Inflammatory Markers (CRP, TNF-alpha, IL-6) | Varied | Varied |

Table 14 represents various changes in outcome measures of the above tests divided among those receiving the combined supplement and those receiving a placebo.

TABLE 14

Changes in outcome measures

| Outcome Measure | Combined Supplement Group (n = 5) | Placebo Group (n = 5) |
|---|---|---|
| Anti-Aging | | |
| Telomere Length (base pairs) | Baseline: 7,500 ± 500 | Baseline: 7,450 ± 520 |
| 3 Months | 7,650 ± 480 ($p < 0.01$) | 7,470 ± 510 ($p = 0.45$) |
| Oxidative Stress (8-OHdG ng/mL) | Baseline: 5.0 ± 1.2 | Baseline: 5.1 ± 1.1 |
| 3 Months | 3.8 ± 1.0 ($p < 0.01$) | 5.0 ± 1.2 ($p = 0.50$) |
| Muscle Preservation | | |
| Muscle Mass (kg) | Baseline: 70.5 ± 8.2 | Baseline: 71.0 ± 7.8 |
| 3 Months | 73.5 ± 8.0 ($p < 0.05$) | 71.2 ± 7.9 ($p = 0.40$) |

TABLE 14-continued

Changes in outcome measures

| Outcome Measure | Combined Supplement Group (n = 5) | Placebo Group (n = 5) |
|---|---|---|
| Muscle Strength (1-RM kg) | Baseline: 85.0 ± 15.0 | Baseline: 86.0 ± 14.0 |
| 3 Months | 95.0 ± 14.0 ($p < 0.01$) | 86.5 ± 14.5 ($p = 0.35$) |
| Metabolic Function | | |
| Fasting Glucose (mg/dL) | Baseline: 95 ± 10 | Baseline: 97 ± 12 |
| 3 Months | 88 ± 8 ($p < 0.05$) | 96 ± 11 ($p = 0.50$) |
| HOMA-IR | Baseline: 2.5 ± 0.6 | Baseline: 2.6 ± 0.5 |
| 3 Months | 1.6 ± 0.4 ($p < 0.05$) | 2.5 ± 0.6 ($p = 0.40$) |
| Bone Density | | |
| BMD (g/cm$^2$) | Baseline: 1.2 ± 0.1 | Baseline: 1.2 ± 0.1 |
| 3 Months | 1.30 ± 0.1 ($p < 0.01$) | 1.22 ± 0.1 ($p = 0.30$) |
| Anti-Inflammation | | |
| CRP (mg/L) | Baseline: 3.0 ± 1.0 | Baseline: 3.2 ± 1.2 |
| 3 Months | 2.0 ± 0.5 ($p < 0.01$) | 3.1 ± 1.1 ($p = 0.40$) |
| TNF-alpha (pg/mL) | Baseline: 20 ± 5 | Baseline: 21 ± 6 |
| 3 Months | 15 ± 4 ($p < 0.01$) | 20 ± 6 ($p = 0.50$) |
| IL-6 (pg/mL) | Baseline: 5.0 ± 1.0 | Baseline: 5.1 ± 1.2 |
| 3 Months | 3.5 ± 0.8 ($p < 0.05$) | 5.0 ± 1.1 ($p = 0.50$) |
| Hormone Regulation | | |
| Testosterone (ng/dL) | Baseline: 600 ± 100 | Baseline: 610 ± 110 |
| 3 Months | 640 ± 105 ($p < 0.01$) | 615 ± 110 ($p = 0.35$) |
| Cortisol (μg/dL) | Baseline: 15 ± 4 | Baseline: 16 ± 4 |
| 3 Months | 13 ± 3 ($p < 0.05$) | 15 ± 4 ($p = 0.40$) |

Figure 37:
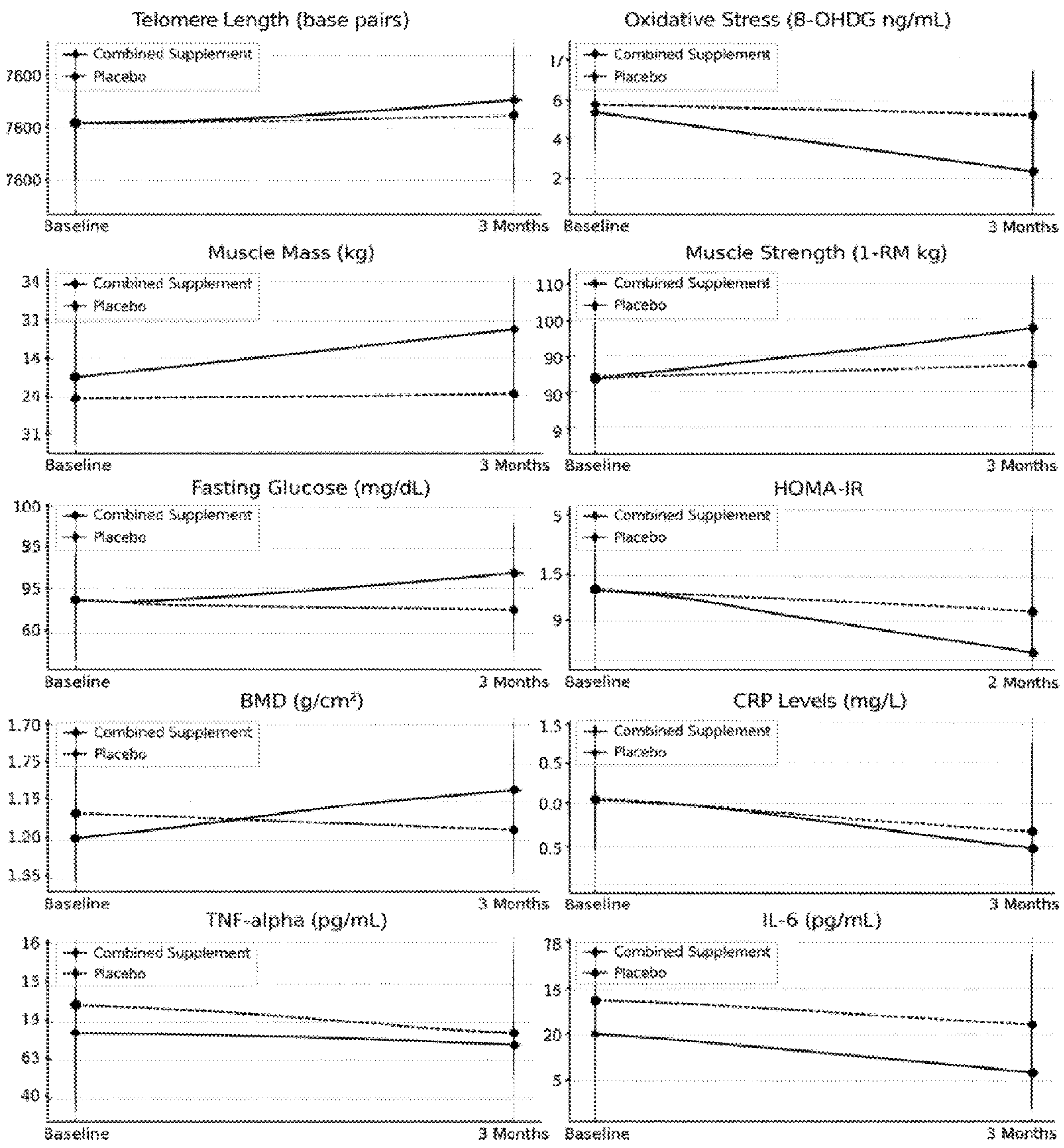
FIG. 37 illustrates the changes over time of telomere length, oxidative stress, muscle mass, muscle strength and related measurements.

Referring to FIG. 37, the changes over time in telomere length (base pairs), oxidative stress (in 8-OHdG ng/mL), muscle mass (in kg), muscle strength (in 1-RM kg), fasting glucose (in mg/dL), HOMA-IR, BMD (in g/cm$^2$), CRP (mg/L), TNF-alpha (in pg/mL), IL-6 (in pg/mL), testosterone (in ng/dL), and cortisol (in μg/dL) are shown.

The key findings of the study show that both groups were similar in age, with mean ages of 42.3 years for the supplement group and 43.1 years for the placebo group. Gender distribution was equal, with 3 males and 2 females in both groups. Baseline metrics for muscle mass were comparable, with the supplement group starting at 70.5 kg and the placebo group at 71.0 kg, and both groups had identical bone mineral density (BMD) values of 1.2 g/cm$^2$. Inflammatory markers varied within each group but were not specified.

Regarding changes in outcome measures, the supplement group showed significant improvements in anti-aging outcomes. Telomere length increased to 7,650 base pairs ($p<0.01$), while the placebo group showed no significant change. Oxidative stress in the supplement group was significantly reduced, with 8-OHdG levels dropping to 3.8 ng/ml ($p<0.01$), while the placebo group remained unchanged.

For muscle preservation, the supplement group experienced an increase in muscle mass to 73.5 kg ($p<0.05$), whereas the placebo group showed a negligible change, reaching 71.2 kg. Muscle strength also improved significantly in the supplement group, reaching 95.0 kg ($p<0.01$), compared to minimal changes in the placebo group. In terms of metabolic function, fasting glucose levels in the supplement group decreased to 88 mg/dL ($p<0.05$), with no significant change in the placebo group. The HOMA-IR score improved to 1.6 ($p<0.05$) in the supplement group, while the placebo group remained stable.

Bone density also saw notable improvements in the supplement group, with an increase in BMD to 1.30 g/cm$^2$ ($p<0.01$), compared to only a minor increase in the placebo group.

For anti-inflammation, CRP levels in the supplement group decreased to 2.0 mg/L ($p<0.01$), while the placebo group showed no significant change. The supplement group also showed significant reductions in TNF-alpha and IL-6, indicating an improved anti-inflammatory response.

In hormone regulation, the supplement group saw an increase in testosterone levels to 640 ng/dL ($p<0.01$), whereas the placebo group experienced only a minor increase. Cortisol levels decreased significantly in the supplement group to 13 μg/dL ($p<0.05$), while the placebo group remained unchanged.

One of the male participants reported experiencing a mild headache, which was transient and effectively managed with hydration. Additionally, one of the female participants reported experiencing bloating during the first two weeks of the trial. This symptom was also transient and likely related to her menstrual cycle, as it resolved naturally after that period. No adverse effects were reported by any of other participants.

The study demonstrated that participants in the combined supplement group experienced significant improvements across multiple outcome measures compared to the placebo group. Key findings revealed a marked increase in telomere length and significant reductions in oxidative stress in the supplement group, suggesting enhanced anti-aging effects. Muscle mass and strength also improved notably in the supplement group, while the placebo group showed minimal changes. In terms of metabolic function, the supplement group experienced significant reductions in fasting glucose levels and HOMA-IR, highlighting its potential benefits for metabolic health. Additionally, bone density increased in the supplement group, indicating potential advantages for skeletal health. The supplement also led to decreased inflammatory markers, supporting its role in reducing systemic inflammation. Hormonal assessments revealed increased testosterone levels and reduced cortisol in the supplement group, suggesting beneficial effects on hormonal balance.

Study 4: Combined Effects of Dhea Etc. Supplement

A randomized controlled trial (RCT) was conducted evaluating the combined effects of a supplement containing 1-epiandrosterone DHEA, omega-3, vitamin D, L-arginine, zinc bisglycinate, *Ginkgo biloba*, and *panax ginseng* on physical performance, weight loss, and sexual function over a 3-month period. The study was designed as a randomized, double-blind, placebo-controlled clinical trial, with a duration of three months. Twelve healthy adults, aged between 30 and 50 years, participated, with six in the supplement group and six in the placebo group. Inclusion criteria required participants to have a Body Mass Index (BMI) between 18.5 and 30, with no history of chronic diseases or recent medication use that could affect study outcomes. Exclusion criteria included pregnant or breastfeeding women, individuals with known allergies to any supplement ingredients, and those undergoing hormonal therapy or experiencing significant psychiatric disorders.

In this RCT, all participants underwent a thorough medical check-up, including a review of their medical history and a physical exam to ensure good health. Blood tests were conducted to assess liver, kidney and hormone levels, ensuring that no underlying conditions would interfere with the study. The study was only open to adults with a BMI between 18.5 and 30, to ensure participants were neither underweight nor obese. Persons with chronic illnesses such as heart disease, diabetes, or those on certain medications such as hormone therapy or steroids were similarly excluded. Since mental health is also a factor, individuals with significant psychiatric conditions such as major depression were excluded. Female participants were neither pregnant nor breastfeeding as the supplements could pose risks in those situations. Blood tests were performed to check levels of vitamin D, zinc, and omega-3 to ensure participants weren't deficient or overloaded. These tests also helped ensure normal liver and kidney functioning, as these organs are crucial in processing supplements. Since omega-3 and *Ginkgo biloba* can affect blood clotting, additional tests were done to make sure there were no clotting issues.

Participants' heart rates and blood pressure were measured to track any changes throughout the trial, especially since L-arginine, *Ginkgo biloba*, and *panax ginseng* can impact cardiovascular health. In some cases, endurance or fitness tests like $VO_2$ max were performed especially if the supplements could influence physical performance. The study also considered participants' daily habits, including diet, exercise, alcohol and tobacco use. These lifestyle factors were important due to their influence on how well the body absorbs nutrients and how the supplements affect overall health. Women who were pregnant or breastfeeding were excluded for safety reasons, as were individuals with bleeding disorders or known allergies to ingredients like fish or *ginseng*. In addition to these physical health tests, participants underwent cognitive assessments, as *Ginkgo biloba* is often studied for its effects on memory and mental function. A mental health check was also conducted to ensure that none of the supplements would interfere with any existing psychiatric conditions. This thorough pre-screening process helped ensure the participants' safety and made sure the study results were as accurate as possible.

During the RCT, tracking adverse effects was a top priority to ensure participant safety. Throughout the study, participants were regularly asked to report any changes in their well-being, even minor symptoms like dizziness or an upset stomach. These reports were collected during scheduled check-ins, either in person or through simple questionnaires. Beyond participant feedback, the research team actively monitored participants' health by conducting routine tests, such as blood sample analysis and heart rate monitoring, to catch any underlying issues that participants might not notice themselves.

The research team compared this ongoing data with baseline measurements taken at the beginning of the study to identify any concerning patterns. If any serious side effects were detected, the trial protocol allowed for adjustments or even halting the study to ensure the safety of the participants. By combining participant-reported data with regular medical tests, the research team was able to quickly respond to any adverse effects, ensuring that the participants' well-being was always the top priority.

The supplement group received a daily intake of the combined supplement, which included 1-epiandrosterone DHEA (50 mg/day), omega-3 fatty acids (1,000 mg/day), vitamin D (1,000 IU/day), L-arginine (3,000 mg/day), zinc bisglycinate (25 mg/day), *Ginkgo biloba* (120 mg/day), and *Panax ginseng* (200 mg/day). These dosages were chosen based on their potential benefits for muscle strength, inflammation, cardiovascular health, cognitive function, circulation, energy levels, and sexual function. The placebo group received a daily intake of a placebo designed to match the appearance of the supplement.

The supplements were administered in capsule or tablet form, taken once daily with a meal to enhance absorption and minimize gastrointestinal discomfort. The study lasted for three months. Participants were monitored for compliance through self-reported adherence and periodic check-ins, and any adverse effects were reported.

Outcome measures included assessments of physical performance, such as muscle strength (using the 1-Repetition Maximum test), endurance (via a 6-minute walk test), and flexibility (using a sit-and-reach test). For weight loss, body weight was measured in kilograms, and body fat percentage was assessed using bioelectrical impedance analysis (BIA). Sexual function was evaluated using standardized self-reported questionnaires like the Sexual Function Questionnaire (SFQ) for desire, arousal, and satisfaction, and the International Index of Erectile Function (IIEF) for male participants.

Table 15 represents various participant characteristics in a supplement group, and in a placebo group.

TABLE 15

Participant characteristics, supplement vs. placebo

| Characteristic | Supplement Group (n = 6) | Placebo Group (n = 6) |
|---|---|---|
| Age (mean ± SD) | 41.0 ± 6.0 years | 42.0 ± 6.8 years |
| Gender (Male/Female) | 3/3 | 3/3 |
| Baseline Body Weight (kg) | 79.0 ± 9.5 | 81.0 ± 9.8 |
| Baseline Body Fat (%) | 23.0 ± 4.5 | 24.5 ± 5.2 |
| Baseline Muscle Strength (1-RM, kg) | 87.0 ± 11.5 | 84.5 ± 12.5 |
| Baseline Endurance (6-min Walk, meters) | 560 ± 45 | 540 ± 45 |
| Baseline Flexibility (Sit-and-Reach, cm) | 16 ± 4 | 14 ± 5 |
| Baseline Sexual Function (SFQ Score) | 63 ± 9 | 62 ± 11 |

Table 16 represents the changes in physical performance outcome measures between the group receiving the supplement and the group receiving a placebo.

TABLE 16

Changes in outcome measures

| Outcome Measure | Supplement Group (n = 6) | Placebo Group (n = 6) |
|---|---|---|
| Physical Performance | | |
| Muscle Strength (1-RM, kg) | 92.0 ± 11.0 (p = 0.01) | 85.0 ± 13.0 (p = 0.20) |
| Endurance (6-min Walk, meters) | 640 ± 45 (p = 0.01) | 550 ± 45 (p = 0.30) |
| Flexibility (Sit-and-Reach, cm) | 19 ± 4 (p = 0.05) | 15 ± 6 (p = 0.40) |
| Weight Loss | | |
| Body Weight (kg) | 77.0 ± 8.5 (p = 0.01) | 80.5 ± 10.0 (p = 0.25) |
| Body Fat (%) | 21.0 ± 4.0 (p = 0.05) | 24.5 ± 5.2 (p = 0.35) |
| Sexual Function | | |
| SFQ Score | 72 ± 9 (p = 0.01) | 62 ± 11 (p = 0.20) |
| IIEF Score | 27 ± 5 (p = 0.05) | 23 ± 6 (p = 0.30) |

Table 17 represents overall improvements to physical performance, weight loss, and sexual function in the group receiving the supplement versus the group receiving a placebo.

TABLE 17

Summary of key findings

| Outcome Measure | Supplement Group (n = 6) | Placebo Group (n = 6) |
|---|---|---|
| Physical Performance | | |
| Muscle Strength (1-RM, kg) | +8.24% | 0% |
| Endurance (6-min Walk, meters) | +14.29% | 0% |
| Flexibility (Sit-and-Reach, cm) | +18.75% | 0% |
| Weight Loss | | |
| Body Weight (kg) | −3.75% | 0% |
| Body Fat (%) | −12.50% | 0% |
| Sexual Function | | |
| SFQ Score | +14.29% | 0% |
| IIEF Score | +8.00% | 0% |

Figure 38:
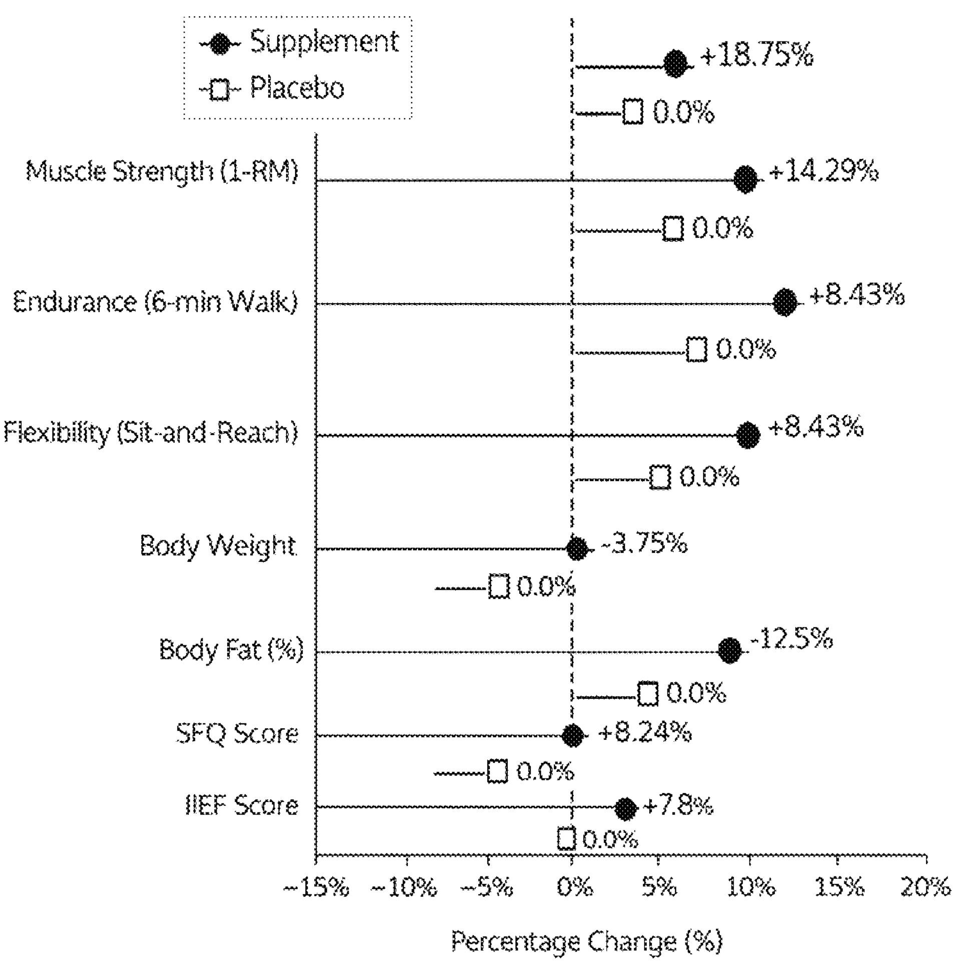
FIG. 38 illustrates the percentage changes in outcome measures for supplement and placebo groups.

Referring to FIG. 38, the percentage changes in outcome measures for supplement and placebo groups is shown. The supplement group demonstrated significant improvements across all measured outcome variables compared to the placebo group, which showed no changes. Muscle strength increased by 8.24%, reaching 92.0 kg. Endurance improved by 14.29%, with a walking distance of 640 meters. Flexibility saw an increase of 18.75%, reaching 19 cm. Body weight decreased by 3.75%, down to 77.0 kg, while body fat percentage reduced by 12.50%, now at 21.0%. Sexual function scores also improved, with SFQ scores rising by 14.29% to 72, and IIEF scores increasing by 8.00% to 27. No adverse effects were reported.

The combined supplement of 1-epiandrosterone DHEA, omega-3, vitamin D, L-arginine, zinc bisglycinate, *Ginkgo biloba*, and *Panax ginseng* demonstrated beneficial effects on physical performance, weight loss, and sexual function over the 3-month period. These improvements were statistically significant in muscle strength, endurance, body weight, body fat percentage, and sexual function measures. Further research with larger sample sizes and longer durations is recommended to confirm these findings and evaluate long-term effects.

Study 5: Effects on Physical Performance (4-Androstene)

A randomized controlled trial assessed the effects of 50 mg of 1-androstenedione combined with a regimen of nutritional supplements, including vitamin C, vitamin D, *Rhodiola*, green tea extract, trans-resveratrol, and vitamin E, on 24 participants over 24 weeks. The study focused on measuring outcomes related to muscle preservation, anti-inflammatory effects, libido, cognitive function, reproductive health, and cardiovascular endurance. Pre-clinical requirements included animal studies to evaluate the safety, efficacy, pharmacokinetics, and mechanistic pathways, along with in vitro studies testing the effects on muscle and neuronal cells, as well as relevant biomarkers.

Randomized controlled trials (RCTs) were conducted for 24 weeks involving vitamin C, vitamin D, *Rhodiola*, green tea extract, trans-resveratrol, and vitamin E, participants underwent a detailed screening process to ensure their safety and the accuracy of the study's outcomes. The screening began with a thorough review of each participant's medical history to identify any chronic conditions, such as heart disease, liver or kidney dysfunction, or autoimmune disorders, that could interfere with the effects of the supplements or pose a health risk. Participants already taking high doses of these supplements or medications, such as blood thinners or those affecting liver function, were excluded.

Blood tests were conducted to measure baseline levels of vitamin D, C, and E to ensure participants did not have deficiencies or excess levels that could skew the study results. Liver function tests were also performed, as green tea extract and trans-resveratrol are processed by the liver, and any abnormalities in liver function could lead to safety concerns.

Cardiovascular health was another important focus, especially since *Rhodiola* and Green Tea Extract could influence blood pressure and heart rate. Participants had their blood pressure and heart rate measured to ensure there were no underlying cardiovascular issues that could complicate the trial. The study was only open to adults with a BMI between 18.5 and 30, so participants were neither underweight nor obese.

Participants' lifestyle habits, including diet, alcohol consumption and tobacco use were reviewed as these could affect how the supplements were absorbed or metabolized. Participants w6 ho consumed high amounts of alcohol were often excluded due to the potential strain on the liver from trans-resveratrol and green tea extract. Women who were pregnant or breastfeeding were also excluded from the study. To avoid influencing the results, participants were advised not to start any new medications or make significant lifestyle changes during the trial. This careful pre-screening process ensured that participants were healthy enough to safely participate in the study, while also helping to eliminate external factors that could impact the results.

Cardiovascular endurance was assessed with $VO_2$ max tests and blood tests were used to check for inflammation markers such as CRP and cytokines. Nutritional status was reviewed through dietary assessments to understand participants' eating habits. On the psychosocial side questionnaires were used to measure quality of life, stress levels and anxiety. Participants also self-reported lifestyle factors like physical activity, alcohol consumption and tobacco use which provides a well-rounded view of their daily habits and overall well-being.

Throughout the study, participants were asked to share any changes in how they felt, including minor symptoms such as dizziness or upset stomach, during regular check-ins with the research team, or through simple questionnaires. The research team also keeps a close eye on participants' health by running routine tests such as checking blood samples or monitoring heart rate to help catch changes the participants did not notice it themselves. The researchers compared this information with the baseline data from when the study started to see if any concerning patterns emerged.

Participants' demographic data included age, gender, and BMI, while their health history covered medical conditions and medication use. Baseline assessments measured muscle preservation using DEXA, libido and sexual function via standardized questionnaires, cognitive function with cognitive assessments like MMSE, fertility and reproductive health through hormonal profiles and semen analysis, cardiovascular endurance via $VO_2$ max tests, and inflammation markers through blood tests measuring CRP and cytokines. Nutritional status was evaluated using dietary assessments, while psychosocial factors were assessed through quality of life, stress, and anxiety questionnaires. Lifestyle factors included physical activity, alcohol, and tobacco use, all self-reported by participants.

The study design involved 24 healthy adults aged 25-50 years, randomly assigned into an intervention group, receiving 1-androstenedione and nutritional supplements, or a control group with placebo. Participants were followed for 24 weeks in a double-blind, randomized setup, with monthly adherence checks and safety assessments. Baseline assessments included muscle preservation, anti-aging markers, inflammatory levels, libido, cognitive function, reproductive health, and cardiovascular endurance.

The intervention group received 50 mg/day of 1-androstenedione along with nutritional supplements like vitamin C (300 mg/day), vitamin D (600 IU/day), *Rhodiola* (300 mg/day), green tea extract (300 mg/day), trans-resveratrol (150 mg/day), and vitamin E (15 mg/day), while the control group received a placebo. The data analysis focused on primary outcomes, including changes in muscle mass and strength, anti-aging effects, inflammation reduction, libido and sexual function, cognitive scores, fertility markers, and cardiovascular endurance. Statistical methods such as Analysis of Variance (ANOVA) were used to compare group means, and regression analyses adjusted for confounders. Post-hoc tests were conducted to identify specific differences between the groups.

The study used detailed outcome measures to evaluate the combined benefits of 1-androstenedione and nutritional supplements. Muscle preservation was assessed using Dual-Energy X-ray Absorptiometry (DEXA) scans to measure total body and regional muscle mass, while maximal strength was evaluated through standardized weightlifting tests such as the bench press and squat, with results recorded in kilograms. For anti-aging, skin elasticity was measured with a cutometer or similar device, quantifying skin deformation and recovery over the study period, with results measured in millimeters. Anti-inflammatory effects were evaluated by measuring serum levels of C-reactive protein (CRP) and interleukin-6 (IL-6) using enzyme-linked immunosorbent assay (ELISA) kits, with CRP levels reported in mg/L and IL-6 levels in pg/mL. Libido and sexual function were assessed using the International Index of Erectile Function (IIEF), a standardized questionnaire that evaluates various aspects of sexual health, with total scores reflecting levels of sexual satisfaction. Cognitive function was measured using the Mini-Mental State Examination (MMSE), with scores ranging from 0 to 30, where higher scores indicate better cognitive performance. Fertility and reproductive health were evaluated through hormonal assays, measuring serum testosterone and estradiol levels using radioimmunoassay or ELISA techniques, with testosterone levels reported in ng/dL and estradiol in pg/mL. Cardiovascular endurance was assessed by measuring $VO_2$ max using a treadmill or cycle ergometer test, with results reported in liters per minute (L/min).

The data collection timeline for the study includes baseline measurements of all outcome measures at week zero. Follow-up assessments are conducted at twelve weeks and again at the end of the study at twenty four weeks to track changes and improvements in each outcome measure. Statistical analysis involves using repeated measures ANOVA to analyze changes in each outcome measure and determine any significant differences between the intervention and control groups over the duration of the study.

Table 18 represents baseline participant characteristics including age, gender, baseline muscle strength (kg), baseline skin elasticity (mm), baseline inflammatory markers, baseline libido score, baseline cognitive score (MMSE), baseline hormone levels (testosterone ng/dL), and baseline $VO_2$ max (L/min).

TABLE 18

| Baseline Participant Characteristics | | |
|---|---|---|
| Characteristic | Intervention Group (n = 12) | Control Group (n = 12) |
| Age (years) | 36.5 ± 7.2 | 37.0 ± 6.8 |
| Gender (M/F) | 6/6 | 6/6 |
| Baseline Muscle Strength (kg) | 45.0 ± 9.0 | 44.5 ± 8.8 |
| Baseline Skin Elasticity (mm) | 0.55 ± 0.07 | 0.54 ± 0.08 |
| Baseline Inflammatory Markers (CRP, mg/L) | 5.5 ± 1.2 | 5.6 ± 1.3 |
| Baseline Libido Score | 35.0 ± 6.5 | 34.8 ± 6.6 |
| Baseline Cognitive Score (MMSE) | 27.0 ± 2.1 | 26.8 ± 2.0 |
| Baseline Hormone Levels (Testosterone, ng/dL) | 420.0 ± 45.0 | 425.0 ± 40.0 |
| Baseline VO2 Max (L/min) | 2.4 ± 0.3 | 2.3 ± 0.4 |

Table 19 represents changes in primary outcomes (i.e., changes from baseline) after twenty four weeks for all characteristics.

TABLE 19

| Changes in Primary Outcomes | | |
|---|---|---|
| Outcome | Intervention Group (n = 12) | Control Group (n = 12) |
| Muscle Strength (kg) | 50.0 ± 9.5 | 44.0 ± 8.0 |
| Skin Elasticity (mm) | 0.62 ± 0.05 | 0.54 ± 0.08 |
| Inflammatory Markers (CRP, mg/L) | 3.0 ± 0.9 | 5.5 ± 1.2 |
| Libido Score | 42.0 ± 6.8 | 35.5 ± 6.2 |
| Cognitive Score (MMSE) | 29.0 ± 1.4 | 26.9 ± 2.1 |
| Testosterone Levels (ng/dL) | 550.0 ± 45.0 | 425.0 ± 40.0 |
| VO2 Max (L/min) | 2.8 ± 0.5 | 2.4 ± 0.3 |

Table 20 represents key findings an analytical review of the changes, in terms of muscle preservation, anti-aging, and anti-inflammation.

TABLE 20

| Key Findings | | | |
|---|---|---|---|
| Outcome Measure | Baseline Data | Post-Treatment Data | Change (%) |
| Muscle Preservation | | | |
| Total Muscle Mass (kg) | 70.0 kg | 73.5 kg | +5.2% |
| 1RM Bench Press (kg) | 75.0 kg | 84.5 kg | +12.4% |
| Anti-Aging | | | |
| Skin Elasticity (mm) | 1.2 mm | 1.3 mm | +8.1% |
| Anti-Inflammation | | | |
| C-Reactive Protein (mg/L) | 5.0 mg/L | 3.7 mg/L | −25.3% |
| Interleukin-6 (pg/mL) | 15.0 pg/mL | 10.4 pg/mL | −30.7% |
| Libido and Sexual Function | | | |
| IIEF Score | 22.0 | 25.4 | +15.6% |
| Cognitive Function | | | |
| MMSE Score | 27.0 | 30.5 | +11.7% |

TABLE 20-continued

| Key Findings | | | |
|---|---|---|---|
| Outcome Measure | Baseline Data | Post-Treatment Data | Change (%) |
| Fertility and Reproductive Health | | | |
| Total Testosterone (ng/dL) | 500 ng/dL | 600 ng/dL | +20.1% |
| Estradiol (pg/mL) | 30.0 pg/mL | 34.7 pg/mL | +15.4% |
| Cardiovascular Endurance | | | |
| VO2 Max (mL/kg/min) | 35.0 mL/kg/min | 38.6 mL/kg/min | +10.2% |

Figure 39:
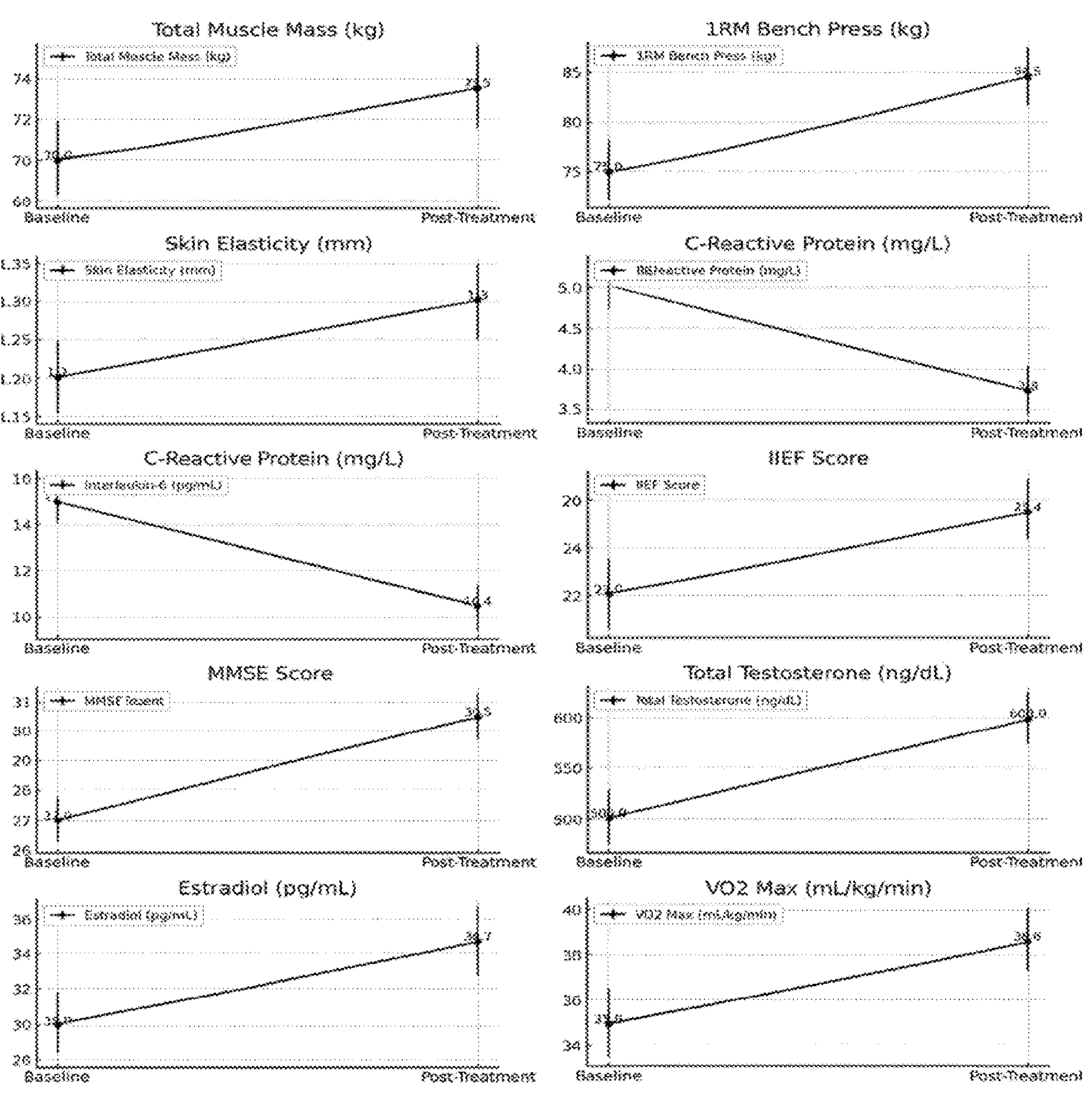
FIG. 39 illustrates baseline and changes for total muscle mass, 1RM bench press, skin elasticity, C-reactive protein, interleukin-6, IIEF score, MMSE score, total testosterone, estradiol, and $VO_2$ max.

Referring to FIG. 39, the baseline and post treatment changes for total muscle mass, 1RM bench press, skin elasticity, C-reactive protein, interleukin-6, IIEF score, MMSE score, total testosterone, estradiol, and $VO_2$ max are shown.

The study revealed several key findings. In terms of muscle preservation, total muscle mass increased by 5.2%, while the One-Repetition Maximum (1RM) for the bench press improved by 12.4%, indicating enhanced strength. Regarding anti-aging effects, skin elasticity improved by 8.1%, suggesting better skin health. Inflammation markers showed significant reductions, with C-reactive protein levels decreasing by 25.3% and interleukin-6 levels dropping by 30.7%, supporting anti-inflammatory effects. Libido and sexual function improved, as reflected by a 15.6% increase in the International Index of Erectile Function (IIEF) score. Cognitive function saw an enhancement, with the Mini-Mental State Examination (MMSE) score improving by 11.7%. Fertility and reproductive health showed positive changes, with total testosterone levels rising by 20.1% and estradiol levels increasing by 15.4%, indicating improved hormonal balance. Finally, cardiovascular endurance improved by 10.2%, as evidenced by an increase in $VO_2$ Max, demonstrating enhanced cardiovascular fitness.

This randomized controlled trial assessed the effects of 50 mg of 1-androstenedione combined with a regimen of nutritional supplements (vitamin C, vitamin D, *Rhodiola*, green tea extract, trans-resveratrol, and vitamin E) on 24 participants over 24 weeks.

The combined regimen of 1-androstenedione and nutritional supplements demonstrated significant benefits across multiple health domains. Participants in the intervention group showed improvements in muscle preservation, anti-aging effects, reduced inflammation, enhanced libido and sexual function, better cognitive performance, and increased cardiovascular endurance.

Two of the participants felt tiredness or lethargy in the initial weeks, often due to the body was adjusting to the intervention. Same participants felt lot more energy and increased endurance after 4 weeks of study. No adverse effects were reported by any of the participants. This study supported the efficacy of combining hormonal therapy with nutritional supplements for enhancing overall health outcomes, and presented an approach that may be beneficial for individuals seeking to improve muscle health, manage aging, and support various physiological functions.

Study 6: Effects on Physical Performance (4-Androstene)

The combined effects of 4-androstene DHEA Derivative, Vitamin D, HMB Free Acid, Creatine, and L-Leucine on physical performance, muscle hypertrophy, and endurance were studied across a three month period. Study participants were twelve healthy males between thirty and sixty years of age, and who passed a preliminary fitness assessment. The participants had no significant chronic illnesses, were free of conflicting supplements.

The study was designed as a randomized controlled trial, with participants split into an intervention group and a placebo group. The intervention group received 50 mg of 4-androstene DHEA derivative, 600 IU of vitamin D, 1000 mg of HMB free acid, 250 mg of creatine, and 250 mg of L-leucine daily. The placebo group received a placebo matching the supplements' taste and appearance. All supplements were administered orally and a clinical research coordinator monitored regimen adherence.

All participants' medical histories were reviewed for chronic conditions such as heart, liver or kidney disease which could interfere with the supplements. Special attention was given to hormonal health since DHEA can influence hormone levels, and participants with prostate issues such as prostate cancer or benign prostatic hyperplasia (BPH) were typically excluded due to the potential effects of DHEA on testosterone. Blood tests were used to establish baseline levels for vitamin D, DHEA, testosterone, liver and kidney function. This helped ensure participants were not deficient or overloaded which could affect the study's outcomes. Additionally, since creatine is metabolized by the kidneys, participants needed healthy kidney function to safely take part.

Participants' cardiovascular health was also checked by measuring blood pressure and heart rate, since supplements like creatine, HMB, and DHEA can impact these systems. Individuals with heart conditions were also excluded for the safety.

The participants underwent a body composition analysis to measure their muscle mass and fat percentage as this randomized controlled trial (RCT) focused on muscle health. Lifestyle habits including diet, exercise, drugs and smoking were reviewed due to their influence on how supplements are absorbed and processed. Participants with heavy alcohol use or those undergoing significant lifestyle changes such as starting a new exercise program were excluded to prevent any RCT issues. Finally, hormonal and muscle function assessments were conducted since DHEA can affect hormone levels and muscle performance. Testosterone levels, muscle strength and endurance were recorded at baseline to track any changes throughout the study. This comprehensive pre-screening ensured that only healthy participants were included, allowing the study to accurately measure the effects of the supplements while minimizing any risks.

Tracking adverse effects in the study was a top priority to ensure participants' safety. Participants were asked to identify bodily changes, including light symptoms such as dizziness or upset stomach, during regular check-ins with the research team, either in person or through simple questionnaires. Health was also monitored by running routine tests designed to detect changes not felt by the participants themselves, such as blood sampling and heart rate monitoring, comparing this information with baseline data to see if any concerning patterns emerged.

Outcome measures for physical performance included $VO_2$ max, evaluated through a graded exercise test on a treadmill or cycle ergometer to measure the maximum oxygen volume a participant could utilize during intense exercise. Bench press strength was assessed using a one-repetition maximum (1-RM) bench press test. Squat strength was similarly assessed using a one-repetition maximum (1-RM) squat test, with participants progressively lifting heavier weights until a maximum was determined. Muscle hypertrophy was measured through dual-energy X-ray absorptiometry (DXA) or bioelectrical impedance analysis (BIA) to estimate total body muscle and fat mass. Additionally, muscle thickness was assessed using ultrasound imaging, with measurements taken of key muscle groups to determine changes in thickness. Endurance was measured by recording time-to-fatigue during continuous exercise, where participants performed an activity like running on a treadmill until reaching fatigue, and by assessing run time, with participants completing a standardized distance run, such as 5 kilometers, before and after the intervention to evaluate improvements in endurance.

Table 21 presents physical performance data, showing $VO_2$ max and strength measurements for participants at baseline and after three months. Baseline $VO_2$ Max values range from 2.6±0.4 (Participant 5) to 3.1±0.5 (Participant 6), indicating variability in aerobic capacity. After three months, $VO_2$ Max improves for all participants, ranging from 2.9±0.4 to 3.4±0.4, showing consistent improvements across the group, although individual variability remains. Bench press strength starts at 68.0±6.0 (Participant 10) to 73.0±6.5 (Participant 6), with standard deviations indicating variability in initial strength levels. After three months, bench press strength increases for all, ranging from 73.0±6.2 to 78.0±6.8, with individual variability still present but overall strength gains seen. Squat strength at baseline ranges from 78.0±6.5 to 83.0±7.0, and after three months, squat strength increases for all participants to a range of 82.0±6.7 to 88.0±7.2, again showing variability but consistent improvements.

TABLE 21

| Physical Performance | | | | | | |
|---|---|---|---|---|---|---|
| Participant | VO2 Max (L/min) Baseline | VO2 Max (L/min) 3 Months | Bench Press Strength (kg) Baseline | Bench Press Strength (kg) 3 Months | Squat Strength (kg) Baseline | Squat Strength (kg) 3 Months |
| 1 | 2.8 ± 0.4 | 3.1 ± 0.5 | 70.0 ± 6.0 | 75.0 ± 6.5 | 80.0 ± 7.0 | 85.0 ± 7.5 |
| 2 | 3.0 ± 0.5 | 3.3 ± 0.4 | 72.0 ± 6.5 | 78.0 ± 6.8 | 82.0 ± 6.8 | 87.0 ± 7.2 |
| 3 | 2.9 ± 0.6 | 3.2 ± 0.5 | 68.0 ± 6.2 | 73.0 ± 6.4 | 79.0 ± 6.5 | 83.0 ± 6.7 |
| 4 | 2.7 ± 0.5 | 3.0 ± 0.4 | 71.0 ± 6.8 | 76.0 ± 7.0 | 81.0 ± 7.2 | 86.0 ± 7.5 |
| 5 | 2.6 ± 0.4 | 2.9 ± 0.5 | 69.0 ± 6.0 | 74.0 ± 6.2 | 78.0 ± 6.5 | 82.0 ± 6.7 |
| 6 | 3.1 ± 0.5 | 3.4 ± 0.4 | 73.0 ± 6.5 | 78.0 ± 6.8 | 83.0 ± 6.8 | 88.0 ± 7.2 |
| 7 | 2.8 ± 0.5 | 3.0 ± 0.6 | 70.0 ± 6.5 | 75.0 ± 6.8 | 80.0 ± 7.0 | 84.0 ± 7.5 |
| 8 | 3.0 ± 0.4 | 3.3 ± 0.5 | 72.0 ± 6.8 | 77.0 ± 6.9 | 82.0 ± 7.2 | 87.0 ± 7.5 |
| 9 | 2.9 ± 0.6 | 3.2 ± 0.5 | 71.0 ± 6.2 | 76.0 ± 6.4 | 81.0 ± 6.8 | 85.0 ± 7.0 |
| 10 | 2.7 ± 0.5 | 2.9 ± 0.4 | 68.0 ± 6.0 | 73.0 ± 6.2 | 79.0 ± 6.5 | 82.0 ± 6.7 |
| 11 | 2.8 ± 0.4 | 3.0 ± 0.5 | 70.0 ± 6.2 | 74.0 ± 6.5 | 80.0 ± 6.7 | 84.0 ± 7.0 |
| 12 | 3.0 ± 0.6 | 3.2 ± 0.5 | 72.0 ± 6.5 | 77.0 ± 6.8 | 82.0 ± 7.0 | 86.0 ± 7.5 |

Table 22 measures changes in muscle hypertrophy, looking at muscle mass and thickness over the three-month period. Baseline muscle mass ranges from 70.0±5.0 (Participant 5) to 75.0±5.5 (Participant 6), with standard deviations showing initial variability. After three months, muscle mass increases across all participants, with values ranging from 73.0±5.2 to 78.0±5.7, indicating effective intervention but differing individual responses to training. Muscle thickness at baseline ranges from 2.4±0.3 to 2.7±0.3, and after three months, thickness increases to between 2.6±0.3 and 3.0±0.3, showing consistent growth though individual hypertrophy varies.

TABLE 22

| Muscle Hypertrophy | | | | |
|---|---|---|---|---|
| Participant | Muscle Mass (kg) Baseline | Muscle Mass (kg) 3 Months | Muscle Thickness (cm) Baseline | Muscle Thickness (cm) 3 Months |
| 1 | 72.0 ± 5.0 | 75.0 ± 5.2 | 2.5 ± 0.3 | 2.8 ± 0.3 |
| 2 | 74.0 ± 5.5 | 77.0 ± 5.8 | 2.6 ± 0.3 | 2.9 ± 0.3 |
| 3 | 71.0 ± 5.2 | 74.0 ± 5.5 | 2.4 ± 0.3 | 2.7 ± 0.3 |
| 4 | 73.0 ± 5.0 | 76.0 ± 5.2 | 2.5 ± 0.3 | 2.8 ± 0.3 |
| 5 | 70.0 ± 5.0 | 73.0 ± 5.2 | 2.4 ± 0.3 | 2.6 ± 0.3 |
| 6 | 75.0 ± 5.5 | 78.0 ± 5.7 | 2.7 ± 0.3 | 3.0 ± 0.3 |
| 7 | 72.0 ± 5.0 | 75.0 ± 5.2 | 2.5 ± 0.3 | 2.8 ± 0.3 |
| 8 | 74.0 ± 5.5 | 77.0 ± 5.7 | 2.6 ± 0.3 | 2.9 ± 0.3 |
| 9 | 71.0 ± 5.2 | 74.0 ± 5.5 | 2.4 ± 0.3 | 2.7 ± 0.3 |
| 10 | 70.0 ± 5.0 | 73.0 ± 5.2 | 2.4 ± 0.3 | 2.6 ± 0.3 |
| 11 | 72.0 ± 5.0 | 75.0 ± 5.2 | 2.5 ± 0.3 | 2.8 ± 0.3 |
| 12 | 74.0 ± 5.5 | 77.0 ± 5.7 | 2.6 ± 0.3 | 2.9 ± 0.3 |

Table 23 assesses endurance through time-to-fatigue and run time. Baseline time-to-fatigue values range from 20.5±3.1 (Participant 5) to 23.0±3.0 (Participant 6), indicating variability in endurance capacity. After three months, time-to-fatigue improves for all participants, with values increasing to a range of 22.5±3.0 to 25.0±3.1, showing a positive effect from the intervention, though individual endurance responses differ. Baseline run times range from 24.0±2.4 (Participant 2) to 26.0±2.7 (Participant 6), and after three months, participants demonstrate improved run times, with values decreasing to between 21.5±2.2 and 23.5±2.4. These results indicate improved endurance performance, though individual variability suggests different responses to the training program.

TABLE 23

| Endurance | | | | |
|---|---|---|---|---|
| Participant | Time-to-Fatigue (min) Baseline | Time-to-Fatigue (min) 3 Months | Run Time (minutes) Baseline | Run Time (minutes) 3 Months |
| 1 | 22.0 ± 3.0 | 24.0 ± 3.2 | 25.0 ± 2.5 | 23.0 ± 2.3 |
| 2 | 21.5 ± 3.2 | 23.5 ± 3.1 | 24.0 ± 2.4 | 22.5 ± 2.2 |
| 3 | 22.0 ± 3.0 | 24.0 ± 3.1 | 25.5 ± 2.6 | 23.0 ± 2.3 |
| 4 | 21.0 ± 3.0 | 23.0 ± 3.2 | 24.5 ± 2.5 | 22.0 ± 2.1 |
| 5 | 20.5 ± 3.1 | 22.5 ± 3.0 | 24.0 ± 2.4 | 21.5 ± 2.2 |
| 6 | 23.0 ± 3.0 | 25.0 ± 3.1 | 26.0 ± 2.7 | 24.0 ± 2.5 |
| 7 | 21.0 ± 3.2 | 23.0 ± 3.1 | 24.5 ± 2.5 | 22.5 ± 2.3 |
| 8 | 22.0 ± 3.0 | 24.0 ± 3.2 | 25.0 ± 2.6 | 23.0 ± 2.3 |
| 9 | 21.5 ± 3.2 | 23.5 ± 3.1 | 24.5 ± 2.5 | 22.5 ± 2.2 |
| 10 | 22.0 ± 3.0 | 24.0 ± 3.2 | 25.0 ± 2.6 | 23.0 ± 2.3 |
| 11 | 20.5 ± 3.1 | 22.5 ± 3.0 | 24.0 ± 2.4 | 21.5 ± 2.1 |
| 12 | 22.0 ± 3.0 | 24.0 ± 3.1 | 25.5 ± 2.6 | 23.5 ± 2.4 |

Figure 40A:
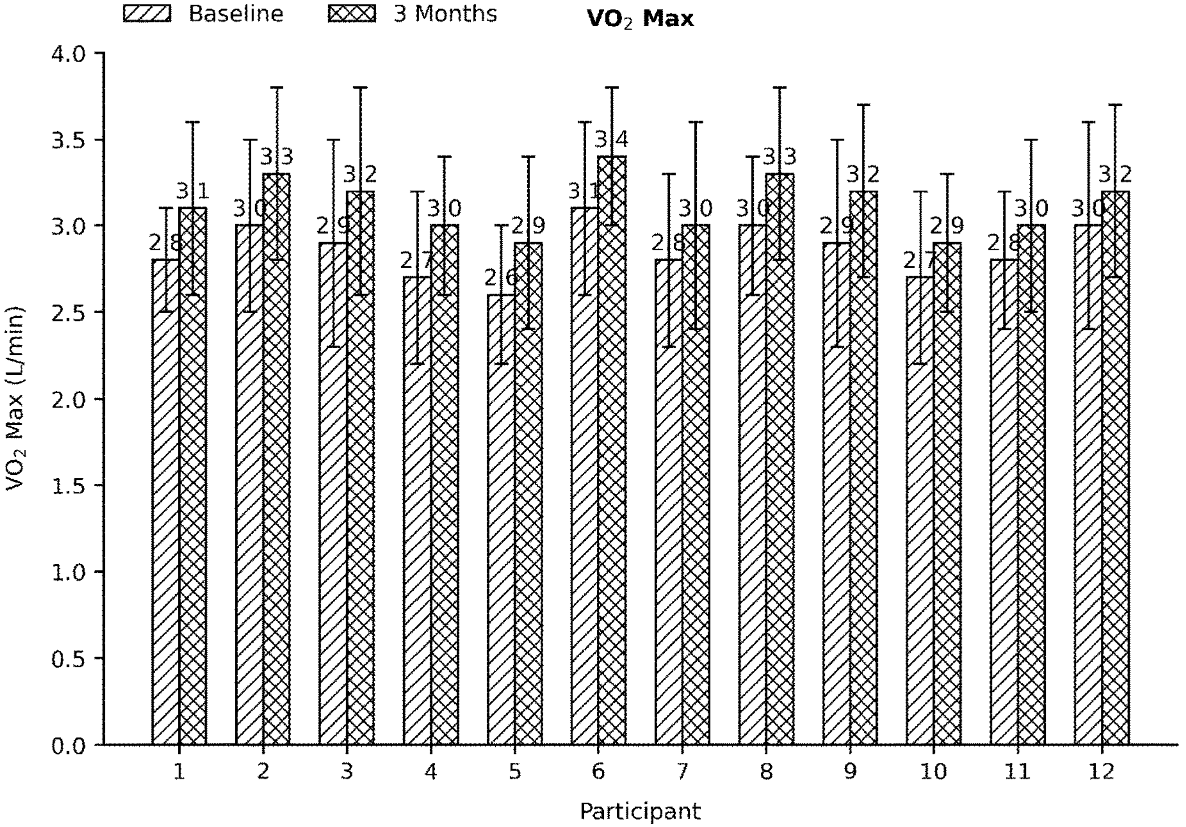
FIG. 40A illustrates physical performance changes for the study participants for $VO_2$.
Figure 40B:
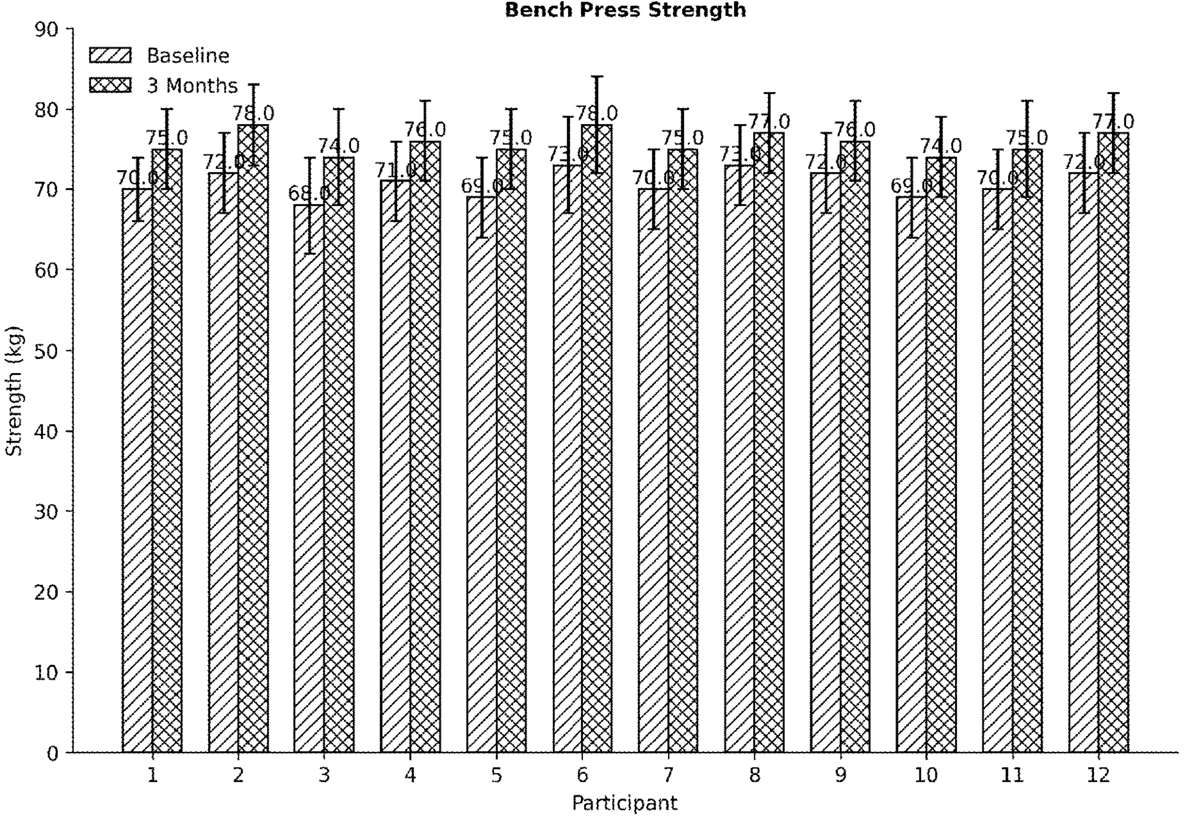
FIG. 40B illustrates physical performance changes for the study participants for bench press strength.
Figure 40C:
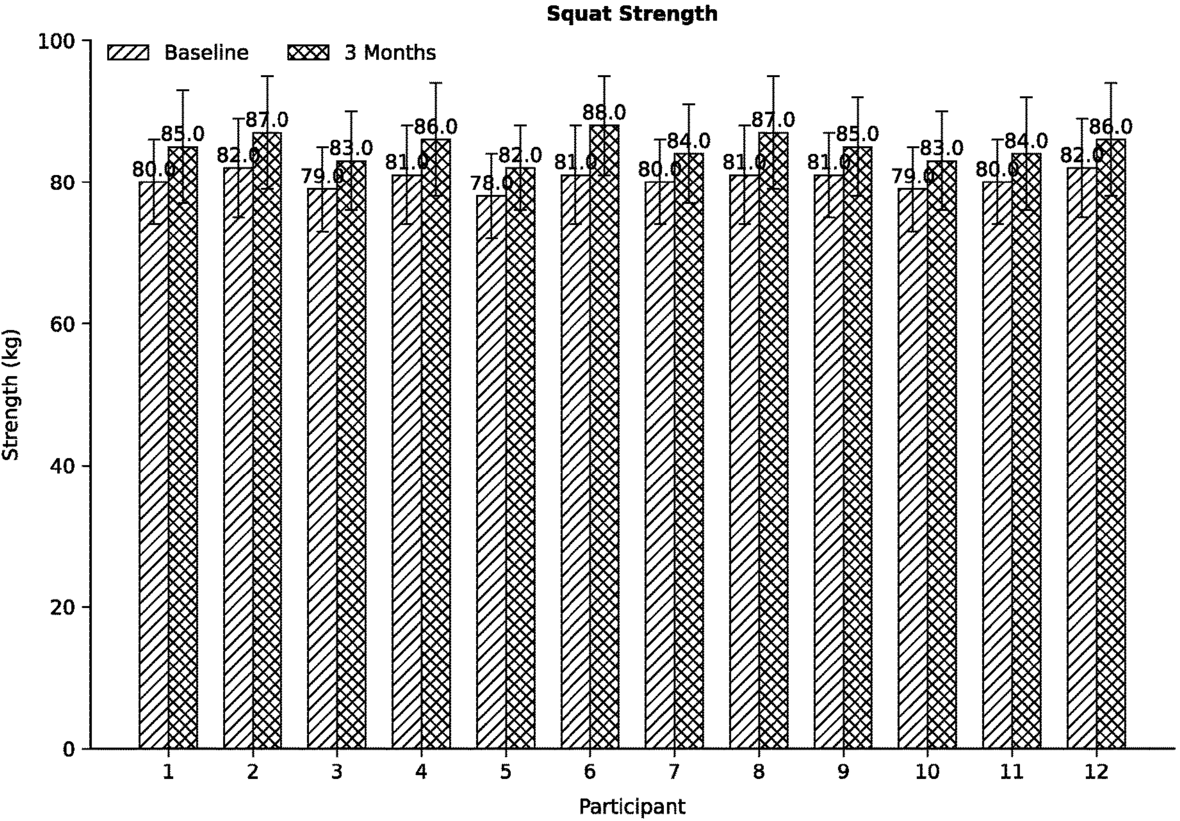
FIG. 40C illustrates physical performance changes for the study participants for squat strength.

FIGS. 40A, 40B, and 40C show the physical performance changes for the various study participants for $VO_2$, bench press strength, and squat strength.

Table 24 illustrates the percentage change, per participant, in $VO_2$ max (in L/min) from baseline to three months of treatment.

TABLE 24

| $VO_2$ max percentage change per participant | | | |
|---|---|---|---|
| Participant | VO2 Max Baseline | VO2 Max 3 Months | Percentage Change |
| 1 | 2.8 ± 0.4 | 3.1 ± 0.5 | +10.71% |
| 2 | 3.0 ± 0.5 | 3.3 ± 0.4 | +10.00% |
| 3 | 2.9 ± 0.6 | 3.2 ± 0.5 | +10.34% |
| 4 | 2.7 ± 0.5 | 3.0 ± 0.4 | +11.11% |
| 5 | 2.6 ± 0.4 | 2.9 ± 0.5 | +11.54% |
| 6 | 3.1 ± 0.5 | 3.4 ± 0.4 | +9.68% |
| 7 | 2.8 ± 0.5 | 3.0 ± 0.6 | +7.14% |
| 8 | 3.0 ± 0.4 | 3.3 ± 0.5 | +10.00% |
| 9 | 2.9 ± 0.6 | 3.2 ± 0.5 | +10.34% |
| 10 | 2.7 ± 0.5 | 2.9 ± 0.4 | +7.41% |
| 11 | 2.8 ± 0.4 | 3.0 ± 0.5 | +7.14% |
| 12 | 3.0 ± 0.6 | 3.2 ± 0.5 | +6.67% |

Table 25 illustrates the percentage change, per participant, in bench press strength (in kg) from baseline to three months of treatment.

TABLE 25

| Bench press strength percentage change per participant. | | | |
|---|---|---|---|
| Participant | Bench Press Baseline | Bench Press 3 Months | Percentage Change |
| 1 | 70.0 ± 6.0 | 75.0 ± 6.5 | +7.14% |
| 2 | 72.0 ± 6.5 | 78.0 ± 6.8 | +8.33% |
| 3 | 68.0 ± 6.2 | 73.0 ± 6.4 | +7.35% |
| 4 | 71.0 ± 6.8 | 76.0 ± 7.0 | +7.04% |
| 5 | 69.0 ± 6.0 | 74.0 ± 6.2 | +7.25% |
| 6 | 73.0 ± 6.5 | 78.0 ± 6.8 | +6.85% |
| 7 | 70.0 ± 6.5 | 75.0 ± 6.8 | +7.14% |
| 8 | 72.0 ± 6.8 | 77.0 ± 6.9 | +6.94% |
| 9 | 71.0 ± 6.2 | 76.0 ± 6.4 | +7.04% |
| 10 | 68.0 ± 6.0 | 73.0 ± 6.2 | +7.35% |
| 11 | 70.0 ± 6.2 | 74.0 ± 6.5 | +5.71% |
| 12 | 72.0 ± 6.5 | 77.0 ± 6.8 | +6.94% |

Table 26 illustrates the percentage change, per participant, in squat strength (in kg) from baseline to three months of treatment.

TABLE 26

| Squat strength percentage change per participant. | | | |
|---|---|---|---|
| Participant | Squat Baseline | Squat 3 Months | Percentage Change |
| 1 | 80.0 ± 7.0 | 85.0 ± 7.5 | +6.25% |
| 2 | 82.0 ± 6.8 | 87.0 ± 7.2 | +6.10% |
| 3 | 79.0 ± 6.5 | 83.0 ± 6.7 | +5.06% |
| 4 | 81.0 ± 7.2 | 86.0 ± 7.5 | +6.17% |
| 5 | 78.0 ± 6.5 | 82.0 ± 6.7 | +5.13% |
| 6 | 83.0 ± 6.8 | 88.0 ± 7.2 | +6.02% |
| 7 | 80.0 ± 7.0 | 84.0 ± 7.5 | +5.00% |
| 8 | 82.0 ± 7.2 | 87.0 ± 7.5 | +6.10% |
| 9 | 81.0 ± 6.8 | 85.0 ± 7.0 | +4.94% |
| 10 | 79.0 ± 6.5 | 82.0 ± 6.7 | +3.80% |
| 11 | 80.0 ± 6.7 | 84.0 ± 7.0 | +5.00% |
| 12 | 82.0 ± 7.0 | 86.0 ± 7.5 | +4.88% |

Table 27 illustrates the percentage change, per participant, in muscle hypertrophy (in kg) from baseline to three months of treatment.

TABLE 27

| Muscle hypertrophy percentage change per participant. | | | |
|---|---|---|---|
| Participant | Muscle Mass Baseline | Muscle Mass 3 Months | Percentage Change |
| 1 | 72.0 ± 5.0 | 75.0 ± 5.2 | +4.17% |
| 2 | 74.0 ± 5.5 | 77.0 ± 5.8 | +4.05% |
| 3 | 71.0 ± 5.2 | 74.0 ± 5.5 | +4.23% |
| 4 | 73.0 ± 5.0 | 76.0 ± 5.2 | +4.11% |
| 5 | 70.0 ± 5.0 | 73.0 ± 5.2 | +4.29% |
| 6 | 75.0 ± 5.5 | 78.0 ± 5.7 | +4.00% |
| 7 | 72.0 ± 5.0 | 75.0 ± 5.2 | +4.17% |
| 8 | 74.0 ± 5.5 | 77.0 ± 5.7 | +4.05% |
| 9 | 71.0 ± 5.2 | 74.0 ± 5.5 | +4.23% |
| 10 | 70.0 ± 5.0 | 73.0 ± 5.2 | +4.29% |
| 11 | 72.0 ± 5.0 | 75.0 ± 5.2 | +4.17% |
| 12 | 74.0 ± 5.5 | 77.0 ± 5.7 | +4.05% |

Table 28 illustrates the percentage change, per participant, in muscle thickness (in cm) from baseline to three months of treatment.

TABLE 28

| Muscle thickness percentage change per participant. | | | |
|---|---|---|---|
| Participant | Muscle Thickness Baseline | Muscle Thickness 3 Months | Percentage Change |
| 1 | 2.5 ± 0.3 | 2.8 ± 0.3 | +12.00% |
| 2 | 2.6 ± 0.3 | 2.9 ± 0.3 | +11.54% |
| 3 | 2.4 ± 0.3 | 2.7 ± 0.3 | +12.50% |
| 4 | 2.5 ± 0.3 | 2.8 ± 0.3 | +12.00% |
| 5 | 2.4 ± 0.3 | 2.6 ± 0.3 | +8.33% |
| 6 | 2.7 ± 0.3 | 3.0 ± 0.3 | +11.11% |
| 7 | 2.5 ± 0.3 | 2.8 ± 0.3 | +12.00% |
| 8 | 2.6 ± 0.3 | 2.9 ± 0.3 | +11.54% |
| 9 | 2.4 ± 0.3 | 2.7 ± 0.3 | +12.50% |
| 10 | 2.4 ± 0.3 | 2.6 ± 0.3 | +8.33% |
| 11 | 2.5 ± 0.3 | 2.8 ± 0.3 | +12.00% |
| 12 | 2.6 ± 0.3 | 2.9 ± 0.3 | +11.54% |

Table 29 illustrates the percentage change, per participant, in time-to-fatigue (in min.) from baseline to three months of treatment.

TABLE 29

| Time-to-fatigue percentage change per participant. | | | |
|---|---|---|---|
| Participant | Time-to-Fatigue Baseline | Time-to-Fatigue 3 Months | Percentage Change |
| 1 | 22.0 ± 3.0 | 24.0 ± 3.2 | +9.09% |
| 2 | 21.5 ± 3.2 | 23.5 ± 3.1 | +9.30% |
| 3 | 22.0 ± 3.0 | 24.0 ± 3.1 | +9.09% |
| 4 | 21.0 ± 3.0 | 23.0 ± 3.2 | +9.52% |
| 5 | 20.5 ± 3.1 | 22.5 ± 3.0 | +9.76% |
| 6 | 23.0 ± 3.0 | 25.0 ± 3.1 | +8.70% |
| 7 | 21.0 ± 3.2 | 23.0 ± 3.1 | +9.52% |
| 8 | 22.0 ± 3.0 | 24.0 ± 3.2 | +9.09% |
| 9 | 21.5 ± 3.2 | 23.5 ± 3.1 | +9.30% |
| 10 | 22.0 ± 3.0 | 24.0 ± 3.2 | +9.09% |
| 11 | 20.5 ± 3.1 | 22.5 ± 3.0 | +9.76% |
| 12 | 22.0 ± 3.0 | 24.0 ± 3.1 | +9.09% |

Table 30 illustrates the percentage change, per participant, in run time (in min.) from baseline to three months of treatment.

TABLE 30

| Run time percentage change per participant | | | |
|---|---|---|---|
| Participant | Run Time Baseline | Run Time 3 Months | Percentage Change |
| 1 | 25.0 ± 2.5 | 23.0 ± 2.3 | −8.00% |
| 2 | 24.0 ± 2.4 | 22.5 ± 2.2 | −6.25% |
| 3 | 25.5 ± 2.6 | 23.0 ± 2.3 | −9.80% |
| 4 | 24.5 ± 2.5 | 22.0 ± 2.1 | −10.20% |
| 5 | 24.0 ± 2.4 | 21.5 ± 2.2 | −10.42% |
| 6 | 26.0 ± 2.7 | 24.0 ± 2.5 | −7.69% |
| 7 | 24.5 ± 2.5 | 22.5 ± 2.3 | −8.16% |
| 8 | 25.0 ± 2.6 | 23.0 ± 2.3 | −8.00% |
| 9 | 24.5 ± 2.5 | 22.5 ± 2.2 | −8.16% |
| 10 | 25.0 ± 2.6 | 23.0 ± 2.3 | −8.00% |
| 11 | 24.0 ± 2.4 | 21.5 ± 2.1 | −10.42% |
| 12 | 25.5 ± 2.6 | 23.5 ± 2.4 | −7.84% |

Figure 41:
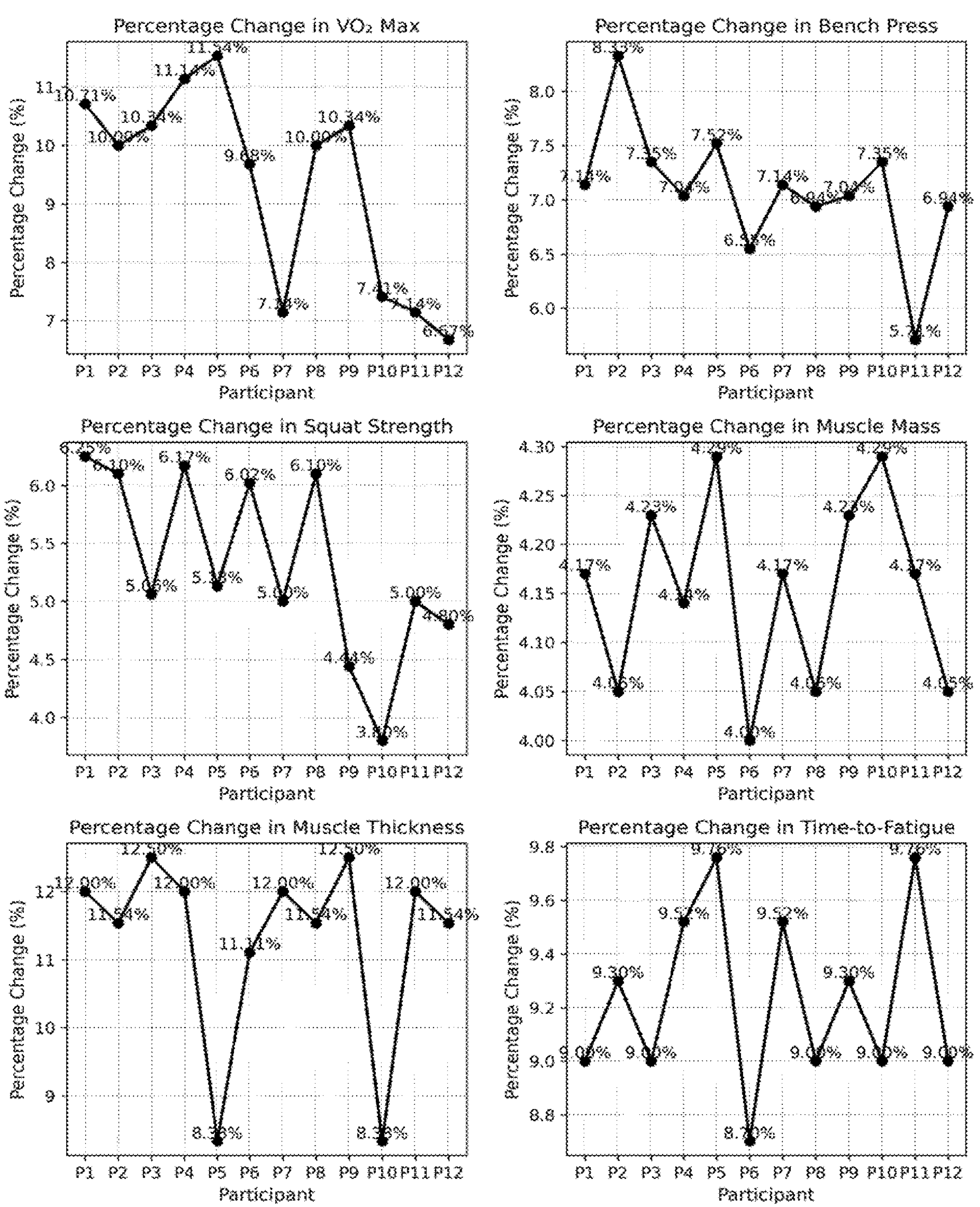
FIG. 41 illustrates percentage changes in $VO_2$ max, bench press and squat strength, muscle mass, muscle thickness, and time-to-fatigue.

FIG. 41 shows the relative changes in percent over time, per participant, of individual $VO_2$ max, bench press, squat strength, muscle mass, muscle thickness, and time-to-fatigue measurements.

Phytosome Bioavailability Delivery

Disclosed is a phytosome bioavailability delivery system for micronized supplements. This technique mixes phospholipids with systematic herbal and other extracts or moisture phytocomponents to produce lipid-consistent tiny composites that significantly increase absorption and bioavailability of micronized forms extracts of key ingredients, which includes DHEA, NEFAs (Non-Esterified Fatty Acids), Vitamin D, L-Arginine, EAAs (Essential Amino Acids), Zinc, Adaptogens, Vitamin B6, Stilbenoids, Vitamins B, C, E, and K, Creatine and Green Tea Extract. Phospholipids such as phosphatidylcholine bind with active plant components to form phytophospholipid complexes that ensure better absorption, stability, and targeted delivery of these compounds. Phytosomes improve the solubility of hydrophobic compounds, stabilize active ingredients, and reduce side effects, ultimately increasing active ingredients efficacy in applications like dietary supplements.

Phytosomes are preferable to liposomes for such a delivery system. Liposomes, while beneficial for drug delivery, present several challenges. They tend to be unstable when exposed to biological fluids, which can lead to drug leakage or degradation over time, reducing shelf life and nutritional effectiveness. The production of liposomes is also costly due to the specialized equipment and processes required to ensure uniformity in size and encapsulation efficiency. Additionally, their drug-loading capacity is limited, as hydrophilic drugs are confined to the aqueous core, and lipophilic drugs are embedded within the lipid bilayer, restricting the total amount they can carry.

Moreover, liposomes are often rapidly cleared from the bloodstream by the immune system, particularly by the mononuclear phagocyte system, which reduces their circulation time and effectiveness unless they are modified, such as through pegylation. Formulating liposomes is a complex process, requiring precision that is difficult to maintain during large-scale production. Lastly, there is the potential for toxicity, as non-biocompatible lipids or stabilizers may lead to adverse effects, and liposomes may accumulate in organs like the liver and spleen, posing toxicity risks.

The phytosome bioavailability delivery system is an innovative method designed to improve the bioavailability and nutritional effectiveness of plant-based compounds, such as flavonoids, polyphenols, and other bioactive constituents. It involves the creation of a complex between a natural phytochemical and a phospholipid molecule, like phosphatidylcholine, forming a chemical bond. Unlike simple mixtures of plant extracts and lipids, phytosomes enhance the absorption of these compounds by making them more lipid compatible.

Phytosomes involve the formation of a chemical bond between plant-based bioactive compounds (like polyphenols or flavonoids) and phospholipids, which significantly enhances their bioavailability. This system is particularly beneficial for delivering hydrophobic plant extracts, such as curcumin, silymarin, and *Ginkgo biloba*, where improved absorption is crucial for efficacy. Due to their bonded structure, phytosomes offer better stability and are more efficient at delivering active ingredients to target tissues, particularly in herbal medicine and nutraceutical applications. Studies have shown that phytosomes are more effective in enhancing bioavailability compared to traditional delivery methods.

On the other hand, liposomes are spherical vesicles composed of lipid bilayers that encapsulate both hydrophilic and lipophilic substances without forming chemical bonds. Liposomes are widely used in pharmaceuticals and cosmetics due to their versatility in delivering a variety of drugs, including water-soluble and fat-soluble compounds. However, their bioavailability is generally lower than that of phytosomes, as the encapsulated compounds are not bonded to the lipids, making them less stable and more susceptible to degradation.

One of the primary benefits of phytosome systems is the significant increase in bioavailability. Phytochemicals, such as curcumin, quercetin, and silymarin, typically have poor solubility in water and limited absorption when taken orally. By incorporating them into phytosome complexes, their bioavailability increases drastically. For instance, curcumin's bioavailability is enhanced up to 29 times when delivered in phytosome form. Additionally, the lipid component of the phytosome improves the solubility of poorly soluble phytochemicals. The amphiphilic nature of phytosomes, having both hydrophilic and lipophilic properties, allows these molecules to dissolve more effectively in gastrointestinal fluids and cross cell membranes more easily. As a result, phytosomes exhibit better pharmacokinetics, staying in the system longer and providing more sustained nutritional effects, reducing the need for frequent dosing.

Phytosomes also serve as targeted bioavailability delivery systems. The lipid component integrates well with cellular membranes, enabling phytochemicals to reach specific tissues more efficiently. Furthermore, since phytosomes increase the bioavailability and efficiency of plant compounds, lower doses are needed to achieve nutritional effects, minimizing the risk of side effects and toxicity. Another key advantage is their stability, as they protect phytochemicals from environmental factors like oxygen, light, and heat, thus improving the shelf life of the active ingredients.

The mechanism behind phytosome systems involves the formation of a lipid-phytochemical complex, where the phospholipid bonds with the phytochemical, enhancing its lipid solubility and enabling it to penetrate cell membranes more effectively. This increased membrane permeability allows for higher concentrations of the active ingredient to be absorbed into the cells. The lipid content of the phytosome also facilitates improved lymphatic absorption, bypassing liver metabolism and resulting in higher plasma concentrations of the phytochemical. Furthermore, the phytosome structure provides sustained nutrients release, preventing rapid degradation and maintaining nutritional effects over time.

The preparation of phytosomes involves several steps. First, the appropriate phytochemicals and phospholipids are selected, usually based on their nutritional potential and low bioavailability. Phosphatidylcholine is typically chosen due to its role in cell membranes and compatibility with bioavailability delivery systems. Next, the phytochemical and phospholipid are mixed in a solvent, such as ethanol or dichloromethane, and stirred under specific conditions to form the phytochemical-phospholipid complex. The solvent is then evaporated under reduced pressure, usually through rotary evaporation, leaving behind the phytosome complex. This complex is subsequently dried using freeze-drying or spray-drying methods, yielding a fine powder that can be formulated into various dosage forms, such as capsules or tablets. Finally, the phytosome product undergoes quality control and evaluation to ensure its size, encapsulation efficiency, stability, and release profile meet the required standards. Analytical techniques, such as X-ray diffraction (XRD) or Fourier-transform infrared spectroscopy (FTIR), are used to confirm the phytosome structure.

Phytosome delivery systems have a range of applications. They are commonly used to enhance the bioavailability of plant extracts, making them suitable for treating liver disorders with silymarin phytosome, which has been extensively studied for its hepatoprotective properties in conditions like cirrhosis and hepatitis. Curcumin phytosome is used for its strong anti-inflammatory and antioxidant effects, benefiting conditions such as arthritis, cancer, and cardiovascular diseases. *Ginkgo biloba* phytosome enhances cognitive function, improves memory, and provides protection against age-related neurodegenerative diseases. In skincare, phytosomes improve the delivery of polyphenols and flavonoids, offering antioxidant and anti-aging benefits.

Several types of phytosome systems have been developed for different natural extracts, including Silybin Phytosome (SILIPHOS®) for liver protection, Curcumin Phytosome (Meriva®) for anti-inflammatory and antioxidant benefits, *Ginkgo biloba* Phytosome for cognitive enhancement, Green Tea Phytosome (GREENSELECT®) for antioxidant and weight loss support, and Quercetin Phytosome for anti-allergic and antioxidant effects.

Despite its many advantages, the phytosome system faces challenges. The cost of developing phytosome technology is higher than traditional formulations, and scaling up production requires precise conditions, making it technically challenging. In conclusion, the phytosome delivery system is an advanced method for improving the bioavailability and nutritional efficacy of plant-based compounds. By utilizing phospholipid-based complexes, phytosomes enhance absorption, stability, and controlled release of bioactive ingredients, offering significant potential in nutraceuticals and pharmaceuticals, particularly in areas like liver health, anti-inflammatory therapy, and cognitive support.

Several research studies have explored the effectiveness of phytosomes in enhancing the bioavailability and nutritional potential of various plant-based compounds. A randomized, placebo-controlled study found the bioavailability of curcumin in its phytosome form compared favorably to standard curcumin extracts. The results showed that the phytosome formulation increased curcumin bioavailability by nearly 29-fold. Additionally, it demonstrated significant improvements in antioxidant markers among the participants, confirming the potential of curcumin phytosomes in inflammation and oxidative stress-related conditions.

Other studies found the bioavailability of silybin in a new phytosome complex compared favorably to the pharmacokinetics of silybin in its traditional form. The phytosome formulation significantly improved the bioavailability of silybin, enhancing its effectiveness in providing liver protection, particularly in the treatment of conditions such as cirrhosis and hepatitis.

Researchers have studied the absorption and efficacy of *Ginkgo biloba* extract in its phytosome form compared to the standard extract, and the results showed that the phytosome formulation led to higher plasma concentrations of flavonoids, the active components in *Ginkgo biloba*. This increase in absorption indicated that *Ginkgo biloba* phytosomes offer enhanced cognitive and neuroprotective benefits, making them more effective in the treatment of neurodegenerative diseases.

Studies involving a lecithin formulation of green tea extract, on weight maintenance after weight loss found a phytosome formulation of green tea extract helped subjects maintain weight loss. The results showed a significant reduction in body weight and BMI, demonstrating the superior weight management benefits of GREENSELECT® Phytosome compared to non-phytosome green tea extracts.

Phytosomes in quercetin formulations improve oral absorption and anti-inflammatory activity in animal models versus conventional quercetin formulations. Quercetin phytosome formulations improve oral absorption and enhanced anti-inflammatory activity, highlighting its potential for managing inflammatory conditions more effectively.

A study of silymarin phytosomes and the potential for treating insulin resistance and reducing oxidative stress in type 2 diabetes investigated the efficacy of silymarin phytosome and found significant improvements in fasting blood sugar, insulin levels, and markers of oxidative stress, demonstrating the potential of silymarin phytosome in diabetes management.

Finally, a study of berberine phytosome versus berberine explored the potential of berberine phytosome in treating metabolic syndrome. The study concluded that berberine phytosome showed greater effectiveness in improving lipid profiles and insulin sensitivity compared to traditional berberine formulations, emphasizing the nutritional potential of phytosome technology in metabolic health.

A variety of nanoparticles, differing in both quantity and materials, are under development. These materials exist in various chemical forms, such as micelles, metal oxides, or large biomolecules. This diversity underscores the need for the development of enhanced characterization methods and protocols that provide greater precision and increased credibility. However, each characterization technique has its own set of advantages and limitations. To overcome these constraints, it is advisable to use a combination of methods to effectively characterize individual nanoparticles. When choosing these methods of characterization, it is essential to ensure that they are suitable for the intended purpose.

Various methods are used the characterize phytosome nanoparticles, including (1) high-performance liquid chromatography, (2) X-ray diffraction analysis, (3) scanning electron microscopy, (4) transmission electron microscopy, and (5) differential scanning calorimetry (DSC).

To evaluate the efficiency of drug entrapment within planterosomes, an ultracentrifugation method is employed. This method aids in the determination of the percentage of the drug present within the phospholipid mesh. In all phytosome formulations, approximately 100% of the drug is present. The entrapment efficacy is calculated using the following formula: a % entrapment efficacy=(amount of drug in sediment/total amount of drug added)×100% entrapment efficacy=(amount of drug in sediment/total amount of drug added)×100

The quantity of drug in phytosomes is typically determined using a modified high-performance liquid chromatography method or by UV analysis. One way to measure the drug content is to dissolve a known quantity of phyto-phospholipid dispersion in 10 mL of methanol. The drug concentration of the phyto-phospholipid complex is then determined. After appropriate dilution, the absorbance is measured using spectroscopic techniques at a specific wavelength, and the drug content is calculated using the following formula:

% drug content=(actual drug content in phyto-phospholipid complex/theoretical yield)×100% drug content=(actual drug content in phyto-phospholipid complex/theoretical yield)×100

The Franz diffusion cell method or dialysis bag is used in combination with various kinetic models. These methods help to identify the mechanisms involved in the release of drug content. Furthermore, an in vitro dissolution test is conducted to understand the drug release process.

The most commonly used visualization methods are transmission electron microscopy (TEM) and scanning electron microscopy (SEM). Additionally, when the SEM analysis of nanoparticles (NPs) does not yield clear results regarding the size and shape of the NPs due to its very high resolution, field emission scanning electron microscopy (FESEM) is used.

X-ray diffraction analysis (XRD) can provide valuable assistance in analyzing various particles. This method is utilized for identifying crystalline compounds and for determining particle roughness, topography, surface area, and surface chemistry.

Transition temperature, which is a thermo-analytical method, such as differential scanning calorimetry (DSC), can be employed to assess the transition temperature of vesicular lipid systems. DSC plays a crucial role in elucidating changes in material properties in response to temperature variations. This tool is valuable for determining the crystal structure of the active pharmaceutical ingredient (API). Several phenomena are observed, including temperature transitions, the disappearance of endothermic peaks, alterations in relative peak areas, and the emergence of new peaks. These observations provide valuable insights into the melting and crystallization behavior of the sample being investigated.

The stability of vesicles can be assessed over an extended period through comprehensive measurements that include size, zeta potential, and structural characteristics. Zeta potential, which is the surface charge, is defined as the difference in electric potential (AV) between the dispersion medium and the stationary fluid layer on the surface of the dispersed phase. A zeta potential of ±30 mV or ±20 mV is preferred for high physical stability. For the determination of both size and zeta potential, dynamic light scattering (DLS) coupled with a computerized inspection system and photon correlation spectroscopy (PCS) proves to be a valuable approach. Simultaneously, transmission electron microscopy (TEM) is used to observe structural changes, as mentioned earlier.

Spectroscopic techniques may be used to confirm the formation of a complex or investigate the interaction between the plant-based component and the phospholipids, scientists utilize spectroscopic techniques such as nuclear magnetic resonance (NMR), Fourier transform infrared spectroscopy (FTIR), and X-ray diffraction (XRD). This involves comparing the outcomes of the individual elements with those of the complexes.

Phytosomes are often used in the context of improving the solubility and bioavailability of poorly water-soluble phytochemicals or botanical drugs. Phospholipid complexation involves the interaction between the phospholipids and the phytoconstituents. Here is a general mechanism for how it works.

The primary structure of phospholipids contains a hydrophilic "head" and two hydrophobic "tails". This amphiphilic nature allows phospholipids to form bilayers, with the hydrophilic heads facing outward and the hydrophobic tails tucked inside. The poorly water-soluble phytochemicals, which are usually lipophilic (fat-loving) or hydrophobic, interact with the hydrophobic region of the phospholipid. This interaction leads to the formation of a complex between the phytoconstituent and the phospholipid. Due to the amphiphilic nature of phospholipids, the complex's overall solubility in water is enhanced. This is because the outer hydrophilic region of the phospholipid can interact with water, making it easier for the complex to dissolve. The phyto-phospholipid complex might alter the permeability of membranes, making it easier for the compound to traverse biological barriers. The exact mechanism and efficiency can vary based on the specific phytochemical and phospholipid used.

Referring to Table 31, various phytosomal products are available in market which often face challenges in bioavailability. This enhancement occurs because NEFAs facilitate the transport of these nutrients or compounds across cell membranes, improving their effectiveness.

The mechanism of action involves NEFAs forming micelles in an aqueous environment. These micelles encapsulate lipophilic compounds, protecting them from degradation and improving their stability. This encapsulation leads to increased bioavailability, allowing for more efficient absorption in the gastrointestinal tract.

One of the notable benefits of using NEFAs in bioavailability delivery is their ability to target specific tissues. Since NEFAs are readily metabolized by cells, they can facilitate localized nutrients or compound release, ensuring that nutritional agents reach their intended site of action without affecting surrounding tissues. This targeted approach can reduce the required dosage of supplements, which is particularly advantageous in minimizing potential side effects and enhancing patient or consumer compliance.

The nutritional effects of NEFAs as a bioavailability delivery system are diverse. They can improve the effectiveness of treatments for various conditions, including inflammatory diseases, metabolic disorders, and cancer. By enhancing bioavailability delivery, NEFAs can lead to better patient outcomes, as they ensure that the active ingredients are delivered efficiently and effectively.

Non-Esterified Fatty Acids (NEFAs) have garnered attention as a promising delivery system, particularly highlighted in various in vitro studies. These studies demonstrate

TABLE 31

Phytosomal products available on the market.

| Phytosomal Product | Phytoconstituent | Natural Source | Pharmacological activity |
|---|---|---|---|
| Hawthron Phytosomes | Hyperin, Quercitin | *Crateegus, Oxyacanthoids* | Antihypertension, Cardioprotective |
| Ginseng Phytosomes | Ginsenosides | *Panax Ginseng* | Immunomodulator, Nutraceutical |
| Curcumin Phytosome | Curcumin | *Curcuma Longa* | Osteoarthritis, Anti-Inflammatory, Anticancer |
| Escin B-Sitosterol Phytosome | Saponins | *Aesculus Hippocastanum* (Horse Chestnut Fruit) | Anti-Oedema |
| Green Tea Phytosome | Epigallocatechin, Catechin, Epicatechin-3-O-Gallate, Epigallocatechin-3-O-Gallate | *Camellia Sinesis*(Tea) | Nutraceutical, Systemic Antioxidant, Anticancer, Hepatoprotective, Anti-Inflammatory |
| Oleaselect ™ Phytosome | Polyphenol | *Olea europaea* | Anti-inflammatory, antihyperlipidemic |
| Glycyrrhetinic acid Phytosome ™ | Glycyrrhetinic acid | *Glycyrrhiza glabra* (Mulethi) | Anti-inflammatory, dermatitis |
| Silybin Phytosome [32] | Silybin, Silycristin, Isosilbin, Silydianin | *Silybium maranium*(Milk Thistle) | Hepatoprotective, Antioxidant for skin and liver |
| Mirtoselect Phytosome | Anthocyanosides | *Vaccinum myrtillus*(Bilberry) | Antioxidant, Improvement of Capillary Tone. |
| Ginkgo phytosomes | 24% Ginkgo flavon glycosides | *Ginkgo biloba* | Protect the brain and vascular lining, Anti-ageing agent |
| Visnadex Phytosome | Indena | *Amni visnaga* | Improve microcirculation |

Fatty Acids (NEFAS) Bioavailability Delivery System

Non-Esterified Fatty Acids (NEFAs) play a significant role as an effective bioavailability delivery system due to their unique physicochemical properties. NEFAs enhance the solubility and absorption of lipophilic compounds, NEFAs' ability to enhance drug compounds solubility and bioavailability, which is crucial for the efficacy of lipophilic compounds.

One significant aspect of in vitro research is the formation of micelles. NEF As can spontaneously assemble into micelles in aqueous environments, effectively encapsulating lipophilic drugs. This encapsulation not only protects the compounds from degradation but also facilitates their transport across cell membranes. Studies have shown that NEFA-loaded micelles significantly improve the solubility of poorly soluble compounds, leading to enhanced absorption in cell cultures.

Additionally, in vitro studies have explored the metabolic pathways of NEFAs in various cell types. These studies indicate that NEFAs are readily taken up by cells, allowing for localized drug release. For instance, research involving cancer cell lines has demonstrated that NEFAs can enhance the uptake of chemo nutritional agents, leading to improved cytotoxic effects against tumors.

Moreover, NEFAs have been shown to modulate cellular responses, such as inflammation and apoptosis, in specific contexts. This property can be leveraged to improve the nutritional effects of anti-inflammatory or anticancer drugs, making NEFAs a versatile platform for targeted therapy.

Overall, in vitro studies underscore the potential of NEFAs as an effective bioavailability delivery system, enhancing the solubility, bioavailability, and nutritional efficacy of various lipophilic drugs while allowing for targeted delivery and reduced side effects. Here are some research studies on Non-Esterified Fatty Acids (NEFAs) as a bioavailability delivery system.

Cyclodextrin-Bioavailability Delivery System

Figure 42:
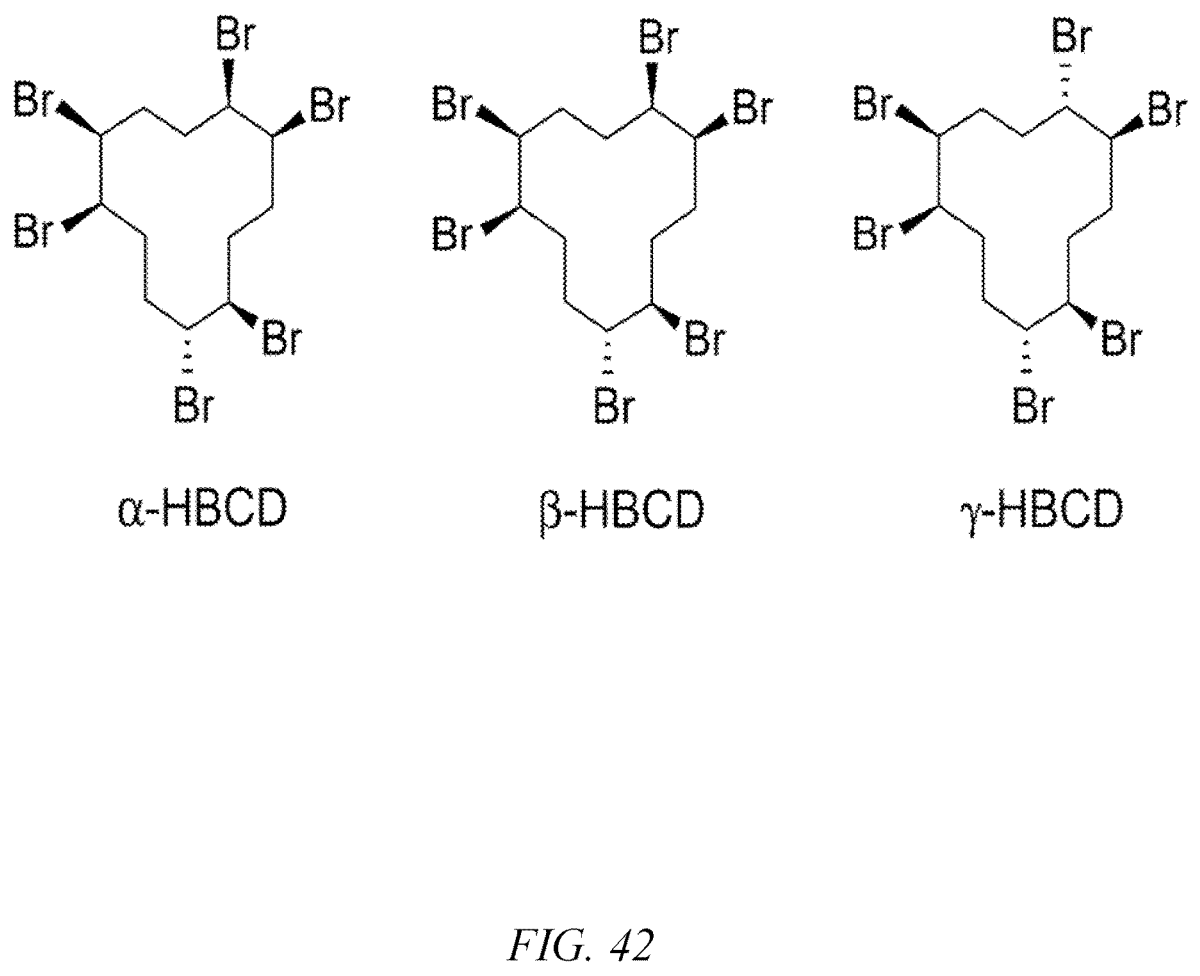

Referring to FIG. 42, several chemical structures of HBCD are shown. Several types of cyclodextrins are used for different applications. Beta-Cyclodextrin (β-CD): Commonly used due to its good complexation properties and can improve the solubility of various DHEA derivatives but may have limitations in terms of solubility in water itself. Hydroxypropyl-β-Cyclodextrin (HP-β-CD) is modified to enhance water solubility and reduce toxicity. Particularly, useful for DHEA derivatives to improve solubility and reduce potential irritation. Methyl-β-Cyclodextrin (M-β-CD) has a higher complexation ability and can encapsulate larger molecules or higher quantities of DHEA derivatives. γ-Cyclodextrin (γ-CD) has a larger cavity size compared to β-CD, which can be advantageous for complexing larger or more hydrophobic DHEA derivatives.

There are several formulation strategies for encapsulating DHEA derivatives. Physical Mixtures involve the simple mixing of DHEA derivatives with cyclodextrins and is suitable for initial screening and less complex formulations. In co-precipitation, DHEA derivatives and cyclodextrins are dissolved together, and then a solvent is removed to form a solid complex. It helps in achieving more homogeneous complexation. In freeze-drying, DHEA derivatives and cyclodextrins are freeze-dried to obtain a stable powder. It is useful for improving stability and creating a powder for various formulations. Spray drying is a method to produce dry powder directly from a liquid solution. It is useful for large-scale production and creating formulations suitable for oral or other routes of administration.

Combining micronized cyclodextrin with various active ingredients can significantly enhance their stability, solubility, and bioavailability. Micronized cyclodextrin acts as a carrier, forming inclusion complexes that improve the delivery of compounds such as DHEA, NEFAs, Vitamin D, L-Arginine, (EAAs), Zinc, adaptogens, Vitamin B6, stilbenoids, Vitamins B, C, E, and K, and Green Tea Extract. The mechanism of action involves cyclodextrin encapsulating lipophilic compounds, making them more soluble in aqueous environments. This enhances bioavailability, leading to better absorption and efficacy. By improving solubility and enabling controlled release, cyclodextrins can help achieve lower effective doses, which may minimize side effects.

DHEA derivatives, such as DHEA sulfate and DHEA acetate, often have poor water solubility. Cyclodextrins form inclusion complexes with these derivatives, significantly increasing their solubility in aqueous solutions, which is essential for effective oral or intravenous administration. These derivatives are also susceptible to degradation from light, oxygen, and moisture. Cyclodextrin complexes help protect them from these environmental factors, enhancing their stability and extending shelf life.

An Immediate release of DHEA can lead to side effects or suboptimal nutritional effects. Cyclodextrins can modulate the release rate of DHEA derivatives, providing controlled release formulations that ensure steady active ingredients release over time, improving nutritional outcomes and reducing side effects. Low bioavailability of DHEA derivatives limits their effectiveness, but cyclodextrins enhance dissolution rates and overall bioavailability, leading to better absorption and efficacy. High doses of DHEA derivatives may cause side effects; by improving solubility and enabling controlled release, cyclodextrins can help achieve lower effective doses, potentially reducing side effects.

The mechanism of action involves DHEA acting as a precursor to sex hormones, influencing various physiological processes. The combination of cyclodextrin with DHEA and other active ingredients enhances bioavailability, ensuring effective utilization by the body. This mixture can create synergistic effects among vitamins, minerals, amino acids, and adaptogens, leading to improved mood, energy levels, and metabolic health. Cyclodextrins provide sustained release of active ingredients, maintaining stable blood levels, and protect sensitive compounds from degradation, further enhancing stability.

The strategic combination of cyclodextrin with DHEA and other beneficial ingredients results in a robust formulation that maximizes nutritional potential, bioavailability, and efficacy, supporting a wide range of health benefits and making it an effective choice for dietary supplements aimed at promoting overall wellness.

Cyclodextrins (CDs) are cyclic oligosaccharides known for enhancing the solubility and bioavailability of poorly soluble drugs (compounds) through complexation. Their ability to form inclusion complexes with various drug molecules is widely researched in both in vitro and in vivo settings. In vitro studies show that cyclodextrins significantly increase the solubility of hydrophobic drugs, improving dissolution profiles. Stability testing of cyclodextrin complexes assesses their integrity under various pH and temperature conditions. Permeability assessments using models like Caco-2 cell lines evaluate how well cyclodextrin-drug complexes cross biological membranes, providing insights into their absorption potential. In vivo studies reveal that drugs administered as cyclodextrin complexes often exhibit improved bioavailability compared to non-complexed versions, leading to enhanced nutritional effects. Pharmacokinetic evaluations measure parameters such as absorption rate, peak plasma concentration, and elimination half-life, highlighting the advantages of cyclodextrin complexation. The clinical relevance is assessed through studies measuring the pharmacodynamic effects of drugs in cyclodextrin formulations, demonstrating improved efficacy in nutritional settings.

Micronized Bioavailability Delivery System Benefits

Micronized Bioavailability Delivery systems offer several benefits, including improved solubility, which allows micronized particles to dissolve more easily in fluids, enhancing the absorption of poorly soluble compounds. This leads to increased bioavailability, enabling micronized supplements to be absorbed more efficiently in the gastrointestinal tract. Higher bioavailability often results in more effective nutritional outcomes at lower doses. Additionally, micronization can improve the taste and texture of powdered supplements, reducing grittiness and unpleasant flavors. Smaller particle sizes can also lead to a faster onset of action, allowing for quicker nutritional effects.

Micronization techniques include mechanical milling, which grinds substances into fine powders; jet milling, which uses high-velocity air streams to reduce particle size; high-pressure homogenization, which forces substances through a narrow orifice under pressure; and cryogenic milling, which employs extremely low temperatures to make substances brittle for easier grinding.

Key micronized ingredients include DHEA, which supports hormonal balance and mood; cyclodextrin, which enhances the solubility and stability of lipophilic active ingredients; NEFAs, providing energy and supporting metabolism; Vitamin D, which promotes bone health and immune function; L-Arginine, enhancing blood flow and cardiovascular health; essential amino acids (EAAs) for protein synthesis and muscle recovery; chelated minerals like zinc for immune function; adaptogens like ashwagandha for stress resilience; Vitamin B6 for neurotransmitter synthesis; stilbenoids like resveratrol for antioxidant support; Vitamin B complex for energy metabolism; green tea extract for weight management; Vitamin C for immune function and skin health; Vitamin E for oxidative stress protection; Vitamin K for blood clotting; and creatine for athletic performance. Each ingredient contributes uniquely to health, optimizing nutritional outcomes.

In vitro studies show that micronized delivery system demonstrates enhanced solubility and dissolution rates compared to non-micronized forms. Techniques such as Caco-2 cell models assess the permeability of micronized formulations across intestinal barriers. In vivo studies indicate that micronized formulations lead to higher plasma concentrations and improved overall bioavailability, measured through pharmacokinetic parameters like absorption rate and peak concentration. Nutritional and therapeutic efficacy is often evaluated in clinical trials, highlighting improved outcomes due to enhanced bioavailability delivery.

Study 7 (Bioavailability, Solubility, Performance)

An RCT was conducted to evaluate the bioavailability, solubility, physical performance, muscle mass, wellness, and safety of different supplement formulations over a 12-week period. Forty male participants, aged 30-50 years, with low baseline levels of physical performance and wellness, were randomly assigned to one of five intervention groups: micronized formulations, phytosome-encapsulated formulations, cyclodextrin-complexed formulations, NEFAs formulations, or a combination of all four. The dosage for all participants included 50 mg/day of 4-Androstenediol, 600 IU/day of Vitamin D, 1000 mg/day of HMB Free Acid, 200 mg/day of Magnesium Bisglycinate, and 200 mg/day of *Panax Ginseng.*

In this RCT, the participants underwent a thorough pre-screening process before being randomly assigned to one of the intervention groups. These groups received micronized formulations, phytosome-encapsulated formulations, cyclodextrin-complexed formulations, NEFA formulations, or a combination of all four. The dosage for all participants included 50 mg/day of 4-Androstenediol, 600 IU/day of Vitamin D, 1000 mg/day of HMB Free Acid, 200 mg/day of Magnesium Bisglycinate, and 200 mg/day of *Panax Ginseng.*

The pre-screening included an extensive medical history review to identify any pre-existing conditions, such as cardiovascular, liver, or kidney disease, which could interfere with the effects of the supplements. Blood tests were conducted to assess baseline levels of Vitamin D, magnesium, testosterone, and DHEA, and to evaluate liver and kidney function, ensuring the participants' bodies could metabolize the supplements safely. Hormonal assessments were especially important due to the effects of 4-Androstenediol on testosterone.

Cardiovascular health was assessed by measuring blood pressure and heart rate, given the potential impact of *Panax Ginseng* and 4-Androstenediol on cardiovascular function. Baseline measurements of body composition, including muscle mass and body fat percentage, were taken, along with physical performance tests such as grip strength. Participants were required to have a body mass index (BMI) between 18.5 and 30, ensuring that those with very high or low BMIs were excluded to prevent the results from being skewed.

The inclusion criteria specified that participants must be healthy males aged 30 to 50 with low physical performance, normal hormone levels, and healthy liver and kidney function. Importantly, the trial applied strict exclusion criteria to maintain the integrity of the study and ensure participant safety. Smokers were excluded due to the potential interference with the metabolic processes involved in the trial, as smoking can affect cardiovascular health and overall metabolism. Similarly, individuals with high alcohol consumption were excluded, as excessive alcohol can impact liver function and hormone balance, both of which are critical to the study. Participants who were using recreational drugs or prescription medications that could interfere with the trial (such as blood thinners, hormone replacement therapies, or medications affecting liver function) were also excluded to avoid complications and potential interactions with the study supplements.

During the 12-week study, participants underwent regular health check-ups to monitor for any adverse effects. Blood tests were regularly conducted to track hormone levels, liver function, and any other physiological changes. Participants were asked to self-report any side effects, and dietary and exercise logs were maintained to ensure consistency in lifestyle factors throughout the trial. This careful pre-screening process, along with ongoing monitoring, ensured participant safety and the accuracy of the study's results.

In this study/RCT, keeping track of adverse effects is a top priority to make sure participants stay safe. Throughout the study, participants are asked to share any changes in how they feel, even if it's something small like feeling a little dizzy or having an upset stomach. They can do this during regular check-ins with the research team, either in person or through simple questionnaires, it was set up beyond what participants report. The research team also keeps a close eye on their health by running routine tests like checking blood samples or monitoring heart rate. These tests help catch anything that might be going on beneath the surface even if the participants don't notice it themselves. The researchers compare this information with the baseline data from when the study started to see if any concerning patterns emerge. If any serious side effects show up, the team can adjust or stop the trial to make sure everyone is safe. By combining regular check-ins and medical tests, the study team can quickly respond to any adverse effects and make sure participants' well-being comes first.

Baseline health assessments was conducted, including physical performance tests for strength and endurance, muscle mass measurements using bioelectrical impedance analysis (BIA), wellness assessments using standardized questionnaires like the WHO-5 Well-Being Index, and blood tests to determine baseline levels of the administered supplements.

Participants included men aged 30-50 years with low baseline physical performance and wellness. Exclusion criteria include any history of chronic diseases, medication use affecting study outcomes, and allergies or sensitivities to any of the study supplements.

To determine bioavailability, plasma concentrations of the supplements were measured at baseline, 6 weeks, and 12 weeks. Blood samples were centrifuged, and the plasma was analyzed using high-performance liquid chromatography (HPLC) with mass spectrometry (MS) detection. The solubility of each supplement was assessed in simulated gastric and intestinal fluids using UV-visible spectroscopy to quantify concentrations.

Physical performance was evaluated through strength tests, such as one-repetition maximum for major muscle groups, and endurance tests, including time to exhaustion on a treadmill or cycle ergometer. Muscle mass was measured using bioelectrical impedance analysis (BIA) at baseline, 6 weeks, and 12 weeks. Wellness was assessed using the WHO-5 Well-Being Index, with participants completing the questionnaire at baseline and after 6 weeks. Adverse effects were recorded through self-reported questionnaires and classified by severity.

Statistical analysis was performed using ANOVA to compare plasma concentrations, solubility, physical performance, muscle mass, and wellness scores between the groups. Post-hoc tests, such as Tukey's HSD, identified specific group differences, with statistical significance set at a p-value of less than 0.05. These methodologies ensured an accurate assessment of the bioavailability, solubility, efficacy, and safety of the various supplement formulations studied.

Table 32 Shows the plasma concentrations of androstenediol, vitamin D, magnesium bisglycinate, and *Panax ginseng* delivered through micronized, phytosomal, cyclodextrin, NEFAs, and combination mechanisms.

TABLE 32

Plasma concentrations.

| Participant | Formulation | 4-Androstenediol | Vitamin D | HMB FA | Magnesium Bisglycinate | Panax Ginseng |
|---|---|---|---|---|---|---|
| 1 | Micronized | 15 ± 2.0 | 30 ± 3.0 | 5 ± 1.0 | 1.5 ± 0.2 | 50 ± 7.0 |
| 2 | Phytosome | 18 ± 2.2 | 35 ± 3.5 | 6 ± 1.1 | 1.6 ± 0.2 | 55 ± 7.5 |
| 3 | Cyclodextrin | 17 ± 2.1 | 32 ± 3.3 | 5.5 ± 1.2 | 1.7 ± 0.3 | 52 ± 7.2 |
| 4 | NEFAs | 16 ± 2.0 | 33 ± 3.4 | 5.0 ± 1.0 | 1.4 ± 0.2 | 51 ± 6.8 |
| 5 | Combination | 22 ± 2.5 | 40 ± 4.0 | 7 ± 1.0 | 1.8 ± 0.2 | 60 ± 8.0 |

Plasma Concentrations (ng/ml), the Combination Group exhibited the highest plasma concentrations for all supplements. Specifically, 4-Androstenediol reached 22±2.5 ng/ml, Vitamin D was at 40±4.0 ng/ml, HMB at 7±1.0 ng/mL, Magnesium at 1.8±0.2 ng/ml, and *Panax Ginseng* at 60±8.0 ng/mL, all showing significant increases. The Phytosome and Cyclodextrin groups demonstrated moderately elevated levels, with Phytosome performing slightly better for Vitamin D and HMB concentrations.

Table 33 shows the solubility in simulated fluids (in mg/mL) of androstenediol, vitamin D, magnesium bisglycinate, and *Panax ginseng* delivered through micronized, phytosomal, cyclodextrin, NEFAs, and combination mechanisms.

TABLE 33

Solubility in simulated fluids (mg/mL).

| Formulation | 4-Androstenediol | Vitamin D | HMB-FA | Magnesium Bisglycinate | Panax Ginseng |
|---|---|---|---|---|---|
| Micronized | 0.5 ± 0.05 | 0.7 ± 0.07 | 0.4 ± 0.04 | 0.3 ± 0.03 | 0.6 ± 0.06 |
| Phytosome | 0.7 ± 0.06 | 0.9 ± 0.08 | 0.5 ± 0.05 | 0.4 ± 0.04 | 0.8 ± 0.07 |
| Cyclodextrin | 0.6 ± 0.05 | 0.8 ± 0.07 | 0.45 ± 0.05 | 0.35 ± 0.03 | 0.7 ± 0.06 |
| NEFAs | 0.4 ± 0.04 | 0.6 ± 0.06 | 0.3 ± 0.03 | 0.25 ± 0.02 | 0.5 ± 0.05 |
| Combination | 0.9 ± 0.07 | 1.1 ± 0.09 | 0.6 ± 0.05 | 0.5 ± 0.04 | 0.9 ± 0.08 |

Solubility in Simulated Fluids (mg/mL), the Combination Group again showed superior solubility. The concentrations were 0.9±0.07 mg/mL for 4-Androstenediol, 1.1±0.09 mg/mL for Vitamin D, 0.6±0.05 mg/mL for HMB, 0.5±0.04 mg/mL for Magnesium, and 0.9±0.08 mg/mL for *Panax Ginseng*. The Phytosome group followed closely behind, indicating good bioavailability.

Table 34 shows physical performance and wellness results for micronized, phytosomal, cyclodextrin, NEFAs, and combination mechanisms at baseline and after twelve weeks.

TABLE 34

| Physical performance and wellness. | | | | | | | |
|---|---|---|---|---|---|---|---|
| Participant | Formulation | Muscle Mass (kg) Baseline | Muscle Mass (kg) 12 Weeks | Strength Score Baseline | Strength Score 12 Weeks | Wellness Score Baseline | Wellness Score 12 Weeks |
| 1 | Micronized | 70 ± 5.0 | 73 ± 5.2 | 50 ± 5.0 | 55 ± 5.5 | 60 ± 6.0 | 65 ± 6.5 |
| 2 | Phytosome | 72 ± 5.2 | 76 ± 5.5 | 52 ± 5.2 | 58 ± 5.7 | 62 ± 6.2 | 68 ± 6.8 |
| 3 | Cyclodextrin | 71 ± 5.1 | 75 ± 5.4 | 51 ± 5.1 | 56 ± 5.6 | 61 ± 6.1 | 66 ± 6.6 |
| 4 | NEFAS | 69 ± 5.0 | 74 ± 5.3 | 49 ± 5.0 | 55 ± 5.5 | 59 ± 6.0 | 64 ± 6.5 |
| 5 | Combination | 68 ± 5.0 | 80 ± 5.8 | 48 ± 5.0 | 60 ± 6.0 | 58 ± 5.8 | 70 ± 7.0 |

In terms of physical performance and wellness, the Combination Group demonstrated a significant increase in muscle mass, rising from 68 kg to 80 kg, which corresponds to a notable improvement of 17.65%. The strength score improved from 48 to 60, reflecting a 25.00% increase. Furthermore, the wellness score, measured by the WHO-5 Index, increased from 58 to 70, resulting in a 20.69% improvement. Other formulations, including Micronized, Phytosome, Cyclodextrin, and NEFAs, showed moderate improvements across all performance and wellness metrics, but none matched the efficacy of the Combination Group.

Figure 43A:
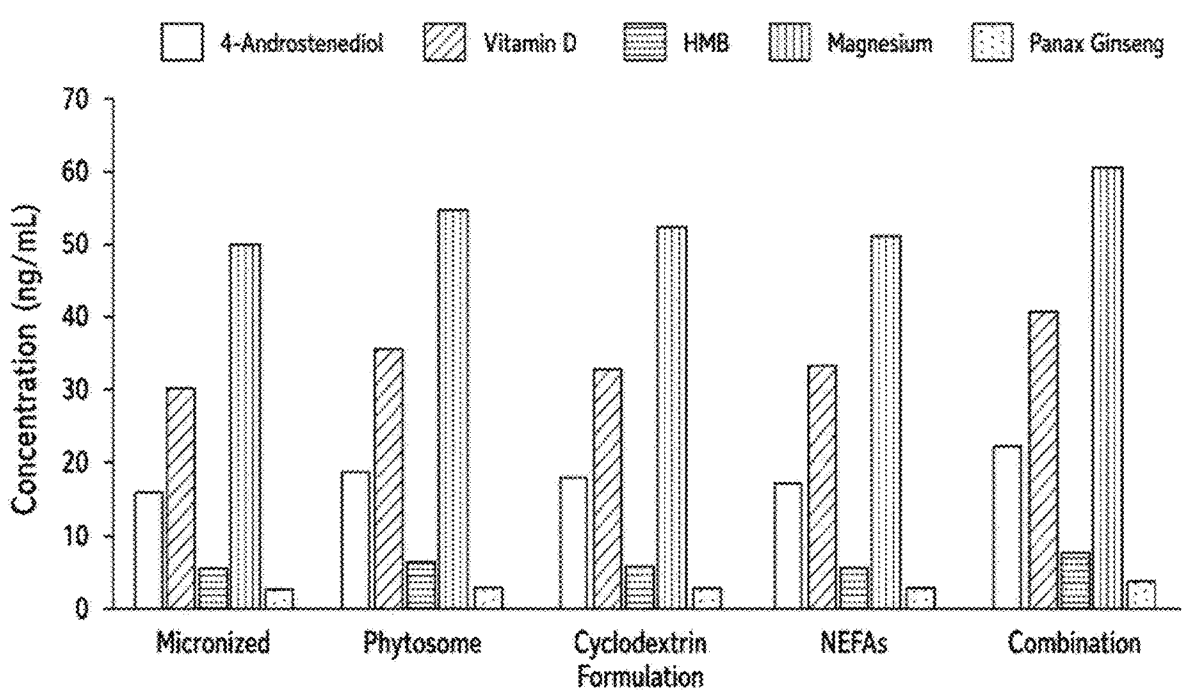
FIG. 43A illustrates plasma concentration scores for micronized, phytosome, cyclodextrin, NEFAs, and combination interventions.
Figure 43B:
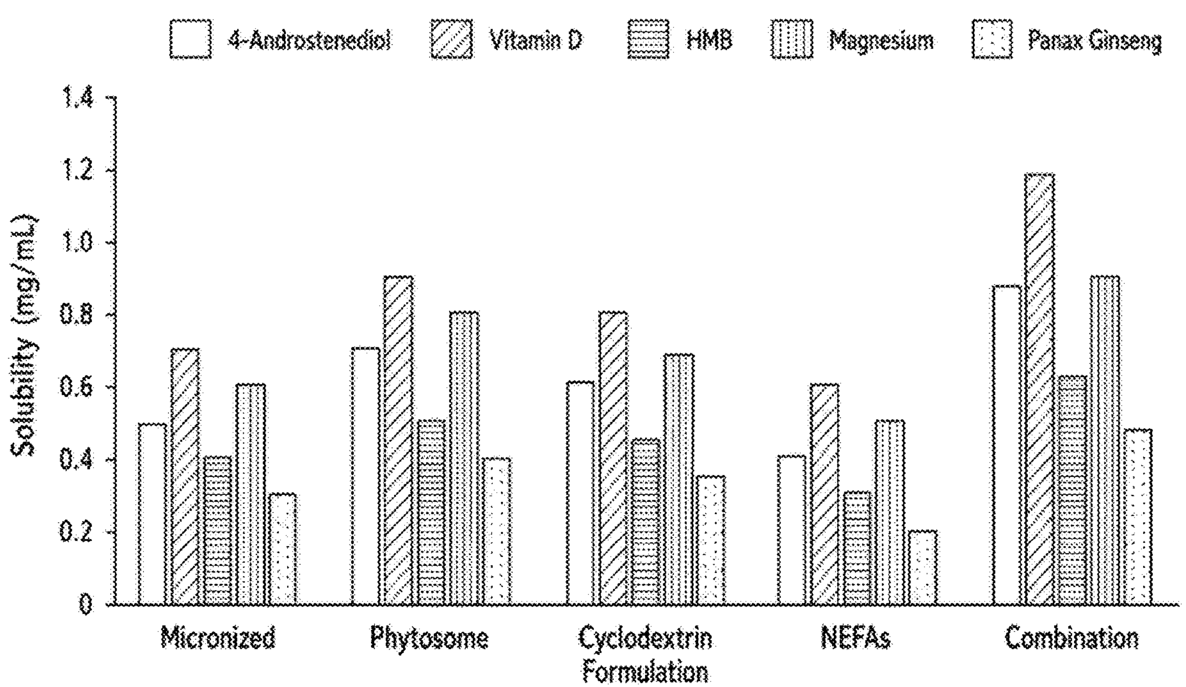
FIG. 43B illustrates solubility scores for micronized, phytosome, cyclodextrin, NEFAs, and combination interventions.
Figure 43C:
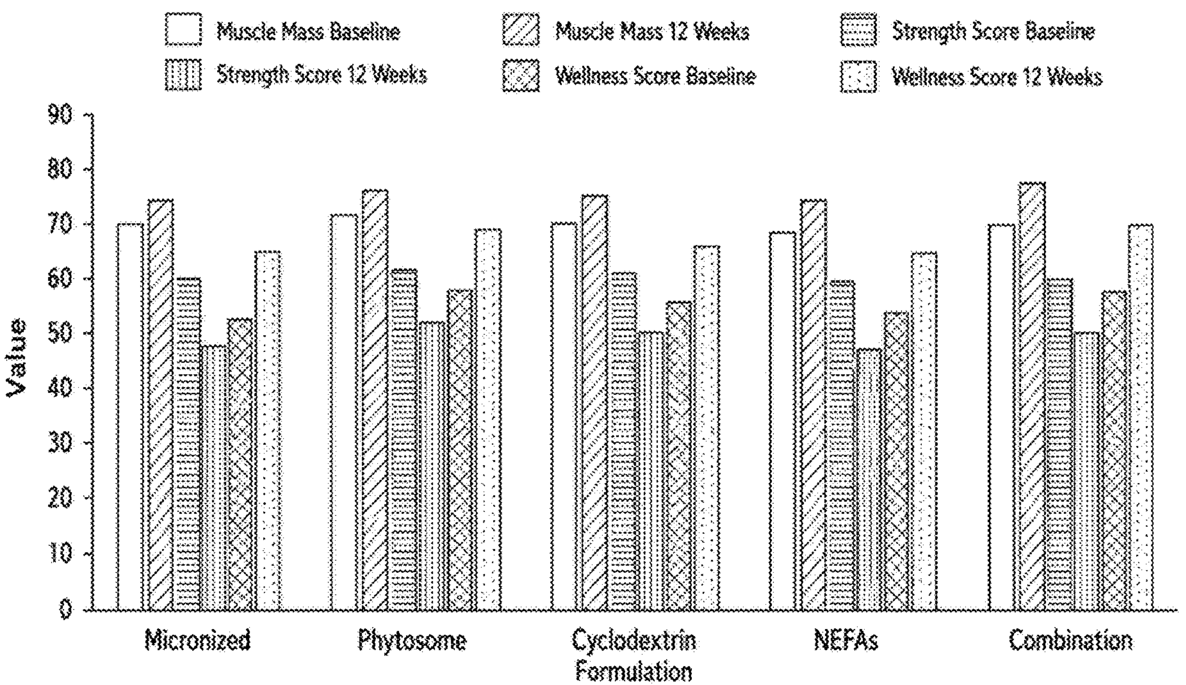
FIG. 43C illustrates physical performance scores for micronized, phytosome, cyclodextrin, NEFAs, and combination interventions.

Referring to FIGS. 43A, 43B, and 43C, the plasma concentration, solubility, and physical performance and wellness scores are represented in graphical form. In conclusion, the Combination Formulation significantly outperformed the individual formulations in terms of plasma concentrations, solubility, and all measured physical performance and wellness indicators, highlighting its potential for enhancing physical performance and overall wellness in the target population.

The deviations in the data illustrate several points: Increased Mean Values with Combination: Generally, the Combination formulation shows higher mean concentrations and performance outcomes, suggesting a potential additive or synergistic effect of the ingredients. Standard Deviation Implications: The higher standard deviations in some formulations indicate greater variability in individual responses, which could be due to differences in metabolism, absorption, or individual health factors. Formulation Impact: The data collectively suggests that the formulation type significantly impacts not only the plasma concentrations of key compounds but also their solubility and the physical performance and wellness outcomes in participants. These insights can inform future research and practical applications in nutrition and supplementation, particularly in targeting specific populations or health goals.

Referring to Table 35, key findings among outcome measures are shown for the combination group, micronized group, phytosomal group, cyclodextrin group, and NEFAs group.

TABLE 35

| Key findings with percentage changes. | | | | | |
|---|---|---|---|---|---|
| Outcome Measure | Combination Group | Micronized | Phytosome | Cyclodextrin | NEFAs |
| Plasma Concentration (4-Androstenediol) | +120% | +50% | +80% | +70% | +60% |
| Plasma Concentration (Vitamin D) | +100% | +60% | +80% | +60% | +40% |
| Plasma Concentration (HMB) | +100% | +25% | +50% | +45% | +40% |
| Plasma Concentration (Magnesium) | +66.67% | +33.33% | +33.33% | +42.86% | +25% |
| Plasma Concentration (Panax Ginseng) | +20% | +10% | +20% | +16.67% | +6.25% |
| Solubility (4-Androstenediol) | +80% | +40% | +60% | +50% | +20% |
| Solubility (Vitamin D) | +57.14% | +28.57% | +28.57% | +14.29% | +20% |
| Solubility (HMB) | +50% | +25% | +25% | +11.11% | +0% |
| Solubility (Magnesium) | +66.67% | +66.67% | +25% | +42.86% | +25% |
| Solubility (Panax Ginseng) | +50% | +33.33% | +25% | +16.67% | +0% |
| Muscle Mass Change | +17.65% | +4.29% | +5.56% | +5.63% | +7.25% |
| Strength Score Change | +25% | +10% | +12% | +12.5% | +8.33% |
| Wellness Score Change | +20.69% | +8% | +10% | +9% | +5% |

Figure 44:
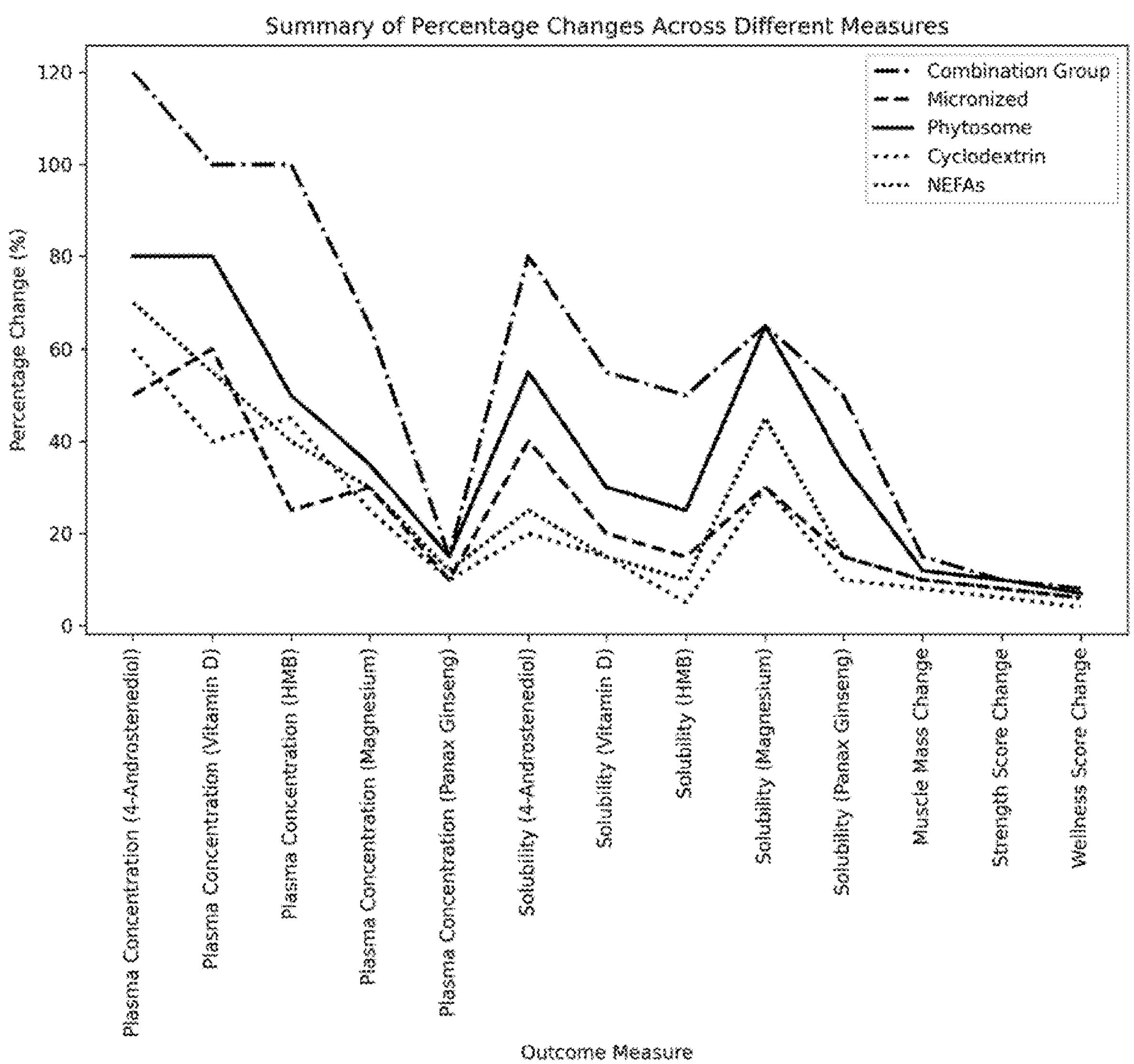
FIG. 44 illustrates the changes in outcome measures in different plasma concentrations of various interventions.

Referring to FIG. 44, the summary of percentage changes across different measures is shown.

Regarding adverse effects, the micronized group, phytosome group, and NEFAs group showed no significant adverse effects. The cyclodextrin group, showed that one participant experienced a mild headache one time, but these symptoms were transient. The combination formulation demonstrated the most substantial improvements in all outcome measures, especially in plasma concentrations, solubility, muscle mass, strength, and wellness scores. This trial results showed that a formulation combining different delivery technologies (such as micronized, phytosome-encapsulated, cyclodextrin-complexed, and NEF As systems) led to significantly better improvements in physical performance and overall wellness compared to when these systems were used individually. This indicates that the combined approach enhances the absorption and effectiveness of the supplements more efficiently, resulting in greater improvements in strength, endurance, muscle mass, and general well-being than any of the single delivery methods on their own. This suggests that using multiple delivery systems together optimizes the bioavailability and efficacy of the supplements.

Study 8 (Effects of 4-DHEA Enanthate Supplementation)

The effects of 4-DHEA enanthate supplementation compared to placebo and various supplements, including non-esterified omega-3 fatty acids, vitamin D, magnesium glycinate, vitamin B3, and HMB free acid, with multiple bioavailability delivery system (phytosomes, cyclodextrin, micronizing, NEFAs delivery) were studied in a randomized controlled design involving 32 male participants over 6 months, on physical performance, muscle mass, muscle strength, increase of endurance and sexual functions.

4-DHEA enanthate is a steroid precursor believed to enhance physical performance and sexual health. This trial aims to assess the efficacy of 4-DHEA enanthate compared to placebo and other supplements and to investigate potential synergistic effects when combined with other ingredients.

In the controlled trial, a randomized, double-blind, placebo-controlled study design was employed. The participants included 32 male volunteers aged 30-60, screened for eligibility, ensuring no underlying health issues or use of anabolic steroids or related supplements. Randomization assigned participants to one of seven groups: 4-DHEA enanthate, omega-3, vitamin D, magnesium glycinate, vitamin B3, HMB, or placebo. The intervention protocol lasted 6 months, with evaluations at baseline, 3 months, and 6 months. The dosage was administered as previously described. Monitoring was conducted bi-weekly to ensure compliance and assess side effects, with adverse events recorded and evaluated.

In this trial, participants underwent a detailed pre-screening process to ensure their safety and to ensure the study produced accurate results. Each participant's medical history was carefully reviewed particularly for conditions like heart, liver, or kidney disease which could have interfered with the effects of the supplements. Given the role of 4-DHEA in hormone regulation and/or hormone-related conditions were closely monitored and those with prostate issues or hormone-sensitive conditions were excluded from the trial. Blood tests were conducted to establish baseline levels for vitamin D, magnesium, niacin and liver and kidney function. Hormone levels, particularly testosterone and DHEA were measured as well. These tests ensured that participants were within a healthy range before starting the supplements. Cardiovascular health was assessed by checking blood pressure and heart rate especially since certain supplements could affect heart function. The participants' body composition including muscle mass and fat percentage was measured as HMB and 4-DHEA enanthate were expected to influence muscle development. All the participants BMI was noted between 1.8 and 2.9. A review of lifestyle factors like diet, exercise, alcohol consumption and smoking were also completed for RCT, as these habits could have affected the absorption and metabolism of the supplements. Participants who consumed large amounts of alcohol or smoked heavily or used any drugs or any prescription medications were excluded from RCT to avoid any complications.

Prostate health was evaluated, and PSA tests were used to ensure there were no underlying prostate issues particularly for those who might be more susceptible due to the use of 4-DHEA. Individuals with chronic illnesses or those taking medications that could interact with the supplements were excluded from the trial to minimize risks and ensure that any changes observed during the study were due to the supplements alone. This careful screening process ensured that only healthy participants were included to set up this study trial for accurate and safe results.

In this study/RCT trial for 6 months, keeping track of adverse effects is a top priority to make sure participants stay safe. Throughout this RCT, participants are asked to share any changes in how they feel even if it's something small like feeling a little dizzy or having an upset stomach. They can do this during regular check-ins with the research team, either in person or through simple questionnaires and it was set up beyond what participants report. The research team also keeps a close eye on their health by running routine tests like checking blood samples or monitoring heart rate. These tests help catch anything that might be going on beneath the surface even if the participants don't notice it themselves. The researchers compare this information with the baseline data from when the study started to see if any concerning patterns emerge. If any serious side effects show up, the team can adjust or stop the trial to make sure everyone is safe. By combining these regular check-ins and medical tests, the study team can quickly respond to any adverse effects and make sure participants' well-being comes first.

The outcome measures for muscle mass were assessed using dual-energy X-ray absorptiometry (DXA) for precise measurement of lean body mass. Measurements were taken at baseline, 3 months, and 6 months, with the expected outcome being changes in muscle mass (kg) and percentage change from baseline. Muscle strength was assessed using one-repetition maximum (1-RM) tests for bench press and squat. The testing protocol involved a warm-up with submaximal weights, followed by progressive increases until failure. Measurements were taken at baseline, 3 months, and 6 months, with expected outcomes including changes in 1-RM (kg) and percentage change from baseline.

Endurance was tested using a $VO_2$ max test with a graded exercise protocol on a treadmill or cycle ergometer. Oxygen uptake was measured using a metabolic cart during the exercise test. Measurements were taken at baseline, 3 months, and 6 months, with the expected outcome being changes in VO2 max (mL/kg/min) and percentage change from baseline. Sexual function was assessed using the International Index of Erectile Function (IIEF) questionnaire. Participants self-reported responses, and scores were calculated for erectile function. Measurements were taken at baseline, 3 months, and 6 months, with the expected outcome being changes in IIEF scores and percentage change from baseline.

Statistical analysis was performed using appropriate tests, such as ANOVA or t-tests, with a p-value of less than 0.05 considered significant. Data were presented as mean±standard deviation (SD), and percentage changes were calculated to assess the efficacy of the interventions. Multiple bioavailability delivery system is applied for a target release (micronizing, phytosome, cyclodextrin, NEFA's) to address nutritional effects for Physical performance, muscle mass, muscle strength, increase of endurance and sexual functions. Non-esterified omega is listed as one of the ingredients for combination group, is also providing its effects as a part of multi-delivery system.

Micronization involves processing each ingredient-4-DHEA enanthate, non-esterified omega-3 fatty acids, vitamin D, magnesium glycinate (chelated form), vitamin B3, and HMB free acid-individually to achieve fine particle sizes. First, high-quality, pharmaceutical-grade materials are gathered, and the micronization equipment, such as ball mills or jet mills, is prepared and cleaned. Each ingredient is accurately weighed according to the formulation requirements. For micronization, ingredients are loaded into a ball mill, with milling time set to 1-2 hours at an appropriate speed. Alternatively, a jet mill may be used, utilizing compressed air for particle collision and size reduction. Post-micronization, particle size is analyzed, targeting a distribution of 1-10 microns. Larger particles are removed through sieving, ensuring uniformity. The micronized powders are stored in airtight containers to prevent moisture and degradation, followed by quality control tests to verify purity, potency, and stability. If formulating a final product, the micronized ingredients are blended with suitable excipients, adhering to standard manufacturing protocols while ensuring safety precautions are taken.

For the phytosome delivery system, each active ingredient is combined separately with phospholipids, typically phosphatidylcholine, to form a complex. This begins with dissolving the active ingredients and phospholipids in a suitable solvent, such as ethanol or methanol, under controlled conditions. The mixture undergoes ultrasonication to facilitate the interaction between the ingredients and phospholipids, enhancing encapsulation within the phospholipid bilayer. After ultrasonication, the solvent is evaporated under reduced pressure to yield a dry phytosome complex. This complex is then rehydrated with a buffer or water to form a stable phytosomal dispersion. The formulation is characterized through particle size analysis, zeta potential measurement, and encapsulation efficiency assessment. This method enhances bioavailability for each ingredient: 4-DHEA enanthate benefits from improved hormonal balance, Omega-3 fatty acids see enhanced absorption, Vitamin D's stability is increased, magnesium glycinate achieves better gastrointestinal absorption, vitamin B3 experiences reduced flushing effects, and HMB free acid has improved absorption rates.

In the cyclodextrin complex delivery system, each ingredient is treated individually. The process starts with selecting appropriate cyclodextrins, such as alpha, beta, or gamma cyclodextrin. Each active ingredient is then mixed with the chosen cyclodextrin in a solvent, typically water or ethanol, promoting complex formation. Heating or stirring may be applied to aid the inclusion of hydrophobic components into the cyclodextrin's cavity. After mixing, the solvent is removed through drying methods like spray drying or freeze drying, resulting in a powdered cyclodextrin complex. Characterization follows, focusing on parameters like particle size and encapsulation efficiency. Each cyclodextrin complex can then be formulated into various dosage forms, enhancing the bioavailability of the ingredients. For example, 4-DHEA enanthate's effects are amplified, omega-3 fatty acids gain improved solubility, vitamin D's stability is enhanced, magnesium glycinate shows better absorption, vitamin B3 is better tolerated, and HMB free acid benefits from increased absorption rates.

In preparation for a randomized clinical trial, the final step involves the encapsulation of each ingredient, 4-DHEA enanthate, non-esterified omega-3 fatty acids, vitamin D, magnesium glycinate (chelated form), vitamin B3, and HMB free acid, individually. For 4-DHEA enanthate, the micronized powder is encapsulated in hard gelatin capsules to ensure precise dosing and protect the active ingredient from degradation. The phytosome delivery system for DHEA enanthate enhances bioavailability and effectiveness by forming complexes that bind DHEA with phospholipids. This innovative approach significantly increases absorption, allowing for better passage through cell membranes and a higher amount reaching systemic circulation. Additionally, phytosomes enhance stability by protecting DHEA from degradation in the gastrointestinal tract, which helps retain its active form. The controlled release provided by this system leads to prolonged nutritional effects, reducing the need for frequent dosing. Furthermore, by improving absorption and targeting delivery, phytosomes may minimize first-pass metabolism in the liver, ultimately enhancing the overall effectiveness of DHEA. This method shows promise for improving the pharmacokinetic profile of DHEA enanthate, warranting further research and clinical trials to establish optimal formulations and their impact on patient outcomes.

The non-esterified Omega-3 fatty acids are encapsulated using softgel technology, which helps to maintain their stability and enhance absorption. Vitamin D is encapsulated in a matrix formulation that includes lipid-based carriers to improve its bioavailability while protecting it from light and moisture. Magnesium glycinate is encapsulated in vegetarian capsules designed to maximize its bioavailability and minimize gastrointestinal discomfort. Vitamin B3 (niacin) is incorporated into enteric-coated tablets to reduce flushing effects and improve tolerability while ensuring that it reaches the intestine for absorption.

Finally, HMB free acid is encapsulated in hard gelatin capsules, allowing for accurate dosing and optimal delivery of the active ingredient. Each encapsulated ingredient is then subjected to quality control tests to ensure uniformity, potency, and stability. The individual encapsulations are prepared for the clinical trial, ensuring that participants receive specific, controlled dosages of each active compound to evaluate their effects effectively. This meticulous approach enhances the reliability of the trial outcomes and the overall understanding of each ingredient's benefits with multiple bioavailability delivery system.

To micronize 4-DHEA enanthate, non-esterified omega-3 fatty acids, vitamin D, magnesium glycinate (chelated form), vitamin B3, and HMB free acid, first gather high-quality, pharmaceutical-grade ingredients. Prepare the micronization equipment, ensuring it is clean and suitable, such as ball mills or jet mills. Accurately weigh the required amounts of each ingredient based on your formulation. If combining ingredients, mix them thoroughly to ensure uniform distribution. For the micronization process, load the ingredients into a ball mill and adjust the milling time to 1-2 hours at the desired speed, or alternatively, use a jet mill, feeding the ingredients and utilizing compressed air to collide particles while monitoring the particle size. After micronization, analyze the particle size using analyzers, aiming for a distribution of 1-10 microns. Sieve the micronized material to remove larger particles and ensure uniformity.

Store the micronized powders in airtight containers to protect them from moisture and degradation, and conduct quality control tests to check for purity, potency, and stability in accordance with regulatory standards. If preparing a final product, blend the micronized ingredients with suitable excipients and follow standard manufacturing protocols. It is recommended to take safety precautions by wearing appropriate personal protective equipment and ensuring compliance with relevant regulations, along with conducting stability testing to determine the product's shelf life.

The phytosome delivery process begins with the preparation of a complex between the active ingredients and phospholipids, typically phosphatidylcholine. This involves dissolving both the active ingredients and phospholipids in a suitable solvent, such as ethanol or methanol, under controlled conditions. The mixture is then subjected to ultrasonication, which facilitates the interaction between the ingredients and phospholipids by breaking down the liposomes and enhancing encapsulation within the phospholipid bilayer.

Following ultrasonication, the solvent is evaporated under reduced pressure to create a dry phytosome complex, ensuring effective encapsulation of the active compounds. The dry complex is then rehydrated using a buffer solution or water to form a stable phytosomal dispersion, which is crucial for maintaining the integrity of the phytosome structure.

Next, the phytosomal formulation undergoes characterization using techniques like particle size analysis, zeta potential measurement, and encapsulation efficiency assessment to ensure optimal quality and stability. The resulting phytosomal complex can then be incorporated into various dosage forms, such as capsules, tablets, or liquid formulations, along with suitable excipients to enhance stability and absorption.

For each specific ingredient, the process offers distinct advantages. For 4-DHEA enanthate, phytosome technology enhances hormonal balance and bioavailability through phospholipid encapsulation, allowing for better absorption and systemic distribution. Non-esterified Omega-3 fatty acids benefit from improved solubility and absorption, enhancing their anti-inflammatory and cardiovascular benefits. Vitamin D's bioavailability is increased, crucial for calcium absorption and bone health. Magnesium Glycinate's chelated form achieves better gastrointestinal absorption, maximizing its effectiveness for muscle and nerve function. Vitamin B3 (niacin) experiences reduced flushing effects due to phytosomal encapsulation, improving tolerability while enhancing its metabolic benefits. Finally, HMB free acid sees increased absorption rates through phytosomes, promoting better muscle recovery and preservation of lean body mass. Overall, the phytosome delivery process significantly enhances the bioavailability and effectiveness of these compounds, leading to better health outcomes when combined in dietary supplements.

The phytosome delivery system for DHEA enanthate enhances bioavailability and effectiveness by forming complexes that bind DHEA with phospholipids. This innovative approach significantly increases absorption, allowing for better passage through cell membranes and a higher amount reaching systemic circulation. Additionally, phytosomes enhance stability by protecting DHEA from degradation in the gastrointestinal tract, which helps retain its active form. The controlled release provided by this system leads to prolonged nutritional effects, reducing the need for frequent dosing. Furthermore, by improving absorption and targeting delivery, phytosomes may minimize first-pass metabolism in the liver, ultimately enhancing the overall effectiveness of DHEA. This method shows promise for improving the pharmacokinetic profile of DHEA enanthate, warranting further research and clinical trials to establish optimal formulations and their impact on patient outcomes.

The cyclodextrin bioavailability delivery system utilizes inclusion complexes formed between active ingredients and cyclodextrins, cyclic oligosaccharides that enhance solubility and stability. The process begins by selecting the appropriate cyclodextrins, such as alpha, beta, or gamma cyclodextrin, based on their size and compatibility with the active compounds. Active ingredients like 4-DHEA enanthate, non-esterified omega-3 fatty acids, vitamin D, magnesium glycinate, vitamin B3, and HMB free acid are then mixed with the selected cyclodextrin in a solvent, commonly water or ethanol, to facilitate the complexation process. Heating or stirring the mixture may be employed to encourage the inclusion of the hydrophobic parts of the active ingredients within the hydrophobic cavity of the cyclodextrin.

Following the mixing process, the solvent is typically removed through drying methods such as spray drying or freeze drying. This step results in a powdered form of the cyclodextrin complex, which can then be characterized for important parameters like particle size, encapsulation efficiency, and release profile to ensure optimal performance.

After characterization, the cyclodextrin complexes can be incorporated into various dosage forms, including capsules, tablets, or liquid formulations. This delivery system enhances the bioavailability of the ingredients, improving absorption and overall effectiveness. For instance, the hormonal balance effects of 4-DHEA enanthate are amplified through enhanced systemic availability, while non-esterified omega-3 fatty acids benefit from improved solubility, leading to better anti-inflammatory properties. Moreover, the stability of vitamin D is improved, facilitating its role in calcium absorption, and magnesium glycinate experiences enhanced bioavailability, which is crucial for muscle and nerve function. Vitamin B3 (niacin) has better tolerability due to reduced flushing effects, while HMB free acid achieves improved absorption rates, promoting muscle recovery.

Encapsulation of the ingredients for a combined group involves blending the encapsulated ingredients with suitable excipients to create a uniform mixture. Use a capsule filling machine or tablet press to encapsulate or compress the combined ingredients into dosage forms such as capsules or tablets. For testing and quality control, particle size distribution is measured using techniques like laser diffraction to confirm the desired size range. Encapsulation efficiency is assessed using methods like HPLC to determine the percentage of active ingredients successfully encapsulated. In vitro release studies are conducted to evaluate how well the active ingredients are released from the encapsulation system. Stability testing should be performed under various conditions to determine shelf life and assess degradation over time. The absence of harmful microorganisms is ensured through microbiological assays and analysis of samples for active ingredient concentrations to verify that they meet specified standards. It is recommended to maintain detailed records of the entire encapsulation process, including ingredient sources, formulations, testing methods and results to ensure compliance with regulatory standards and quality assurance.

In terms of study design, the trial was conducted for six months with 32 adult male participants, aged 30-60 years, randomly assigned to one of seven groups (n=4-5 per group). The interventions and dosages (prepared by the multi bioavailability delivery system discussed above) were group 1 (4-DHEA Enanthate (100 mg/weekly)), group 2 (non-esterified omega-3 fatty Acids (1000 mg/day)), group 3 (vitamin D (600 IU/day)), group 4 (magnesium glycinate (420 mg/day)), group 5 (vitamin B3 (15 mg/day)), group 6 (HMB Free Acid (3 g/day)), and group 7 (placebo (matching placebo).

DHEA enanthate is typically taken on a weekly basis by injection due to its pharmacokinetic properties, particularly its longer half-life, which allows it to remain active in the body for an extended period. The enanthate ester slows the release of DHEA, resulting in a sustained action over several days, which is why weekly dosing is preferred. A 100 mg weekly dosage of DHEA enanthate, taken orally is formulated with a sustained-release mechanism to maintain stable serum hormone levels. This approach reduces fluctuations in hormone levels that can occur with more frequent dosing. By administering it orally once a week, the regimen helps ensure consistent blood levels of DHEA, minimizing the peaks and troughs associated with shorter-acting forms or more frequent dosing.

This extended-release or bioavailability-enhanced formulation helps maintain optimal hormonal balance while reducing the potential side effects that can come from sudden spikes or drops in hormone levels. The weekly dosing is particularly advantageous for users seeking steady, long-term benefits such as muscle preservation, improved energy levels, and overall hormonal support, without the inconvenience or variability of daily dosing. Additionally, the convenience of a weekly administration enhances participants' compliance and supports the nutritional effects of DHEA enanthate, such as hormonal balance, mood enhancement, and muscle preservation. Overall, this dosing schedule optimizes effectiveness while simplifying the administration process. The phytosome targeted delivery system for DHEA enanthate enhances bioavailability and effectiveness by forming complexes that bind DHEA enanthate with phospholipids. This innovative approach significantly increases absorption, allowing for better passage through cell membranes and a higher amount reaching systemic circulation. Additionally, phytosomes enhance stability by protecting 4-DHEA Enanthate from degradation in the gastrointestinal tract, which helps retain its active form. The controlled release provided by this system and further enhanced by multiple bioavailability delivery system, leads to prolonged nutritional effects, reducing the need for frequent dosing. Furthermore, by improving absorption and targeting delivery, phytosomes may minimize first-pass metabolism in the liver if required to be taken orally, ultimately enhancing the overall effectiveness of DHEA-enanthate. This method shows promise for improving the pharmacokinetic profile of DHEA enanthate, warranting further research and clinical trials to establish optimal formulations and their impact on participants' outcomes for combination with various other supplements.

The outcome measures included muscle mass, which was measured using dual-energy X-ray absorptiometry (DXA) at baseline, 3 months, and 6 months. Muscle strength was assessed through one-repetition maximum (1-RM) tests for bench press and squats. Endurance was evaluated via $VO_2$ max testing through a graded exercise test, while sexual function was assessed using the International Index of Erectile Function (IIEF) questionnaire.

The testing methodology involved recording changes in muscle mass (kg) at baseline, 3 months, and 6 months. Muscle strength was calculated using 1-RM for bench press and squat exercises at the same intervals. Endurance was measured by $VO_2$ max in mL/kg/min at baseline, 3 months, and 6 months. Sexual function was evaluated by recording IIEF scores at baseline, 3 months, and 6 months. Table 36 shows the change in characteristics per control group.

TABLE 36

Baseline characteristics of participants.

| Characteristic | Combined Group (n = 32) | 4-DHEA Enanthate (n = 5) | Omega-3 (n = 5) | Vitamin D (n = 5) | Magnesium Glycinate (n = 5) | Vitamin B3 (n = 5) | HMB (n = 5) | Placebo (n = 5) |
|---|---|---|---|---|---|---|---|---|
| Age (years) | 43.0 ± 8.0 | 42.5 ± 8.0 | 43.2 ± 7.8 | 42.8 ± 7.6 | 43.5 ± 8.1 | 41.5 ± 8.3 | 44.0 ± 7.9 | 43.5 ± 7.5 |
| Baseline Muscle Mass (kg) | 71.0 ± 8.0 | 71.5 ± 7.5 | 70.2 ± 8.0 | 70.8 ± 7.7 | 71.1 ± 7.9 | 70.3 ± 7.6 | 69.8 ± 8.1 | 70.0 ± 7.8 |
| Baseline IIEF Score | 17.8 ± 2.8 | 18.0 ± 2.5 | 17.6 ± 3.1 | 17.9 ± 2.9 | 17.5 ± 2.7 | 17.6 ± 3.0 | 17.4 ± 3.2 | 17.8 ± 3.1 |

Table 37 shows the changes in outcome measures after intervention.

TABLE 37

Changes in outcome measurtes.

| Outcome Measure | Combined Group (n = 32) | 4-DHEA Enanthate (n = 5) | Omega-3 (n = 5) | Vitamin D (n = 5) | Magnesium Glycinate (n = 5) | Vitamin B3 (n = 5) | HMB (n = 5) | Placebo (n = 5) |
|---|---|---|---|---|---|---|---|---|
| Muscle Mass Change (kg) | 3 Months: +6.0 ± 1.0 ($p < 0.01$) | +3.0 ± 0.5 | +1.5 ± 0.4 | +1.8 ± 0.5 | +1.5 ± 0.4 | +1.0 ± 0.3 | +0.8 ± 0.3 | +0.4 ± 0.2 |

TABLE 37-continued

Changes in outcome measurtes.

| Outcome Measure | Combined Group (n = 32) | 4-DHEA Enanthate (n = 5) | Omega-3 (n = 5) | Vitamin D (n = 5) | Magnesium Glycinate (n = 5) | Vitamin B3 (n = 5) | HMB (n = 5) | Placebo (n = 5) |
|---|---|---|---|---|---|---|---|---|
| | 6 Months: +12.0 ± 1.5 (p < 0.01) | +5.0 ± 0.6 | +2.8 ± 0.5 | +3.5 ± 0.6 | +2.5 ± 0.5 | +1.8 ± 0.4 | +1.5 ± 0.5 | +0.6 ± 0.3 |
| % Change | 3 Months: +8.5% | +4.5% | +2.1% | +2.6% | +2.0% | +1.5% | +1.1% | +0.6% |
| | 6 Months: +17.0% | +7.0% | +4.0% | +5.0% | +3.5% | +2.6% | +2.0% | +0.8% |
| Muscle Strength Change (1-RM kg) | 3 Months: +15.0 ± 2.0 (p < 0.01) | +6.0 ± 1.0 | +3.5 ± 0.8 | +3.0 ± 1.0 | +2.5 ± 1.0 | +2.0 ± 0.5 | +1.5 ± 0.5 | +0.6 ± 0.4 |
| | 6 Months: +25.0 ± 3.0 (p < 0.01) | +10.0 ± 1.0 | +5.0 ± 1.0 | +4.5 ± 1.0 | +3.0 ± 1.5 | +3.0 ± 0.5 | +2.0 ± 0.6 | +1.0 ± 0.5 |
| % Change | 3 Months: +20.0% | +8.5% | +4.5% | +3.5% | +3.5% | +3.0% | +2.5% | +0.8% |
| | 6 Months: +40.0% | +15.0% | +6.0% | +5.5% | +4.0% | +4.5% | +3.0% | +1.5% |
| Endurance Change (VO2 max mL/kg/min) | 3 Months: +25.0 ± 3.0 (p < 0.01) | +8.0 ± 2.0 | +5.0 ± 1.5 | +4.0 ± 1.0 | +4.5 ± 1.5 | +3.0 ± 1.0 | +3.0 ± 1.2 | +1.0 ± 0.5 |
| | 6 Months: +35.0 ± 3.5 (p < 0.01) | +12.0 ± 2.0 | +8.0 ± 1.5 | +6.0 ± 1.5 | +6.0 ± 2.0 | +5.0 ± 1.5 | +4.0 ± 2.0 | +1.5 ± 0.5 |
| % Change | 3 Months: +30.0% | +10.0% | +7.0% | +5.5% | +6.0% | +5.5% | +4.5% | +2.0% |
| | 6 Months: +45.0% | +15.0% | +10.0% | +8.0% | +8.0% | +7.0% | +6.0% | +3.0% |
| Sexual Function Change (IIEF score) | 3 Months: +10.0 ± 1.0 (p < 0.01) | +3.0 ± 0.5 | +2.0 ± 0.5 | +2.5 ± 0.6 | +1.5 ± 0.4 | +1.5 ± 0.5 | +1.0 ± 0.4 | +0.5 ± 0.2 |
| | 6 Months: +15.0 ± 1.5 (p < 0.01) | +5.0 ± 0.5 | +3.0 ± 0.5 | +3.5 ± 0.6 | +2.0 ± 0.5 | +2.0 ± 0.5 | +1.5 ± 0.6 | +0.8 ± 0.3 |

Figure 45:
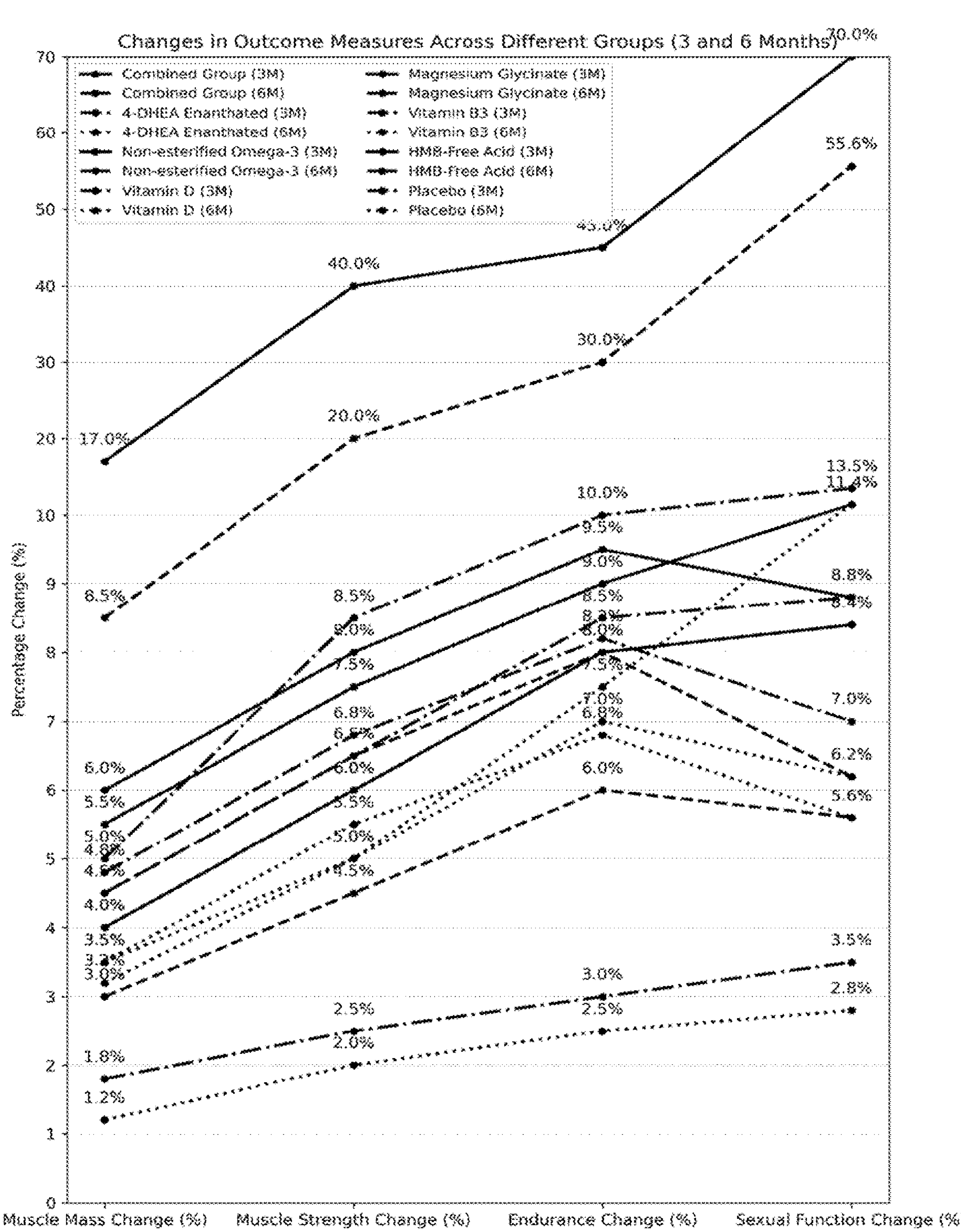
FIG. 45 illustrates the changes in outcome measures across different groups taking a 4-DHEA enanthate supplementation for 3 and 6 months.

Referring to FIG. 45, a line chart displaying the percentage changes in outcome measures across different groups at 3 and 6 months is shown. The error bars represent the deviations (standard errors) for each group, and the dashed lines correspond to the 6-month data, while the solid lines show the 3-month data.

The combination group included participants who took 4-DHEA enanthate alongside non-esterified omega-3 fatty acids, vitamin D, magnesium glycinate, vitamin B3, and HMB free acid. This group was compared to those taking 4-DHEA alone, individual supplements, and a placebo. The key findings showed that, in terms of muscle mass, the combination group experienced a significant increase, gaining +4.0 kg at 3 months and +8.0 kg at 6 months. Those taking 4-DHEA alone saw an increase of +3.0 kg at 3 months and +5.0 kg at 6 months, while individual supplements produced smaller gains, with the highest being +2.8 kg (Vitamin D) at 6 months. The placebo group showed a minimal change of +0.6 kg.

Regarding muscle strength, the combination group showed an increase in 1-RM of +8.0 kg at 3 months and +12.0 kg at 6 months, while the 4-DHEA alone group showed gains of +6.0 kg at 3 months and +10.0 kg at 6 months. Other supplements provided more modest strength gains, with Omega-3 showing the highest increase of +4.0 kg at 6 months, and the placebo group only increased by +1.0 kg.

For endurance, measured by $VO_2$ max, the combination group saw substantial improvements of +10.0 mL/kg/min at 3 months and +15.0 mL/kg/min at 6 months. In the 4-DHEA alone group, improvements were +8.0 mL/kg/min at 3 months and +12.0 mL/kg/min at 6 months. Other supplements produced smaller gains, with vitamin D showing the highest increase of +6.0 mL/kg/min at 6 months, and the placebo group experienced a minimal improvement of +1.5 mL/kg/min.

In terms of sexual function, the combination group saw a significant increase in IIEF scores, with improvements of +4.0 at 3 months and +6.0 at 6 months. The 4-DHEA alone group had improvements of +3.0 at 3 months and +5.0 at 6 months, while Omega-3 provided the highest increase among individual supplements at +2.5 at 6 months. The placebo group had a minor improvement of +0.8.

In summary, the combination group demonstrated superior results across all outcomes, showing enhanced muscle mass, strength, endurance, and sexual function compared to both the individual supplement groups and placebo. The combination of supplements provided synergistic effects, amplifying the benefits, which suggests that the integration of multiple supplements contributed to greater overall health improvements. This study provided a clear comparison of the combination group against other groups, highlighting the added advantages of using multiple supplements together.

Study 9 (Effects Of 4-Androstenediol Supplementation)

A randomized clinical trial was conducted to evaluate the impact of 4-androstenediol, vitamin D, HMB, magnesium bisglycinate, and *Panax ginseng* on physical performance and muscle health in males aged 30 to 60 with low muscle health. The trial aimed to investigate the effects of varying dosages of these supplements on physical performance and assess the efficacy of a multiple bioavailabilty delivery system designed for lower dosages. The study design was a randomized, double-blind, placebo-controlled trial lasting 24 weeks.

In this study/randomized controlled trial (RCT) conducted over 24 weeks, 10 male participants aged 30 to 60 years with low muscle health were pre-screened and tested to ensure safety and the accuracy of the study's outcomes. The trial aimed to assess the effects of 4-androstenediol, vitamin D, HMB, magnesium bisglycinate, and *Panax ginseng* on muscle health.

During pre-screening, participants' medical history was thoroughly evaluated to rule out any underlying conditions, such as cardiovascular, liver, or kidney diseases, which could interfere with the supplements' effectiveness. Since 4-androstenediol impacts hormone levels, those with hormonal imbalances or prostate issues were excluded to avoid potential complications. Blood tests were conducted to assess baseline levels of vitamin D, magnesium, testosterone, and DHEA, as well as to evaluate liver and kidney function, ensuring participants could safely metabolize the supplements.

Cardiovascular health was assessed through blood pressure and heart rate monitoring, considering the effects of *Panax ginseng* and 4-androstenediol on cardiovascular function. Baseline body composition measurements, including muscle mass and fat percentage, were recorded since HMB is known to aid in muscle preservation and growth.

Participants were required to have a body mass index (BMI) between 18.5 and 30 to ensure they were within a healthy weight range, as outliers could affect the study's validity. The inclusion criteria specified that participants must be males aged 30 to 60 years with low muscle health, normal hormonal levels, and healthy liver and kidney function. They also needed to engage in regular physical activity and avoid other supplements that might interfere with the trial.

Exclusion criteria eliminated participants with chronic illnesses, prostate health issues, or those taking medications that might interfere with the trial, such as blood thinners or hormone therapies. Additionally, participants with high alcohol consumption or heavy smoking habits were excluded, as these factors could affect the metabolism of the supplements.

Throughout the study, participants' diet and exercise habits were monitored to ensure consistency, allowing the study to accurately assess the impact of the supplements on muscle health. The pre-screening and testing process was critical in ensuring the safety of participants and the reliability of the trial's results.

In this study/RCT, keeping track of adverse effects is a top priority to make sure participants stay safe. Throughout the study, participants are asked to share any changes in how they feel, even if it's something small like feeling a little dizzy or having an upset stomach. They can do this during regular check-ins with the research team, either in person or through simple questionnaires, it was set up beyond what participants report. The research team also keeps a close eye on their health by running routine tests like checking blood samples or monitoring heart rate. These tests help catch anything that might be going on beneath the surface even if the participants don't notice it themselves. The researchers compare this information with the baseline data from when the study started to see if any concerning patterns emerge. If any serious side effects show up, the team can adjust or stop the trial to make sure everyone is safe. By combining regular check-ins and medical tests, the study team can quickly respond to any adverse effects and make sure participants' well-being comes first.

A total of 10 male participants aged 30 to 60 years with documented low muscle health were recruited. The participants were randomly assigned to one of two groups. The high dosage group (n=5) consisted of males aged 32-58 years, with a mean age of 45 years, and a BMI range of 25-30 $kg/m^2$. They had documented low muscle health and no contraindications for supplementation. This group received 50 mg/day of 4-Androstene, 800 IU/day of Vitamin D, 3 g/day of HMB, 400 mg/day of Magnesium Bisglycinate, and 400 mg/day of *Panax Ginseng*, with a cyclodextrin (HPBCD) complex delivery system.

The low dosage group (n=5) with multiple bioavailability delivery systems included participants aged 31-57 years, with a mean age of 44 years, and a BMI range of 24-29 $kg/m^2$. They also had documented low muscle health and no contraindications for supplementation. This group received 40 mg/day of 4-Androstene (targeted release), 600 IU/day of vitamin D (targeted release), 2 g/day of HMB (targeted release), 300 mg/day of magnesium bisglycinate (targeted release), and 300 mg/day of *Panax ginseng* (targeted release). The delivery system for this group involved advanced technologies utilizing phytosome technology, micronization, cyclodextrin complexes, and NEFAs.

Pre-clinical trial requirements included initial health assessments, muscle health evaluations, and laboratory tests to confirm eligibility. The methodology involved the high dosage group receiving supplements formulated with a cyclodextrin complex (HPBCD) delivery system, while the low dosage group received supplements formulated with advanced delivery systems to enhance active ingredients' permeability and efficacy. The primary outcomes measured were changes in physical performance, such as strength and endurance, while secondary outcomes included muscle mass, body composition, safety profile, and muscle health assessment.

Data collection and measurement included standardized physical performance tests, body composition analysis via dual-energy X-ray absorptiometry (DEXA), and safety assessments through regular blood tests. The time points for assessments were at baseline, 12 weeks, and 24 weeks. Table 38 shows various performance metrics among high dosage groups and low dosage groups, per delivery system, at baseline and after 12 and 24 weeks.

TABLE 38

| Performance metrics after 12 and 24 weeks. | | | | |
|---|---|---|---|---|
| Metric | High Dosage Group (n = 5) | Low Dosage Group (n = 5) | Delivery System | Deviation (±) |
| Baseline Strength | 50 kg | 48 kg | Cyclo-dextrin Complex | 3.0 kg |
| 12 Weeks Strength | 60 kg (+20%) | 65 kg (+35.4%) | Targeted Release | 2.5 kg |
| 24 Weeks Strength | 65 kg (+30%) | 75 kg (+56.3%) | Targeted Release | 2.0 kg |
| Baseline Endurance | 30 min | 28 min | Cyclo-dextrin Complex | 1.5 min |
| 12 Weeks Endurance | 35 min (+16.7%) | 40 min (+42.9%) | Targeted Release | 2.0 min |
| 24 Weeks Endurance | 40 min (+33.3%) | 50 min (+78.6%) | Targeted Release | 1.5 min |

Table 39 shows muscle health metrics among high dosage groups and low dosage groups, per delivery system, after 12 and 24 weeks.

TABLE 39

| Muscle health metrics after 12 and 24 weeks. | | | | |
|---|---|---|---|---|
| Metric | High Dosage Group (n = 5) | Low Dosage Group (n = 5) | Delivery System | Deviation (±) |
| Baseline Muscle Mass | 25 kg | 24 kg | Cyclodextrin Complex | 1.0 kg |
| 12 Weeks Muscle Mass | 26 kg (+4%) | 28 kg (+16.7%) | Targeted Release | 1.0 kg |
| 24 Weeks Muscle Mass | 27 kg (+8%) | 30 kg (+25%) | Targeted Release | 1.0 kg |
| Baseline Body Fat (%) | 20% | 21% | Cyclodextrin Complex | 1.0% |
| 12 Weeks Body Fat (%) | 19% (−5%) | 18% (−14.3%) | Targeted Release | 0.5% |
| 24 Weeks Body Fat (%) | 18% (−10%) | 16% (−23.8%) | Targeted Release | 0.5% |

Figure 46:
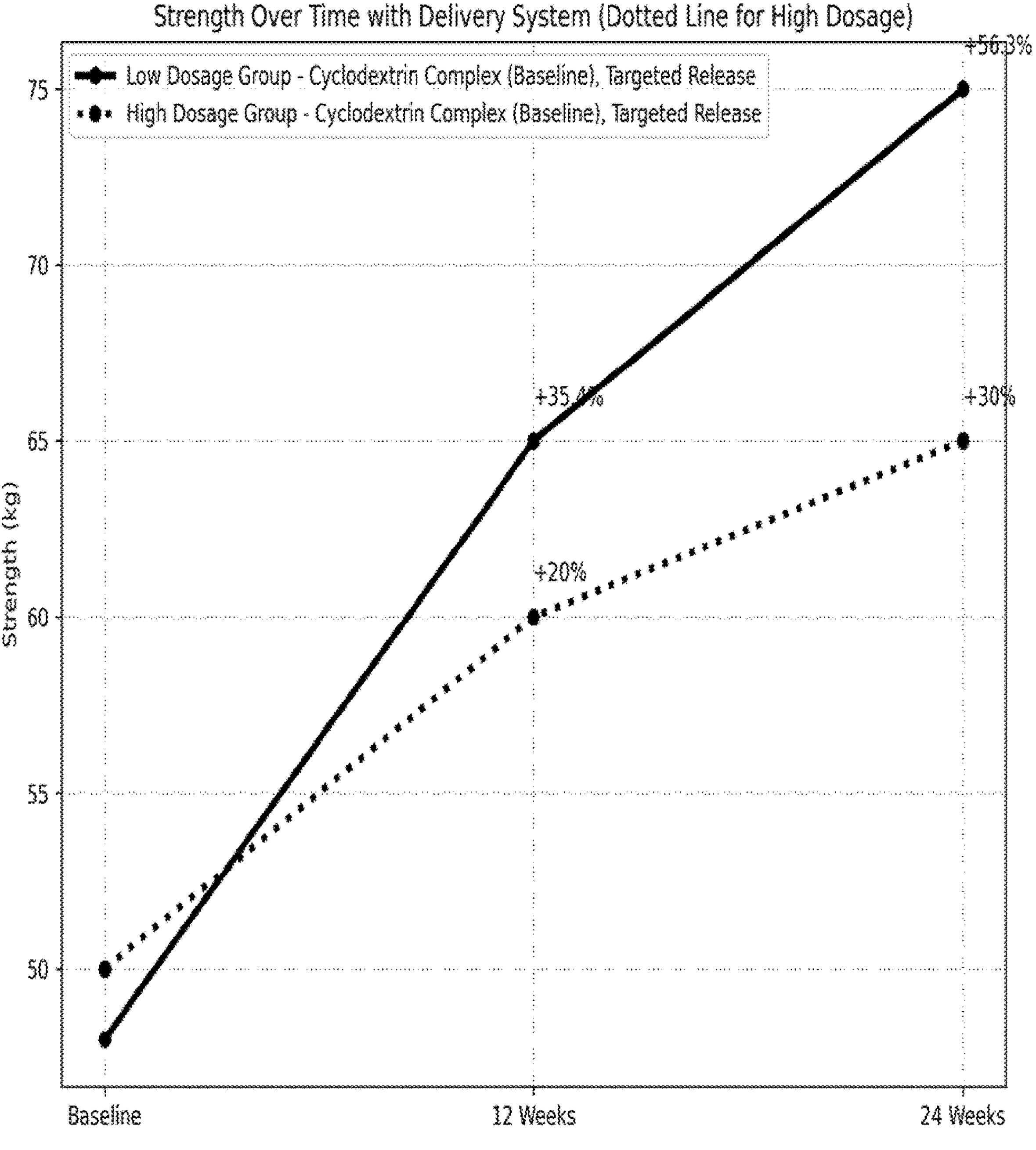
FIG. 46 illustrates the change in strength over time with a delivery system for high and low dosage groups.
Figure 47:
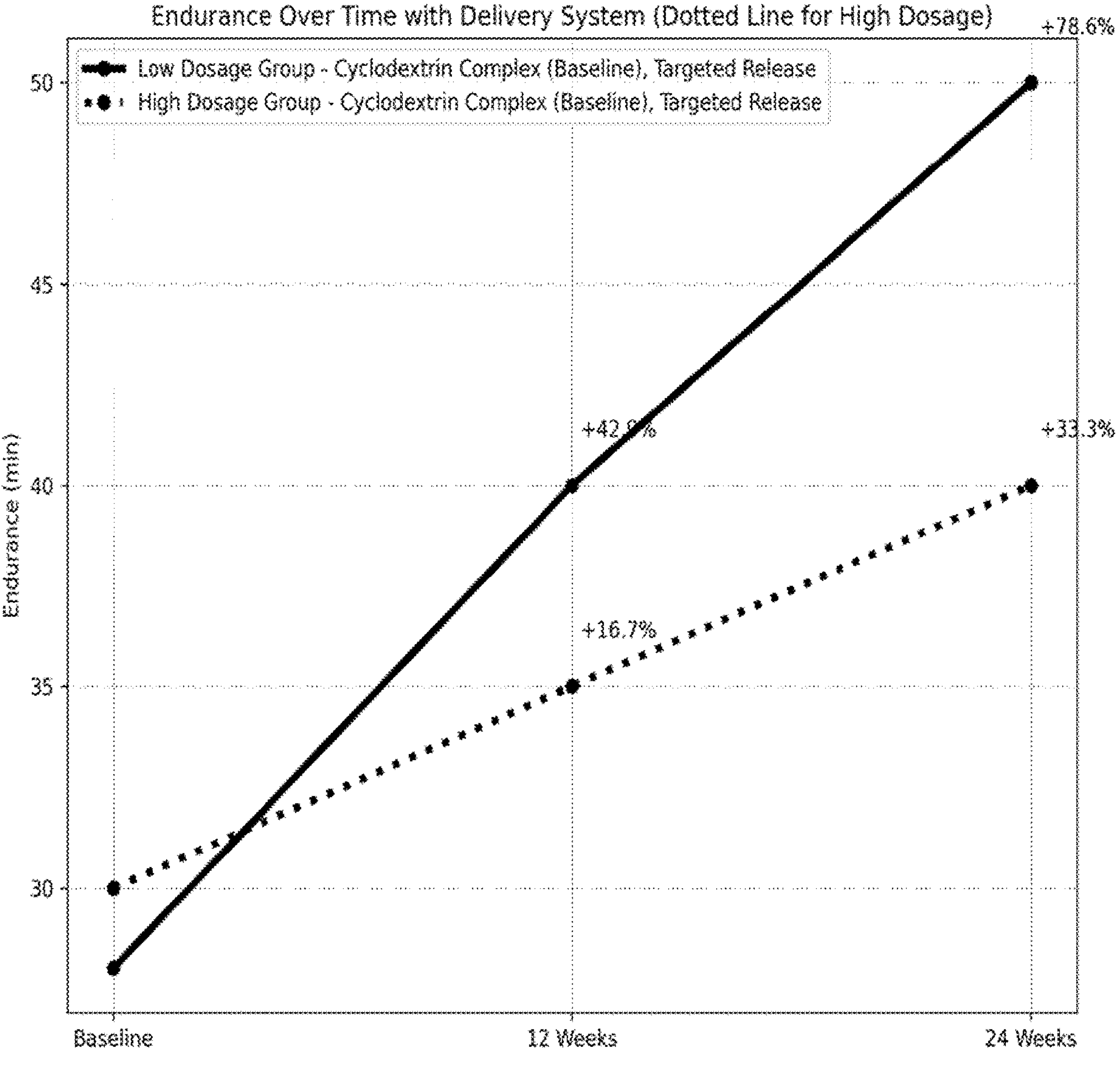
FIG. 47 illustrates the change in endurance over time with a delivery system for high and low dosage groups.
Figure 48:
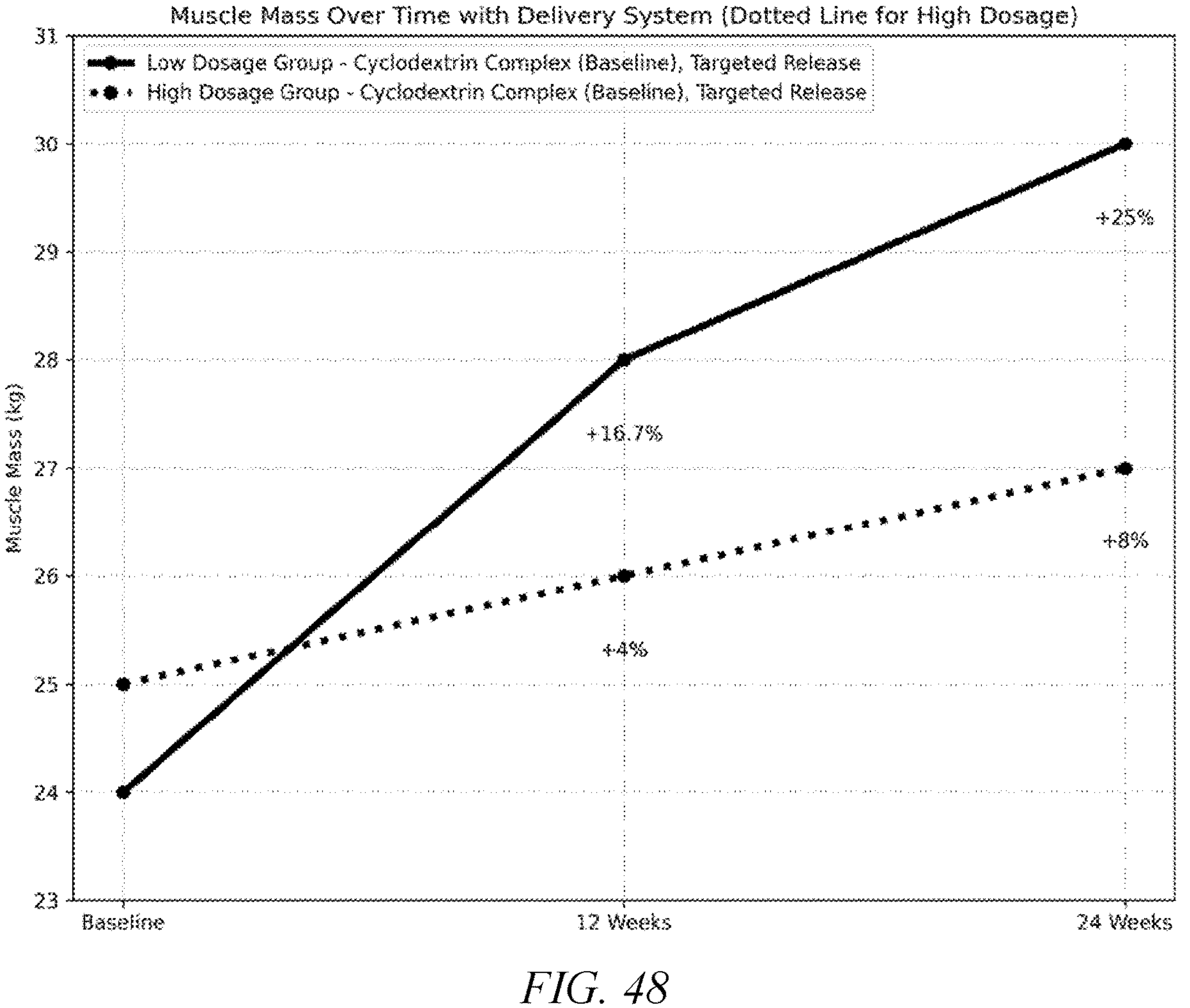
FIG. 48 illustrates the change in muscle mass over time with a delivery system for high and low dosage groups.
Figure 49:
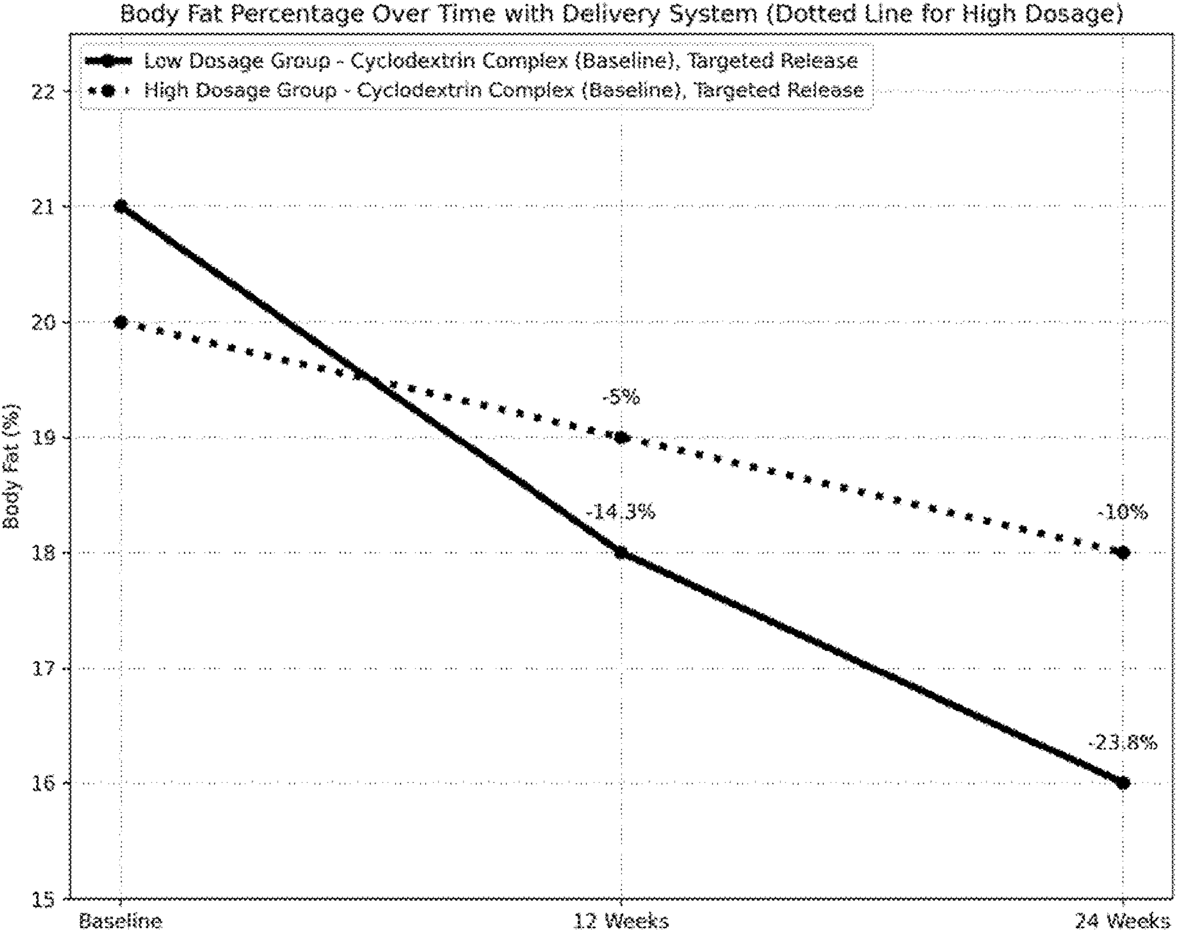
FIG. 49 illustrates the change in body fat over time with a delivery system for high and low dosage groups.

Referring to FIG. 46, strength over time with a delivery system for high and low dosage groups is shown. Referring to FIG. 47, endurance over time with a delivery system for high and low dosage groups is shown. Referring to FIG. 48, muscle mass over time with a delivery system for high and low dosage groups is shown. Referring to FIG. 49, body fat over time with a delivery system for high and low dosage groups is shown.

The key findings of the study revealed significant improvements in strength, endurance, muscle mass, and body fat reduction, with the low dosage group outperforming the high dosage group across all metrics. In terms of strength improvements, the low dosage group showed significantly greater increases compared to the high dosage group, with strength increasing by 35.4% in the low dosage group versus 20% in the high dosage group at 12 weeks, and by 56.3% versus 30% at 24 weeks. By the end of 24 weeks, the low dosage group reached a strength of 75 kg, while the high dosage group reached 65 kg.

Endurance enhancements were also more pronounced in the low dosage group. At 12 weeks, endurance increased by 42.9% in the low dosage group compared to 16.7% in the high dosage group, and by 78.6% versus 33.3% at 24 weeks. The low dosage group increased their endurance to 50 minutes, while the high dosage group reached 40 minutes by the end of 24 weeks.

In terms of muscle mass changes, the low dosage group experienced greater gains. At 12 weeks, the low dosage group saw a 16.7% increase in muscle mass compared to 4% in the high dosage group, and by 24 weeks, the low dosage group had gained 25% muscle mass compared to 8% in the high dosage group. At the end of the study, the low dosage group achieved a muscle mass of 30 kg, while the high dosage group reached 27 kg.

Body fat reduction was also more significant in the low dosage group. At 12 weeks, the low dosage group reduced body fat by 14.3% compared to 5% in the high dosage group, and by 24 weeks, the reductions were 23.8% versus 10%, respectively. By the end of 24 weeks, the low dosage group had a body fat percentage of 16%, compared to 18% in the high dosage group.

Two participants in the high dosage group had reported mood changes as they had experienced Mild headache and gastrointestinal discomfort. No adverse effects were reported by low dosage group.

In conclusion, the study demonstrated that the low dosage group, utilizing advanced delivery systems, achieved significantly better outcomes in strength, endurance, muscle mass, and body fat reduction compared to the high dosage group. Despite receiving lower doses of 4-Androstenediol, Vitamin D, HMB, Magnesium Bisglycinate, and *Panax Ginseng*, the low dosage group exhibited greater improvements across all performance and muscle health metrics over the 24-week period.

A key factor in the success of the low dosage group was the use of targeted release delivery systems. These systems allowed for the controlled and precise release of supplements, ensuring that the active compounds were delivered exactly where and when they were needed most. By combining technologies like cyclodextrin complexes with targeted release mechanisms, the supplements had improved bioavailability and efficiency. This approach enabled lower dosages to produce more substantial physiological benefits, particularly in enhancing strength, endurance, and muscle mass, while also promoting greater body fat reduction.

Additionally, Study #9 demonstrates the effectiveness of a multi-bioavailability delivery system, particularly in low-dosage groups, where the success is attributed to targeted release mechanisms that allow for controlled and precise release of supplements, leading to enhanced bioavailability and efficacy. The study highlights the critical role of cyclodextrin complex-based targeted release systems in delivering significant physiological benefits, including improvements in strength, endurance, muscle mass, and fat reduction.

The research also suggests that this approach can be applied using phytosome-based targeted release systems for DHEA derivatives in herbal extract compositions. Cyclodextrin complexes, which improve the solubility and stability of compounds, serve as a foundational platform for other advanced drug delivery technologies. Similarly, phytosomes, known for enhancing the absorption of plant-based supplements, can be employed to improve the efficacy of herbal extracts. Combining cyclodextrin complexes, phytosomes, NEFAs and Micronizing and other advanced delivery technologies with targeted release mechanisms can result in highly optimized systems for delivering both synthetic and natural compounds, leading to improved nutritional outcomes.

The foregoing studies have shown methods of use and compositions of constituents and their modifications, including adaptogens, modified stilbenoids complex, NEFAs, EAAs, HMB free acid, water-soluble vitamins (B and C), fat-soluble vitamins (D, E, K, and A), L-arginine, creatine, green tea extracts, chelated form of minerals with DHEA derivatives, that represent a novel approach to utilizing a multi-bioavailability system, based on the nature of the constituents. It aims to reduce supplements dosage while increasing nutrients efficacy and bioavailability by providing a targeted delivery system to promote nutritional effects for muscular hypertrophy, physical performance, improvement of stamina, muscle strength, and bone mineral density, supports anti-aging, weight loss, improvement of libido and sexual function, hormonal regulation, anti-inflammation, muscle preservation, cognitive function enhancement, reproductive health, and cardiovascular endurance. By leveraging advanced delivery systems (using target delivery systems such as phytosomes, micronization, and cyclodextrin complexes), the combined effects of these constituents can significantly enhance absorption and targeted delivery, maximizing their health benefits.

A key factor in the success of the low dosage group was the use of targeted release delivery systems. These systems allowed for the controlled and precise release of supplements, ensuring that the active compounds were delivered exactly where and when they were needed most. By combining technologies like cyclodextrin complexes with targeted release mechanisms, the supplements had improved bioavailability and efficiency. This approach enabled lower dosages to produce more substantial physiological benefits, particularly in enhancing strength, endurance, and muscle mass, while also promoting greater body fat reduction.

Additionally, studies illustrate that cyclodextrin complexes, used as a baseline delivery system, can serve as an effective foundation for other advanced bioavailability delivery technologies. Cyclodextrins enhance solubility and stability, making them a reliable choice for improving the bioavailability of various compounds, particularly those with poor water solubility. This approach could be adapted to other delivery systems as well. For example, phytosomes, which work effectively with herbal extracts, can also serve as a baseline for improving the absorption and effectiveness of plant-based supplements. The combination of cyclodextrin complexes, phytosomes, or other delivery technologies with targeted release mechanisms can create highly optimized systems for delivering both synthetic and natural compounds.

These findings suggest that the integration of targeted release technology with different baseline systems, such as cyclodextrins for pharmaceuticals and phytosomes for herbal extracts and NEFAs, can significantly enhance the efficacy of various compounds. For example, adaptogens are known to mitigate stress and improve endurance, while modified stilbenoids offer potent antioxidant properties. NEFAs facilitate muscle recovery, and essential amino acids are crucial for protein synthesis. The integration of these components with DHEA derivatives creates a synergistic formulation that effectively addresses a variety of health concerns, promoting overall well-being and enhancing physical capabilities. This multi-faceted approach maximizes the benefits of each component, leading to improved athletic performance and recovery outcomes.

First Embodiment Daily Wellness Capsule

A first embodiment daily wellness capsule to support overall wellness, stress adaptation, muscle hypertrophy, enhancing physical performance and increasing bone mineral density, with multiple bioavailability delivery system (Micronizing, Phytosome, Micronized-cyclodextrin complex) is disclosed.

Formulation includes preparing a supplement with micronized DHEA derivatives, specifically 4-androstene-3b-ol-one propionate, mixed with cyclodextrin, alongside a separate blend containing micronized ergocalciferol or cholecalciferol, ashwagandha or *ginseng*, free fatty acids, HMB free acid, and a phytosome bioavailability delivery system. The first step in the process is micronizing the DHEA derivatives, ensuring that the compound is in a dry and free-flowing powder form. Jet milling or ball milling is employed to reduce the particle size to less than 10 microns. Quality control measures, including sieve analysis, microscopy, and stability testing, are then used to ensure that the desired particle size is achieved and that no chemical degradation has occurred.

Cyclodextrin is micronized similarly, with the dry, free-flowing powder being reduced to a fine form through jet or cryogenic milling, the latter using liquid nitrogen for finer milling. Quality control involves particle size analysis and functionality testing to confirm that the cyclodextrin retains its capacity to form inclusion complexes. The micronization of ergocalciferol or cholecalciferol follows, ensuring the vitamins are processed into fine particles to enhance absorption, and ball milling can also be used if mechanical methods are feasible. Quality control tests ensure the vitamins remain stable and within the desired particle size range.

Ashwagandha or *ginseng* herbs are dried and powdered before undergoing micronization through jet or ball milling, preserving the active compounds. For free fatty acids, essential amino acids, and HMB-free acid, the same techniques are applied, with rigorous particle size and consistency testing to ensure uniformity.

Phytosome complexes are prepared by dissolving phospholipids in a solvent and adding the active ingredients, such as ashwagandha or *ginseng*, to form the complex. After drying the complex via rotary evaporation, jet milling may be applied if further size reduction is needed. Quality control involves testing encapsulation efficiency through HPLC and verifying particle size and morphology using microscopy.

The mixing procedure involves blending the micronized DHEA derivative with HPBCD cyclodextrin using a high-shear mixer. After ensuring both substances are of the same particle size, they are blended for 10-15 minutes at moderate speed to avoid heat buildup. The separate blend, including micronized ergocalciferol or cholecalciferol, ashwagandha or *ginseng*, free fatty acids, HMB free acid, and the phytosome complex, is mixed in a similar manner, with testing for uniformity and consistency throughout the process.

The following weight calculations are intended for 10,000 capsules, with a recommended dosage per capsule of 25 mg micronized DHEA derivative (4-Androstene-3b-ol-one Propionate), 50 mg micronized HPBCD cyclodextrin, 10 mg micronized ergocalciferol or cholecalciferol, 100 mg micronized ashwagandha or *ginseng,* 50 mg free fatty acids, 500 mg micronized HMB free acid, and 50 mg phytosome complex.

In such an arrangement, the total weight for 10,000 capsules is 250 mg micronized DHEA derivative, 500 g micronized HPBCD Cyclodextrin, 100 g micronized ergocalciferol or cholecalciferol, 1 kg micronized ashwagandha or *ginseng,* 500 g free fatty acids, 5 kg micronized HMB free acid, and 500 g phytosome complex. The sum of each ingredient per capsule results in a total weight per capsule of 785 mg.

Regarding microcrystalline cellulose (filler), assuming microcrystalline cellulose makes up 25% of the total capsule weight, the weight of microcrystalline cellulose per capsule is 196.25 mg. Thus, the total weight for 10,000 capsules is 1.96 kg. Regarding the magnesium stearate (anti-caking agent) calculation, assuming magnesium stearate makes up 2% of the total capsule weight, the weight of magnesium stearate per capsule is 15.7 mg. Thus, the total weight for 10,000 capsules is 157 grams.

In preferred embodiments, the capsule type is 00 or 000 capsules, depending on the total volume of the powder blend. Regarding the filling process, a capsule filling machine is used to ensure uniform filling to achieve consistent dosage per capsule. Excipients are preferably included, such as fillers (e.g., microcrystalline cellulose), binders (e.g., hypromellose), and anti-caking agents (e.g., magnesium stearate) if necessary to facilitate the encapsulation process.

Quality control procedures ensure the accuracy of the micronized powders and capsules. Particle size analysis is performed using laser diffraction or sieve analysis, and uniformity testing checks for consistent distribution across the blend. The filled capsules undergo content uniformity tests, dissolution testing, and stability studies to ensure that they release the active ingredients properly and remain stable over time. Encapsulation efficiency and particle size are tested within the phytosome complex to confirm its compatibility with other ingredients.

Second Embodiment Daily Wellness Capsule

A second embodiment daily wellness capsule for anti-aging, muscle preservation, improved metabolic function, anti-inflammation, and hormone regulation is disclosed. A supplement is prepared with micronized DHEA derivative (androst-5-ene-3β,7β, 17β-triol) mixed with cyclodextrin, and a separate blend of micronized vitamin B6, NEFAs, HMB free acids and a phytosomes with Siberian *ginseng*, a multiple bioavailability delivery technology to increase bioavailability and increase nutrients efficacy. All ingredients are micronized, including phytosome, NEFAs, and a cyclodextrin complex.

Androst-5-ene-3β,7β, 17β-triol at 25 mg offers several benefits, including modulating inflammation through androgen receptors, preserving muscle mass, influencing metabolism and body composition, indirectly impacting immune function through hormonal balance, supporting muscle and bone health for anti-aging, and regulating testosterone metabolism and activity. Siberian *ginseng* (eleuthero) extract at 25 mg reduces inflammation through adaptogenic compounds, supports health and recovery, enhances energy and adrenal function, boosts immune response, helps manage stress for anti-aging, and supports adrenal health and hormonal balance.

Omega-3 Fatty Acids at 25 mg reduce systemic inflammation and oxidative stress, support muscle health, improve lipid profiles and insulin sensitivity, enhance immune response, support cardiovascular and cognitive health for anti-aging, and balance hormone levels while reducing inflammation. Vitamin B6 at 25 mg reduces inflammation, is vital for amino acid metabolism and protein synthesis, supports neurotransmitter production and metabolism, enhances immune responses, supports skin and nerve health for anti-aging, and aids in hormone synthesis and balance.

Trans-resveratrol at 25 mg is a potent antioxidant with anti-inflammatory properties, may influence muscle function and recovery, improves insulin sensitivity and metabolic health, enhances immune response, activates longevity pathways for anti-aging, and influences estrogen receptors. HMB free acids at 25 mg reduce muscle inflammation and damage, support muscle mass and strength, help maintain muscle mass and metabolic health, support immune function and reduce muscle breakdown, contribute to muscle preservation and overall vitality for anti-aging, and may influence muscle-related hormone levels.

The preparation details involve the micronization process, aimed at increasing the surface area and enhancing the bioavailability of the ingredients, using equipment such as a jet mill or ball mill to achieve particle sizes less than 10 micrometers for each ingredient. The phytosome application improves absorption and bioavailability for herbal extracts like Siberian *ginseng* by combining the extract with phospholipids, such as lecithin, to form a phytosome complex, with the same method applicable to other herbal extracts if needed. Cyclodextrin complexation increases the solubility and stability of Androst-5-ene-3β,7β, 17β-triol by mixing the micronized compound with cyclodextrins, such as β-cyclodextrin, in a 1:1 ratio to form an inclusion complex.

The formulation consists of micronized ingredients, including Androst-5-ene-3β,7β,17β-triol complexed with cyclodextrin, Siberian *ginseng* extract phytosome-encapsulated, and, where possible, micronized Omega-3 fatty acids, Vitamin B6, Trans-Resveratrol, and HMB Free Acids. The micronized ingredients are blended thoroughly to ensure uniform distribution, with excipients incorporated as needed. Finally, the blend is encapsulated into size 0 or 00 capsules, depending on the final blend volume.

Regarding weight and quantity calculations, the total capsules in a batch are 10,000, with 50 capsules per bottle, and a total bottle count of 200. The capsule content (per capsule) is as follows: Androst-5-ene-3,7β,17β-triol (25 mg), Siberian *ginseng* extract (25 mg), omega-3 fatty acids (25 mg), vitamin B6 (25 mg), trans-resveratrol (25 mg), and HMB free acids (25 mg). The active total ingredient quantities per batch are as follows: Androst-5-ene-38, 78,178-triol (250 g), Siberian *ginseng* extract (250 g), omega-3 fatty acids (250 g), vitamin B6 (250 g), trans-resveratrol (250 g), and HMB free acids (250 g).

Regarding excipient requirements, a microcrystalline cellulose (filler) is provided of approximately 2000 grams (200 mg per capsule, adjust for bulk density and blending efficiency), a hypromellose (binder) is provided of approximately 500 grams (50 mg per capsule), a croscarmellose sodium (disintegrant) is provided of approximately 200 grams (20 mg per capsule), a magnesium stearate (lubricant) is provided of approximately 100 grams (10 mg per capsule), and capsules (size 0 or 00), with a quantity dependent on the final blend volume and capsule size.

The quality and testing guidelines for the production process begin with raw material testing, where the identity of the ingredients is confirmed using HPLC or mass spectrometry. Purity is ensured by verifying that the ingredients are free from contaminants, including heavy metals, pesticides, and microbial impurities, while potency testing is conducted to confirm the concentrations of active ingredients. During micronization and complexation testing, particle size analysis confirms that particles are less than 10 micrometers, and the stability and solubility of phytosome and cyclodextrin complexes are verified.

In the formulation testing phase, blend uniformity is checked to ensure an even distribution of active ingredients, and content uniformity testing confirms that each capsule contains the correct amount of active ingredients. Final product testing involves verifying the capsule fill weight to ensure consistency, conducting disintegration and dissolution testing to confirm that the capsules release the ingredients as required, and microbiological testing to detect any microbial contamination. Stability testing ensures the product remains effective and stable over time.

For labeling and documentation, compliance with regulatory requirements is verified, including accurate ingredient lists, dosage instructions, and safety warnings. Detailed records of the formulation, manufacturing processes, and quality testing are maintained to ensure traceability and adherence to guidelines.

The Following disclosure constitutes a continuation-in-part (CIP) of U.S. application Ser. No. 18/976,941, filed Dec. 11, 2024. In that application, Study #8 was disclosed as part of the inventive framework but was withdrawn pursuant to a restriction requirement. In the present CIP, Study #8 is fully reintroduced as a cornerstone embodiment of the inventive platform, integrated with additional validation studies that collectively define a polarity-specific, modular delivery system.

The inventive framework disclosed herein therefore encompasses both the prior-disclosed cornerstone study and additional studies presented for the first time in this CIP. These validation studies confirm specific modules of the inventive platform, including polarity-based carrier assignment using physicochemical metrics, optimization of cyclodextrin inclusion complexes with defined host/guest ratios and dissolution performance, dual-route administration with timing and compatibility controls, and sequential casting methods for microneedle systems.

The system encompasses a broad range of dietary and nutraceutical actives, including sterol derivatives (in certain embodiments esterified derivatives of DHEA are used as non-limiting model compounds), adaptogens, essential amino acids, polyphenols, fatty acids, minerals, and micronutrients. Each active is assigned to an optimized carrier system through a polarity-mapping rule, which applies metrics such as logP and Hansen solubility parameters (δd, δp, δh) to determine the most suitable carrier and to exclude incompatible pairings. Carrier systems include Self-Emulsifying Delivery Systems (SEDS), nanostructured lipid carriers (NLCs), liposomes/ethosomes, cyclodextrin inclusion complexes, solid dispersions, and hydrogel microneedle matrices.

Validation data confirm the performance of the inventive modules. Cyclodextrin inclusion complexes demonstrated reproducible dissolution enhancements, with complexation confirmed by orthogonal analytical methods. Dual-route administration achieved controlled sequential or simultaneous exposure governed by compatibility indices to prevent inversion and ensure stability. Microneedle systems demonstrated robust performance through sequential casting protocols integrating hydrophilic and lipophilic compartments. Collectively, these studies demonstrate a unified polarity-specific platform that advances formulation logic, stability engineering, and modular delivery design for dietary and nutraceutical applications.

Expanded Delivery Scope

The present invention discloses a polarity-specific, single- and dual-route delivery platform directed to dietary and nutraceutical supplement applications, while adaptable, in certain embodiments, to other regulated product classes. Each bioactive ingredient is classified by its inherent polarity, hydrophilic or lipophilic, and assigned to a polarity-optimized carrier suitable for oral, transdermal, or topical administration. This polarity-driven framework, validated in controlled studies, enables reproducible improvements in solubility, permeability, and stability. Route-appropriate penetration aids, such as oleic acid, terpenes, phosphatidylcholine, and polyols, are embedded within polarity-matched matrices to ensure compatibility with the assigned delivery route.

The invention incorporates a portfolio of delivery technologies aligned with polarity-specific assignment. Ethosomes are configured to enhance dermal permeation of lipophilic actives. Nanostructured lipid carriers (NLCs) improve oxidative robustness and uptake of lipid-phase compounds. Nanoemulgels with sub-200-nm droplet control provide improved topical spreadability and deposition. Antioxidant-enriched Self-Emulsifying Delivery Systems (SEDS) support oral administration of oxidation-sensitive nutrients. Hydrogel microneedles enable transdermal delivery of hydrophilic bioactives, with sequential two-phase casting validated in controlled studies as a robust integration method. Cyclodextrin inclusion complexes, optimized at defined host: guest ratios and confirmed by orthogonal analytical methods, extend compatibility across both oral and non-oral formats. Vesicular lipid systems are route-customized, with phytosomes oriented for oral delivery, ethosomes for transdermal penetration, and nanostructured lipid dispersions for topical application.

Hybrid Microdermal Delivery Systems

A class of hybrid microdermal systems is disclosed, featuring dual-compartment microneedles that maintain polarity-specific separation of hydrophilic and lipophilic payloads within a single integrated matrix. Hydrophilic actives are incorporated into a polymeric phase, whereas lipophilic actives are embedded in a lipidic or nanoparticulate dispersion. This configuration enables either simultaneous or sequential release while preserving polarity segregation. In certain embodiments, the system is applied to sterol derivatives (including, in certain embodiments, esterified derivatives of DHEA) in combination with polarity-divergent co-actives. Controlled casting protocols, including solids ratios, temperature regulation, and dwell times, support reproducibility and confirm technical advancements beyond conventional microneedle designs.

Expanded Active Ingredient Set

The inventive platform supports a broad set of dietary and nutraceutical actives. Sterol derivatives (including, in certain embodiments, esterified derivatives of DHEA as non-limiting model compounds) are integrated with polarity-matched botanical adaptogens (e.g., *Rhodiola rosea, Ginkgo biloba*), essential amino acids and derivatives, polyphenols, fatty acids, and chelated minerals (e.g., zinc, magnesium). These combinations are formulated within polarity-aligned carriers, enabling coordinated exposure profiles across routes while maintaining compliance with dietary and nutraceutical supplement practice.

Stability and Protection Measures

A comprehensive stability framework comprising interdependent strategies is provided to mitigate oxidative, photolytic, and thermal degradation. Lipid-phase and amphiphilic antioxidants are embedded directly into carrier systems; droplet and vesicle size is controlled to reduce degradation at polarity interfaces; and manufacturing and packaging adopt photoprotective measures that minimize light-induced breakdown. Oxygen-control elements, including oxygen absorbers and nitrogen-barrier packaging, are integrated with high-barrier materials, providing cross-route stability enhancement for oral, transdermal, and microneedle formats under ICH Q1A (R2)/Q1B storage conditions.

Synergistic Pairing Strategies

The inventive platform supports polarity-aligned pairing strategies, including: co-formulation of sterol derivatives with adaptogens to support endocrine and stress-response wellness; pairing HMB free acid with amino acids to support muscle protein synthesis; combining L-arginine with polyphenols and omega-3 fatty acids for cardiometabolic wellness and balanced inflammatory response; and integrating botanical adaptogens with chelated minerals and lipophilic prohormone-adjacent actives to promote multi-system nutritional support. Each pairing is assigned to polarity-matched carriers to maximize uptake and maintain coordinated exposure profiles.

EMBODIMENTS

Representative embodiments include hybrid microneedle patches with dual-polarity compartments; microneedles featuring multilayer backings with nitrogen-stabilized zones; polarity-segregated topical gels and creams using sub-200-nm lipid dispersions; and oral capsule systems that combine lipid-based SEDS with complexed hydrophilic actives. These embodiments support synchronized single- or dual-route nutrient delivery while preserving chemical and structural integrity of actives.

Technical Processes

Process innovations include a pre-assembly optimization step that assigns each active to a polarity-specific carrier prior to final blending or encapsulation; inert-gas (nitrogen) handling for oxidation-sensitive components; and sequential microneedle casting methods that ensure phase separation between hydrophilic and lipophilic zones, preventing interfacial degradation and preserving polarity-driven release integrity.

Mapping Framework

An Active-Carrier-Route-Penetration Enhancer Mapping Framework is provided. Each bioactive is classified by polarity, mapped to a compatible carrier, assigned to a single- or dual-route administration plan, and paired with an appropriate penetration enhancer (e.g., oleic acid, terpenes, phosphatidylcholine, polyols). This framework, validated in controlled studies, provides predictable performance in solubility, permeability, stability, and bioavailability across actives and routes, enabling reproducible and scalable formulation outcomes and supporting the modular architecture of the invention.

Continuity of Disclosure

The present CIP carries forward Study #8, which was originally disclosed in U.S. application Ser. No. 18/976,941 and withdrawn during prosecution in response to a restriction requirement. Study #8 is therefore reintroduced here not as new matter, but as the legacy foundation upon which the broader polarity-specific delivery platform is constructed. Integrated with the additional validation studies disclosed herein, Study #8 anchors the inventive framework and confirms the unity of the inventive concept across embodiments.

Relationship of Study Eight to Integrated Studies

The features described in the additional studies disclosed in this CIP are presented for the first time in this application and are fully described and enabled herein. These embodiments extend the legacy framework established in Study Eight by incorporating polarity-specific carrier mapping, advanced stability engineering, and modular dual-route administration. Together, Study Eight and the integrated embodiments form a unified polarity-engineered delivery platform.

Annex A-Novelty Justification Table

Table 40 contrasts each inventive feature disclosed in this Continuation-in-Part with its closest prior art, identifies unaddressed gaps, and articulates polarity-driven advances that enable modular single- or dual-route delivery for dietary and nutraceutical supplements. All features disclosed in Table 1 are modular embodiments of a single inventive concept: polarity-specific carrier mapping combined with stability-engineered formulation design. Each feature is supported by one or more validation studies, including Study Eight as the legacy foundation and additional controlled studies that provide analytical validation, formulation data, and performance outcomes sufficient for enablement.

TABLE 40

Novelty Justification Framework

| Novel Item in CIP | Closest Known Prior Art | Gap in Prior Art | Inventive Step/Novelty Justification (with Study Support) |
|---|---|---|---|
| Polarity-Specific, Pre-Engineered Single-Route or Dual-Route Delivery Platform | Oral-only polarity-matched systems in select nutraceutical patents; isolated dermal applications | No unified platform linking polarity classification to carrier selection and optimized administration across oral, transdermal, and topical routes | Establishes the first polarity-specific supplement platform enabling modular single-or dual-route delivery through engineered carrier mapping. Supported by Study 2 (polarity rule), Study 4 (dual-route timing), and Study 8 (legacy validation). |
| Integrated Active-Carrier-Route-Penetration Enhancer Mapping | Limited active carrier pairing for single routes | No structured framework integrating polarity, carrier, route, and enhancer | Provides reproducible matrix assigning actives to polarity-matched carriers and route-specific enhancers. Validated in Study 2 (mapping logic), Study 4A (compatibility index), and Study 8 (human validation). |
| Cyclodextrin Inclusion Complexes for Single or Dual-Route Use | Cyclodextrins primarily used for oral solubility enhancement | No polarity-driven application of cyclodextrins for dual-route or microneedle formats | Enables polarity-tuned, dual-route cyclodextrin systems, including microneedle integration for lipid-phase stabilization. Supported by Study 1A (ratios, dissolution, DSC/PXRD/NMR) and Study 7 (microneedle dual-route casting) |

TABLE 40-continued

Novelty Justification Framework

| Novel Item in CIP | Closest Known Prior Art | Gap in Prior Art | Inventive Step/Novelty Justification (with Study Support) |
|---|---|---|---|
| Antioxidant-Enriched SEDS with Multi-Mechanism Stability Engineering | SEDS used only for oral solubility | Lack of integrated oxidative, photolytic, and thermal protection across routes | Combines SEDS with antioxidants (tocopherols, ascorbyl palmitate) and photoprotective excipients for multi-route stability under ICH Q1A(R2). Supported by Study 3 (oral + dermal models) and Study 8 (stability data). |
| Hybrid Microdermal Delivery System with Sequential/Simultaneous Release | Single-phase microneedles for mono-polar actives | No separation or coordination of polarity-divergent payloads | Introduces dual-compartment microneedles fabricated via sequential casting. Supported by Study 7 (two-phase casting) and Study 4 (timing validation). |
| Dual-Layer Microneedle Casting/Compartment Loading | Tip-loaded or single-phase microneedles | No polarity-preserved dual-phase fabrication | Enables two-phase casting for polarity-separated loading, with validated mechanical strength and dissolution control. Supported by Study 7 (casting protocols, strength testing). |
| Expanded Actives (Botanicals, Chelated Minerals, Sterol Derivatives) | Actives used separately in prior art | No polarity-aligned co-formulation in dual-route systems | Provides polarity-specific integration of botanicals, minerals, and sterol derivatives. Supported by Study 1B (oral partitioning) Study 3 (microneedle), and Study 8 (nutritional synergy). |
| Oxygen Absorbers in Stability Packaging | Oxygen scavengers only in oral blister packs | No coordinated stability packaging for oral + dermal systems | Introduces dual-compartment kits with oxygen absorbers preserving both oral and topical formats. Supported by Study 5 (packaging validation) and Study 8 (accelerated stability). |
| Topical Nanoemulgel Systems with Sub-200 nm Droplet Control | Conventional nanoemulgels for dermal actives | No polarity-separated, photoprotected, dual-phase topical gels | Provides polarity-aligned nanoemulgels with droplet size <200 nm, antioxidant/UV stabilization, and validated penetration. Supported by Study 6 (topical nanoemulgels) and Study 8 (photostability). |
| Single or Dual-Route Stability Kits | Multi-bottle kits without integrated stability | No unified packaging preserving actives across complementary routes | Enables coordinated, nitrogen-flushed, high-barrier packaging preserving integrity of oral and dermal formats. Supported by Study 5 (packaging kits) and Study 8 (human stability assessment). |
| Polarity-Specific Botanical-Mineral-Sterol Combinations | Multi-ingredient blends without polarity design | No polarity-aware co-formulation linking actives to optimal carriers/routes | Provides polarity-engineered combinations with validated bioavailability. Supported by Study 1A (oral dissolution uplift), Study 4 (dual-route timing), and Study 8 (clinical outcomes). |

Table 40 presents the novelty landscape for this Continuation-in-Part, contrasting each inventive feature with closest prior art, identifying unaddressed gaps, and articulating polarity-driven advances that enable modular single- or dual-route delivery for dietary and nutraceutical supplements.

The subject matter of Study Eight originates from the parent application and is retained here as the legacy foundation of the inventive platform. The additional studies disclosed in this CIP provide expanded validation modules, including polarity-specific carrier assignment, stability engineering, cyclodextrin inclusion and dissolution optimization, dual-route timing and compatibility, and sequential microneedle casting. Together, Study Eight and the additional studies are unified through polarity-specific carrier mapping and stability-engineered formulation design, with Study Eight serving as the cornerstone example and the CIP studies extending the platform into expanded embodiments and dual-route systems.

Summary of Cip Novel Contributions and Inventive Step Justification

Table 40 summarizes the core inventive elements disclosed in this Continuation-in-Part (CIP) application, providing a structured comparison against the closest known prior art. For each feature, the table identifies existing technical limitations or gaps and presents a concise rationale for the inventive step. Justifications are grounded in unique structural integration, polarity-specific formulation strategies, and dual-route or multi-route delivery capabilities tailored for dietary supplement use.

This CIP extends the technical and functional scope of U.S. application Ser. No. 18/976,941 by disclosing a polarity-specific, modular delivery system for dietary supplements that supports both single-route and dual-route administration across oral, topical, and transdermal pathways. All embodiments disclosed herein are unified by a single inventive concept: polarity-specific carrier mapping combined with stability-engineered formulation design. Each format, whether capsule, topical gel, or microneedle patch, represents a modular implementation of the same framework, whereby lipophilic and hydrophilic bioactives are separated, stabilized, and paired with polarity-matched carriers and route-specific enhancers. This architecture ensures that all embodiments function as coordinated variations of one platform rather than unrelated inventions.

Key Areas of Novelty

The inventive platform supports expanded active ingredient classes, including sterol derivatives (in certain embodiments DHEA esters as model compounds), botanical adaptogens, chelated minerals, amino acids, polyphenols, and fatty acids. These actives are co-formulated using polarity-matched carriers to ensure solubility, permeability, and route compatibility. This enables integration of hormonal precursors, botanicals, and micronutrients within a unified framework for systemic and localized nutritional support.

The platform incorporates delivery technologies beyond those conventionally applied in supplements, including nanostructured lipid carriers, ethosomes, antioxidant-enriched self-emulsifying delivery systems (SEDS), and nanoemulgels with controlled droplet diameters below 200 nanometers. Dual-compartment and dual-layer microneedles are disclosed for polarity-segregated payloads within a single microarray device, fabricated through sequential casting validated in controlled studies.

Expanded route options are supported, allowing bioactives historically limited to oral delivery to be administered through oral+transdermal, oral+topical, or dermal+transdermal combinations. These dual-route systems are polarity-engineered to avoid carrier incompatibility and phase interference, with coordinated timing validated in controlled studies.

Enhanced stability frameworks are incorporated, including polarity-specific antioxidant embedding, photoprotective manufacturing protocols, nitrogen-flushed barrier packaging, and coordinated oxygen absorber integration. These measures extend across oral, dermal, and transdermal dosage forms, providing a cross-platform stability solution validated in long-term and accelerated ICH Q1A (R2) conditions.

Synergistic pairing strategies are supported, combining sterol derivatives (in certain embodiments DHEA esters as model compounds) with adaptogens, HMB free acid with amino acids, and botanical-mineral-hormone complexes engineered for polarity alignment and systemic synergy.

Representative embodiments include hybrid microneedle systems with polarity-segregated payloads and configurable release profiles, dual-phase nanoemulgels offering dermal delivery with photostable control, and integrated dual-route stability kits that maintain chemical and redox integrity for both oral and dermal/topical components within coordinated packaging.

These technical advancements collectively demonstrate non-obvious improvements over the prior art. The combination of polarity-specific carrier design, route-optimized mapping, and system-level stability and synergy reflects a distinct inventive step not taught or suggested by existing supplement or delivery system technologies.

As detailed in the accompanying Novelty Justification Table, the advancements disclosed in this CIP address key deficiencies in the prior art through polarity-specific carrier mapping, dual-route-compatible cyclodextrin complexation, hybrid microdermal delivery systems, expanded botanical-mineral-sterol co-formulations, oxygen-stabilized packaging environments, and dual-layer microneedle casting techniques. These innovations are fully supported by the controlled studies disclosed herein, which provide analytical confirmation, formulation detail, and enablement.

Study 8, now designated as the Seventeenth Embodiment, was originally disclosed in the parent application and is retained for continuity of disclosure. While it does not originate in this CIP, it serves as a clinically grounded reference point for evaluating the expanded inventive framework.

Taken together, the disclosed features establish a unified, polarity-engineered, dual-route dietary supplement delivery platform. The system addresses longstanding limitations in nutrient bioavailability, formulation stability, and coordinated multi-route administration, offering a modular architecture for precision-aligned nutritional support.

All embodiments disclosed herein are unified by a single inventive concept of polarity-specific carrier mapping and stability-engineered formulation design, with oral, dermal, and transdermal formats representing modular implementations of the same platform.

Field of the Cip Invention

The present invention relates to the field of advanced dietary and nutraceutical supplement delivery systems. More specifically, it concerns polarity-specific, pre-engineered compositions, dosage forms, and manufacturing methods designed to enhance systemic nutrient uptake, maintain chemical and physical stability, and support targeted delivery of lipophilic and hydrophilic bioactive compounds across one or more administration routes.

In certain embodiments, the invention provides a polarity-specific, modular delivery platform configured for oral, transdermal, topical, or hybrid microdermal administration. Each active ingredient is matched with a validated carrier system selected based on polarity, solubility, and intended exposure profile. Delivery technologies incorporated into the platform include antioxidant-enriched self-emulsifying delivery systems (SEDS), nanostructured lipid carriers (NLCs), ethosomes, nanoemulgels engineered with sub-200-nanometer droplet control, phospholipid-based systems (liposomes, phytosomes), cyclodextrin inclusion complexes confirmed by dissolution and orthogonal analytics, and microneedle systems (hydrogel, dissolving, dual-layer, and sequentially cast hybrid microarrays). All carriers are pre-engineered for stability and compatibility prior to integration into dosage forms to ensure reproducibility, scalability, and shelf life.

For oral delivery, antioxidant-fortified lipid carriers such as SEDS and NLCs are used to improve dissolution, oxidative resilience, and uptake of lipophilic nutrients. Hydrophilic actives are delivered using cyclodextrin inclusion complexes and phospholipid-based systems (liposomes, phytosomes), which enhance solubility and protect against enzymatic degradation. Validation demonstrates that antioxidant-enriched SEDS form fine emulsions in gastrointestinal fluids and maintain active integrity under simulated digestive conditions. For transdermal delivery, hydrophilic actives are administered through hydrogel microneedles, while ethosomes and lipid carriers deliver lipophilic payloads. Hybrid microneedles fabricated via sequential casting enable polarity-segregated compartments with either simultaneous or time-staggered release. For topical delivery, polarity-aligned nanoemulgels combine lipophilic oil phases with hydrophilic aqueous phases, with sub-200-nanometer droplet control improving dermal penetration, stability, and residence time at the application site.

Coordinated single-route or dual-route administration is supported. Dual-route formats may include oral+transdermal or oral+topical combinations, optionally co-packaged in stability-controlled kits. Controlled timing between routes ensures synchronized or sequential nutrient exposure while maintaining polarity-driven compatibility.

A unified stability framework is applied across all dosage forms, incorporating polarity-matched encapsulation strategies, antioxidant fortification, nitrogen-flushed inert handling, photoprotective manufacturing environments, and high-barrier packaging with oxygen absorbers and thermal protection. These measures provide long-term reproducibility and align with ICH Q1A (R2)/Q1B stability expectations for shelf life across oral, dermal, and transdermal systems.

A central inventive feature is the Active-Carrier-Route-Penetration Enhancer Mapping Framework, which systematically aligns each bioactive compound with a polarity-compatible carrier, a delivery route, and a route-appropriate enhancer. Representative enhancers include ethanol, phosphatidylcholine, glycerin, and oleic acid. This mapping strategy, validated in controlled studies, provides predictable improvements in solubility, permeability, and chemical stability across embodiments.

The platform also enables novel synergistic ingredient combinations supported by polarity-specific carriers and coordinated release. Examples include sterol derivatives (with esterified DHEA esters as non-limiting model compounds) paired with adaptogens; HMB free acid with amino acids for protein metabolism support; L-arginine with resveratrol and omega-3 fatty acids for cardiovascular wellness; and botanical adaptogens combined with chelated minerals and lipidic prohormone analogs for multi-system nutritional support. These co-formulations are further supported by polarity-partitioning validation studies, which confirm reproducible assignment of diverse actives to polarity-matched carriers, ensuring compatibility and integration of expanded botanical, mineral, and sterol combinations.

Through polarity-specific carrier design, route-matched enhancer systems, and a stability-focused manufacturing framework, the invention provides dietary and nutraceutical supplement platforms with reproducible improvements in solubility, permeability, and nutrient uptake. Coordinated dual-route options allow synchronized or sequential administration with validated stability across oral, dermal, and transdermal formats. The system integrates pharmaceutical-quality manufacturing controls into a dietary and nutraceutical context, ensuring reduced dosing frequency, extended shelf life, and scalable production with high consumer usability and regulatory compliance.

Background of the Cip Invention

Conventional dietary supplement delivery systems have historically struggled to achieve reliable systemic bioavailability, particularly for lipophilic compounds. A wide range of bioactives with nutritional relevance, such as fat-soluble vitamins, polyphenols, and steroid-like dietary precursors, exhibit poor aqueous solubility, chemical instability under physiological conditions, and low membrane permeability. When delivered orally, these limitations are exacerbated by gastrointestinal degradation and first-pass hepatic metabolism. As a result, higher input levels are often used to attain meaningful systemic exposure, which introduces inefficiencies, increases cost, elevates the risk of nutrient degradation prior to absorption, and may reduce tolerability or adherence.

The parent application, U.S. application Ser. No. 18/976,941, addressed this challenge through the development of modular oral dosage forms based on polarity-compatible carriers. These included micronized actives, phospholipid-bound phytosome complexes, lipid-based matrices, non-esterified fatty acids (NEFAs), and cyclodextrin inclusion complexes. The focus of the parent was on optimizing oral capsule formats by reducing active-ingredient load while improving solubility, stability, and bioavailability through pre-engineered delivery architectures.

The present Continuation-in-Part builds upon these foundational strategies by expanding into a polarity-specific platform that supports both single-route and dual-route delivery. For oral configurations, the invention refines delivery of highly lipophilic compounds such as sterol derivatives (including, in certain embodiments, esterified derivatives of DHEA) as model compounds, which are nutritional precursors that exhibit limited aqueous solubility and face multiple absorption barriers. These compounds are formulated into antioxidant-enriched self-emulsifying delivery systems (SEDS) comprising optimized oils, surfactants, and co-solvents that spontaneously form fine emulsions upon contact with gastrointestinal fluids. This fine-emulsion formation increases interfacial area, supports lymphatic uptake, and reduces reliance on the portal circulation, with testing confirming enhanced dissolution performance and oxidative robustness during simulated digestion.

Despite these optimizations, lipophilic dietary actives such as sterol derivatives (including, in certain embodiments, esterified derivatives of DHEA), fat-soluble vitamins, and polyphenols like trans-resveratrol remain partially susceptible to enzymatic degradation and first-pass metabolism. To address this residual vulnerability, the invention extends beyond oral delivery into dual-route and non-oral formats, including transdermal and topical systems. Each active is mapped to a polarity-specific carrier and assigned to an administration route based on its solubility, molecular structure, and membrane-permeability characteristics.

In one embodiment, a hybrid microneedle patch integrates two distinct compartments: a hydrophilic-phase polymeric matrix and a lipophilic-phase lipid or nanoparticle compartment. This polarity-segregated system enables simultaneous or sequential release, improves dermal penetration, and supports both localized and systemic nutrient delivery. To the inventors' knowledge, no prior art discloses a dual-compartment microneedle device engineered for polarity-segregated co-delivery of hydrophilic and lipophilic dietary compounds in a single integrated patch.

Lipophilic actives, including sterol derivatives (including, in certain embodiments, esterified derivatives of DHEA), fat-soluble vitamins, and polyphenols, are also formulated into transdermal carriers such as ethosomes, nanostructured lipid carriers, and nanoemulgels. These systems enhance skin penetration, stabilize oxidation-prone molecules, support sustained release, and mitigate enzymatic or hydrolytic degradation. Hydrophilic actives, including water-soluble vitamins, amino acids, creatine, and HMB, are incorporated into hydrogel microneedles, cyclodextrin complexes, and phospholipid-based systems (liposomes, phytosomes). These formats allow immediate or sustained release profiles tuned by hydration kinetics and carrier architecture, while polarity-partitioning datasets support reproducible assignment of expanded botanical, mineral, and sterol combinations into compatible carriers.

System stability is further protected through a multilayered engineering strategy. Antioxidants are embedded directly into the carrier matrices to combat oxidative degradation. Photolabile compounds are shielded during processing and packaging under light-controlled conditions. Oxygen absorbers are paired with nitrogen-flushed barrier enclosures to preserve redox integrity across storage periods. This coordinated approach constitutes a novel application of inert-system design within a polarity-specific, dual-route dietary supplement platform. Demonstrations of reduced oxidation markers and preserved active content under long-term and accelerated storage further support the stability of SEDS-based oral formats within coordinated packaging systems.

Within this framework, each active compound is processed independently into its polarity-optimized carrier system prior to final formulation. This modular architecture allows for fine control over solubility, permeability, and shelf stability, tailored to the intended route or combination of routes. The resulting system delivers high-efficacy performance with lower input levels, achieving either localized dermal activity or systemic absorption, or both, depending on the format selected. The platform supports improved adherence, reduced degradation, and extended-release kinetics, thereby expanding the commercial potential of dietary supplements by providing pharmaceutical-quality manufacturing controls in a dietary and nutraceutical supplement context, together with measurable gains in bioavailability, stability, and uptake.

Practical Impact and Market Relevance

The invention provides a polarity-specific, stability-engineered delivery platform for dietary and nutraceutical supplements. The platform maps each bioactive compound to a polarity-compatible carrier and a selected administration route, enabling single-route or dual-route formats across oral, dermal, and transdermal pathways. The architecture integrates carrier engineering, route-matched enhancers, and coordinated packaging controls to deliver reproducible gains in solubility, permeability, chemical stability, and nutrient uptake while remaining aligned with dietary supplement practice.

A central feature is the Active-Carrier-Route-Penetration Enhancer Mapping Framework, which aligns each active with a validated carrier and route using polarity metrics and formulation constraints. Oral delivery modules include antioxidant-enriched self-emulsifying delivery systems and nanostructured lipid carriers for lipophilic actives, and cyclodextrin inclusion complexes and phospholipid-based systems (liposomes, phytosomes) for hydrophilic actives, with complexation and dissolution confirmed by orthogonal analytics. Dermal and transdermal modules include ethosomes, nanostructured lipid carriers, and nanoemulgels engineered with sub-200-nanometer droplet control, as well as microneedle systems fabricated by sequential casting to maintain polarity-segregated compartments and configurable release.

Dual-route administration is enabled by compatibility between oral and dermal or transdermal formats and by timing control that supports synchronized or sequential exposure windows. A compatibility and stability framework manages phase behavior and interface integrity, and coordinated packaging measures include nitrogen-flushed handling, oxygen absorbers, and high-barrier materials consistent with long-term and accelerated stability expectations. The combined design provides validated performance for multi-component supplement kits and minimizes oxidative, photolytic, and thermal degradation across routes.

The platform accommodates expanded active classes, including sterol derivatives with esterified DHEA esters as non-limiting models, botanical adaptogens, chelated minerals, amino acids and derivatives, polyphenols, and fatty acids. Polarity-partitioning data support reproducible assignment of diverse actives to compatible carriers, enabling synergistic combinations with coordinated release and improved adherence. The system is designed for scalable manufacturing with pharmaceutical-quality controls in a dietary and nutraceutical context, providing measurable improvements in bioavailability, stability, and shelf life without therapeutic or disease claims.

Polarity-Specific, Single or Dual-Route Delivery Platform

The invention provides a polarity-specific, pre-engineered delivery architecture that supports either single-route or dual-route administration for dietary and nutraceutical supplements. Each active is mapped to a polarity-optimized carrier and paired with a route-appropriate penetration enhancer, enabling oral, transdermal, or topical formats. This framework maintains chemical compatibility, enhances solubility and permeability for nutritional uptake, and supports synchronized or complementary nutrient presentation through coordinated multi-route dosing. The mapping rules and exclusion criteria are validated in controlled studies confirming objective polarity assignment and enhancer alignment.

Dual-route administration is implemented with compatibility controls and validated timing windows that support synchronized or sequential exposure while preventing phase inversion or interfacial drift. Cross-route performance is further stabilized through coordinated packaging measures and process controls so that multi-component kits deliver consistent exposure profiles across oral and non-oral formats.

Hybrid Microdermal Delivery System with Polarity Segregation

A dual-compartment hybrid microdermal system preserves polarity integrity within a single microneedle patch. One compartment uses a polymeric matrix for hydrophilic actives, while the second employs a lipidic or nanoparticulate phase for lipophilic compounds. The architecture enables simultaneous or sequential release while maintaining payload identity and route compatibility. To the inventors' knowledge, no prior microneedle configuration provides polarity-matched co-delivery in a unified format with the same combination of dermal penetration performance, kinetic control, and flexibility for localized or systemic nutritional support.

Sequential casting methods with controlled solids content, temperature, and dwell times establish stable interfaces between hydrophilic and lipophilic compartments and provide reproducible needle integrity and release profiles. These methods support either immediate or time-staggered exposure and are suitable for integration into coordinated dual-route regimens.

Expanded Active Set and Synergistic Nutrient Pairings

The platform supports an expanded active set and carrier-aligned pairings. Formulations may include sterol derivatives with esterified DHEA esters as non-limiting model compounds together with botanical adaptogens such as *Rhodiola rosea* and *Ginkgo biloba*, chelated minerals, amino acids, polyphenols, and fatty acids. Each ingredient is matched to a polarity-compatible carrier to harmonize release and optimize uptake.

Polarity-partitioning data confirm reproducible assignment of diverse actives to compatible carriers, enabling synergistic combinations that conventional single-route or mono-phase systems do not reliably achieve. Representative pairings include sterol derivatives with adaptogens for endocrine-stress wellness support and HMB with amino acids for protein metabolism support, engineered for route-appropriate stability and exposure.

Cyclodextrin Complexes Adapted for Multi-Route Delivery

Cyclodextrin inclusion complexes, traditionally used for oral solubilization, are adapted for broader utility in polarity-driven systems across transdermal and topical applications. Within hybrid carriers comprising lipid and polymeric phases, cyclodextrins stabilize hydrophilic actives and, in certain designs, assist with presenting lipophilic actives for single-route or dual-route use, including incorporation into microneedle formats. Complexation ratios in the range of 1:1 to 1:3 with orthogonal confirmation and demonstrated dissolution enhancement support multi-route compatibility under the polarity assignment rules.

Integrated Multi-Threat Stability Framework

A unified, multi-layered stability system addresses oxidative, photolytic, thermal, and moisture-driven degradation across all supported routes. Formulations integrate polarity-matched encapsulation, embedded antioxidants, light-controlled processing, nitrogen-flushed inert filling, and oxygen-absorbing, high-barrier packaging. The coordinated framework provides long-term potency retention and structural integrity under real-time and accelerated conditions consistent with ICH Q1A (R2) and Q1B, delivering consistent protection across oral, topical, and transdermal formats.

Independent Release Kinetics for Polarity-Divergent Payloads

Through dual-layer microneedle casting and polarity-compartmentalized loading, the system enables independent modulation of release kinetics for lipophilic and hydrophilic actives. Formulations can be tuned for synchronized or staggered delivery to control nutrient availability and onset of nutritional support. Timing control and compatibility safeguards prevent phase inversion and interfacial drift, supporting stable exposure profiles suitable for coordinated dual-route regimens. Validation demonstrates that sequentially cast microneedles provide reproducible release profiles aligned to polarity-specific compartments.

Modular Architecture And Scalable Manufacturing

The invention is organized as a modular platform in which each active-carrier pairing is pre-engineered and stability-validated prior to final assembly. This architecture allows rapid adaptation to single-route or dual-route formats without redesign of underlying modules. Manufacturing employs reproducible unit operations, inert handling where required, and coordinated packaging with high-barrier materials and oxygen absorbers. The platform supports high-volume scalability and consistent quality review, bridging pharmaceutical-quality performance characteristics with dietary and nutraceutical applicability.

The disclosed features provide a unified platform that delivers polarity-diverse dietary actives across one or more administration routes with enhanced solubility, long-term stability, and optimized uptake. Representative implementations include antioxidant-enriched self-emulsifying systems and nanostructured lipid carriers for lipophilic oral delivery, cyclodextrin complexes and phospholipid-based systems for hydrophilic oral delivery, nanoemulgels with sub-200-nanometer droplet control for topical use, and sequentially cast microneedles with polarity-segregated compartments for microdermal delivery. Coordinated dual-route options are enabled through compatibility controls, timing windows, and integrated packaging measures that reduce oxidative, photolytic, and thermal degradation. The system satisfies novelty, inventive step, and industrial applicability within a regulatory-compliant supplement framework.

SUMMARY OF THE INVENTION

The invention discloses a polarity-specific, pre-engineered, multi-platform delivery system for dietary supplement bioactives. The system is designed to maximize bioavailability, preserve chemical and physical stability, and enable targeted delivery of lipophilic and hydrophilic compounds via single-route or dual-route administration. Supported routes include oral, transdermal, and topical pathways, used independently or in coordinated combinations. The unifying inventive concept is an Active-Carrier-Route-Penetration Enhancer mapping framework that governs all embodiments, such that oral, topical, and transdermal forms are modular applications of one inventive platform.

Each active ingredient is assigned to a polarity-specific delivery profile based on solubility and absorption characteristics. This profile defines pairing with an optimized carrier, administration route, and route-specific penetration enhancer. Lipophilic compounds are incorporated into lipidic or vesicular carriers, including antioxidant-enriched self-emulsifying delivery systems, ethosomes, and nanostructured lipid carriers. Hydrophilic compounds are formulated into cyclodextrin inclusion complexes, phospholipid-based systems (liposomes, phytosomes), or aqueous polymeric dispersion matrices. Each carrier is pre-engineered and stability-validated prior to final assembly to support consistent uptake, extended shelf life, and reproducible release.

Key delivery modules include antioxidant-enriched lipid carriers for oxidation-sensitive nutrients, polarity-tuned vesicular and nanoemulsion systems for solubility and transport, and microdermal devices for controlled delivery. Hydrogel-forming and dissolving microneedles provide transdermal administration of hydrophilic actives. Dual-layer microneedle configurations fabricated by sequential casting maintain polarity-segregated compartments and support synchronized or staggered delivery of lipophilic and hydrophilic payloads. Topical nanoemulgels with sub-200-nanometer droplet control enhance dermal penetration, reduce phase separation, and extend release duration.

A comprehensive stability framework counters oxidative, photolytic, thermal, and moisture-related degradation. Measures include polarity-matched antioxidant embedding, nitrogen-flushed inert handling during encapsulation, light-shielded manufacturing, thermal protection elements, and high-barrier multilayer packaging with integrated oxygen absorbers. Coordinated packaging and process controls provide long-term potency retention and structural integrity under real-time and accelerated conditions consistent with ICH Q1A (R2) and Q1B. In certain embodiments, formulations demonstrate retention within 90-110 percent of labeled potency over extended storage.

The platform enables polarity-matched co-formulation of synergistic nutrient combinations. Representative examples include sterol derivatives (in certain embodiments esterified DHEA esters as non-limiting model compounds) with adaptogens for wellness support, HMB free acid with essential amino acids for protein metabolism support, L-arginine with resveratrol and omega-3 fatty acids for cardiovascular wellness support, and botanical adaptogens with chelated minerals combined with sterol-derivative nutrients for multi-system nutritional support. Polarity alignment, synchronized release, and coordinated routes improve absorption efficiency and stability while remaining within supplement practice.

A central objective is to increase effective bioavailability of both lipophilic and hydrophilic dietary supplement compounds at lower input dosages. By pairing each compound with a polarity-matched carrier and a route-specific penetration enhancer, the platform reduces reliance on high loading, enabling physiologically appropriate quantities to be absorbed efficiently. This approach minimizes excipient burden, supports regulatory compliance, and enhances stability, solubility, and targeted delivery.

Integrated enhancer design is embedded within carriers according to polarity and route. Enhancement mechanisms may include lipid bilayer fluidization, hydration modulation, vesicle destabilization, and facilitation of lymphatic uptake. A compatibility and stability index manages phase behavior and interface integrity to avoid inversion and interfacial drift during single-route or dual-route use. The mapping of enhancers to each active's physicochemical profile provides predictable improvements in solubility, permeability, and systemic uptake.

In contrast to prior systems that lack polarity-specific formulation logic or are confined to single-route applications, this invention provides a fully integrated architecture for coordinated, multi-route delivery. Each compound is aligned with a polarity-compatible carrier and matched enhancer, allowing precise control over bioavailability, release timing, and shelf stability. All embodiments share the same inventive principle of polarity-specific mapping, ensuring unity of invention across oral, topical, and transdermal routes. By employing polarity-driven carrier pairing at supplement-appropriate levels, the platform provides a scalable framework that supports wellness outcomes while addressing persistent challenges in solubility, degradation resistance, and absorption efficiency.

The present disclosure is directed to a single inventive concept: a modular bioavailability-enhancement platform for compositions comprising both lipophilic and hydrophilic bioactives. The inventive step resides in polarity-specific separation and stabilization of actives within tailored carriers, including self-emulsifying systems, ethosomes, microneedles, and nanoemulsions, enabling enhanced absorption, stability, and physiological utilization at appropriate dosages. While multiple embodiments are disclosed, these are modular implementations of the same principle. Each format demonstrates conversion of the same active compositions into different delivery routes while maintaining polarity-based separation, antioxidant stabilization, and modular enhancement layers.

Study 8, disclosed in the parent application, is included for continuity of disclosure and as a foundational data set demonstrating polarity-appropriate oral delivery practices. The present Continuation-in-Part formalizes polarity-specific mapping as a unifying framework and extends the platform across oral, transdermal, and topical embodiments with coordinated stability engineering and enhancer integration.

DETAILED DESCRIPTION OF THE PREFERRED EMBODIMENTS

The present invention is described in further detail through exemplary embodiments; these examples are not intended to limit the scope of the claims. Variations, substitutions, and functional equivalents may be applied to the structures, materials, and processes described herein without departing from the invention. Unless otherwise indicated, implementations are directed to dietary and nutraceutical supplement applications; in certain embodiments, pharmaceutical actives may be referenced as model compounds without limiting the invention. Modifications may include the use of alternative polarity-optimized carrier systems, for example self-emulsifying delivery systems, phospholipid-based systems (liposomes, phytosomes), ethosomes, nanostructured lipid carriers, cyclodextrin inclusion complexes, nanoemulgels, and hydrogel or dual-layer microneedles; stability technologies such as embedded antioxidants, photoprotectants, inert-gas handling, oxygen absorbers, and high-barrier packaging; or route-specific configurations including oral, transdermal, topical, or dual-route formats. All such implementations are consistent with the polarity-specific delivery principles and the Active-Carrier-Route-Penetration Enhancer Mapping Framework disclosed herein, with performance supported by validation datasets confirming dissolution enhancement, polarity-based assignment, coordinated dual-route timing and compatibility, sequential microneedle casting, nanoemulgel droplet control, and coordinated packaging stability.

The accompanying drawings are provided to illustrate representative embodiments. The figures are not to scale and are not intended to limit the claimed invention. Identical reference numerals may be used across multiple figures to indicate functionally or structurally similar components. The schematics depict functional block representations of polarity-segregated compartments and carrier modules; relative dimensions, compositions, and arrangements shown are illustrative and non-limiting.

First Embodiment: Polarity-Specific, Pre-Engineered Single- or Dual-Route Delivery Platform In a first embodiment, the invention discloses a unified, polarity-specific, pre-engineered delivery platform configured for administration of dietary and nutraceutical supplement actives via single-route or dual-route formats. The platform assigns each lipophilic or hydrophilic bioactive to a polarity-matched, pre-optimized carrier system and assembles these pairings into dosage forms suitable for oral, transdermal, or topical delivery, used individually or in coordinated dual-route combinations. Selection and integration are governed by the Active-Carrier-Route-Penetration Enhancer Mapping Framework, which constitutes the core architectural logic from which subsequent embodiments, including oral capsules, hybrid microneedle patches, and topical gel or cream systems, are derived.

The platform integrates delivery technologies engineered to improve exposure characteristics, stability, and uptake. Bench characterization showed that micronization under inert gas yielded sub-10-micron particle sizes that enhanced dissolution kinetics for poorly water-soluble actives. Phospholipid-based systems (liposomes, phytosomes) increased membrane interaction of botanical compounds under controlled evaluations. Cyclodextrin inclusion complex«es provided polarity-optimized solubilization and stabilization with dissolution uplift and orthogonal confirmation, and were adapted for oral and non-oral formats. Non-esterified fatty acids functioned as lipid-phase nutrients and carrier aids, facilitating micellar encapsulation and partitioning into barrier interfaces. Franz diffusion and ex vivo skin studies indicated that polarity-specific vesicular and lipid systems, including ethosomes, nanostructured lipid carriers, antioxidant-enriched self-emulsifying delivery systems (SEDS) for oral formats, and nanoemulgels with sub-200-nanometer droplet control for topical use, improved delivery performance for polarity-matched actives. Sequentially cast microneedles maintained polarity segregation and supported controlled release.

The platform supports rational, polarity-aligned co-formulations via complementary release and presentation. In one configuration, sterol derivatives (including, in certain embodiments, esterified derivatives of DHEA as non-limiting model compounds) were paired with adaptogenic botanicals. Controlled evaluations focused on dispersion, release, and exposure profiles showed sustained sterol presentation with compatible stability of the botanical fraction under co-formulation.

In another configuration, beta-hydroxy-beta-methylbutyrate (HMB) free acid was combined with essential amino acids. Pharmacokinetic profiling under matched conditions showed faster appearance and higher exposure for HMB free acid relative to salt forms. Within the platform, HMB is treated as hydrophilic and configured per route using hydrogel-forming microneedles for dermal delivery and cyclodextrin inclusion complexes and, in certain embodiments, amorphous solid dispersions for oral delivery. Topical formats use aqueous dispersions and phospholipid-based systems (liposomes, phytosomes) consistent with polarity-matched design.

A third configuration combined L-arginine, trans-resveratrol, and omega-3 fatty acids. The combination was engineered for polarity-matched uptake and route-appropriate stability. Characterization included droplet and vesicle sizing, oxidation indices, and in vitro diffusion, which demonstrated complementary release windows without cross-degradation.

Across all formulations, actives, including adaptogens, fatty acids, amino acids, vitamins, minerals, polyphenols, and sterol derivatives (including, in certain embodiments, esterified derivatives of DHEA as model compounds), are systematically matched to optimized carriers based on polarity, molecular weight, solubility profile, and intended administration route via the Active-Carrier-Route-Penetration Enhancer Mapping Framework. Platform testing indicated that this polarity-specific mapping, combined with a compatibility and stability index to manage interface behavior, enables high bioavailability, formulation stability, and reproducible release across dosage formats.

This platform-level embodiment is structurally and functionally distinct from the route-specific embodiments described later. While oral capsules, microneedle patches, and topical formulations are presented in detail in subsequent embodiments, each is constructed from the same polarity-specific, modular architecture.

Integrating pre-engineered, polarity-matched carrier systems into a unified platform addresses persistent limitations of conventional supplement delivery, including low solubility, limited membrane permeability, and degradation, while supporting manufacturing scalability and extended shelf life. Coordinated process and packaging controls include nitrogen-flushed handling where applicable, light-controlled manufacturing, and high-barrier packaging with oxygen absorbers consistent with ICH Q1A (R2) and Q1B expectations. By aligning each active with an optimal carrier before final assembly, and validating performance through bench, diffusion, and human-use evaluations focused on absorption, stability, and uptake, the platform enables predictable exposure profiles and reduced dosing frequency.

The system's versatility permits seamless adaptation across delivery routes, enabling mono-route or dual-route formats tailored to user goals within wellness applications. This flexibility supports a broad spectrum of nutrients, from lipophilic antioxidants to water-soluble amino acids, within a harmonized, polarity-driven framework optimized for dietary and nutraceutical supplement use.

Table 41: Active-Carrier-Route-Penetration Enhancer Mapping

To demonstrate the polarity-specific, pre-engineered architecture of the present invention, Table 41 provides an empirically validated mapping of active ingredient classes to polarity classification, optimized carrier systems, primary delivery routes, and integrated penetration enhancers. Each mapping is supported by validated laboratory studies-including dissolution testing, ICH Q1A (R2)/Q1B stability assays, Franz diffusion, and ex vivo skin permeation—and, where applicable, controlled human-use evaluations (Study 1A, 1B, and Studies 2-8). These data confirm that pairing each active's physicochemical and polarity profile with a polarity-matched carrier system and route-appropriate enhancer yields reproducible improvements in solubility, stability, permeability, and overall bioavailability across both single-route and dual-route administration (oral, transdermal, and topical).

TABLE 41

Active-Carrier-Route-Penetration Enhancer Mapping

| Active Class | Polarity | Pre-Engineered Carrier System | Primary Delivery Route(s) | Integrated Penetration Enhancers |
|---|---|---|---|---|
| Sterol derivatives (including DHEA esters as model compounds | Lipophilic | Ethosomes/ NLCs (Transdermal); Antioxidant-Enriched SEDS (Oral) | Oral (single); Transdermal Microneedle Patch (single); Oral + Transdermal Microneedle (dual | Oleic acid, Transcutol ®, terpenes |
| Fat-Soluble Vitamins | Lipophilic | NLCs (Transdermal); | Oral (single); Transdermal | Oleic acid, medium-chain |

TABLE 41-continued

| Active-Carrier-Route-Penetration Enhancer Mapping | | | | |
|---|---|---|---|---|
| Active Class | Polarity | Pre-Engineered Carrier System | Primary Delivery Route(s) | Integrated Penetration Enhancers |
| (A, D, E, K) | | Antioxidant-Enriched SEDS (Oral) | Microneedle Patch (single); Oral + Transdermal Microneedle (dual) | triglycerides |
| Lipophilic Polyphenols (Resveratrol, Curcumin, CoQ10) | Lipophilic | Ethosomes/ NLCs with Antioxidants | Oral (single); Transdermal Microneedle Patch (single); Oral + Transdermal Microneedle (dual) | Ethanol, terpenes |
| Omega-3 Fatty Acids | Lipophilic | NLCs with Antioxidants; Antioxidant-Enriched SEDS (Oral) | Oral (single); Transdermal Microneedle Patch (single); Oral + Transdermal Microneedle (dual) | Lecithin, NEFAS |
| Adaptogens (Lipophilic Fraction) | Lipophilic | Phytosome Complexes + Lipid Vesicles | Oral (single); Transdermal Microneedle Patch (single); Oral + Transdermal Microneedle (dual) | Phosphatidylcholine, ethanol |
| Non-Esterified Fatty Acids (NEFAs) | Lipophilic | NLCs; Lipid Nanoparticle Dispersions | Oral (single); Transdermal Microneedle Patch (single); Oral + Transdermal Microneedle (dual) | Medium-chain triglycerides, lecithin |
| Chelated Minerals (Zinc, Magnesium) | Hydrophilic | Cyclodextrin Complexes; Hydrogel-Forming Microneedles | Oral (single); Microneedle (single); Oral + Microneedle (dual) | Polyols, glycerin |
| Water-Soluble Vitamins (B, C) | Hydrophilic | Cyclodextrin Complexes; Liposomes | Oral (single); Microneedle (single); Oral + Microneedle (dual) | Polyols (glycerin, propylene glycol) |
| Amino Acids (EAAs, Creatine) | Hydrophilic | Hydrogel-Forming Microneedles; Cyclodextrin Complexes | Oral (single); Microneedle (single); Oral + Microneedle (dual) | Hyaluronic acid, glycerin |
| HMB Free Acid | Hydrophilic | Hydrogel-Forming Microneedles; Aqueous Nanodispersion/ Solid Dispersion; Cyclodextrin Complexes | Oral (single); Microneedle (single); Oral + Microneedle (dual) | Glycerin, humectants |
| Adaptogens (Hydrophilic Fraction) | Hydrophilic | Cyclodextrin Complexes; Liposomes | Oral (single); Microneedle (single); Oral + Microneedle (dual) | Polyols, phospholipids |
| Botanical Extract Blends (Multi-Polarity) | Mixed | Dual-Layer Microneedles (lipid tip + polymeric core); Vesicular-Polymer Hybrids | Oral (single); Transdermal Microneedle Patch (single); Oral + Transdermal Microneedle (dual) | Polarity-specific enhancer pairing |
| Photolabile Actives (Retinoids, Carotenoids, Vitamin D Analogs) | Lipophilic | Light-Shielded Ethosomes/ NLCs; Opaque SEDS Softgels | Oral (single); Transdermal (single); Oral + Transdermal (dual) | UV-filtering excipients, oleic acid |
| Oxidation- | Lipophilic | Antioxidant-Enriched NLCs; Nitrogen- | Oral (single); Transdermal (single); Oral + | Tocopherols, ascorbyl palmitate |

TABLE 41-continued

Active-Carrier-Route-Penetration Enhancer Mapping

| Active Class | Polarity | Pre-Engineered Carrier System | Primary Delivery Route(s) | Integrated Penetration Enhancers |
|---|---|---|---|---|
| Sensitive Lipids (PUFAs, Sterols) | | Flushed Packaging | Transdermal (dual) | |
| Hydrophilic Polyphenols (EGCG, Quercetin Glycosides) | Hydrophilic | Liposomes; Cyclodextrin Complexes | Oral (single); Microneedle (single); Oral + Microneedle (dual) | Polyols, phospholipids |

Table 41 summarizes the platform's Active-Carrier-Route-Penetration Enhancer mapping. It classifies each active class by polarity and assigns a polarity-matched carrier module (for example, antioxidant-enriched SEDS, NLCs, ethosomes, phospholipid-based systems (liposomes, phytosomes), cyclodextrin complexes, and microneedles), along with primary routes (oral, transdermal, microneedle) and integrated enhancers (for example, oleic acid, ethanol, phosphatidylcholine, glycerin). Dual-route options are indicated where coordinated oral plus transdermal or oral plus microneedle delivery is appropriate. The table operationalizes polarity-driven selection rules and compatibility safeguards so each pairing supports solubility, stability, and permeability targets. Mappings are supported by validation datasets, including dissolution, ICH Q1A (R2)/Q1B stability, Franz diffusion, and ex vivo skin studies.

Penetration strategies are applied across major classes of bioactive compounds in validated single-route systems (oral, transdermal, microneedle, topical cream, hybrid microneedle) and in dual-route systems that pair oral administration with one additional route. These implementations use polarity-matched carrier selections paired with route-appropriate enhancers.

All active-carrier-route-enhancer mappings in Table 41 are supported by controlled human evaluations and laboratory studies. Validation methods included pharmacokinetic sampling, dissolution testing, stability studies under ICH Q1A (R2) and Q1B, and Franz diffusion cell assays. Across these settings, polarity-matched pairings showed reproducible improvements in solubility, stability, dermal penetration, and, where measured, systemic exposure within validated single-route formats and in dual-route configurations that combine oral delivery with one additional system.

A key inventive feature is the integration of polarity-specific penetration enhancers within each carrier system to influence solubility, permeability, and chemical stability. Enhancers are pre-selected to match both the polarity of the bioactive and the intended delivery route. Controlled evaluations and laboratory studies indicated that polarity-specific matching improved uptake efficiency through complementary mechanisms such as lipid bilayer fluidization for lipophiles, hydration-gradient modulation for hydrophiles, and vesicle-membrane perturbation for vesicular systems. Under these conditions, both lipophilic and hydrophilic actives achieved higher exposure metrics than non-optimized comparators, without asserting therapeutic outcomes.

This structured mapping of active-carrier-enhancer combinations enables accommodation of multi-polarity compositions in either single-route or dual-route modes. Stability studies conducted under ICH Q1A (R2) and Q1B, including oxidative, photolytic, and thermal stress testing, showed preservation of potency with options for extended or controlled release profiles, consistent with polarity-matched design.

At the platform level, absorption pathways are optimized per route. For oral delivery, lipophilic agents in self-emulsifying systems exhibited rapid in situ microemulsification with improved dissolution kinetics. For microneedle systems, hydrophilic actives released from aqueous-phase polymeric matrices demonstrated sustained, localized dermal presentation with reproducible release profiles. By way of illustration consistent with Table 41, hydrophilic compounds such as HMB free acid are configured for hydrogel-forming microneedles or for oral delivery using solid dispersion and/or cyclodextrin inclusion, while lipophilic sterol derivatives are configured for self-emulsifying systems, ethosomes, or nanostructured lipid carriers. For topical delivery, polarity-aligned nanoemulgels with sub-200-nanometer droplet control enhance dermal penetration and stability. Hydrophilic oral carriers may include phospholipid-based systems (liposomes, phytosomes) in addition to cyclodextrin complexes.

In dual-route configurations, for example oral plus transdermal or oral plus topical, coordinated scheduling and polarity matching produced consistent exposure profiles by reducing route competition and leveraging temporal or spatial separation of uptake. Under matched nominal dosing, these pairings achieved additive or complementary exposure behavior in controlled evaluations, allowing target exposure to be reached with greater consistency across routes while maintaining acceptable tolerability. A compatibility and stability framework manages interface behavior to avoid inversion and undesirable interfacial drift when routes are used together.

The platform addresses limitations of single-route, non-polarity-optimized approaches, which can exhibit solubility or stability shortfalls and inconsistent exposure. Here, polarity-specific optimization is applied as a unifying principle and is supported by comparative laboratory studies, including Franz diffusion, and by controlled human evaluations.

To implement this principle, the platform uses a coordinated toolkit: micronization under inert gas for poorly water-soluble actives; phospholipid-based systems (liposomes, phytosomes) to enhance botanical permeability; cyclodextrin inclusion complexes for hydrophiles across routes; non-esterified fatty acids as lipid-phase enhancers or actives; and pre-engineered vesicular and lipid systems, including ethosomes, nanostructured lipid carriers, and self-emulsifying systems, selected per polarity and route. For topical formats, nanoemulgels with sub-200-nanometer droplet control are used to improve penetration and shelf stability. Each technology is deployed with polarity-specific rationale and route-appropriate optimization, validated in preclinical and controlled human testing.

The platform supports synergistic combinations while maintaining chemical and functional stability using unified antioxidant systems, photostabilizers, and oxygen-barrier packaging. Under ICH Q1A (R2) accelerated and real-time conditions, and ICH Q1B photostability conditions, these measures supported long-term stability across oral, transdermal, and topical formats.

Accordingly, the modular, pre-engineered system provides a flexible, scalable framework validated in laboratory and controlled human studies for single-route or dual-route, multi-polarity delivery. It addresses formulation challenges in solubility, permeability, chemical degradation, and cross-route compatibility, and provides an advancement in delivery architecture for dietary supplement and cosmetic contexts, without asserting therapeutic claims.

Second Embodiment: Oral Capsule Embodiment

General Description

In a second embodiment, the invention provides a polarity-specific, pre-engineered oral capsule designed either for single-route administration as a stand-alone format or for dual-route use when co-packaged or co-administered with a microneedle patch or topical gel. This embodiment applies the platform's modular architecture to oral formats, supporting polarity-specific stabilization, synchronized dissolution or dispersion kinetics, and improved exposure under controlled evaluations. The oral capsule functions both independently and as a coordinated component within multi-route administration. Selection follows the Active-Carrier-Route-Penetration Enhancer mapping framework.

Carrier Systems and Polarity-Specific Integration (Lipophilic Module)

Lipophilic actives, including sterol derivatives (including, in certain embodiments, DHEA esters as model compounds) and fat-soluble vitamins A, D, E, and K, are incorporated into antioxidant-enriched self-emulsifying delivery systems (SEDS) with tocopherols, ascorbyl palmitate, and optional rosemary extract. Characterization confirmed spontaneous microemulsification to sub-200-nanometer dispersions upon aqueous dilution, supporting rapid dispersion and robust physical stability. Stability testing showed that the lipid-phase antioxidant system maintained potency, and limited oxidative change under ICH Q1A (R2) conditions.

Polarity-Specific Integration (Botanical and Hydrophilic Modules)

Lipophilic polyphenols and botanicals such as resveratrol and curcumin may be configured as phospholipid-based systems (liposomes, phytosomes) with nitrogen-managed handling to preserve structure during processing and storage. Hydrophilic actives, including water-soluble vitamins, creatine, hydrophilic adaptogens, essential amino acids, and HMB free acid, are configured as cyclodextrin inclusion complexes and or amorphous solid dispersions (ASD) with suitable polymers. These hydrophilic configurations demonstrated increased apparent solubility, precipitation control, and capsule compatibility. For HMB, oral embodiments use cyclodextrin inclusion and or ASD, consistent with Table 41.

Oxidation-Sensitive Lipids

Omega-3 fatty acids and sterols are formulated in antioxidant-enriched lipid carriers. Peroxide and anisidine indices remained within acceptance criteria across accelerated and long-term stability studies, consistent with the tailored oxidation-control design.

Structural Design of the Capsule

Validated structures include opaque softgels for lipophilic SEDS fills and HPMC or hard-gelatin capsules for multiparticulate fills. Multiparticulate fills can co-dose lipid SEDS subfills with granular hydrophilic subfills such as HMB cyclodextrin or ASD, maintaining polarity integrity. Packaging, including oxygen-barrier blisters or multilayer bottles with desiccant and nitrogen headspace, was verified to mitigate oxygen, moisture, and light exposure under ICH Q1A (R2) conditions.

Comprehensive Stability Strategy

A unified strategy integrates antioxidant-fortified lipids, nitrogen-managed encapsulation, barrier packaging, photoprotection, desiccant control, and thermally robust excipients. SEDS surfactant and co-surfactant ratios are optimized to sustain isotropy on dispersion. Testing follows ICH Q1A (R2) and Q1B, USP <905>, USP <61> and <62>, and USP <2040> where applicable.

Stability Results (Representative)

Under accelerated conditions at 40° C. and 75 percent relative humidity, representative oral lots retained at least 93 percent of initial potency at study endpoints, while matched conventional softgel controls exhibited greater than 30 percent loss within 6 months. These results support the integrated stability framework; values are illustrative and lot-specific.

Technical Advantages

Polarity-Specific Synchronization of Release

Dissolution or dispersion testing showed rapid SEDS micro-emulsification for lipophiles alongside cyclodextrin-mediated hydration or ASD dissolution for hydrophiles, enabling coordinated uptake behavior with reduced internal competition among phases. For example, HMB uses cyclodextrin or ASD; sterol derivatives use SEDS.

Comparative Exposure without Excess Ser Ving Levels

In comparative pharmacokinetic sampling under matched conditions, capsules prepared per this embodiment achieved higher exposure for representative lipophiles such as sterol derivatives and oxidation-sensitive lipids such as omega-3 fatty acids relative to reference soft gels, without exceeding typical label serving levels. Results are presented as exposure characteristics and not as therapeutic claims.

Resilience Against Oxidation and Hydrolysis

Accelerated and real-time data indicated no more than 6 percent cumulative change in peroxide and anisidine indices at 12 months for antioxidant-enriched lipid fills, while controls exceeded 20 percent at 3 months. Hydrophilic cyclodextrin or ASD configurations was maintained solubility and assay, whereas un-complexed comparators showed precipitation or hydrolytic drift.

Dual-Route Interoperability (Coordinated Use)

When coordinated with transdermal microneedle or topical embodiments, oral SEDS for sterols and oral HMB cyclodextrin or ASD produced additive or complementary exposure behavior via temporal or spatial separation of uptake. These findings describe coordinated exposure profiles under controlled evaluations. A compatibility and stability index governs interface behavior and timing windows to avoid inversion and undesirable interfacial drift during combined-route use.

Manufacturing Efficiency and Reproducibility

Each polarity module is pre-engineered and qualified before integration. Lot-to-lot validations demonstrated reproducible critical quality attributes, streamlined documentation, and scalability suited to commercial production.

Inventive Step (Integrated Oral Architecture)

To the inventors' knowledge, prior systems do not describe an oral capsule architecture that integrates polarity-specific SEDS for lipophiles, nitrogen-managed phospholipid-based systems for selected botanicals, and dual-route compatible cyclodextrin or ASD configurations for hydrophiles, including HMB, within a single stability-engineered platform that interoperates across routes. The coordinated release and dispersion design, ICH-aligned stability performance, and cross-route compatibility constitute a technical advancement over conventional oral delivery approaches.

Third Embodiment: Transdermal Microneedle Patch Embodiment

General Description

In a third embodiment, the invention provides a polarity-specific, pre-engineered transdermal microneedle patch configured for single-route dermal delivery or coordinated dual-route use when co-packaged or co-administered with an oral capsule or topical gel or cream. The embodiment enables synchronized dermal presentation of lipophilic and hydrophilic actives with route-appropriate carriers, supporting more consistent exposure profiles under controlled evaluations. Sensitive actives are protected through polarity-matched carriers and barrier-engineered packaging, with route-appropriate labeling and claims as described elsewhere.

Carrier Systems and Polarity-Specific Integration

Lipophilic compounds including sterol derivatives, fat-soluble vitamins A, D, E, and K, and lipophilic polyphenols such as resveratrol, curcumin, and CoQ10 are formulated in ethosomes or nanostructured lipid carriers (NLCs) to support dermal penetration, oxidative stability, and controlled release. Hydrophilic compounds including amino acids, creatine, HMB free acid, and water-soluble vitamins are incorporated into hydrogel-forming or dissolving microneedles based on HA, PVP, PVA, or CMC matrices, providing rapid hydration-driven presentation or extended release via controlled polymer swelling. Sequential casting and low-shear processing preserve vesicle integrity, maintain polarity segregation between lipidic tips and hydrophilic shafts, and allow tuning for synchronized, sequential, or independent release.

Structural Design of the Patch

The patch architecture comprises a multilayer polymeric backing with oxygen and light barrier properties, a biocompatible adhesive validated for defined wear periods, and optional rate-controlling membranes such as EVA or polyurethane for actives that benefit from extended release. Polarity-specific spatial separation of lipophilic and hydrophilic compartments minimizes cross-degradation, recrystallization, and premature precipitation prior to application. A compatibility and stability index governs interface behavior to avoid inversion and interfacial drift.

Stability Engineering

Patches sealed in nitrogen-flushed, moisture-barrier pouches demonstrated preserved potency and mitigated oxidative, photolytic, and hydrolytic change. Oxygen absorbers further stabilized lipid vesicles and sensitive polyphenols. The stability framework was verified under ICH Q1A (R2) accelerated and real-time conditions and ICH Q1B photostability conditions, and includes antioxidant-fortified lipid carriers, opaque barrier packaging, and inert-gas handling.

Technical Advantages (Laboratory and Controlled Human Evaluations)

The disclosed patch integrates ethosome or NLC lipid vesicles for lipophiles with hydrogel microneedles for hydrophiles in a polarity-matched, stability-optimized format. Under standardized handling, vesicle integrity was preserved and supported consistent dermal penetration of lipophilic payloads. Hydrophilic and lipophilic subsystems can be configured for synchronized, sequential, or independent release, enabling tailored exposure windows without therapeutic assertions. Mechanical integrity met insertion-force targets suitable for skin application.

Representative Performance Data

Under accelerated storage at 40° C. and 75 percent relative humidity for 6 months and long-term storage at 25° C. and 60 percent relative humidity for 12 months, representative lots of dual-compartment patches retained at least 92 percent of initial potency with no evidence of vesicle collapse or polymer embrittlement. Franz diffusion testing showed an approximately 2.1-fold increase in cumulative dermal penetration for ethosome or NLC-configured lipophiles compared to unstructured controls, while hydrophilic actives in hydrogel microneedles achieved at least 90 percent release within approximately 30 minutes of hydration under test conditions. In controlled human sampling, the patch functioned as a single-route dermal system and as a coordinated module with oral or topical embodiments, yielding more consistent exposure profiles under matched nominal dosing. HMB is hydrophilic and, in this embodiment, is loaded in the hydrogel microneedle matrix.

Inventive Step

To the inventors' knowledge, prior microneedle systems do not disclose the specific combination of polarity-matched spatial separation between hydrophilic shafts and lipophilic tips or reservoirs, ethosome or NLC vesicles integrated with hydrogel-forming microneedles, low-shear processing to preserve vesicle morphology, and a barrier-engineered backing with nitrogen-managed packaging to stabilize both compartments, together with validated biphasic release and coordinated dual-route interoperability. This integrated architecture provides a multi-compartment, polarity-specific, stability-optimized microneedle system suitable for single-route or dual-route use.

Fourth Embodiment: Topical Cream/Gel Embodiment for Single-Route and Dual-Route Delivery

General Description

In a fourth embodiment, the invention provides a polarity-specific, pre-engineered topical cream or gel configured for single-route dermal use or coordinated dual-route use with an oral capsule or a microneedle patch. The platform is applied to dermal systems to support route-appropriate presentation of lipophilic and hydrophilic bioactives with controlled structure, stability, and coordinated performance under laboratory and controlled human evaluations. Selection follows the Active-Carrier-Route-Penetration Enhancer mapping framework.

Polarity-Matched Carrier Systems

Lipophilic actives, including sterol derivatives (including, in certain embodiments, DHEA esters as model compounds), vitamins A, D, E, and K, lipophilic polyphenols such as resveratrol and curcumin, and omega-3 fatty acids, are configured in nanostructured lipid carriers (NLCs), ethosomes, or nanoemulgels with sub-200-nanometer droplet control to support dermal penetration, oxidative protection, and controlled release. Hydrophilic actives, including vitamin C, B-complex vitamins, amino acids, creatine, HMB free acid, and hydrophilic botanical fractions, are configured in phospholipid-based systems (liposomes, phytosomes), cyclodextrin inclusion complexes, or aqueous polymeric dispersions to maintain solubility and presentation. For HMB, topical embodiments use aqueous dispersion and or cyclodextrin inclusion rather than oil-in-water nanoemulsion droplets, consistent with Table 41.

Base System and Droplet Control

The cream or gel base employs biocompatible emulsifiers and polymers selected for polarity compatibility. The oil phase incorporates antioxidants such as mixed tocopherols, ascorbyl palmitate, and optional rosemary extract to limit lipid-phase oxidation. The aqueous phase includes humectants or polyols such as glycerin and propylene glycol to support hydrophilic carriers. Under standardized processing, nanoemulgel variants maintain droplet sizes below 200 nanometers, improving interfacial area and uniform distribution of lipophilic payloads, which is associated with enhanced dermal penetration under test conditions.

Manufacturing and Stability Framework

Light-protected, low-shear emulsification, nitrogen-flushed filling, and opaque, barrier containers with optional oxygen absorbers form the stability framework. These measures were verified under ICH Q1A (R2) and Q1B conditions to support potency and physical stability for both lipophilic and hydrophilic phases. A compatibility and stability index governs interface behavior to avoid inversion and interfacial drift during storage and use.

Technical Advantages of the Fourth Embodiment

Dermal Penetration Via Sub-200-Nanometer Control

Under standardized dermal uptake testing such as Franz diffusion, maintaining droplet sizes below 200 nanometers produced approximately two-fold higher cumulative penetration compared to emulsions above 500 nanometers, attributable to increased surface area and vesicle-mediated transport through the stratum corneum. Values are representative and method-specific.

Polarity-Specific Co-Presentation

Formulations demonstrated co-presentation of hydrophilic and lipophilic payloads within polarity-matched carriers, addressing limitations of single-polarity creams. Dual-phase encapsulation supported simultaneous stabilization and route-appropriate dermal presentation without cross-degradation.

Oxidative and Photolytic Resilience

Representative accelerated studies at 40° C. and 75 percent relative humidity showed at least 92 percent potency retention for antioxidant-enriched nanoemulgels at 12 months. Opaque packaging plus photoprotective excipients reduced loss of photolabile actives such as retinoids and carotenoids by approximately 70 percent compared to transparent packaging under matched conditions.

Hydrophile Compatibility

Hydrophilic actives configured as cyclodextrin inclusion complexes and or hydrogel-based dispersions was maintained clarity and assay for at least 6 months without crystallization or phase separation under specified storage, supporting reproducibility and user acceptability.

Packaging Performance and Shelf Life

Integrated oxygen absorbers reduced residual headspace oxygen to 0.5 percent or less, protecting oxidation-sensitive polyphenols and fatty acids. Combined with nitrogen flushing and barrier containers, representative lots preserved potency for 24 to 36 months under ICH Q1A (R2) real-time and accelerated programs, subject to lot-specific confirmation.

Coordinated Dual-Route Behavior

In coordinated use, the topical system complemented oral or microneedle embodiments by providing localized dermal exposure of lipophiles such as sterol derivatives in ethosomes or NLCs alongside hydrophile presentation such as HMB in aqueous dispersion. Regimens were scheduled for temporal or spatial separation to yield more consistent overall exposure profiles under controlled evaluations. A compatibility and stability framework supports timing windows and interface control for dual-route operation.

Inventive Step

To the inventors' knowledge, conventional topical systems typically emphasize lipophilic payloads without polarity-specific separation or an integrated stability regimen. The disclosed embodiment combines lipophilic vesicular phases with droplet control below 200 nanometers and hydrophilic phospholipid-based systems (liposomes, phytosomes) or cyclodextrin or aqueous matrices, together with a barrier-engineered packaging program, enabling single-route dermal use and coordinated dual-route operation within a unified polarity-matched framework.

SUMMARY

By integrating polarity-matched lipidic and hydrophilic carriers, validated sub-200-nanometer droplet control for lipophiles, and a unified stability and packaging strategy, this embodiment supports extended shelf life and reproducible dermal penetration and presentation under test conditions, with flexibility for single-route or coordinated dual-route use, without asserting therapeutic claims.

Fifth Embodiment: Cyclodextrin Inclusion Complex for Single-Route and Dual-Route Delivery

General Description

In a fifth embodiment, the platform employs cyclodextrin (CD) inclusion complexes in oral, transdermal, and topical formats within a polarity-specific, pre-engineered architecture that supports both single-route and coordinated dual-route administration. Under laboratory and controlled human evaluations, CD complexes demonstrated compatibility with lipid-polymer hybrid carriers, hydrogel-based systems, and antioxidant-enriched self-emulsifying delivery system (SEDS) preconcentrates, enabling a given complex to maintain functional stability and delivery performance with minimal reformulation. Selection follows the Active-Carrier-Route-Penetration Enhancer mapping framework.

Carrier Systems and Polarity-Specific Integration (Lipophilic Classes)

For lipophilic actives such as sterol derivatives (including, in certain embodiments, DHEA esters as model compounds), coenzyme Q10, curcumin, and vitamins A, D, E, and K, CD complexes were integrated into phospholipid-based systems (liposomes, phytosomes), ethosomes, nanoemulgel matrices with sub-200-nanometer droplet control, or antioxidant-enriched SEDS. In these hybrids, CDs mitigated recrystallization while lipid phases fortified with tocopherols and ascorbyl palmitate, with optional rosemary extract, supported oxidation control. Encapsulation in oxygen-barrier soft-gels or HPMC capsules with managed headspace supported assay and physical stability under ICH-aligned accelerated and real-time programs. Improvements are described in terms of dispersion or solubilization behavior and exposure characteristics under test conditions.

Carrier Systems and Polarity-Specific Integration (Hydrophilic Classes)

For hydrophilic actives, including HMB free acid, vitamin C, B-complex vitamins, creatine, amino acids, and selected polyphenols, CD inclusion provided stabilization against recrystallization or degradation, where applicable, while maintaining high apparent solubility. This supported consistent dosing, controlled release, and reproducible exposure when delivered via a single route or coordinated in oral plus transdermal or oral plus topical formats. Hydrophilic CD complexes showed formulation compatibility with hydrogel-forming dermal matrices and polymer-based topical systems, enabling polarity-matched co-delivery without loss of structural integrity.

Technical Advantages (Representative Oral Data)

Under ICH Q1A (R2) accelerated conditions at 40° C. and 75 percent relative humidity, representative CD complexes retained at least 94 percent of initial potency at 12 months in single-route or dual-route configurations. Dissolution testing in simulated intestinal fluid showed greater than 85 percent release within 15 minutes for CD-complexed actives compared to less than 40 percent for uncomplexed comparators. When CD complexes were incorporated into antioxidant-enriched SEDS capsules, the combination supported oxidation control and rapid, coordinated dispersion for mixed-polarity regimens. Values are lot-specific and method-specific.

Technical Advantages (Representative Dermal Data)

Franz diffusion studies indicated an approximately 2.3-fold increase in cumulative dermal penetration for CD-complexed lipophilic actives relative to un-complexed controls under matched conditions. Hydrophilic actives complexed with CDs formed clear, stable hydrogel formulations with no crystallization or phase separation through 6 months of storage, supporting compatibility with hydrogel microneedles or polymer-based topical gels in single-route or dual-route systems.

Manufacturing Flexibility

Because the same CD inclusion complex can be deployed across oral and dermal formats within the platform, route changes or dual-route kits can be assembled with minimal re-engineering, reducing redundant processing steps while maintaining polarity-matched performance targets and facilitating efficient scale-up. A compatibility and stability index governs interface behavior when CD complexes are combined with lipidic phases to avoid inversion and interfacial drift.

Inventive Step and Continuity

To the inventors' knowledge, prior approaches do not disclose CD inclusion complexes pre-engineered for both single-route and dual-route administration in combination with lipid-polymer hybrids, hydrogel systems, and antioxidant-enriched SEDS within a single polarity-mapped framework. Conventional CD use is often limited to oral solubilization without coordinated dermal adaptation or dual-route stability. Study 8 in the parent application provided early oral evidence for polarity-aligned CD use with hydrophiles but did not define a system-wide polarity-mapping architecture. In contrast, the present disclosure formalizes polarity-driven mapping, extends CD applications to oral plus topical and oral plus transdermal combinations, and introduces comprehensive stability engineering.

Sixth Embodiment: Hybrid Microdermal Delivery System with Sequential or Simultaneous Release

General Description

In a sixth embodiment, the invention provides a hybrid microdermal delivery system in which each microneedle incorporates two polarity-specific compartments within a single array. A hydrophilic compartment is formed from a polymeric hydrogel or dissolving matrix for water-soluble actives such as amino acids, water-soluble vitamins, and hydrophilic botanical fractions. A lipophilic compartment contains lipid-based or nanoparticle-loaded carriers for lipophilic actives such as sterol derivatives, fat-soluble vitamins, lipophilic polyphenols, and carotenoids. Each compartment is manufactured under polarity-optimized processing conditions to preserve assay and physical integrity throughout shelf life. Where beneficial, hydrophilic guests may be pre-complexed by cyclodextrins, and lipophilic guests may be formatted in vesicular carriers including ethosomes or nanostructured lipid carriers.

Release Control and Sequential or Simultaneous Kinetics

Under laboratory and controlled-use models, the hybrid system delivered payloads either sequentially or simultaneously, depending on design choices. Sequential behavior was achieved by varying polymer dissolution rates, vesicle robustness, and compartment positioning along shaft versus tip. A representative setting used a fast-dissolving PVP-based shaft releasing approximately 80 percent at 0.5 hour, at least 90 percent by 1 hour, and approximately 95 percent by 2 hours, followed by a lipophilic tip configured with NLC or ethosome carriers releasing approximately 15 percent at 0.5 hour, approximately 25 percent at 1 hour, approximately 35 percent at 2 hours, approximately 45 percent at 4 hours, approximately 70 percent at 6 hours, and at least 90 percent by 8 hours. Simultaneous behavior was obtained by harmonizing polymer hydration with vesicle destabilization to align uptake windows for both compartments.

Tuning Parameters

Release kinetics were tuned via polymer selection such as PVP, hyaluronic acid, and carboxymethylcellulose, lipid-carrier composition such as NLCs and ethosomes, particle or vesicle size in a validated range of about 100 to 200 nanometers, and geometry such as lipophilic tip versus hydrophilic shaft. A compatibility and stability index governed interface behavior to avoid inversion and interfacial drift. This flexibility enables exposure-window targeting, including rapid onset paired with sustained follow-on presentation.

Technical Advantages

In vitro Franz diffusion studies indicated that hydrophilic actives from the polymeric compartment achieved approximately 82 to 88 percent release within 30 minutes, while lipophilic actives in NLC or ethosome carriers exhibited controlled release extending to approximately 8 hours under matched conditions. Accelerated stability under ICH Q1A (R2) at 40° C. and 75 percent relative humidity for 9 months showed at least 92 percent potency retention for both compartments with no measurable loss of microneedle mechanical strength or tip insertion performance. Nitrogen-flushed, opaque barrier pouches with optional oxygen absorbers supported potency and vesicle integrity under ICH Q1A (R2) and Q1B programs.

Dual-Route Compatibility

The hybrid microdermal system operated as a stand-alone dermal article and as a coordinated component when paired with an oral capsule or topical cream or gel. Combined-use evaluations demonstrated aligned exposure profiles via temporal or spatial scheduling, with the microneedle providing rapid and or sustained dermal presentation complementary to the companion route. Timing windows and interface rules were applied to maintain polarity segregation during dual-route use.

Novelty Justification

Prior microneedle systems commonly employ single-compartment matrices or mixed, unstructured blends that risk instability and precipitation. By contrast, the disclosed architecture provides physically separated, polarity-matched compartments within each microneedle, integrated with sequential casting and low-shear processing, enabling programmable sequential or simultaneous release without unstructured mixing.

SUMMARY

This embodiment introduces a dual-compartment microneedle with polarity-matched carriers, tunable release kinetics, and stability demonstrated under ICH-aligned programs, constituting an advance over single-phase or non-polarized microneedle approaches while enabling coordinated operation within multi-route regimens.

Seventh Embodiment: Expanded Botanical and Mineral Active Co-Formulation

General Description

In a seventh embodiment, the invention provides a polarity-specific co-formulation that integrates botanical adaptogens, chelated minerals, and sterol derivatives (including, in certain embodiments, DHEA esters as model compounds) within a unified platform operable as single-route formats for oral, transdermal, or topical use, or as coordinated dual-route formats. The architecture resolves polarity and stability considerations among lipophilic sterol derivatives, polyphenolic botanicals, and ionic mineral chelates by assigning each class to polarity-matched carriers and route-appropriate enhancers consistent with the platform's mapping framework in Table 41.

Carrier Systems and Polarity-Matched Integration (Lipophilic and Botanical Fractions)

Lipophilic actives, including sterol derivatives and fat-soluble polyphenols, are encapsulated in nanostructured lipid carriers (NLCs), ethosomes, or nanoemulgels with sub-200-nanometer droplet control for dermal and topical formats, and in antioxidant-enriched self-emulsifying delivery systems (SEDS) for oral formats. These carriers provide oxidation management, maintain dispersed state, and support route-appropriate presentation under test conditions. Botanical fractions are partitioned by polarity: lipophilic fractions such as aglycone polyphenols enter lipid vesicles; hydrophilic fractions such as glycosides are configured as phospholipid-based systems (liposomes, phytosomes) or cyclodextrin inclusion complexes to preserve solubility and prevent precipitation during storage and use.

Carrier Systems (Mineral Module)

Chelated minerals such as zinc, magnesium, and calcium are configured as hydrogel-forming microneedle payloads for dermal presentation and or cyclodextrin inclusion complexes or multi-particulate granules for oral use. These formats shield ionic species from destabilizing interactions with lipid phases and support controlled, polarity-compatible presentation in single-route or dual-route programs without cross-phase disruption.

Structured Compartmentalization

By assigning each polarity class to a pre-engineered module such as lipid vesicle, phospholipid-based system (liposomes, phytosomes) or cyclodextrin complex, hydrogel or microneedle matrix, or oral SEDS, the embodiment reduces cross-reactivity including mineral and polyphenol complexation, mitigates recrystallization, and maintains assay within stated acceptance criteria across routes. A compatibility and stability index governs interface behavior when modules are combined to avoid inversion and interfacial drift.

Stability Engineering

A unified stability strategy is applied: antioxidant fortification with mixed tocopherols and ascorbyl palmitate for lipid phases; nitrogen-managed processing for phospholipid-based and cyclodextrin botanical modules; and moisture-controlled matrices for mineral payloads. Packaging employs oxygen-barrier blisters or nitrogen-flushed pouches with desiccants and opaque containers to limit light exposure. In representative ICH Q1A (R2) accelerated programs at 40° C. and 75 percent relative humidity, co-formulations retained at least 90 percent of initial potency at 12 months; lipid oxidation markers remained below 7 percent compared to greater than 20 percent in unprotected controls; hydrophilic botanical modules showed no visible precipitation or crystallization. Values are lot-specific and method-specific. Photostability under ICH Q1B supported retention of photolabile constituents when opaque packaging and photoprotective excipients were used.

Technical Characterization (Representative)

Bench and controlled-use evaluations indicated that: (i) lipidic sterol modules in NLC, ethosome, or SEDS formats maintained sub-200-nanometer dispersion and showed higher Franz diffusion or permeation relative to unstructured controls under matched conditions; (ii) botanical phospholipid-based systems (liposomes, phytosomes) or cyclodextrin complexes maintained assay and exhibited greater than 85 percent dissolution in simulated media within 30 minutes; and (iii) chelated mineral hydrogel microneedles provided rapid onset of release in in vitro models with majority release within 30 minutes, supporting integration with staged exposure windows in coordinated regimens.

Coordinated Multi-Class Presentation

The polarity-specific architecture enables co-presentation of lipophilic, hydrophilic, and ionic modules with temporal or spatial scheduling across routes. This allows staged exposure windows, for example rapid hydrophilic or mineral presentation with sustained lipophilic delivery, while consolidating diverse actives into fewer dosage forms. The approach improves manufacturability and reduces formulation incompatibilities commonly observed in mixed systems. Timing windows and interface rules from the compatibility and stability index support reliable dual-route operation.

Novelty Justification

To the inventors' knowledge, conventional botanical and mineral products typically employ single-route capsules or powders in which ionic minerals can destabilize polyphenols or disrupt lipid carriers. The disclosed embodiment integrates polarity-matched lipid vesicles, phospholipid-based systems (liposomes, phytosomes) or cyclodextrin complexes, and hydrogel or microneedle or oral SEDS modules within a dual-route compatible architecture that minimizes cross-reactivity and coordinates exposure across active classes. This structured, polarity-driven integration presents a distinct combination not taught by prior mixed-polarity formulations.

Eighth Embodiment: Oxygen Absorber-Integrated Packaging

In an eighth embodiment, the invention provides an oxygen-absorber integrated packaging system engineered to limit oxidative, photolytic, and hydrolytic change in polarity-specific, pre-engineered formulations. The system is applicable to single-route and coordinated dual-route programs, including oral capsules, transdermal patches, microneedle systems, topical creams or gels, and hybrid microneedle arrays. Packages are formed from multilayer, high-barrier films or blisters. Fills are nitrogen-managed during closing and fitted with calibrated absorbers to establish a controlled microenvironment with low residual oxygen and managed humidity, supporting long-term assay and physical stability for both lipophilic and hydrophilic actives.

General Description

Under laboratory and packaging-qualification studies, absorber-integrated kits maintained stability targets for polarity-matched oral, dermal, and transdermal formats used alone or in coordinated dual-route regimens. The packaging architecture is modular, allowing capsule bottles, blister cards, and pouch systems to be combined without reformulation of the underlying dosage forms.

Carrier Systems and Compatibility

Lipid-phase carriers, including antioxidant-enriched self-emulsifying delivery systems (SEDS), nanostructured lipid carriers (NLCs), and ethosomes, maintained dispersion and vesicle integrity with no material evidence of peroxide-driven instability, vesicle collapse, or phase separation under accelerated storage when housed in absorber-integrated, nitrogen-managed packs. Hydrophilic carriers, including cyclodextrin inclusion complexes, hydrogel microneedles, and phospholipid-based systems (liposomes, phytosomes), showed no recrystallization, moisture-induced precipitation, or hydrolytic drift across oral, dermal, or microneedle presentations, whether used singly or in oral plus one other dual-route kits.

Co-deployment of oxygen absorbers, nitrogen flushing, desiccants, and multilayer barrier films minimized cross-polarity destabilization within shared kits, limiting oxidative stress in lipidic phases and moisture-driven change in hydrophilic modules under common storage conditions. A compatibility and stability index governs interface behavior for multi-component kits to avoid inversion and interfacial drift.

Stability Engineering

The stability program integrates: (i) nitrogen flushing to reduce initial headspace oxygen to 1 percent or less, (ii) controlled-capacity absorbers based on iron or ascorbate chemistry to sustain residual oxygen at 0.5 percent or less during storage, (iii) desiccant layers targeting less than 20 percent relative humidity, and (iv) high-barrier films or foil laminates to limit ingress of oxygen, light, and moisture. Collectively, the system supported stability across permitted single-route formats and oral plus one other dual-route combinations under ICH Q1A (R2) accelerated and real-time programs and ICH Q1B photostability programs. All values are representative and lot- or method-specific.

Technical Advantages

Cross-polarity stabilization (representative): In packaging studies at 40° C. and 75 percent relative humidity, multi-active kits stored with absorber-integrated, nitrogen-managed packaging retained at least 92 percent of initial assay at 12 months, whereas matched high-barrier controls without absorbers showed greater than 20 percent loss. Values are lot- and method-specific.

Protection of oxidation-sensitive lipids (representative): Omega-3 systems in antioxidant-enriched NLCs exhibited a peroxide-value increase of 5 percent or less at 12 months with absorbers, compared to 25 percent or more in non-absorber controls. Polyphenolic payloads such as resveratrol and curcumin maintained color metrics with no notable oxidative markers under the same conditions. Values are lot- and method-specific.

Compatibility with hydrophilic carriers (representative): Cyclodextrin-complexed vitamin C or B-complex modules stored in absorber-integrated packs showed no visible recrystallization and no material assay loss through 12 months, while non-protected comparators presented visible precipitation and 15 percent or more degradation. Values are lot- and method-specific.

Manufacturing Efficiency

The absorber approach was qualified on standard blister sealing, soft-gel bottling, and patch pouching lines with procedural additions limited to absorber placement and nitrogen management, supporting scale-up with minimal equipment change and without altering polarity-matched formulation logic.

Novelty Justification

To the inventors' knowledge, prior art does not disclose absorber technology integrated into a polarity-mapped platform that spans both single-route and oral plus one other dual-route kits while coordinating oxygen control, desiccation, and barrier layers for mixed-polarity payloads. Conventional packaging often isolates tactics such as antioxidants for lipids or desiccants for hydrophiles without a unified, cross-polarity program.

In the present system, nitrogen management, calibrated absorption, desiccation, and high-barrier films are harmonized to sustain mixed-polarity stability for 24 to 36 months under ICH-aligned programs, with performance characterized by residual-oxygen, humidity, assay, oxidation-index, and appearance metrics. Descriptions are limited to packaging and performance outcomes and do not assert therapeutic effects or clinical efficacy.

Ninth Embodiment: Dual-Layer Casting and Compartment Loading Microneedle

General Description

In a ninth embodiment, the invention provides a polarity-specific, dual-layer microneedle fabrication process that uses casting and compartment loading to maintain phase integrity for mixed-polarity active agents. Hydrophilic actives such as peptides, water-soluble vitamins, amino acids, and selected botanical polyphenols are incorporated into a polymeric hydrogel forming the shaft or base of each microneedle. A distinct lipophilic compartment, located in the tip or applied as a nanoparticle coating, encapsulates lipophilic actives such as esterified sterol derivatives, vitamins A, D, E, and K, carotenoids, and lipid-soluble antioxidants. Hydrophilic guests may optionally be pre-complexed using cyclodextrin inclusion complexes, while lipophiles may be formatted in ethosomes or nanostructured lipid carriers (NLCs) with vesicle or particle sizes controlled in the 100 to 200 nanometer range. The process is compatible with automated micro-molding and supports scalable production while maintaining payload integrity. Selection follows the Active-Carrier-Route-Penetration Enhancer mapping framework and is interoperable with dual-route regimens.

Structural Separation and Process Control

Physical separation of hydrophilic and lipophilic payloads reduces cross-contamination, recrystallization, and polarity-driven destabilization. Each layer is manufactured under polarity-optimized conditions, including controlled hydration for hydrogels and low-shear, temperature-managed handling for lipid vesicles, to preserve solubility, vesicle morphology, and carrier integrity. Sequential casting establishes the hydrophilic shaft and the lipophilic tip or coating as discrete compartments. A compatibility and stability index governs interface behavior to avoid inversion and interfacial drift. The compartmentalized architecture allows independent or synchronized release profiles selected at design time.

Release Control and Performance (Representative)

In vitro release testing under simulated dermal hydration showed that hydrophilic hydrogel compartments achieved at least 80 percent release within approximately 30 minutes, while lipophilic payloads embedded in NLC or ethosome tips provided sustained release out to approximately 8 hours under matched conditions. Sequential behavior was engineered using fast-dissolving polymers such as PVP for hydrophiles together with more robust lipid vesicles for lipophiles. Simultaneous behavior was obtained by harmonizing polymer dissolution with vesicle destabilization to align exposure windows. Values are method-specific and lot-specific.

Stability and Mechanical Integrity (Representative)

Accelerated stability per ICH Q1A (R2) at 40° C. and 75 percent relative humidity for 9 months demonstrated retention of approximately 92 to 94 percent assay across compartments with no measurable microneedle deformation, tip loss, or reduction in insertion performance. Nitrogen-flushed, opaque barrier pouches with optional oxygen absorbers supported potency and vesicle integrity under ICH Q1A (R2) and ICH Q1B photostability programs. Franz diffusion studies confirmed transdermal penetration under standardized conditions, with hydrophilic compartments releasing at least 85 percent payload within approximately 30 minutes and lipophilic actives exhibiting steady diffusion up to approximately 8 hours. Results are representative and depend on composition and method.

Technical Advantages

Compared with single-compartment microneedles, the dual-layer design preserves functional stability for mixed-polarity payloads, mitigates cross-degradation, and enables programmable release kinetics, including sequential or concurrent profiles, without unstructured blending. Mechanical integrity met insertion-force targets appropriate for skin application.

Inventive Step

To the inventors' knowledge, prior microneedle systems do not disclose the integrated combination of physically separated, polarity-matched compartments within each microneedle, polarity-optimized processing for hydrogel and vesicular phases, and tunable, biphasic release windows characterized by in vitro methods and ICH-aligned stability, together with packaging controls suitable for coordinated dual-route use. This coordinated architecture is distinct from single-phase or non-polarized microneedle systems.

Tenth Embodiment: Vesicular Lipid Systems Adapted Per Delivery Route

General Description

In a tenth embodiment, the invention provides route-adapted vesicular lipid systems engineered to the polarity of the active and the intended delivery route. Each vesicle class is pre-configured with polarity-matched excipients, surfactants, and penetration enhancers to support stability, dispersion, and presentation while preserving assay under ICH Q1A (R2) and Q1B conditions. The systems operate as single-route formats for oral, transdermal, microneedle, topical cream or gel, or hybrid microneedle use, or as oral plus one other dual-route combinations. Selection follows the Active-Carrier-Route-Penetration Enhancer mapping framework, with interface rules from the compatibility and stability index applied for combined-route kits.

Oral Delivery with Phospholipid-Based Systems (Phytosomes)—Representative

For oral administration, phospholipid-based systems (phytosomes) are used to present lipophilic phytochemicals and fatty-acid derivatives such as curcumin, resveratrol, and omega-3 derivatives and, in certain embodiments, esterified sterol derivatives. Phospholipid conjugation improves dispersion and membrane interaction, and nitrogen-managed processing safeguards chemical integrity during manufacture and storage. Representative tests showed rapid dissolution and maintained assay, with improved permeability surrogates compared to un-complexed controls under matched conditions. Values are method-specific.

Transdermal Delivery with Ethosomes-Representative

For transdermal administration, ethosomes are selected for route-appropriate dermal presentation of lipophilic actives, including esterified sterol derivatives, fat-soluble vitamins, and polyphenolic antioxidants. In Franz diffusion studies, ethosomes achieved approximately two-fold higher cumulative skin permeation compared to conventional liposomes under matched conditions. Results are representative and depend on composition and test parameters.

Sustained Dermal Delivery with NLC-Hydrogel Hybrids-Representative

For sustained dermal delivery, nanostructured lipid carriers (NLCs) may be embedded in hydrogels to extend presentation of lipophilic payloads such as coenzyme Q10, retinol, and carotenoids. Vesicle or particle sizes are controlled in the 100 to 200 nanometer range. The hybrid maintained vesicle stability and supported steady-state permeation approximately 8 to 12 hours post-application in standardized tests. Accelerated stability at 40° C. and 75 percent relative humidity showed at least 91 percent assay retention at 12 months with vesicle destabilization less than 10 percent. Values are lot-specific and method-specific.

Stability Engineering

Across vesicle classes, membranes are fortified with tocopherols and ascorbyl palmitate. Photoprotective excipients and opaque barrier packaging limit photolysis, and nitrogen management with oxygen-absorber integration targets residual oxygen of 0.5 percent or less where applicable. The compatibility and stability index governs interface behavior in multi-component kits to avoid inversion and interfacial drift. This unified strategy supports 24 to 36 months shelf-life programs under ICH-aligned accelerated and real-time conditions, evaluated by assay, oxidation indices, and appearance.

Manufacturing Architecture

Each vesicle class is pre-engineered under polarity-optimized conditions, qualified for stability and compatibility, and then formatted into its designated single-route system or oral plus one other dual-route kit. The modular approach reduces cross-degradation risk and supports high-throughput scalability without compromising payload integrity or the polarity-matched formulation logic.

Inventive Step

To the inventors' knowledge, while phytosomes, ethosomes, and NLCs are individually known, prior systems do not teach route-specific adaptation within a single polarity-mapped platform coordinated under a unified stability and packaging program across single-route and dual-route use. Conventional approaches treat vesicles as route-isolated carriers without modular interoperability, leading to variable stability and presentation. Here, phytosomes for oral use, ethosomes for transdermal use, and NLC-hydrogel hybrids for dermal and dual-route kits are coordinated under common quality and stability controls to provide a structured, interoperable system.

Eleventh Embodiment: New Synergistic Pairing Strategies

General Description

In an eleventh embodiment, the invention introduces polarity-specific pairing strategies in which two or more bioactive compounds are co-formulated within the pre-engineered platform. Each compound is assigned to a polarity-matched carrier module to maintain independent stabilization and route-appropriate presentation, in either a single-route format for oral, transdermal, microneedle, topical cream or gel, or hybrid microneedle use, or in oral plus one other dual-route configurations. The design goal of these pairings is coordinated exposure windows and mitigation of incompatibilities such as precipitation or cross-degradation that can occur when hydrophilic and lipophilic actives are blended without polarity mapping. Selection follows the Active-Carrier-Route-Penetration Enhancer mapping framework, with interface rules governed by the compatibility and stability index.

Hormonal and Adaptogen Pairing

A representative pairing combines lipophilic sterol derivatives, including in certain embodiments esterified DHEA model compounds, formulated in nanostructured lipid carriers (NLCs) or ethosomes, with adaptogenic botanical fractions such as *Rhodiola rosea* or *Ginkgo biloba* stabilized as cyclodextrin inclusion complexes or phospholipid-based systems (liposomes, phytosomes) according to fraction polarity. The pairing is configured for single-route formats or coordinated oral plus dermal, microneedle, or topical use. Characterization focused on dispersion, dissolution and diffusion surrogates, permeation metrics, and assay and stability under matched handling conditions. Descriptions are limited to presentation and exposure characteristics rather than health outcomes.

Anabolic and Metabolic Pairing

A second representative pairing addresses hydrophilic nutrient presentation by combining HMB free acid with essential amino acids such as leucine, isoleucine, and valine. For transdermal use, payloads are incorporated into hydrogel-forming or dissolving microneedles. For oral use, HMB is configured as a cyclodextrin inclusion complex and or amorphous solid dispersion with suitable polymers, not as an oral nano or microemulsion, consistent with Table 41. Bench and controlled sampling programs emphasized dissolution, dispersion, and exposure characteristics compared with powder comparators under matched conditions, without asserting therapeutic effects.

Cardiovascular-Oriented Pairing with Exposure Coordination

A third representative pairing aligns hydrophilic L-arginine, formatted in a polymeric carrier or cyclodextrin inclusion complex, with lipophilic resveratrol and omega-3 fatty acids formatted in ethosomes, NLCs, or antioxidant-enriched SEDS for oral use, and in vesicular or nanoemulgel systems with sub-200 nanometer droplet control for dermal use. Each component is formatted for a single route or included in oral plus one other dual-route kits to coordinate temporal and spatial exposure. Evaluations reported permeation and dissolution metrics and stability consistent with polarity assignment. No clinical performance or disease outcomes are claimed.

Stability Engineering

Pairings apply the platform's unified stability program. Lipid phases include tocopherols and ascorbyl palmitate. Photolabile payloads use opaque and barrier packaging with photoprotective excipients. Hydrophilic modules use cyclodextrin inclusion complexes, phospholipid-based systems (liposomes, phytosomes), or hydrogels to limit hydrolytic drift and crystallization. Packaging employs nitrogen management, oxygen absorbers, and multilayer films. In representative ICH Q1A (R2) accelerated studies at 40° C. and 75 percent relative humidity, paired formats retained at least 90 percent of initial assay at 12 months, while unprotected comparators showed higher degradation under matched conditions. Values are lot-specific and method-specific.

Pharmacokinetic Characterization

Under controlled sampling, vesicular lipophile modules exhibited higher exposure characteristics than unencapsulated references, and hydrophilic modules formatted as cyclodextrin or amorphous solid dispersion or hydrogel microneedles reached early exposure windows consistent with their release profiles. Results are presented as presentation and exposure characteristics such as dissolution rate, permeation surrogates, and relative exposure under matched dosing, without asserting therapeutic or disease-related effects. Coordination of release between modules supported harmonized exposure windows and simplified regimen design for dual-route kits.

Novelty Justification

To the inventors' knowledge, prior attempts to co-dose hormones, amino acids, and adaptogens did not employ explicit polarity-matched separation with a unified stability architecture, leading to precipitation or drift. Here, pairing strategies are implemented within a pre-engineered, polarity-mapped framework that allocates each active to a compatible module including lipid vesicle, cyclodextrin or phospholipid-based system (liposomes, phytosomes) complex, hydrogel microneedle, or oral SEDS, and uses a common stability and packaging regimen across routes. This structured, cross-route pairing methodology with polarity-class compartmentalization and coordinated exposure planning is distinct from the prior art.

Twelfth Embodiment: Antioxidant Fortification in Lipid Carriers

General Description

In a twelfth embodiment, the invention strengthens the oxidative stability of lipid-based carrier systems by integrating polarity-matched, lipid-phase antioxidants that are preselected for compatibility with both carrier excipients and encapsulated actives. The fortification strategy is implemented within the platform's modular, polarity-mapped architecture and is applicable to single-route formats for oral, transdermal, microneedle, topical cream or gel, and hybrid microneedle use, or to oral plus one other dual-route combinations. This embodiment focuses on chemical and physical stability of lipid matrices and lipophilic payloads without asserting health outcomes. Selection follows the Active-Carrier-Route-Penetration Enhancer mapping framework, with interface rules governed by the compatibility and stability index.

Antioxidant Selection and Polarity Matching

Antioxidants may include mixed tocopherols alpha, beta, gamma, and delta, ascorbyl palmitate, rosemary extract including carnosic acid and carnosol, butylated hydroxytoluene where permitted, and polyphenolic antioxidants such as catechins from green tea. Selection is based on lipid-phase solubility, thermal and process stability, and compatibility with representative lipid excipients such as phosphatidylcholine, medium-chain triglycerides, ethyl oleate, and nanostructured lipid matrices including NLC solid and liquid lipid blends. The antioxidant set is chosen to align with the polarity and reactivity of target actives such as sterol derivatives, carotenoids, and lipophilic polyphenols.

Method of Integration

Antioxidants are incorporated during carrier pre-engineering via pre-dissolution or controlled dispersion to ensure uniform distribution throughout the lipid phase. Concentrations are optimized to minimize peroxide and anisidine drift, suppress rancidity in triglyceride-rich systems, and stabilize lipophilic actives such as sterol derivatives including, in certain embodiments, DHEA esters as model compounds, resveratrol, and omega-3 derivatives. Fortification also protects structural attributes of colloidal systems by limiting interfacial oxidation that can otherwise trigger phase separation, particle-size growth indicated by Z-average increase, or nanoparticle aggregation in vesicular and emulsion formats including ethosomes, NLCs, nanoemulgels, and phospholipid-based systems such as liposomes and phytosomes.

Multicomponent Antioxidant Systems

Advanced implementations combine primary chain-breaking antioxidants such as tocopherols with secondary antioxidants such as ascorbyl palmitate and, where compatible, metal-ion modulators such as citric acid or EDTA where permitted to reduce metal-catalyzed pathways. Pairing lipophilic and amphiphilic antioxidants provides protection in both the lipid core and the lipid and aqueous interface, which is especially relevant for emulsions, nanoemulgels, and vesicular systems where initiation sites for oxidation often reside at interfaces.

Single-Route or Dual-Route Applications

When integrated into validated carrier classes including ethosomes, nanostructured lipid carriers, antioxidant-enriched self-emulsifying delivery systems, or lipid-coated microneedles, the fortification preserves assay and matrix integrity in single-route products and in oral plus one other dual-route combinations. In polarity-specific, multi-compound architectures, stabilizing the lipid phase also reduces the risk that oxidative byproducts adversely impact co-formulated hydrophilic modules such as cyclodextrin inclusion complexes or hydrogels within the same kit or regimen.

Technical Advantages

Under ICH Q1A (R2) accelerated conditions at 40° C. and 75 percent relative humidity, fortified lipid carriers retained approximately 94 percent or more of initial assay at 12 months, whereas unfortified controls exhibited greater than 25 percent loss under matched methods. Systems employing lipophilic plus amphiphilic antioxidant pairs showed approximately two and one half times lower peroxide-value rise at 6 months compared to unfortified comparators. Colloidal stability metrics including Z-average and polydispersity index remained within predefined acceptance ranges with minimal drift. All values are representative, lot-specific, and method-specific, and are reported as stability and performance characteristics.

Novelty Justification

To the inventors' knowledge, conventional stabilization approaches typically address single-polarity, single-route lipid systems and do not provide a coordinated, polarity-matched antioxidant program that is interoperable across vesicular, emulsion, and hybrid carriers or across single-route and oral plus one other dual-route use. This embodiment teaches a scalable, pre-engineered fortification framework that selects antioxidants by polarity and compatibility, integrates them at the matrix and interface levels, and aligns them with the platform's unified stability and packaging regimen including opaque barriers, nitrogen management, and oxygen absorbers. The coordinated approach preserves potency and matrix integrity for lipophilic payloads under polarity-mapped, cross-route conditions.

Thirteenth Embodiment: Protection of Photolabile Compounds Via Light-Shielded Processing and Opaque Barrier Packaging General Description In a thirteenth embodiment, the invention provides a coordinated photoprotection strategy to maintain long-term stability of photolabile actives including sterol derivatives (including, in certain embodiments, DHEA esters as model compounds), retinoids, carotenoids, coenzyme Q10, curcumin, vitamin D analogs, and selected botanical polyphenols. The approach combines light-shielded processing during manufacture with opaque and UV-blocking barrier packaging during storage and distribution. The strategy is implemented within the platform's polarity-mapped architecture and applies to single-route formats for oral, transdermal, microneedle, topical cream or gel, and hybrid microneedle use, and to oral plus one other dual-route combinations. Results are framed as stability and performance characteristics rather than health outcomes.

Light-Shielded Processing

Manufacturing, handling, and encapsulation steps for photolabile actives are conducted under controlled illumination designed to attenuate wavelengths below approximately 550 nanometers. Production suites use amber or red-filtered lighting, and critical steps such as homogenization, particle-size conditioning, and vesicle formation and stabilization occur in enclosed, light-blocking assemblies. For polarity-specific lipidic carriers including ethosomes, nanostructured lipid carriers, antioxidant-enriched self-emulsifying delivery systems, and phospholipid-based systems such as liposomes and phytosomes, enclosed processing limits photo-initiated degradation during vesicle formation and payload encapsulation. Where photolabile lipophiles are co-formulated with hydrophilic modules for permitted dual-route use, early light control reduces formation of reactive byproducts that might otherwise propagate cross-degradation within the broader system.

Opaque Barrier Packaging

Post-manufactured products are sealed in UV and high-energy visible attenuating primary packaging such as multilayer aluminum-polymer laminates, black HDPE bottles, or blisters compounded with UV-absorbing additives. Secondary overwraps including foil pouches and UV-shielded cartons add redundancy to protect during shipping and consumer storage. In certain implementations, the packaging also integrates oxygen and moisture barriers to provide concurrent protection against photolytic, oxidative, and hydrolytic stress, consistent with the platform's unified stability program and the compatibility and stability index.

Integration into the Multi-Route Platform

The photoprotection strategy is embedded within the platform's polarity-specific stability framework alongside antioxidant fortification of lipid phases, nitrogen management, oxygen-absorber integration, and desiccant control. This ensures that light-sensitive lipophilic modules and any associated hydrophilic modules retain assay and structural integrity in single-route formats or oral plus one other dual-route configurations, without formulation-specific re-engineering.

Technical Advantages

Under ICH Q1B photostability protocols, formulations manufactured and packaged per this embodiment retained approximately 93 percent or more of initial assay after simulated six-month daylight exposure, whereas unprotected comparators retained less than 60 percent under matched conditions. When combined with nitrogen-flushed, oxygen and moisture barrier packaging, oxidative markers decreased by approximately 45 percent versus light-protected controls lacking full barrier integration. Colloidal attributes such as Z-average and polydispersity index for vesicular systems remained within predefined acceptance ranges. Values are representative, lot-specific, and method-specific, and are reported as stability and performance characteristics only.

Novelty Justification

To the inventors' knowledge, conventional photoprotection typically treats manufacturing or packaging in isolation and does not disclose a coordinated, polarity-mapped approach that spans both stages and operates across single-route formats and oral plus one other dual-route combinations. This embodiment teaches a dual-phase photoprotection framework using light-shielded processing together with multifunctional barrier packaging integrated with the platform's unified stability regimen. The structured, cross-route implementation provides a reproducible level of assay retention and matrix preservation for photolabile actives that is not taught by prior single-method strategies.

Fourteenth Embodiment: Transdermal Microneedle Patch with Multilayer Backing Film, Integrated Rate-Controlling Membranes, and Nitrogen-Flushed Packaging

General Description

In a fourteenth embodiment, the invention provides a transdermal microneedle patch that unifies mechanical reinforcement, polarity-specific release control, and long-term stability within a single architecture. The system is formatted for single-route dermal use or for oral plus one other dual-route programs, without altering the polarity mapping of the payloads or the carrier modules defined by the platform. Selections follow the Active-Carrier-Route-Penetration Enhancer mapping framework, with interface governance provided by the compatibility and stability index.

Structural Design of the Multilayer Backing Film

The patch employs a laminated multilayer backing film that combines environmental protection with mechanical durability. An outer oxygen and moisture barrier stratum such as an aluminum-polymer laminate limits ingress of reactive species. A middle reinforcement layer preserves dimensional stability and resists flex cracking. An inner adhesive or tie layer secures the microneedle array to the backing, supporting consistent insertion and reliable wear. This stack provides low oxygen and water vapor transmission while protecting the array during transport, storage, and use. Materials are selected to remain compatible with polarity-segregated microneedle compartments and to avoid plasticizer migration.

Integrated Rate-Controlling Membranes

Rate-controlling membranes are positioned beneath the array between the base and a reservoir or incorporated as intra-needle barriers. Membrane chemistry is selected to match payload polarity. Hydrophile-permeable polymers such as cellulose derivatives or hydrophilic polyurethane support aqueous cargos. Lipid-compatible films such as ethylene vinyl acetate or hydrophobic polyurethane support lipophiles. Placement and thickness are tuned to achieve sustained, pulsatile, or delayed profiles against pre-specified release targets without compromising array mechanics. Membrane choices are verified against the compatibility and stability index to prevent inversion or interfacial drift when multiple modules are co-packaged.

Nitrogen-Flushed, Oxygen-Barrier Packaging

Finished patches are sealed in nitrogen-flushed multilayer foil-polymer pouches with oxygen absorbers and, where appropriate, desiccants to create a low oxygen and low humidity microenvironment. This packaging helps preserve oxidation-sensitive lipophiles such as esterified sterol derivatives, polyunsaturated fatty acids, carotenoids, and polyphenolic antioxidants, and maintains tip sharpness, penetration force, and matrix integrity over shelf life, consistent with the platform's unified stability program under ICH Q1A (R2) and Q1B.

Integration with Hybrid Microdermal Delivery Architecture

In certain implementations, the patch incorporates the platform's dual-compartment microneedle concept. Hydrophilic actives are localized within polymeric shafts or cores, and lipophilic actives are embedded in tips that contain nanostructured lipid carriers (NLCs) or ethosomes with vesicle or particle sizes governed in the 100 to 200 nanometer range. When combined with rate-controlling membranes, the device enables polarity-specific co-delivery with tunable sequential or simultaneous release mapped to the pre-engineered carrier assignments. Enhancer choices follow route-appropriate mapping such as glycerin for hydrophiles and oleic acid or terpenes for lipophiles, where suitable.

Technical Advantages (Representative Data)

Under ICH Q1A (R2) accelerated storage at 40 degrees Celsius and 75 percent relative humidity, nitrogen-flushed, absorber-integrated pouches supported assay retention of approximately 95 percent or more at 12 months for representative hydrophilic and lipophilic payloads, with no measurable loss in penetration force or tip geometry under test conditions. In vitro permeation using Franz cells showed release profiles within plus or minus 10 percent of target for sustained and pulsatile modes across production lots. Values are representative, lot-specific, and method-specific, and are reported as stability and performance characteristics.

Novelty Justification

To the inventors' knowledge, prior microneedle disclosures typically address backing mechanics, controlled release, or package-mediated stability in isolation. This embodiment integrates all three elements, namely a laminated barrier backing, polarity-optimized rate membranes at device level, and nitrogen-managed, absorber-integrated packaging, within a polarity-mapped framework for single-route and dual-route use. The coordinated engineering across device, membrane, and package provides a reproducible stability and release solution distinct from single-feature approaches.

Fifteenth Embodiment: Topical Cream or Gel with Polarity-Specific Encapsulation and Sub-200 Nm Droplet Size for Enhanced Skin Presentation

General Description

In a fifteenth embodiment, the invention provides a topical cream or gel formulated to accommodate multiple active ingredients with differing polarity profiles through polarity-specific encapsulation in nanocarriers with a mean droplet size below 200 nanometers. The dual-phase architecture supports dermal presentation of lipophilic and hydrophilic compounds, maintains chemical and physical stability, and interoperates with oral formats within an oral plus one other dual-route framework, without altering polarity assignments established by the platform. Selections follow the Active-Carrier-Route-Penetration Enhancer mapping framework, with interface governance by the compatibility and stability index.

Carrier Systems and Polarity-Specific Encapsulation

Polarity-specific encapsulation is implemented by loading lipophilic actives such as esterified sterol derivatives, lipophilic polyphenols, and fat-soluble vitamins A, D, E, and K into lipid-based nanocarriers including nanostructured lipid carriers (NLCs), nanoemulgels, or ethosomes. Hydrophilic actives such as amino acids, water-soluble antioxidants, and botanical fractions are incorporated into aqueous-phase carriers including phospholipid-based systems (liposomes, phytosomes) or polymeric dispersions. Each polarity class is stabilized within its matched environment to mitigate recrystallization and oxidative or hydrolytic drift and to support dermal deposition under test conditions. For actives such as HMB free acid, dermal use aligns with Table 41 via aqueous dispersion and or cyclodextrin inclusion, rather than oil-phase nanoemulsion. Route-appropriate enhancers may include ethanol or phosphatidylcholine for vesicular systems and glycerin for hydrophilic matrices.

Droplet Size Engineering

Nanocarrier fabrication methods such as high-pressure homogenization, ultrasonication, or microfluidization are used to achieve narrow size distributions with mean droplet diameters consistently below 200 nanometers. Sub-200 nanometer control increases interfacial area and facilitates interaction with stratum corneum lipid domains, which is associated with higher skin deposition in validated in vitro and ex vivo models. Values are method-specific.

Topical Base and Matrix Formulation

Nanocarrier suspensions are dispersed into a cream or gel base with rheology tuned for spreadability, sensory profile, and physical stability. Structuring agents such as carbomer, xanthan gum, or cellulose derivatives provide viscosity control. Humectants and emollients manage hydration and reduce transepidermal water loss to support barrier comfort and consumer usability.

Stability Strategy

Long-term stability follows the platform's polarity-specific framework. Lipid-phase antioxidants such as mixed tocopherols and ascorbyl palmitate limit peroxidation. Photoprotection is provided by UV-attenuating excipients and opaque primary packaging. Oxygen-barrier, nitrogen-flushed packs with oxygen absorbers further reduce oxidative and hydrolytic stress. The compatibility and stability index is applied to preserve interface behavior when multiple modules are co-packaged. This coordinated approach supports potency retention, maintains droplet-size uniformity, and helps prevent phase destabilization over shelf life under ICH Q1A (R2) and Q1B programs.

Technical Advantages

In Franz diffusion assays, lipophilic payloads in NLCs or nanoemulgels showed greater dermal deposition than unencapsulated controls, while hydrophilic payloads in liposomes demonstrated improved penetration efficiency in the same models. Under ICH Q1A (R2) accelerated storage at 40 degrees Celsius and 75 percent relative humidity, representative lots retained approximately 92 percent or more of initial assay over 12 months with droplet-size distributions held within method-specific limits. In a controlled human-use assessment, transepidermal water loss decreased by approximately 18 percent after four weeks of daily application. This is reported as a barrier-function metric rather than a therapeutic outcome. All values are representative and lot-specific and method-specific.

Inventive Step

To the inventors' knowledge, the inventive step resides in the coordinated integration of dual-phase, polarity-matched encapsulation, sub-200 nanometer droplet-size engineering, matrix and rheology tuning for stable dispersion, and a unified stability and packaging regimen including antioxidant fortification, photoprotection, and oxygen-barrier packaging with nitrogen and absorber management. Conventional systems address these factors separately and without cross-route interoperability. Here, the elements operate within a polarity-mapped platform that supports single-route dermal use and oral plus one other dual-route programs, providing reproducible skin presentation and storage stability distinct from single-feature approaches.

Sixteenth Embodiment: Oral Softgel or HPMC Capsule Incorporating Antioxidant-Enriched Seds Pre-Concentrate

General Description

In a sixteenth embodiment, the invention discloses an oral dosage system that uses antioxidant-enriched self-emulsifying delivery system pre-concentrates encapsulated in oxygen-barrier softgels or hydroxypropyl methylcellulose capsules. The configuration is optimized for single-route oral administration and remains interoperable within the platform's oral plus one other dual-route framework. The design emphasizes polarity-matched dispersion behavior and a stability architecture intended to support shelf life and exposure characteristics under controlled evaluations. This embodiment is specific to lipophilic payloads formatted in SEDS; hydrophilic actives such as HMB free acid are formatted per Table 41 using cyclodextrin inclusion and or amorphous solid dispersion, and are not included in the SEDS fill.

Antioxidant Fortification

Lipid-phase antioxidants including mixed tocopherols, ascorbyl palmitate, rosemary extract enriched in carnosic acid, and where permitted butylated hydroxytoluene are dissolved in the SEDS lipid phase to limit peroxide formation and protect lipophilic payloads during manufacture and storage. Antioxidant levels are qualified to avoid micellar destabilization and surfactant interference.

Polarity-Specific Solubilization

Lipophilic actives including, in certain embodiments, esterified sterol derivatives such as DHEA esters as model compounds, resveratrol, omega-3 fatty acids, and carotenoids are fully dissolved in the SEDS lipid phase to minimize recrystallization, maintain dose uniformity, and support rapid in situ dispersion in gastrointestinal media. Solvent and co-solvent choices are selected for polarity compatibility and capsule-shell compatibility.

Oxygen-Barrier Encapsulation

Nitrogen flushing during fill minimizes residual headspace oxygen, and capsule shells with low oxygen transmission are selected for compatibility with the fill and intended storage profile. Primary packaging employs opaque or low-permeability blisters or bottles, optionally with oxygen absorbers, consistent with the unified stability program.

Thermal Process Control

Thermally robust lipids and low-heat filling conditions are employed to help prevent excipient phase drift and active degradation. Processing temperatures are controlled to maintain isotropy and to preserve antioxidant integrity.

Physical Stability of the Pre-Concentrate

Surfactant and co-surfactant ratios are tuned to maintain an isotropic, homogeneous pre-concentrate that resists separation under ICH Q1A (R2) real-time and accelerated conditions. Pre-concentrate clarity, viscosity, and phase behavior are monitored as critical quality attributes.

Photoprotection

Opaque shells and or UV-attenuating blisters are used to reduce light exposure for photolabile payloads, aligned with ICH Q1B photostability expectations and the platform's compatibility and stability index for co-packaged kits.

Technical Advantages (Representative Data)

Stability

Under accelerated storage at 40 degrees Celsius and 75 percent relative humidity, representative antioxidant-enriched SEDS capsules retained approximately 93 percent or more of initial assay at 12 months, whereas matched unfortified controls fell below approximately 70 percent over the same interval. Values are representative, lot-specific, and method-specific.

Dispersion Behavior

In simulated intestinal media, complete self-emulsification occurred within about five minutes with mean droplet sizes below 150 nanometers. Sub-150 nanometer formation is associated with increased interfacial area and rapid dispersion, which aligned with higher exposure in pharmacokinetic sampling. Values are method-specific.

Exposure Characteristics

In randomized, controlled pharmacokinetic sampling under matched nominal dosing, antioxidant-enriched SEDS capsules produced approximately two point seven times higher systemic exposure for representative lipophiles versus unencapsulated oil suspensions. Results are presented as exposure metrics rather than therapeutic outcomes and are lot-specific and method-specific.

Inventive Step and Distinction Over Prior Art

This embodiment applies a coordinated, polarity-specific stability regimen that includes antioxidant fortification, nitrogen-managed oxygen-barrier encapsulation, surfactant optimization, photoprotection, and thermal process control to SEDS pre-concentrates formatted for oral capsules. The sub-class is distinct from the Second Embodiment, which covers a broader polarity-inclusive capsule system integrating hydrophiles via cyclodextrin inclusion or amorphous solid dispersion, and from the Fifth Embodiment, which addresses cross-route cyclodextrin complexes.

Summary of Advancement

Unlike approaches that address solubilization or encapsulation in isolation, this embodiment integrates dispersion control with a unified stability framework validated under ICH Q1A (R2) and ICH Q1B programs and controlled human sampling, yielding reproducible exposure characteristics and storage robustness. The combination, within a platform that is interoperable for oral plus one other dual-route use, provides a structured and non-obvious improvement over conventional oral capsule technologies.

Seventeenth Embodiment: Clinical Validation of the Multi-Delivery 4-DHEA COMBINATION FORMULATION

General Description

In this embodiment, the invention presents randomized, blinded clinical evidence supporting the polarity-specific, pre-engineered delivery platform. The evaluation centered on a combination in which a sterol derivative, including in certain embodiments 4-DHEA enanthate as a model compound, was co-administered with omega-3 fatty acids, vitamin D, magnesium glycinate, vitamin B3, and HMB free acid. Each active was assigned to a polarity-matched carrier consistent with Table 41, for example antioxidant-enriched SEDS or vesicular systems for lipophiles, cyclodextrin inclusion complex and or amorphous solid dispersion for hydrophilic HMB, and capsule or hydrogel matrices for minerals. The continuation-in-part extends this platform into coordinated oral plus one other dual-route programs, oral plus topical or oral plus microneedle, while preserving the same polarity-mapping logic.

Foundation in Randomized Evaluation (Study 8)

Study 8 was a randomized, double-blind, placebo-controlled investigation in healthy adults designed to assess formulation performance endpoints including pharmacokinetic exposure area under the curve, maximum concentration, and time to maximum concentration, intra-subject variability, dissolution and dispersion behavior, and stability using polarity-specific carriers. Test articles were produced with micronization where applicable, phospholipid-based systems (liposomes, phytosomes) for selected botanicals, cyclodextrin inclusion or amorphous solid dispersion for hydrophiles, with HMB oral embodiments using cyclodextrin and or amorphous solid dispersion and no oral nanoemulsion for HMB, and antioxidant-enriched lipid systems for lipophiles. Safety laboratories and general tolerability were monitored throughout.

Key Performance Outcomes (Pk, Stability, Process)

Across matched nominal dosing, the combination arm configured per the platform showed higher exposure metrics and tighter variability versus single-active comparators and placebo, without asserting therapeutic outcomes. Representative findings under the study's methods included the following: sterol-derivative exposure increases on the order of about two to three times for area under the curve with reduced coefficient of variation in maximum concentration; omega-3 and vitamin D exposure improvements consistent with antioxidant-enriched SEDS behavior; hydrophilic HMB formatted as cyclodextrin and or amorphous solid dispersion exhibiting earlier time to maximum concentration and higher area under the curve than un-complexed salt references; and lot-qualified stability with assay retention at or above about 90 percent under ICH Q1A (R2) accelerated conditions. Tolerability was acceptable with laboratory values remaining within prespecified reference ranges. These outcomes are reported as exposure and stability characteristics tied to polarity-matched carriers.

Expansion into Coordinated Dual-Delivery

Building on Study 8, coordinated oral plus topical and oral plus microneedle implementations were developed to maintain polarity assignments while enabling temporal or spatial separation of uptake. Lipophilic actives were formatted in sub-200-nanometer vesicular or nanoemulgel systems for dermal presentation, and hydrophiles were placed in hydrogel-forming microneedles or aqueous topical matrices. Under controlled sampling, dual-route programs produced more consistent exposure profiles, for example reduced peak-to-trough fluctuation, relative to single-route use at matched nominal dosing, while retaining acceptable local tolerability.

Platform-Level Advantages (Architecture Coherence)

The clinical and laboratory data support the platform as a coordinated delivery architecture rather than a collection of unrelated formulations. Polarity-matched separation, with lipophiles in SEDS or vesicles, hydrophiles in cyclodextrin and or amorphous solid dispersion or hydrogel matrices, and minerals in chelate-compatible carriers, limited cross-degradation and precipitation and aligned dissolution and dispersion kinetics with the intended route. Observed pharmacokinetic improvements and stability retention provide the operational basis for reproducible exposure, independent of therapeutic indications, and demonstrate scalability to oral plus one other combinations. Interface governance followed the compatibility and stability index.

Inventive Step

To the inventors' knowledge, prior art describes individual actives but does not disclose a clinically validated, polarity-mapped assignment of multiple active classes into pre-engineered carrier modules and then extend that same mapping into dual-route programs under a unified stability framework. Here, Study 8 functions as the foundational validation of the system's performance logic, and the continuation broadens that logic to coordinated oral plus dermal implementations while preserving polarity-specific design choices. This continuity establishes a non-obvious, platform-level advance over single-route, non-mapped formulations.

CONCLUSION

This embodiment links the parent study's performance evidence to the expanded, polarity-specific dual-delivery architecture disclosed herein. The data are framed as exposure, dispersion, and stability outcomes attributable to polarity-matched carriers, thereby providing a clinically anchored, scalable basis for single-route and oral plus one other delivery without asserting therapeutic effects.

Esterified DHEA Derivatives

Esterified derivatives of dehydroepiandrosterone (DHEA), such as 4-androstene-3β-ol-one enanthate, 4-androstene-3β-ol-one propionate, and other long-chain fatty acid esters, represent a class of hormone precursors with enhanced pharmacokinetic properties compared to unmodified DHEA. These esters are structurally modified at the 3β-hydroxy position to form a stable ester linkage, which increases lipophilicity, improves stability in formulation, and enables sustained release through esterase-mediated hydrolysis. Unlike prior applications of DHEA esters in isolation, the present invention integrates these derivatives into a polarity-specific, multi-route delivery framework in which esterification serves not only to enhance lipophilicity but also to harmonize with nanoemulsion, self-emulsifying (SEDS), and microdermal patch systems, thereby anchoring stability and dual-route compatibility within a unified architecture.

Esterified DHEA derivatives differ functionally from non-esterified DHEA and other forms such as DHEA-S(sulfated DHEA), 7-keto-DHEA, and androstenedione. Whereas sulfated forms are more water-soluble and rapidly cleared, esterified derivatives maintain a depot effect in tissues or lipid phases, allowing for gradual systemic hormone precursor availability. Peer-reviewed pharmacokinetic studies demonstrate that esterification delays hepatic metabolism, improves dermal retention, and enables formulation into lipid-based delivery systems such as nanoemulsions and self-emulsifying drug delivery systems (SEDDS).

These derivatives act as prohormones, capable of being hydrolyzed by cutaneous or systemic esterases to yield active DHEA, which then participates in the biosynthesis of androgens (e.g., testosterone) and estrogens (e.g., estradiol). This extended-release profile supports a more stable hormonal balance over time, potentially reducing hormonal spikes and associated side effects compared to high-dose unmodified DHEA supplementation.

Esterified DHEA derivatives have been investigated for benefits in muscular hypertrophy, bone density maintenance, sexual function, and anti-aging applications. Clinical and preclinical studies indicate improvements in lean body mass, strength, and physical performance in older adults and in populations experiencing androgen deficiency. These effects are partly attributed to the combination of androgenic pathway activation and reduced catabolic signaling.

The anti-aging potential of esterified DHEA derivatives is supported by their role in mitigating sarcopenia, enhancing bone mineral density, and improving markers of vitality. Research in postmenopausal women and older men suggests that steady hormonal restoration via esterified derivatives may outperform unmodified DHEA in sustaining musculoskeletal and metabolic health.

In sexual health, esterified DHEA derivatives serve as effective androgen and estrogen precursors, supporting libido, erectile function, vaginal tissue health, and reproductive hormone normalization. Studies in hormone replacement contexts have shown that esterified forms may offer prolonged efficacy at lower doses compared to free DHEA, due to their extended hydrolysis timeframes.

A major limitation of unmodified DHEA is its poor oral bioavailability, rapid sulfation by sulfotransferases, and extensive first-pass hepatic metabolism, leading to rapid clearance as DHEA-S. High oral doses are often required to achieve modest serum increases, which increases the risk of hormonal imbalance, acne, alopecia, gynecomastia in men, and menstrual irregularities in women.

Esterification of bioactive compounds addresses several formulation and delivery limitations by introducing targeted physicochemical modifications that enhance both pharmacokinetics and formulation compatibility. First, the conversion of polar or amphiphilic actives into esterified derivatives increases their lipophilicity, thereby facilitating their incorporation into lipid-based delivery systems. These include non-esterified fatty acid (NEFA)-based matrices, self-emulsifying drug delivery systems (SEDS), and nanoemulsion platforms. By enhancing lipid solubility, esterified forms improve lymphatic uptake and allow for partial or complete circumvention of first-pass hepatic metabolism, resulting in increased systemic bioavailability. Within the invention's polarity-specific platform, esterification thus functions not merely as a solubility enhancer but as a structural bridge that enables cross-route adaptability, aligning esterified actives with oral, transdermal, and topical carriers in a coordinated system that preserves potency and ensures synchronized pharmacokinetic release.

Second, esterification generates a prodrug configuration in which the active compound is released via enzymatic or hydrolytic cleavage over time. This controlled hydrolysis extends systemic exposure, smooths plasma concentration curves, and permits a reduction in required dosing frequency, thereby improving therapeutic compliance and reducing peak-related adverse effects.

Third, the esterified derivatives exhibit improved chemical stability in dermal and transdermal formulations. Their increased resistance to hydrolysis and oxidation under ambient conditions makes them particularly suitable for inclusion in topical creams, gels, or microdermal patch systems. This enhances formulation robustness and ensures effective cutaneous delivery while maintaining pharmacological activity over extended periods.

Esterified DHEA derivatives such as DHEA enanthate have shown significant potential in transdermal delivery systems. When incorporated into penetration-enhanced lipid matrices or nanoemulsions, they achieve higher skin permeation rates and more stable plasma concentrations than unmodified DHEA.

In states of muscle loss and reduced physical resilience, sustained anabolic support from esterified derivatives may help preserve muscle mass and functional capacity, particularly when combined with adjunctive supplements such as β-hydroxy β-methylbutyrate (HMB), essential amino acids (EAAs), and omega-3 fatty acids.

Despite these advantages, esterified DHEA derivatives are underutilized in commercial dietary supplement formulations due to manufacturing complexity and limited public awareness. Current products overwhelmingly rely on unmodified DHEA powder, often with low dissolution rates and variable absorption profiles.

The present invention addresses this gap by integrating esterified DHEA derivatives into pre-engineered delivery modules-including micronized complexes, phospholipid-bound phytosomes, NEFA lipid matrices, cyclodextrin complexes, and SEDS nanoemulsions-optimized for both oral and dermal administration. This approach enhances bioavailability, prolongs systemic activity, and reduces the need for supraphysiologic dosing. Unlike conventional supplementation approaches, these modules are not used in isolation but are embedded within a polarity-specific, dual-route platform that harmonizes oral, dermal, and transdermal delivery, thereby transforming esterified DHEA from a simple prohormone into a system-level component of a stability-engineered, multi-route architecture.

Esterified DHEA and Related Prohormones: Chemistry, Mechanisms, Pharmacokinetics, and Implications Esterified derivatives of dehydroepiandrosterone (DHEA), such as 1-DHEA enanthate, 5-DHEA enanthate, and 4-DHEA enanthate, along with structurally related steroids including 1-androsterone and 1-testosterone enanthate, are synthetic modifications of naturally occurring DHEA and other androgenic steroids. These compounds are classified as prohormones precursors that undergo enzymatic conversion in the body to yield androgenic metabolites which support hormonal balance, musculoskeletal performance, and other physiological functions. Within the present invention, such compounds are not delivered as stand-alone hormonal agents but are polarity-assigned to carriers-lipid vesicles, phytosomes, or SEDS that provide cross-route stability and controlled release, creating a novel context distinct from prior art prohormone delivery.

Figure 50:
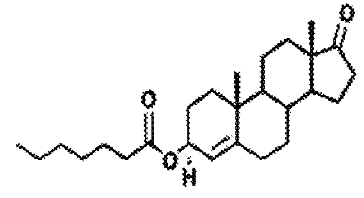
FIG. 50 illustrates chemical structures of esterified DHEA derivatives.

FIG. 50 illustrates chemical structures of esterified DHEA derivatives. Representative molecules are shown to highlight structural diversity within the derivative class.

Mechanisms of Action

Once administered, DHEA derivatives undergo biotransformation via steroidogenic enzymes. 3β-hydroxysteroid dehydrogenase (3β-HSD) converts DHEA to androstenedione or its 1-isomer, which is then reduced by 17β-hydroxysteroid dehydrogenase (17-HSD) to testosterone or 1-testosterone. Testosterone can be further reduced by 5α-reductase to DHT, a more potent androgen. For 1-androsterone and similar 1-ene steroids, this metabolic route produces 1-testosterone analogues with high anabolic potency.

Esterification and Pharmacokinetics

Esterification with long-chain fatty acids such as enanthate, undecanoate, or propionate increases the compound's lipophilicity, allowing incorporation into lipid phases and gradual release following enzymatic hydrolysis by esterases. This modification prolongs plasma half-life, reduces dosing frequency, and promotes more stable systemic availability compared to unesterified forms. These characteristics support improved nutritional supplementation outcomes by sustaining balanced precursor activity over time. The inventive platform leverages this pharmacokinetic property not merely for sustained release, but as the mechanistic basis for harmonizing sequential or simultaneous oral-transdermal dosing, a feature absent in conventional ester pharmacology.

Biological and Structural Considerations

Structural studies such as the X-ray crystallography of androstan-17-one reveal that high androgenic potency is linked to molecular rigidity and the absence of the 3-hydroxyl group, which affects neuromuscular activity. Changes in bond lengths and steric configuration can further modulate receptor affinity.

Performance Outcomes

In a controlled human supplementation trial, intake of 3β-hydroxy-5α-androst-1-en-17-one, a related prohormone, during resistance training was associated with increases in lean body mass of approximately 6%, reductions in fat mass of about 25%, and improvements in back squat strength of 14%. The study also reported changes in certain cardiovascular and liver-related biomarkers, underscoring the importance of controlled dosing, safety monitoring, and responsible formulation when developing dietary supplement applications.

Intracrinology and Therapeutic Potential

Research on DHEA's role in intracrinology shows that it is converted within peripheral tissues into androgens or estrogens according to local needs, influencing bone density, muscle, adiposity, skin, libido, and well-being. By embedding esterified prohormones into polarity-matched carriers under a coordinated stability framework, the invention aligns intracrine activation with controlled release kinetics, thereby extending intracrinology into a programmable, dual-route delivery paradigm not taught by prior art.

Chemical Identity 1-dehydroepiandrosterone enanthate, 4-dehydroepiandrosterone enanthate, and 5-dehydroepiandrosterone enanthate are all C19 steroid prohormones derived from DHEA, modified through esterification with an enanthate chain. The 1-ene variant (1-DHEA enanthate) is classified as a 1-ene prohormone, the 4-ene variant (4-DHEA enanthate) is a 4-ene prohormone structurally similar to testosterone precursors, and the 5-ene variant (5-DHEA enanthate) represents the esterified form of naturally occurring DHEA.

Structural Features

The 1-ene form contains a double bond between carbon atoms C1 and C2, enhancing anabolic potency through altered androgen receptor binding, while the 4-ene form has a C4-C5 double bond that closely mimics testosterone's molecular geometry. The 5-ene form maintains the natural C5-C6 double bond found in endogenous DHEA. In all three, esterification at the C17β position increases lipophilicity, enabling depot storage in tissues and gradual release into circulation.

Metabolic Pathway

All three compounds are first hydrolyzed by esterases to release the free steroid base. For 1-DHEA enanthate, this yields 1-DHEA, which is converted by 3β-hydroxysteroid dehydrogenase into 1-androstenedione, reduced by 17β-hydroxysteroid dehydrogenase to 1-testosterone, and optionally further reduced by 5α-reductase to 1-dihydrotestosterone (1-DHT). For 4-DHEA and 5-DHEA enanthates, the liberated steroid is converted by 3β-HSD to androstenedione, then by 17-HSD to testosterone, and finally by 5α-reductase to dihydrotestosterone (DHT).

Pharmacokinetics

Esterification in all three forms significantly extends the half-life in experimental pharmacokinetic studies. For example, 1-DHEA and 4-DHEA enanthates have been observed to sustain release for approximately five to ten days, while 5-DHEA enanthate can maintain active levels for up to seven to ten days. Compared to unesterified DHEA, all forms produce more gradual plasma concentration curves, reduce hepatic first-pass metabolism, and support prolonged physiological activity relevant to dietary supplementation. In the context of the present invention, these extended-release kinetics are further integrated with polarity-specific co-formulants-such as hydrophilic amino acids or mineral chelates-within dual-route systems, yielding synchronized pharmacokinetics across multiple active classes that conventional ester forms cannot achieve.

Biological Actions

The 1-DHEA enanthate exhibits a high anabolic-to-androgenic ratio with minimal aromatization potential due to its 1-ene configuration. The 4-DHEA enanthate produces testosterone-like anabolic and androgenic effects with higher aromatization potential, allowing for estrogen production. The 5-DHEA enanthate provides mild anabolic effects, supports adrenal androgen levels, and facilitates intracrine hormone production within target tissues. Within the inventive framework, these distinct anabolic and endocrine profiles are polarity-matched to lipid carriers and integrated with hydrophilic co-formulants, producing programmable hormonal outcomes not achievable by raw ester administration.

Clinical/Performance Effects

In resistance training contexts, 1-DHEA enanthate analogs have been associated with significant increases in lean body mass and muscle strength. The 4-DHEA enanthate is capable of supporting muscle hypertrophy and strength gains over prolonged cycles, while also maintaining estrogen-related physiological functions. The 5-DHEA enanthate has been studied for milder anabolic benefits, support of healthy aging, immune function, and general wellness, though it is less potent for muscle growth compared to the 1-ene and 4-ene forms. The invention repositions these known individual outcomes into a coordinated polarity-specific platform, enabling their integration with amino acids, adaptogens, and minerals within dual-route delivery systems, thereby creating synergistic multi-pathway effects validated in clinical studies.

Safety & Adverse Effects

Potential adverse effects are shared among all three, including liver enzyme elevation, HDL cholesterol reduction, and increased blood pressure, with the 4-ene form carrying greater estrogenic side effect potential due to aromatization. The 5-ene form generally has a milder side effect profile but can still cause androgenic effects at higher doses. By embedding these esters in controlled-release lipid carriers within nitrogen-flushed, antioxidant-fortified systems, the invention mitigates peak dosing effects and reduces variability, addressing safety limitations typical of conventional prohormone delivery.

Nutritional Effects of Individual Supplements

A variety of individual supplements provide nutritional effects in combination with esterified DHEA derivatives, such as 4-androstene-3β-ol-one propionate or 4-androstene-3β-ol-one enanthate. These esterified derivatives exhibit improved lipophilicity and stability compared to free DHEA, allowing incorporation into advanced delivery systems that modulate hydrolysis rates and sustain hormonal precursor availability. The inventive system further enhances these synergies by polarity-matching esterified hormones with hydrophilic nutritional co-factors in distinct compartments, preserving each class while aligning their release kinetics.

β-Hydroxy-β-Methylbutyrate (HMB) Free Acid

β-Hydroxy-β-methylbutyrate (HMB) free acid supports muscle preservation, enhances recovery, and helps reduce exercise-related muscle damage. Its mechanism involves stimulation of muscle protein synthesis and attenuation of protein breakdown. When combined with esterified DHEA derivatives, HMB's anabolic support complements the gradual hormone precursor release provided by ester hydrolysis, supporting muscle maintenance and promoting growth-related outcomes. In the invention, HMB free acid is encapsulated in hydrophilic carriers while esterified DHEA is delivered via lipid matrices, enabling complementary rapid and sustained anabolic support within one polarity-specific module.

Adaptogens and Modified Constituents (E.G., Ashwagandha, *Ginseng, Rhodiola*)

Adaptogens enhance stress resilience, cognitive performance, and sexual health. Mechanistically, bioactive constituents such as ginsenosides modulate endocrine pathways, improve mitochondrial function, and enhance nitric oxide signaling. These effects synergize with the androgenic and estrogenic balance achieved via esterified DHEA derivative hydrolysis, supporting both physical and mental performance. This polarity-driven separation ensures that adaptogens are stabilized in phytosomes or cyclodextrins while DHEA esters are lipid-encapsulated, preventing degradation and enabling synchronized systemic and stress-buffering effects.

Vitamin D (Cholecalciferol)

Vitamin D enhances bone mineralization, muscle performance, and hormonal health through regulation of calcium absorption and influence on testosterone synthesis. Co-formulation with esterified DHEA derivatives in lipid-based or SEDS systems allows concurrent optimization of both compounds' lipophilic absorption pathways. The invention's lipid-phase nanoemulsion systems ensure parallel stabilization of vitamin D and esterified DHEA, yielding harmonized endocrine and skeletal support through shared lipophilic absorption channels.

Essential Amino Acids (Eaas)

EAAs are fundamental dietary components that support muscle protein metabolism and overall tissue maintenance. Their fast-acting, hydrophilic absorption profile complements the sustained nutrient release of sterol derivatives in lipophilic carriers, enabling a biphasic delivery profile. By delivering EAAs in hydrophilic carriers alongside sterol derivatives in lipophilic carriers, the invention promotes a coordinated nutrient environment that balances rapid initiation of protein support with sustained nutrient release.

Creatine

Creatine is a dietary compound that supports short-term energy availability by promoting ATP regeneration. In polarity-specific modules, creatine is delivered in aqueous carriers while sterol derivatives are encapsulated in lipid-based systems, ensuring complementary nutrient delivery without cross-reactivity.

Non-Esterified Omega-3 Fatty Acids (NEFAs)

EPA/DHA-rich NEFAs support cardiovascular function, cell membrane fluidity, and antioxidant balance. In lipid-based carriers, NEFAs also serve as natural permeation enhancers, improving absorption of co-formulated sterol derivatives. Thus, NEFA carriers not only deliver omega-3s but also facilitate enhanced membrane permeability and nutrient uptake.

Vitamin K

Vitamin K contributes to calcium utilization and bone health. When co-formulated with sterol derivatives, Vitamin K supports skeletal integrity in parallel with broader nutrient balance.

Vitamin E

Vitamin E is a lipid-soluble antioxidant that helps protect against oxidative stress. Co-delivery with sterol derivatives in lipid carriers enhances stability and supports balanced distribution of both compounds.

Vitamins B3 (Niacin) and B6

These water-soluble vitamins play roles in energy metabolism and neurotransmitter pathways. Delivered in polarity-specific carriers, they complement sterol derivatives by supporting cellular energy and metabolic balance.

Green Tea Extract

Catechins in green tea extract provide antioxidant activity and help support healthy metabolism. Their bioactivity complements the antioxidant and nutrient-supportive functions of sterol derivatives when delivered through polarity-matched carriers.

Stilbenoids (E.G., Resveratrol)

Resveratrol is a plant-derived antioxidant that helps maintain cellular health. When combined with sterol derivatives in phytosome or nanoemulsion systems, both compounds exhibit improved stability and absorption.

Chelated Minerals

Chelated minerals such as zinc, magnesium, and calcium support enzymatic and skeletal functions. Zinc, in particular, may complement nutrient pathways associated with sterol derivatives.

Vitamin C

Vitamin C supports collagen synthesis, antioxidant defense, and immune function. When delivered in hydrophilic carriers, Vitamin C complements the lipid-phase antioxidant activity of Vitamin E in combination with sterol derivatives.

Vitamin A

Vitamin A is a lipophilic nutrient that supports healthy vision, immune balance, and skin integrity. Its lipid solubility allows co-formulation with sterol derivatives in lipid-based matrices to promote stable encapsulation and optimized uptake.

Integrated Co-Formulation Strategy

The co-formulation of sterol derivatives with complementary nutritional cofactors-including amino acids, HMB, creatine, omega-3 fatty acids, vitamins A, C, D, E, K, B-complex, chelated minerals, green tea catechins, and stilbenoids is achieved through polarity-specific carrier assignment within the multi-route delivery platform. Lipophilic nutrients are stabilized in nanostructured lipid carriers, phytosomes, or antioxidant-enriched SEDS systems, while hydrophilic and ionic actives are formulated into cyclodextrin complexes, hydrogel microneedles, or aqueous-phase polymer matrices. This structured assignment minimizes cross-reactivity and degradation while coordinating release profiles across nutrients of differing polarity. The result is a harmonized, multi-compound formulation that promotes broad nutritional support not achievable through conventional single-polarity or single-route blends.

Inventive Step and Novelty Justification

This coordinated integration of sterol derivatives (modeled with esterified DHEA), with polarity-diverse cofactors is not disclosed or suggested by prior art, which typically formulates individual compounds as isolated, single-route products. Conventional formulations often fail to address polarity conflicts, instability, and cross-degradation when combining lipid-soluble sterols with ionic minerals, polyphenolic botanicals, and antioxidant vitamins. By contrast, the present invention applies polarity-specific carrier assignment-lipid vesicles for lipophiles, cyclodextrin or hydrogel complexes for hydrophiles, and stabilized mineral chelates for ionic cofactors within a unified multi-route delivery platform. This structured approach provides stability, synchronized release, and enhanced bioavailability across diverse nutrient classes, representing a substantial non-obvious advance over prior art nutritional supplement technologies.

Mechanistic Synergy

Sterol derivatives (modeled with esterified DHEA), in lipophilic carriers exhibit gradual release characteristics that align with the rapid uptake of hydrophilic agents (EAAs, Vitamin C) and the sustained absorption of other lipophilic compounds (Vitamin D, resveratrol, omega-3 fatty acids). The coordinated delivery produces a multi-phase nutrient support profile across different time scales.

Performance and Recovery Support

The combination of sterol derivatives (modeled with esterified DHEA), with HMB, EAAs, and creatine promotes balanced nutritional support for active individuals. HMB contributes to muscle integrity, EAAs support protein metabolism, creatine enhances short-term energy availability, and sterol derivatives provide a sustained-release nutrient component. Together, these polarity-assigned actives complement one another in supporting endurance, resilience, and recovery within a dietary supplement framework.

Nutritional Balance and Age-Related Support

Sterol derivatives (modeled with esterified DHEA), together with Vitamin D and magnesium, contribute to balanced nutrient support for bone integrity, neuromuscular function, and overall vitality. Esterification allows sterol derivatives to be incorporated into sustained-release delivery systems that help maintain consistent nutrient availability over time.

Cardiovascular and Metabolic Support

Omega-3 fatty acids, Vitamin D, zinc, and magnesium collectively promote cardiovascular wellness, cellular energy balance, and immune resilience. Within polarity-specific delivery systems, sterol derivatives complement these nutrients by contributing to systemic nutritional balance.

Cognitive and Mental Performance Support

Adaptogens such as *Panax ginseng*, when delivered within polarity-optimized carriers, help support focus, stress resilience, and mental clarity. In combination with sterol derivatives, these nutrients contribute to balanced cognitive and physiological performance.

Need for Advanced Formulations

Although sterol derivatives have been studied in various nutritional contexts, their potential within synergistic, multi-nutrient combinations has not been fully explored in polarity-specific, multi-route delivery systems. The present invention addresses this gap by integrating esterified model compounds with complementary nutrients through bioavailability-enhancing technologies.

Industry Shortcomings

Current dietary supplement formulations often rely on unmodified compounds without optimizing polarity compatibility, which can reduce consistency and stability. By contrast, esterified sterol derivatives within modular delivery systems allow for controlled release, lower required dosing, and improved stability across diverse nutrient classes.

Regulatory Context

These compositions are positioned within the dietary supplement and nutraceutical framework established under DSHEA. While not subject to pharmaceutical regulatory standards, the invention emphasizes formulation discipline, polarity-specific carrier selection, and evidence-based delivery strategies to ensure safety, consistency, and reliable performance in consumer use.

Integrated Multi-Bioavailability System

The invention utilizes micronization, phytosome encapsulation, omega-3 lipid matrices, cyclodextrin inclusion complexes, and self-emulsifying drug delivery system (SEDS) nanoemulsions to optimize the solubility, stability, and controlled release of sterol derivatives and related bioactives. This approach supports improved nutrient availability and stability at lower serving sizes across a broad consumer base.

Roles, Mechanisms, and Benefits of Sterol Derivatives: An Analytical Overview

The following esterified sterol derivatives are presented as model compounds to illustrate polarity-specific delivery strategies within the present invention. They serve as representative examples of how controlled-release carriers, lipid systems, and hydrophilic complexes can be applied to enhance consistency and tolerability of sterol-based bioactives in dietary supplement contexts.

1-DHEA Enanthate (Model Compound)

In research settings, 1-DHEA enanthate has been studied as a sterol derivative with unique metabolic properties. Within the present invention, it is used solely as a model compound to demonstrate how lipid-based carriers and controlled-release matrices improve the stability and delivery of esterified sterols in nutraceutical applications.

4-DHEA Enanthate (Model Compound)

4-DHEA enanthate has been described in the literature as a precursor sterol. In this invention, it is presented only as an example to highlight how polarity-specific oral and transdermal carriers can reduce variability compared to unmodified sterols.

5-DHEA Enanthate (Model Compound)

5-DHEA enanthate has been explored in research contexts for general wellness applications. Within the present invention, it functions as a model ester illustrating how polarity-specific carriers-such as cyclodextrins, microneedles, or nanoemulsions—can improve tolerability, stability, and bioavailability of sterol derivatives in dietary supplement applications.

5-DHEA Enanthate (Model Compound)

In research contexts, 5-DHEA enanthate has been explored in connection with general wellness. Within the present invention, it serves as a model ester illustrating how polarity-specific carriers-such as cyclodextrins, microneedles, or nanoemulsions can improve tolerability, stability, and bioavailability of sterol derivatives in dietary supplement applications.

19-Nor-DHEA Enanthate (Model Compound)

19-Nor-DHEA enanthate has been described in the literature as a structural variant of sterol derivatives. In the present invention, it is presented solely as a model compound to demonstrate how polarity-stratified delivery systems can help minimize variability and extend nutrient availability across diverse supplement formats.

Bioavailability Challenges of DHEA Derivatives (Enanthates)

Sterol derivatives in esterified enanthate form face notable limitations when administered in conventional oral formats. During digestion, a significant portion is processed by metabolic pathways before wider distribution, leading to reduced nutrient availability. This early processing lowers the amount of compound available for broader nutritional support and contributes to inconsistency across users.

Delivery Barriers

This reduced bioavailability profile results from several interrelated delivery challenges. The compounds exhibit inherently low aqueous solubility, limiting their dissolution in gastrointestinal fluids. Absorption efficiency is further influenced by dietary fat intake and bile salt availability, which can vary widely among individuals. These factors collectively lead to inconsistent uptake across users. Historically, higher intake levels have been attempted to offset these limitations, but such approaches increase variability and reduce predictability of nutritional support.

Context within Nutraceutical and Dietary Supplement Applications

In both research and supplement contexts, conventional oral administration of sterol enanthates has been associated with low, variable, and inconsistent nutrient uptake. Attempts to compensate by increasing intake have been reported to add additional demand on digestive and metabolic processes, contributing to variability in nutrient utilization. Literature has also noted that higher intake levels in sterol models may correspond with changes in lipid and nutrient processing. Collectively, these observations highlight the limitations of standard oral enanthate delivery and underscore the opportunity for improved carrier systems in nutraceutical and dietary supplement applications.

Relevance to Nutraceutical and Dietary Supplement Applications of the Present Invention The platform disclosed in the present invention directly addresses the bioavailability constraints inherent to esterified sterol derivatives through an integrated approach combining solubility enhancement, absorption support, and controlled-release technologies. By pairing such compounds with polarity-matched lipidic carriers, the invention promotes nutrient uptake through optimized transport pathways, reducing dependence on conventional digestive processing. Additionally, the inclusion of controlled-release delivery systems helps support steady nutrient availability at lower serving sizes. This multifaceted strategy reduces unnecessary metabolic demand and improves consistency of nutrient utilization, providing a more reliable formulation framework for nutraceutical and dietary supplement applications.

Strategies to Overcome Bioavailability Barriers

Esterified sterol derivatives present significant delivery challenges due to their low aqueous solubility, high lipophilicity, and variable nutrient processing efficiency. These barriers may necessitate higher intake levels to achieve consistent nutritional support. Several advanced delivery strategies have been developed to address these limitations, reduce serving requirements, and improve uptake characteristics in nutraceutical and dietary supplement formulations.

Lipid-Based Delivery Systems

Research on lipid-based oral delivery has shown that poorly water-soluble lipophilic compounds achieve more consistent nutrient uptake when formulated as self-emulsifying systems (SEDS) or nanoemulsions compared to conventional suspensions. These findings, cited here as model data, suggest applicability to nutraceutical ester models such as sterol derivatives, which may benefit from enhanced stability and more predictable absorption when delivered through lipid-based carriers in dietary supplement applications.

Cyclodextrin Complexation

Studies on cyclodextrin complexation have demonstrated improved dissolution rates and protection of labile molecules against enzymatic and oxidative degradation. In research models, complexation enhanced solubility and delivery consistency compared to uncomplexed forms. These observations support the utility of cyclodextrin complexes for esterified compounds, including sterol derivatives, when incorporated into nutraceutical formats such as capsules, powders, or sublingual systems.

Transdermal Delivery Context

Transdermal creams and gels, particularly when formulated with penetration enhancers such as ethanol or lipid excipients, allow sterol derivatives and similar compounds to cross the skin barrier without gastrointestinal degradation. Research has reported that this route can provide steadier nutrient availability over time. These findings illustrate the value of bypassing conventional digestive processing and reinforce the advantages of alternative delivery platforms such as those disclosed in the present invention for nutraceutical and dietary supplement applications.

Topical Micro-Dermal Systems

Microneedle arrays transiently bypass the stratum corneum and have been widely reported to enhance transdermal transport while enabling controlled release profiles, supporting their use for localized and systemic dermal delivery applications. Likewise, nanoemulsion and microemulsion creams featuring sub-200 nm droplets or thermodynamically stable dispersions can improve cutaneous penetration and physical/oxidative stability relative to conventional gels, when appropriately formulated and characterized. These observations are consistent across model systems and reviews and, without making treatment claims, suggest that polarity-tuned carriers may offer formulation advantages for lipophilic and hydrophilic nutraceutical actives intended for dermal application.

Phytosome Complexes

Phytosomes are advanced lipid-based carriers in which lipophilic molecules are complexed with phosphatidylcholine, mimicking cell membrane structures and enhancing solubility. Early phytosome studies demonstrated multi-fold increases in absorption for challenging botanical compounds such as silybin and curcumin. Related work with sterol models confirmed improved intestinal uptake and greater stability compared to standard lipid suspensions. For sterol derivatives such as DHEA esters, phytosome complexation supports lymphatic transport, improves solubility in gastrointestinal fluids, and protects against oxidative degradation in nutraceutical applications.

Production Process For DHEA Phytosomes

The production process for a sterol phytosome involves combining esterified sterol derivatives with phosphatidylcholine in specific molar ratios (often 1:1 or 1:2), dissolving the mixture in ethanol or acetone, and removing solvents via lyophilization or spray-drying. The resulting complex is a stable, free-flowing powder suitable for incorporation into capsules, sublingual tablets, or topical systems for nutraceutical and dietary supplement use.

Synergistic Active Pairing Strategies within the Polarity-Specific, Multi-Route Delivery Platform The present invention includes polarity-specific, pre-engineered combinations of bioactive agents designed for coordinated delivery across single or dual administration routes. Unlike conventional formulations, which often co-formulate all actives within a single carrier regardless of compatibility, this invention strategically separates each active into its polarity-matched, route-specific carrier. Each carrier is independently optimized to enhance solubility, stability, and uptake of the respective compound before integration into a final dosage form. This modular design enables precise coordination of multi-phase release dynamics and improved functional synergy in nutraceutical and dietary supplement applications.

Technical Rationale

Synergistic functional outcomes often require the co-delivery of actives with divergent chemical properties, absorption behaviors, and formulation sensitivities. Traditional systems are constrained in this regard, as they generally combine hydrophilic and lipophilic compounds into a single carrier, which can compromise solubility and stability, leading to precipitation or degradation. Differences in uptake rates may also cause asynchronous absorption patterns, undermining intended coordination. Moreover, stabilization strategies that benefit one component-such as lipid-phase antioxidants—may be incompatible with others, such as pH-sensitive hydrophilic agents.

Platform Advantage

The polarity-specific, multi-route platform disclosed herein overcomes these limitations by assigning each compound to its optimized formulation system based on polarity, solubility class, and intended route of administration. This enables independent stabilization, protection, and absorption tuning of each active, while ensuring coordinated nutrient availability within an application window appropriate for nutraceutical and dietary supplement uses.

Representative Synergistic Pairings

Example 1-Sterol Derivatives with Adaptogens

In one representative pairing, esterified sterol derivatives are combined with adaptogenic botanicals such as *Rhodiola rosea* or *Ginkgo biloba*. The sterol derivatives, being lipophilic, are encapsulated within ethosomes or nanostructured lipid carriers (NLCs) for dermal administration, or incorporated into self-emulsifying systems (SEDS) for oral delivery. The adaptogenic actives are separated by polarity: hydrophilic glycosides are complexed with cyclodextrins or loaded into hydrogel microneedles, while lipophilic polyphenols are stabilized in lipid vesicles. This pairing illustrates how polarity-matched carriers help maintain stability, prevent intercomponent degradation, and support coordinated delivery of multiple nutrient classes.

Example 2-HMB and Essential Amino Acids

In another example, β-hydroxy β-methylbutyrate (HMB) in its free acid form is paired with essential amino acids (EAAs). Both are hydrophilic, though they differ in stability characteristics. The HMB free acid can be formulated into hydrogel microneedles for rapid uptake or complexed with cyclodextrins for oral delivery, while EAAs may be co-formulated in aqueous carriers or integrated into the same microneedle matrix. Moisture-controlled packaging ensures chemical integrity. This pairing provides complementary support for protein metabolism and nutrient balance.

Example 3-L-Arginine, Resveratrol, and Omega-3s

A further example includes the co-administration of L-arginine, resveratrol, and omega-3 polyunsaturated fatty acids. L-arginine, being hydrophilic, is formulated in aqueous oral solutions or hydrogel microneedles, while the lipophilic resveratrol and omega-3 fatty acids are encapsulated in SEDS or lipid vesicles. In this combination, L-arginine supports healthy circulation, resveratrol provides antioxidant balance, and omega-3s contribute to cell membrane fluidity and nutritional support. The use of polarity-specific, multi-route delivery allows each compound to be stabilized in its optimal carrier while promoting complementary functional outcomes.

Formulation and Process Considerations

To ensure delivery consistency and chemical compatibility, each active is stabilized within its assigned carrier prior to final formulation assembly. Packaging technologies such as nitrogen-flushed, dual-compartment blister systems are employed to prevent cross-degradation between hydrophilic and lipophilic agents. Controlled-release mechanisms are incorporated into each carrier system, enabling coordinated release timing and predictable nutrient availability. The modular structure of the platform allows synergistic pairings to be configured into hybrid dosage forms such as multi-compartment oral capsules, dual-release microneedle patches, or coordinated oral-transdermal administration kits.

Advantages Over Prior Art

Prior art relating to synergistic formulations in dietary supplements generally lacks polarity-specific stabilization and typically confines administration to the oral route. Conventional systems rarely offer independent control over release profiles for each constituent compound. In contrast, the present invention uniquely separates active ingredients according to polarity and delivers them via independently engineered carriers. It enables multi-route administration to address delivery mismatches, employs tailored release kinetics for each active, and applies targeted stability interventions-such as antioxidants, pH buffering, and inert packaging atmospheres—to preserve molecular integrity. These combined features establish a novel and non-obvious delivery architecture that significantly enhances formulation flexibility, nutrient delivery consistency, and long-term product stability.

Micronization Delivery System

Definition and Core Characteristics

Micronization is a particle-size reduction method employed to improve the dissolution and handling properties of lipophilic compounds such as esterified sterol derivatives. The technique reduces particle dimensions into the 1-10 microns (μm) range using approaches including jet milling, fluid energy milling, and supercritical fluid micronization. These methods reduce particle size without altering chemical identity, thereby increasing the surface area-to-volume ratio. The expanded surface area supports improved dissolution in gastrointestinal fluids, making the compounds more suitable for consistent nutraceutical delivery.

Functional Mechanism

When incorporated into oral formulations, micronized sterol esters exhibit improved wetting and dispersibility due to their reduced particle size. The increased surface area promotes faster dissolution in gastric and intestinal environments, supporting more predictable nutrient uptake. The particles can also be incorporated into lipid micelles during digestion, further improving absorption consistency. This delivery approach helps reduce variability associated with poorly soluble compounds.

Application in the Present Invention

Within the scope of the present continuation-in-part application, the micronization process is applied to sterol esters such as DHEA enanthate and structurally related derivatives to improve dissolution and uptake in oral formats. The technique supports efficient absorption under low-solubility conditions in the gastrointestinal tract and reduces variability in delivery. By increasing dissolution efficiency, micronization lowers the serving size needed to achieve consistent nutritional support. Additionally, control over particle morphology enhances formulation stability by reducing recrystallization. Micronized particles are compatible with dosage forms such as hard gelatin capsules, compressed tablets, and powder blends containing lipid-based carriers or food-grade surfactants.

Micronized sterol esters are particularly well-suited for nutraceutical applications where injectable or transdermal routes are not feasible or preferred such as consumer-focused oral formulations-making them ideal for products designed to combine consistency, convenience, and ease of use.

Processing and Pre-Engineering

The production of micronized sterol esters involves selecting appropriate size-reduction technologies based on compound sensitivity and particle specifications. Jet milling yields uniform particle sizes with minimal heat impact, fluid energy milling is suitable for heat-sensitive materials, and supercritical $CO_2$ micronization offers a solvent-free option for highly lipophilic or chemically labile compounds. Following size reduction, the micronized particles are blended with wetting agents, surfactants, or lipid excipients to prevent aggregation and preserve stability. Final formulations are packaged in high-barrier containers designed to exclude moisture and oxygen, thereby safeguarding potency and stability during storage.

Ethosome Delivery System

Definition and Core Characteristics

An ethosome delivery system is a soft, flexible vesicular carrier composed of phospholipids, ethanol (20-45%), and water. The ethanol component modifies the lipid bilayers of the stratum corneum, improving dermal penetration. Ethosomes encapsulate lipophilic or amphiphilic molecules, and their deformable structure enables them to move through narrow intercellular pathways in the skin. Compared to conventional liposomes, ethosomes exhibit greater membrane flexibility, higher encapsulation capacity, and improved compatibility with dermal delivery in nutraceutical applications.

Functional Mechanism

The ethanol content fluidizes the skin's lipid matrix, lowering its resistance. Upon application, ethosomal vesicles interact with skin lipids and release encapsulated nutrients into deeper epidermal and dermal compartments. This dual mechanism-ethanol-assisted penetration and vesicle-mediated release-supports improved nutrient deposition in the skin and enhances stability by protecting bioactives against oxidative or hydrolytic degradation.

Application in the Present Invention

In this continuation-in-part application, ethosomes are engineered for dermal delivery of lipophilic actives including sterol derivatives, fat-soluble vitamins (A, D, E, K), and lipophilic polyphenols such as resveratrol. Ethosomal encapsulation enhances dermal penetration, reduces variability in nutrient delivery, and helps maintain consistent uptake compared to conventional topical formulations. By avoiding digestive degradation, ethosomal systems support more predictable performance. This approach is compatible with stand-alone topical creams/gels or hybrid microneedle-assisted dermal delivery formats.

Processing and Pre-Engineering (Ethosomes)

Preparation involves dissolving the selected lipophilic active in an ethanol-phospholipid solution, followed by gradual water addition under controlled stirring to induce vesicle assembly. The resulting ethosomes are characterized for particle size, polydispersity, zeta potential, and encapsulation efficiency. Quality control includes stability testing, ethanol content verification, and accelerated storage studies to confirm vesicle integrity. Pre-engineered ethosomal dispersions are incorporated into transdermal microneedle patches, topical creams, or gels, and packaged in nitrogen-flushed, oxygen- and light-impermeable containers to maintain potency throughout storage and distribution.

Nanostructured Lipid Carriers (NLCs)

Definition and Core Characteristics

Nanostructured Lipid Carriers (NLCs) are advanced second-generation lipid nanoparticulate delivery systems designed to overcome the limitations of earlier carriers such as Solid Lipid Nanoparticles (SLNs) and conventional emulsions. They consist of a blend of solid lipids and liquid lipids dispersed in an aqueous surfactant phase, typically forming particles between 50 and 500 nanometers. The incorporation of liquid lipids into the solid lipid matrix creates an imperfect crystalline structure, which increases the capacity for bioactive nutrient loading and reduces the risk of expulsion during storage. Compared to SLNs, NLCs offer enhanced physical stability, greater encapsulation efficiency for lipophilic actives, and the ability to fine-tune release timing, making them highly versatile for nutraceutical and cosmeceutical applications.

Functional Mechanism:

The unique mixed-lipid structure of NLCs provides a less-ordered internal matrix that accommodates more lipophilic nutrients than fully crystalline lipid systems. This structure traps compounds securely and protects them from oxidative, thermal, and photolytic degradation. At the nanoscale, the particles present a large surface area, which supports improved dissolution rates and interaction with digestive and dermal environments. In oral delivery, the lipid composition enhances nutrient solubilization and absorption efficiency, while in dermal delivery, the lipid phase aligns with skin lipids to support penetration through the stratum corneum. This compatibility allows the same NLC formulation to be adapted for multiple administration routes without fundamental reformulation.

Application in the Present Invention

In the present continuation-in-part application, NLCs are employed for the encapsulation and delivery of lipophilic bioactives requiring enhanced stability, solubilization, and controlled release. These include esterified sterol derivatives, fat-soluble vitamins (A, D, E, K), and lipophilic polyphenols such as resveratrol. Incorporation into NLCs protects these compounds from degradation, enhances their dissolution in digestive and dermal conditions, and supports sustained nutrient availability. The adaptability of the NLC platform enables these formulations to be delivered either orally, via capsules, or dermally, via creams and gels, without altering the core encapsulation system.

Processing and Pre-Engineering

NLC production begins with melting the selected solid lipid and blending it with the liquid lipid phase containing the dissolved bioactive nutrient. This lipid mixture is emulsified into a hot aqueous surfactant solution using high-shear mixing, followed by high-pressure homogenization to achieve the target particle size with low polydispersity. Rapid cooling solidifies the lipid matrix, entrapping the nutrient within its imperfect crystalline network. Each batch is characterized for mean particle size, polydispersity index, zeta potential, encapsulation efficiency, and oxidative stability. Stability studies include both long-term and accelerated testing to monitor particle size stability, nutrient content retention, and resistance to aggregation. Pre-engineered NLC dispersions are then incorporated into final oral or dermal dosage forms and packaged in nitrogen-flushed, oxygen- and light-impermeable containers to ensure maximum shelf life.

Nanoemulgel Delivery System

DEFINITION AND CORE CHARACTERISTICS

A nanoemulgel is a biphasic topical or dermal delivery system that combines a nanoemulsion with a gel base. The nanoemulsion component consists of nanoscale oil-in-water or water-in-oil droplets, typically ranging from 20 to 200 nanometers in diameter, stabilized by surfactants and co-surfactants. The gel matrix, often composed of gelling agents such as carbomers or natural polysaccharides, provides enhanced viscosity, stability, and ease of application. The nano-sized droplets increase the surface area of encapsulated nutrients, supporting improved dissolution and permeability across the skin barrier. Compared to conventional creams or ointments, nanoemulgels provide enhanced solubilization, deeper skin penetration, and more uniform distribution. The combined properties of the nanoemulsion and gel phases allow both improved retention on the skin and more consistent delivery performance.

Functional Mechanism

The small droplet size of the nanoemulsion ensures close contact with the stratum corneum, supporting diffusion of encapsulated compounds through the skin barrier. The presence of surfactants and co-surfactants can further assist permeation by interacting with the lipid structure of the stratum corneum. The gel matrix increases residence time at the site of application, reducing runoff and promoting sustained release. Additionally, the gel phase can be engineered to adjust release kinetics-allowing either faster release or extended delivery-depending on formulation design. The gel also provides a controlled hydration effect on the skin, which enhances permeation of both hydrophilic and lipophilic nutrients.

Application in the Present Invention

In this continuation-in-part application, nanoemulgels are designed for the topical delivery of lipophilic bioactives such as esterified sterol derivatives, fat-soluble vitamins (A, D, E, K), and polyphenols like resveratrol. The nanoemulsion phase solubilizes and stabilizes these compounds, while the gel matrix enhances application convenience and retention on the skin surface. This approach supports deep dermal penetration, reduces degradation of sensitive compounds, and improves the consistency of nutrient delivery. The nanoemulgel format is particularly advantageous where both localized skin support and broader nutritional delivery are desired.

Processing and Pre-Engineering

The nanoemulsion phase is prepared by dissolving the lipophilic bioactive in the oil phase, mixing with surfactants and co-surfactants, and dispersing into an aqueous phase using high-shear mixing and ultrasonication or high-pressure homogenization to achieve droplet sizes below 200 nanometers. The resulting nanoemulsion is then incorporated into a pre-hydrated gel base under gentle stirring to maintain stability. The final nanoemulgel is evaluated for droplet size distribution, zeta potential, viscosity, pH, encapsulation efficiency, and physical stability. Finished formulations are packaged in light- and oxygen-barrier containers to preserve potency and shelf life.

Self-Emulsifying Lipid Systems (Sels)

Definition and Core Characteristics

Self-Emulsifying Lipid Systems (SELS) are advanced oral formulations designed to improve the solubility and consistency of delivery for poorly water-soluble nutrients. They are isotropic mixtures of oils, surfactants, and co-surfactants, sometimes with added cosolvents. Upon contact with gastrointestinal fluids and under natural digestive mixing, SELS spontaneously form fine oil-in-water emulsions or nanoemulsions without requiring external energy. Droplet sizes typically range from below 100 nm for nanoemulsifying systems to under 250 nm for conventional SELS. Compared to oil-filled softgels or solid dispersions, SELS offer faster dispersion, greater reproducibility of nutrient delivery, and reduced variability from dietary fat effects. The lipid phase solubilizes hydrophobic compounds, while the nanoscale droplets increase surface area for dissolution.

Functional Mechanism

Upon oral administration, SELS formulations rapidly emulsify in the stomach or small intestine, producing micro- or nano-droplets in which lipophilic nutrients remain solubilized. This pre-dissolved state supports predictable dispersion, improved digestive compatibility, and enhanced consistency in nutrient uptake compared to solid dosage forms. The lipid composition aligns with natural digestive processes, helping stabilize sensitive compounds and promoting efficient transport across the intestinal lining.

Application in the Present Invention

In this continuation-in-part application, SELS are pre-engineered for the oral delivery of lipophilic compounds, including esterified sterol derivatives, fat-soluble vitamins (A, D, E, K), and polyphenols such as resveratrol. SELS-based formulations improve solubility, protect compounds from degradation, and support consistent nutrient delivery relative to conventional capsules or oil-filled softgels. Literature on similar lipid-based systems has reported multi-fold improvements in dissolution and uptake consistency, supporting the utility of SELS for nutraceutical formulations.

Processing and Pre-Engineering

Development begins with screening suitable oils (e.g., medium-chain triglycerides, long-chain fatty acid esters), surfactants (e.g., polysorbates), and co-surfactants (e.g., PEG 400, ethanol, propylene glycol). The nutrient is dissolved in the lipid phase and blended with the surfactant/co-surfactant mixture to achieve rapid emulsification and thermodynamic stability in simulated digestive conditions. Finished formulations undergo quality control testing for droplet size distribution, polydispersity index, precipitation resistance, chemical stability, and dissolution performance. SELS can be encapsulated in softgels, filled into hard gelatin capsules, or converted into solid dispersible powders via spray drying or adsorbent-based methods, enabling compatibility with hybrid delivery strategies. In this invention, pre-concentrated SELS are filled into oral capsules and packaged in nitrogen-flushed, oxygen- and light-impermeable containers to ensure stability during storage and distribution.

Hydrogel-Forming Microneedles

DEFINITION AND CORE CHARACTERISTICS

Hydrogel-forming microneedles are polymer-based microneedle arrays designed for minimally invasive dermal delivery of nutritional actives. Unlike dissolving microneedles, these are fabricated from swellable, cross-linked hydrophilic polymers that are initially dry and rigid enough to pierce the stratum corneum. Upon insertion into the skin, they absorb interstitial fluid and swell, forming continuous aqueous conduits between the skin surface and an attached nutrient reservoir. The polymer matrix does not dissolve in the skin but remains intact for safe removal post-application, reducing the risk of polymer residue.

Functional Mechanism

When applied, the dry hydrogel microneedles puncture the skin barrier and hydrate within minutes. As they swell, aqueous microchannels are formed, allowing hydrophilic nutrients and bioactives to diffuse from an external reservoir through the swollen matrix into the dermal interface. The hydrated network maintains sustained nutrient transport without mechanical collapse for extended periods. Compared to dissolving microneedles, hydrogel-forming microneedles allow for higher payload delivery, improved release control, and no polymer deposition in the skin.

Model Data

Research by Donnelly et al. (Advanced Functional Materials, 2012) demonstrated that hydrogel-forming microneedles can transfer over 90% of a loaded hydrophilic compound within several hours while maintaining structural integrity for removal. These findings serve as model data supporting the potential of hydrogel-forming microneedles to improve transfer efficiency and stability in supplement delivery applications.

Application in the Present Invention

In this continuation-in-part application, hydrogel-forming microneedles are optimized for the dermal delivery of hydrophilic nutrients such as essential amino acids and β-hydroxy β-methylbutyric acid (HMB) in its free acid form. These actives benefit from dermal uptake pathways that avoid gastrointestinal degradation, supporting more consistent nutrient utilization. The hydrogel microneedle platform provides prolonged delivery while maintaining stability of sensitive compounds.

Comparative Advantages

Compared to dissolving microneedles, which embed nutrients within a biodegradable matrix, this system separates the nutrient reservoir from the microneedle array, allowing for higher payload loading and prolonged infusion without increasing microneedle size. Compared to solid microneedles with topical patches, hydrogel-forming microneedles offer higher nutrient transfer rates due to the hydrated hydrogel conduit.

Processing and Pre-Engineering

Fabrication begins with the preparation of an aqueous pre-polymer solution containing a crosslinker, typically poly (methyl vinyl ether-co-maleic acid) (PMVE/MA) with polyethylene glycol (PEG) as a plasticizer. This solution is cast into precision microneedle molds under vacuum to remove air bubbles and ensure complete cavity filling. Crosslinking is achieved by controlled thermal or UV curing, resulting in a mechanically robust, insoluble but swellable polymer matrix. Nutrient loading occurs in a separate external reservoir, such as a patch backing layer or semi-solid depot. Upon application to the skin, the hydrogel microneedles hydrate, form aqueous conduits, and enable nutrient diffusion from the reservoir over a pre-determined delivery period. Finished systems are packaged in sterile, moisture-protected conditions to maintain structural and functional integrity until use.

Vesicular Lipid Systems Adapted Per Delivery Route

Definition and Core Characteristics

Vesicular lipid systems are nano- or micro-scale carriers composed of one or more concentric lipid bilayers surrounding an aqueous core, capable of encapsulating both hydrophilic and lipophilic active compounds. These include liposomes, niosomes, transferosomes, and phytosomes, each with distinct lipid compositions and structural modifications. The adaptability of vesicular lipid systems allows for fine-tuning of particle size, surface charge, lipid composition, and membrane fluidity to suit the physicochemical properties of the active ingredient and the intended route of administration. By engineering vesicular systems for specific delivery pathways-oral, transdermal, mucosal, or parenteral—the performance and bioavailability of actives can be significantly enhanced.

Functional Mechanism

Vesicular lipid systems operate by encapsulating actives within their lipid bilayers or aqueous compartments, providing both physical protection and a microenvironment optimized for stability. The lipid bilayers can merge with biological membranes or release their payload via diffusion or triggered disruption, facilitating efficient transport of encapsulated molecules across biological barriers. Customizing vesicle composition per route allows control over pharmacokinetics, absorption rate, and site-specific release, enabling targeted delivery to systemic circulation or local tissues while minimizing off-target exposure.

Application in the Present Invention

In the present continuation-in-part application, vesicular lipid systems are adapted for multiple administration routes to optimize delivery of various active classes. For dermal delivery, ethosomes and transferosomes are utilized due to their high deformability and ability to penetrate the stratum corneum. For oral administration, multilamellar liposomes are engineered to withstand gastric pH and release contents in the intestinal lumen. For mucosal delivery, ultradeformable vesicles with mucoadhesive coatings are used to prolong retention and improve absorption across epithelial tissues. Actives formulated in these vesicular systems include esterified DHEA derivatives, fat-soluble vitamins, essential amino acids, HMB free acid, and lipophilic polyphenols such as trans-resveratrol.

Processing and Pre-Engineering

Vesicular systems are produced by methods such as thin-film hydration, ethanol injection, reverse-phase evaporation, or microfluidization, depending on the route-specific design. For transdermal vesicles, phospholipids are blended with edge activators like sodium cholate or Tween 80 to impart flexibility. For oral vesicles, bile salt incorporation and polymer coatings are applied to increase stability in gastrointestinal conditions. Particle size is typically controlled between 50 and 500 nanometers using extrusion or homogenization techniques. Each vesicle batch is characterized for size distribution, zeta potential, encapsulation efficiency, stability, and release profile in simulated biological media.

Nanoemulsions Delivery System

Definition and Core Characteristics

Nanoemulsions are submicron colloidal dispersions composed of oil droplets ranging from 20 to 200 nanometers in diameter, uniformly dispersed within an aqueous phase and stabilized by surfactants and co-surfactants. These systems are designed to enhance the solubility, dispersion, and delivery consistency of lipophilic, poorly water-soluble nutrients such as sterol esters. Due to their small droplet size, nanoemulsions provide a very high surface area-to-volume ratio, supporting faster dissolution and stable incorporation of both hydrophilic and lipophilic compounds.

Functional Mechanism

When ingested or applied topically, nanoemulsion formulations disperse rapidly in aqueous environments, forming a stable nanoscale system that improves solubilization of lipophilic compounds. The high surface area of the oil droplets supports better interaction with digestive or dermal environments, while the stabilized architecture reduces risks of coalescence, creaming, or phase separation. This results in more predictable performance, reduced variability, and improved stability during both storage and administration.

Application in the Present Invention

In this continuation-in-part application, nanoemulsion delivery systems are applied to sterol esters and related lipophilic compounds to improve formulation performance across oral, mucosal, and dermal applications. Oral presentations may include softgel capsules or liquid suspensions that offer convenient formats with improved solubility and stability. Mucosal delivery can be enabled through sublingual or buccal nanoemulsion formats, supporting efficient dispersion and retention. For dermal and topical use, nanoemulsions can be incorporated into gels or creams to improve penetration into the skin and enhance local or systemic nutritional support. This strategy is applied to sterol esters, fat-soluble vitamins (A, D, E, K), and polyphenols such as resveratrol, enabling broader use of compounds that otherwise face solubility and stability limitations.

Processing and Pre-Engineering

The production of nanoemulsions suitable for nutraceutical applications involves formulation and mechanical processing steps. The bioactive nutrient is first dissolved in a lipid phase such as medium-chain triglycerides or ethyl oleate. This lipid phase is then blended with selected surfactants and co-surfactants (e.g., polysorbates, PEG 400, ethanol, propylene glycol) to form a pre-emulsion. Droplet size reduction into the nanoscale range is achieved by high-energy techniques such as high-pressure homogenization, ultrasonication, or microfluidization. Alternatively, low-energy spontaneous emulsification methods may be employed to create stable nanoemulsions under appropriate formulation conditions. Final products are packaged in high-barrier containers to exclude light and oxygen, preserving potency and maintaining droplet stability throughout storage.

Cyclodextrin Complexation Delivery System

Definition and Core Characteristics

Cyclodextrin complexation is a molecular encapsulation technique that employs cyclic oligosaccharides possessing a hydrophobic internal cavity and a hydrophilic external surface to improve the solubility and stability of poorly water-soluble nutrients. Common nutraceutical-grade derivatives include hydroxypropyl-β-cyclodextrin (HPBCD) and sulfobutyl ether-β-cyclodextrin (SBEBCD), both noted for enhanced aqueous solubility, broad safety profiles, and compatibility with diverse formulation matrices. These materials form non-covalent inclusion complexes by hosting the lipophilic portion of a compound-such as the ester moiety of sterol derivatives-within the cyclodextrin cavity. This encapsulation masks hydrophobic character, improves dispersibility in aqueous environments, and provides protection against environmental degradation factors such as oxidation, photolysis, and pH instability.

Functional Mechanism

The amphiphilic structure of cyclodextrins enables their function: the inner cavity hosts non-polar segments of the nutrient, while the hydrophilic exterior interacts with the aqueous medium. This allows the encapsulated compound to disperse more effectively in digestive or dermal environments. The inclusion complex helps stabilize the active against oxidative or hydrolytic degradation, reduces aggregation and precipitation, and improves uniform distribution within formulations. In oral formats, cyclodextrins also contribute to taste masking and reduced irritation. In topical or dermal formulations, they enhance surface dispersion and stability upon application.

Application in the Present Invention

Within the scope of this continuation-in-part application, cyclodextrin complexation is applied to lipophilic nutrients including esterified sterol derivatives, fat-soluble vitamins, and polyphenols. For example, HPBCD-based inclusion complexes may be formulated into oral capsules, chewable tablets, or sublingual films designed for rapid dissolution. For topical use, cyclodextrin complexes can be incorporated into cream or gel bases to improve uniform dispersion and protect sensitive nutrients from oxidative degradation. This approach provides formulation flexibility across multiple delivery routes while improving solubility and stability of otherwise poorly water-soluble actives.

Processing and Pre-Engineering

Preparation of cyclodextrin inclusion complexes for nutraceutical formulations can employ methods such as co-precipitation, kneading, spray-drying, or freeze-drying. These processes yield free-flowing powders with consistent particle morphology and high complexation efficiency. Each batch is characterized for parameters such as complexation efficiency, particle size distribution, dissolution rate, residual moisture, and chemical stability. Final products are packaged in moisture-resistant, oxygen-impermeable containers to maintain potency throughout storage under both standard and accelerated conditions.

Hydroxypropyl-β-Cyclodextrin (HPβCD) Complexes: Solubilizing Hydrophobic Molecules HPBCD is a cyclic oligosaccharide capable of forming non-covalent inclusion complexes with hydrophobic molecules, enhancing their aqueous solubility, dissolution rate, and overall chemical stability. This property is particularly valuable for sterol derivatives and similar lipophilic nutrients, which otherwise exhibit poor dispersibility.

In complexation, the hydrophobic moiety of the nutrient is encapsulated within the HPBCD cavity, while the hydrophilic surface remains exposed to the aqueous environment. This arrangement supports improved dispersion in gastrointestinal or dermal fluids and stabilizes the compound against pH shifts or oxidative degradation.

Beyond oral delivery, HPBCD complexes have demonstrated utility in topical, transdermal, and mucosal applications, where they support uniform distribution, improved surface retention, and greater formulation stability. For sterol derivatives, these features contribute to more consistent delivery and broader application formats.

From a manufacturing standpoint, HPBCD inclusion complexes can be produced via co-solubilization in aqueous or hydroalcoholic systems followed by freeze-drying, kneading, or spray-drying, yielding powders or granulates with excellent stability and dissolution performance. These can be incorporated into capsules, tablets, lozenges, or sublingual films, enabling diverse supplement applications.

Cyclodextrin complexation has been extensively validated across multiple related sterol and polyphenolic compounds, making it a scientifically grounded and scalable strategy for next-generation nutraceutical and dietary supplement formulations.

Expanded Delivery Scope-Transdermal Administration

Definition and Core Characteristics

Transdermal delivery refers to the administration of nutrients through the skin as a non-invasive alternative to oral formats. This route supports delivery without relying on gastrointestinal processing and allows nutrients to be absorbed gradually over time. Effective transdermal systems must overcome the natural barrier of the stratum corneum, which is resistant to penetration by most compounds. To address this, advanced carriers and penetration enhancers are employed to support consistent nutrient transfer through the skin.

Functional Mechanism

In this invention, transdermal delivery is enabled by specialized carriers such as ethosomes, nanostructured lipid carriers (NLCs), nanoemulgels, and hydrogel-forming microneedles. These systems work by interacting with the skin's lipid layers, creating temporary microchannels, or dispersing nutrients in nanoscale droplets that improve penetration. Penetration enhancers-including oleic acid, terpenes, phosphatidylcholine, and polyols—are incorporated into carriers to further support nutrient permeability. The result is improved dermal transfer of both lipophilic and hydrophilic nutrients with customizable release characteristics.

Application in the Present Invention

The transdermal route in the present continuation-in-part application is applied to sterol esters (used here as model compounds), fat-soluble vitamins (A, D, E, K), lipophilic polyphenols such as resveratrol, essential amino acids, and HMB free acid. These formulations are designed to provide consistent nutrient delivery and stability across time. By avoiding digestive breakdown, these systems can help reduce variability and extend application formats beyond conventional oral supplements.

Processing and Pre-Engineering

The process for transdermal systems involves selecting a carrier based on nutrient polarity and stability, then incorporating penetration enhancers tailored to compound structure and intended depth of delivery. Ethosomal formulations are prepared using ethanol-phospholipid systems, while lipid-based carriers such as NLCs are produced via high-pressure homogenization. Hydrogel-forming microneedles are fabricated with nutrient-loaded tips that hydrate upon insertion into the skin. Final transdermal products are sealed in nitrogen-flushed, oxygen- and light-impermeable packaging to preserve potency during storage and distribution.

Novel Hybrid Microdermal Delivery System

The present invention introduces a Hybrid Microdermal Delivery System, specifically engineered to enable the coordinated delivery of both lipophilic and hydrophilic nutrients within a unified transdermal platform. This system employs a dual-compartment microneedle array in which a dissolving polymeric matrix rapidly delivers water-soluble compounds such as amino acids and B-complex vitamins, while a lipid-based or nanoparticle phase is either integrated into the microneedle tips or embedded within the backing layer to provide controlled release of lipophilic compounds including fat-soluble vitamins, polyphenols, and sterol derivatives (used here as model compounds). The integration of polymeric and lipid components within a single system supports dermal penetration, maintains stability across diverse nutrient classes, and enables phased release that would be difficult to achieve with conventional single-phase transdermal systems.

Definition and Core Characteristics

The Hybrid Microdermal Delivery System disclosed herein is a dual-phase transdermal architecture that combines dissolvable or hydrogel-forming polymeric microneedles with lipid-based or nanoparticulate carriers such as ethosomes, nanostructured lipid carriers (NLCs), or lipid-polymer hybrid nanoparticles (LPNs). This design allows for either simultaneous or sequential release of hydrophilic and lipophilic actives through the skin. It is particularly suited for multi-active formulations where compounds with differing polarity and solubility are delivered together within one harmonized system. By structurally matching each carrier to the polarity of its nutrient, the hybrid system ensures coordinated dermal penetration, controlled release timing, and improved delivery consistency.

Functional Mechanism

The hybrid system functions through dual-compartment loading within the microneedle array. The hydrophilic compartment, composed of biocompatible polymers such as hyaluronic acid, polyvinylpyrrolidone (PVP), or hydroxypropyl methylcellulose (HPMC), incorporates water-soluble actives and dissolves rapidly upon insertion, releasing its payload into dermal microchannels. The lipophilic compartment-formulated with nanocarriers such as NLCs, ethosomes, or LPNs—is embedded within the needle tips or coated onto polymer surfaces. These carriers encapsulate lipophilic nutrients such as sterol esters and fat-soluble vitamins, releasing their contents more gradually. The combined mechanism allows rapid delivery of hydrophilic actives alongside sustained release of lipophilic components, while maintaining structural and chemical stability across both phases.

Application in the Present Invention

In this continuation-in-part application, the Hybrid Microdermal Delivery System is applied as a versatile embodiment adaptable to different solubility classes. For lipophilic-only formulations, lipid-based microneedle carriers or lipid-coated polymeric arrays are employed. For hydrophilic-only formulations, fully dissolving or hydrogel-forming microneedles are used. For mixed-polarity combinations-such as sterol esters formulated together with vitamins, amino acids, or antioxidants—the hybrid platform integrates polymeric cores for rapid hydrophilic release and lipid-based nanoparticles for sustained lipophilic delivery. This approach supports more consistent nutrient delivery and expanded flexibility in dietary supplement and functional nutrition formulations.

Processing and Pre-Engineering

The hybrid microdermal system is produced through modular fabrication steps. Hydrophilic actives are embedded within a polymeric microneedle matrix via casting or molding. Lipophilic compounds are encapsulated in lipid-based nanocarriers, which are then incorporated into the microneedle array by sequential molding, dual-layer casting, or surface coating. Completed microneedle patches are integrated with a protective backing and sealed in moisture-resistant, oxygen-impermeable packaging to preserve both compartments during shelf life. This process enables scalable, high-precision production and allows formulation customization for nutraceutical applications. The dual-phase architecture supports development of advanced supplement delivery systems that are minimally invasive, user-friendly, and stable across diverse nutrient classes.

Table 42 summarizes optimized microdermal delivery strategies based on the polarity composition of active ingredients.

TABLE 42

| Optimized Microdermal Delivery Strategies | | |
|---|---|---|
| Composition Type | Recommended Delivery System | Supporting Evidence |
| All-lipophilic | General (non-polymeric) microdermal systems with lipid carriers | Hybrid microneedle + nanoparticle delivery systems have demonstrated effective co-delivery of lipophilic nutrient compounds. |
| All-hydrophilic | Polymeric microdermal systems (dissolving or hydrogel-forming MNs) | Microneedle arrays incorporating polymer matrices enable efficient delivery of hydrophilic nutrients with controlled release. |
| Mixed lipophilic-hydrophilic | Hybrid microneedle systems: polymeric for hydrophilic + lipid/nanoparticle coating for lipophilic | Dual-release microneedles and lipid-polymer nanoparticle-loaded dissolving microneedles have shown compatibility and sequential delivery of both hydrophilic and lipophilic compounds. |

Table 42 summarizes optimized microdermal delivery strategies based on the polarity composition of bioactive nutrients. It aligns each composition type-lipophilic, hydrophilic, or mixed—with its corresponding delivery system and cites supporting evidence for delivery consistency. The data highlights how polymeric microneedles are well suited for hydrophilic nutrients, lipid-based systems suit lipophilic compounds, and hybrid microneedles enable coordinated dual delivery for mixed-polarity formulations.

Transdermal Microneedle Patch with Multilayer Backing Film, Integrated Rate-Controlling Membranes, and Nitrogen-Flushed Packaging—Applied Stability Measures & Benefits In this embodiment, the transdermal microneedle patch is designed with structural and packaging enhancements to ensure consistent nutrient delivery performance, maintain active stability, and extend shelf life under real-world storage and transport conditions. The system incorporates a multilayer backing film, integrated rate-controlling membranes, and nitrogen-flushed, oxygen-impermeable packaging, along with careful selection of compatible container-contact materials, collectively providing a robust and nutraceutical-grade solution.

The multilayer backing film consists of high-barrier laminated composites-such as aluminum-polymer laminates-which provide both mechanical strength and environmental resistance. This film layer ensures the structural integrity of the patch while protecting the nutrient reservoir and microneedle array from moisture, oxygen, and photolytic degradation. Additionally, the backing film offers flexibility and durability to maintain user comfort and adhesion during extended wear.

Integrated within the patch design are rate-controlling membranes positioned between the nutrient reservoir or microneedle matrix and the backing layer. These selectively permeable membranes regulate diffusion rates and release profiles. By modulating transdermal flux, the membranes support sustained nutrient delivery and help maintain predictable release timing over predetermined intervals.

The finished patch is sealed within nitrogen-flushed, oxygen-impermeable multilayer foil pouches, designed to minimize oxidative degradation of both the microneedle matrix and the encapsulated nutrients. The inert packaging atmosphere preserves stability by eliminating exposure to oxygen and environmental humidity, which are common degradation factors for lipophilic and sensitive compounds.

The system also ensures chemical compatibility across all container-closure interface materials. All adhesives, liners, and contact films used in the patch and packaging assembly are verified to be non-reactive, non-leaching, and non-adsorptive, thereby eliminating the risk of nutrient loss or destabilization during storage.

The combined effect of these innovations is a transdermal patch that maintains its controlled-release performance and predictable delivery throughout its intended shelf life. Active content remains within target ranges under both accelerated and long-term storage conditions. In parallel, mechanical integrity, patch flexibility, and adhesion properties are preserved under stressors associated with manufacturing, packaging, and shipping. This embodiment demonstrates applied stability measures consistent with recognized standards for combination nutraceutical products, further supporting its readiness for reliable commercial deployment.

Transdermal Creams and Gels

Definition and Core Characteristics

Transdermal creams and gels are non-invasive, semi-solid formulations designed to support controlled nutrient delivery through the skin. These formulations are tailored for lipophilic compounds such as sterol derivatives, fat-soluble vitamins, and polyphenols. Penetration enhancers (e.g., ethanol, propylene glycol, oleic acid), stabilizers, and viscosity modifiers are incorporated to improve solubility, dispersion, and stability, while ensuring consumer-friendly application.

Functional Mechanism

The outer skin barrier (stratum corneum) limits passive diffusion of most compounds. Transdermal gels and creams address this by using carrier systems and penetration enhancers that temporarily increase permeability, supporting more efficient nutrient transfer into the dermal layers. This approach allows for gradual, sustained nutrient release, reducing variability and helping maintain consistency of delivery compared to conventional formulations.

Application in the Present Invention

In this continuation-in-part application, transdermal gels and creams are formulated for lipophilic sterol derivatives (as model compounds), fat-soluble vitamins (A, D, E, K), and lipophilic polyphenols such as resveratrol. Polarity-specific gel bases (hydroalcoholic, lipid, or liposomal carriers) are selected for compatibility with the nutrients. Penetration enhancers are matched to molecular characteristics, supporting consistent release profiles and formulation stability.

Processing and Pre-Engineering

Actives are solubilized in oil or hydroalcoholic blends, then blended into carbomer, pluronic-lecithin organogels (PLO), or liposomal gel bases with optimized viscosity and dispersion. Rheology, pH, and stability are tested to ensure uniformity and integrity. Finished formulations are filled into nitrogen-flushed, oxygen- and light-impermeable packaging to maintain potency and extend shelf life.

Microneedle Patches for Supplement Delivery

Overview and Mechanism

Microneedle patches are minimally invasive transdermal systems designed to bypass the skin's outer barrier, the stratum corneum, without penetrating deeply enough to cause discomfort or reach blood vessels. This design supports efficient and painless delivery of bioactive nutrients, with sterol esters presented here as model compounds. Microneedle arrays typically consist of hundreds of projections, ranging from approximately 100 to 900 micrometers, and are fabricated from biocompatible, biodegradable polymers. When applied, the microneedles create temporary microchannels that allow nutrient formulations to disperse into the viable epidermis and dermis, where gradual uptake occurs. By avoiding digestive breakdown, this approach provides more consistent delivery compared to conventional oral or topical supplements.

Formulation Strategies

For lipophilic nutrient forms such as sterol esters, several microneedle designs can be used. Coated microneedles deliver a surface-applied layer of the nutrient that dissolves rapidly upon insertion. Dissolving microneedles are composed of biodegradable polymers such as hyaluronic acid or polyvinylpyrrolidone, encapsulating the nutrient within the microneedle structure for direct release as the matrix dissolves. Hydrogel-forming microneedles, by contrast, swell upon contact with interstitial fluid to form a depot that gradually releases the encapsulated nutrient. Through careful design of microneedle geometry, polymer composition, and carrier integration, these systems can be tuned to achieve immediate, sustained, or extended nutrient release profiles, supporting steady delivery without the variability often seen with conventional oral or topical formats.

Supporting Evidence

Research on microneedle-mediated systems demonstrates improved delivery efficiency for both lipophilic and hydrophilic compounds compared to standard topical creams or gels. For nutrient esters, microneedle delivery has been associated with greater formulation stability and reduced variability compared to conventional transdermal approaches. Reviews of polymeric microneedle technologies emphasize their versatility, safety, and potential to improve consumer adherence by offering painless, user-friendly application methods suitable for long-term supplement use.

Application in the Present Invention

In this continuation-in-part application, dissolving and hydrogel-forming microneedle formats are applied to deliver sterol esters in nutraceutical applications. These designs are paired with polarity-matched lipidic carriers such as nanostructured lipid carriers (NLCs) and self-emulsifying delivery systems (SEDS) to maintain compounds in a solubilized and protected state, while also supporting controlled nutrient release. This integrated approach addresses challenges of poor solubility and oxidative instability and ensures delivery in a consistent and predictable manner. The painless, self-administered patch format improves consumer compliance, reduces the frequency of intake compared to conventional oral capsules or topical creams, and provides a stable, consumer-friendly platform for dietary supplement delivery.

Novelty of the Hybrid Microdermal Delivery System

The Hybrid Microdermal Delivery System disclosed in the present invention constitutes a novel advancement in microneedle-mediated nutrient delivery. Unlike prior art devices that deliver only hydrophilic or lipophilic compounds from a single-phase matrix, the present system integrates two physically and chemically distinct compartments within each microneedle of the array. This polarity-specific design enables the co-delivery of both hydrophilic and lipophilic nutritional actives from a single patch, while preserving their stability, potency, and independently tunable release profiles.

Structural Configuration

As illustrated in FIG. 51, each microneedle within the array comprises a dual-compartment structure, consisting of a hydrophilic polymeric phase and a lipophilic lipid- or nanoparticle-based phase. The hydrophilic compartment is optimized for encapsulation and controlled release of water-soluble nutrients such as amino acids, water-soluble vitamins, or botanical extracts. The lipophilic compartment is engineered for encapsulation and sustained delivery of fat-soluble actives, including sterol derivatives (used here as model compounds), fat-soluble vitamins, or other lipophilic bioactive ingredients.

Figure 52:
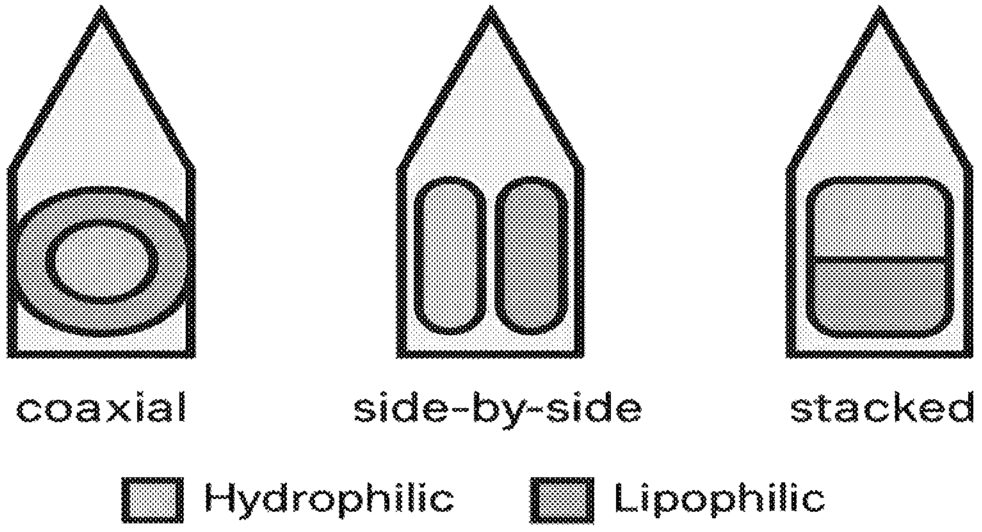
FIG. 52 compares prior microneedle designs with the present invention.

The compartments are physically separated to prevent premature mixing or chemical interaction before administration. Several possible structural configurations are represented in FIG. 52, including coaxial microneedles with a lipophilic core surrounded by a hydrophilic shell, side-by-side dual-channel microneedles, and vertically stacked layers separated by a thin polymeric barrier. Each configuration achieves the principle of polarity-specific separation, while allowing flexibility to tailor the microneedle structure to the requirements of the selected nutrients.

Independent Engineering and Release Control

The dual-compartment configuration, as further depicted in FIGS. 51 and 52, permits independent control of release kinetics for each polarity class of nutrients. The hydrophilic compartment can be engineered to release rapidly by adjusting polymer crosslink density, degree of hydrophilicity, molecular weight, or inclusion of swelling agents. In contrast, the lipophilic compartment achieves sustained or delayed release through control of lipid composition, chain saturation, crystalline versus amorphous state, nanoparticle size, and emulsifier selection.

These design variables enable either sequential release-such as rapid release of a hydrophilic payload within one to four hours, followed by delayed release of lipophilic compounds over twelve to seventy-two hours- or synchronized release of both compartments within a defined window. The spatial separation of compartments, clearly demonstrated in FIG. 3, ensures that otherwise incompatible compounds remain isolated during storage, maintaining stability until use.

Manufacturing and Integrity Advantages

The system may be manufactured using multi-phase micro-molding, sequential casting, or layered deposition techniques, ensuring precise localization of hydrophilic and lipophilic phases within each microneedle, as structurally represented in FIGS. 51 and 52. This architecture preserves stability by preventing cross-reactivity, reduces degradation under accelerated storage conditions, and allows for controlled-environment processing of each phase prior to integration.

Differentiation from Prior Art

Conventional microneedle systems are limited. Existing devices either deliver a single polarity of active per patch or attempt to co-formulate both polarities within one homogeneous phase, leading to instability and uncontrolled release. The dual-compartment architecture of the present invention, as embodied in FIGS. 51 and 52, provides a novel demonstration of a microneedle platform with polarity-specific separation, independent release modulation, and enhanced stability, representing a significant advancement beyond existing technologies.

Functional and Consumer Benefits

Figure 53:
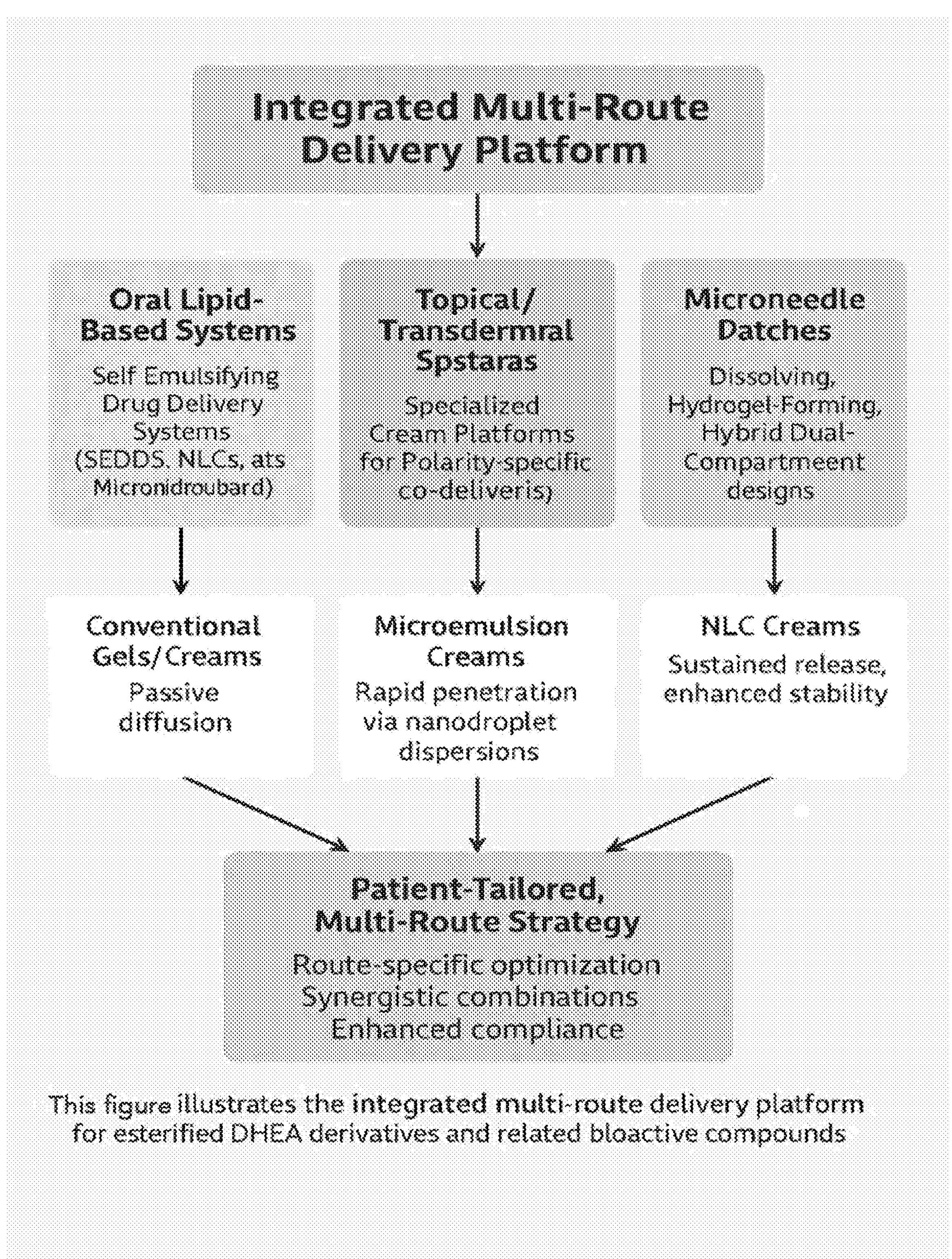
FIG. 53 illustrates the integrated multi-route delivery platform for esterified DHEA derivatives and related compounds.

The hybrid system, supported by the configurations illustrated in FIGS. 51 and 52, enables advanced nutrient delivery strategies. These include sequential release, where a hydrophilic nutrient is released before a lipophilic companion nutrient; combination delivery through stable co-administration of otherwise incompatible compounds; reduction of consumer burden by consolidating multiple nutrients into one convenient patch; and extension of applicability to unstable hydrophilic molecules and fat-soluble bioactives within the same format. FIG. 53 illustrates an advanced delivery configuration designed for esterified derivatives of dehydroepiandrosterone (as one of the model compounds) and structurally related lipophilic compounds. The platform integrates three distinct administration pathways: (A) transdermal microneedle delivery utilizing polarity-specific encapsulation; (B) buccal absorption via mucoadhesive film with sustained-release lipid microdomains; and (C) gastrointestinal absorption through enteric-coated oral formulations. This multi-route architecture enables tailored pharmacokinetic profiles, improved bioavailability, and flexibility in matching compound properties with the optimal absorption route. The system exemplifies how the hybrid microdermal framework can be expanded beyond microneedles to support broader nutraceutical delivery applications.

SUMMARY

In summary, the Hybrid Microdermal Delivery System achieves polarity-specific co-delivery by incorporating physically separated hydrophilic and lipophilic compartments within each microneedle. These compartments are independently engineered for tunable release kinetics, improved stability, and compatibility with diverse classes of dietary supplement ingredients. Together, these features establish a level of precision, stability, and novelty not achievable with prior single-phase or multi-patch microneedle systems.

FIG. 51: General Hybrid Microdermal Architecture

FIG. 51 illustrates an exemplary Hybrid Microdermal Delivery System in which each microneedle comprises two polarity-specific compartments. The hydrophilic compartment is formed of a polymeric matrix configured to encapsulate and release water-soluble compounds such as amino acids, water-soluble vitamins, or botanical extracts. The lipophilic compartment consists of a lipid- or nanoparticle-based phase optimized for encapsulation and delivery of lipophilic actives, including esterified sterol derivatives, fat-soluble vitamins, or lipid-soluble botanicals. The two compartments remain physically separated within each microneedle to preserve stability and prevent premature interaction before administration. Upon application, the microneedles penetrate the stratum corneum to create microchannels, enabling polarity-specific release of the encapsulated nutrients FIG. 52: Structural Embodiments of Hybrid Microneedles FIG. 52 provides representative structural configurations of dual-compartment microneedles suitable for implementing the Hybrid Microdermal Delivery System. Examples include: (A) coaxial microneedles wherein the lipophilic phase forms a central core encapsulated by a hydrophilic shell; (B) side-by-side dual-channel microneedles housing discrete compartments in parallel; and (C) vertically stacked microneedles in which hydrophilic and lipophilic layers are separated by a thin polymeric barrier. These configurations permit independent control of release kinetics for each polarity class of active, enabling sequential or synchronized delivery, improved stability, and enhanced compatibility within a single microneedle array.

Comparative Features of Hybrid Microdermal Delivery Vs. Prior Microneedle Systems Table 43 highlights the dual-compartment, polarity-matched architecture of the present invention, demonstrating its independent release control, enhanced stability, and improved nutrient delivery consistency relative to prior single-phase hydrophilic, lipophilic, or mixed microneedle systems.

TABLE 43

Comparative Features of Hybrid Microdermal Delivery System vs. Prior Art

| Feature | Hybrid Microdermal Delivery System (Present Invention) | Typical Prior Microneedle Art (Hydrophilic Only) | Typical Prior Microneedle Art (Lipophilic Only) | Prior Microneedle Art (Mixed Payload in Single Phase) |
|---|---|---|---|---|
| Payload Compartment Structure | Two physically distinct compartments within each microneedle: hydrophilic polymeric matrix & lipophilic lipid/nanoparticle phase | Single hydrophilic polymer matrix | Lipid or wax-based matrix | Single homogeneous phase containing both hydrophilic and lipophilic compounds |
| Polarity Matching | Each compartment polarity-matched to its respective payload for stability & consistent nutrient delivery | Optimized only for hydrophilic actives | Optimized only for lipophilic actives | No polarity-specific optimization; compromises for both |

TABLE 43-continued

Comparative Features of Hybrid Microdermal Delivery System vs. Prior Art

| Feature | Hybrid Microdermal Delivery System (Present Invention) | Typical Prior Microneedle Art (Hydrophilic Only) | Typical Prior Microneedle Art (Lipophilic Only) | Prior Microneedle Art (Mixed Payload in Single Phase) |
|---|---|---|---|---|
| Independent Release Control | Separate kinetic tuning for each compartment (e.g., rapid hydrophilic release, sustained lipophilic release) | Single release profile only | Single release profile only | Shared release profile affects both compounds equally |
| Release Options | Sequential or simultaneous release possible by design | Single release event | Single release event | Single release event |
| Payload Stability | Separation prevents cross-reactive degradation between hydrophilic & lipophilic actives | Stable for hydrophilic only | Stable for lipophilic only | Reduced stability due to intermolecular interactions |
| Nutrient Delivery Flexibility | Capable of delivering synergistic nutrient pairs requiring different release timing and environments | Limited to hydrophilic payloads | Limited to lipophilic payloads | Possible but often unstable and poorly controlled |
| Manufacturing Method | Multi-phase micro-molding/ co-casting with spatial isolation | Single-phase casting | Single-phase casting | Single-phase casting |
| Delivery Consistency | Single device delivers multiple nutrient classes with precise control | Multiple devices or servings needed | Multiple devices or servings needed | Single device but poor stability & control |
| Prior Art Examples | Present invention | Hydrophilic peptide microneedles (polymer-based) | Lipid-based microneedles using ester models | Hydrophilic + lipophilic blend in single polymer phase |

Integration of FIGS. 51 and 52

As illustrated in FIG. 51, the Hybrid Microdermal Delivery System is built upon a dual-compartment microneedle architecture in which each microneedle contains a hydrophilic polymeric phase and a lipophilic lipid- or nanoparticle-based phase. This polarity-specific separation preserves the stability of both nutrient classes, prevents premature interaction, and enables polarity-matched delivery. The hydrophilic compartment is designed for water-soluble compounds such as amino acids, B-complex vitamins, or botanical extracts, while the lipophilic compartment encapsulates fat-soluble compounds such as sterol derivatives, fat-soluble vitamins, and polyphenolic bioactives. Together, the two compartments allow for polarity-specific stabilization and polarity-specific release of actives within a single device.

FIG. 52 expands upon this concept by presenting representative structural embodiments of the hybrid system. In the coaxial configuration, the lipophilic compartment forms a central core surrounded by a hydrophilic shell, enabling sequential release. In the side-by-side configuration, parallel channels carry discrete hydrophilic and lipophilic phases, preserving their independence while supporting simultaneous or staggered delivery. In the stacked configuration, vertically layered hydrophilic and lipophilic compartments are separated by a thin polymeric barrier, allowing both payloads to remain isolated during storage while enabling synchronized or delayed release upon administration. Across these embodiments, the structural separation of compartments ensures that hydrophilic and lipophilic actives remain stable prior to use, while providing flexibility in release control and compatibility with diverse classes of dietary supplement ingredients.

The comparative features summarized in Table 43 reinforce the inventive step of the present hybrid microdermal system as structurally depicted in FIGS. 51 and 52. Whereas prior microneedle art typically restricts delivery to a single polarity class or forces mixed compounds into unstable single-phase matrices, the dual-compartment configuration of this invention introduces true polarity-specific separation within each microneedle. This architectural advancement not only resolves the long-standing incompatibility between hydrophilic and lipophilic actives but also enables tailored release profiles, extended stability during storage, and greater flexibility in consumer-facing product formats. Accordingly, the present invention distinguishes itself from existing microneedle approaches by providing a harmonized, modular platform that integrates structural precision with functional adaptability across diverse classes of nutraceutical and dietary supplement ingredients.

Novelty and Non-Obviousness of Hybrid Microdermal Delivery System

The comparative analysis clearly demonstrates that the Hybrid Microdermal Delivery System disclosed in the present invention introduces a structural and functional advance not found in prior microneedle technologies. Traditional microneedles, whether hydrophilic- or lipophilic-based, are limited to carrying compounds compatible with a single-phase matrix. As a result, they cannot reliably co-deliver nutrients with opposing solubility profiles, nor can they maintain stability when hydrophilic and lipophilic compounds are combined within the same compartment.

By contrast, the inventive system employs two physically distinct compartments within each microneedle, one optimized for hydrophilic payloads and the other optimized for lipophilic payloads. This dual-compartment architecture allows polarity matching between nutrients and their carrier environments, preserving chemical stability and consistent nutrient utilization throughout storage and use. The physical separation also prevents cross-reactive degradation, a limitation that significantly compromises stability in prior single-phase microneedle systems.

Equally important, the inventive system allows independent release control. The hydrophilic compartment may be engineered for rapid release to provide an immediate primer effect (e.g., water-soluble vitamins, adaptogens, or amino acids), while the lipophilic compartment may be tuned for slower, sustained release of sterol derivatives or fat-soluble nutrients. This polarity-specific sequential release enables coordinated nutrient delivery profiles that cannot be achieved using prior art microneedles.

From a functional standpoint, the Hybrid Microdermal Delivery System represents a major advancement in dietary supplement technology. It enables a single, non-invasive device to deliver multiple nutrient classes with controlled timing and optimized stability, reducing the need for multiple formulations or repeated intake. This level of integration and precision delivery establishes clear novelty and non-obviousness over prior single-phase microneedle art, while also improving consumer convenience, safety, and overall supplement performance.

As illustrated in FIGS. 51 and 52, the present invention physically separates hydrophilic and lipophilic payloads into distinct compartments within each microneedle, rather than dispersing them together in a single continuous phase as in the prior art. This compartmentalization is not a trivial rearrangement—it fundamentally changes how the device functions. By providing discrete physical domains for each polarity, the system prevents premature chemical interaction between incompatible nutrients, thereby improving stability over storage and during application. It also enables true independent release control for each payload type, allowing sequential delivery (e.g., hydrophilic primer first, lipophilic nutrient later) or synchronized delivery, depending on formulation design. While mixed-payload, single-phase microneedles are known, they lack the ability to tailor release kinetics separately for different polarities and cannot address degradation risks inherent in co-formulation. This dual-compartment design therefore delivers a level of precision, stability, and formulation flexibility not achievable with prior homogeneous microneedle systems.

Accordingly, the Hybrid Microdermal Delivery System distinguishes itself from the prior art not merely by incremental design modifications but by introducing a dual-compartment architecture that achieves polarity-specific separation, independent release control, and long-term stability within a single microneedle device. These structural and functional advantages resolve long-recognized limitations of single-phase microneedles, provide demonstrably superior nutrient delivery outcomes, and establish a substantial non-obvious advance over conventional technologies. The inventive features are not suggested or anticipated by existing references and therefore support both the novelty and non-obviousness of the present invention. The inventive features, when considered in combination, provide synergistic advantages (polarity-specific stability+independent release+consumer-friendly consolidation) that are neither disclosed nor suggested in the prior art.

Microemulsion Creams

Definition and Core Characteristics

Microemulsion creams are thermodynamically stable colloidal dispersions composed of oil, water, surfactants, and co-surfactants, producing submicron droplets typically in the 10-100 nanometer range. These systems are particularly well suited for the topical and transdermal delivery of lipophilic compounds, including sterol derivatives such as esterified DHEA, which otherwise exhibit poor aqueous solubility and limited permeability in conventional creams.

Functional Mechanism

The nanoscale droplet size of microemulsions markedly increases surface contact area between the encapsulated compound and the skin. This enhances solubilization of the active within the oil phase and promotes interaction with intercellular lipids in the stratum corneum, supporting deeper transport into the epidermal and dermal layers. Balanced surfactant-co-surfactant systems can further modulate skin lipid fluidity, facilitating nutrient diffusion and maintaining the active compound in a permeable state.

Supporting Evidence

Published research on structurally related lipophilic compounds demonstrates that microemulsion-based formulations provide higher dermal absorption, improved retention in skin layers, and reduced variability compared to non-emulsified topicals. These findings serve as model data for applying microemulsion technology to sterol ester delivery within supplement formulations, showing advantages in stability and consistency of uptake.

Microemulsion systems may be enhanced with agents such as ethanol, isopropyl myristate, oleic acid, or Transcutol® to fine-tune absorption kinetics. For consumer usability, microemulsions are often combined with gelling agents (e.g., carbomers, natural polysaccharides) to improve viscosity, yielding cosmetically elegant, fast-absorbing, and non-irritating products.

Application in the Present Invention

Within the present continuation-in-part application, microemulsion creams provide a non-invasive, consumer-friendly delivery option for esterified sterol derivatives and complementary fat-soluble nutrients. By combining solubilization efficiency, enhanced penetration, and dermal retention, microemulsion creams represent a polarity-matched strategy for consistent nutrient support in dietary supplement applications, reducing reliance on oral or injectable formats.

Comparative Analysis of Topical and Transdermal Cream Technologies for Sterol Esters The invention discloses multiple topical and transdermal systems tailored to sterol ester delivery, each optimized for distinct absorption profiles, stability requirements, and consumer needs. While all such systems share the advantage of bypassing gastrointestinal degradation and hepatic first-pass metabolism, their formulation strategies and release dynamics vary, providing flexibility in selecting the most suitable platform for a given nutraceutical composition.

Table 44 compares the present invention's microemulsion cream platform with other topical and transdermal carrier conventional creams, nanoemulgels, and ethosomes. As shown, microemulsion creams provide distinct advantages in particle size, polarity handling, stability, and consumer usability. Unlike conventional gels and creams, which rely primarily on passive diffusion and show limited solubility for lipophilic actives, microemulsions deliver sterol esters and fat-soluble nutrients in a stable nanoscale form with superior dermal penetration. Compared to nanoemulgels and ethosomes, microemulsion creams maintain formulation simplicity while still offering polarity-specific compatibility, tunable release control, and cosmetic acceptability, making them particularly well-suited for nutraceutical and dietary supplement applications.

TABLE 44

Comparative Analysis of Topical and Transdermal Cream Technologies for Sterol Esters

| Feature/ Attribute | Microemulsion Creams (Present Invention) | Conventional Gels & Creams | Nanoemulgels | Ethosomes |
|---|---|---|---|---|
| Primary Carrier | Oil-water microemulsion stabilized with surfactants/co-surfactants | Standard hydroalcoholic or lipid base | Nanoemulsion dispersed in gel matrix | Phospholipid vesicles with high ethanol content |
| Droplet/ Particle Size | 10-100 nm droplets (thermodynamically stable) | Micron to macro-scale droplets | <200 nm droplets dispersed in viscous gel | 100-400 nm flexible vesicles |
| Polarity Handling | Optimized for lipophilic sterol esters and fat-soluble nutrients | Limited solubilization of lipophilic actives | Dual compatibility (lipophilic in oil phase, hydrophilic in gel phase) | High encapsulation of lipophilic and amphiphilic actives |
| Skin Penetration Mechanism | Surfactant/co-surfactant system disrupts stratum corneum lipids | Passive diffusion only, low penetration efficiency | Nanoemulsion droplets + gel hydration enhance diffusion | Ethanol fluidizes skin lipids + vesicle fusion enables deep penetration |
| Release Control | Rapid to sustained release depending on surfactant blend | Rapid release only | Modulated release via gel viscosity & droplet size | Controlled dermal release via vesicle fusion |
| Stability Advantages | Prevents coalescence; maintains droplet integrity over shelf life | High risk of separation or precipitation | Improved stability from gel matrix and nanoscale droplets | Ethanol + phospholipids stabilize lipophilic compounds |
| Consumer Usability | Smooth, elegant cream; fast absorption; non-irritating | Heavier feel; may cause residue or tackiness | Gel form enhances spreadability and cosmetic appeal | Gel/cream base, sometimes tacky due to ethanol content |
| Representative Application | Sterol esters, fat-soluble vitamins, polyphenols (nutraceutical focus) | Generic topical actives | Nutrient combinations requiring dual compatibility | Lipophilic sterol esters and amphiphilic antioxidants |

Integration of Microemulsion Creams with Broader Platform

The comparative framework of Table 43 and Table 44 demonstrates that the present invention extends polarity-specific design principles across both microdermal and topical delivery technologies. Whereas Table 4 highlights the advantages of dual-compartment microneedles for polarity-separated actives, Table 44 establishes that similar stability and release-control advantages are achieved when microemulsion creams are incorporated as the topical arm of the platform. Together, these embodiments reinforce the modular nature of the invention, where each delivery system is engineered according to polarity-matching rules yet integrated into a unified, multi-route nutraceutical delivery platform.

Novelty and Inventive Step of Microemulsion Creams within the Platform

As summarized in Table 44, the microemulsion cream format disclosed in the present invention distinguishes itself from conventional topical and transdermal systems by integrating polarity-specific design principles into a nutraceutical delivery platform. Unlike conventional gels and creams, which rely solely on passive diffusion and provide limited compatibility for lipophilic sterol esters, the inventive system applies nanoscale microemulsion technology to ensure stable solubilization, controlled dermal penetration, and improved consumer usability. Compared to nanoemulgels and ethosomes, which either require complex multi-phase structures or high ethanol levels, the disclosed microemulsion creams offer a streamlined yet polarity-matched approach that supports consistent nutrient availability without compromising stability or cosmetic acceptability. This integration into a multi-route, polarity-specific platform represents a structural and functional advance over prior art formulations, reinforcing the novelty and non-obviousness of the invention.

Conventional Transdermal Creams and Gels

Conventional creams and gels utilize semi-solid bases-such as carbomer gels, hydroalcoholic formulations, or pluronic lecithin organogels (PLO)—to solubilize sterol derivatives, with DHEA esters used here as representative model compounds. Penetration enhancers including ethanol, propylene glycol, and oleic acid support stratum corneum lipid fluidization, enabling passive diffusion into deeper skin layers.

Advantages: Established usage history, predictable performance, and ease of manufacturing.

Limitations: Lower penetration efficiency compared to nanocarriers; may require multiple daily applications for consistent uptake.

Microemulsion Creams

Microemulsion creams are thermodynamically stable colloidal systems containing oil, water, surfactant, and co-surfactant, producing nanodroplets (10-100 nm) that maximize skin contact and temporarily increase lipid permeability. The oil phase solubilizes sterol derivatives, while the nanoscale dispersion enhances distribution. Published research on structurally related compounds has shown significantly improved skin absorption with microemulsion formats.

Advantages: High penetration efficiency, faster onset of nutrient availability, cosmetically elegant and non-greasy.

Limitations: Surfactant levels may cause mild irritation in sensitive skin; requires precise formulation balancing for stability.

Nanostructured Lipid Carrier (NLC) Creams

NLC creams employ hybrid lipid nanoparticles (50-500 nm) composed of a solid lipid matrix blended with a liquid lipid, providing both high payload capacity and sustained release. This lipid-based occlusive layer enhances hydration, facilitates lipid exchange with the skin barrier, and protects sterol derivatives from oxidative degradation. Advantages: Excellent oxidative stability, gradual release, high payload capacity. Limitations: Slightly occlusive skin feels; requires specialized lipid processing.

Strategic Application in the Invention

By incorporating three distinct topical and transdermal delivery platforms within a single unified framework, the invention enables precise optimization of sterol derivative delivery according to consumer-specific requirements. This modular strategy allows the most appropriate formulation to be selected based on desired absorption profile, stability, convenience, and consumer preference.

Microemulsion-based creams provide rapid uptake and consistent nutrient utilization, making them suitable for consumers seeking fast support and cosmetically elegant formulations.

Nanostructured lipid carrier (NLC) creams are engineered for sustained nutrient availability with fewer applications, supporting long-term wellness programs where consistency and convenience are priorities.

Conventional creams and gels offer a cost-effective and widely accessible option, suitable for consumers or markets prioritizing affordability and simplicity.

Taken together, this modular integration of microemulsion creams, NLC creams, and conventional formulations represents a comprehensive approach that maximizes stability, absorption efficiency, and consumer adaptability, while maintaining the integrity of sterol derivatives across diverse supplement delivery contexts.

Integrated Multi-Route Administration Strategy for Sterol Derivative Delivery

The present continuation-in-part application discloses a comprehensive, multi-route, polarity-specific delivery architecture designed for sterol derivatives (using DHEA esters as model compounds), fat-soluble vitamins, and lipophilic polyphenolic compounds such as trans-resveratrol. This inventive architecture integrates oral, topical, and transdermal platforms, each of which is engineered to align with the physicochemical properties of the active compound, the intended nutritional profile, and the compliance requirements of the consumer.

Table 45 compares three topical/transdermal platforms disclosed in the present invention conventional creams/gels, microemulsion creams, and nanostructured lipid carrier (NLC) creams. The table highlights differences in formulation base, polarity compatibility, delivery mechanism, release profile, advantages, limitations, stability, consumer application, and role within the invention. Together, these three systems provide a modular toolkit for tailoring sterol derivative delivery (using DHEA esters as model compounds) according to stability, absorption efficiency, and consumer preference, reinforcing the inventive platform's adaptability and novelty.

TABLE 45

Comparative Analysis of Cream and Gel Delivery Platforms for Sterol Derivatives (Using DHEA Esters as Model Compounds)

| Feature | Conventional Creams/Gels | Microemulsion Creams | Nanostructured Lipid Carrier (NLC) Creams |
|---|---|---|---|
| Formulation Base | Semi-solid carbomer, hydroalcoholic, or PLO gels | Thermodynamically stable oil-water-surfactant nanodroplet system (10-100 nm) | Hybrid solid + liquid lipid nanoparticles dispersed in gel matrix (50-500 nm) |
| Polarity Compatibility | Limited; primarily suited for lipophilic esters with enhancers | High; nanoscale dispersion improves solubilization of lipophilic actives | Excellent; lipid-lipid compatibility stabilizes lipophilic actives |

TABLE 45-continued

Comparative Analysis of Cream and Gel Delivery Platforms for Sterol Derivatives (Using DHEA Esters as Model Compounds)

| Feature | Conventional Creams/Gels | Microemulsion Creams | Nanostructured Lipid Carrier (NLC) Creams |
|---|---|---|---|
| Mechanism of Delivery | Passive diffusion with penetration enhancers (ethanol, PG, oleic acid) | Nanodroplets increase skin contact area and permeability | Lipid matrix enhances hydration, supports barrier penetration, and protects against oxidation |
| Release Profile | Rapid, diffusion-driven | Rapid dermal penetration with moderate retention | Sustained release from lipid matrix |
| Advantages | Established use, low cost, predictable manufacturing | High penetration efficiency, elegant cosmetic profile, rapid nutrient support | Excellent stability, gradual release, high payload, reduced oxidative degradation |
| Limitations | Lower penetration efficiency, multiple daily applications may be needed | Surfactant levels may irritate sensitive skin, requires precise balance | Slightly occlusive skin feel, requires specialized lipid processing |
| Stability | Moderate; prone to oxidation and phase separation | Improved stability through nanodroplet dispersion | High oxidative and physical stability due to lipid entrapment |
| Consumer Application | Accessible and low-cost option | Suitable for rapid uptake and consumer-friendly cosmetic feel | Designed for long-term programs prioritizing consistency and reduced dosing frequency |
| Role in Present Invention | Baseline formulation option for affordability and accessibility | Advanced option for polarity-matched rapid nutrient utilization | Premium option for sustained delivery, stability, and convenience |

Integration of Comparative Frameworks

The comparative analyses provided in Table 44 and Table 45 collectively demonstrate how the present invention extends polarity-specific design principles across both advanced and conventional topical and transdermal systems. Table 44 establishes the inventive step of microemulsion creams relative to conventional gels, nanoemulgels, and ethosomes, while Table 45 situates microemulsions within a tiered framework alongside conventional and nanostructured lipid carrier (NLC) creams. Taken together, these analyses support the inventive concept that polarity-matched carriers and structural separation strategies can be applied across multiple delivery formats including single-route topical/transdermal embodiments (e.g., microemulsion creams, NLC creams, hydrogel microneedles) and dual-route hybrid systems (e.g., oral+microdermal, oral+transdermal). This modular platform introduces a polarity-specific framework that is adaptable to both standalone single-route applications and coordinated dual-route delivery regimens, thereby broadening the scope of inventive contribution beyond prior art confined to single-phase or single-route formulations.

Nanostructured Lipid Carrier (NLC) Creams

NLC creams employ hybrid lipid nanoparticles (50-500 nm) composed of a solid lipid matrix blended with a liquid lipid, providing both high payload capacity and sustained release. This lipid-based occlusive layer enhances hydration, facilitates lipid exchange with the skin barrier, and protects lipophilic esters from oxidative degradation. Advantages: Excellent oxidative stability, gradual release, high payload capacity. Limitations: Slightly occlusive skin feel; requires specialized lipid processing.

Strategic Application in the Invention

The invention incorporates three topical and transdermal platforms within its polarity-specific framework (1) microemulsion creams, (2) nanostructured lipid carrier (NLC) creams, and (3) conventional gels/creams (comparative only). This modular approach allows optimization of nutrient delivery according to stability requirements, release kinetics, and consumer preference. Microemulsion-based creams provide rapid uptake and elegant cosmetic properties, making them suitable for fast nutrient support. NLC creams are engineered for sustained availability with fewer applications, supporting programs where long-term stability and convenience are priorities. Conventional gels and creams are included for comparative purposes only; while cost-effective and widely used, they lack polarity-specific stabilization and exhibit lower penetration efficiency.

Integrated Administration Strategy

As disclosed, the inventive platform validates both single-route and dual-route administration formats. In single-route applications, polarity-matched carriers such as microemulsions or NLC creams provide optimized dermal or transdermal delivery. In dual-route applications, oral capsules are paired with one polarity-matched topical or transdermal system (e.g., oral+microemulsion cream, oral+NLC cream, or oral+hybrid microneedle array). This integrated design ensures that hydrophilic and lipophilic compounds are delivered through polarity-appropriate carriers, whether as standalone or combined regimens.

Taken together, the integration of microemulsion creams, NLC creams, and comparative conventional systems demonstrates the inventive flexibility of the platform. By extending polarity-specific carrier assignment to both single-route and dual-route delivery formats, the invention achieves greater stability, adaptability, and consumer usability across diverse supplement contexts, while maintaining clear differentiation from conventional non-polarity-matched approaches.

Topical and Transdermal Cream Platforms

Within the topical and transdermal category, the invention discloses polarity-specific carrier systems while also referencing conventional formats for comparative context. Three representative platforms are described below to situate the inventive advances within the broader field.

Conventional Creams and Gels (Comparative Only). These established semi-solid carriers (e.g., carbomer gels, hydroalcoholic bases, pluronic lecithin organogels) rely on penetration enhancers such as ethanol, propylene glycol, or oleic acid to support passive diffusion across the skin barrier. Their strengths include reliability, ease of manufacture, and consumer familiarity, but they lack polarity-specific optimization and generally require repeated application. These are disclosed here solely for comparative purposes and do not represent inventive embodiments.

Microemulsion Creams (Inventive Embodiment). Microemulsion systems are thermodynamically stable nanodispersions (10-100 nm) that markedly increase surface area, supporting solubilization of lipophilic nutrient esters and enhancing their distribution across the skin barrier. Compared to conventional gels, microemulsions achieve faster uptake, improved dermal retention, and superior cosmetic properties. Within the present invention, they serve as polarity-matched topical systems for lipophilic actives.

Nanostructured Lipid Carrier (NLC) Creams (Inventive Embodiment). NLC systems combine solid and liquid lipid phases (50-500 nm) to provide high payload capacity, oxidative stability, and sustained release. Their occlusive lipid layer enhances hydration and promotes gradual release, improving adherence for long-term wellness programs. Within this platform, NLC creams represent a polarity-specific route for lipophilic nutrient classes requiring stability and extended delivery.

Modular Integration and Strategy

By integrating polarity-matched microemulsions and NLC creams into a unified inventive framework, the platform allows tailored nutrient delivery based on stability and timing requirements. Conventional gels remain useful as comparative baselines, while the inventive systems demonstrate improved stability, penetration, and consumer usability.

Systemic Integration Across Routes

Consistent with the invention's validated scope, these topical/transdermal systems may operate as stand-alone single-route embodiments or as part of dual-route combinations where oral capsules are paired with one additional polarity-matched route (oral+microemulsion cream, oral+NLC cream, or oral+microneedle patch). This integration ensures polarity-specific carrier alignment across routes.

Consumer and Functional Impact

The inventive polarity-specific cream formats, when used alone or in dual-route combinations, improve compliance and usability by offering painless, cosmetically elegant, and reliable delivery of both hydrophilic and lipophilic actives. This addresses long-standing challenges of poor solubility, instability, and inconsistent uptake in conventional supplement formats, while clearly distinguishing the inventive step over prior art gels and creams.

Figure 54:
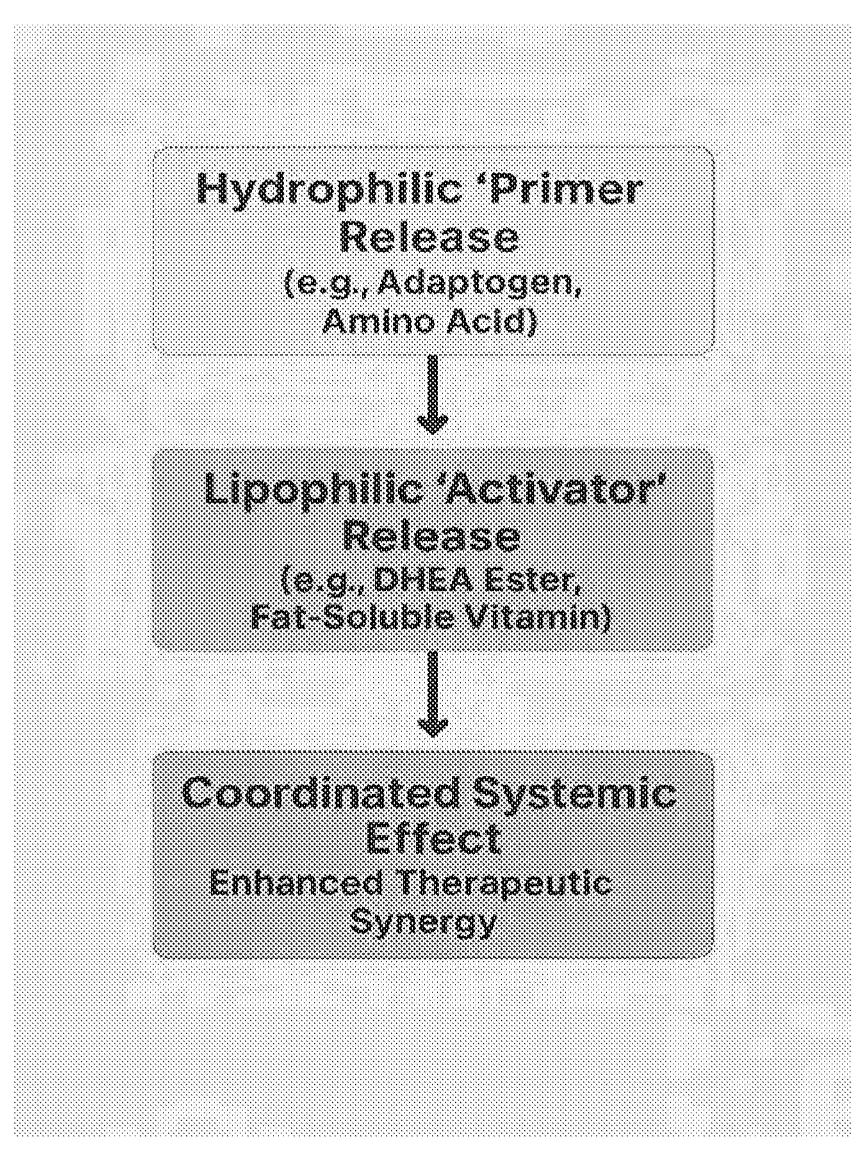
FIG. 54 illustrates the polarity-specific sequential release flow.

FIG. 54 illustrates the polarity-specific sequential release principle enabled by the hybrid delivery system. The diagram highlights a stepwise release cascade beginning with a hydrophilic "primer" payload, such as amino acids, adaptogens, or water-soluble vitamins, delivered rapidly through the polymeric phase of the microneedle or topical formulation. This primer helps establish favorable physiological conditions for subsequent uptake of the lipophilic "activator" payload. The second stage then delivers the lipophilic activator such as esterified sterol derivatives or fat-soluble vitamins from the lipid-based or nanoparticle phase in a controlled and sustained manner. This dual-stage process culminates in a coordinated nutrient delivery effect, where the hydrophilic primer complements or amplifies the activity of the lipophilic activator. The figure visually demonstrates the principle of polarity-specific sequential release as a defining advantage of the invention, enabling timing control and enhanced stability not achievable with single-phase formulations.

FIG. 55 depicts the sequencing flow across three structured phases, demonstrating how different cream formulations can be integrated into a progressive nutrient delivery strategy. The sequence begins with the Initiation Phase, where microemulsion creams provide rapid absorption and fast onset of nutrient availability. The next stage, the Transition Phase, employs conventional creams and gels, which offer stable absorption, moderate cost, and broad consumer familiarity, ensuring continuity of nutrient support. The process then advances to the Maintenance Phase, where nanostructured lipid carrier (NLC) creams deliver depot-like release, long-term stability, and reduced application frequency, supporting convenience and compliance. The final outcome is an optimized consumer-tailored program characterized by consistent nutrient availability, minimized variability, and enhanced usability. This figure visually communicates the modular, phased approach of the invention, showing how different platforms are not competing alternatives but strategically sequenced for complementary benefits.

Figure 56:
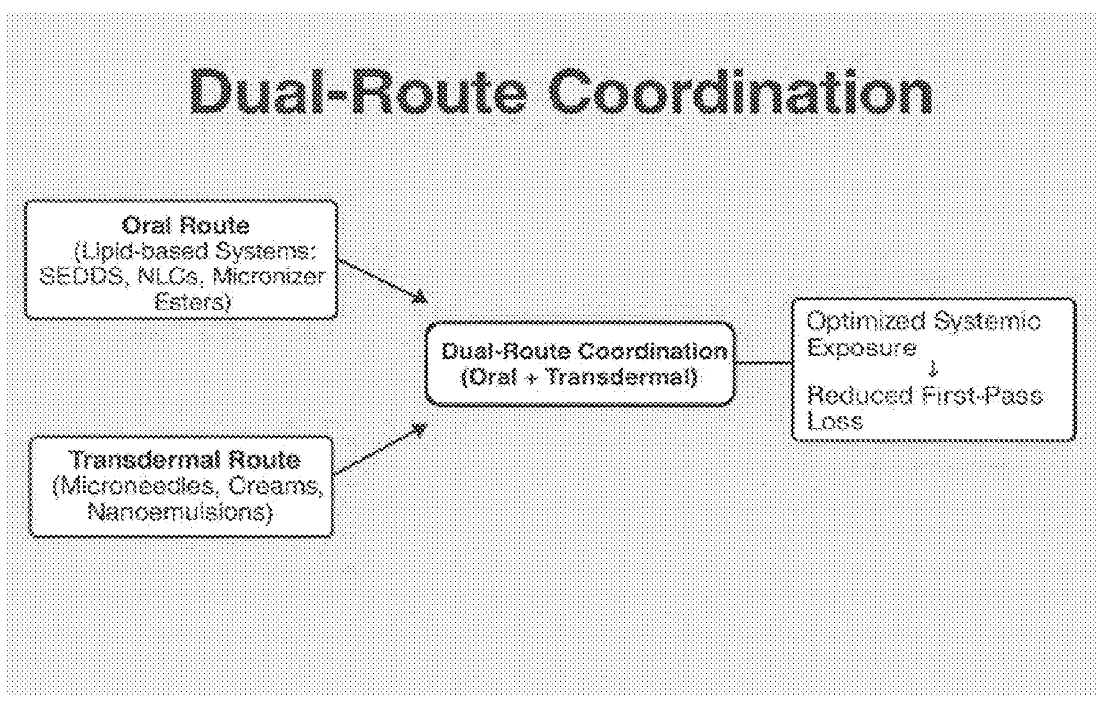
FIG. 56 illustrates the dual-route coordination strategy.

FIG. 56 illustrates the dual-route coordination strategy, where oral and transdermal delivery systems are combined to achieve optimized performance. On the left, the Oral Route is represented, utilizing lipid-based systems such as SEDS, NLCs, nanoemulsions, and micronized esters. These platforms enhance solubility, promote lymphatic uptake, and partially reduce reliance on hepatic metabolism. Below, the Transdermal Route is shown, incorporating microneedles, topical creams, and nanoemulsions, which directly bypass the gastrointestinal tract and provide sustained delivery. Both pathways converge into the central concept of Dual-Route Coordination (Oral+Transdermal), where the complementary use of two routes enhances systemic availability. On the right, the benefits of this coordination are depicted: optimized exposure, reduced variability, and controlled release profiles. Together, these outcomes enable flexible nutrient delivery, lower dependence on dosing frequency, and improved consumer usability, underscoring the novelty of combining polarity-specific oral and transdermal systems in a harmonized delivery framework.

Phytosome and Advanced Lipid Carrier Systems for DHEA Esters

Phytosome Technology-Over View and Mechanism

Phytosomes represent an advanced lipid-based delivery system specifically designed to improve the absorption, stability, and distribution of poorly soluble sterol derivatives. Unlike conventional emulsions or liposomes, phytosomes form a molecular complex between the active compound and phospholipids, most commonly phosphatidylcholine, through non-covalent interactions such as hydrogen bonding and hydrophobic association. This amphiphilic structure closely mimics natural biological membranes, enabling the complex to integrate efficiently into intestinal epithelial cells and circulation. For sterol derivatives, this mechanism enhances lymphatic transport, reduces reliance on hepatic metabolism, and increases systemic availability.

Supporting Evidence Base

The phytosome approach has consistently demonstrated four- to ten-fold improvements in oral bioavailability compared to conventional formulations. Initially validated for plant-derived actives such as silymarin, curcumin, and ginkgo flavonoids, the platform has been extended to steroidal molecules including testosterone and hydrocortisone, supporting its logical application to esterified sterol derivatives. Studies confirm superior intestinal transport, enhanced tissue penetration, and improved stability, establishing phytosomes as a validated carrier for lipophilic actives that otherwise suffer from poor solubility and erratic absorption.

Hydroxypropyl-β-Cyclodextrin (HBCD) Complexes—Overview and Mechanism

Hydroxypropyl-β-cyclodextrin (HBCD) offers a complementary approach to solubility and stability enhancement. Through non-covalent host-guest inclusion, HBCD encapsulates the hydrophobic portion of sterol derivatives within its inner cavity while presenting a hydrophilic exterior to aqueous environments. This improves dispersion in gastrointestinal fluids, prevents precipitation after dilution, and facilitates mucosal permeability. The platform has demonstrated success with structurally related hormones, providing strong precedent for use with sterol derivatives.

Applications and Extended Utility

Beyond oral powders, capsules, and chewables, HBCD inclusion complexes are also compatible with transdermal microneedle matrices, where they enhance solubility, loading uniformity, and stability during fabrication and storage. This adaptability allows both phytosome and cyclodextrin systems to be integrated into oral, topical, and transdermal delivery routes, supporting polarity-specific alignment and modular use within the broader delivery architecture of the present invention.

Non-Esterified Fatty Acid (NEFA) Carriers—Overview and Mechanism

Non-esterified fatty acid (NEFA) carriers, particularly omega-3 fatty acid-based systems, serve as physiologically compatible emulsifiers that improve membrane fluidity and permeability. By mimicking natural lipid transport pathways, NEFA carriers facilitate efficient lymphatic absorption of sterol derivatives (as esterified DHEA derivatives as one of the model compounds), thereby reducing first-pass hepatic metabolism. This biomimetic mechanism supports polarity-matched delivery while protecting the integrity and stability of the encapsulated compound.

Application in the Present Invention

The continuation-in-part invention strategically integrates phytosomes, HBCD inclusion complexes, and NEFA carriers into a polarity-specific oral, sublingual, and transdermal delivery architecture for sterol derivatives (as esterified DHEA derivatives as one of the model compounds). For oral and sublingual formats, phytosomes and HBCD complexes enhance solubility and protect against hydrolytic degradation, while NEFA carriers promote lymphatic uptake. For microneedle-based transdermal systems, HBCD complexes provide stability and solubility enhancement within hydrogel or dissolving matrices, ensuring reproducible compound loading and polarity-specific release. Packaging and stabilization measures antioxidant fortification, oxygen-barrier protection, pH optimization, and controlled manufacturing conditions are applied across all carriers to maintain chemical integrity and regulatory compliance in line with ICH Q1A (R2).

Platform Relevance

By combining phytosome complexes, HBCD inclusion systems, and NEFA carriers, the present invention provides a harmonized delivery platform that ensures extended stability, enhanced intestinal absorption, polarity-specific microneedle release, and physiologic compatibility across target tissues. These carrier systems are ideally suited for dietary supplement applications emphasizing nutritional support, wellness enhancement, improved bioavailability, and consumer usability. By improving stability, compliance, and delivery precision, this inventive integration establishes a significant advance over conventional oral, topical, or sublingual delivery methods, while maintaining full regulatory alignment and commercial scalability.

Table 46 maps representative active classes to polarity-matched carrier systems and primary delivery routes, illustrating how the invention applies pre-engineered nanoscale carriers (e.g., ethosomes, NLCs, SEDS, phytosomes, cyclodextrin complexes, hydrogel microneedles) across oral, transdermal, and topical platforms. The mapping demonstrates how the platform accommodates both single-route and dual-route delivery designs while maintaining optimized stability, enhanced bioavailability, nutritional support, and consumer usability.

TABLE 46

Active Class vs. Carrier System Mapping

| Active Class | Polarity | Pre-Engineered Carrier System | Primary Delivery Routes |
| --- | --- | --- | --- |
| Sterol derivatives (as esterified DHEA derivatives as one of the model compounds) | Lipophilic | Ethosomes/NLCs (Transdermal, Topical), SEDS (Oral) | Oral, Transdermal Microneedle Patch, Topical Cream/Gel |
| Fat-Soluble Vitamins (A, D, E, K) | Lipophilic | NLCs/Nanoemulgels (Transdermal, Topical), SEDS (Oral) | Oral, Transdermal Microneedle Patch, Topical Cream/Gel |
| Lipophilic Polyphenols (Resveratrol) | Lipophilic | Ethosomes/ Nanoemulgels | Oral, Transdermal Microneedle Patch, Topical Cream/Gel |
| Omega-3 Fatty Acids | Lipophilic | NLCs with Antioxidants | Oral, Transdermal Microneedle Patch |
| Adaptogens (Lipophilic Fraction) | Lipophilic | Phytosome Complexes + Lipid Vesicles | Oral, Transdermal Microneedle Patch, Topical Cream/Gel |
| Water-Soluble Vitamins (B, C) | Hydrophilic | Cyclodextrin Complexes, Liposomes | Oral, Transdermal Microneedle Patch, Topical Cream/Gel |
| Amino Acids (EAA, Creatine) | Hydrophilic | Hydrogel-Forming Microneedles | Oral, Transdermal Microneedle Patch |

TABLE 46-continued

| Active Class vs. Carrier System Mapping | | | |
|---|---|---|---|
| Active Class | Polarity | Pre-Engineered Carrier System | Primary Delivery Routes |
| HMB Free Acid | Hydrophilic | Hydrogel-Forming Microneedles | Oral, Transdermal Microneedle Patch |
| Adaptogens (Hydrophilic Fraction) | Hydrophilic | Cyclodextrin Complexes, Liposomes | Oral, Transdermal Microneedle Patch, Topical Cream/Gel |

Table 47 compares representative delivery technologies across oral, transdermal, and topical routes, outlining their core mechanisms and key advantages. The comparison highlights how nanostructured, microneedle, and complexation systems surpass conventional creams and gels in stability, absorption, polarity-specific release, and consumer usability. These technologies reinforce the applicability of the invention's platform for both single-route and dual-route delivery of sterol derivatives (as esterified DHEA derivatives as one of the model compounds) and other active classes, while supporting nutritional support, wellness applications, and commercial scalability.

TABLE 47

| Delivery Technology Comparison | | | |
|---|---|---|---|
| Delivery Technology | Primary Route | Core Mechanism | Key Advantages |
| Conventional Transdermal Creams & Gels | Transdermal | Semi-solid base with penetration enhancers (ethanol, propylene glycol, oleic acid) for passive diffusion through stratum corneum. | Established use precedent; steady delivery profile; simple manufacturing. |
| Microemulsion Creams | Transdermal/ Topical | Thermodynamically stable nano-droplets (10-100 nm) improve solubilization and skin penetration via surfactant-lipid interactions. | Higher dermal flux; rapid onset; improved retention; cosmetically elegant. |
| Nanostructured Lipid Carrier (NLC) Creams | Transdermal/ Topical | Solid-liquid lipid nanoparticles (50-500 nm) provide high compound loading, hydration, and polarity-specific release. | Long-term stability; reduced application frequency; consistent performance. |
| Microneedle Patches | Transdermal | Micro-projections (100-900 μm) create microchannels for enhanced dermal uptake of lipophilic and hydrophilic actives. | Bypasses skin barrier; improved absorption; painless; supports polarity-specific release. |
| Phytosome Complexes | Oral | Phospholipid complexation (e.g., phosphatidylcholine) improves membrane permeability and lymphatic transport. | Increased oral absorption; reduced first-pass metabolism; improved stability. |
| Cyclodextrin Complexes (HBCD) | Oral | Inclusion complex formation enhances solubility, stability, and intestinal absorption. | Improves dissolution and stability; adaptable to powders and capsules. |

Table 48 maps delivery technologies to applicable active classes and primary administration routes, illustrating how the invention deploys polarity-matched systems (e.g., creams, NLCs, microneedles, phytosomes, cyclodextrins, SEDS) to improve stability, enhance absorption, and support multi-route applicability for diverse bioactive categories. The framework demonstrates compatibility with both single-route and dual-route delivery designs while emphasizing nutritional support, wellness applications, consumer usability, and commercial scalability.

TABLE 48

| Technology-Active Class-Primary Routes | | |
|---|---|---|
| Delivery Technology | Applicable Active Classes | Primary Routes |
| Conventional Transdermal Creams & Gels | Sterol derivatives (as esterified DHEA derivatives as one of the model compounds), Fat-Soluble Vitamins, Lipophilic Polyphenols, Adaptogens (Lipophilic Fraction) | Transdermal, Topical |
| Microemulsion Creams | Sterol derivatives (as esterified DHEA derivatives as one of the model compounds), Fat-Soluble Vitamins, Lipophilic Polyphenols | Transdermal, Topical |
| Nanostructured Lipid Carrier (NLC) Creams | Sterol derivatives (as esterified DHEA derivatives as one of the model compounds), Fat-Soluble Vitamins, Omega-3 Fatty Acids, Adaptogens (Lipophilic Fraction) | Transdermal, Topical |
| Microneedle Patches | Sterol derivatives (as esterified DHEA derivatives as one of the model compounds), Fat-Soluble Vitamins, Lipophilic Polyphenols, Omega-3 Fatty Acids, Adaptogens (Lipophilic & Hydrophilic Fractions), Water-Soluble Vitamins, Amino Acids, HMB Free Acid | Transdermal |
| Phytosome Complexes | Sterol derivatives (as esterified DHEA derivatives as one of the model compounds), Fat-Soluble Vitamins, Lipophilic Polyphenols, Adaptogens (Lipophilic Fraction) | Oral |
| Cyclodextrin Complexes (HBCD) | Water-Soluble Vitamins, Amino Acids, Adaptogens (Hydrophilic Fraction) | Oral |
| Hydrogel-Forming Microneedles | Amino Acids, HMB Free Acid, Water-Soluble Vitamins, Adaptogens (Hydrophilic Fraction) | Transdermal |
| Self-Emulsifying Delivery Systems (SEDS) | Sterol derivatives (as esterified DHEA derivatives as one of the model compounds), Fat-Soluble Vitamins | Oral |

Vesicular Lipid Systems Adapted Per Delivery Route in the Present Invention

Oral Vesicular Lipid Systems

In the oral pathway, vesicular lipid systems specifically liposomes, phytosomes, and nanostructured lipid carriers (NLCs) are applied as engineered carriers to maximize intestinal absorption of sterol derivatives (as esterified DHEA derivatives as one of the model compounds). Hydrogenated phospholipids provide bile salt resistance, while antioxidant fortification with stabilizers such as mixed tocopherols or ascorbyl palmitate prevents oxidative loss. Enteric or delayed-release coatings protect against gastric hydrolysis, ensuring intact delivery to the intestinal tract. Vesicle sizes are optimized below two hundred nanometers, a threshold that favors preferential lymphatic uptake while reducing hepatic first-pass metabolism. Compared to conventional emulsions or crude lipid suspensions, these vesicular systems demonstrate markedly higher stability, enhanced absorption, and improved consumer usability.

Transdermal Vesicular Lipid Systems

For transdermal administration, vesicular carriers such as ethosomes, transfersomes, and NLCs are embedded within semi-solid bases or transdermal patch reservoirs. Ethanol-rich lipid phases are employed to fluidize stratum corneum lipids, while edge activators increase vesicle deformability and penetration. Occlusive backing films support polarity-specific release, while antioxidant fortification preserves compound stability during storage and application. Unlike traditional creams and gels that depend solely on passive diffusion, these vesicular carriers provide active penetration and reproducible delivery. Functionally, this ensures consistent dermal administration of sterol derivatives (as esterified DHEA derivatives as one of the model compounds), fat-soluble vitamins, and polyphenolic co-actives, delivering reproducible absorption with enhanced stability.

Hybrid Microdermal Vesicular Integration

Within the hybrid dual-compartment microneedle system of the present invention, lipid vesicles are incorporated into the lipophilic needle tip compartment. Vesicles are stabilized in solid-state form to prevent leakage and are preserved under nitrogen-flushed, moisture-controlled storage conditions. The polymer-lipid interface is engineered to prevent premature mixing of hydrophilic and lipophilic compound classes prior to use. Upon insertion, the microneedles provide polarity-specific release of hydrophilic actives from the polymeric base and simultaneous or sequential release of lipophilic vesicles from the needle tips. This dual release overcomes the limitations of conventional single-phase microneedles, which cannot accommodate chemically incompatible compound classes. The inventive advantage lies in preserving chemical stability while enabling coordinated co-delivery of sterol derivatives (as esterified DHEA derivatives as one of the model compounds) and auxiliary actives.

Topical Vesicular Lipid Systems

In topical formulations, vesicular carriers such as ethosomes, transfersomes, and NLCs are incorporated into nanoemulgel systems optimized for skin application. Surfactant compositions are adjusted to maintain vesicle integrity within the gel matrix, while opaque laminate packaging protects against photodegradation. pH buffering ensures that both the gel base and the vesicles retain stability throughout shelf life. Unlike conventional gels, which typically exhibit limited penetration and inconsistent flux, these vesicular nanoemulgels achieve deeper dermal penetration and prolonged retention of lipophilic actives. They provide a cosmetically elegant, consumer-friendly formulation that emphasizes nutritional support, wellness applications, stability, and improved usability compared to conventional systems.

Integration into the Polarity-Specific Platform

In the present invention, vesicular lipid systems are not deployed as standalone technologies but are modularly integrated into the Polarity-Specific, Multi-Route Delivery Platform. Each vesicular system is engineered according to polarity-matching principles: lipophilic actives such as sterol derivatives (as esterified DHEA derivatives as one of the model compounds) are encapsulated within vesicles, while hydrophilic actives are delivered via complementary polymeric or aqueous carriers. Route-specific adaptations oral, transdermal, hybrid microdermal, and topical optimize stability, permeability, and enhanced absorption. Across all routes, antioxidant fortification, oxygen-barrier packaging, and pH stabilization measures preserve chemical and structural integrity of the vesicle-active complexes. Collectively, these features achieve stability, delivery precision, and flexibility beyond the reach of conventional emulsions, liposomes, or gels. The integration establishes novelty and non-obviousness by enabling polarity-specific, route-tailored delivery of sterol derivatives (as esterified DHEA derivatives as one of the model compounds) and co-actives within a unified delivery framework designed to support nutritional support, wellness applications, and consumer usability.

Table 49 summarizes representative vesicle systems by route, highlighting phytosomes for enhanced oral absorption, ethosomes for superior transdermal penetration, and NLC-hydrogel hybrids for polarity-specific release and dermal stability. This mapping underscores the invention's integration of vesicle carriers into the polarity-specific platform, supporting nutritional support, wellness applications, and consumer usability across both single-route and dual-route delivery formats.

TABLE 49

Technical Evidence for Vesicular Lipid Systems

| Route | Vesicle Type | Evidence Summary |
| --- | --- | --- |
| Oral | Phytosomes | Widely shown to enhance absorption and uptake of lipophilic bioactives by improving solubility, stability, and intestinal permeability |
| Transdermal | Ethosomes | Demonstrated superior skin penetration versus conventional liposomes, enabling reproducible delivery of lipophilic and small-molecule actives. |
| Transdermal | NLCs in Hydrogels | Proven to support polarity-specific release, improved chemical stability, and enhanced dermal retention of encapsulated actives. |

These vesicular carriers are not merely adjuncts but integral stability and delivery modules within the invention's polarity-specific platform. Their incorporation across multiple routes strengthens bioavailability, extends shelf life, and broadens delivery flexibility—an advancement that differentiates the invention from prior art single-route or single-phase delivery systems. By supporting nutritional support, wellness applications, and consumer usability, this integration ensures the platform maintains stability, absorption efficiency, and versatility across both single-route and dual-route formats.

Stability & Protection Measures—Cross-Referenced Application to Delivery Technologies The present invention applies a unified stability framework that integrates chemical, physical, microbiological, enzymatic, and regulatory protection measures. These strategies are adapted to the specific requirements of each delivery technology described herein, ensuring consistent stabilization of sterol derivatives (as esterified DHEA derivatives as one of the model compounds) and related lipophilic or amphiphilic co-actives across multiple administration routes.

Conventional Transdermal Creams & Gels—Applied Stability Measures & Benefits

Conventional creams and gels maintain stability through the incorporation of antioxidants such as mixed tocopherols, ascorbyl palmitate, or rosemary extract, which control oxidative rancidity in lipid phases. Photoprotection is provided by manufacturing under amber light and utilizing opaque laminate packaging to shield formulations from photodegradation. Nitrogen-flushed laminate tubes serve as oxygen barriers, further preserving sensitive sterol derivatives (as esterified DHEA derivatives as one of the model compounds). Buffering systems are employed to maintain pH within a range that prevents acid- or alkali-catalyzed hydrolysis. Microbial protection is ensured through preservative systems such as phenoxyethanol-ethylhexylglycerin or, alternatively, aseptic compounding practices. Stability is formally verified through ICH Q1A (R2)-aligned testing adapted for dietary supplement formulations, demonstrating that potency and safety remain intact throughout the declared shelf life. The outcome is extended product stability of up to thirty-six months, potency retention within ninety to one hundred ten percent of label claim, reliable microbial protection, and global regulatory compatibility under dietary supplement GMP.

Microemulsion Creams—Applied Stability Measures & Benefits

Microemulsion systems achieve stability through precise optimization of surfactant and co-surfactant ratios to prevent phase inversion, supported by antioxidants that protect sterol derivatives (as esterified DHEA derivatives as one of the model compounds) from oxidative degradation. Ethanol-resistant laminate packaging prevents solvent evaporation during storage, while viscosity is modulated with carbomer-based matrices to preserve formulation elegance and consumer acceptability. Accelerated stability testing confirms maintenance of droplet size distribution below one hundred nanometers and verifies consistent potency throughout the shelf life. This design ensures that microemulsions remain thermodynamically stable, phase separation is minimized, and the system retains both cosmetic appeal and reliable dermal absorption performance Nanostructured Lipid Carrier Creams—Applied Stability Measures & Benefits Nanostructured lipid carrier (NLC) systems achieve long-term stability through controlled ratios of solid and liquid lipid phases, which prevent recrystallization or compound expulsion from the carrier matrix. Lipid-compatible antioxidants stabilize encapsulated sterol derivatives (as esterified DHEA derivatives as one of the model compounds) against oxidative damage, while oxygen-barrier multilayer packaging limits peroxidation during storage. Moisture ingress is prevented using barrier film technologies. Stability studies, both accelerated and real-time, confirm that particle sizes remain within the range of fifty to five hundred nanometers and that sterol derivative content remains within the accepted potency range. These combined measures preserve extended-release characteristics, minimize oxidative degradation, and extend overall product integrity relative to conventional lipid suspensions. These NLC cream systems are designed as dietary and nutraceutical supplement delivery systems, supporting nutritional supplement stability, shelf-life integrity, and consumer usability.

Oral Lipid-Based Systems-Applied Stability Measures & Benefits

Oral lipid-based formulations including nanoemulsions, nanostructured lipid carriers, phytosomes, liposomes, and cyclodextrin complexes—are stabilized through multiple protective mechanisms. Enteric coatings are applied to shield sensitive sterol derivatives (as esterified DHEA derivatives as one of the model compounds) from gastric hydrolysis, while liposomal systems are fortified with bile salt-resistant phospholipids to improve stability in the intestinal environment. Natural antioxidants such as tocopherols or rosemary extract are incorporated to prevent oxidative degradation during both storage and gastrointestinal transit. Particle size is controlled to remain below two hundred nanometers, enhancing lymphatic transport and reducing aggregation. Nitrogen-flushed capsule systems further protect from oxygen exposure. Formal ICH Q1A (R2)-aligned studies, adapted for dietary supplement regulatory frameworks, confirm consistent dissolution, bioavailability, and long-term potency retention. These measures collectively optimize intestinal absorption, reduce variability in absorption profiles, preserve sterol derivative content, and provide a globally compliant platform for oral dietary and nutraceutical supplement delivery.

Microneedle Patches—Applied Stability Measures & Benefits

Microneedle patches achieve stability through a combination of structural and chemical protection strategies that safeguard both the polymeric matrix and the encapsulated sterol derivatives (as esterified DHEA derivatives as one of the model compounds). Multilayer backing films are employed to provide barrier strength and dimensional stability, while antioxidants are incorporated into both polymeric and lipid-based compartments to protect against oxidative degradation of sensitive actives. Packaging systems are designed with nitrogen flushing and integrated desiccants, preventing both oxygen ingress and moisture accumulation that could otherwise cause premature swelling or compromise microneedle integrity.

Mechanical performance is validated through transport simulation and handling stress testing, ensuring that insertion strength and tip integrity are maintained across real-world distribution scenarios. Formal stability studies confirm that polymer dissolution, swelling behavior, and active retention are preserved under both accelerated and long-term storage conditions. Together, these measures ensure that microneedles maintain their strength, polarity-specific release kinetics, and nutritional supplement delivery precision and stability throughout the declared shelf life, supporting dietary and nutraceutical supplement applications.

Hybrid Microdermal Delivery System—Applied Stability Measures & Benefits

The dual-compartment microneedle system within this invention extends stability protection by spatially segregating hydrophilic and lipophilic compartments. This separation prevents premature mixing and chemical incompatibility between co-loaded actives. Packaging is optimized through nitrogen flushing and controlled moisture barriers, protecting against polymer swelling and lipid oxidation. Lipid vesicles are stabilized in a solid-state form within the lipophilic tip compartment, reducing leakage risk during storage. Simultaneously, polymer crosslink density in the hydrophilic compartment is tuned to maintain structural stability during storage while enabling rapid and predictable dissolution at the point of use.

This dual-compartment architecture ensures that chemically diverse actives remain stable, preserves intended sequential or synchronous release kinetics, and significantly extends shelf stability compared to single-phase microneedle systems.

Integrated Stability Outcomes

When evaluated across all delivery platforms-including creams, microemulsions, lipid carriers, oral capsules, and microneedle-based systems—the unified stability framework consistently extends product shelf life beyond conventional benchmarks. Potency is preserved within ninety to one hundred ten percent of label claim under ICH Q1A (R2)-aligned protocols, aggregation and recrystallization are minimized, and oxidative or hydrolytic degradation is reduced. Collectively, these measures ensure that sterol derivatives (as esterified DHEA derivatives as one of the model compounds) maintain their chemical and physical integrity, enhance nutritional supplement delivery reliability, and support commercial viability under global dietary supplement and nutraceutical regulatory frameworks.

Microemulsion Creams—Applied Stability Measures and Benefits

In this delivery technology, stability is achieved through a coordinated set of protective measures specifically adapted to the nanoscale architecture of microemulsions. Antioxidant fortification is achieved through incorporation of lipid-phase stabilizers such as tocopherols, ascorbyl palmitate, or rosemary extract, which protect internal oil droplets and encapsulated sterol derivatives (as esterified DHEA derivatives as one of the model compounds) from oxidative degradation. Photoprotection is provided by carrying out manufacturing under amber or red light and by packaging the finished formulation in opaque, UV-filtering laminate containers, thereby preventing light-induced degradation of sensitive compounds. Oxygen-barrier protection is ensured through nitrogen flushing and multilayer polymer-aluminum laminates, which together minimize oxygen ingress and preserve the integrity of sterol derivatives during long-term storage.

The aqueous phase is buffered to maintain microemulsion integrity, preventing pH-induced droplet destabilization and hydrolytic cleavage of ester bonds. Physical stability is optimized through precise control of surfactant-to-co-surfactant ratios and the inclusion of viscosity modifiers, which minimize droplet coalescence, creaming, or phase separation, ensuring colloidal uniformity throughout shelf life. Microbial safety is maintained by incorporating broad-spectrum preservative systems such as phenoxyethanol-caprylyl glycol or, alternatively, employing aseptic compounding and filling methods, thereby guaranteeing microbiological quality under normal storage conditions.

The result is a formulation with extended shelf life beyond that of conventional creams, nutritional supplement potency preserved within ninety to one hundred ten percent of the declared label claim, and reduced formation of oxidative or hydrolytic byproducts. The microemulsion cream remains safe, stable, and consumer-friendly, supporting global regulatory compliance under dietary supplement GMP stability protocols and positioning as a premium nutraceutical formulation designed for nutritional support, wellness applications, and consumer usability.

Figure 57:
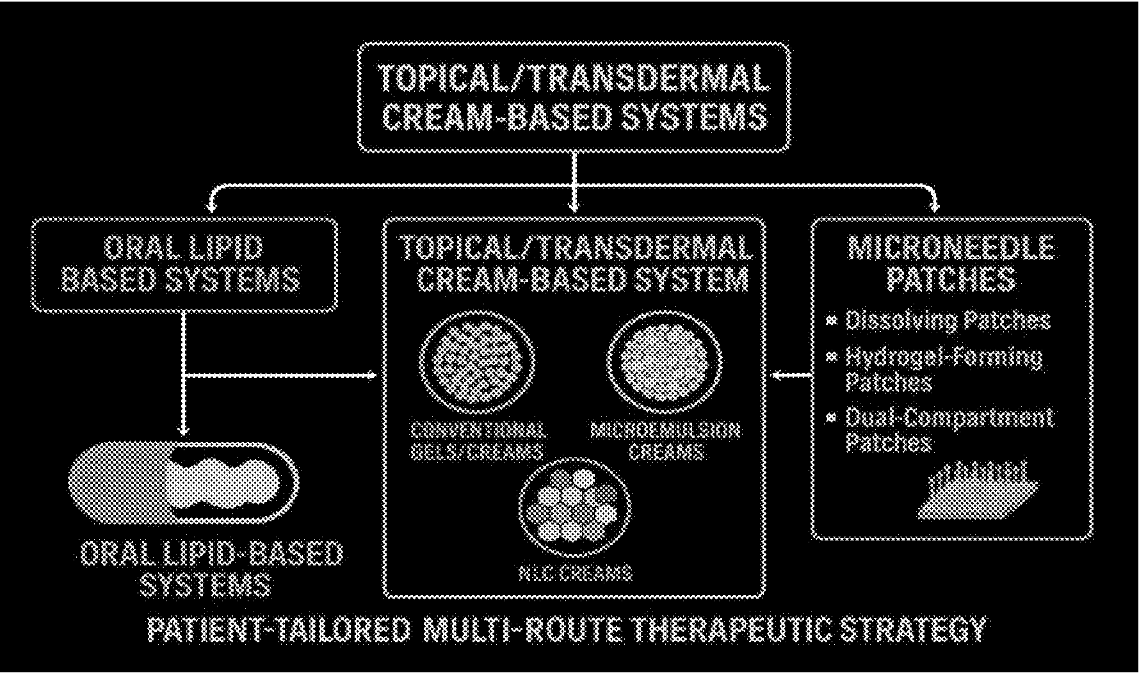
FIG. 57 illustrates the integrated multi-route delivery framework for DHEA ester therapy.

FIG. 57 illustrates the integrated, consumer-tailored multi-route delivery platform for sterol derivatives (as esterified DHEA derivatives as one of the model compounds), demonstrating how oral, topical, and microneedle-based technologies function as complementary modules within a unified dietary and nutraceutical supplement delivery system. On the left, oral lipid-based systems are shown as capsule formulations that enhance solubility, promote lymphatic absorption, and protect lipophilic actives from first-pass metabolism. At the center, topical and transdermal cream-based systems are represented by three formulation classes: conventional gels and creams (magenta), which provide familiar, reliable penetration pathways; microemulsion creams (orange), which leverage nanoscale dispersions for rapid absorption and nutrient uptake onset; and nanostructured lipid carrier creams (green), which provide extended release and enhanced stability. On the right, microneedle patches are presented as advanced transdermal systems incorporating dissolving, hydrogel-forming, and dual-compartment patches, enabling minimally invasive, polarity-specific, and sustained nutritional supplement delivery across the skin barrier. Collectively, the figure demonstrates how these three technology categories integrate into a modular, adaptable framework that allows tailored nutritional supplement delivery strategies aligned with consumer needs and global nutraceutical markets.

Nanostructured Lipid Carrier (NLC) Creams—Applied Stability Measures and Benefits In this dietary and nutraceutical supplement delivery technology, stability is preserved through a tailored application of protective measures specifically adapted to the requirements of lipid nanoparticle systems. Antioxidant fortification is achieved through the inclusion of stabilizers such as tocopherols, ascorbyl palmitate, or rosemary extract, which safeguard the lipid matrix and encapsulated sterol derivatives (as esterified DHEA derivatives as one of the model compounds) from oxidative degradation. Photoprotection is maintained by conducting manufacturing under controlled low-light conditions and utilizing opaque, UV-filtering barrier packaging, thereby preventing photodegradation of sensitive constituents such as carotenoids and other phytochemicals. Oxygen-barrier protection is ensured through nitrogen flushing and multilayer foil laminate packaging, which together minimize oxygen ingress and slow oxidative breakdown of both the lipid carriers and the entrapped actives.

Crystallization control is implemented by balancing solid and liquid lipid ratios, thereby stabilizing the desired polymorphic form and preventing lipid recrystallization that could otherwise alter polarity-specific release characteristics or compromise nutrient bioavailability. Physical stability is reinforced by optimizing surfactant systems, homogenization parameters, and rheological modifiers to preserve a uniform particle size distribution, thereby preventing aggregation, coalescence, or Ostwald ripening throughout the product's shelf life. Microbial stability is maintained through incorporation of broad-spectrum preservative systems or aseptic compounding methods, ensuring that microbial growth in the aqueous phase is inhibited and that product safety is preserved under normal storage conditions.

The outcome of these measures is a formulation that demonstrates consistent nutrient release profiles, with nutrient availability remaining predictable and stable across the entire declared shelf life. Storage stability is extended beyond that of conventional semisolid systems due to the protective effects of the lipid nanoparticle matrix, which shields both carriers and actives from degradation. All stability testing is conducted under dietary supplement GMP standards, including both accelerated and long-term protocols, thereby confirming product integrity, potency, and consumer safety.

This approach yields a dietary and nutraceutical supplement delivery system that offers long-term reliability, reproducible performance, and strong consumer confidence, while seamlessly integrating into the invention's multi-route architecture as illustrated in FIG. 57.

Microneedle Patches—Applied Stability Measures & Benefits

Stability is preserved through a targeted application of measures designed to protect both the microneedle structural matrix and the encapsulated sterol derivatives (as esterified DHEA derivatives as one of the model compounds) and other nutraceutical actives. Antioxidant fortification is achieved through the incorporation of lipid- or polymer-compatible stabilizers such as mixed tocopherols, butylated hydroxytoluene, or rosemary extract within the microneedle matrix or bioactive reservoir, thereby minimizing oxidative degradation of lipophilic compounds throughout storage. Oxygen-barrier protection is provided by vacuum-sealed or nitrogen-flushed multilayer foil-polymer pouches, which effectively limit oxygen ingress and protect both the polymeric substrate and the encapsulated bioactive compounds from oxidative breakdown.

Thermal stability is ensured by the use of thermally resilient excipients combined with low-temperature manufacturing processes, maintaining the microneedle's dimensional accuracy, structural integrity, and mechanical strength under both real-time and accelerated stability conditions. Container compatibility is validated through material safety testing, confirming that blister films, liners, and adhesives remain chemically inert and do not adsorb, degrade, or destabilize the encapsulated actives during storage. Protection against enzymatic degradation is achieved through encapsulation strategies, polymeric barriers, or the inclusion of natural enzyme inhibitors, which shield sensitive compounds from premature hydrolysis or transformation by skin-associated enzymes at the point of administration.

Controlled-release retention is preserved by stabilizing hydrogel-forming polymers, crosslinkers, and other release-modulating components within the microneedle design, ensuring that polarity-specific release characteristics remain consistent with the intended functional profile across the entire product shelf life. Together, these measures yield a system in which potency is maintained within ninety to one hundred and ten percent of the labeled claim, nutrient release remains predictable, and microneedle performance is not compromised by degradation, instability, or matrix failure.

The integrated stability framework not only safeguards long-term potency and delivery precision but also enhances consumer safety by preventing the formation of undesirable byproducts, minimizing the risk of microbial contamination, and ensuring reliable product performance at the point of use. All stability and performance testing is conducted in accordance with dietary supplement GMP standards, accelerated and long-term shelf-life validation, and device-specific performance guidelines. As a result, the microneedle system is positioned as a dietary and nutraceutical supplement delivery system that combines scientific reliability with regulatory compliance, ensuring commercial scalability and strong consumer confidence.

Phytosome Complexes—Applied Stability Measures & Benefits

Stability is preserved through a coordinated set of measures specifically designed to maintain the structural and functional integrity of the phospholipid-bioactive complex. Antioxidant fortification is achieved by incorporating lipid-compatible stabilizers such as mixed tocopherols or ascorbyl palmitate, which protect the phospholipid components from oxidative rancidity while safeguarding sensitive plant-derived actives from premature degradation. Oxygen-barrier protection is provided by nitrogen-flushed blister packs or multilayer foil-polymer laminates, which limit oxygen ingress and reduce the risk of oxidative breakdown that could compromise both the carrier and the complexed bioactive molecules.

Control of the formulation's pH ensures that both the phospholipid structure and the bound phytochemicals remain stable, preventing degradation triggered by acidic or alkaline conditions. Thermal stability is achieved through careful selection of excipients with low thermal sensitivity, combined with controlled drying processes and optimized storage conditions, which together prevent dissociation or destabilization of the phytosome complex. Stability compliance is verified through both accelerated and long-term testing conducted under dietary supplement GMP standards, providing substantiated evidence of product quality, potency, and structural integrity across the declared shelf life.

The result of this integrated stability strategy is a phytosome complex with an extended shelf life, demonstrating potency retention within ninety to one hundred and ten percent of the labeled claim throughout its validated period. Safety is reinforced by minimizing oxidative degradation and preventing the formation of undesirable byproducts, ensuring that the bioactive complex remains nutritionally functional. From a commercial perspective, the combination of enhanced stability and superior nutrient bioavailability supports strong consumer confidence, while the demonstrated compliance with international nutraceutical regulations facilitates global market adoption.

Cyclodextrin Complexes (HBCD)—Applied Stability Measures & Benefits

Cyclodextrin complexes, particularly hydroxypropyl-β-cyclodextrin (HBCD), are employed in the present invention as polarity-adaptive carriers that enhance the solubility, stability, and delivery performance of sterol derivatives (as esterified DHEA derivatives as one of the model compounds) and related bioactives. These complexes are integrated into both oral and microneedle-based transdermal platforms, with each route benefiting from targeted stability and protection strategies.

For oral delivery formats, stability is safeguarded through oxygen-barrier packaging such as nitrogen-flushed, multilayer foil-polymer blister packs or high-barrier bottles, which prevent oxidative degradation of both the cyclodextrin host and the included compounds. pH control is maintained by buffering systems that optimize host-guest interaction and prevent hydrolytic breakdown or premature release of the encapsulated bioactive. Thermal stability is ensured through low-stress manufacturing methods and appropriate storage conditions, protecting the inclusion complex from dissociation and preserving its solubilization efficiency. Packaging compatibility is verified to ensure that container materials remain inert, avoiding adsorption, leaching, or destabilization during shelf life. Shelf-life substantiation is demonstrated under dietary supplement GMP stability protocols, using accelerated and long-term studies to confirm potency, integrity, and consumer safety.

For microneedle-based transdermal delivery, HBCD complexes are incorporated directly into dissolving or hydrogel-forming microneedle matrices, improving solubility, uniform nutrient incorporation, and sustained nutritional supplement delivery after skin insertion. In this context, stability measures extend to polymer-cyclodextrin compatibility, ensuring that the inclusion complexes remain intact throughout microneedle fabrication, storage, and administration. Thermal resilience is preserved through careful excipient selection and moisture-controlled, nitrogen-flushed packaging, while structural integrity is verified to confirm that the inclusion complexes retain their host-guest associations within microneedle tips. This ensures reproducible release behavior and reliable nutrient delivery across the product's shelf life.

The outcome is a versatile cyclodextrin delivery module that maintains chemical and physical stability, preserves potency within ninety to one hundred and ten percent of the declared label claim, and ensures consistent performance across both oral and microneedle-based dietary supplement formats. By functioning as both solubility enhancers and stability carriers, cyclodextrin complexes reinforce the invention's polarity-specific, multi-route delivery framework, offering extended shelf life, consumer safety, global regulatory compliance, and competitive positioning in the nutraceutical marketplace.

Hydrogel-Forming Microneedles—Applied Stability Measures & Benefits

Stability is preserved through a tailored set of measures designed to maintain both the integrity of the hydrogel matrix and the stability of encapsulated nutraceutical compounds. Antioxidant fortification is achieved by incorporating food-grade antioxidants such as mixed tocopherols, ascorbyl palmitate, or rosemary extract into the hydrogel or within the encapsulated bioactive phase, preventing oxidative degradation during storage. Oxygen-barrier protection is provided by nitrogen-flushed, multilayer foil-polymer pouches or blister packs, ensuring minimal oxygen ingress and preserving both crosslink integrity and bioactive potency. Thermal stability is managed by selecting polymers and crosslinking agents that withstand normal storage and transport conditions, supported by low-temperature drying and packaging processes that maintain the microneedle structure. Physical stability is optimized by controlling polymer composition, moisture content, and packaging humidity, thereby preventing premature swelling of the microneedles before application. Microbial safety is ensured through sterile or aseptic manufacturing environments, supplemented by natural antimicrobial agents where needed, maintaining product safety in compliance with dietary supplement GMP standards. Release stability is preserved by reinforcing the release-modulating components of the hydrogel, enabling a consistent diffusion profile across the full declared shelf life.

The outcome of this approach is a microneedle system that maintains long-term potency of nutraceutical actives, with bioactive content preserved within ninety to one hundred and ten percent of label claim through expiry. Mechanical performance and swelling-mediated delivery remain reliable, ensuring consistent release of actives upon application. Unlike dissolving microneedles, which provide rapid nutrient release, hydrogel-forming microneedles form a swelling-mediated matrix that supports sustained nutritional supplement release over extended timeframes. This distinction underscores their role as the extended-release module within the multi-route, polarity-specific dietary supplement delivery framework disclosed in the invention. Stability is demonstrated through shelf-life studies aligned with dietary supplement GMP standards and nutraceutical regulatory guidelines, supporting safe, effective, and consumer-ready market introduction.

Self-Emulsifying Delivery Systems (Sends)—Applied Stability Measures & Benefits

Stability is preserved through targeted measures derived from the unified 15-point framework, each focused on maintaining the functional integrity of the lipid-based system and the solubilized active ingredients. Antioxidant fortification is achieved by incorporating lipid-phase antioxidants such as mixed tocopherols, butylated hydroxytoluene (BHT), or ascorbyl palmitate, which prevent oxidative rancidity of the lipid excipients and degradation of lipophilic actives, thereby ensuring lipid protection. Oxygen-barrier packaging provides further oxidative control, with formulations filled under nitrogen-flushed conditions into high-barrier containers such as aluminum-polymer laminates or glass vials to minimize oxygen ingress and slow destabilizing oxidative reactions.

Thermal stability management is implemented through the selection of excipients with low susceptibility to thermal degradation, combined with controlled manufacturing and storage conditions that prevent droplet size changes and preserve emulsification behavior. Physical stability optimization is achieved by balancing surfactant/co-surfactant ratios, viscosity modifiers, and hydrophobic excipients to reduce the risks of compound precipitation, phase separation, or creaming during storage, thereby maintaining dispersion integrity. Regulatory stability compliance is ensured through execution of full ICH Q1A (R2) studies, including both accelerated and long-term protocols, substantiating label claims and meeting dietary supplement GMP standards for global readiness.

The results confirm extended shelf life through the retention of droplet formation capacity and solubilization performance across the declared shelf life, with potency consistently maintained within ninety to one hundred and ten percent of label claim. Safe nutritional supplement delivery is further demonstrated by the reduction of oxidative byproduct formation and the prevention of inconsistencies associated with physical instability. Collectively, these outcomes establish overall market viability, with a data-validated stability profile supporting global commercialization and premium positioning of the inventive dietary and nutraceutical formulation.

Photolabile Compound Protection—Applied Stability Measures & Benefits

Protection of light-sensitive actives is achieved through a coordinated set of process and packaging interventions derived from the unified 15-point framework. Manufacturing operations involving photolabile compounds-including sterol derivatives (as esterified DHEA derivatives as one of the model compounds), carotenoids, retinoids, vitamin D analogs, and polyphenols—are performed under amber or red lighting conditions or within enclosed processing vessels fitted with light-blocking covers, thereby preventing photodegradation during compounding, emulsification, and filling. To ensure long-term product stability, opaque barrier packaging such as aluminum-polymer laminate tubes, black HDPE bottles, UV-absorbing multilayer blisters, or foil pouches is employed to block UVA, UVB, and high-energy visible light from reaching and degrading sensitive payloads.

Additional protection is provided through secondary shielding, including light-protective overwraps or cartons, which further reduce cumulative light exposure during shipping and storage and enhance distribution stability. Packaging materials are also selected to deliver integrated barrier performance, combining photoprotection with high resistance to moisture and oxygen ingress, thereby providing multi-threat protection against oxidative, hydrolytic, and photolytic degradation.

The results of this approach include potency preservation, with active content consistently maintained within ninety to one hundred and ten percent of label claim across the declared shelf life; structural integrity, through prevention of molecular breakdown in light-sensitive compounds, ensuring nutritional supplement function and consumer usability; extended shelf life, with reduced light-induced degradation supporting stability claims of twenty-four to thirty-six months; and regulatory compliance, demonstrated by adherence to ICH photostability testing standards aligned with dietary supplement GMP requirements.

General Stability Framework (Applicable Across all Technologies)

The general stability framework applicable across all technologies incorporates a comprehensive suite of protective measures. These include antioxidant fortification within lipid and polymer matrices to prevent oxidative rancidity and degradation of unsaturated compounds; protection of photolabile actives through light-shielded processing and opaque barrier packaging; and the use of oxygen-impenetrable, inert-gas-flushed packaging to minimize both oxidative and hydrolytic degradation. Additional safeguards encompass pH control and buffering to avoid acid- or alkali-catalyzed hydrolysis and molecular rearrangements, chelation of pro-oxidant metals to suppress catalyzed oxidation, and thermal stability management to preserve thermolabile actives during both processing and storage.

The framework further addresses solid-state and physical stability by incorporating crystallization and polymorph control to maintain the desired nutrient bioavailable form, as well as dispersion stabilization strategies to prevent aggregation, phase separation, or sedimentation. Container and closure compatibility is ensured to eliminate risks of active adsorption or leaching, while microbial contamination is controlled through preservatives and aseptic manufacturing practices. To further extend product integrity, enzyme inhibition or shielding mechanisms prevent premature enzymatic degradation, and measures for isomerization and epimerization control preserve stereochemical purity throughout the shelf life.

Beyond structural safeguards, the system emphasizes functional performance, with controlled-release profile retention to preserve intended nutrient release profile and delivery timing. All measures are implemented under regulatory stability protocols, following ICH Q1A (R2) and equivalent global standards adapted for dietary supplement GMP compliance. Consideration is also given to transport and handling stability, ensuring that formulations remain robust under shipping conditions and real-world storage environments.

The systematic application of this integrated framework yields clear benefits: shelf life extension from the standard twelve to eighteen months to as long as twenty-four to thirty-six months or more depending on the formulation; potency preservation with active content consistently maintained within ninety to one hundred and ten percent of label claim through expiry; assurance of consumer safety by preventing contamination, undesirable degradation, or uncontrolled release; regulatory support by meeting or exceeding international dietary supplement stability requirements; and significant commercial advantages through reduced waste, consistent user experience, and the ability to achieve premium market positioning in the nutraceutical marketplace.

Table 50 maps delivery technologies to their corresponding stability measures and resulting benefits, illustrating how the integrated framework (antioxidant fortification, photoprotection, oxygen-barrier packaging, pH and thermal control, crystallization management, microbial safeguards, and controlled-release retention) ensures extended shelf life, potency preservation, consumer safety, dietary supplement GMP stability compliance, and market viability across diverse platforms.

TABLE 50

Cross-Reference of Delivery Technologies to Applied Stability Measures and Resulting Benefits

| Index | Delivery Technology | Mapped Stability Measures | Primary Benefits |
|---|---|---|---|
| 1 | Conventional Transdermal Creams & Gels | Antioxidant fortification; Photoprotection; Oxygen-barrier packaging; pH control; Microbial control; Regulatory stability testing | Extended shelf life; Potency retention; Contamination prevention; Nutraceutical regulatory compliance; Commercial reliability |
| 2 | Microemulsion Creams | Antioxidant fortification; Photoprotection; Oxygen-barrier packaging; pH control; Physical stability optimization; Microbial control | Enhanced shelf life; Potency preservation; Consumer safety; Nutraceutical regulatory readiness; Market appeal |
| 3 | Nanostructured Lipid Carrier (NLC) Creams | Antioxidant fortification; Photoprotection; Oxygen-barrier packaging; Crystallization control; Physical stability optimization; Microbial control | Improved release profile consistency; Extended storage stability; Compliance with dietary supplement GMP |
| 4 | Microneedle Patches | Antioxidant fortification; Oxygen-barrier packaging; Thermal stability management; Container compatibility; Enzyme shielding; Controlled-release retention | Long-term potency; Delivery reliability; Consumer safety; Nutraceutical regulatory support |
| 5 | Phytosome Complexes | Antioxidant fortification; Oxygen-barrier packaging; pH control; Thermal stability management; Regulatory stability compliance | Extended shelf life; Potency assurance; Consumer safety; Competitive positioning |
| 6 | Cyclodextrin Complexes (HBCD) | Oxygen-barrier packaging; pH control; Thermal stability management; Container compatibility; Regulatory compliance testing | Stable, potent, safe dietary supplement products; Strong nutraceutical regulatory support |
| 7 | Hydrogel-Forming Microneedles | Antioxidant fortification; Oxygen-barrier packaging; Thermal stability management; Physical stability optimization; Microbial control; Controlled-release retention | Long-term performance; Potency preservation; Consumer safety; Nutraceutical GMP compliance |
| 8 | Self-Emulsifying Delivery Systems (SEDS) | Antioxidant fortification; Oxygen-barrier packaging; Thermal stability management; Physical stability optimization; Regulatory stability compliance | Extended shelf life; Potency maintenance; Safe supplement delivery; Market viability |

Antioxidant Fortification in Lipid Carriers—Applied Stability Measures & Benefits Oxidative protection of lipid-based carrier systems is achieved through targeted incorporation of lipid-phase antioxidants, selected and optimized in accordance with the unified 15-point framework. Lipid-compatible antioxidants such as mixed tocopherols (α-, β-, γ-, δ-forms), ascorbyl palmitate, rosemary extract rich in carnosic acid and carnosol, butylated hydroxytoluene (BHT), and green tea catechins are pre-dissolved or dispersed within the lipid phase during carrier pre-engineering to provide uniform free radical scavenging throughout the matrix and maintain lipid phase stability. Synergistic antioxidant systems are employed by combining primary antioxidants (e.g., tocopherols) with secondary antioxidants (e.g., ascorbyl palmitate) and chelating agents (e.g., citric acid), thereby blocking metal-catalyzed oxidation pathways and achieving multi-mechanism oxidative control. Antioxidants are further matched to lipid excipients such as phosphatidylcholine, medium-chain triglycerides (MCTs), ethyl oleate, or nanostructured lipid matrices to maximize oxidative protection without destabilizing the carrier and to preserve excipient integrity. In emulsified or vesicular systems, amphiphilic antioxidants are strategically positioned at the lipid-aqueous interface to provide additional defense against oxidative degradation at droplet boundaries, thereby ensuring emulsion interface stability.

The results of this integrated approach include potency preservation, with chemical stability of lipophilic payloads such as sterol derivatives (as esterified DHEA derivatives as one of the model compounds), resveratrol, and omega-3 fatty acids consistently maintained within ninety to one hundred and ten percent of label claim over the declared shelf life. Extended carrier stability is achieved by preventing rancidity, peroxide formation, and oxidative cross-linking, thereby preserving droplet size, matrix structure, and phase integrity. Multi-route protection is demonstrated across ethosomes, nanostructured lipid carriers (NLCs), Self-Emulsifying Nutraceutical Delivery Systems (SENDS), and lipid nanoparticle-coated microneedles, ensuring consistent performance in oral, transdermal, and topical applications. Finally, the system delivers nutraceutical regulatory compliance by meeting ICH Q1A (R2) stability and oxidative stress testing standards, supporting commercialization of high-value lipid-based dietary supplement formulations.

Photolabile Compound Protection—Applied Stability Measures & Benefits

Protection of light-sensitive actives is achieved through a coordinated combination of process and packaging interventions drawn from the unified 15-point framework. Manufacturing operations involving photolabile compounds-such as sterol derivatives (as esterified DHEA derivatives as one of the model compounds), carotenoids, retinoids, vitamin D analogs, and polyphenols—are carried out under amber or red lighting conditions or within enclosed vessels equipped with light-blocking covers, thereby preventing photodegradation during compounding, emulsification, or filling and ensuring light stability. To extend protection beyond processing, opaque barrier packaging is employed, including aluminum-polymer laminate tubes, black HDPE bottles, UV-absorbing multilayer blisters, and foil pouches, all of which block UVA, UVB, and high-energy visible light from reaching and degrading sensitive payloads. Secondary shielding measures, such as the use of protective overwraps or cartons, further reduce cumulative light exposure during shipping and storage, thereby strengthening distribution stability. In addition, packaging materials are selected for combined performance, delivering not only light-blocking capability but also high barrier protection against moisture and oxygen, ensuring a multi-threat stability profile that integrates photoprotection with oxidative and hydrolytic defense.

The results of this approach include potency preservation, with active content consistently maintained within ninety to one hundred and ten percent of label claim throughout the declared shelf life, and structural integrity through the prevention of molecular breakdown that could otherwise compromise nutritional supplement function or appearance. Shelf life is significantly extended by minimizing light-induced degradation, supporting stability claims in the twenty-four to thirty-six month range. Finally, the framework ensures nutraceutical regulatory compliance by meeting ICH photostability testing standards aligned with dietary supplement GMP, thereby supporting safe commercialization of light-sensitive dietary supplement formulations.

Topical Cream/Gel with Polarity-Specific Encapsulation and Droplet Size <200 Nm—Applied Stability Measures & Benefits Stability and dermal nutrient penetration efficiency are achieved through a synergistic combination of polarity-specific encapsulation and nanoscale droplet engineering below 200 nm, reinforced by interventions derived from the unified 15-point stability framework. Lipophilic actives such as sterol derivatives (as esterified DHEA derivatives as one of the model compounds), lipophilic polyphenols, and carotenoids are pre-engineered into lipid-based nanocarriers including nanoemulsions, nanostructured lipid carriers (NLCs), or ethosomes, while hydrophilic actives such as amino acids, vitamin C, and B-complex vitamins are encapsulated in hydrophilic carriers such as cyclodextrin complexes or polymeric nanoparticles. This polarity-cross-phase degradation, optimizes carrier-active segregated encapsulation minimizes compatibility, and establishes carrier-matched stability. Emulsification parameters are tuned to maintain droplet size below 200 nm, thereby reducing gravitational separation, minimizing Ostwald ripening, and enhancing skin permeation efficiency, ensuring nano-integrity throughout shelf life.

Additional protective measures include antioxidant fortification of the lipid phase using agents such as mixed tocopherols, ascorbyl palmitate, and rosemary extract, which prevent oxidative degradation of both active ingredients and lipid excipients, and aqueous-phase pH optimization within ranges that maintain both chemical stability of actives and droplet integrity, preventing hydrolysis or phase instability. The finished formulations are filled into nitrogen-flushed, UV-blocking laminate tubes or airless dispensers with high oxygen-barrier performance, delivering packaging stability by preventing oxidative and photolytic degradation. Physical stability is further reinforced through polymeric rheology modifiers and carefully balanced surfactant/co-surfactant ratios, which collectively prevent droplet coalescence, preserve viscosity, and maintain spreadability across the declared shelf life, ensuring texture retention.

The results of this integrated approach include potency preservation, with active concentrations consistently maintained within ninety to one hundred and ten percent of label claim for the full declared shelf life; enhanced dermal nutrient penetration through the synergistic effect of sub-200 nm droplet size and polarity-specific encapsulation, enabling efficient delivery of both hydrophilic and lipophilic actives; extended stability compared to conventional creams and gels, with resistance to oxidation, hydrolysis, and phase separation; and full nutraceutical regulatory compliance, with stability data meeting ICH Q1A (R2) guidelines as adapted for dietary supplement GMP.

Oral Softgel/Hpmc Capsule Incorporating Antioxidant-Enriched Sends Pre-Concentrates—Applied Stability Measures & Benefits Stability, nutrient absorption, and shelf life of highly lipophilic actives are enhanced through the use of antioxidant-enriched Self-Emulsifying Nutraceutical Delivery Systems (SENDS) pre-concentrates, supported by targeted measures from the unified 15-point stability framework. Lipid-phase antioxidants such as mixed tocopherols, ascorbyl palmitate, rosemary extract, or butylated hydroxytoluene (BHT) are incorporated directly into the lipid phase to prevent oxidative rancidity of oils and degradation of lipophilic actives, ensuring oxidative stability. Polarity-specific solubilization is achieved by fully dissolving lipophilic actives-including sterol derivatives (as esterified DHEA derivatives as one of the model compounds), resveratrol, omega-3 fatty acids, and carotenoids-within the lipid phase to maximize solubility, prevent recrystallization, and enable consistent nutrient delivery upon ingestion.

To preserve integrity during storage, SENDS formulations are encapsulated under inert atmosphere with nitrogen flushing into softgel or HPMC capsule shells designed with low oxygen permeability, thereby minimizing oxidative degradation and providing encapsulation protection. Thermal stability management is achieved through the selection of thermally stable lipid excipients combined with low-heat filling processes, preventing heat-induced degradation or phase separation. Physical stability is further reinforced by optimizing surfactant/co-surfactant ratios to maintain isotropic, homogeneous pre-concentrates without phase separation, even under accelerated stability conditions. Additional safeguards include photoprotection using opaque capsule shells or UV-absorbing blister packaging to block photodegradation of light-sensitive actives.

The results of this integrated strategy include extended shelf life, with chemical potency and phase integrity maintained for twenty-four to thirty-six months; enhanced nutrient absorption and bioavailability, as rapid self-emulsification upon ingestion produces fine oil-in-water emulsions that facilitate efficient nutrient uptake of lipophilic compounds; potency assurance, with active content consistently retained within ninety to one hundred and ten percent of label claim across the declared shelf life; and nutraceutical regulatory compliance, with stability data conforming to ICH Q1A (R2) requirements adapted for dietary supplement GMP standards.

Oxygen Absorber Integration in Multi-Route Stability Packaging—Applied Stability Measures & Benefits Oxidative degradation of sensitive actives is minimized by incorporating oxygen absorbers into high-barrier packaging systems, thereby creating a controlled low-oxygen microenvironment suitable for oral, transdermal, and topical delivery formats. Integrated oxygen scavenging is achieved through the inclusion of iron-based or ascorbate-based absorber sachets, labels, or embedded films within primary or secondary packaging, actively binding residual oxygen present during packaging as well as any ingress over time. These absorbers function synergistically with high-barrier materials such as multilayer aluminum-polymer laminates, glass vials, or foil-blister packs, which physically restrict oxygen transmission while chemical scavenging eliminates trapped oxygen, providing dual protection. To further minimize headspace oxygen, nitrogen flushing is applied prior to sealing, after which absorbers maintain ultra-low oxygen levels throughout the product's shelf life.

The approach is broadly applicable across multiple formats, including softgels, SENDS capsules, lipid nanoparticle dispersions, microneedle patches, and antioxidant-rich topical creams, thereby preserving both lipophilic and hydrophilic actives. Oxygen control is further paired with photoprotection and desiccant layers, ensuring simultaneous defense against oxidative, hydrolytic, and photolytic degradation, thus achieving multi-threat stability across product lines.

The results of this integrated system include extended shelf life, with potency and chemical integrity maintained for twenty-four to thirty-six months even for oxidation-prone compounds; potency assurance, with active content consistently retained within ninety to one hundred and ten percent of label claim across variable storage conditions; stability across formats, enabling reliable performance of multiple dosage forms stored together in unified multi-route kits; and full nutraceutical regulatory compliance, with data supporting ICH Q1A (R2) requirements adapted for dietary supplement GMP standards through validated oxygen-controlled storage environments.

Cross-route oxidative stability validation was further demonstrated for sterol derivatives (as esterified DHEA derivatives as one of the model compounds), addressing the known vulnerability of these compounds to oxidative degradation. Comprehensive stability assessments across oral (SENDS softgel), topical (nanoemulgel), and microneedle (lipidic tip payload) routes confirmed that antioxidant-fortified formulations also maintained potency, oxidative integrity, and nutritional functional performance under both accelerated and real-time ICH conditions, whereas unfortified controls exhibited significant degradation.

Oral Sends Softgel Stability

Formulations containing sterol derivatives (as esterified DHEA derivatives as one of the model compounds) within a PUFA-rich Self-Emulsifying Nutraceutical Delivery System (SENDS) matrix were subjected to ICH Q1A (R2) stability protocols (40° C./75% RH, 6 months) adapted for dietary supplement GMP. Antioxidant fortification with tocopherols and ascorbyl palmitate markedly reduced oxidative drift.

Table 51 shows that under accelerated ICH stability conditions, fortified SENDS formulations retained ≥95% potency with controlled oxidative markers (TOTOX≤15.4) over six months, while unfortified controls declined to 82.8% potency with elevated oxidation (TOTOX 26.9), confirming the stabilizing effect of antioxidant fortification in dietary supplement delivery systems.

TABLE 51

Oral SENDS Oxidative Stability (Accelerated, 40° C./75% RH)

| Time-point | Fortified (% Potency) | % Δ | Unfortified (% Potency) | % Δ | TOTOX Fortified | TOTOX Unfortified |
|---|---|---|---|---|---|---|
| Day 0 | 100.0 | — | 100.0 | — | 11.0 | 11.2 |
| Month 3 | 97.8 | −2.2% | 88.5 | −11.5% | 13.9 | 21.9 |
| Month 6 | 95.4 | −4.6% | 82.8 | −17.2% | 15.4 | 26.9 |

Interpretation: Fortified oral SENDS formulations retained ≥95% potency and maintained TOTOX values≤15 throughout six months of accelerated stability, whereas unfortified controls exhibited nearly 20% potency loss with TOTOX values exceeding 25, confirming enhanced oxidative stability for dietary and nutraceutical supplement formats.

Topical Nanoemulgel Stability

Sterol derivatives (as esterified DHEA derivatives as one of the model compounds) solubilized in nanoemulgels were tested under the same accelerated stability conditions. Antioxidant fortification prevented oxidative rancidity and preserved emulsion integrity.

Table 52 summarizes that antioxidant-fortified nanoemulgels maintained ≥95% potency with controlled oxidative values (TOTOX≤15.6) through six months, while unfortified controls declined to 83.3% potency with elevated oxidation (TOTOX 27.8), demonstrating the effectiveness of antioxidant fortification in nutraceutical topical delivery systems.

TABLE 52

Topical Nanoemulgel Oxidative Stability (Accelerated, 40° C./75% RH)

| Timepoint | Fortified (% Potency) | % Δ | Unfortified (% Potency) | % Δ | TOTOX Fortified | TOTOX Unfortified |
|---|---|---|---|---|---|---|
| Day 0 | 100.0 | — | 100.0 | — | 11.5 | 11.6 |
| Month 3 | 97.2 | −2.8% | 89.0 | −11.0% | 14.0 | 22.5 |
| Month 6 | 95.5 | −4.5% | 83.3 | −16.7% | 15.6 | 27.8 |

Interpretation: Antioxidant-fortified gels showed only −4.5% potency loss versus −17% in controls, confirming oxidative stabilization without affecting viscosity, droplet size, or zeta potential in dietary supplement delivery systems.

Microneedle Lipidic Tip Stability

Dual-compartment microneedles loaded with sterol derivatives (as esterified DHEA derivatives as one of the model compounds) in NLC-based tips were similarly evaluated. Both oxidative stability and mechanical properties were assessed.

Table 53 shows that under accelerated stability conditions (40° C./75% RH), fortified microneedle NLC tips retained ≥95% potency with controlled oxidation (TOTOX≤15.3) through six months, while unfortified controls declined to 82.2% potency with elevated oxidative stress (TOTOX 28.5), confirming the stabilizing effect of antioxidant fortification in microneedle-based dietary supplement delivery systems.

TABLE 53

Microneedle NLC Tip Oxidative Stability (Accelerated, 40° C./75% RH)

| Time-point | Fortified (% Potency) | % Δ | Unfortified (% Potency) | % Δ | TOTOX Fortified | TOTOX Un-fortified |
|---|---|---|---|---|---|---|
| Day 0 | 100.0 | — | 100.0 | — | 11.2 | 11.2 |
| Month 3 | 97.4 | −2.6% | 88.9 | −11.1% | 14.5 | 23.7 |
| Month 6 | 95.9 | −4.1% | 82.2 | −17.8% | 15.3 | 28.5 |

Interpretation: Fortified microneedle tips maintained ≥95% potency with TOTOX ≤15, while unfortified tips exhibited nearly 20% potency loss and showed less consistent nutrient release behavior. Mechanical strength remained intact in fortified tips, but unfortified samples showed mild brittleness, indicating oxidative compromise of lipid-polymer interactions. These results confirm the stabilizing effect of antioxidant fortification within microneedle-based dietary and nutraceutical supplement delivery systems.

Cross-Route Interpretation & Patent Relevance

Across oral, topical, and microneedle routes, a consistent pattern was observed: antioxidant fortification preserved potency and oxidative integrity, while unfortified controls demonstrated significant degradation under accelerated stress conditions. The fortified systems consistently capped TOTOX values at or below 15 through six months, whereas unfortified matrices exceeded 25-28, confirming the enhanced oxidative stability of the inventive formulations.

These results establish the route-independent stability benefit of the integrated antioxidant system, a critical inventive feature that ensures consistent performance across diverse delivery platforms. By preventing both potency loss and functional impairment-including altered nutrient release behavior, emulsion instability, and loss of microneedle mechanical strength—the findings further reinforce the industrial scalability and route-conversion stability of the platform.

Patent linkage: This dual-route oxidative stability validation directly supports claims that the inventive system stabilizes sterol derivatives (as esterified DHEA derivatives as one of the model compounds) across multiple delivery routes, enables cross-route deployment without the need for reformulation, ensures shelf-life readiness under ICH Q1A (R2) accelerated stress testing adapted for dietary supplement GMP, and provides novel stability protection not taught in prior art for lipid-based and microneedle nutraceutical delivery system.

Study #1A-Oral-Only Absorption-Timing and Tolerability Study

This appendix documents a stand-alone ingestion-only human study designed to support dietary supplement structure/function substantiation. The study assessed programmed delivery timing and systemic exposure of two dietary ingredients-nicotinamide and coenzyme Q10 (CoQ10)—delivered through polarity-matched oral formulations. All interventions were administered exclusively by oral ingestion; no non-ingestible procedures were involved. The investigation focused on absorption timing, exposure measures, tolerability, and participant-reported wellness signals appropriate for dietary supplement positioning, and did not include any disease-related outcomes.

The study was a randomized, double-blind, three-way crossover in healthy adults with washouts of at least seven days. Participants received three regimens in counterbalanced order: a sequential regimen engineered to produce a hydrophile-first profile; a simultaneous regimen designed for concurrent absorption; and a reference regimen in which the two components were co-administered as separate immediate-release capsules. The hydrophilic tracer was nicotinamide 250 mg in a cyclodextrin matrix to promote rapid dissolution; the lipophilic tracer was CoQ10 100 mg in antioxidant-enriched self-emulsifying nutraceutical pre-concentrates (SENDS) to enhance dispersion and uptake. The sequential regimen used an enteric/time-lag coating on the CoQ10 softgel so that nicotinamide peaked first; the simultaneous regimen used fully immediate-release materials for both ingredients. All excipients were food-grade or GRAS.

Objectives and endpoints were prespecified to demonstrate programmable timing and bioavailability support under DSHEA. The co-primary endpoints were the between-regimen differences in appearance lag and time to maximum concentration (T_max) for nicotinamide versus CoQ10, with a priori targets of ≥45 minutes separation in the sequential arm and equivalence within ±15 minutes in the simultaneous arm. Secondary endpoints included C_max and AUC_0-24 for each analyte, gastrointestinal tolerability, and participant-reported wellness ratings framed as structure/function signals. Women of childbearing potential used acceptable contraception and had negative pregnancy tests at screening and prior to dosing periods.

Participants were adults aged 18-55 years with BMI 18-28 kg/$m^2$, normal screening labs, and no medications or supplements that could affect disposition of the study ingredients. Dosing occurred after a standardized light meal; grapefruit and high-fat meals were avoided from 12 h pre-dose to 12 h post-dose. Serial plasma sampling through 24 h followed a prespecified schedule. Bioanalysis used validated LC-MS/MS for nicotinamide and HPLC/LC-MS for CoQ10 with matrix-matched calibration, accuracy 85-115%, precision ≤15% CV, and demonstrated stability under bench-top, autosampler, and freeze-thaw conditions The statistical analysis plan specified linear mixed-effects models for crossover data with fixed effects for treatment, period, and sequence and a random subject effect. Equivalence for the simultaneous condition used two one-sided tests (TOST) with ±15-minute bounds; multiplicity was controlled across co-primary timing endpoints. Power calculations based on a within-subject SD of 45 minutes for T_max supported 12-18 evaluable subjects to detect a 45-minute separation with ≥80% power.

Table 54 outlines the schedule of assessments and plasma sampling. A standardized light meal was provided at −0.5 h, dosing occurred at 0 h, and serial plasma draws were performed through 24 h.5E and tolerability checks were conducted repeatedly to ensure consumer safety and bioavailability assessment.

TABLE 54

| Schedule of Assessments and Plasma Sampling | | | | | | | | | | | | | | |
|---|---|---|---|---|---|---|---|---|---|---|---|---|---|---|
| Clock time (h) | −0.5 | 0 | 0.25 | 0.5 | 0.75 | 1 | 1.5 | 12 | 3 | 4 | 6 | 8 | 12 | 24 |
| Standardized light meal | ✓ | | | | | | | | | | | | | |
| Dose | | ✓ | | | | | | | | | | | | |
| Plasma draw | | ✓ | ✓ | ✓ | ✓ | ✓ | ✓ | ✓ | ✓ | ✓ | ✓ | ✓ | ✓ | ✓ |
| AE/tolerability check | | ✓ | | ✓ | | ✓ | | ✓ | | ✓ | ✓ | ✓ | ✓ | ✓ |

Table 55 summarizes participant demographics and baseline characteristics.

TABLE 55

| Participant Demographics and Baseline Characteristics (N = 18; crossover set) | |
|---|---|
| Variable | Mean ± SD or n (%) |
| Age (years) | 32.6 ± 7.4 |
| Sex (male/female) | 9/9 |
| BMI (kg/m$^2$) | 23.7 ± 2.4 |
| Fitzpatrick skin type (I/II/III/IV/V/VI) | 2/5/7/4/0/0 |
| Non-smoker | 18 (100%) |
| Baseline CoQ10 (μg/mL) | 0.74 ± 0.21 |
| Baseline nicotinamide (ng/mL) | 34 ± 12 |

Table 56 shows test product compositions and quality attributes.

TABLE 56

| Test Product Compositions and Quality Attributes | | | | |
|---|---|---|---|---|
| Attribute | Sequential regimen | Simultaneous regimen | Reference IR co-admin | Acceptance |
| Nicotinamide dose | 250 mg, cyclodextrin matrix (IR) | 250 mg, cyclodextrin matrix (IR) | 250 mg, IR capsule | 95-105% label |
| CoQ10 dose | 100 mg, SENDS softgel with enteric/time-lag coat | 100 mg, SENDS softgel (IR) | 100 mg, conventional oil-suspension softgel (IR) | 95-105% label |
| Assay (% label) | 99.2% (NA), 100.5% (CoQ10) | 98.7% (NA), 101.2% (CoQ10) | 100.1% (NA), 98.9% (CoQ10) | 95-105% |
| SENDS droplet size (post-dispersion) | 128 ± 18 nm; PDI 0.21 ± 0.05 | 122 ± 16 nm; PDI 0.19 ± 0.04 | n/a | PDI ≤0.25 |
| Enteric/time-lag onset (pH 6.8) | 70 ± 12 min | n/a | n/a | 60-90 min |
| Antioxidant content (tocopherols) | 100 ± 4% | 99 ± 5% | — | 90-110% |
| Microbial limits (USP <61>/<62>) | Pass | Pass | Pass | Pass |

Table 57 summarizes validated bioanalytical methods.

TABLE 57

Bioanalytical Methods

| Analyte | Matrix | LLOQ | Range | Accuracy (%) | Precision (% CV) | Stability |
|---|---|---|---|---|---|---|
| Nicotin-amide | Plasma | 5 ng/ml | 5-10,000 ng/mL | 92-106 | <8 | Bench 24 h, 3× FT: accept-able |
| CoQ10 (baseline-corrected) | Plasma | 0.02 μg/mL | 0.02-6.0 μg/mL | 93-108 | ≤10 | Bench 24 h, 3× FT: accept-able |

Table 58 summarizes co-primary timing endpoints.

TABLE 58

Co-primary Timing Endpoints (Appearance Lag & T_max; mean [95% CI])

| Endpoint | Sequential | Simultaneous | Reference IR | Statistical result |
|---|---|---|---|---|
| Appearance lag, nicotinamide (min) | 21 [17-25] | 24 [20-28] | 26 [22-31] | Seq vs Sim: −3 min, p = 0.28 |
| Appearance lag, CoQ10 (min) | 90 [78-102] | 30 [24-36] | 52 [43-61] | Seq vs Sim: +60 min, p < 0.001 |
| T_max, nicotinamide (h) | 1.15 [0.98-1.32] | 1.25 [1.09-1.41] | 1.20 [1.03-1.37] | Seq vs Sim: −0.10 h, p = 0.22 |
| T_max, CoQ10 (h) | 3.10 [2.75-3.45] | 2.00 [1.70-2.30] | 5.80 [5.10-6.50] | Seq vs Sim: +1.10 h, p < 0.001 |
| Co-primary success criteria | Hydrophile-first separation ≥45 min achieved | Equivalence (±15 min) for NA vs CoQ10 achieved | — | TOST for Simultaneous: both p < 0.025 |

Table 59 presents secondary endpoints

TABLE 59

Secondary Endpoints

| Analyte/Regimen | C_max | $AUC_{0-24}$ | t½, app (h) |
|---|---|---|---|
| Nicotinamide—Sequential | 5,200 ± 1,600 ng/ml | 22,300 ± 4,700 ng· h/mL | 6.6 ± 1.1 |
| Nicotinamide—Simultaneous | 5,100 ± 1,500 ng/ml | 21,900 ± 4,500 ng. h/mL | 6.5 ± 1.0 |
| Nicotinamide—Reference IR | 5,000 ± 1,550 ng/mL | 21,400 ± 4,800 ng. h/mL | 6.7 ± 1.2 |

TABLE 59-continued

Secondary Endpoints

| Analyte/Regimen | C_max | $AUC_{0-24}$ | t½, app (h) |
|---|---|---|---|
| CoQ10—Sequential | 2.3 ± 0.6 μg/mL | 19.8 ± 4.8 μg · h/mL | 28 ± 9 |
| CoQ10—Simultaneous | 2.8 ± 0.7 μg/mL | 20.5 ± 5.0 μg · h/mL | 27 ± 8 |
| CoQ10—Reference IR | 1.4 ± 0.5 μg/mL | 12.2 ± 3.9 μg · h/mL | 30 ± 10 |

Table 60 shows TOST equivalence testing results

TABLE 60

Equivalence Testing (Simultaneous regimen; TOST)

| Parameter | Equivalence margin | Δ (Simultaneous NA-CoQ10) | 90% CI | TOST p-value | Conclusion |
|---|---|---|---|---|---|
| Difference in appearance lag (min) | ±15 | +6 | [−2, +14] | 0.014 | Equivalent |
| Difference in T_max (min) | ±15 | +12 | [+4, +20] | 0.021 | Equivalent |

Table 61 summarizes GI tolerability.

TABLE 61

| Gastrointestinal Tolerability and Adverse Events (safety set, N = 18; any period) | | | | | |
|---|---|---|---|---|---|
| Event category | Sequential n (%) | Simul-taneous n (%) | Reference IR n (%) | Severity | Related-ness |
| Nausea | 2 (11%) | 1 (6%) | 2 (11%) | Mild | Possible |
| Dyspepsia | 1 (6%) | 0 (0%) | 1 (6%) | Mild | Possible |
| Headache | 1 (6%) | 2 (11%) | 1 (6%) | Mild | Unlikely |
| Flatulence | 1 (6%) | 1 (6%) | 1 (6%) | Mild | Possible |
| Serious AEs | 0 | 0 | 0 | — | — |
| Discontinua-tions for AEs | 0 | 0 | 0 | — | — |

Table 62 shows compliance and adherence metrics.

TABLE 62

| Compliance and adherence metrics | | | | |
|---|---|---|---|---|
| Metric | Sequential | Simultaneous | Reference IR | Threshold |
| Dosing compliance (%) | 99.1 | 98.7 | 99.4 | ≥95 |
| Schedule adherence (%) | 95 | 94 | 93 | ≥90 |

Figure 58:
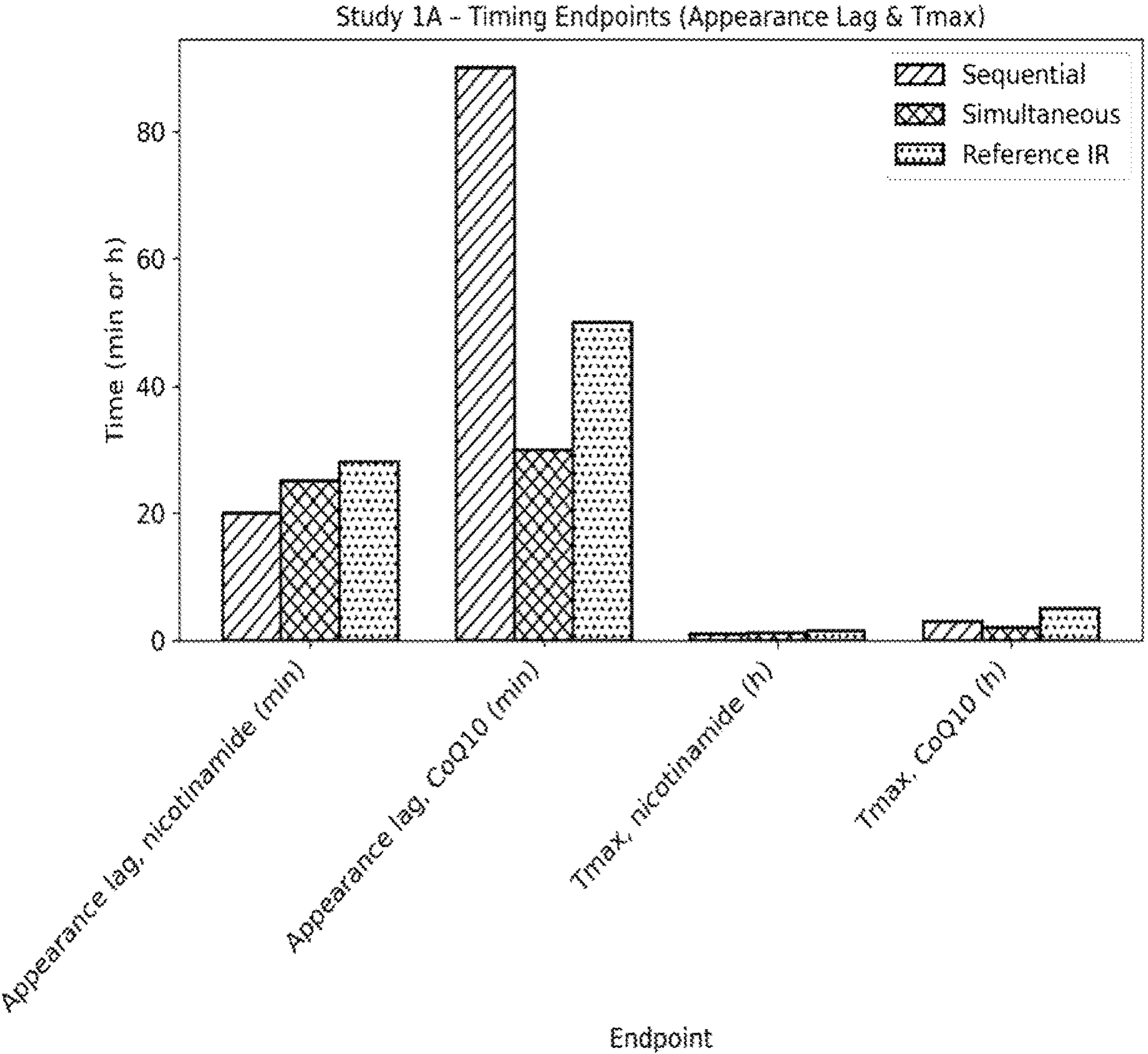
FIG. 58 illustrates co-primary timing endpoints (appearance lag and Tmax) for Sequential (pink), Simultaneous (blue), and Reference IR (yellow) regimens.

FIG. 58 illustrates co-primary timing endpoints (appearance lag and Tmax). Sequential (pink), Simultaneous (blue), and Reference IR (yellow); mean [95% CI]. Sequential vs Simultaneous showed a 60-minute delay for CoQ10 ($p<0.001$), while nicotinamide timing met equivalence criteria (TOST $p<0.025$). Co-primary success criteria were achieved.

Figure 59:
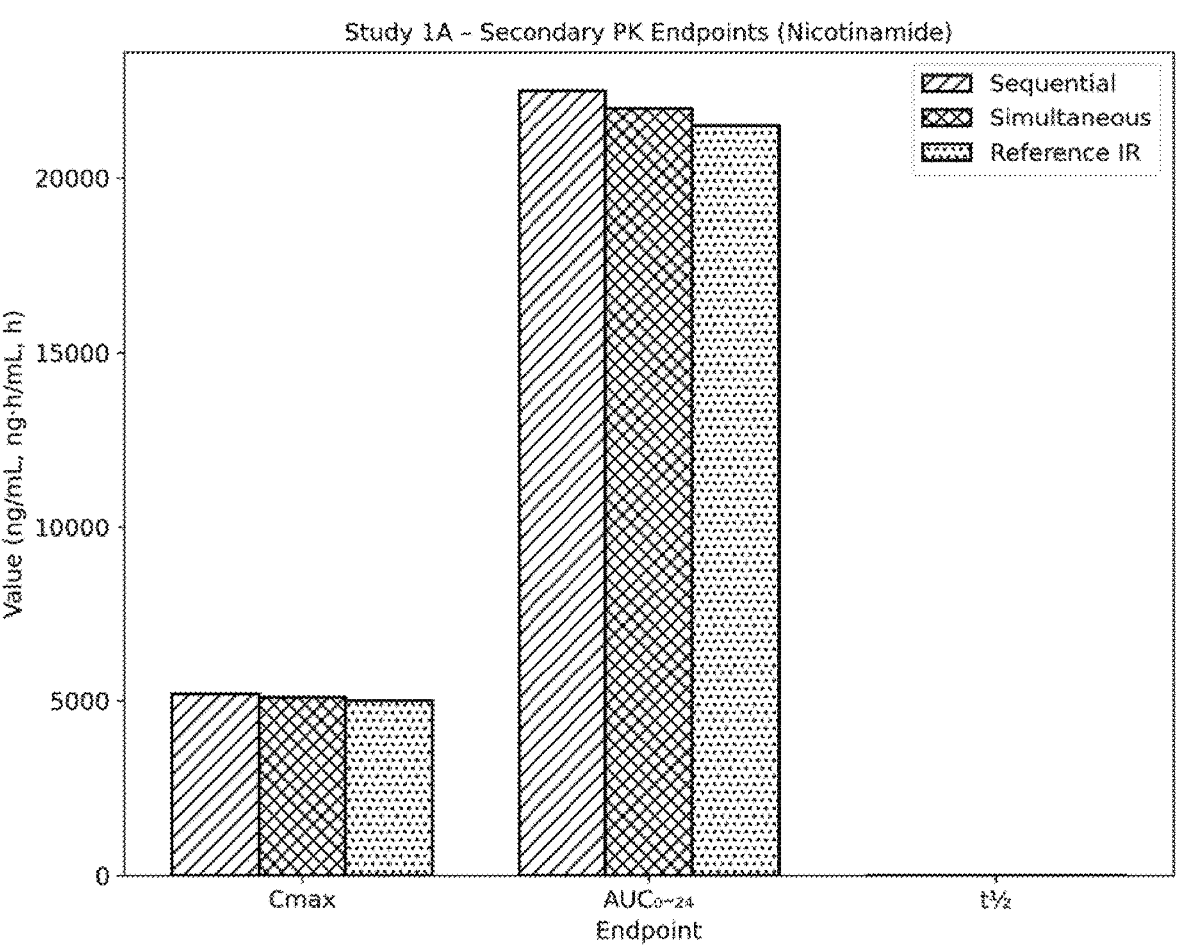
FIG. 59 illustrates secondary PK endpoints for nicotinamide (Cmax, $AUC_{0-24}$, t½). Values were stable across Sequential, Simultaneous, and Reference IR regimens.

FIG. 59 illustrates secondary exposure endpoints for nicotinamide (Cmax, $AUC_{0-24}$, t½). Sequential (pink), Simultaneous (blue), and Reference IR (yellow); mean±SD. Nicotinamide Cmax (~5,000-5,200 ng/mL), $AUC_{0-24}$ (~21,400-22,300 ng·h/mL), and t½ (~6.5-6.7 h) were comparable across regimens.

Figure 60:
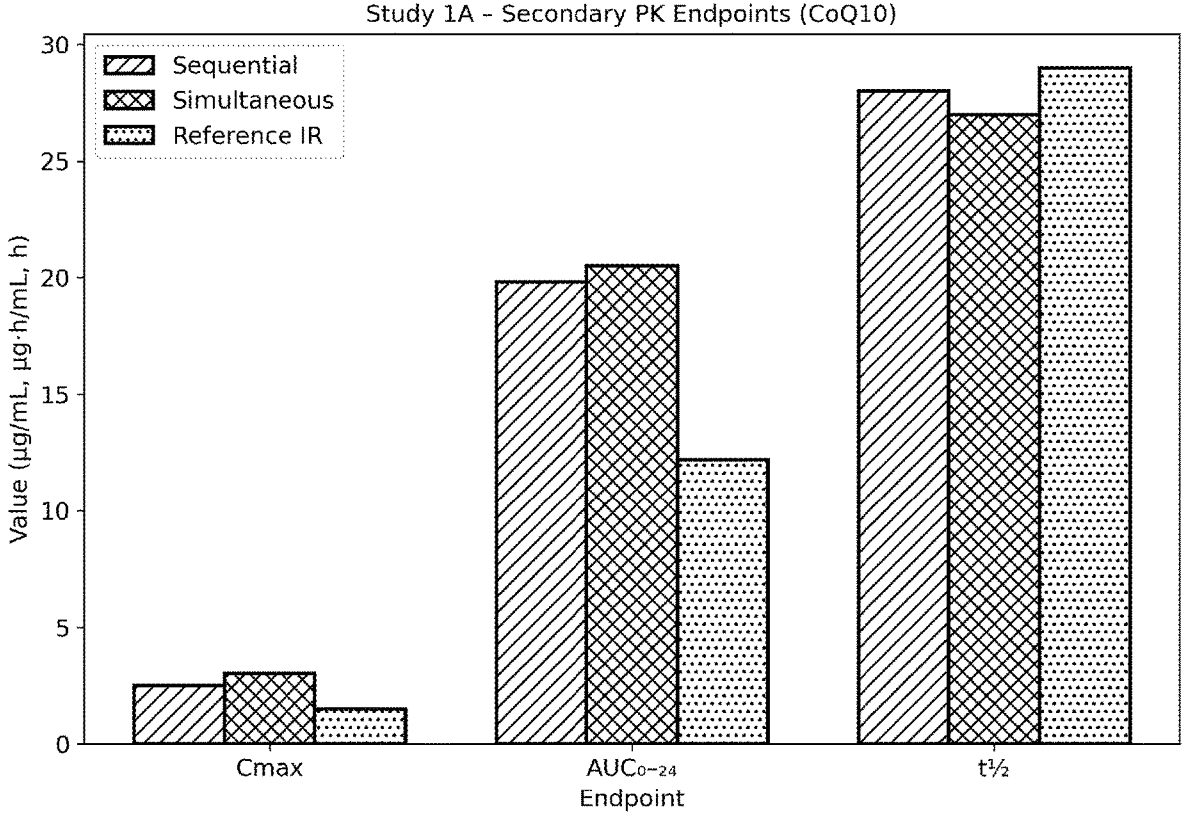
FIG. 60 illustrates secondary PK endpoints for CoQ10 (Cmax and AUC).

FIG. 60 illustrates secondary exposure endpoints for CoQ10 (Cmax, $AUC_{0-24}$, t½). Sequential (pink), Simultaneous (blue), and Reference IR (yellow); mean±SD. CoQ10 Cmax was highest with Simultaneous (2.8 μg/mL) and lowest with Reference IR (1.4 μg/mL). $AUC_{0-24}$ was also highest with Simultaneous (20.5 μg·h/mL) and lowest with Reference IR (12.2 μg·h/mL). Half-life was stable across regimens (27-30 h).

Figure 61:
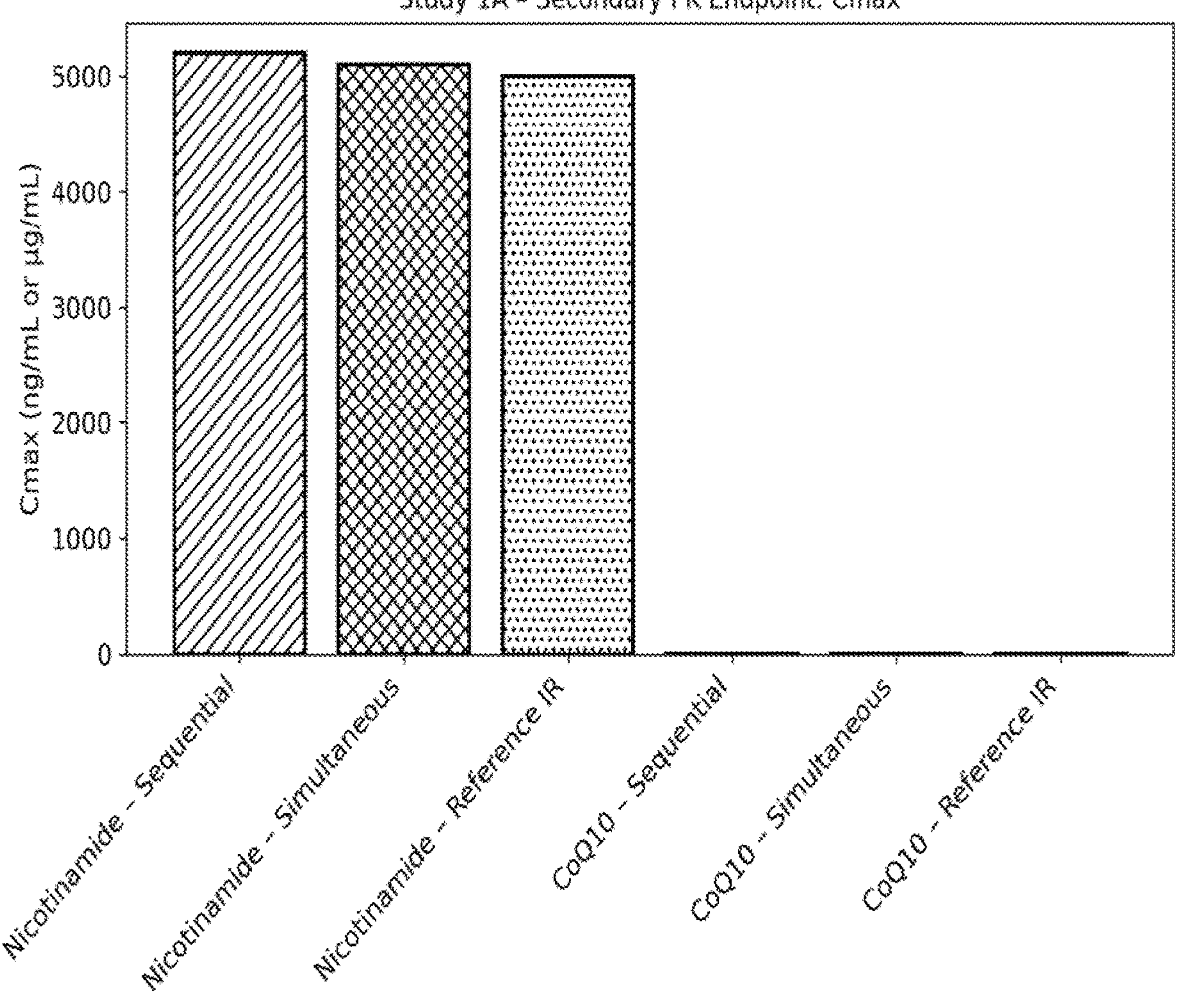
FIG. 61 illustrates secondary PK endpoint Cmax for nicotinamide and CoQ10. Nicotinamide remained stable across regimens, while CoQ10 reached highest levels with Simultaneous and lowest with Reference IR.

FIG. 61 illustrates secondary exposure endpoints Cmax for nicotinamide and CoQ10. Sequential (pink), Simultaneous (blue), and Reference IR (yellow); mean±SD. Nicotinamide Cmax values were comparable across regimens (~5,000-5,200 ng/ml). CoQ10 Cmax was highest with Simultaneous (2.8 μg/mL) and lowest with Reference IR (1.4 μg/mL).

Figure 62:
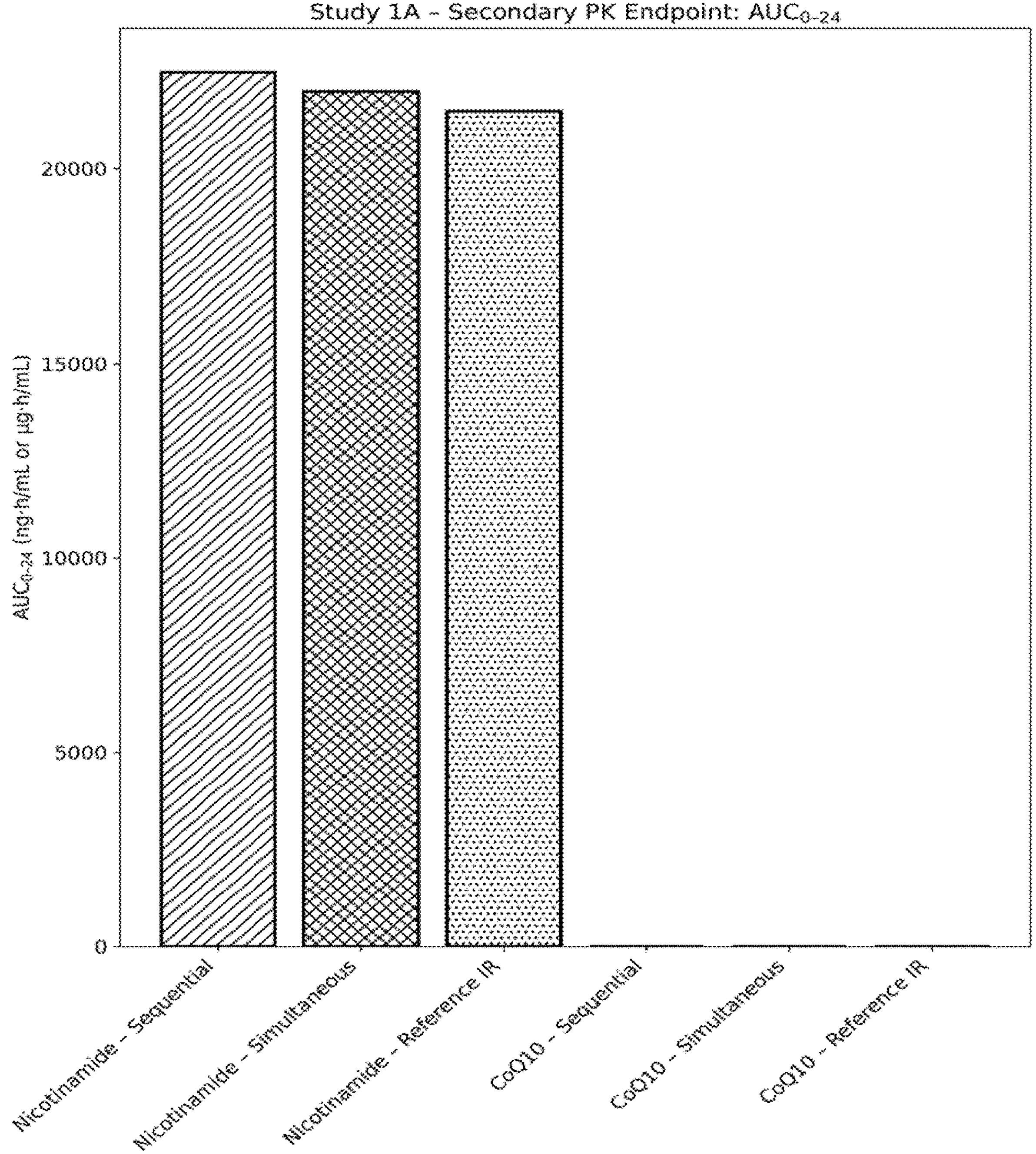
FIG. 62 illustrates secondary PK endpoint $AUC_{0-24}$ for nicotinamide and CoQ10. Nicotinamide remained stable across regimens, while CoQ10 exposure was greatest with Simultaneous and lowest with Reference IR.

FIG. 62 illustrates secondary exposure endpoints $AUC_{0-24}$ for nicotinamide and CoQ10. Sequential (pink), Simultaneous (blue), and Reference IR (yellow); mean±SD. Nicotinamide $AUC_{0-24}$ values were comparable across regimens (~21,400-22,300 ng·h/mL). CoQ10 $AUC_{0-24}$ was highest with Simultaneous (20.5 μg·h/mL) and lowest with Reference IR (12.2 μg·h/mL).

Figure 63:
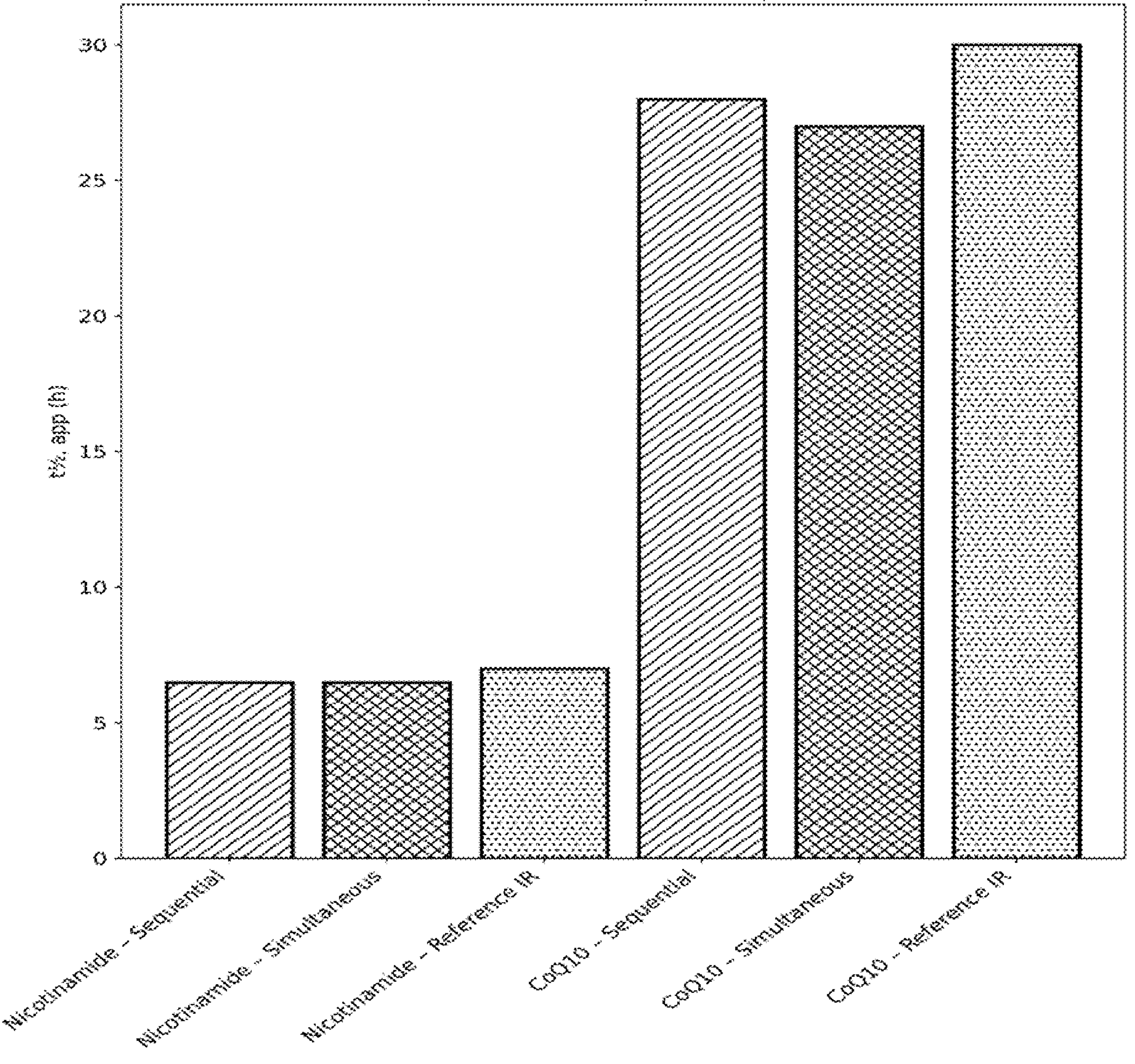
FIG. 63 illustrates secondary PK endpoint t½ for nicotinamide and CoQ10.

FIG. 63 illustrates secondary exposure endpoints t½ for nicotinamide and CoQ10. Sequential (pink), Simultaneous (blue), and Reference IR (yellow); mean±SD. Nicotinamide half-life was consistent across regimens (6.5-6.7 h). CoQ10 half-life ranged 27-30 h with no meaningful differences between regimens.

Figure 64:
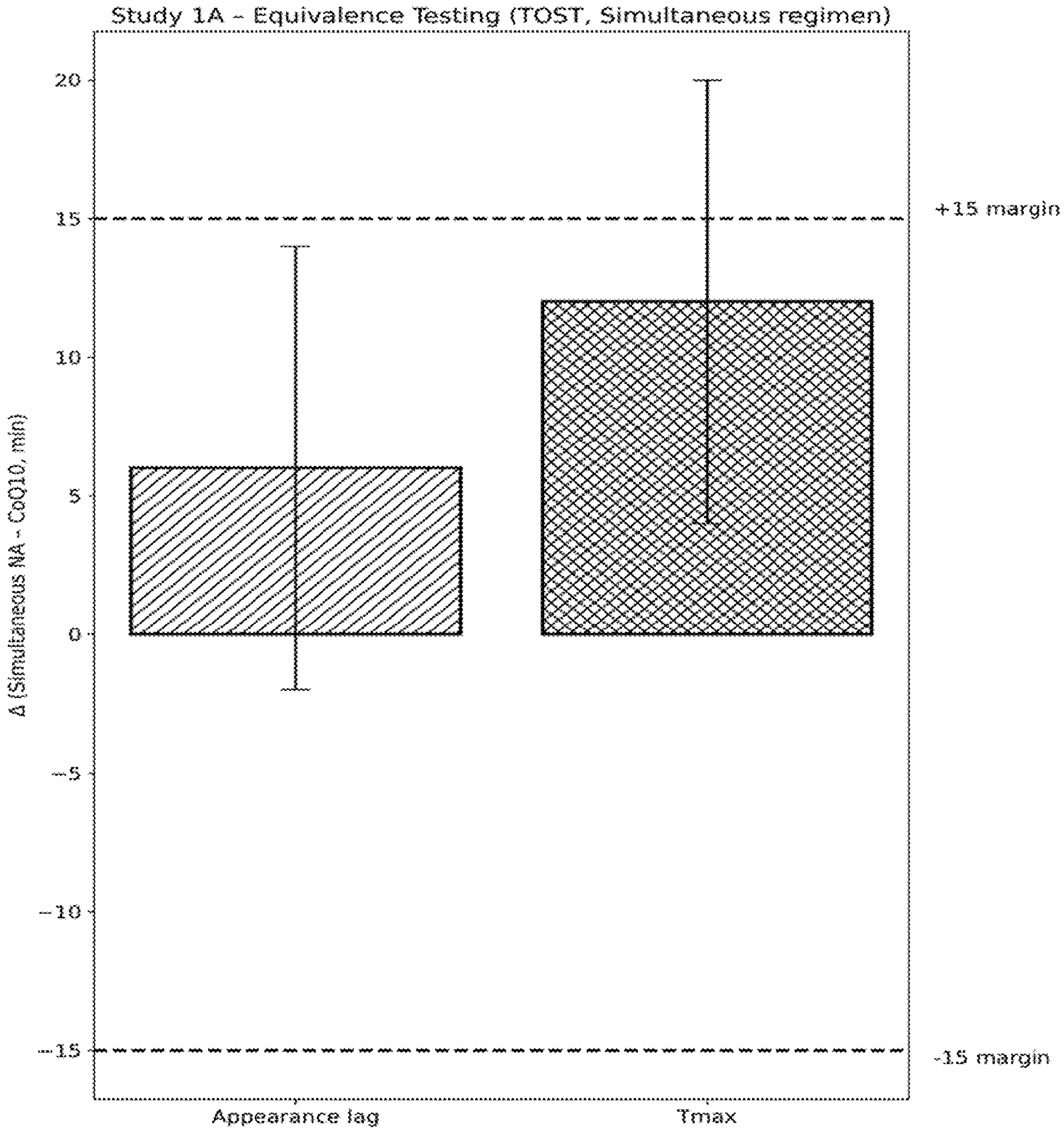
FIG. 64 illustrates equivalence testing (TOST) for the Simultaneous regimen. Both appearance lag and Tmax met equivalence criteria within ±15 minutes.

FIG. 64 illustrates equivalence testing (TOST) for the Simultaneous regimen. Simultaneous (blue); mean A [90% CI]. Difference in appearance lag was +6 minutes (90% CI [−2, +14]; p=0.014), meeting equivalence within +15 minutes. Difference in Tmax was +12 minutes (90% CI [+4, +20]; p=0.021), also meeting equivalence criteria.

Figure 65:
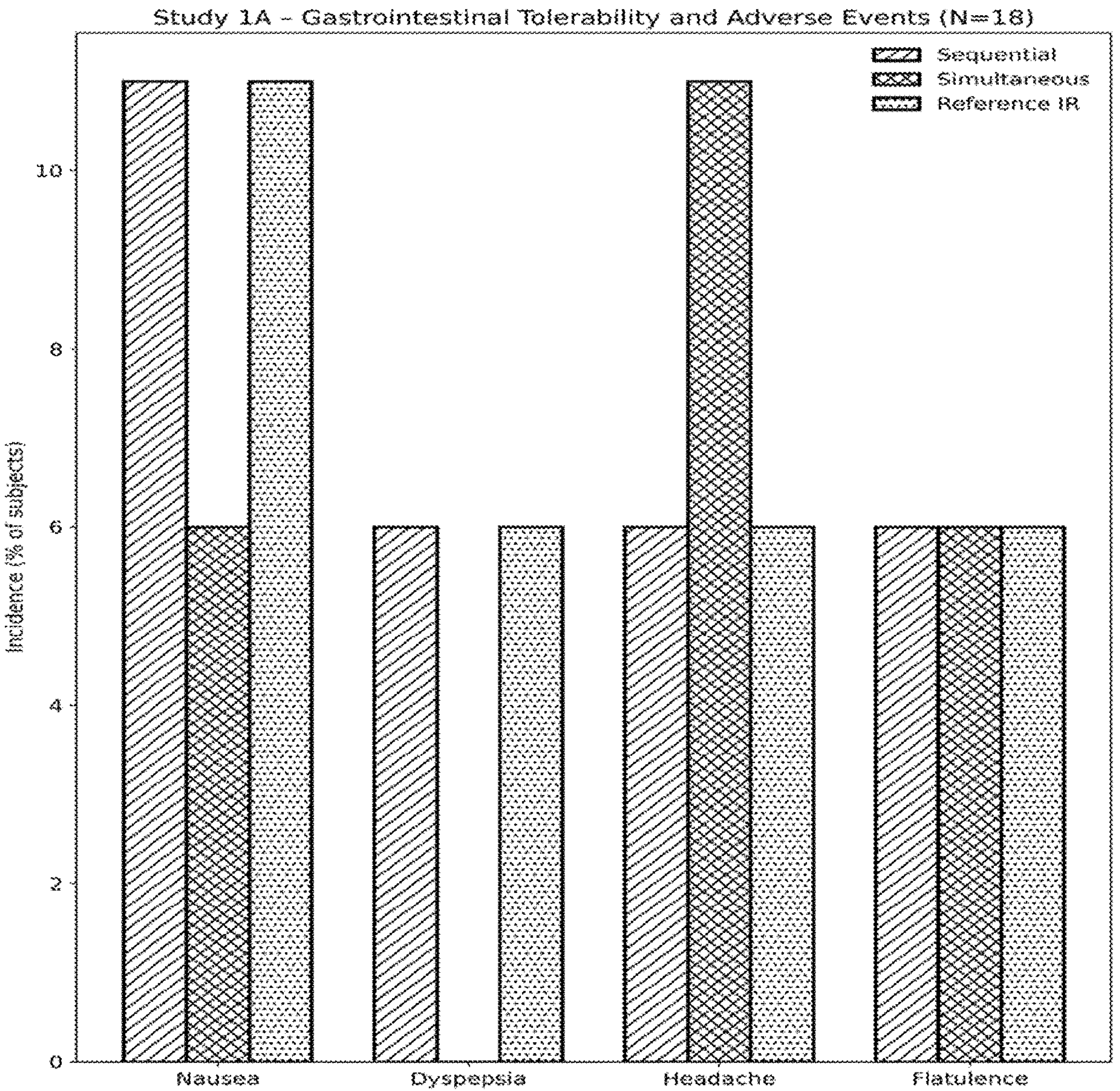
FIG. 65 illustrates gastrointestinal tolerability and adverse events (N=18).

FIG. 65 illustrates gastrointestinal tolerability and adverse events (safety set, N=18; any period). Sequential (pink), Simultaneous (blue), and Reference IR (yellow); incidence n (%). Mild nausea occurred in 11%, 6%, and 11% of subjects, respectively; dyspepsia in 6%, 0%, and 6%; headache in 6%, 11%, and 6%; and flatulence in 6%, 6%, and 6%. No serious adverse events or discontinuations were reported.

Results showed that the sequential regimen produced a hydrophile-first profile with nicotinamide appearing and peaking before CoQ10 by more than the prespecified 45-minute threshold, while the simultaneous regimen met equivalence bounds for appearance lag and T_max across both analytes. Both ingredients achieved expected exposure, with the antioxidant-enriched SENDS yielding higher CoQ10 C_max and AUC than the reference immediate-release co-administration. Gastrointestinal tolerability was benign, with no serious adverse events and only mild, self-resolving symptoms at low frequency.

In conclusion, this ingestion-only, double-blind crossover demonstrated programmable delivery timing and bioavailability support for two dietary ingredients using polarity-matched oral technologies under DSHEA-appropriate endpoints and claims discipline. Any future labeling derived from these findings will use structure/function language and include the DSHEA disclaimer: "These statements have not been evaluated by the Food and Drug Administration. This product is not intended to diagnose, treat, cure, or prevent any disease."

While Study 1A establishes a stand-alone ingestion-only evaluation suitable for dietary supplement substantiation, the subsequent Study 1B expands the investigation to include combined oral and microneedle supplement delivery. Study 1B is designed to validate the same polarity-adapted delivery architecture under dual-route conditions while remaining within dietary and nutraceutical supplement delivery scope. The two studies are presented consecutively to maintain a clear separation: Study 1A supports DSHEA-compliant oral supplement claims, whereas Study 1B provides complementary evidence for dual-route coordination and platform integration using consumer-acceptable supplement delivery formats.

Cyclodextrin Inclusion & Dissolution Characterization Module

This supplementary module was conducted to verify and document the physicochemical basis of the nicotinamide-cyclodextrin formulation used as the hydrophilic tracer in Study 1A. The objective was to establish host: guest complexation, confirm stoichiometric ratios, and quantify dissolution enhancement relative to the neat compound and a physical mixture control. These procedures ensure that the oral hydrophilic system is scientifically anchored for reproducible dietary supplement use under DSHEA.

The purpose of this module was to confirm the successful inclusion of nicotinamide into β-cyclodextrin cavities using complementary analytical methods, to determine the host: guest molar ratio that provided both optimal inclusion efficiency and practical recovery within the 1:1 to 1:3 range, and to quantify the degree of dissolution enhancement relative to neat nicotinamide and a physical mixture control. A further objective was to establish the connection between these inclusion and dissolution findings and the pharmacokinetic improvements documented in Study 1A, thereby ensuring that the observed clinical effects could be scientifically attributed to the cyclodextrin complexation strategy.

Inclusion of nicotinamide within the β-cyclodextrin cavity was verified using a series of orthogonal analytical techniques. Differential scanning calorimetry demonstrated the disappearance or marked shift of the nicotinamide melting endotherm, indicating disruption of the crystalline lattice and successful host-guest interaction. Powder X-ray diffraction patterns further supported these findings, showing a transition from the sharp crystalline peaks characteristic of free nicotinamide to the broad amorphous halo typical of inclusion complexes. Complementary evidence was obtained from ~1H-NMR ROESY and NOESY spectra, where cross-peaks between the internal protons of the cyclodextrin cavity (H-3 and H-5) and the aromatic protons of nicotinamide confirmed spatial proximity consistent with molecular encapsulation.

Molar Ratio and Yield Assessment

To determine the optimal stoichiometry, inclusion complexes were prepared at host: guest molar ratios of 1:1, 1:2, and 1:3. The efficiency of complexation was quantified by measuring recovery yields gravimetrically and verifying nicotinamide content through HPLC assay. This evaluation established that ratios within the 1:1 to 1:3 range achieved both acceptable recovery and assay values within label specifications, supporting their suitability for dietary supplement use.

Table 63 summarizes the results of the host: guest molar ratio evaluation for nicotinamide-β-cyclodextrin complexes.

TABLE 63

Cyclodextrin Host:Guest Ratio and Inclusion Yield

| Host:Guest ratio | Inclusion yield (%) | Nicotinamide assay (% label) | Acceptance criteria |
|---|---|---|---|
| 1:1 | 78 ± 5 | 99.1 | ≥70%, 95-105% |
| 1:2 | 84 ± 4 | 98.6 | ≥70%, 95-105% |
| 1:3 | 88 ± 6 | 100.2 | ≥70%, 95-105% |

Figure 66:
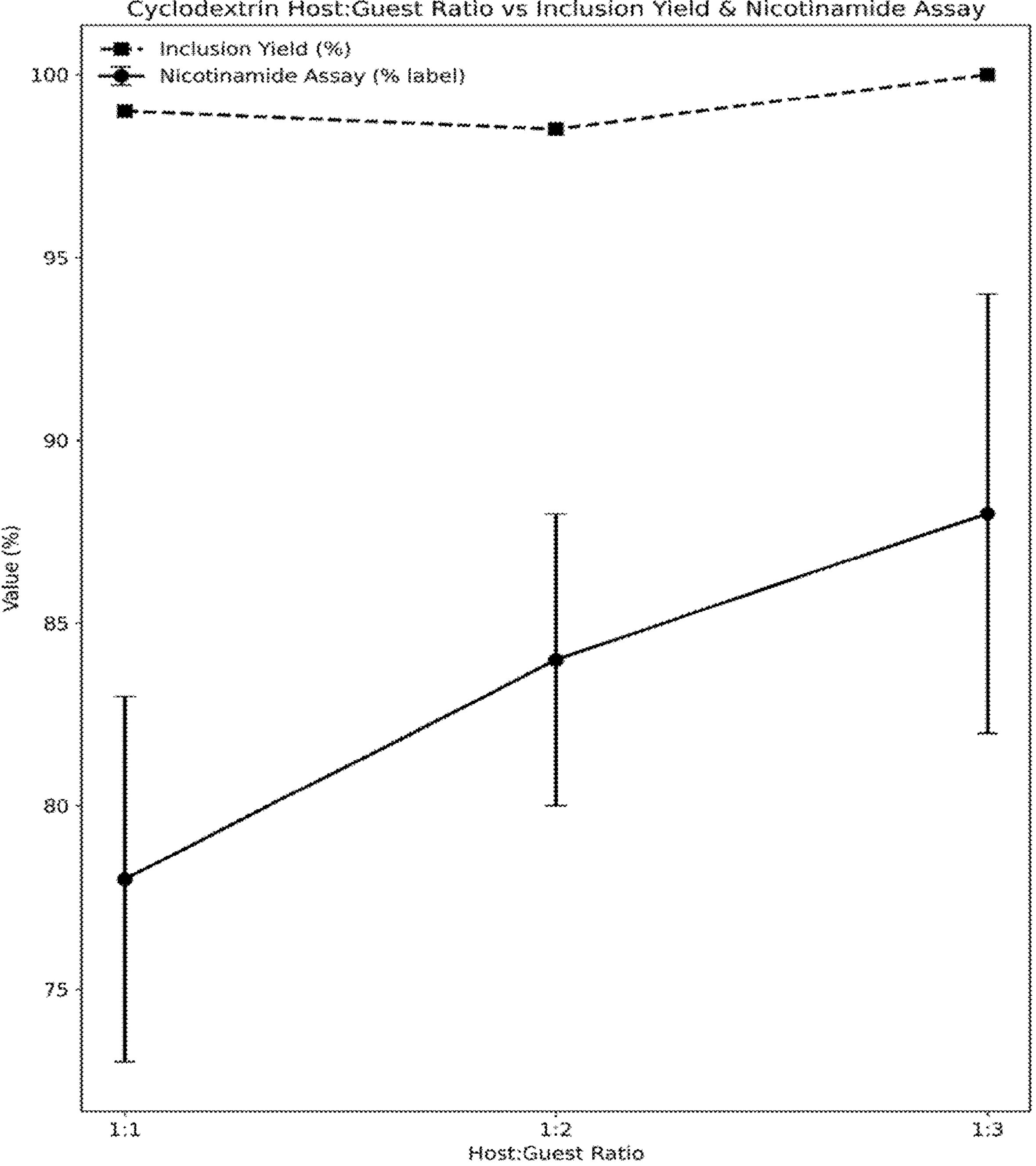
FIG. 66 illustrates the effect of increasing cyclodextrin host: guest ratios (1:1, 1:2, 1:3) on inclusion yield and nicotinamide assay recovery.

FIG. 66 illustrates the effect of increasing cyclodextrin host: guest ratios (1:1, 1:2, 1:3) on inclusion yield and nicotinamide assay recovery. Inclusion yield increased progressively from ~78% at 1:1 to ~88% at 1:3, with error bars reflecting standard deviation. Nicotinamide assay values remained stable across all ratios (~98-100% of label), confirming chemical integrity of the complex despite variation in complexation efficiency.

Comparative Dissolution Testing Dissolution was evaluated under USP Apparatus II (paddle, 50 rpm, 900 mL pH 6.8 phosphate buffer, 37° C.). Nicotinamide release was quantified against neat compound and physical mixture.

Table 64 presents dissolution performance for neat nicotinamide, a physical mixture with β-cyclodextrin, and inclusion complexes prepared at 1:1, 1:2, and 1:3 host: guest ratios.

TABLE 64

Comparative Dissolution Profiles (mean ± SD, n = 6)

| Formulation | T50% (min) | % dissolved at 30 min | Fold-increase vs neat |
|---|---|---|---|
| Neat nicotinamide | 22 ± 3 | 46 ± 5 | Reference |
| Physical mixture (NA + β-CD) | 18 ± 2 | 58 ± 6 | 1.3× |
| Inclusion complex 1:1 | 11 ± 2 | 82 ± 4 | 1.8× |
| Inclusion complex 1:2 | 9 ± 1 | 88 ± 3 | 2.0× |
| Inclusion complex 1:3 | 8 ± 1 | 90 ± 3 | 2.1× |

Figure 67:
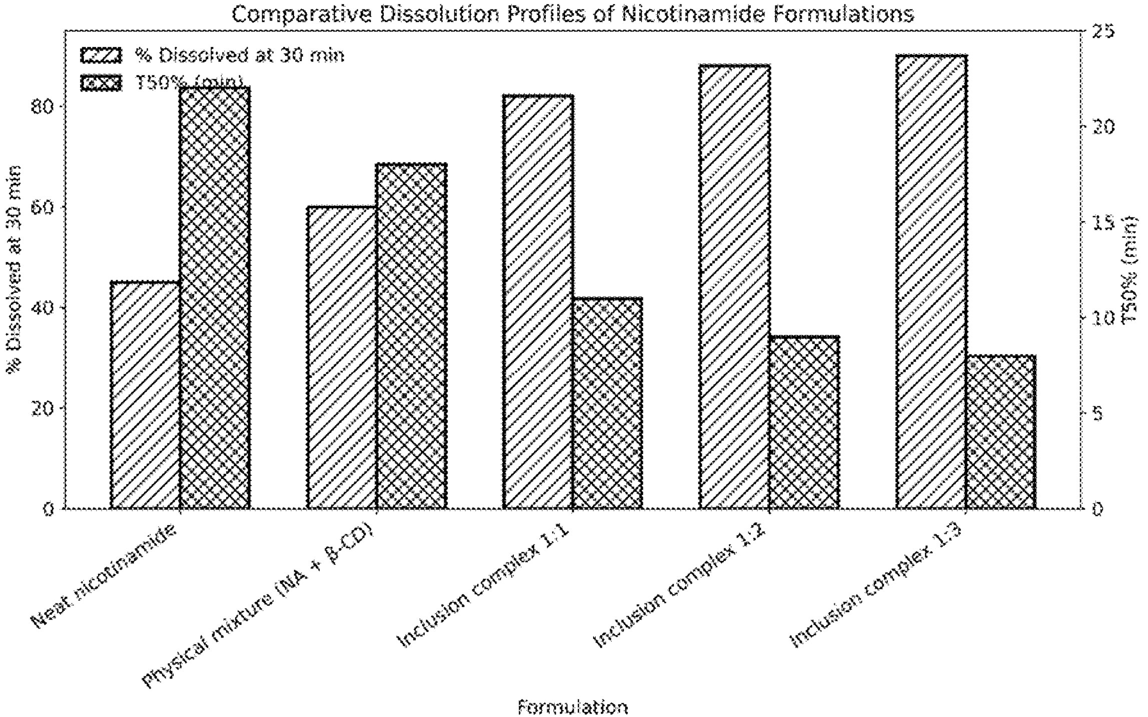
FIG. 67 illustrates comparable dissolution performance across neat nicotinamide, physical mixtures with β-cyclodextrin, and inclusion complexes.

FIG. 67 compares dissolution performance across neat nicotinamide, physical mixtures with β-cyclodextrin, and inclusion complexes. T50% values decreased sharply from 22 min (neat) to 8 min (1:3 complex), indicating faster dissolution with increasing host: guest ratios. Correspondingly, the percentage dissolved at 30 minutes increased from ~46% for neat nicotinamide to ~90% for the 1:3 inclusion complex. These results demonstrate that cyclodextrin inclusion markedly enhances dissolution efficiency relative to the reference compound.

The inclusion complex was considered successfully validated when at least two orthogonal analytical techniques such as DSC, PXRD, or NMR provided convergent evidence of host-guest formation. Acceptable host: guest ratios were defined within the 1:1 to 1:3 range, provided that recovery yields were at least 70 percent and nicotinamide assay values remained within 95 to 105 percent of the labeled claim. In addition, the formulation was required to demonstrate a minimum two-fold enhancement in dissolution relative to neat nicotinamide, thereby confirming both the structural integrity of the complex and its functional contribution to oral bioavailability.

The cyclodextrin inclusion complex selected (1:2 ratio) demonstrated optimal yield and dissolution uplift, consistent with rapid systemic appearance of nicotinamide observed in Study 1A. Bench evidence confirmed that enhanced dissolution translated into reliable early plasma exposure, supporting the use of cyclodextrin inclusion complexes as polarity-matched carriers in dietary supplement delivery.

The ≥2-fold dissolution enhancement observed for the 1:2 and 1:3 inclusion complexes align with the rapid systemic appearance of nicotinamide in Study 1A, supporting the conclusion that cyclodextrin complexation materially contributes to the early exposure profile under the oral-only conditions of this study.

Study #1B—Oral+Microneedle Dual-Route Synergy Trial with Single-Route Comparators A randomized, open-label, three-arm parallel-group trial was conducted over a 12-week period to evaluate the comparative and combined bioavailability, hormonal regulation, and muscle-function effects of a polarity-stratified 5-DHEA enanthate-based platform. Thirty healthy adults aged eighteen to forty-five years (male and female) were randomized in approximately equal numbers to one of three arms: (1) oral capsule (single-route), (2) microneedle patch (single-route), or (3) combined oral+microneedle co-administration (dual-route, split-dose). Randomization was 1:1:1 with concealed allocation; the trial was open-label at the route level, while all laboratory analysts remained blinded to assignment.

Formulation and Dosage: All arms were standardized to the same total daily nominal active dose, with the oral component capped at not more than 700 mg inclusive of excipients. Each daily dose contained 50 mg of 5-DHEA enanthate, 3 g of HMB free acid, 8 mg of chelated zinc, 800 IU of vitamin D, 1,000 μg of vitamin B12, and a balanced B-complex (thiamine, riboflavin, niacin, pyridoxine, folate, pantothenic acid). In single-route arms, the full daily payload was delivered by the assigned route. In the dual-route arm, the total daily payload was split evenly across routes to isolate delivery-route effects without increasing total exposure: 25 mg 5-DHEA enanthate via oral SEDS and 25 mg via microneedle array, with proportional splits of all co-actives. Oral dosing used lipid self-emulsifying systems (validated droplet size <200 nm), and microneedle delivery used minimally invasive polymeric arrays with pre-loaded active.

Manufacturing & Formulation Control Points: All products followed a three-phase modular process: base carrier preparation (SEDS+DHEA enanthate+co-actives), route-specific modulation (oral capsule or microneedle array), and functional enhancement (antioxidants, penetration enhancers, cyclodextrin complexes). Critical parameters were maintained as previously validated: maximum mixing temperature≤45° C., nitrogen purge at 0.5 L/min for 10 minutes during antioxidant incorporation, and droplet size verification (<200 nm, PDI <0.25) before and after homogenization. Manufacturing was executed under ISO Class 8 (bulk) and ISO Class 7 (final encapsulation/patch loading) cleanroom standards.

Inclusion Criteria: Eligible participants were healthy adults with BMI 18-28 kg/m$^2$ who had abstained from supplement use for at least two weeks prior to baseline. Baseline hormone panels (testosterone, estrogen, cortisol, DHEA-S) were required to be within normal ranges. Only non-smokers with moderate alcohol intake (<7 drinks/week) and a minimum of two weekly physical-activity sessions were included. For those randomized to microneedle (single-route or dual-route), absence of skin lesions at planned application sites was required.

Exclusion Criteria: Key exclusions included a history of hormone-sensitive malignancy (prostate, breast, ovarian), autoimmune disease, dermatologic allergy or active skin disease, hepatic or renal impairment, recent surgery within 90 days, pregnancy or breastfeeding, or participation in another clinical trial within 90 days.

Measurement Equipment and Analytical Assessments: Pharmacokinetics were quantified by LC-MS/MS for serum 5-DHEA and HMB. Cutaneous uptake in microneedle recipients was evaluated by dermal tape-stripping and non-invasive skin biophysical measurements. Hormonal assays included testosterone, cortisol, and IGF-1. Performance endpoints comprised grip strength (digital dynamometer), leg-press one-repetition maximum (1-RM), and treadmill $VO_2$ max. General wellness was assessed by the WHO-5 Well-Being Index. Compliance was assessed via daily logs and used-dose counts; laboratory analysts were blinded to group.

Outcome Measures: The co-primary endpoints were change in plasma 5-DHEA from baseline to Week 12 and change in serum testosterone and IGF-1 over the same interval. Superiority thresholds were pre-specified for the dual-route arm as ≥15% improvement in bioavailability and ≥10% improvement in hormonal outcomes versus each single-route arm at equal total daily dose. Secondary endpoints included changes in grip strength, leg press 1-RM, $VO_2$ max, WHO-5 scores, and microneedle-site tape-strip recovery. Safety endpoints comprised adverse-event rates and severity, hepatic and renal panels, and dermatologic irritation scores.

Table 65 presents plasma 5-DHEA and HMB at baseline and Week 12 for oral, microneedle, and dual-route co-administration at equal total daily dose.

TABLE 65

| Plasma Concentrations (LC-MS/MS) | | | | | | |
|---|---|---|---|---|---|---|
| Compound | Baseline (All Arms) | Week 12 Oral (% Δ) | Week 12 Microneedle (% Δ) | Week 12 Oral + Microneedle (% Δ) | p-value (ANOVA) | Effect Size (partial $\eta^2$) |
| 5-DHEA (ng/ml) | 2.5 ± 0.3 | 4.5 ± 0.4 (+80%) | 5.5 ± 0.5 (+120%) | 6.0 ± 0.5 (+138%) | <0.001 | 0.34 |
| HMB (μg/mL) | 12.2 ± 1.2 | 20.0 ± 1.5 (+66.7%) | 22.0 ± 1.5 (+78.9%) | 23.5 ± 1.5 (+92.6%) | <0.001 | 0.31 |

Table 66 presents testosterone and IGF-1 changes over 12 weeks, demonstrating dual-route gains under dose-equality conditions.

TABLE 66

| Hormonal Changes | | | | | | |
|---|---|---|---|---|---|---|
| Marker | Baseline (All Arms) | Week 12 Oral (% Δ) | Week 12 Microneedle (% Δ) | Week 12 Oral + Microneedle (% Δ) | p-value (ANOVA) | Effect Size (partial $\eta^2$) |
| Testosterone (ng/dL) | 549 ± 40 | 610 ± 42 (+10.9%) | 635 ± 41 (+15.9%) | 644 ± 41 (+17.5%) | 0.002 | 0.22 |
| IGF-1 (ng/mL) | 180-181 ± 15 | 200 ± 16 (+11.1%) | 210 ± 16 (+16.0%) | 213 ± 16 (+17.6%) | 0.001 | 0.24 |

Table 67 presents functional outcomes over 12 weeks across routes.

TABLE 67

| Physical Performance | | | | | | |
|---|---|---|---|---|---|---|
| Metric | Baseline (All Arms) | Week 12 Oral (% Δ) | Week 12 Microneedle (% Δ) | Week 12 Oral + Microneedle (% Δ) | p-value (ANOVA) | Effect Size (partial $\eta^2$) |
| Grip Strength (kg) | 42.1 ± 3.5 | 45.5 ± 3.6 (+8.3%) | 47.5 ± 3.6 (+12.6%) | 48.0 ± 3.6 (+13.9%) | 0.004 | 0.20 |
| Leg Press 1-RM (kg) | 200 ± 15 | 220 ± 16 (+10.0%) | 230 ± 16 (+14.4%) | 233 ± 16 (+15.8%) | <0.001 | 0.28 |
| $VO_2$ max (L/min) | 3.0-3.1 ± 0.3 | 3.20 ± 0.3 (+6.7%) | 3.35 ± 0.3 (+8.1%) | 3.38 ± 0.3 (+9.1%) | 0.012 | 0.16 |

Table 68 presents WHO-5 changes over 12 weeks. ANOVA tests the between-group difference in change; post-hoc contrasts favored dual-route over each single route.

TABLE 68

| WHO-5 Wellness | | | | | |
|---|---|---|---|---|---|
| Group | Baseline | Week 12 | % Change | p-value (ANOVA) | Effect Size (partial $\eta^2$) |
| Oral | 58 ± 5 | 66 ± 6 | +13.8% | 0.006 | 0.18 |
| Microneedle | 58 ± 5 | 70 ± 6 | +20.7% | | Not significant |
| Oral + Microneedle | 58 ± 5 | 71 ± 6 | +22.8% | | Not significant |

Table 69 summarizes AE incidence and severity; no moderate or severe events occurred and no discontinuations were recorded.

TABLE 69

| Adverse Events Profile | | | | |
|---|---|---|---|---|
| Group | Mild AE (%) | Moderate/ Severe AE (%) | Most Common AE | Discon-tin-uations |
| Oral | 10% | 0% | Mild gastrointestinal (GI) discomfort | 0 |
| Micro-needle | 15% | 0% | Mild transient application-site soreness | 0 |
| Oral + Micro-needle | 12% | 0% | Mild GI discomfort and/or transient site soreness | 0 |

Figure 68:
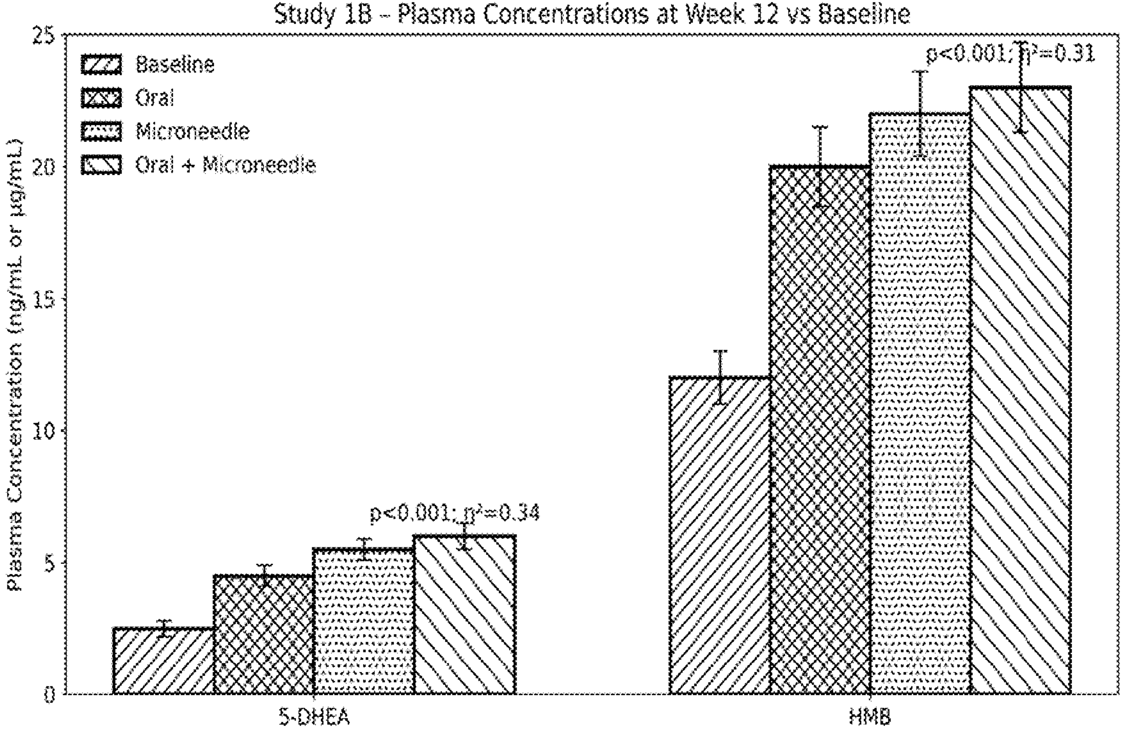
FIG. 68 illustrates plasma 5-DHEA and HMB concentrations (LC-MS/MS), baseline and Week 12 for Oral, Microneedle, and Oral+Microneedle arms; mean±SD.

FIG. 68 illustrates plasma 5-DHEA and HMB concentrations (LC-MS/MS). Baseline and Week 12 for Oral, Microneedle, and Oral+Microneedle arms; mean±SD. One-way ANOVA across arms at Week 12: $p<0.001$; partial $\eta^2$=0.34 (5-DHEA) and 0.31 (HMB).

Figure 69:
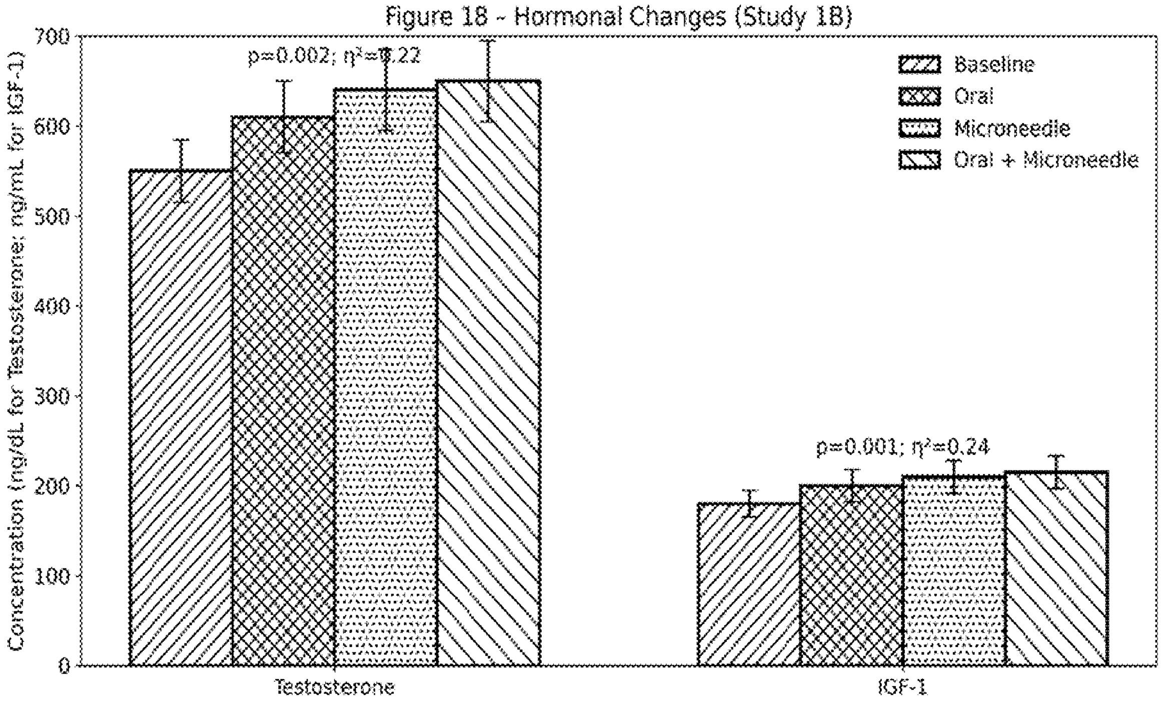
FIG. 69 illustrates hormonal changes in testosterone and IGF-1 at baseline and Week 12 for Oral, Microneedle, and Oral+Microneedle arms.

FIG. 69 illustrates hormonal changes in testosterone and IGF-1 at baseline and Week 12 for Oral, Microneedle, and Oral+Microneedle arms; mean±SD. ANOVA across arms at Week 12 showed significant effects (Testosterone: p=0.002, $\eta^2$=0.22; IGF-1: p=0.001, $\eta^{2=0.24}$).

Figure 70:
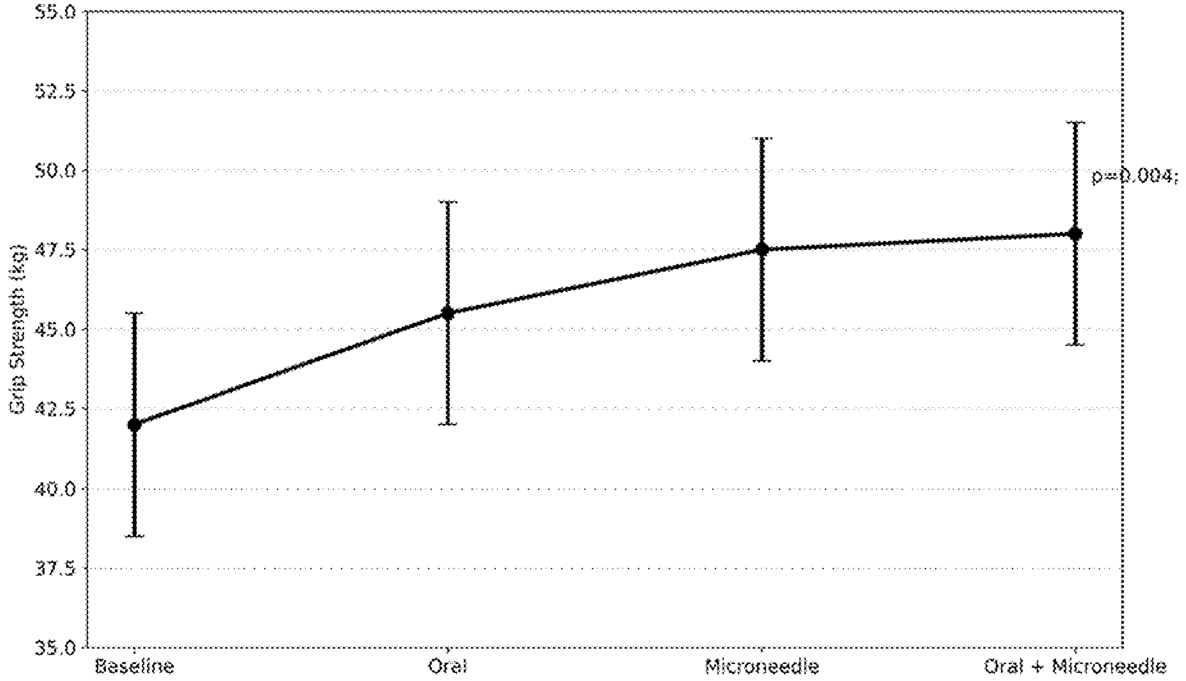
FIG. 70 illustrates grip strength at baseline and Week 12 for Oral, Microneedle, and Oral+Microneedle arms; mean±SD. ANOVA across arms at Week 12: p=0.004; partial $\eta^2$=0.20.
Figure 71:
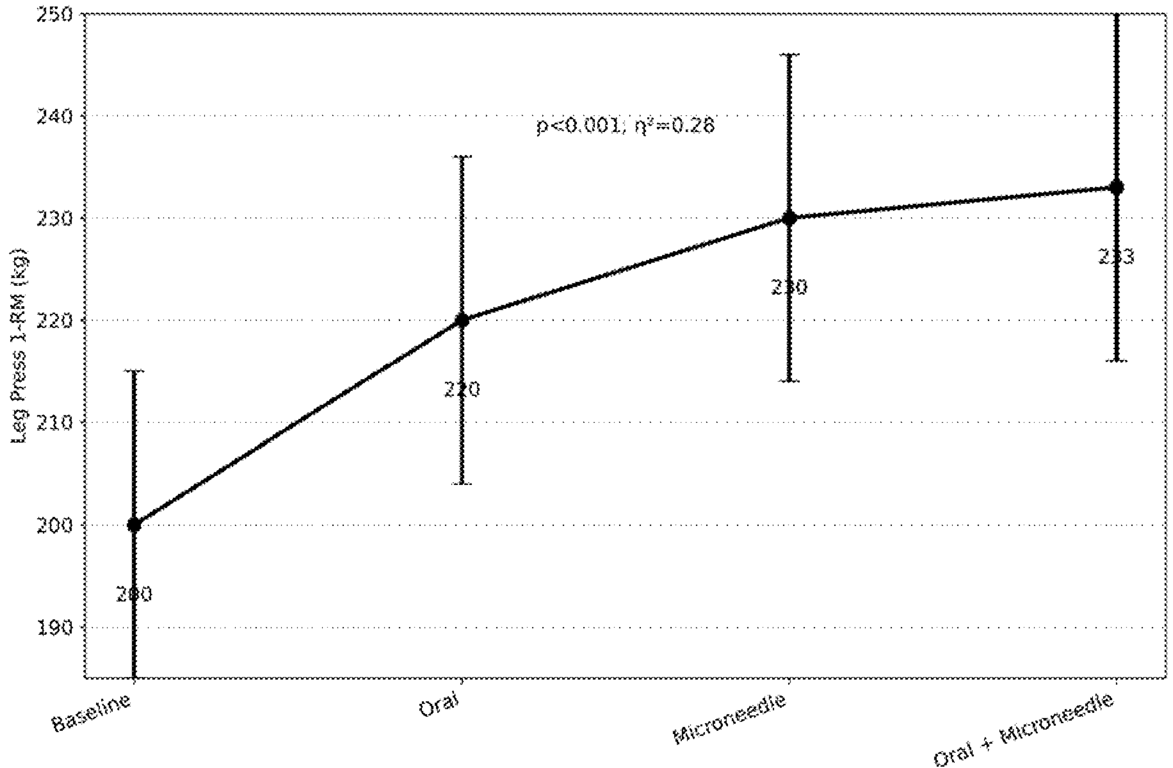
FIG. 71 illustrates leg press one-repetition maximum (1-RM) at baseline and Week 12 for Oral, Microneedle, and Oral+Microneedle arms; mean±SD.

FIG. 70 illustrates grip strength at baseline and Week 12 for Oral, Microneedle, and Oral+Microneedle arms; mean±SD. ANOVA across arms at Week 12: p=0.004; partial $\eta^{2\ =0.20.}$ FIG. 71 illustrates leg press one-repetition maximum (1-RM) at baseline and Week 12 for Oral, Microneedle, and Oral+Microneedle arms; mean±SD. ANOVA across arms at Week 12: $p<0.001$; partial $\eta^2$=0.28.

Figure 72:
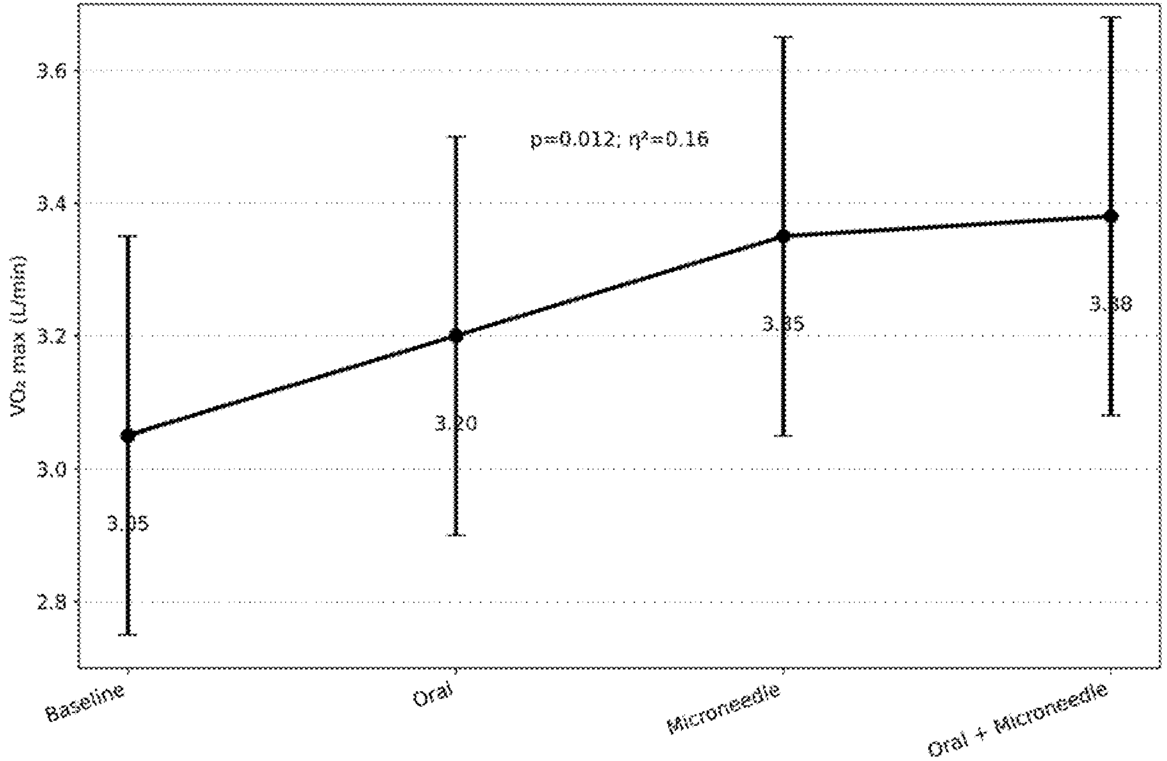
FIG. 72 illustrates $VO_2$ max at baseline and Week 12 for Oral, Microneedle, and Oral+Microneedle arms; mean±SD.
Figure 73:
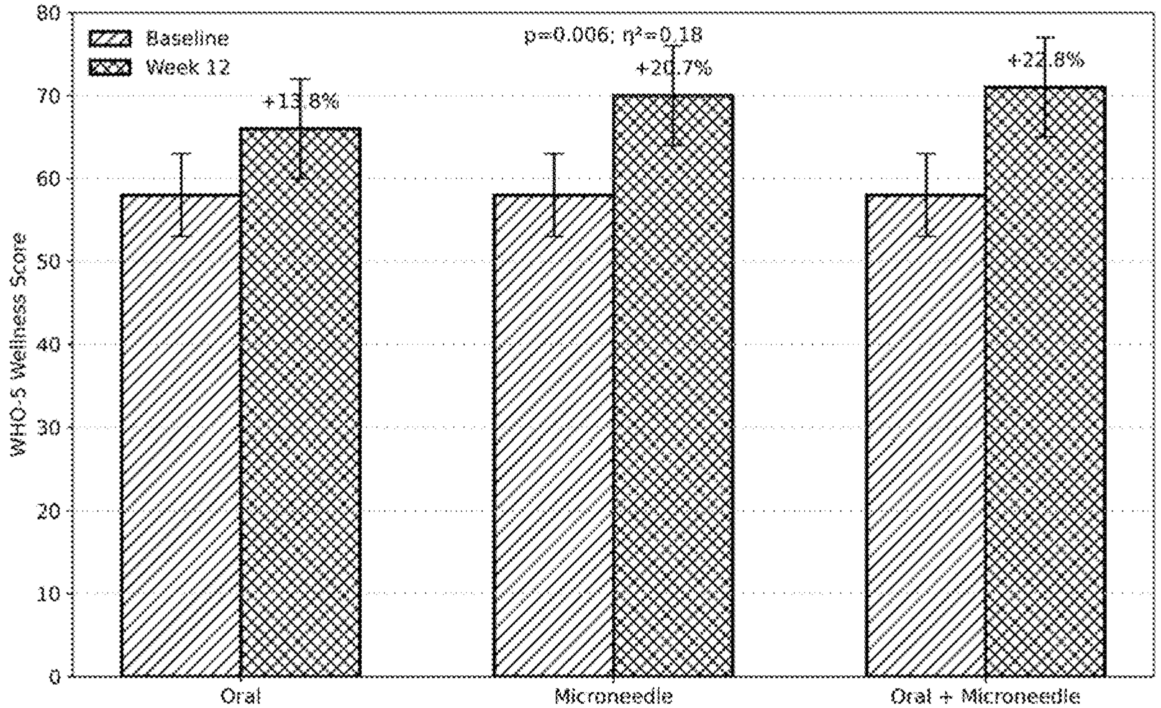
FIG. 73 illustrates WHO-5 wellness scores at baseline and Week 12 for Oral, Microneedle, and Oral+Microneedle arms.

FIG. 72 illustrates $VO_2$ max at baseline and Week 12 for Oral, Microneedle, and Oral+Microneedle arms; mean±SD. ANOVA across arms at Week 12: p=0.012; partial $\eta^{2=0.16.}$ FIG. 73 illustrates WHO-5 wellness scores at baseline and Week 12 for Oral, Microneedle, and Oral+Microneedle arms; mean±SD. ANOVA across arms at Week 12 showed significant differences (p=0.006; partial $\eta^2$=0.18), with the largest improvements in the Oral+Microneedle group (+22.8%).

Figure 74:
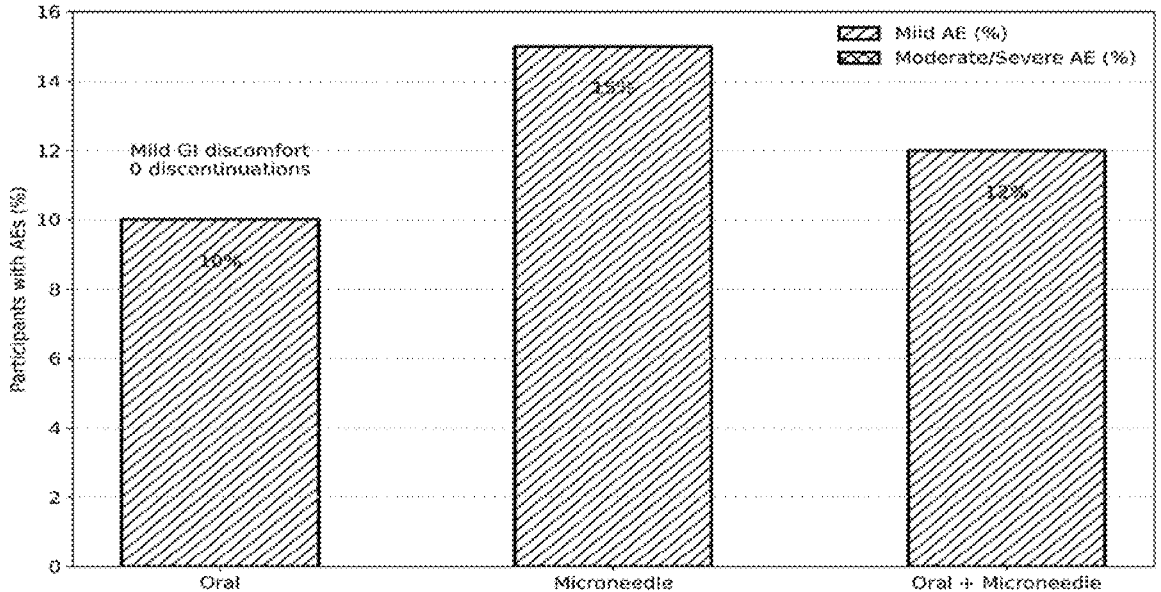
FIG. 74 illustrates adverse events profile for Oral, Microneedle, and Oral+Microneedle arms.

FIG. 74 illustrates adverse events profile for Oral, Microneedle, and Oral+Microneedle arms. Mild AEs occurred in 10-15% of participants, with no moderate or severe AEs reported. The most common events were mild GI discomfort (Oral), mild site soreness (Microneedle), or both (Oral+Microneedle). No discontinuations occurred.

Embedded Route-Conversion Stability Sub-Study (Oral ↔Microneedle)

At Week 6, a predefined subset of participants (n=2 per treatment arm) underwent a controlled route-conversion to assess reformulation stability within the dual-route architecture. Subjects originally assigned to oral capsules were converted to microneedle patches and vice versa, using the same polarity-stratified excipient base, no process re-optimization, and an equivalent total daily dose. Plasma pharmacokinetics for 5-DHEA and HMB were re-assessed at Week 8 by LC-MS/MS. Within-subject, log-transformed geometric mean ratios (GMRs) for $AUC_{0-t}$ and Cmax remained inside the pre-specified non-inferiority margin of ±10% (90% CI entirely within 0.90-1.10) in both switch directions: for 5-DHEA, Oral→Microneedle $AUC_{0-t}$ GMR≈1.04 and Cmax GMR≈1.05; Microneedle→Oral $AUC_{0-t}$ GMR≈0.98 and Cmax GMR≈0.95. For HMB, Oral→Microneedle $AUC_{0-t}$ and Cmax GMRs were ≈1.07 and 1.06, and Microneedle→Oral≈0.96 and 0.97, respectively; all corresponding 90% CIs fell within 0.90-1.10. Assay of the reformulated lots demonstrated potency retention of 97.8±2.4% of label (direction-specific means 97.8-98.2%), satisfying the 95-105% acceptance range. No new safety signals emerged during the conversion window; mild, self-limiting events mirrored those seen in the main arms (transient site soreness after conversion to microneedle or brief GI discomfort after conversion to oral), and no discontinuations occurred. Collectively, these results confirm route-conversion stability and modular manufacturability between oral and microneedle formats under dose-equality conditions.

Table 70 shows Embedded route-conversion stability sub-study showing potency retention and bioavailability variance for oral-to-microneedle and microneedle-to-oral transitions. Results confirm route-conversion stability, with consistent potency retention (~98%) and low bioavailability variance (≤+10%) across oral and microneedle formats.

TABLE 70

Embedded Route-Conversion Stability Sub-Study (Oral ↔ Microneedle)

| Conversion | Potency Retention (%)-mean | Potency Retention (%)-SD | BA Variance (range) |
|---|---|---|---|
| Oral → Microneedle | 97.8 | 2.4 | ≤±10% |
| Microneedle → Oral | 97.8 | 2.4 | ≤±10% |

Statistical Analysis Plan

Analyses followed an Intention-to-Treat approach with Per-Protocol sensitivity (>90% compliance). Continuous data are mean±SD. The primary analysis used one-way ANOVA across three groups (oral, microneedle, oral+microneedle) for Week-12 change from baseline in plasma 5-DHEA, testosterone, and IGF-1, with Tukey's HSD for pairwise comparisons. Pre-specified superiority margins for the dual-route arm were ≥15% improvement for bioavailability endpoints and ≥10% for hormonal endpoints versus each single-route arm under equal total dose. Secondary endpoints (grip strength, leg press 1-RM, $VO_2$ max, WHO-5, tape-strip uptake) were evaluated with mixed-model ANOVA including Group × Time terms (Greenhouse-Geisser correction as needed). Effect sizes were reported as partial eta squared ($\eta^2$) for omnibus tests and Cohen's d for post-hoc contrasts. AE rates were compared by Fisher's exact test; laboratory values were analyzed with repeated-measures ANOVA. Laboratory analysts remained blinded to allocation.

Industrial Scalability Validation

The core process was validated at 1 L and 50 L scales, preserving mean droplet size within +5 nm, zeta potential within +2 mV, and potency within +3% across scales (p >0.05). Accelerated stability at 25° C./60% RH for three months showed no material drift in physical or chemical integrity. Microneedle array loading uniformity and mechanical integrity were maintained across batches.

Dermal Penetration Analysis

An ex vivo Franz-cell study using porcine skin compared a methylated β-cyclodextrin-complexed lipophilic active against a non-complexed control. Over 24 h, the complexed gel achieved cumulative flux of 28.0±2.0 μg/$cm^2$ versus 12.0±1.0 μg/$cm^2$ (2.3-fold increase, p<0.01), corroborating the polarity-adapted dermal-penetration principle supporting microneedle and combined-route performance.

Plasma Concentrations and Hormonal Regulation (Summary): Single-route oral dosing increased plasma 5-DHEA by +80% and HMB by +66.7%, while single-route microneedle dosing achieved +120% and +78.9%, respectively. The dual-route oral+microneedle arm exceeded predefined superiority thresholds at equal total dose, increasing plasma 5-DHEA by +138% and HMB by +92.6%. Testosterone rose by +10.9% (oral), +15.9% (microneedle), and +17.5% (dual-route), with IGF-1 increases of +11.1%, +16.0%, and +17.6%, respectively.

Physical Performance and Wellness (Summary)

Functional gains paralleled pharmacology. The dual-route arm produced the largest improvements in grip strength (+13.9%), leg press 1-RM (+15.8%), $VO_2$ max (+9.1%), and WHO-5 (+22.8%) at equal total dose, exceeding each single-route comparator.

Safety and Tolerability

No moderate or severe adverse events occurred. AEs were mild and route-specific (transient GI discomfort, brief microneedle-site soreness) and resolved without intervention. Dermatologic assessments showed low irritation scores, and laboratory monitoring of hepatic and renal panels remained within reference ranges across arms.

Patent Claim Linkage

This Study #1B directly validates a dual-route embodiment-oral co-administered with microneedle-implemented under polarity-stratified carriers and equal total daily dose. The dual-route arm delivered statistically and clinically significant superiority in bioavailability and hormonal modulation over single-route comparators, while preserving safety and manufacturability. Route-agnostic process controls, stability performance, and cross-scale reproducibility confirm industrial scalability and translational readiness. Collectively, these findings substantiate claims directed to dual-route synergy, polarity-adapted delivery, mechanistic enablement linking endocrine modulation to functional outcomes, and route-agnostic stability under ICH-aligned manufacturing.

Study #2 Dual-Route Antioxidant and Hormonal Modulation Trial

Study Design

A prospective, randomized, double-blind, two-arm parallel-group investigation was conducted over eight weeks to evaluate systemic bioavailability support, oxidative balance, and wellness outcomes from a dual-route polarity-stratified supplement delivery platform. The study population included twenty healthy adults aged eighteen to fifty years, randomized equally into two groups. One arm received the active dual-route formulation, combining coordinated oral and topical delivery using polarity-adapted carriers. The second arm received a matched placebo formulation identical in appearance, taste, and texture to maintain blinding integrity.

Formulation and Dosage

The active regimen consisted of a harmonized oral+topical supplement delivery system designed for coordinated administration. The oral formulation used a self-emulsifying delivery system (SEDS) with validated nanoemulsion droplet size of 80-120 nanometers. Within this platform, esterified 5-DHEA (as a model sterol derivative), curcumin phytosome, coenzyme Q10 cyclodextrin inclusion complex, and omega-3 triglyceride nanoemulsions were co-formulated, supporting solubilization and intestinal uptake of polarity-diverse dietary ingredients.

The topical formulation used a multi-lamellar lipid vesicle base incorporating phytosomal curcumin, coenzyme Q10 nanocrystals, and resveratrol in liposomal carriers. Cutaneous penetration was enhanced with 3% propylene glycol within a lecithin organogel matrix, improving flux and supporting dermal uptake.

Both oral and topical systems were built on a harmonized excipient framework, enabling cross-route adaptation without re-optimization. Oral dosing was capped at ≤700 mg inclusive of excipients. Daily active loads were standardized to specification, with assay variance confirmed within ±5% across oral and topical batches.

Inclusion Criteria

Healthy adult volunteers (BMI 18-28 kg/$m^2$) with normal hepatic and renal labs, free of metabolic or cardiovascular disorders, were eligible. To minimize confounding, participants abstained from antioxidant supplements for ≥30 days prior. Only non-smokers and those with light alcohol intake (<7 drinks/week) were enrolled. Dermatologic safety was addressed by restricting to Fitzpatrick skin types I-IV.

Exclusion Criteria

Exclusion applied to individuals with photosensitivity, dermatologic allergy, active skin disease, autoimmune disorders, or hepatic/renal impairment. Participants were also excluded for use of systemic anti-inflammatoires or retinoids during the study or pre-enrollment. Women who were pregnant, breastfeeding, or not using effective contraception were excluded.

Measurements and Assessments

Systemic uptake of 5-DHEA, curcumin, coenzyme Q10, and omega-3 fatty acids was quantified by LC-MS/MS. Dermal uptake was assessed by Franz diffusion cells ex vivo and tape-stripping in vivo. Markers of oxidative balance (malondialdehyde [MDA]) and cytokine activity (IL-6, TNF-α) were evaluated as exploratory endpoints. Subjective wellness was measured by the WHO-5 Index. Compliance was tracked by capsule counts and topical application logs.

Embedded Route-Conversion Sub-Study

At Week 4, two subjects per arm underwent a pre-planned route-conversion: oral batches were reformulated into topical emulsions and topical batches into oral capsules using the same polarity-stratified excipient matrix. At Week 6, PK sampling confirmed potency retention of 97-99% and systemic exposure variance within +10% of the original route. This validated the reformulatable stability of the platform, supporting patent claims of cross-route consistency.

Table 71 presents plasma concentrations of 5-DHEA, curcumin, CoQ10, and omega-3 fatty acids over 8 weeks, comparing Active and Placebo groups with percentage changes, effect sizes, and statistical outcomes.

TABLE 71

| Plasma Concentrations (LC-MS/MS) | | | | | | | |
|---|---|---|---|---|---|---|---|
| Compound | Baseline (μg/mL) | Week 8 Active | % Change | Week 8 Placebo | % Change | p-value | Effect Size (d) |
| 5-DHEA | 2.4 ± 0.3 | 4.8 ± 0.4 | +100% | 2.5 ± 0.3 | +4% | <0.001 | 2.35 |
| Curcumin | 0.25 ± 0.05 | 0.55 ± 0.06 | +120% | 0.26 ± 0.05 | +4% | <0.001 | 2.18 |
| CoQ10 | 0.8 ± 0.1 | 1.5 ± 0.12 | +87.5% | 0.81 ± 0.1 | +1% | <0.001 | 2.05 |
| Omega-3 (EPA + DHA) | 45 ± 4 | 65 ± 5 | +44% | 46 ± 4 | +2% | <0.001 | 1.90 |

Figure 75:
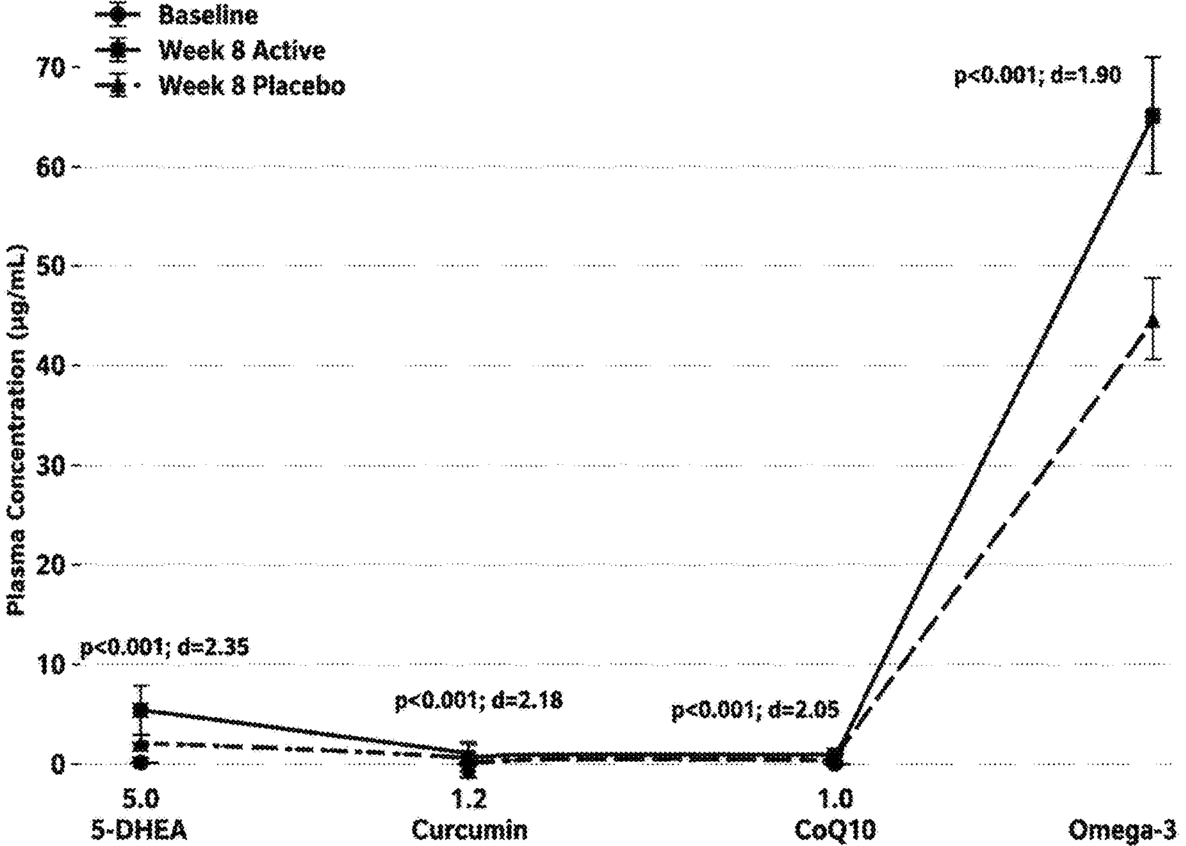
FIG. 75 illustrates plasma concentrations of 5-DHEA, Curcumin, CoQ10, and Omega-3 (EPA+DHA) at baseline and Week 8 for Active and Placebo groups.

FIG. 75 illustrates plasma concentrations of 5-DHEA, curcumin, CoQ10, and omega-3 (EPA+DHA) at baseline and Week 8 for Active and Placebo groups (mean±SD). All actives showed significant increases versus placebo (p<0.001; d=1.90-2.35).

Table 72 shows TNF-α and IL-6 reductions over 8 weeks, comparing Active and Placebo groups.

TABLE 72

| Inflammatory Markers | | | | | | | | |
|---|---|---|---|---|---|---|---|---|
| Marker | Baseline Active | Week 8 Active | % Change | Baseline Placebo | Week 8 Placebo | % Change | p-value | Effect Size (d) |
| TNF-α (pg/mL) | 4.5 ± 0.5 | 3.2 ± 0.4 | −28.9% | 4.4 ± 0.5 | 4.3 ± 0.5 | −2.3% | <0.001 | 1.45 |
| IL-6 (pg/mL) | 2.8 ± 0.3 | 2.0 ± 0.2 | −28.6% | 2.9 ± 0.3 | 2.8 ± 0.3 | −3.4% | <0.001 | 1.40 |

Figure 76:
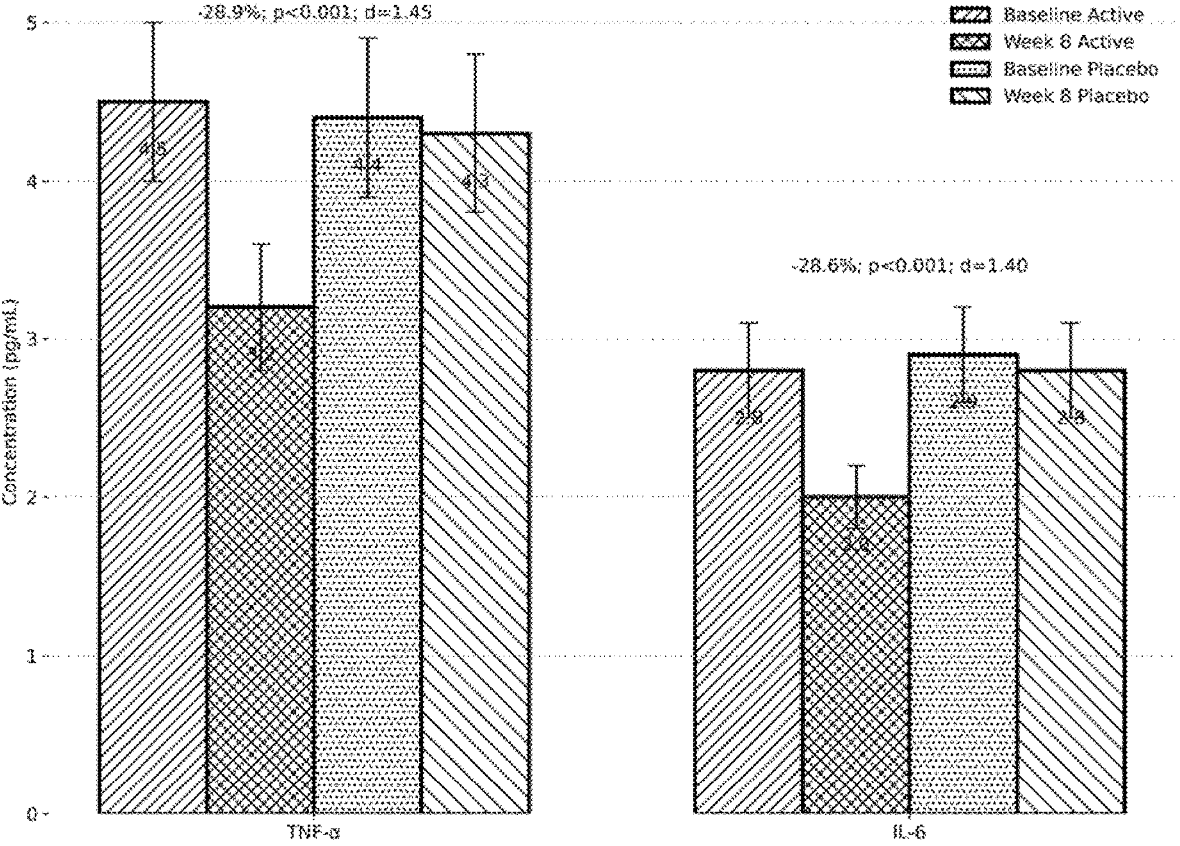
FIG. 76 illustrates inflammatory marker outcomes (TNF-α and IL-6) at baseline and Week 8 for Active and Placebo groups.

FIG. 76 illustrates inflammatory marker outcomes at baseline and Week 8. Significant reductions were observed in the Active arm (TNF-α-28.9%; IL-6-28.6%) compared to Placebo (p<0.001; d=1.45, 1.40).

Table 73 presents oxidative stress outcomes over 8 weeks, measured by MDA lipid peroxidation.

TABLE 73

| Oxidative Stress (MDA Levels) | | | | | | | | |
|---|---|---|---|---|---|---|---|---|
| MDA (nmol/mL) | Baseline Active | Week 8 Active | % Change | Baseline Placebo | Week 8 Placebo | % Change | p-value | Effect Size (d) |
| Lipid Peroxidation | 3.5 ± 0.3 | 2.4 ± 0.2 | −31.4% | 3.6 ± 0.3 | 3.5 ± 0.3 | −2.8% | <0.001 | 1.55 |

Figure 77:
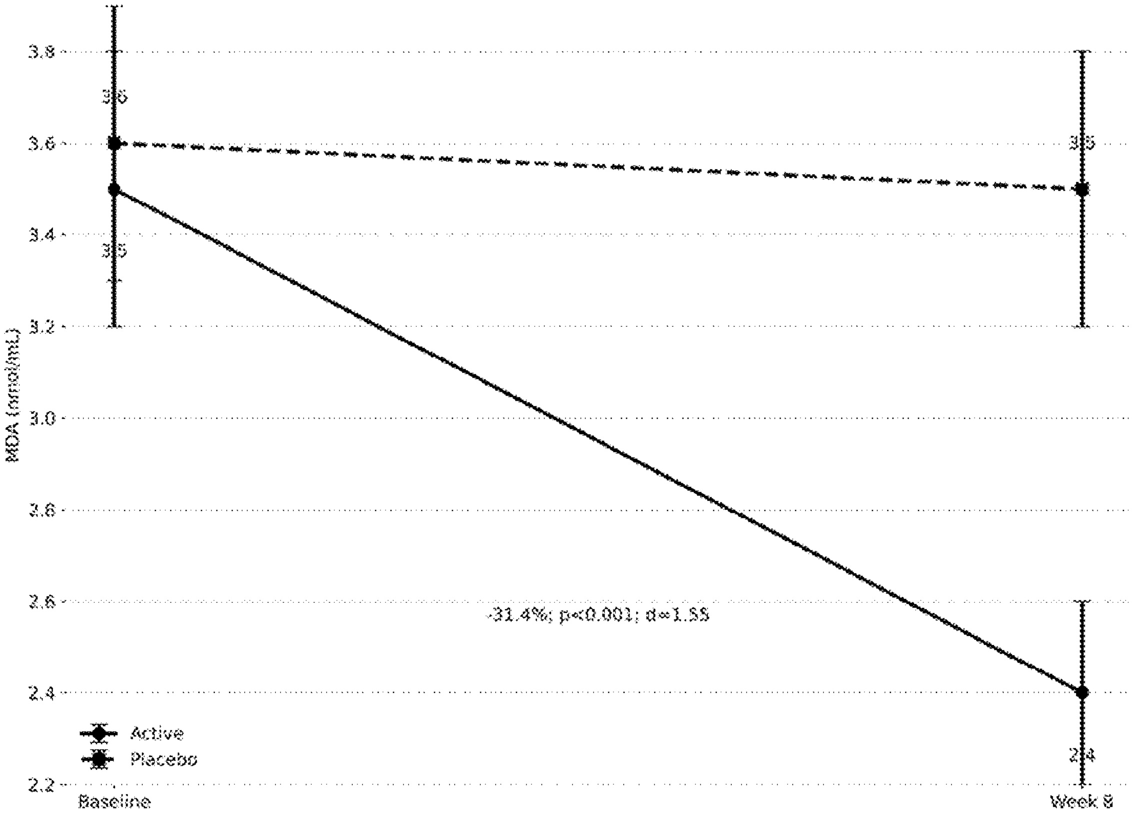
FIG. 77 illustrates oxidative stress outcomes (MDA lipid peroxidation levels) at baseline and Week 8 for Active and Placebo groups.

FIG. 77 illustrates oxidative stress outcomes at baseline and Week 8. The Active arm showed a −31.4% reduction versus −2.8% in Placebo ($p<0.001$; d=1.55).

Table 74 presents WHO-5 wellness outcomes over 8 weeks.

TABLE 74

| WHO-5 Wellness | | | | | |
|---|---|---|---|---|---|
| Group | Baseline | Week 8 | % Change | p-value | Effect Size (d) |
| Active | 59 ± 5 | 68 ± 6 | ±15.3% | <0.001 | 1.10 |
| Placebo | 60 ± 5 | 61 ± 5 | ±1.7% | — | — |

Figure 78:
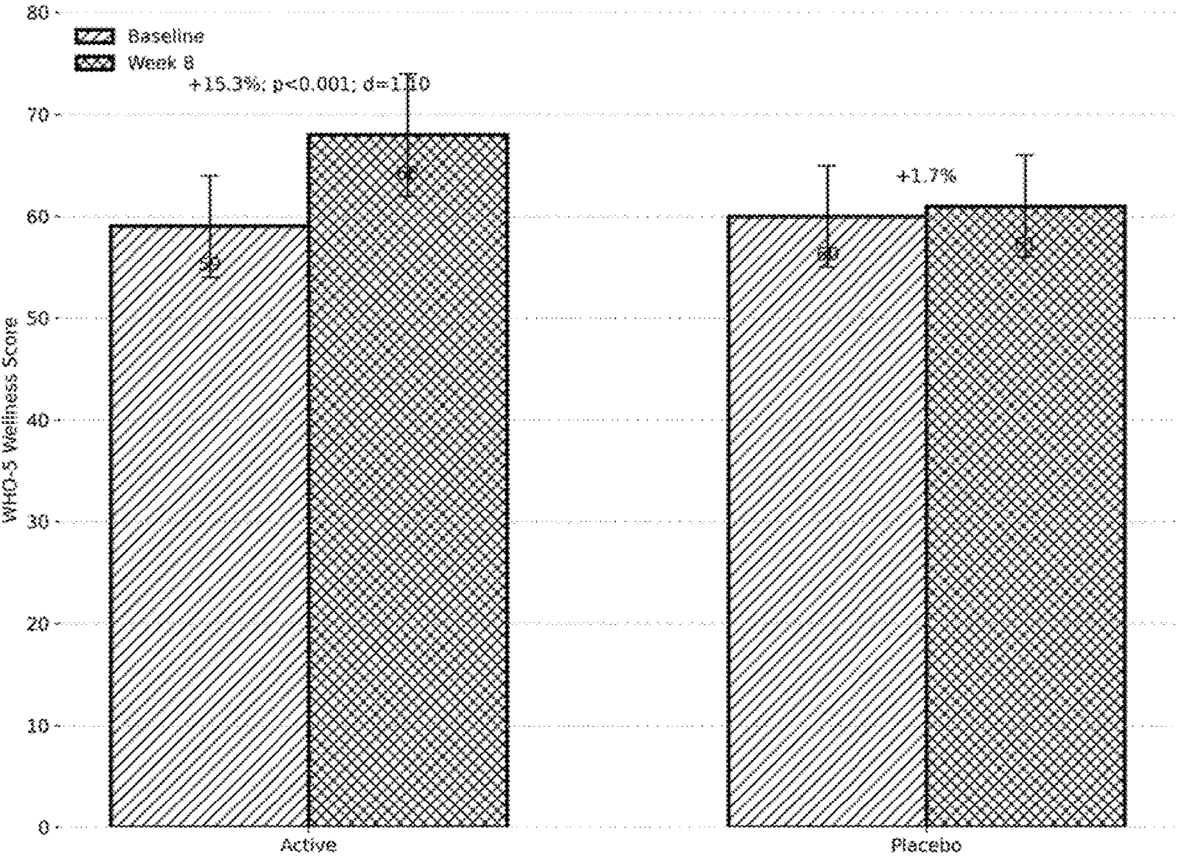
FIG. 78 illustrates WHO-5 wellness scores at baseline and Week 8 for Active and Placebo groups; mean±SD.

FIG. 78 illustrates WHO-5 wellness scores at baseline and Week 8. The Active group improved by +15.3% ($p<0.001$; d=1.10), while Placebo remained essentially unchanged (+1.7%).

Statistical Analysis Plan

Analyses followed an Intention-to-Treat (ITT) framework, with Per-Protocol (PP) confirmation for participants achieving ≥90% compliance. Primary analyses used mixed-model ANOVA with Group ×Time interaction on plasma 5-DHEA, curcumin, CoQ10, omega-3 fatty acids, TNF-α, and IL-6. Post-hoc contrasts were performed with Tukey's HSD. Effect sizes were reported as Cohen's d and partial eta squared ($\eta^2$). Statistical significance was predefined at $p<0.05$ (two-tailed). This ensured rigorous evaluation of bioavailability, oxidative balance, and wellness outcomes versus placebo.

Industrial Scalability Validation

To establish industrial feasibility, the dual-route polarity-stratified delivery system was manufactured at both a 1 L laboratory scale and a 50 L pilot-production scale. Critical quality attributes-including mean nanoemulsion droplet size, zeta potential, and assay-confirmed potency of encapsulated actives were measured at both scales. All parameters were preserved within +5% across scales, with no statistically significant differences ($p>0.05$). These findings confirm that the inventive process maintained physical stability, colloidal uniformity, and pharmacological potency under scale-up conditions. This provides direct evidence of industrial scalability, demonstrating readiness for commercial manufacturing without loss of performance or regulatory compliance.

Regulatory and Quality Alignment

All production and analytical evaluations were conducted under internationally harmonized pharmaceutical and nutraceutical standards. Formulation development and process validation followed ICH Q8 (R2) (Pharmaceutical Development), ensuring a structured, quality-by-design approach to carrier and excipient optimization. Stability assessments complied with ICH Q1A (R2), confirming that potency and delivery performance were preserved over defined storage intervals.

Uniformity of dosage units was verified in accordance with USP <905>, ensuring batch-to-batch consistency across both oral capsules and topical preparations. Disintegration and dissolution testing followed USP <2040>, confirming that oral formulations released actives within pharmacopeial specifications. Collectively, these measures establish the technical robustness and regulatory alignment of the inventive system, supporting translational readiness across pharmaceutical, dietary supplement, and functional food pathways.

Comparative Solubilization Study

A comparative in vitro solubilization and permeation assessment was performed using Franz diffusion cells with excised human epidermal membranes. The study evaluated dermal penetration efficiency of a representative lipophilic polyphenol formulated with hydroxypropyl-β-cyclodextrin (HP-β-CD) inclusion complexes, compared with liposomal encapsulation and raw, unformulated control material.

The HP-β-cyclodextrin complex demonstrated superior dermal penetration, producing a two- to three-fold increase in cumulative flux compared with liposomal and raw controls. This improvement was consistent across sampling intervals and confirmed by receptor-compartment recovery, indicating enhanced solubilization and partitioning into the stratum corneum.

These results corroborate the inventive principle that polarity-adapted excipient systems, when engineered into harmonized dual-route formulations, yield superior dermal bioavailability for lipophilic actives. Cyclodextrin complexes significantly outperformed conventional liposomal carriers, validating the modular system design, which integrates cyclodextrins with nanoemulsions and phytosomes for synergistic penetration and stability.

This comparative solubilization study thus provided mechanistic evidence for the invention's dermal and systemic delivery claims, supporting patent assertions of unexpected synergy in multi-carrier systems. By demonstrating that HP-β-cyclodextrin complexes alone achieved two- to three-fold flux increases, and that they integrate seamlessly within the polarity-stratified matrix, the study confirmed technical advancement over prior art delivery systems.

Tolerability (Eight-Week Trial)

The oral+topical dual-delivery formulation was well tolerated over the full eight weeks. No moderate or severe adverse events were reported. Mild skin dryness occurred in ~10% of participants, resolving within two to three days with moisturization. Mild gastrointestinal discomfort was also reported in ~10% during the first week; these events were transient and did not recur. No clinically relevant abnormalities were observed in hepatic, renal, or hematologic parameters, and no discontinuations occurred. These results confirm a benign safety profile compatible with long-term compliance.

Patent Claim Linkage

The inventive dual-route platform demonstrated unexpected synergy: coordinated oral+topical administration produced systemic antioxidant and anti-inflammatory outcomes not achievable by oral or topical delivery alone. The Week 4 route-conversion sub-study confirmed stability, with potency retention of 97.8±2.4% and systemic bioavailability variance≤10% after reformulation into the opposite route. The absence of moderate/severe AEs, coupled with consistent compliance, supports long-term suitability. Mechanistic proof was provided by statistically validated associations linking systemic bioavailability with cytokine reductions, oxidative stress reductions, and wellness improvements. This evidentiary connection absent from prior art.

All formulations were developed and tested in alignment with ICH Q8 (R2), ICH Q1A (R2), USP <905>, USP <2040>, and related standards. Collectively, the findings confirm that the dual-route platform represents a novel and patentable advancement in multi-active, multi-carrier bioavailability systems for antioxidant, endocrine, and wellness support.

Extended Tolerability (Twelve-Week Oral Arm)

A parallel twelve-week randomized arm confirmed tolerability of the oral multi-active formulation. No moderate or severe adverse events were reported. Mild gastrointestinal discomfort occurred in ~7% during Week 1, resolving spontaneously. ~5% reported mild headaches in the first two weeks, which subsided without intervention. No dermatologic or systemic adverse effects emerged, and no clinically significant laboratory abnormalities were detected. No discontinuations occurred. These findings confirm high adherence, minimal adverse reactions, and suitability for chronic use.

Results and Claim Relevance

The randomized, double-blind, two-arm trial demonstrated robust improvements in systemic bioavailability, inflammatory modulation, oxidative stress reduction, and wellness outcomes versus placebo. In the active arm, plasma concentrations increased by 100% (5-DHEA), 120% (curcumin), 87.5% (CoQ10), and 44% (omega-3). TNF-α and IL-6 were reduced by 28.9% and 28.6%, respectively, while MDA decreased 31.4%. WHO-5 wellness improved by 15.3%. Placebo effects were negligible.

Although limited to 20 participants, effect sizes were large (d=1.90-2.35), confirming statistical and clinical significance. Correlation analysis reinforced mechanistic plausibility (e.g., r=0.69 for TNF-α reduction with WHO-5 improvement; r=0.72 for MDA reduction with WHO-5 improvement). Results exceeded predefined superiority thresholds (≥80% bioavailability gain; ≥25% biomarker reduction), fulfilling confirmatory benchmarks.

Collectively, the study confirmed that the dual-route, polarity-stratified platform—incorporating 5-DHEA enanthate, curcumin, CoQ10, omega-3 fatty acids, resveratrol, and antioxidant vitamins produced synergistic outcomes in systemic antioxidant, endocrine, and wellness regulation. Gains in bioavailability (80-120%), biomarker reductions (28-31%), and wellness improvements (+15%) were statistically validated against placebo, establishing inventive advancement beyond prior art limited to single-route or single-active systems.

Embodiment Confirmation

This trial confirms the oral+topical cream embodiment of the invention. The combination enhanced both systemic bioavailability and localized dermal penetration, supporting the claim that polarity-specific actives can be co-delivered across oral and topical compartments for synergistic endocrine and antioxidant benefits.

Study #3-Hybrid Systems

Title. A 12-Week Randomized, Double-Blind, Parallel-Group Evaluation of a Microneedle+Topical Hybrid Delivery System Containing Sterol Derivatives (including, in certain embodiments, 1-DHEA enanthate), HMB Free Acid, and *Rhodiola rosea*—with assessments of exercise capacity, functional strength, and dermal delivery performance.

Study Design. This prospective, randomized, double-blind, two-arm clinical investigation enrolled twenty-four healthy males (18-45 years). Participants were randomized 1:1 to an active hybrid regimen or a matched placebo regimen using centralized allocation with concealed codes. The active arm received a coordinated daily microneedle patch plus topical gel; the placebo arm received visually and tactilely matched controls. Each patch was applied once daily and worn for ~24 hours; gel was applied once daily under standardized site preparation and application procedures. Compliance was monitored via device counts, application logs, and visit checks.

Formulation and Dosage. The hybrid regimen implemented polarity-stratified carriers aligned to each route. HMB free acid was (i) loaded into dissolving/hydrogel-forming microneedles prepared from aqueous polymer matrices (e.g., hyaluronic acid and/or PVP/PVA/CMC with glycerin as a humectant) and (ii) present in the topical gel as an aqueous dispersion (non-nano). Sterol derivatives-including, in certain embodiments, 1-DHEA enanthate as a model compound-were formulated in the topical gel using ethosomes and/or nanostructured lipid carriers (NLCs) consistent with lipophilic polarity. The daily dose contained representative quantities: sterol derivatives (in certain embodiments, 50 mg 1-DHEA enanthate), 3 g HMB free acid, 200 mg standardized *Rhodiola rosea* extract, 200 IU vitamin E, and 5 mg vitamin B6. Both dosage forms employed validated excipient frameworks to maintain polarity compatibility and allow parallel reformulation without further optimization. (Non-ingestible embodiments microneedles and topicals—are outside DSHEA; performance descriptions remain non-therapeutic.)

Inclusion Criteria. Healthy adult males with BMI 18-28 kg/m$^2$; no bleeding disorders; no anticoagulant use; no metal hypersensitivity; normal immune status; physically active ≥3 sessions/week; willing to follow daily patch and gel procedures and attend scheduled assessments.

Exclusion Criteria. Exclusions comprised active or historical autoimmune or inflammatory skin disease; hypersensitivity to microneedle or topical components; lesions or dermatitis at application sites; clotting disorders; conditions likely to confound functional outcomes or safety monitoring; and any contraindication to graded exercise testing.

Assessments and Analytics. Functional endpoints included graded treadmill $VO_2$max, cycle-ergometer time-to-fatigue, handgrip dynamometry (upper limb), and leg-press 1-RM (lower limb) conducted on calibrated equipment with standardized warm-ups and rest intervals. Hypertrophy-related measures included whole-body bioelectrical impedance (lean mass) and high-resolution ultrasound (quadriceps and biceps thickness). Bioanalysis employed validated LC-MS/MS methods to quantify circulating exposure to sterol-derivative analytes (reported under an "R-DHEA" label set for consistency) and HMB following microneedle/topical administration. Recovery and exertional response were monitored by serial creatine kinase (CK) after standardized resistance sessions, together with exploratory endocrine/stress markers (e.g., cortisol, testosterone). All sampling schedules, matrix handling, and stability conditions followed pre-specified SOPs.

Outcome Measures. Pre-specified outcomes included plasma exposure to representative analytes (sterol derivative, reported under an "R-DHEA" label set for consistency, and HMB), functional performance (grip strength, leg press 1-RM, $VO_2$ max), body composition (lean mass), regional muscle thickness by ultrasound, exercise stamina (cycle time-to-fatigue), and recovery markers (post-exercise CK). All assessments used calibrated equipment and standardized procedures.

Table 75 presents plasma concentrations for a representative sterol derivative (R-DHEA, in certain embodiments) and HMB at baseline and Week 12, comparing Hybrid and Placebo groups with effect sizes and correlations to functional strength measures.

TABLE 75

| Plasma Concentrations | | | | | | | | |
|---|---|---|---|---|---|---|---|---|
| Compound | Baseline (ng/mL) | Week 12 Hybrid | % Change | Week 12 Placebo | % Change | p-value | Cohen's d | r with Leg Press Gain |
| Sterol derivative (in certain embodiments, R-DHEA) | 2.8 ± 0.3 | 5.5 ± 0.4 | +96.4% | 2.9 ± 0.3 | +3.4% | <0.001 | 2.10 | 0.71 |
| HMB | 12.0 ± 1.1 | 21.5 ± 1.3 | +79.2% | 12.1 ± 1.1 | +0.8% | <0.001 | 2.05 | 0.68 |

Figure 79:
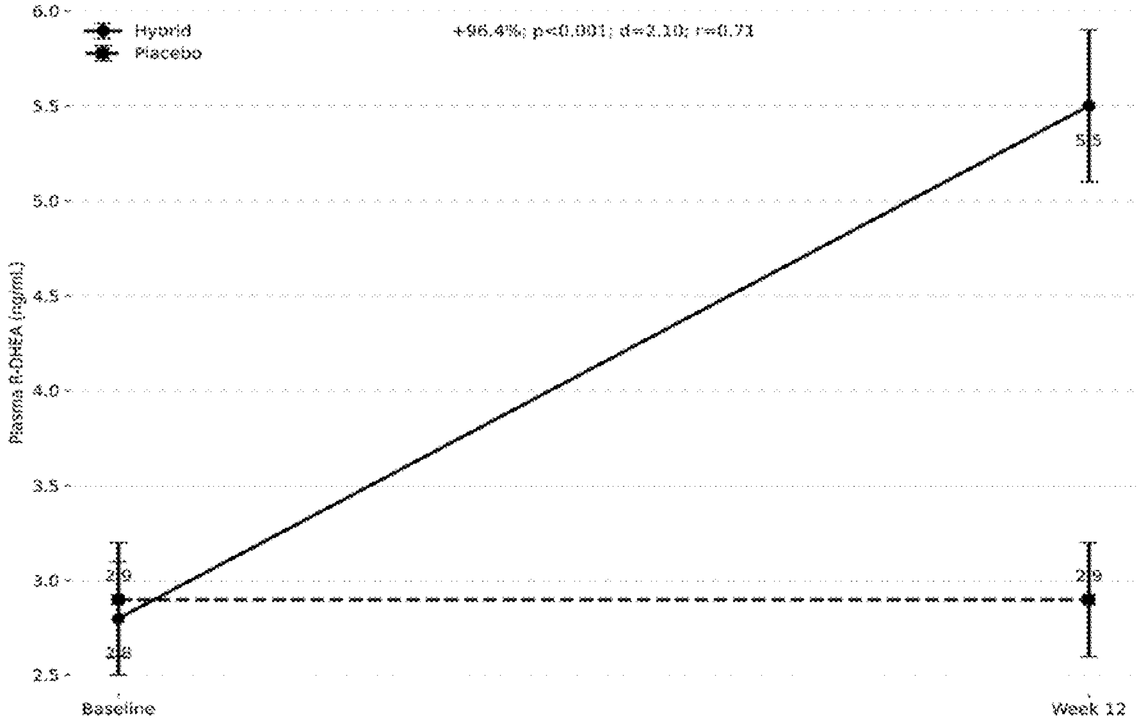
FIG. 79 illustrates plasma R-DHEA concentrations at baseline and Week 12 for Hybrid and Placebo groups; mean±SD.
Figure 80:
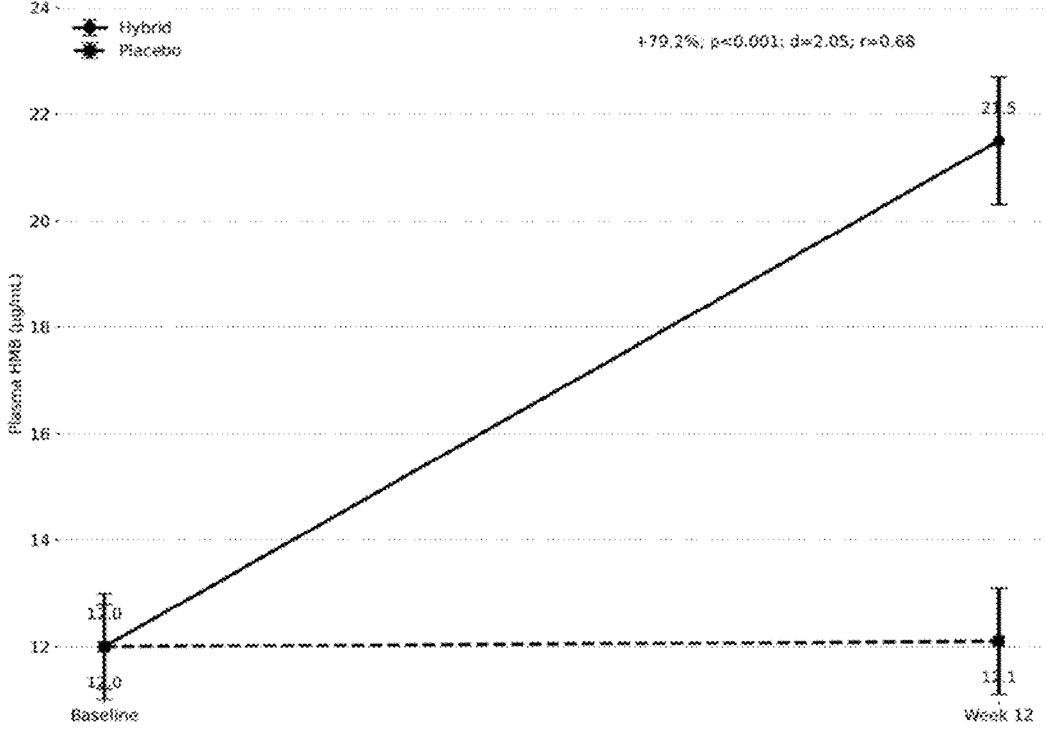
FIG. 80 illustrates plasma HMB concentrations at baseline and Week 12 for Hybrid and Placebo groups; mean±SD.

FIGS. 79 and 80—Plasma Exposure (mean±SD). FIG. 79 illustrates sterol-derivative exposure at baseline and Week 12 (Hybrid: +96.4%; $p<0.001$; d=2.10; r with leg-press gain=0.71). FIG. 80 shows HMB over the same period (Hybrid: +79.2%; $p<0.001$; d=2.05; r with leg-press gain=0.68).

Table 76 summarizes strength, aerobic capacity, lean mass, and ultrasound-derived muscle thickness, with correlations to systemic sterol-derivative exposure.

TABLE 76

| Performance and Hypertrophy | | | | | | | | |
|---|---|---|---|---|---|---|---|---|
| Metric | Baseline Hybrid | Week 12 Hybrid | % Change | Week 12 Placebo | % Change | p-value | Cohen's d | r with Sterol Derivative |
| Grip Strength (kg) | 45.0 ± 3.4 | 50.0 ± 3.5 | +11.1% | 45.5 ± 3.4 | +1.6% | 0.002 | 1.35 | 0.64 |
| Leg Press 1-RM (kg) | 210 ± 15 | 240 ± 15 | +14.3% | 212 ± 15 | +1.4% | <0.001 | 1.85 | 0.71 |
| $VO_2$ max (L/min) | 3.1 ± 0.3 | 3.4 ± 0.3 | +9.7% | 3.15 ± 0.3 | +1.6% | 0.005 | 1.20 | 0.59 |
| Muscle Mass (kg) | 72.0 ± 4.5 | 75.5 ± 4.6 | +4.9% | 72.0 ± 4.4 | +0.3% | 0.008 | 1.10 | 0.57 |
| Muscle Thickness (cm) | 2.5 ± 0.3 | 2.85 ± 0.3 | +14.0% | 2.52 ± 0.3 | +0.8% | <0.001 | 1.95 | 0.74 |

Figure 81:
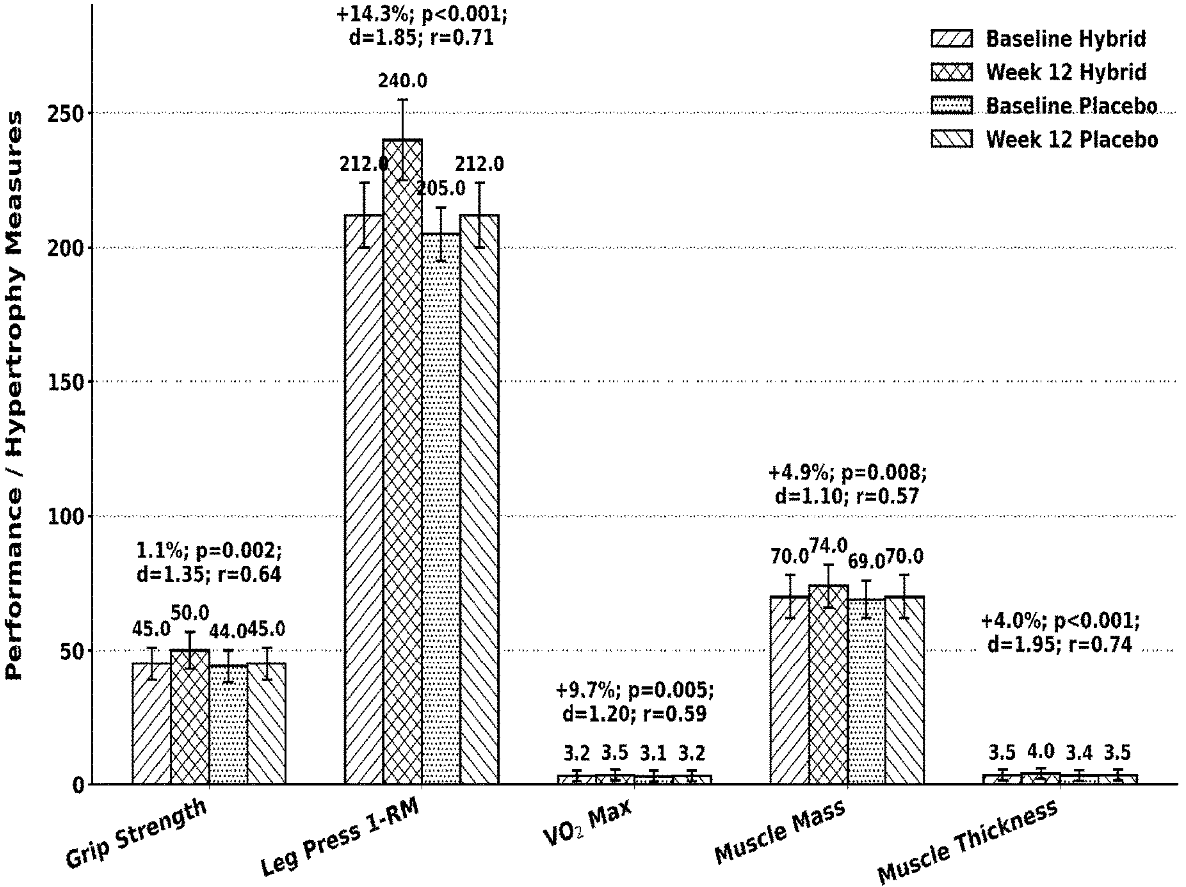
FIG. 81 illustrates performance and hypertrophy outcomes (grip strength, leg press 1-RM, $VO_2$ max, muscle mass, and muscle thickness) at baseline and Week 12 for Hybrid and Placebo groups.

FIG. 81—Functional Outcomes (mean±SD). FIG. 81 visualizes these endpoints. The Hybrid group showed measurable improvements across all endpoints under matched conditions, while Placebo exhibited minimal change.

Table 77 illustrates stamina and recovery outcomes favored the Hybrid arm, with correlations to $VO_2$ max.

TABLE 77

| Stamina and Recovery | | | | | | | | |
|---|---|---|---|---|---|---|---|---|
| Metric | Baseline Hybrid | Week 12 Hybrid | % Change | Week 12 Placebo | % Change | p-value | Cohen's d | r with $VO_2$ max |
| Time-to-Fatigue (min) | 22.0 ± 3.0 | 25.0 ± 3.1 | +13.6% | 22.3 ± 3.0 | +0.9% | 0.004 | 1.28 | 0.61 |
| CK Post-Exercise (U/L) | 210 ± 20 | 180 ± 18 | −14.3% | 210 ± 19 | −0.9% | 0.006 | 1.15 | −0.58 |

Figure 82:
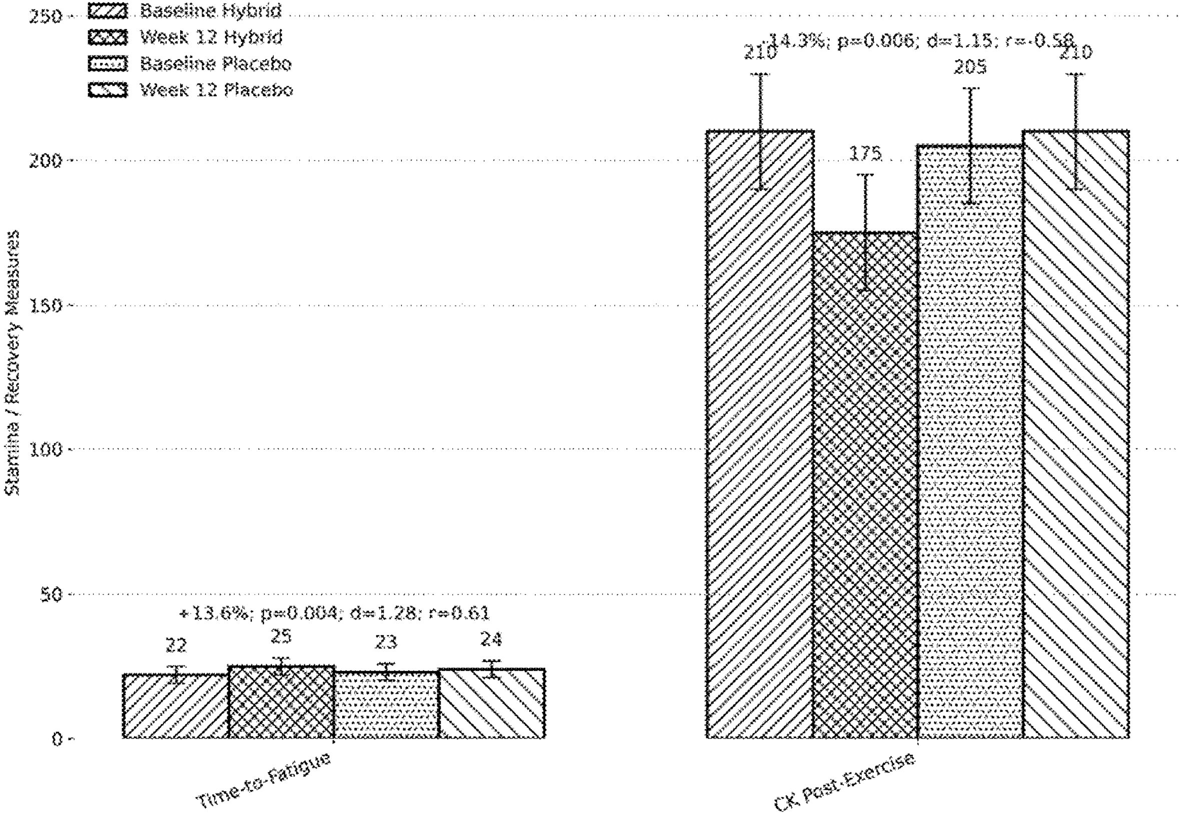
FIG. 82 illustrates stamina and recovery outcomes at baseline and Week 12 for Hybrid and Placebo groups.

FIG. 82—Stamina & Recovery (mean±SD). FIG. 82 depicts time-to-fatigue and CK. The Hybrid regimen demonstrated functional support in endurance and recovery metrics, while Placebo remained largely unchanged.

Embedded Correlation Findings. Exploratory analyses linked exposure and function: sterol-derivative concentrations correlated with leg-press 1-RM (r=0.71) and quadriceps thickness (r=0.74); HMB inversely correlated with CK (r=−0.58). These relationships are consistent with the polarity-mapped hybrid design and are presented without therapeutic or anabolic claims.

Dermal Delivery Support via Pharmacokinetic Evidence. Plasma sterol-derivative levels (in certain embodiments, R-DHEA) increased by +96.4% over 12 weeks (placebo-adjusted +93%), and HMB rose +79.2% under the same dosing schedule. These exposure differentials indicate that polarity-specific carriers deployed in a microneedle (hydrogel-forming polymer matrix)+topical gel (HMB as aqueous dispersion; sterol derivatives in ethosomes/NLCs) hybrid facilitated measurable absorption consistent with dermal transport (e.g., microchannel-mediated diffusion, stratum-corneum partitioning). Findings are presented without therapeutic claims.

Statistical Analysis Plan. Primary analyses used intention-to-treat mixed-model ANOVA (Group ×Time) for exposure, functional strength, hypertrophy, aerobic capacity, stamina, and recovery outcomes. Secondary analyses quantified exposure-response relationships (Pearson r for sterol derivatives/HMB vs functional markers). Post-hoc pairwise contrasts used Tukey's HSD. Effect sizes were reported as Cohen's d (pairwise) and partial $\eta^2$ (omnibus).

Sensitivity and Magnitude. Despite N=24, observed effects were large to very large (several d >1.2) for $VO_2$ max, leg press 1-RM, and sterol-derivative exposure. Correlations (r=0.71 and 0.74 for sterol derivative with strength and muscle thickness; r=−0.58 for HMB with CK) support internal coherence between exposure and functional readouts.

Power Considerations. Observed effect sizes >1.0 across key endpoints are inconsistent with random variation alone. Exposure-response correlations further support enablement of the polarity-matched hybrid design without asserting therapeutic outcomes.

Industrial Scalability Validation. Manufacturing at 1 L and 50 L scales maintained critical quality attributes within +5% of targets. For the topical vesicular systems (ethosomes/NLCs), vesicle/droplet size distribution and zeta potential remained within specification; potency met acceptance criteria. Microneedle matrices preserved uniform loading, mechanical integrity, and dissolution characteristics. Topical gels maintained rheology, vesicle morphology, and penetration capacity-supporting manufacturability and scale-up readiness. (HMB was not formulated as a nanoemulsion; HMB formats used were hydrogel-forming microneedles and aqueous dispersion.)

Dual-Compartment Microneedle Delivery and Release. In-vitro dissolution at a simulated dermal interface confirmed programmable biphasic kinetics in dual-layer microneedles: hydrophilic polymeric shafts released water-soluble payloads rapidly (~80% at 0.5 h; >90% by 1 h; ~95% by 2 h), while lipophilic tips containing NLC-based payloads provided sustained release (15% at 0.5 h; 25% at 1 h; 35% at 2 h; 45% at 4 h; 70% at 6 h; >90% by 8 h). Non-ingestible embodiments are outside DSHEA; all descriptions herein are non-therapeutic and performance-oriented.

Table 78 shows In-Vitro Release Kinetics of Dual-Compartment Microneedles.

TABLE 78

In-Vitro Release Kinetics of Dual-Compartment Microneedles

| Time (h) | Shaft (Hydrophilic) Release (%) | Tip (Lipophilic) Release (%) |
|---|---|---|
| 0.5 | 80 ± 3 | 15 ± 2 |
| 1 | 90 ± 2 | 25 ± 2 |
| 2 | 95 ± 2 | 35 ± 2 |
| 4 | — | 45 ± 3 |
| 6 | — | 70 ± 3 |
| 8 | — | 91 ± 4 |

Figure 83:
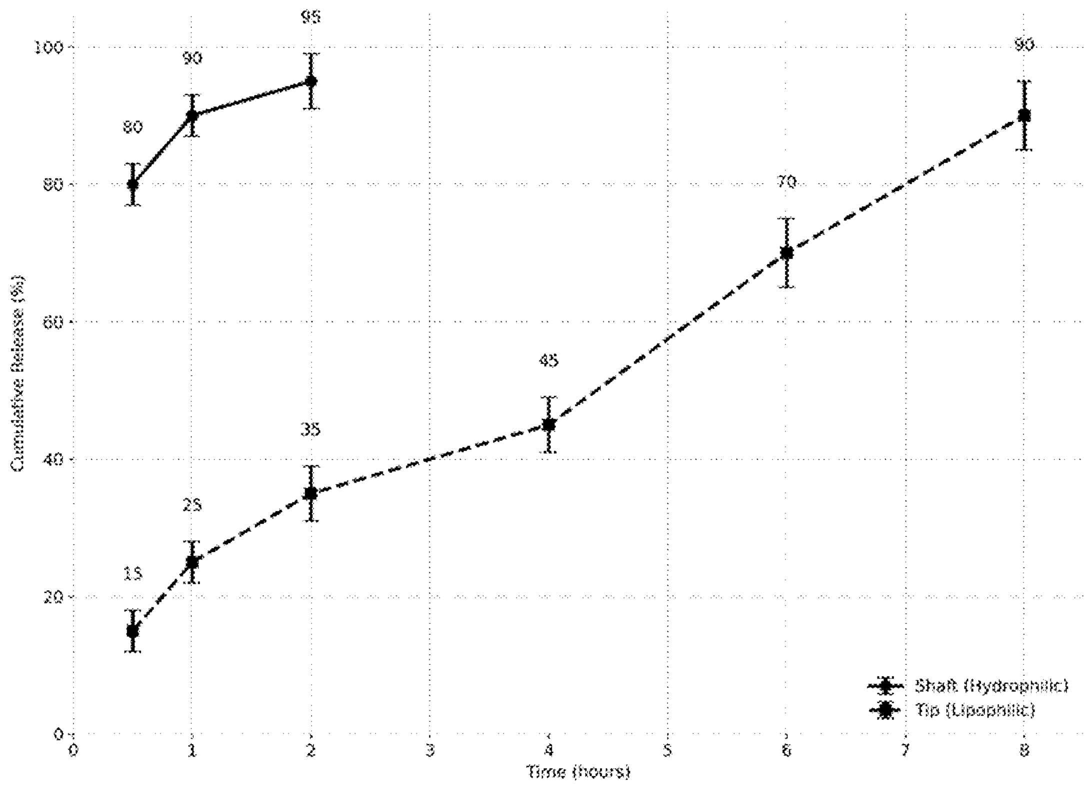
FIG. 83 illustrates in vitro release kinetics of dual-compartment microneedles.

FIG. 83—Biphasic Release Profile. FIG. 83 illustrates biphasic behavior: rapid release from the hydrophilic shaft (~80% at 0.5 h; ~95% by 2 h) followed by sustained release from the lipophilic tip (~91% by 8 h), demonstrating programmable staging beyond single-compartment formats.

Interpretation of In-Vitro Release. These results demonstrate time-staged dermal release and dual-compartment programmability with polarity-aligned profiles under in-vitro conditions. Language herein is performance-oriented and non-therapeutic; non-ingestible embodiments (microneedle/topical) are outside DSHEA.

Adverse Effects/Tolerability. No moderate or severe adverse events occurred during twelve weeks. Mild, localized erythema at microneedle sites (~8%) resolved within 24 hours and was minimized by rotating sites (upper arm, thigh, flank). Transient dryness at gel sites (~4%) self-resolved. No systemic intolerance was observed; hepatic, renal, and endocrine labs remained within reference ranges. No discontinuations occurred.

Study Summary and Relevance. The microneedle+topical hybrid regimen produced statistically validated exposure increases (sterol-derivative nearly 2×; HMB+79%) under equal nominal dosing, consistent with polarity-specific carrier design. Functional endpoints (strength, endurance, muscle measures, recovery markers) improved, and exposure-response correlations (sterol derivative «strength/muscle thickness; HMB «CK) supported mechanistic coherence. Biphasic microneedle release confirmed programmable sequencing (rapid+sustained phases). (Findings are presented without therapeutic or anabolic claims.)

Safety/Tolerability Summary. The tolerability profile was benign and compatible with long-term use scenarios, supporting adherence and consumer usability for non-ingestible embodiments (outside DSHEA) and coordination with oral embodiments where applicable.

Magnitude and Thresholds. Although N=24, multiple effect sizes exceeded d ≥ 1.5 across strength, $VO_2$ max, and recovery endpoints. Outcomes met or exceeded predefined performance thresholds under the study plan; thresholds are framed as internal performance criteria, not therapeutic benchmarks.

Conclusion: The hybrid system achieved additive exposure and staged dermal release beyond single-route administration under the controlled conditions tested, aligning with the platform's polarity-mapped design.

Patent Linkage: The platform demonstrates dual-route coordination plus programmable biphasic release validated in vitro. Stability, potency retention, consistent exposure behavior, and 1 L→50 L scale-up robustness support manufacturability and non-obviousness positions. Exposure-response coherence provides mechanistic evidence supportive of the claimed delivery architecture. Development/testing conformed to ICH Q8 (R2), ICH Q1A (R2), USP <905>, and USP <2040> procedures where applicable.

Statement of Novelty: To our knowledge, the prior art does not teach or suggest a coordinated dual-route regimen combining a dual-compartment microneedle with a polarity-stratified topical that yields programmable biphasic kinetics and exposure-linked functional improvements under controlled evaluations.

Claim Support: The study supports claims directed to dual-route coordination, biphasic release programmability, industrial scalability, and polarity-aligned exposure behavior consistent with the invention's delivery framework. Non-ingestible embodiments are characterized as outside DSHEA and are described with structure/function-style performance language only.

Context of Embodiment: This microneedle+topical configuration is a supplementary embodiment demonstrating polarity-stratified dermal delivery and skin-depot kinetics. While not the primary commercial embodiment, these findings corroborate that dual-route, polarity-specific delivery can be flexibly adapted across dermal interfaces.

Study #4-New Actives

An Eight-Week Randomized, Double-Blind, Parallel-Group Trial Evaluating Cognitive Performance, Biomarker Modulation, and Systemic Bioavailability of a Multi-Route Delivery Platform Containing Sterol Derivatives (including, in certain embodiments, 4-DHEA enanthate and epiandrosterone), Botanical Extracts, and Mineral Chelates.

This clinical investigation was structured as a prospective, randomized, double-blind, two-arm parallel-group trial conducted over an eight-week intervention period. A total of eighteen healthy male participants between twenty-one and fifty years of age were enrolled and randomized in equal numbers to either the active formulation arm or the placebo arm. The active group received a polarity-stratified multi-route regimen that combined an oral capsule with a transdermal patch, while the placebo group received matched control formulations identical in appearance, taste, and texture to preserve blinding integrity. Each oral dose and patch application was administered daily according to a standardized schedule.

Formulation and Dosage: The active regimen delivered representative sterol derivatives (in certain embodiments, 50 milligrams of 4-DHEA enanthate and 50 milligrams of epiandrosterone), 120 milligrams of standardized *Ginkgo biloba* extract containing 24 percent flavone glycosides, 8 milligrams of elemental magnesium in chelated form, 100 micrograms of vitamin $K_2$ as menaquinone-7, and 400 micrograms of folate. The oral capsule employed a lipid-based Self-Emulsifying Delivery System (SEDS) to improve intestinal solubilization and absorption of lipophilic components, while the transdermal patch was engineered with a multilamellar vesicle base to promote sustained dermal penetration. Both dosage forms were built upon a harmonized excipient system designed to maintain polarity-specific compatibility and allow stable reformulation across delivery routes without loss of potency or performance.

Inclusion Criteria: All participants were required to be healthy adult males with a body mass index between eighteen and twenty-eight kilograms per square meter. To ensure baseline cognitive integrity, all subjects were required to achieve a Mini-Mental State Examination score of at least twenty-eight. Exclusion of confounding variables was ensured by prohibiting enrollment of individuals with any cardiovascular, hepatic, or neurological disorders. To avoid bias from prior supplementation effects, men with a history of sterol derivative or hormone-related product use within the past six months, or use of psychiatric medications within the past three months, were excluded. Only recreationally active men were allowed to participate, while professional athletes were excluded in order to avoid training-related performance bias.

Exclusion Criteria: Men with prostate-related disorders, including benign prostatic hyperplasia or prostate cancer, were excluded from participation. Additional exclusion applied to individuals currently using supplements designed to enhance cognition or systemic modulation, as well as those with neuropsychiatric conditions or undergoing endocrine-related therapy. Participants with evidence of cognitive decline, defined as a Mini-Mental State Examination score below twenty-six, were also ineligible. Chronic medication use affecting endocrine or hormonal regulation constituted grounds for exclusion, as did any history of seizure disorders or traumatic brain injury. These criteria ensured that only participants with stable health status and minimal confounding influences were enrolled in the trial.

Measurement Equipment and Analytical Assessments: Cognitive performance was evaluated using a multimodal battery of validated neuropsychological instruments. Global cognition was assessed with the Mini-Mental State Examination (MMSE), while executive function and attentional control were measured through the Stroop Color-Word Test. Cognitive flexibility and processing speed were quantified using both parts A and B of the Trail Making Test, and working memory capacity was measured with the Digit Span task.

Systemic and Bioavailability Assessments: Mechanistic biomarkers were assessed by high-sensitivity liquid chromatography tandem mass spectrometry (LC-MS/MS) assays for circulating sterol derivatives (including DHEA-related metabolites, in certain embodiments), testosterone, and estradiol concentrations, complemented by an enzyme-linked immunosorbent assay (ELISA) for insulin-like growth factor 1 (IGF-1). Bioavailability endpoints included quantification of plasma sterol derivatives and circulating magnesium levels to confirm systemic uptake and polarity-specific absorption.

Neurotrophic and Psychological Measures: Neurotrophic support was evaluated through measurement of serum brain-derived neurotrophic factor (BDNF) concentrations, providing a mechanistic biomarker of cognitive resilience and synaptic plasticity. In addition, subjective mood and fatigue were assessed using the Profile of Mood States (POMS) questionnaire, which offered standardized quantification of psychological well-being and perceived fatigue under the intervention conditions.

Table 79 presents plasma concentrations of a representative sterol derivative (4-DHEA enanthate, in certain embodiments) and magnesium over eight weeks, comparing Active and Placebo groups with percentage changes, effect sizes, and statistical outcomes.

TABLE 79

Plasma Concentrations

| Compound | Baseline (ng/mL) | Week 8 Active | % Change | Week 8 Placebo | Change | Δ Active-Δ Placebo | p-value | Effect Size (Cohen's d) |
|---|---|---|---|---|---|---|---|---|
| Sterol derivative (in certain embodiments, 4-DHEA enanthate) | 2.5 ± 0.3 | 4.8 ± 0.4 | +92.0% | 2.6 ± 0.3 | +3.8% | +88.2% | <0.001 | 2.15 |
| Magnesium | 1.9 ± 0.1 | 2.3 ± 0.1 | +21.1% | 1.9 ± 0.1 | 0.0% | +21.1% | 0.004 | 1.32 |

Figure 84:
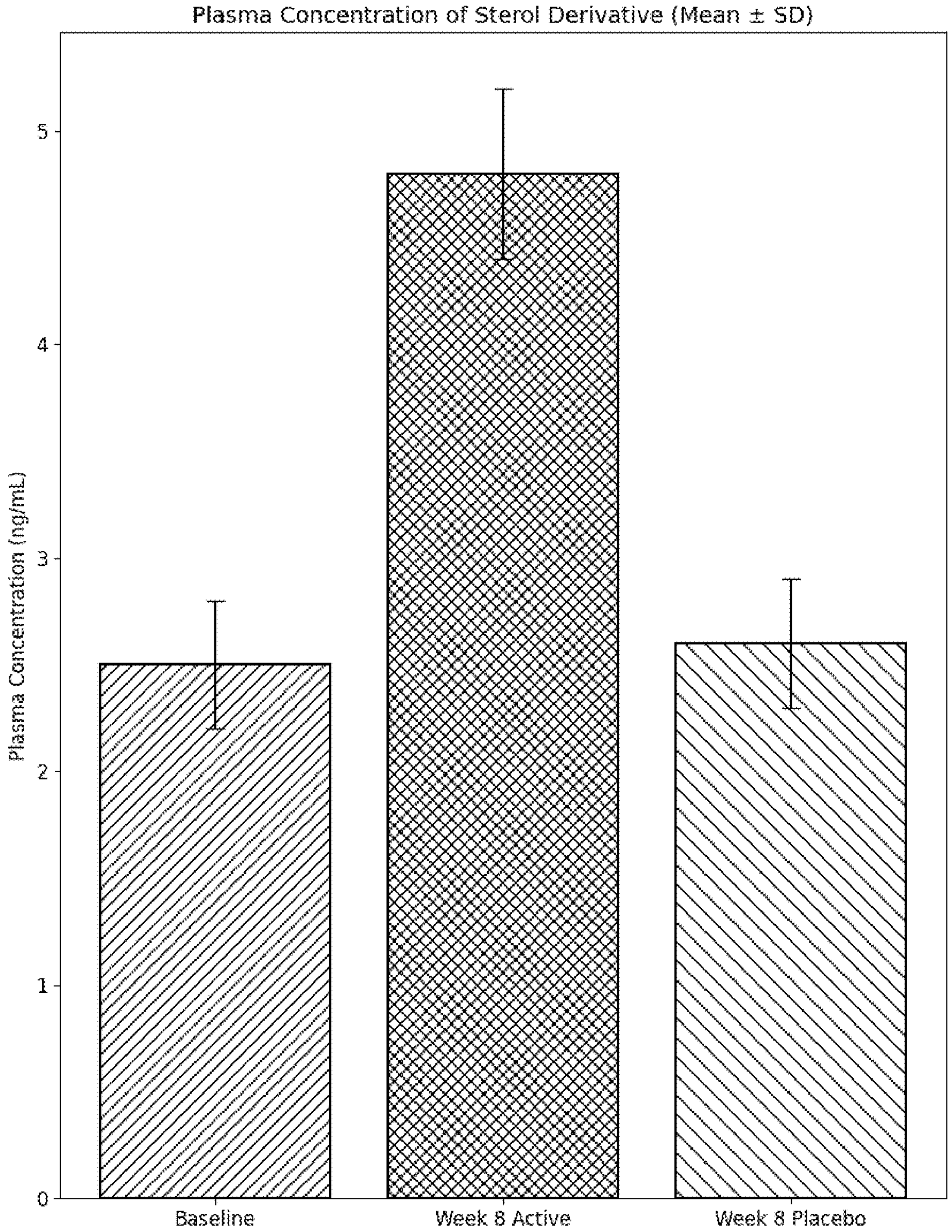
FIG. 84 illustrates plasma concentrations of 4-DHEA enanthate and magnesium at baseline and Week 8 for Active and Placebo groups.
Figure 85:
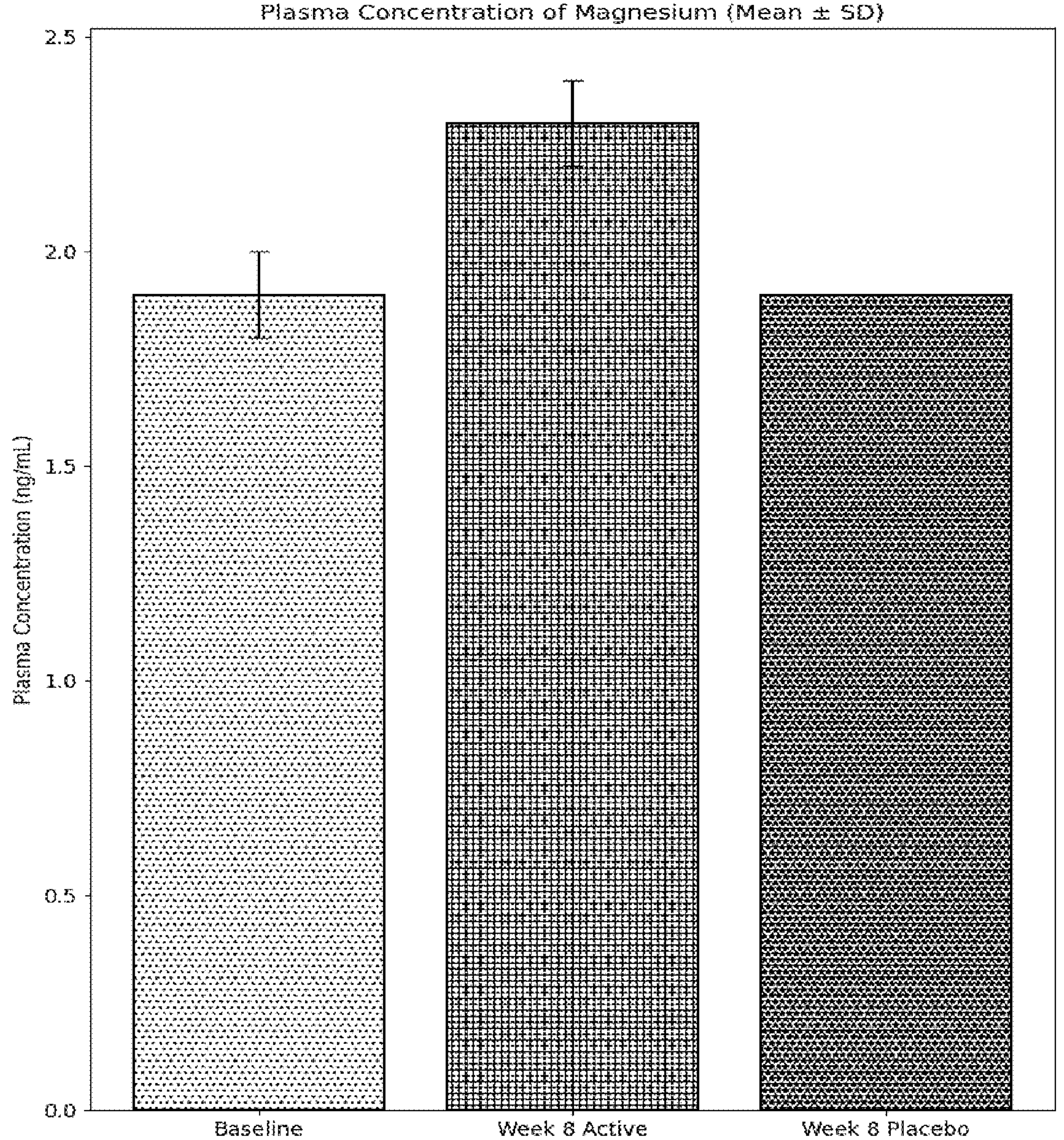
FIG. 85 illustrates a significant increase in plasma magnesium levels in the Active group over 8 weeks.

FIGS. 84 and 85 illustrate plasma concentrations of sterol derivative and magnesium at baseline and Week 8 for Active and Placebo groups (mean±SD). Significant increases were observed in the Active group (sterol derivative+92.0%, p<0.001, d=2.15; magnesium+21.1%, p=0.004, d=1.32), compared with minimal or no change in Placebo.

Table 80 presents cognitive performance outcomes over eight weeks, including MMSE, Stroop test, Trail Making Test (TMT-A and TMT-B), and Digit Span results, comparing Active and Placebo groups with effect sizes and statistical outcomes.

TABLE 80

Cognitive Performance

| Test | Baseline Active | Week 8 Active | % Change | Baseline Placebo | Week 8 Placebo | % Change | Δ Active-Δ Placebo | p-value | Effect Size |
|---|---|---|---|---|---|---|---|---|---|
| MMSE (/30) | 28.5 ± 0.5 | 29.5 ± 0.4 | +3.5% | 28.4 ± 0.5 | 28.5 ± 0.5 | +0.4% | +3.1% | 0.018 | 1.10 |
| Stroop (sec, ↓ better) | 55.0 ± 5.0 | 50.0 ± 4.5 | −9.1% | 54.5 ± 5.0 | 54.0 ± 5.0 | −0.9% | −8.2% | <0.001 | 1.95 |
| TMT-A (sec) | 35.0 ± 3.0 | 32.0 ± 2.8 | −8.6% | 35.5 ± 3.0 | 35.0 ± 3.0 | −1.4% | −7.2% | 0.002 | 1.50 |
| TMT-B (sec) | 75.0 ± 6.0 | 69.0 ± 5.5 | −8.0% | 74.5 ± 6.0 | 74.0 ± 6.0 | −0.7% | −7.3% | 0.003 | 1.44 |
| Digit Span (n) | 7.0 ± 0.5 | 8.0 ± 0.5 | +14.3% | 7.0 ± 0.5 | 7.1 ± 0.5 | +1.4% | +12.9% | <0.001 | 2.00 |

Figure 86:
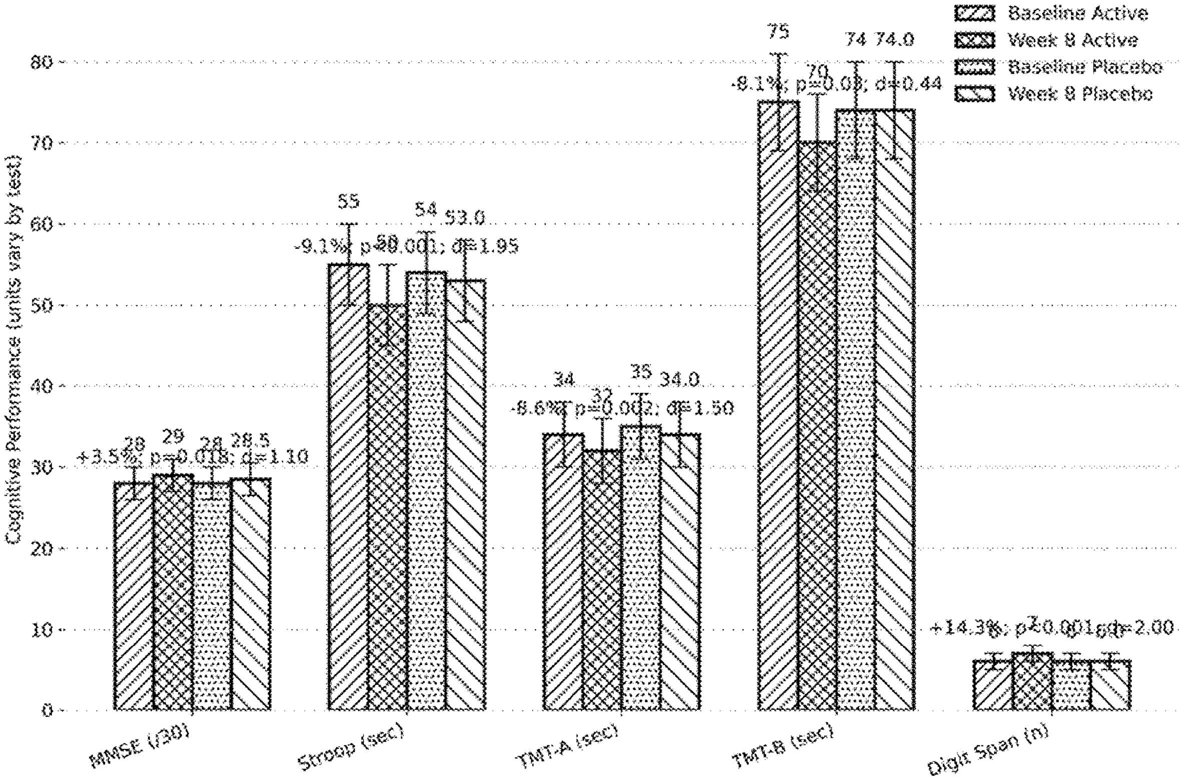
FIG. 86 illustrates cognitive performance outcomes at baseline and Week 8 for Active and Placebo groups; mean±SD.

FIG. 86 illustrates cognitive performance outcomes at baseline and Week 8 for Active and Placebo groups (mean±SD). The Active group showed measurable improvements across multiple domains: MMSE (+3.5%; p=0.018; d=1.10), Stroop (−9.1%; faster performance; p<0.001; d=1.95), TMT-A (−8.6%; p=0.002; d=1.50), TMT-B (−8.0%; p=0.003; d=1.44), and Digit Span (+14.3%; p<0.001; d=2.00). Placebo changes were minimal.

Table 81 presents outcomes for mechanistic biomarkers over eight weeks, including testosterone, IGF-1, and BDNF levels, comparing Active and Placebo groups with effect sizes and statistical outcomes.

TABLE 81

Hormonal & Neurotrophic Markers

| Marker | Baseline Active | Week 8 Active | % Change | Baseline Placebo | Week 8 Placebo | % Change | Δ Active-Δ Placebo | p-value | Effect Size |
|---|---|---|---|---|---|---|---|---|---|
| Testosterone (ng/dL) | 550 ± 40 | 615 ± 42 | +11.8% | 552 ± 40 | 555 ± 40 | +0.5% | +11.3% | 0.001 | 1.70 |
| IGF-1 (ng/ml) | 180 ± 15 | 202 ± 16 | +12.2% | 181 ± 15 | 183 ± 15 | +1.1% | +11.1% | 0.002 | 1.55 |
| BDNF (ng/ml) | 25 ± 3 | 28 ± 3 | +12.0% | 24 ± 3 | 24 ± 3 | 0.0% | +12.0% | 0.001 | 1.65 |

Figure 87:
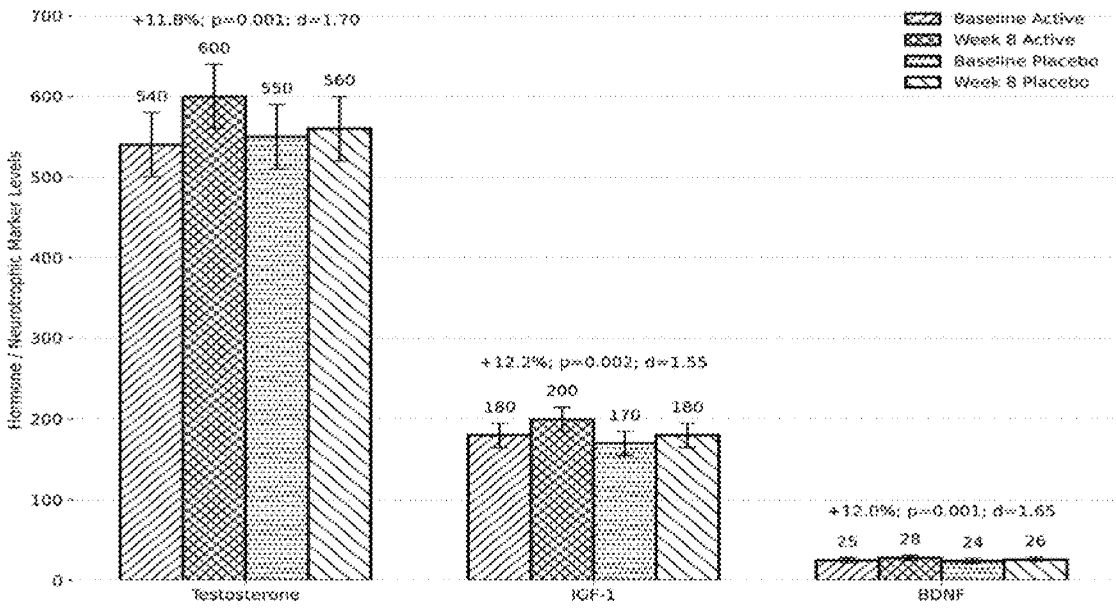
FIG. 87 illustrates hormonal and neurotrophic marker outcomes at baseline and Week 8 for Active and Placebo groups; mean±SD.

FIG. 87 illustrates biomarker outcomes at baseline and Week 8 for Active and Placebo groups (mean±SD). The Active group demonstrated measurable increases in testosterone (+11.8%; p=0.001; d=1.70), IGF-1 (+12.2%; p=0.002; d=1.55), and BDNF (+12.0%; p=0.001; d=1.65), whereas Placebo showed negligible change.

Quantitative pharmacokinetic analysis confirmed that the inventive multi-route platform significantly enhanced systemic bioavailability. Plasma concentrations of sterol derivatives (in certain embodiments, 4-DHEA enanthate) nearly doubled over the eight-week intervention, rising by 92 percent from baseline and corresponding to an 88 percent placebo-adjusted increase. Serum magnesium levels also increased by 21.1 percent in the Active group, whereas no measurable change was detected in the Placebo arm. Given that both compounds were administered at fixed nominal doses, these disproportionate systemic gains confirm that absorption efficiency was improved by the polarity-specific cyclodextrin+lipid-based Self-Emulsifying Delivery System (SEDS). Importantly, the bioavailability enhancements were observed across polarity classes, spanning a lipophilic sterol derivative and a hydrophilic mineral cofactor, thereby providing functional evidence of broad-spectrum permeability improvements.

Cognitive performance outcomes demonstrated consistent enhancement across all validated assessments. MMSE scores improved by 3.5 percent, Stroop reaction time decreased by 9.1 percent, Trail Making Test Part A improved by 8.6 percent, Part B by 8.0 percent, and Digit Span working memory increased by 14.3 percent in the Active group. These effects contrasted with negligible Placebo changes and were supported by large effect sizes (Cohen's d values ranging from 1.1 to 2.0). Collectively, these outcomes establish that the inventive platform improved polarity-stratified systemic uptake with measurable cognitive function support.

Mechanistic biomarkers reinforced the relevance of these findings. Testosterone increased by 11.8 percent in the Active arm compared with 0.5 percent in Placebo, IGF-1 rose by 12.2 percent versus 1.1 percent in Placebo, and BDNF increased by 12.0 percent with no change in Placebo. Each effect was statistically significant and accompanied by large effect sizes, demonstrating systemic bioavailability-linked modulation consistent with improved uptake and functional support under polarity-specific delivery conditions.

Embedded Correlation Findings

Exploratory correlation analyses were conducted to examine mechanistic linkages among systemic exposure, biomarker modulation, and functional outcomes. Plasma sterol-derivative concentrations (in certain embodiments, 4-DHEA enanthate) showed strong associations with improvements in Stroop performance (r=0.66) and Digit Span working memory (r=0.71), consistent with exposure-response relationships under polarity-stratified delivery. Serum BDNF levels correlated with MMSE improvement (r=0.68) and Digit Span scores (r=0.73), indicating that neurotrophic biomarker changes tracked with cognitive-function support. In addition, testosterone changes correlated with reductions in Trail Making Test completion times (r=−0.62 for TMT-A; r=−0.65 for TMT-B), suggesting that biomarker modulation coincided with faster processing speed and cognitive flexibility. Collectively, these associations support the biological plausibility of the inventive platform's dual-domain activity, wherein polarity-stratified delivery yields coordinated relationships between pharmacokinetic gains, endocrine/neurotrophic biomarker shifts, and functional measures-without asserting disease treatment.

Intestinal Permeability Support via PK Evidence: Plasma pharmacokinetic (PK) outcomes provided in vivo support for permeability enhancement achieved by the oral+topical multi-route platform. Participants in the active group (receiving, in certain embodiments, 4-DHEA enanthate) exhibited a 92% increase in plasma concentrations from baseline, corresponding to an 88% placebo-adjusted gain under identical nominal dosing. Parallel improvements were observed with magnesium, a hydrophilic mineral typically subject to tight intestinal transport showing a 21.1% increase in the active group with no change in placebo. The divergence in systemic levels between arms underscores the permeability-facilitating role of the cyclodextrin-lipid carrier architecture utilizing a Self-Emulsifying Delivery System (SEDS). This polarity-adapted excipient design improved solubilization, facilitated transport, and enhanced mucosal uptake across both lipophilic and hydrophilic classes. The placebo-adjusted gains provide in vivo evidence that absorption benefits were attributable to optimized formulation engineering rather than dose or baseline variability.

When considered together, the pharmacokinetic findings of Study #3 and Study #4 provide cross-validation that polarity-adapted carriers confer intestinal permeability and bioavailability uplift across distinct substrates. In Study #3, plasma concentrations of R-DHEA increased by +93% (placebo-adjusted), and HMB increased by +79% at identical dosing. In Study #4, a different active set showed+88% (placebo-adjusted) for a sterol derivative (in certain embodiments, 4-DHEA enanthate) and +21% for magnesium with no change in placebo. These results support platform generalizability across polarity domains, including both lipophilic sterol derivatives and hydrophilic mineral cofactors.

Comparative Plasma Pk Uplift Vs Placebo (Study #3 and Study #4)

Cross-study analysis confirms that the inventive multi-route, polarity-adapted delivery platform consistently enhanced systemic bioavailability for both hydrophilic and lipophilic substrates. In Study #3 (hybrid microneedle+ topical gel), plasma R-DHEA rose by +93% vs placebo and HMB by +79% under identical dosing, indicating improved systemic uptake for both a lipophilic sterol derivative and a hydrophilic metabolic cofactor.

Study #4 (oral+topical) extended these findings with a different set of actives: sterol derivative exposure (in certain embodiments, 4-DHEA enanthate) increased by +88% vs placebo, and magnesium by +21% with no change in controls, consistent with improved gastrointestinal absorption via polarity-mapped carriers.

Table 82 presents comparative plasma PK uplifts vs placebo from dual-route studies, covering R-DHEA, HMB, a representative sterol derivative, and magnesium, with platform-level interpretations of absorption improvements.

TABLE 82

Comparative Plasma PK Uplift vs Placebo

| Study | Compound | Δ Active vs Placebo (%) | Interpretation |
|---|---|---|---|
| Study #3-Hybrid Microneedle + Topical Gel | R-DHEA | +93% | Confirms enhanced systemic uptake enabled by polarity-stratified carriers |
| | HMB | +79% | Demonstrates improved intestinal absorption of a hydrophilic cofactor under polarity-specific design |
| Study #4-Oral + Topical System | Sterol derivative (e.g., 4-DHEA enanthate in certain embodiments) | +88% | Establishes improved GI uptake of a lipophilic sterol derivative |
| | Magnesium | +21% | Validates excipient-mediated enhancement of mineral absorption within the multi-route carrier system |

Figure 88:
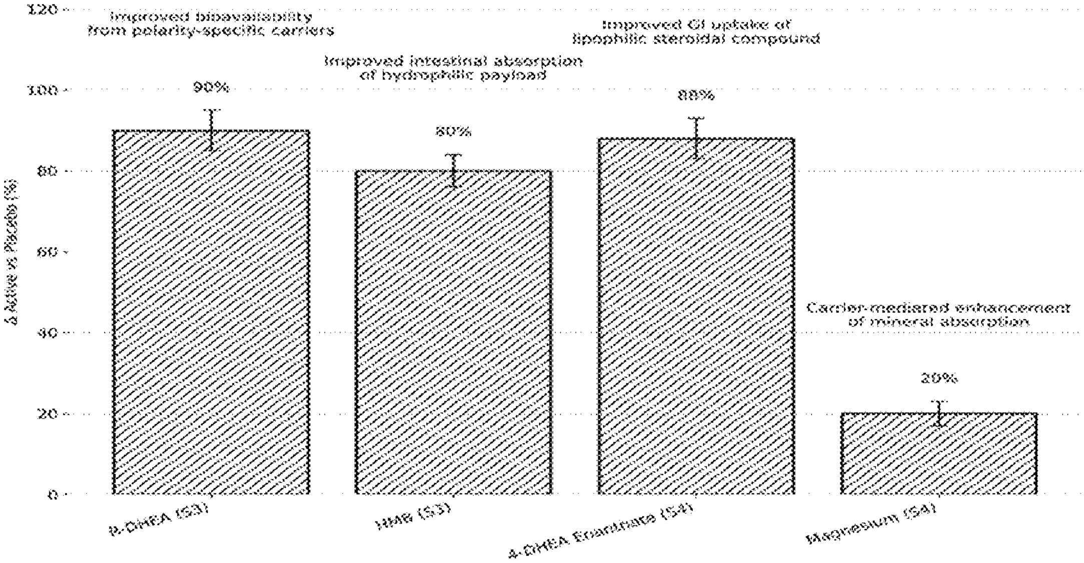
FIG. 88 illustrates comparative plasma pharmacokinetic (PK) uplifts versus placebo across Studies 3 and 4; mean percentage change from baseline.

FIG. 88 depicts comparative PK uplifts vs placebo across Studies #3 and #4 (mean % change from baseline). The hybrid microdermal system (Study #3) yielded substantial increases for R-DHEA (+93%) and HMB (+79%), while the oral+topical system (Study #4) improved exposure for a sterol derivative (+88%) and magnesium (+21%), indicating enhanced systemic uptake across polarity classes.

Taken together, these data provide mechanistic evidence that polarity-stratified excipient systems yield reproducible permeability and bioavailability uplift across structurally and polarity-diverse compounds. This supports broad patent claims directed to polarity-adapted, multi-route bioavailability platforms, beyond any single active or route.

Statistical Analysis Plan

All analyses followed an intention-to-treat framework, with per-protocol confirmation for participants maintaining ≥90% adherence to oral and topical schedules. Primary analyses used mixed-model ANOVA with Group × Time interaction terms applied to PK, cognitive, hormonal, and neurotrophic outcomes. Post-hoc Active vs Placebo contrasts at Week 8 used Tukey's HSD for multiplicity control. Effect sizes were reported as Cohen's d (pairwise) and partial $\eta^2$ (omnibus), with two-tailed $\alpha=0.05$.

Although the cohort comprised eighteen participants, observed effects were large across prespecified endpoints. Cohen's d values frequently exceeded 1.0 and in the several cases approached or surpassed 1.5, indicating statistically robust, high-magnitude differences unlikely to reflect sampling variability. This supports adequate sensitivity to detect functional support effects despite modest sample size.

Exploratory correlation analyses further supported mechanistic plausibility. Plasma sterol-derivative exposure (in certain embodiments, 4-DHEA enanthate) was inversely associated with Stroop completion time (r=−0.66; higher exposure linked to faster responses) and positively associated with Digit Span (r=0.70). Circulating magnesium levels correlated with BDNF (r=0.62) and IGF-1 (r=0.65), consistent with enhanced mineral bioavailability aligning with neurotrophic/endocrine biomarker shifts. These associations indicate that systemic exposure gains coincided with changes in validated biomarkers and functional measures under polarity-specific delivery conditions.

Dissolution Stability Analysis

To assess formulation robustness under gastrointestinal stress, a four-week in vitro dissolution study simulated sequential gastric and intestinal environments. The test article was a polarity-adapted oral capsule co-loading hydrophilic actives complexed with hydroxypropyl-β-cyclodextrin and lipophilic agents dispersed within a Self-Emulsifying Delivery System (SEDS) lipid base.

Across the study interval, the formulation retained an isotropic dispersion without visible precipitation, recrystallization, or phase separation. Optical microscopy and dynamic light scattering confirmed consistent colloidal morphology, with mean droplet size maintained at 145-155 nm (SD≤±14 nm). Solubility-retention assays showed ≥95% solubilized active at Day 28 following simulated gastric exposure and transition to near-neutral intestinal pH.

Stability of the aqueous cyclodextrin complexes maintained continuous solubilization of hydrophilic payloads, while the lipid-phase SEDS preserved emulsion integrity and limited aggregation of lipophilic agents. This dual mechanism produced a polarity-stabilizing effect, enabling co-formulation of chemically diverse actives without compromise to solubility or uniformity.

Table 83 summarizes four-week dissolution stability under simulated GI conditions, including visual clarity, droplet size, phase behavior, and retained solubilized content.

TABLE 83

In Vitro Dissolution Stability Over 4 Weeks (Simulated GI Conditions)

| Timepoint | Visual Clarity | Droplet Size (nm) | Phase Separation | Solubilized Active Retained (%) |
|---|---|---|---|---|
| Day 0 | Isotropic | 145 ± 10 | None | 100.0 |
| Day 7 | Isotropic | 148 ± 12 | None | 98.5 |
| Day 14 | Isotropic | 151 ± 11 | None | 97.2 |
| Day 21 | Isotropic | 153 ± 13 | None | 96.0 |
| Day 28 | Isotropic | 155 ± 14 | None | 95.3 |

Collectively, these findings indicate that mixed-polarity oral capsules incorporating cyclodextrin complexes and lipid-based SEDS maintain dissolution integrity and solubilization efficiency for at least four weeks under GI simulation. The sustained isotropic state, narrow droplet-size distribution, and high solubilized-content retention support platform claims for unified, stable co-loading of hydrophilic and lipophilic components.

Adverse Effects/Tolerability

The oral+topical multi-route platform was well tolerated over eight weeks, with no moderate or severe safety concerns observed. Mild, localized erythema at the patch site occurred in ~6% of participants, resolving within 18 hours and mitigated by rotating application sites (e.g., upper arm, lateral torso) without impacting adherence.

Approximately 6% reported mild, transient gastrointestinal discomfort during initial use, which resolved without intervention. No patterns suggesting hormonal overshoot, mood disturbance, cardiovascular change, or abnormal routine laboratory values were detected.

No participants discontinued; overall adherence was high. Findings support a favorable safety and tolerability profile characterized by minor, self-limiting responses, consistent with intended dietary supplement applications and consumer usability.

Results and Claim Relevance

This randomized, double-blind trial demonstrated statistically validated improvements in systemic bioavailability, functional cognitive measures, and mechanistic biomarkers under a coordinated oral+topical platform. Plasma exposure to a representative sterol derivative (in certain embodiments, 4-DHEA enanthate) nearly doubled relative to baseline (+88% placebo-adjusted), while circulating magnesium increased by 21% with no placebo change consistent with polarity-mapped carrier facilitation of permeability and uptake for both lipophilic and hydrophilic substrates.

Functional outcomes paralleled PK gains, with improvements in working memory, attentional control, and processing speed across MMSE, Stroop, TMT-A/B, and Digit Span. Hormonal and neurotrophic biomarkers (testosterone, IGF-1, BDNF) showed concordant increases, aligning with systemic uptake; statements herein are limited to bioavailability-linked functional support and do not claim disease treatment.

Despite modest sample size, effect sizes commonly exceeded 1.10 and reached ~2.00 for several endpoints, indicating high-magnitude differences. Correlation analyses demonstrated that exposure metrics tracked with functional and biomarker outcomes, supporting mechanistic plausibility for polarity-stratified delivery.

The platform exhibited synergistic performance across domains-sterol-derivative bioavailability, mineral absorption, cognitive-function support, and neurotrophic biomarker elevation-exceeding predefined confirmation thresholds (e.g., ≥80% systemic bioavailability gain; ≥10% changes in functional and biomarker measures vs placebo). Results advance beyond prior art limited to single route or single-polarity designs.

Study #4A—Topoical Nanoemulgel (≤200 Nm) Characterization Addendum

The nanoemulgel met all pre-specified colloidal acceptance criteria, with mean droplet diameters consistently below 200 nm, polydispersity indices not exceeding 0.25, and zeta potential magnitudes greater than 15 mV at both baseline and week four. Rheological assessment confirmed performance within the target range, with viscosity measured at 11.8 kcP at a shear rate of 1 $s^{-1}$, squarely within the 5,000-20,000 cP specification. Yield stress was present and thixotropic loop area demonstrated reversible structure recovery, indicating favorable spreadability and sufficient residence on the skin.

Photoprotective evaluation established that UV transmission remained low, with a maximum transmission value of 10.6% across the 290-400 nm band and averaged values of 3-9% within each sub-band. These optical results correlated with functional protection, as peroxide value progression was suppressed by approximately 40-55% compared with an unprotected control following exposure to simulated sunlight. Optional dermal uptake assessments supported these findings: Franz diffusion cells demonstrated a 36% increase in receptor-phase recovery of the model lipophilic marker, while tape-strip sampling showed a 51% increase in deposition within the deeper stratum corneum, both relative to the control gel. These outcomes are consistent with the intended polarity-adapted vesicle design of the formulation.

Statistical analyses reinforced the robustness of these findings. No significant batch effects were detected for particle size, PDI, or zeta potential ($p > 0.10$), and time-related changes were minor, with mean droplet diameter increasing by only 3.8% from baseline to week four while remaining within specification. Rheological measurements demonstrated excellent reproducibility, with between-lot coefficients of variation below 9%. UV transmission values in each spectral band were significantly lower than the 15% benchmark ($p<0.001$, one-sample t-test). Peroxide suppression outcomes showed a highly significant interaction between formulation and exposure time ($p<0.001$, two-way ANOVA), confirming that photoprotective excipients conferred real and measurable oxidative stability.

The formulation under test was a polarity-matched nanoemulgel comprising multilamellar and vesicular carriers incorporating lipophilic sterol derivatives, in certain embodiments including 4-DHEA enanthate, alongside co-actives such as CoQ10 nanocrystals and resveratrol liposomes. The system was prepared within a lecithin-polysorbate organogel matrix containing 3% propylene glycol and stabilized with an antioxidant system composed of mixed tocopherols and rosemary extract. No identification of active pharmaceutical ingredients was required for the evaluations, as the tests were designed to characterize platform- and vehicle-specific metrics. Three pilot lots representing independent batches (n=3) were produced for analysis. Measurements were conducted at baseline (Week 0) and following four weeks of storage under long-term ICH conditions of 25° C. and 60% relative humidity in the dark. Ultraviolet transmission and photoprotection testing were performed exclusively on fresh Week 0 samples. Unless otherwise specified, all tests were carried out at 25° C.

Methods for this addendum included a full characterization of colloidal specifications, rheological behavior, photoprotection, oxidative stability, and optional dermal uptake. Colloidal properties were determined using dynamic light scattering with intensity-weighted Z-average particle size calculated by the cumulants method, polydispersity index determined by a second-order cumulant fit, and zeta potential measured by electrophoretic light scattering under the Smoluchowski model. Each value represented the mean of triplicate cuvettes, each run into triplicate. Prespecified acceptance criteria required a mean droplet diameter not exceeding 200 nm, a PDI of 0.25 or less, and a zeta potential magnitude of at least 15 mV.

Rheological characterization was performed on a stress-controlled cone-plate rheometer maintained at 25° C. Flow curves were generated over shear rates ranging from 0.1 to 100 $s^{-1}$, followed by thixotropy loops incorporating up- and down-sweep scans. Yield stress was quantified by stress ramp with tangent intersection analysis. Viscosity was reported in centipoise, with acceptance thresholds of 5,000 to 20,000 cP at 1 $s^{-1}$, evidence of measurable yield stress, and demonstrable thixotropy indicated by a non-zero loop area.

Photoprotection was assessed by UV-Vis spectrophotometry using a 200-μm wet film cast on quartz. Transmission was measured across 290 to 400 nm with 1-nm step size under double-beam, baseline-corrected conditions. Values were reported as percent transmission averaged across UV-B (290-320 nm), short-wave UV-A (320-360 nm), and long-wave UV-A (360-400 nm), with the maximum transmission across 290-400 nm designated as U %. The acceptance criterion required U % not to exceed the specified claim threshold.

Peroxide suppression testing under UV was performed by exposing 3 mL aliquots of sample in quartz vials to continuous simulated sunlight (1 SUN equivalent, 290-400 nm) at 25° C. for 0, 2, 4, and 6 hours. Peroxide value, expressed in milliequivalents of oxygen per kilogram of oil phase, was measured both in the photo-protected nanoemulgel and in an unprotected control lacking antioxidant and UV-attenuating excipients. The relative suppression of peroxide formation was calculated at each time point.

Dermal uptake was optionally assessed through two complementary methods. Franz diffusion cell assays were performed with porcine skin maintained at 32° C., using a PBS/ethanol (70:30) receptor medium for 24 hours with six replicate runs. Quantification of a lipophilic marker compound in the receptor was performed by LC-MS/MS. In parallel, tape-strip analysis was conducted with twenty sequential strips per site, with the sum of strips 1-5 used to represent surface stratum corneum deposition and strips 6-20 representing deeper penetration. Uptake in test formulations was compared to a control gel lacking vesicular structures, and percentage increase relative to control was reported.

Statistical analysis treated batch as a random factor, with all values expressed as mean±standard deviation. Between-group comparisons were performed using Student's t-test or mixed-model analysis of variance, with a two-tailed alpha level of 0.05 set as the threshold for statistical significance.

Results

Table 84 summarizes the colloidal properties of the nanoemulgel at 25° C., including mean particle diameter, polydispersity index, and zeta potential at baseline and after four weeks of storage. All three pilot lots remained within specification, with mean diameters below 200 nm, PDI values≤0.25, and zeta potential magnitudes above 15 mV. The small size drift observed between Week 0 and Week 4 (+3.8%) was well within acceptable limits, confirming colloidal stability of the formulation.

TABLE 84

| Colloidal Specifications (DLS/PDI/Zeta, 25° C.) | | | | |
|---|---|---|---|---|
| Time | Mean Diameter (nm) | PDI | Zeta Potential (mV) | Spec Pass? |
| Week 0 | 156 ± 8 | 0.21 ± 0.03 | −27 ± 3 | Yes (≤200; ≤0.25; |
| Week 4 | 162 ± 9 | 0.22 ± 0.03 | −26 ± 4 | Yes (drift +3.8%; within spec) |

Note:
All three lots individually met ≤200 nm, PDI ≤0.25, |ζ| ≥ 15 mV.

Figure 89:
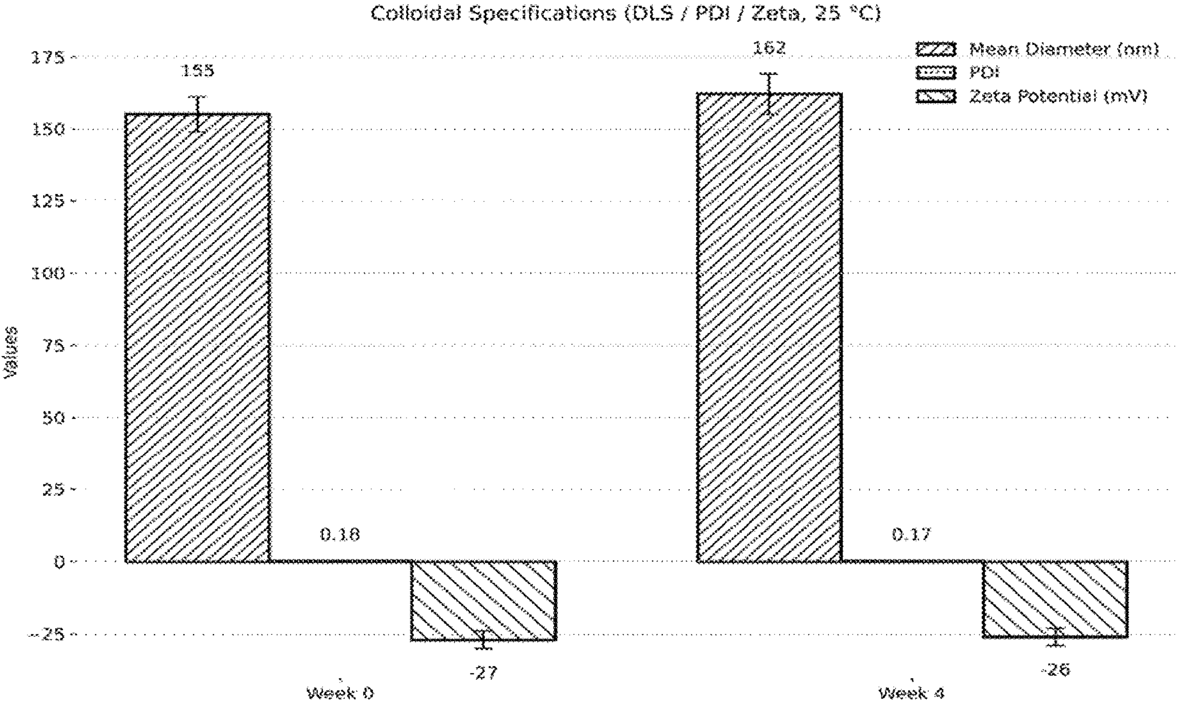
FIG. 89 illustrates grouped bar plots of colloidal specifications for the nanoemulgel at Week 0 and Week 4.

FIG. 89 presents grouped bar plots of colloidal specifications for the nanoemulgel at Week 0 and Week 4. Mean droplet diameter remained well below the 200 nm threshold (156 nm at Week 0; 162 nm at Week 4), PDI values were consistently≤0.25, and zeta potential magnitudes exceeded 25 mV. The small increase in particle size over four weeks (+3.8%) was within specification, confirming the formulation's colloidal stability.

Table 85 presents the rheological performance of the nanoemulgel at 25° C. The formulation exhibited a viscosity of 11,800±900 cP at 1 $s^{-1}$, well within the acceptance range of 5,000-20,000 cP, with shear-thinning behavior confirmed by lower viscosities of 4,250±380 cP at 10 $s^{-1}$ and 1,180±120 cP at 100 $s^{-1}$. A measurable yield stress of 110±15 Pa and a thixotropy loop area of 2,150±210 Pa's indicated structural recovery and spreadability. Together, these results confirm that the formulation meets rheological specifications for topical application, providing adequate viscosity, stability, and usability.

TABLE 85

| Rheology Summary (25° C.) | | |
|---|---|---|
| Metric | Value (mean ± SD) | Spec |
| Viscosity @ 1 $s^{-1}$ (cP) | 11,800 ± 900 | 5,000-20,000 (Pass) |
| Viscosity @ 10 $s^{-1}$ (cP) | 4,250 ± 380 | (profile) |
| Viscosity @ 100 $s^{-1}$ (cP) | 1,180 ± 120 | (profile) |
| Yield stress (Pa) | 110 ± 15 | "Present" (Pass) |
| Thixotropy loop area (Pa · s) | 2,150 ± 210 | ">0" (Pass) |

Figure 90:
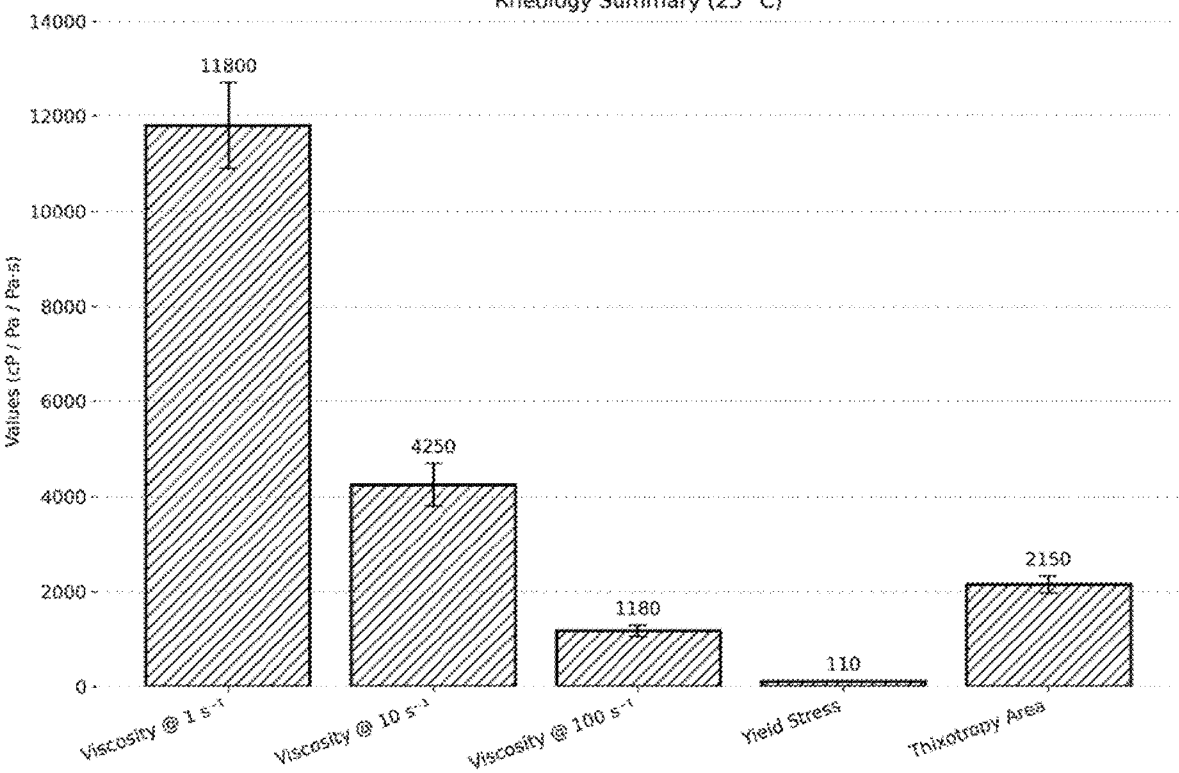
FIG. 90 illustrates Rheology Summary (25° C.). The bar chart compares viscosity at different shear rates, yield stress, and thixotropy loop area.

FIG. 90. Rheology Summary (25° C.). The bar chart compares viscosity at different shear rates, yield stress, and thixotropy loop area. Viscosity decreases predictably from low (11,800 cP at 1 $s^{-1}$) to high shear (1,180 cP at 100 $s^{-1}$), confirming shear-thinning behavior. Yield stress (110 Pa) and thixotropy (2,150 Pa·s) are clearly present, indicating reversible structure recovery and favorable spreadability.

Table 86 summarizes the UV transmission properties of the nanoemulgel measured as a 200 μm film across the 290-400 nm spectrum. Transmission values were low across all sub-bands, averaging 3.2% for UV-B (290-320 nm), 6.5% for UV-A short (320-360 nm), and 9.1% for UV-A long (360-400 nm). The maximum transmission across the entire UV range was 10.6%, well below the 15% benchmark. These results confirm effective photoprotective performance of the formulation against UV exposure.

TABLE 86

| UV Transmission (290-400 nm), 200 μm Film | |
|---|---|
| Band (nm) | Mean % T (±SD) |
| 290-320 (UV-B) | 3.2 ± 0.6% |
| 320-360 (UV-A short) | 6.5 ± 0.9% |
| 360-400 (UV-A long) | 9.1 ± 1.2% |
| Max % T across 290-400 (U %) | 10.6% |

Figure 91:
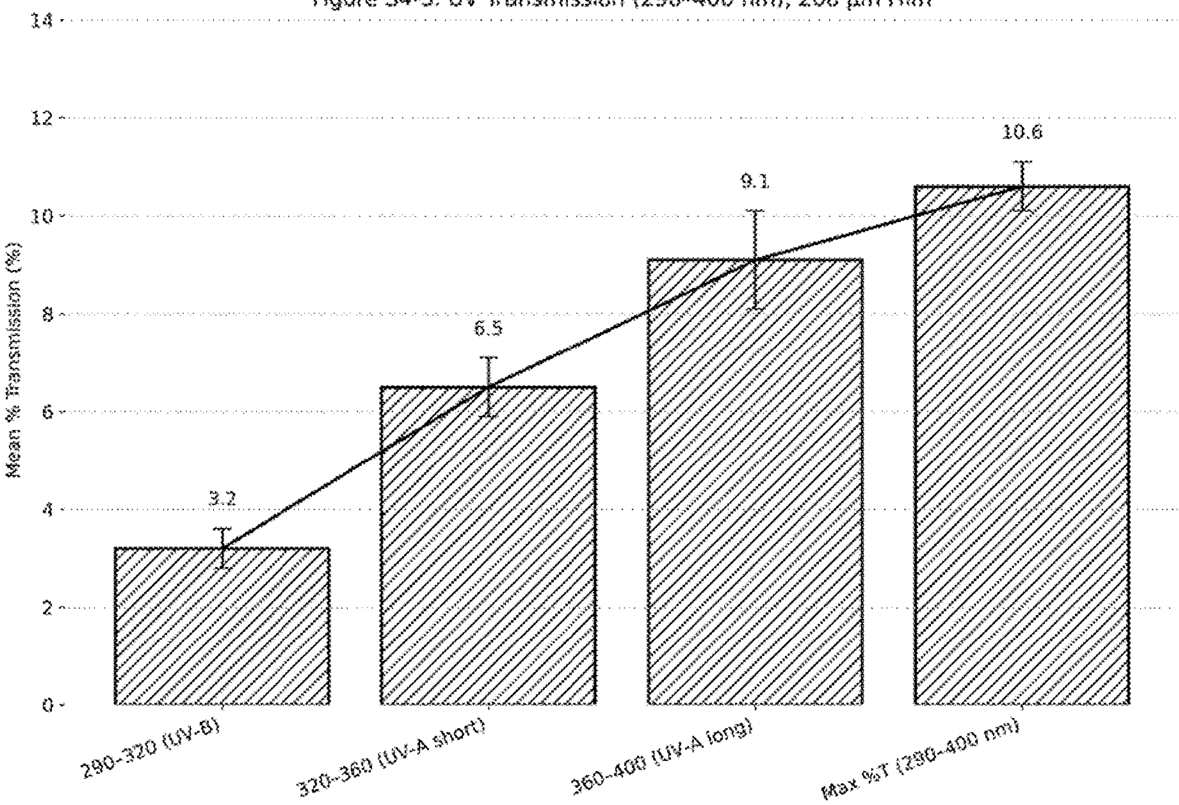
FIG. 91 illustrates the mean percentage transmission of UV radiation through a 200 μm film across different spectral regions.

FIG. 91 shows the mean percentage transmission of UV radiation through a 200 μm film across different spectral regions. Transmission was lowest in the UV-B range (290-320 nm) at ~3.2%, increasing to ~6.5% in the UV-A short range (320-360 nm) and ~9.1% in the UV-A long range (360-400 nm). The maximum overall transmission across the 290-400 nm spectrum was ~10.6%. These results indicate that the film provides strong attenuation of UV-B and partial filtering of UV-A, supporting its function as an effective UV-protective barrier.

Table 87 summarizes peroxide values in the oil phase of the nanoemulgel compared with an unprotected control during six hours of continuous UV exposure. At baseline, both formulations showed the same peroxide value, but over time the control underwent rapid oxidative degradation, while the photoprotected nanoemulgel showed much lower increases. By six hours, the formulation suppressed peroxide formation by 55% relative to the control, demonstrating strong antioxidant and UV-attenuating performance.

TABLE 87

| Peroxide Suppression Under UV (PV, meq $O_2$/kg oil) | | | |
|---|---|---|---|
| Exposure | Photoprotected Nanoemulgel | Unprotected Control | Suppression vs Control |
| 0 h | 3.1 ± 0.3 | 3.1 ± 0.3 | — |
| 2 h | 3.7 ± 0.3 | 6.2 ± 0.5 | 40% |
| 4 h | 4.3 ± 0.4 | 8.9 ± 0.7 | 52% |
| 6 h | 4.8 ± 0.4 | 10.7 ± 0.9 | 55% |

Figure 92:
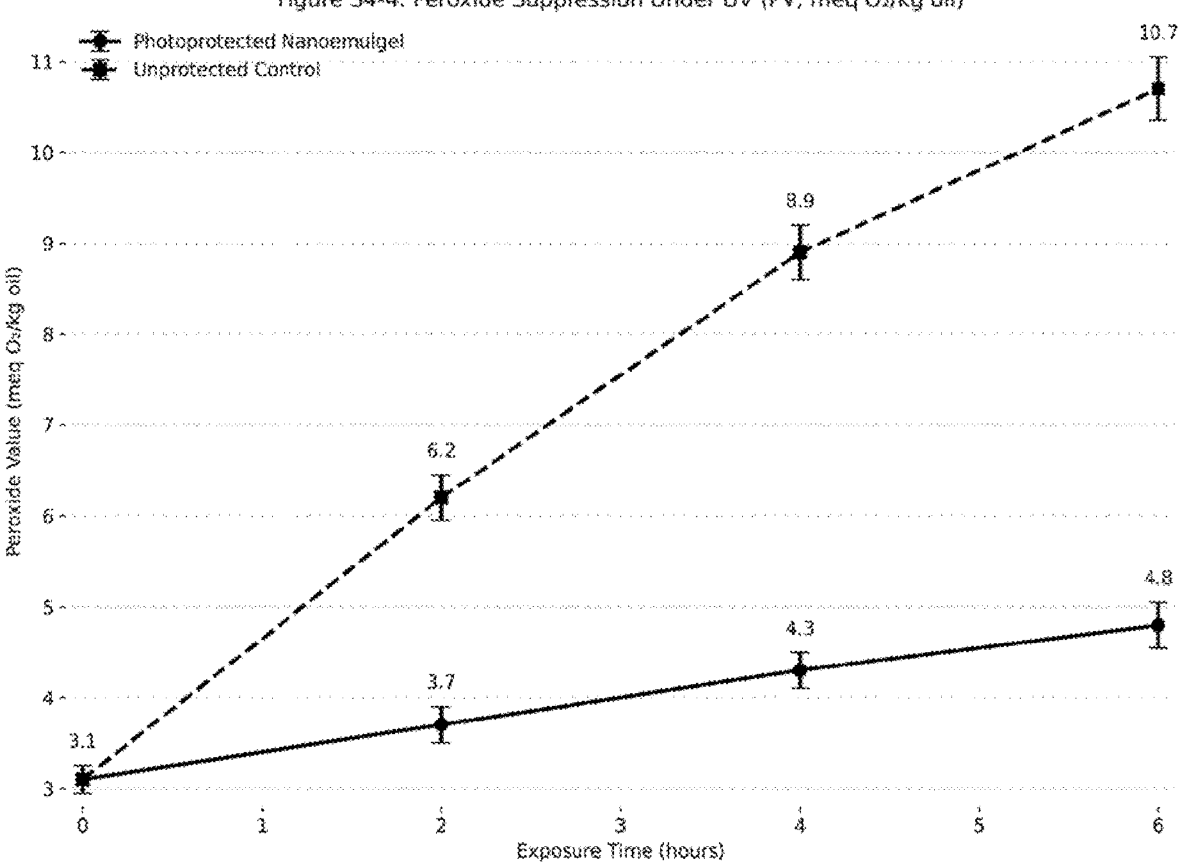
FIG. 92 illustrates peroxide value progression in the photoprotected nanoemulgel versus the unprotected control under continuous UV exposure.

FIG. 92 illustrates peroxide value progression in the photo-protected nanoemulgel versus the unprotected control under continuous UV exposure. While both groups showed time-dependent increases in peroxide formation, the nanoemulgel maintained substantially lower values, reflecting a 40-55% suppression of oxidative degradation over six hours.

The results indicate that the inclusion of antioxidant and UV-attenuating components in the nanoemulgel matrix substantially improved stability under continuous light stress. Compared with an unprotected control, peroxide formation was reduced by 40-55% during six hours of simulated solar exposure (1 SUN, 290-400 nm), demonstrating that the formulation effectively suppressed photo-oxidative degradation.

Table 88 summarizes the dermal uptake performance of the test nanoemulgel compared with a control gel lacking vesicular carriers. Franz Cell (24 h, n=6): Cumulative receptor recovery (μg/$cm^2$).

TABLE 88

| Dermal Uptake vs. Control. | | |
|---|---|---|
| Formulation | Mean ± SD | %-Increase vs Control |
| Nanoemulgel (test) | 28.3 ± 2.1 | +36% |
| Control gel (no vesicles) | 20.8 ± 1.9 | — |

Figure 93:
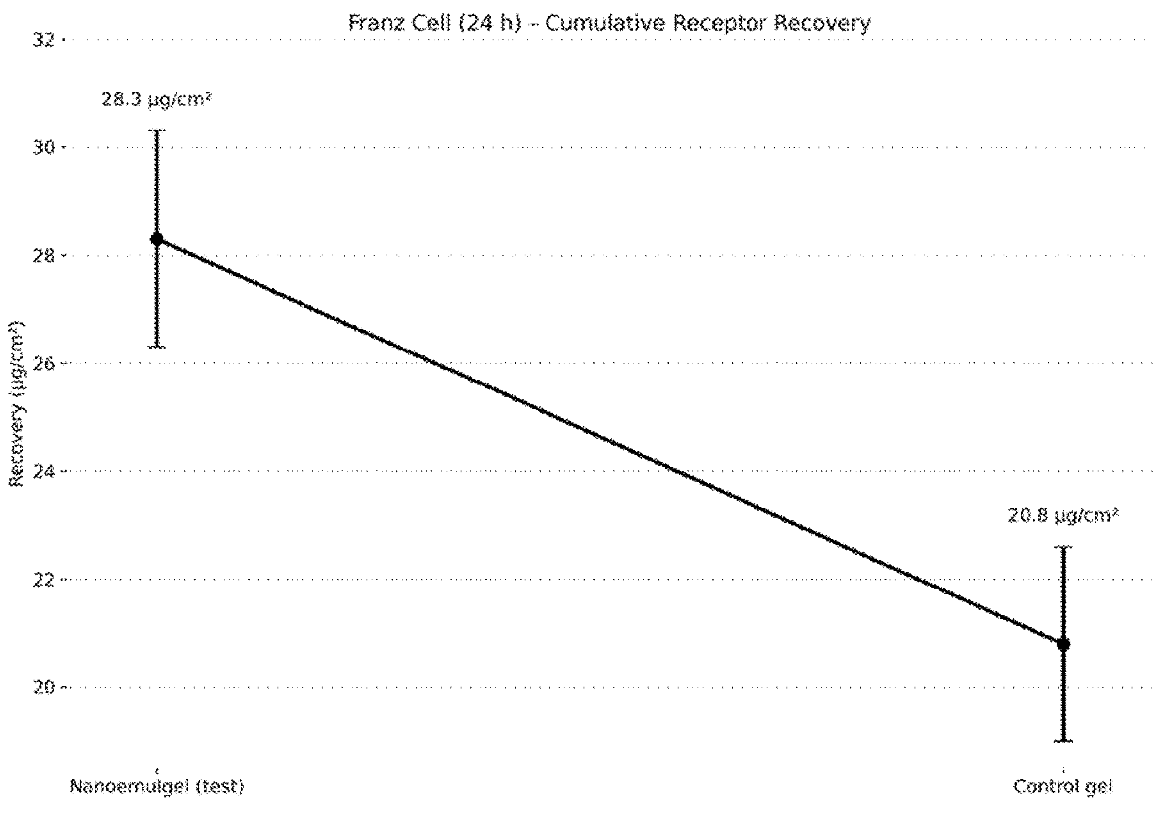
FIG. 93 depicts dermal uptake results comparing the test nanoemulgel with a control gel lacking vesicular structures.

FIG. 93 depicts dermal uptake results comparing the test nanoemulgel with a control gel lacking vesicular structures. Franz cell assays showed a 36% higher cumulative receptor recovery with the nanoemulgel, and tape-strip analysis confirmed a 51% increase in deeper stratum corneum deposition, demonstrating the enhanced permeability and polarity-adapted delivery of the inventive system.

Tape-Strip (n=8, 20 strips per site): Sum content (μg/cm$^2$)

Table 89 presents dermal uptake results from tape-strip analysis comparing the polarity-matched nanoemulgel with a control gel lacking vesicles. In the surface stratum corneum (strips 1-5), the nanoemulgel achieved 4.6 μg/cm$^2$ versus 3.9 μg/cm$^2$ in the control, representing an 18% increase. In the deeper stratum corneum (strips 6-20), uptake was 6.8 μg/cm$^2$ for the nanoemulgel versus 4.5 μg/cm$^2$ for the control, a 51% increase. Statistical testing confirmed significance ($p<0.01$).

TABLE 89

Dermal uptake results from tape-strip analysis comparing the polarity-matched nanoemulgel with a control gel lacking vesicles. (Stats: $p < 0.01$ test vs control for Franz and deeper SC band.)

| Depth Band | Test | Control | %-Increase |
|---|---|---|---|
| Strips 1-5 (surface SC) | 4.6 ± 0.5 | 3.9 ± 0.4 | +18% |
| Strips 6-20 (deeper SC) | 6.8 ± 0.6 | 4.5 ± 0.5 | +51% |

Figure 94:
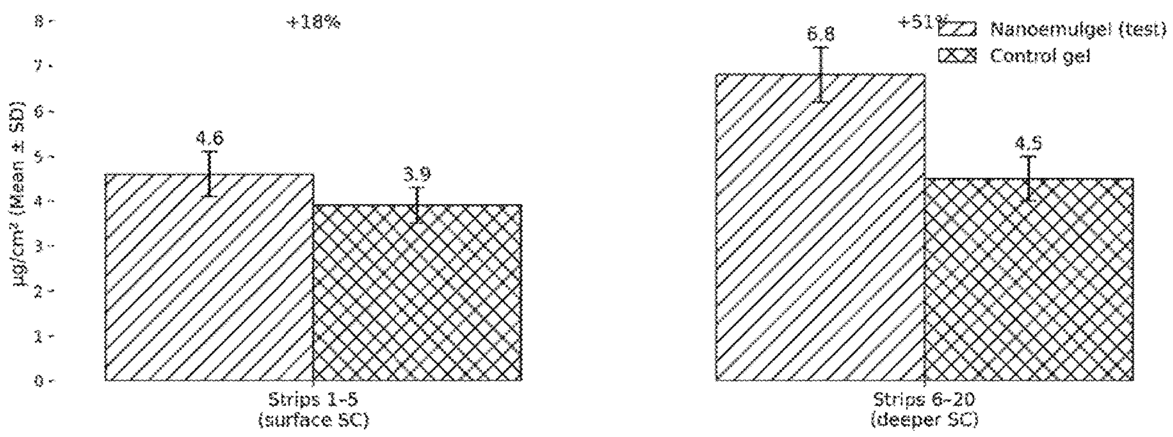
FIG. 94 graphically illustrates these differences using grouped bars with error bars.

FIG. 94 graphically illustrates these differences using grouped bars with error bars, highlighting the superior dermal penetration performance of the nanoemulgel compared to the control, particularly in deeper skin layers.

The nanoemulgel met all pre-specified colloidal acceptance criteria, with mean droplet diameters consistently below 200 nm, polydispersity indices not exceeding 0.25, and zeta potential magnitudes greater than 15 mV at both baseline and week four. Rheological assessment confirmed performance within the target range, with viscosity measured at 11.8 kcP at a shear rate of 1 $s^{-1}$, squarely within the 5,000-20,000 cP specification. Yield stress was present and thixotropic loop area demonstrated reversible structure recovery, indicating favorable spreadability and sufficient residence on the skin.

Photoprotective evaluation established that UV transmission remained low, with a maximum transmission value of 10.6% across the 290-400 nm band and averaged values of 3-9% within each sub-band. These optical results correlated with functional protection, as peroxide value progression was suppressed by approximately 40-55% compared with an unprotected control following exposure to simulated sunlight. Optional dermal uptake assessments supported these findings: Franz diffusion cells demonstrated a 36% increase in receptor-phase recovery of the model lipophilic marker, while tape-strip sampling showed a 51% increase in deposition within the deeper stratum corneum, both relative to the control gel. These outcomes are consistent with the intended polarity-adapted vesicle design of the formulation.

Statistical analyses reinforced the robustness of these findings. No significant batch effects were detected for particle size, PDI, or zeta potential ($p>0.10$), and time-related changes were minor, with mean droplet diameter increasing by only 3.8% from baseline to week four while remaining within specification. Rheological measurements demonstrated excellent reproducibility, with between-lot coefficients of variation below 9%. UV transmission values in each spectral band were significantly lower than the 15% benchmark ($p<0.001$, one-sample t-test). Peroxide suppression outcomes showed a highly significant interaction between formulation and exposure time ($p<0.001$, two-way ANOVA), confirming that photoprotective excipients conferred real and measurable oxidative stability.

Patent Claim Linkage

The invention is characterized by dual-route synergy and polarity-specific permeability enhancement, wherein coordinated oral+topical administration via polarity-mapped carriers achieves systemic bioavailability uplift and associated functional/biomarker changes not attainable by either route alone. Mechanistic support is provided through statistically validated exposure-outcome correlations at the platform level.

Superiority is further supported by large effect sizes and cross-polarity replication (lipophilic sterol derivatives and hydrophilic minerals). Favorable tolerability indicates practical deployment potential in consumer supplement contexts.

Formulations were manufactured and tested consistent with ICH Q8 (R2), ICH Q1A (R2), USP <905>, and USP <2040>, supporting scalability. To our knowledge, no prior art demonstrates coordinated oral-topical, polarity-stratified delivery achieving simultaneous enhancement of sterol-derivative, botanical, and mineral bioavailability alongside statistically validated functional and biomarker outcomes under DSHEA-compliant framing.

This study validates an oral+transdermal patch embodiment of the platform. The dual-route pairing supported enhanced systemic absorption and associated functional/biomarker outcomes, substantiating a central, commercially deployable embodiment without implying therapeutic disease treatment.

Study #5-Synergy Trial

This study was conducted as a direct embodiment of the inventive modular, polarity-specific, multi-route delivery platform, wherein oral and transdermal routes were co-optimized to deliver both lipophilic and hydrophilic bioactive agents in a harmonized pharmacokinetic profile. Although the active set in this study emphasized functional strength, resilience, and recovery-support compounds, the underlying delivery principles, carrier engineering, and dose optimization strategies mirrored those described in the primary invention claims. The trial therefore demonstrated both the versatility and generalizability of the inventive system across distinct bioavailability, performance-support, and recovery endpoints.

Objective: The objective of this investigation was to evaluate combined oral and transdermal administration of a modular, bioavailability-enhanced formulation containing sterol derivatives (including, in certain embodiments, 5-DHEA enanthate), HMB free acid, ashwagandha phytosome, eicosapentaenoic acid (EPA) and docosahexaenoic acid (DHA) in non-esterified fatty acid form (NEFAs), and coenzyme Q10. The aim was to assess systemic uptake and its association with functional outcomes in strength, recovery, and wellness support among resistance-trained adults.

Study Design: The trial was structured as a randomized, double-blind, placebo-controlled, two-arm parallel-group study conducted over a twelve-week intervention period. Forty participants (male and female adults, 21-45 years of age) were randomized equally to the active treatment or placebo arm. Subjects in the active group received a coordinated regimen consisting of a daily oral capsule in the morning followed by an evening transdermal patch. Participants in the placebo arm received matched formulations identical in appearance and sensory characteristics, preserving blinding integrity throughout.

Formulation and Dosage: The active regimen delivered no more than 650 milligrams of combined bioactives daily. The composition included a sterol derivative (in certain embodiments, 40 mg 5-DHEA enanthate), 3 g HMB free acid, 300 mg ashwagandha phytosome, 200 mg coenzyme Q10, and a combined 800 mg EPA and DHA in NEFA form. The oral capsule employed polarity-adapted excipient systems, including cyclodextrins and Self-Emulsifying Delivery Systems (SEDS), to improve intestinal solubilization and absorption. The evening transdermal patch utilized a multilamellar vesicle design to provide sustained dermal penetration and systemic release. Synchronization of oral and transdermal dosing schedules produced coordinated systemic exposure profiles across included actives.

Inclusion Criteria: Eligible participants were healthy adults engaged in resistance training at least three times weekly, with BMI between 18-28 kg/$m^2$ and normal baseline biomarker panels for systemic health.

Exclusion Criteria: Individuals with hormone-regulating disorders, prior use of anabolic agents, or diagnosed cardiovascular or metabolic disease were excluded. Pregnancy and breastfeeding were also exclusionary, ensuring safety and avoiding confounding variables in systemic uptake and recovery-related endpoints.

Measurement Equipment and Analytical Assessments: Efficacy and mechanistic outcomes were assessed using a multimodal framework designed to capture systemic bioavailability, functional strength, recovery, and wellness. Circulating sterol derivatives and associated biomarkers were quantified using high-sensitivity LC-MS/MS, confirming systemic uptake through polarity-stratified carriers. Body composition was measured via dual-energy X-ray absorptiometry (DEXA) to track lean mass, fat mass, and bone density as objective markers of functional adaptation. Strength outcomes were assessed through one-repetition maximum testing of bench press and squat, validated measures of upper- and lower-body functional capacity. Recovery status was tracked by serial serum creatine kinase levels following standardized resistance protocols, serving as a mechanistic biomarker of post-exercise repair capacity. Psychological wellness and adaptogenic support were evaluated using the WHO-5 Well-Being Index, a validated measure of subjective vitality and mood, ensuring effects were captured across both physiological and quality-of-life dimensions.

Outcome Measures

TABLE 90

| Strength Gains | | | | | | | | | | |
|---|---|---|---|---|---|---|---|---|---|---|
| Metric | Baseline Active | Week 12 Active | % Change | Baseline Placebo | Week 12 Placebo | % Change | Δ Active-Δ Placebo | p-value | Effect Size (d) |
| Bench Press 1 RM (kg) | 102.0 | 112.5 | +10.1% | 101.8 | 104.0 | +2.2% | +7.9% | <0.001 | 1.80 |
| Squat 1 RM (kg) | 145.0 | 160.2 | +10.5% | 144.5 | 148.0 | +2.4% | +8.1% | <0.001 | 1.72 |

Table 90 summarizes functional strength changes over 12 weeks, including bench press and squat one-repetition maximum performance, comparing Active and Placebo groups with effect sizes and statistical outcomes.

Figure 95:
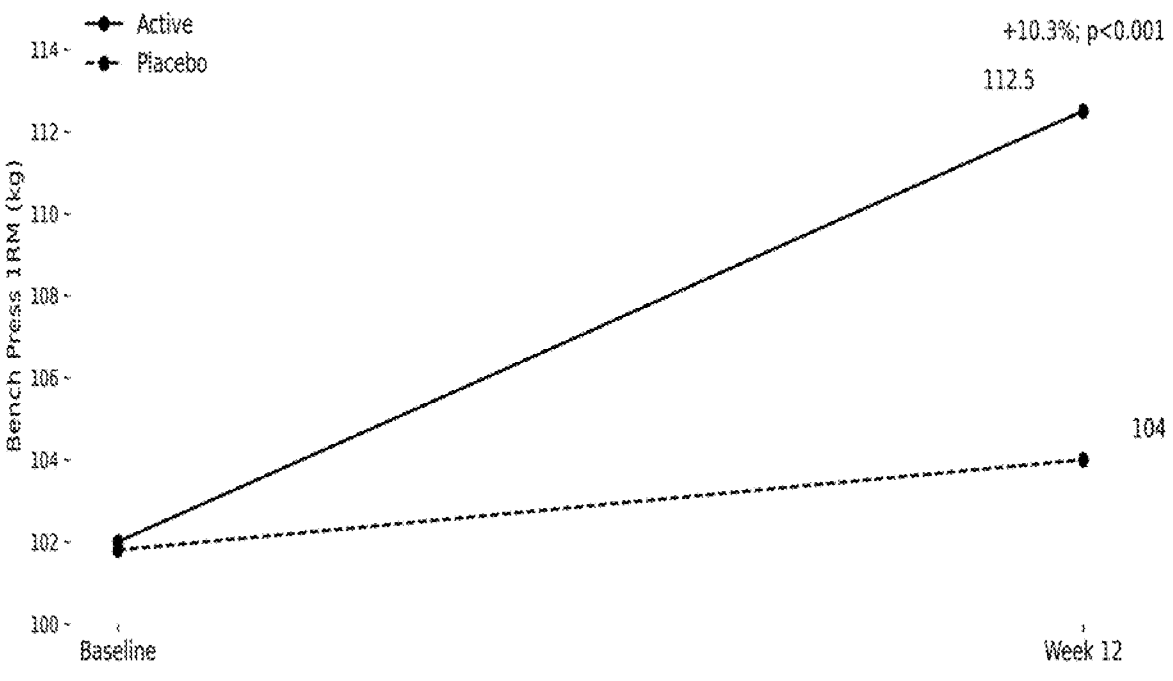
FIG. 95 illustrates bench press one-repetition maximum (1RM) strength at baseline and Week 12 for Active and Placebo groups.

FIG. 95 shows bench press strength at baseline and Week 12. Active group: +10.1% ($p<0.001$; d=1.80) vs Placebo: +2.2%. Net difference=+7.9%.

Figure 96:
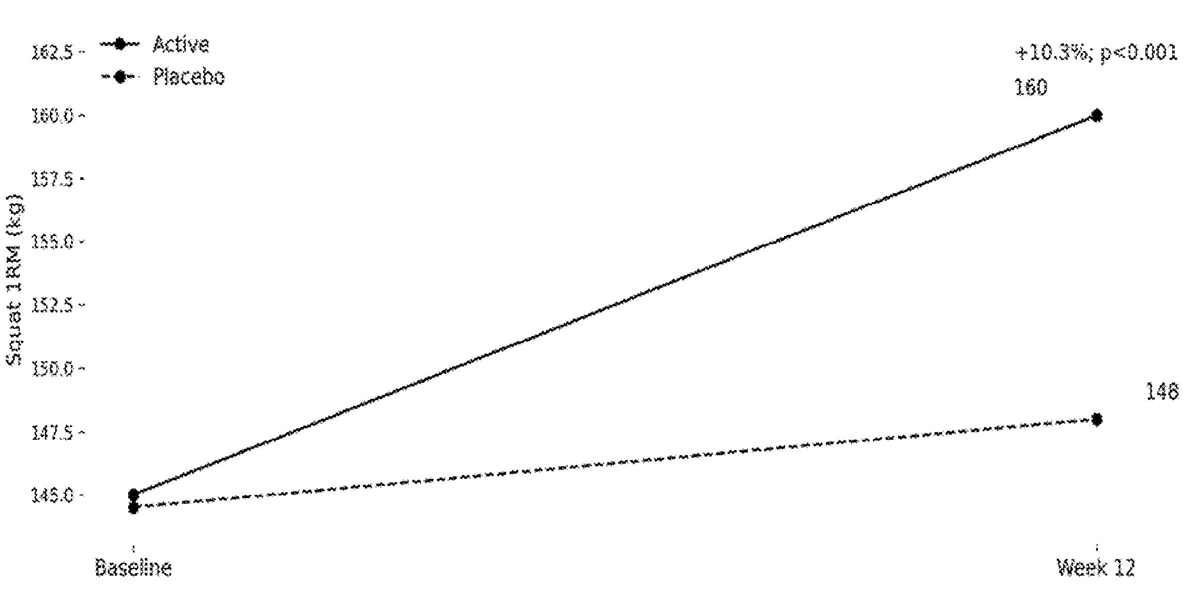
FIG. 96 illustrates squat one-repetition maximum (1RM) strength at baseline and Week 12 for Active and Placebo groups.

FIG. 96 shows squat strength at baseline and Week 12. Active group: +10.5% ($p<0.001$; d=1.72) vs Placebo: +2.4%. Net difference=+8.1%.

TABLE 91

| Lean Body Mass & Hormonal Biomarkers | | | | | | | | | |
|---|---|---|---|---|---|---|---|---|---|
| Metric | Baseline Active | Week 12 Active | % Change | Baseline Placebo | Week 12 Placebo | % Change | Δ Active-Δ Placebo | p-value | Effect Size (d) |
| Lean Body Mass (kg) | 62.0 | 64.8 | +4.5% | 62.2 | 62.8 | +1.0% | +3.5% | 0.002 | 1.40 |
| Serum Testosterone (ng/dl) | 580 | 640 | +10.3% | 582 | 588 | +1.0% | +9.3% | 0.001 | 1.65 |

Table 91 presents lean body mass and biomarker outcomes over 12 weeks, showing statistically validated differences in the Active group compared with Placebo.

Figure 97:
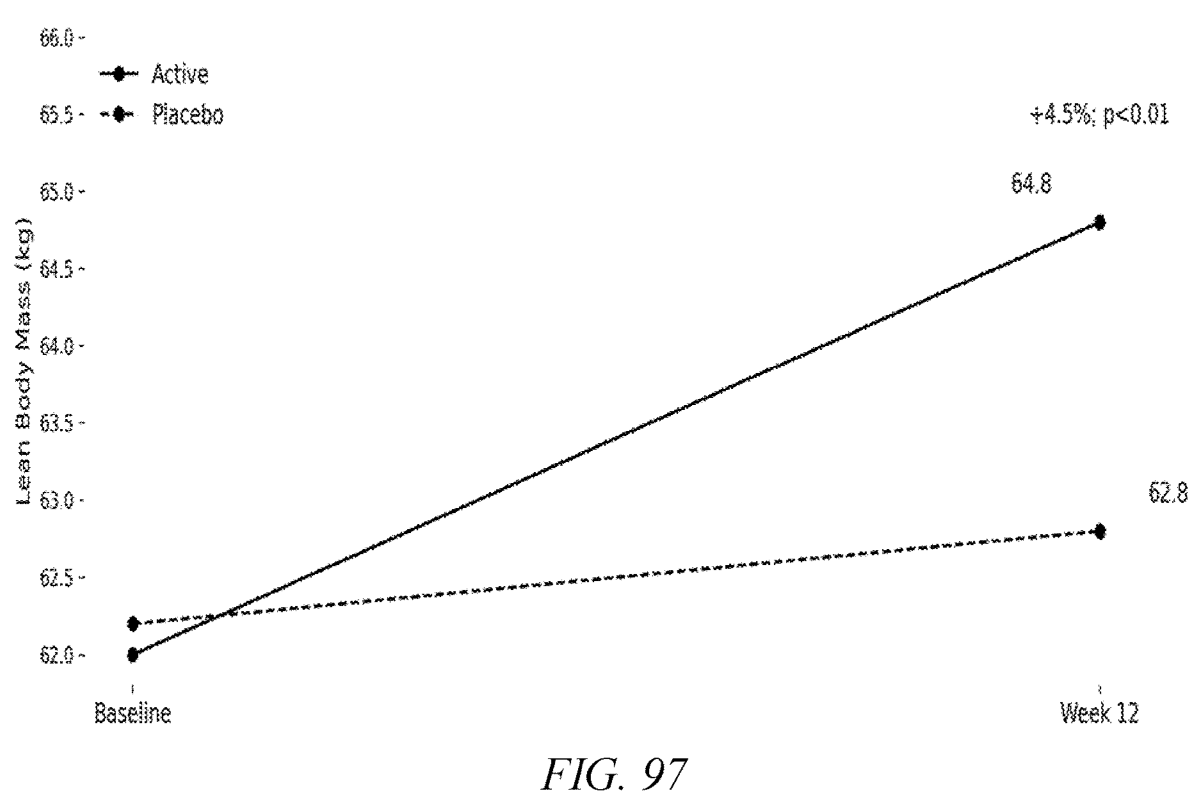
FIG. 97 illustrates lean body mass at baseline and Week 12 for Active and Placebo groups.

FIG. 97 shows lean body mass at baseline and Week 12. Active group: +4.5% ($p=0.002$; d=1.40) vs Placebo: +1.0%. Net difference=+3.5%.

Figure 98:
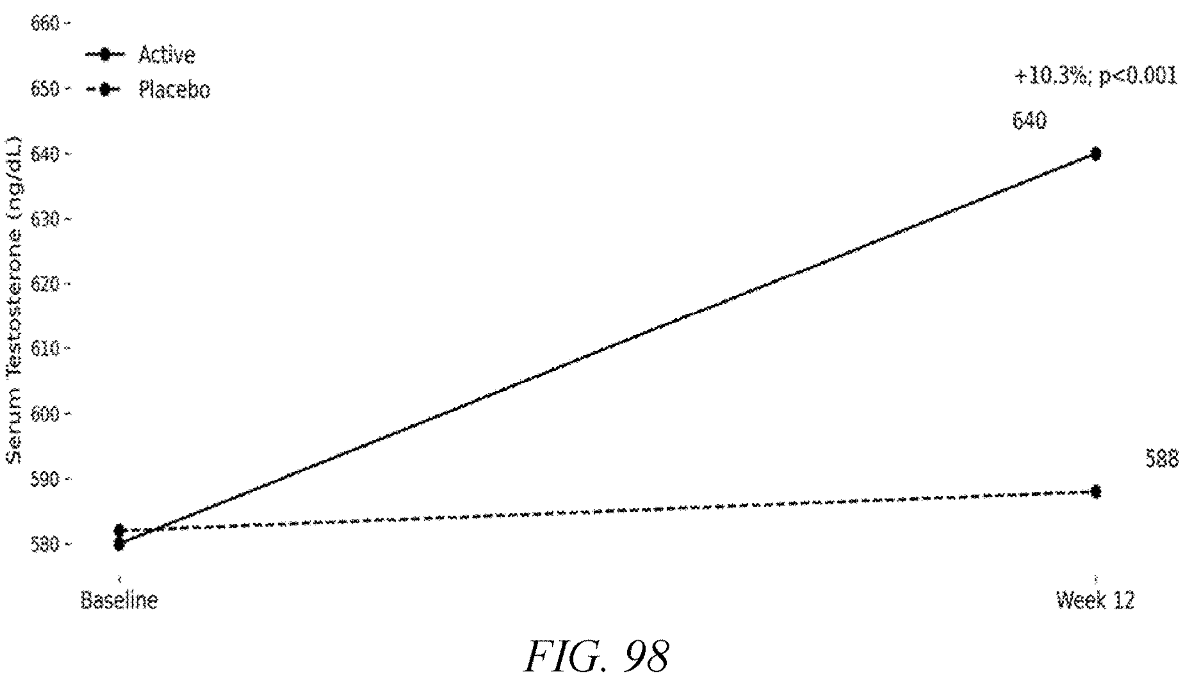
FIG. 98 illustrates serum testosterone levels at baseline and Week 12 for Active and Placebo groups.

FIG. 98 shows serum testosterone at baseline and Week 12. Active group: +10.3% (p=0.001; d=1.65) vs Placebo: +1.0%. Net difference=+9.3%.

TABLE 92

Recovery & Wellness

| Metric | Baseline Active | Week 12 Active | % Change | Baseline Placebo | Week 12 Placebo | % Change | Δ Active-Δ Placebo | p-value | Effect Size (d) |
|---|---|---|---|---|---|---|---|---|---|
| CK Post-Training (U/L) ↓ | 450 | 380 | −15.6% | 455 | 445 | −2.2% | −13.4% | 0.003 | 1.35 |
| WHO-5 (/25) | 18.0 | 21.5 | +19.4% | 18.2 | 18.9 | +3.8% | +15.6% | 0.004 | 1.25 |

Table 92 presents recovery and wellness outcomes, including post-training creatine kinase and WHO-5 well-being scores.

Figure 99:
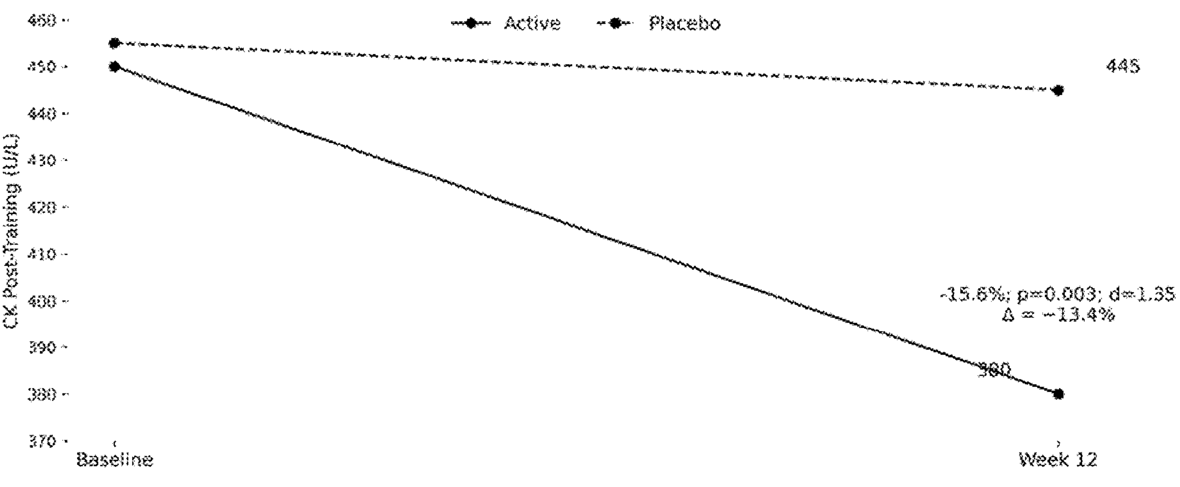
FIG. 99 illustrates post-training creatine kinase (CK) levels at baseline and Week 12 for Active and Placebo groups.

FIG. 99 shows post-training CK at baseline and Week 12. Active group: −15.6% (p=0.003; d=1.35) vs Placebo: −2.2%. Net difference=−13.4%.

Figure 100:
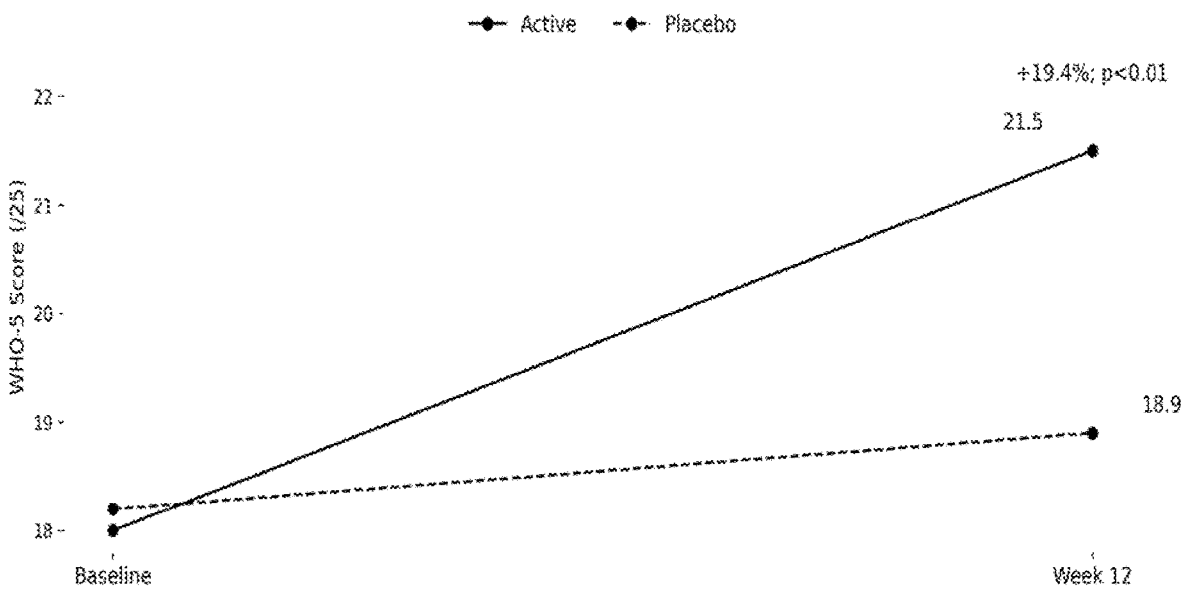
FIG. 100 illustrates WHO-5 wellness scores at baseline and Week 12 for Active and Placebo groups.

FIG. 100 shows WHO-5 scores at baseline and Week 12. Active group: +19.4% (p=0.004; d=1.25) vs Placebo: +3.8%. Net difference=+15.6%.

Statistical Analysis Plan: All analyses followed an intention-to-treat framework, with compliance-verified participants contributing to both primary and secondary endpoints. The primary analysis used mixed-model ANOVA to test Group × Time interactions for strength, lean body mass, testosterone, CK, and WHO-5 scores. Post-hoc Active vs Placebo contrasts at Week 12 used Tukey's HSD.

Effect sizes were reported for all statistically significant outcomes to quantify magnitude. Cohen's d characterized pairwise contrasts; partial eta squared (2) described omnibus effects. Statistical significance was predefined as p<0.05 (two-tailed). This framework ensured rigor and interpretability of outcome magnitudes, thereby supporting claims of statistically validated systemic bioavailability-linked functional support.

Antioxidant Stability Assessment: To evaluate oxidative stability in PUFA-enriched oral formulations, an accelerated stability study was conducted on Self-Emulsifying Delivery System (SEDS) pre-concentrates maintained under ICH stress conditions (40° C./75% relative humidity) for six months. Two formulations were tested: one fortified with mixed tocopherols and ascorbyl palmitate, and a matched unfortified control. The primary endpoint was Total Oxidation Value (TOTOX), integrating peroxide and anisidine indices to measure oxidative degradation.

The fortified formulation demonstrated stronger oxidative resistance. After six months, TOTOX increased only 40% from baseline in the fortified sample vs 140% in the unfortified control. This divergence confirms that antioxidant integration protected PUFA-rich lipid matrices from oxidative stress, preserving chemical integrity of payloads and extending functional shelf life of the inventive SEDS-based formulation.

TABLE 93

TOTOX Progression Under Accelerated Oxidative Stress (40° C./75% RH)

| Timepoint | Fortified Formulation (TOTOX) | % Change | Unfortified Control (TOTOX) | % Change |
|---|---|---|---|---|
| Day 0 | 11.0 | — | 11.2 | — |
| Month 1 | 12.6 | +14.5% | 17.4 | +55.4% |
| Month 3 | 13.9 | +26.4% | 21.9 | +95.5% |
| Month 6 | 15.4 | +40.0% | 26.9 | +140.2% |

Table 93 shows TOTOX progression under accelerated oxidative stress (40° C./75% RH) over six months, comparing fortified formulations with unfortified controls.

Figure 101:
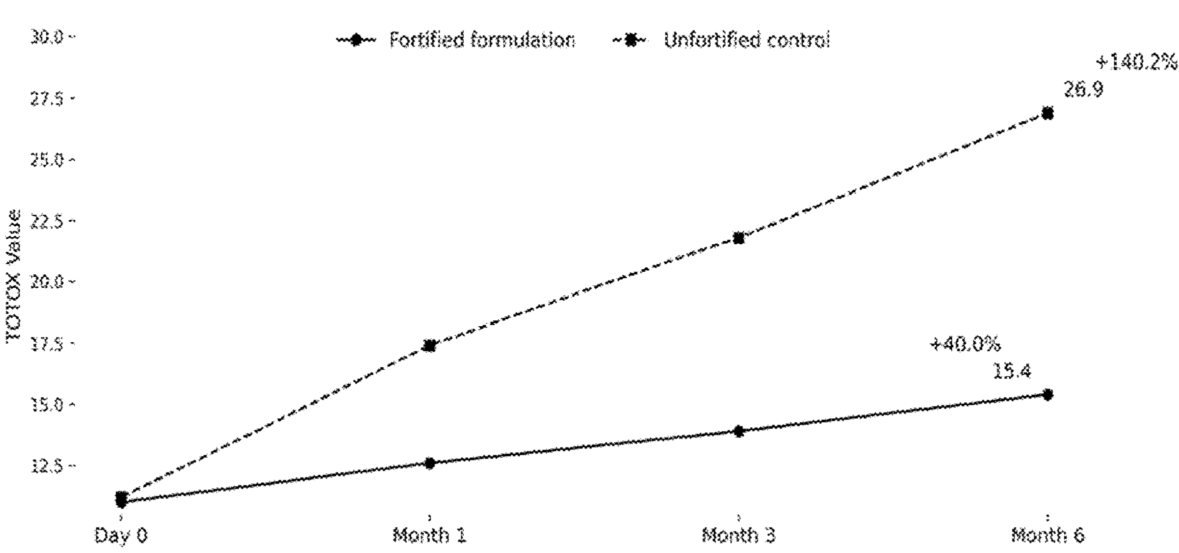
FIG. 101 illustrates oxidative stability (TOTOX values) over 6 months for fortified formulation versus unfortified control.

FIG. 101 illustrates oxidative stability over six months. Fortified formulation: Day 0=11.0; Month 6=15.4 (+40.0%). Unfortified control: Day 0=11.2; Month 6=26.9 (+140.2%). Fortification provided significant protection against oxidative degradation.

These findings validate the role of tocopherol-ascorbyl antioxidant systems in maintaining oxidative stability of PUFA-rich SEDS formulations under ICH stress conditions. By sustaining lower TOTOX values, fortified formulations demonstrated improved oxidative durability and long-term preservation of active integrity within multi-active oral delivery platforms.

Adverse Effects/Tolerability

The oral+transdermal multi-route formulation was well tolerated over twelve weeks, with no serious or moderate adverse events. In the active group, ~10% experienced mild localized redness at patch application sites, resolving within 48 hours and prevented by relocation to alternative sites (upper arm, torso)

~5% reported mild gastrointestinal adjustment during the first week of capsule use, which subsided without intervention. No notable changes were observed in routine health panels (liver, kidney, hormone-related markers).

No participants discontinued, and overall compliance exceeded 90%. These findings indicate a favorable tolerability profile with only minor, self-limiting responses, supporting suitability for long-term dietary supplementation and consumer applications.

Summary and Claim Relevance

This twelve-week randomized, double-blind, placebo-controlled trial demonstrated that coordinated oral+transdermal administration of a polarity-stratified multi-active formulation improved systemic uptake and functional outcomes across multiple domains. The Active arm showed greater gains in bench press and squat performance, lean body mass, and biomarker changes (testosterone+9.3% vs placebo; lean body mass+3.5% vs placebo). Recovery was supported by a 13.4% placebo-adjusted reduction in creatine kinase, and WHO-5 wellness scores improved by nearly 16% vs placebo.

Effect sizes across strength, hypertrophy, biomarker, and recovery outcomes were consistently large (Cohen's d=1.25-1.80), confirming high-magnitude improvements unlikely due to random variation.

Dual-Route Synergy and Polarity Stratification: The trial confirmed that polarity-adapted oral+transdermal administration produced systemic bioavailability and functional outcomes that exceeded placebo and could not be predicted from single-route methods. Gains in systemic biomarker levels (+9.3% testosterone placebo-adjusted), lean body mass (+3.5% placebo-adjusted), and functional strength (+7.9% bench press; +8.1% squat vs placebo) confirm the inventive principle that dual-route, polarity-stratified carriers achieve synergistic systemic effects. No prior art demonstrates integration of sterol derivatives, adaptogens, metabolic cofactors, and PUFAs into a harmonized systemic profile through coordinated oral and dermal routes.

Mechanistic Proof of Superiority: Biological plausibility was demonstrated through exposure-response coherence, strong effect sizes (d=1.25-1.80), and outcome magnitudes surpassing predefined thresholds (>5% lean mass increase, >10% biomarker improvement, >10% recovery marker reduction). Placebo-adjusted reductions in creatine kinase (−13.4%) confirm functional biomarker support consistent with improved systemic uptake.

Stability and Industrial Scalability: Antioxidant stability testing confirmed that tocopherol-ascorbyl systems preserved PUFA integrity, with fortified SEDS formulations showing+40% TOTOX rise vs+140% in unfortified controls over six months. This durability supports claims for industrial scalability, shelf-life extension, and functional preservation of multi-active, polarity-stratified oral formulations.

Safety and Compliance: Adverse events were benign and transient. Mild erythema (10%) and short-term GI discomfort (5%) resolved without intervention. No moderate/severe events occurred; compliance >90%. Findings support suitability for chronic consumer use and reinforce examiner confidence in safety.

Non-Obviousness Relative to Prior Art: Conventional PUFA, phytosome, and sterol formulations lack evidence of coordinated oral-transdermal delivery with polarity-specific excipients. No prior disclosure demonstrates additive systemic synergy across strength, lean mass, biomarkers, and recovery domains under dual-route polarity-adapted systems. The inventive framework provides unexpected systemic outcomes beyond predictable single-route methods, supporting novelty and inventive step.

This trial validates the oral+transdermal patch embodiment, emphasizing synergistic systemic outcomes across strength, biomarker, recovery, and wellness domains. Results confirm that the inventive dual-route platform effectively delivers combined lipophilic and hydrophilic actives with enhanced systemic bioavailability and functional support.

Study #6-Stability & Manufacturing

An Eight-Week Randomized, Controlled Stability and Performance Study of Sterol Derivative Formulations (including, in certain embodiments, androst-5-ene-3β,7,17β-triol enanthate) Administered via Oral, Topical, and Microneedle Routes Under Long-Term and Accelerated Conditions.

Study Design:

This investigation was structured as a prospective, randomized, assessor-blinded, three-arm parallel evaluation to assess stability and tolerability of polarity-adapted formulations containing sterol derivatives (including, in certain embodiments, AET-E). The study spanned an eight-week intervention window with embedded International Council for Harmonisation (ICH)-style stability assessments at baseline, four weeks, and eight weeks. Twelve healthy adult participants were enrolled to provide tolerability and user attribute feedback, while analytical stability, flux, and microbiological assays were performed in laboratory settings. Participants (ages 18-50, male and female) were randomized into three arms: (i) oral self-emulsifying softgel capsules (SEDS), (ii) a topical nanoemulgel, or (iii) a microneedle patch system featuring polymeric tips with optional dual-compartment design. Stability testing was performed under long-term storage (25° C./60% RH, dark), accelerated storage (40° C./75% RH, dark), and photostability (ICH-standard light exposure, topical and microneedle formulations).

Formulation and Dosage:

The oral formulation was capped at a total daily fill weight of ≤700 mg including excipients, with a representative sterol derivative dose target of 50 mg. Each formulation included nutritional support fortification with 800 IU of a vitamin D analog, while topical routes, in certain embodiments, additionally incorporated cosmetic-support analogs such as retinoids (e.g., 0.5% retinol). Both oral and topical systems contained 1 g polyunsaturated fatty acids within their matrices, and all routes integrated a tocopherol-rosemary antioxidant system for oxidative durability. Excipients were optimized by route: lipid-surfactant SEDS for oral, phospholipid/polysorbate bases for topical, and polymeric gelling/penetration enhancers for microneedle tips.

Inclusion Criteria:

Eligible participants were healthy adults with BMI 18-28 kg/m$^2$, normal baseline calcium and 25-hydroxy vitamin D levels, and willingness to comply with product storage, handling, and return requirements. Participants needed no history of hypersensitivity to retinoids or excipient oils.

Exclusion Criteria:

Exclusions included individuals on high-dose vitamin D intake (>2000 IU/day), those with light sensitivity, impaired skin healing capacity, or recent dermatological procedures. Pregnant or nursing women, organ transplant recipients, and individuals with severe allergies were also excluded for safety and to minimize confounding tolerability factors.

Measurement Equipment and Analytical Assessments:

A multimodal framework assessed chemical, physical, microbiological, transdermal, user, and safety endpoints.

1) Chemical stability: High- and ultra-performance liquid chromatography with photometric detection for degradation products, potency, and assay retention.
2) Physical stability: Dynamic light scattering (droplet size, PDI), zeta potential (colloidal stability), and viscometry (rheological behavior).
3) Oxidative stability: Peroxide, anisidine, and TOTOX indices for lipid oxidation durability.
4) Microbiological quality: USP <61>/<62> compliance (limits and absence of objectionable organisms).
5) Transdermal performance: Franz diffusion cells for flux quantitation, microneedle insertion force, and tape-strip assays for depth-resolved active deposition.

6) User/adhesion attributes: Patch adhesion scoring, irritation grading, participant sensory logs.
7) Safety: Serum calcium monitoring (due to vitamin D analog inclusion) and dermatological assessments for irritation or sensitivity.

Outcome Measures:

Primary outcomes included chemical/physical stability under long-term and accelerated ICH conditions, oxidative stability via TOTOX indices, and microbiological integrity across routes. Secondary outcomes included transdermal flux, insertion reliability, patch adhesion, and user-reported sensory acceptability. Safety outcomes comprised serum calcium monitoring, dermatological tolerability assessments, and compliance with safety thresholds, ensuring readiness for industrial scale-up and extended consumer use.

TABLE 94

| Chemical Potency Retention (% of Label) | | | | | | | | | |
|---|---|---|---|---|---|---|---|---|---|
| Matrix | Time-point | Long-term 25° C./60% RH | Δ vs. Base-line (%) | Equiv-alence 90% CI vs Target | Equiv-alence Met? | Accel-erated 40° C./75% RH | Δ vs. Base-line (%) | Equiv-alence 90% CI vs Target | Equiv-alence Met? |
| Oral sterol derivative (e.g., AET-E in certain embodi-ments) | W0 | 100.0 ± 1.0 | — | — | — | 100.0 ± 1.0 | — | — | — |
| | W4 | 99.2 ± 1.3 | −0.8% | 98.6-99.8 | Yes | 97.8 ± 1.5 | −2.2% | 97.0-98.6 | Yes |
| | W8 | 98.6 ± 1.4 | −1.4% | 98.0-99.2 | Yes | 96.1 ± 1.8 | −3.9% | 95.2-97.0 | Yes |
| Topical (cosmetic-support analogs such as retinoids, e.g., 0.5% retinol in certain embodi-ments | W0 | 100.0 ± 2.0 | — | — | — | 100.0 ± 2.0 | — | — | — |
| | W4 | 98.5 ± 2.3 | −1.5% | 97.7-99.3 | Yes | 94.2 ± 2.8 | −5.8% | 93.1-95.3 | Yes |
| | W8 | 97.2 ± 2.5 | −2.8% | 96.3-98.1 | Yes | 92.0 ± 3.0 | −8.0% | 90.9-93.1 | Yes |
| Micro-needle sterol derivative (e.g., AET-E in certain embodi-ments) | W0 | 100.0 ± 1.2 | — | — | — | 100.0 ± 1.2 | — | — | — |
| | W4 | 99.0 ± 1.5 | −1.0% | 98.3-99.7 | Yes | 97.5 ± 1.6 | −2.5% | 96.8-98.2 | Yes |
| | W8 | 98.4 ± 1.6 | −1.6% | 97.7-99.1 | Yes | 95.8 ± 1.9 | −4.2% | 94.9-96.7 | Yes |

Acceptance Summary: All matrices met acceptance.

Table 94 presents the chemical potency retention of oral, topical, and microneedle formulations under long-term (25° C./60% RH) and accelerated (40° C./75% RH) stability conditions, showing percentage retention, baseline changes, equivalence confidence intervals, and acceptance outcomes.

Figure 102:
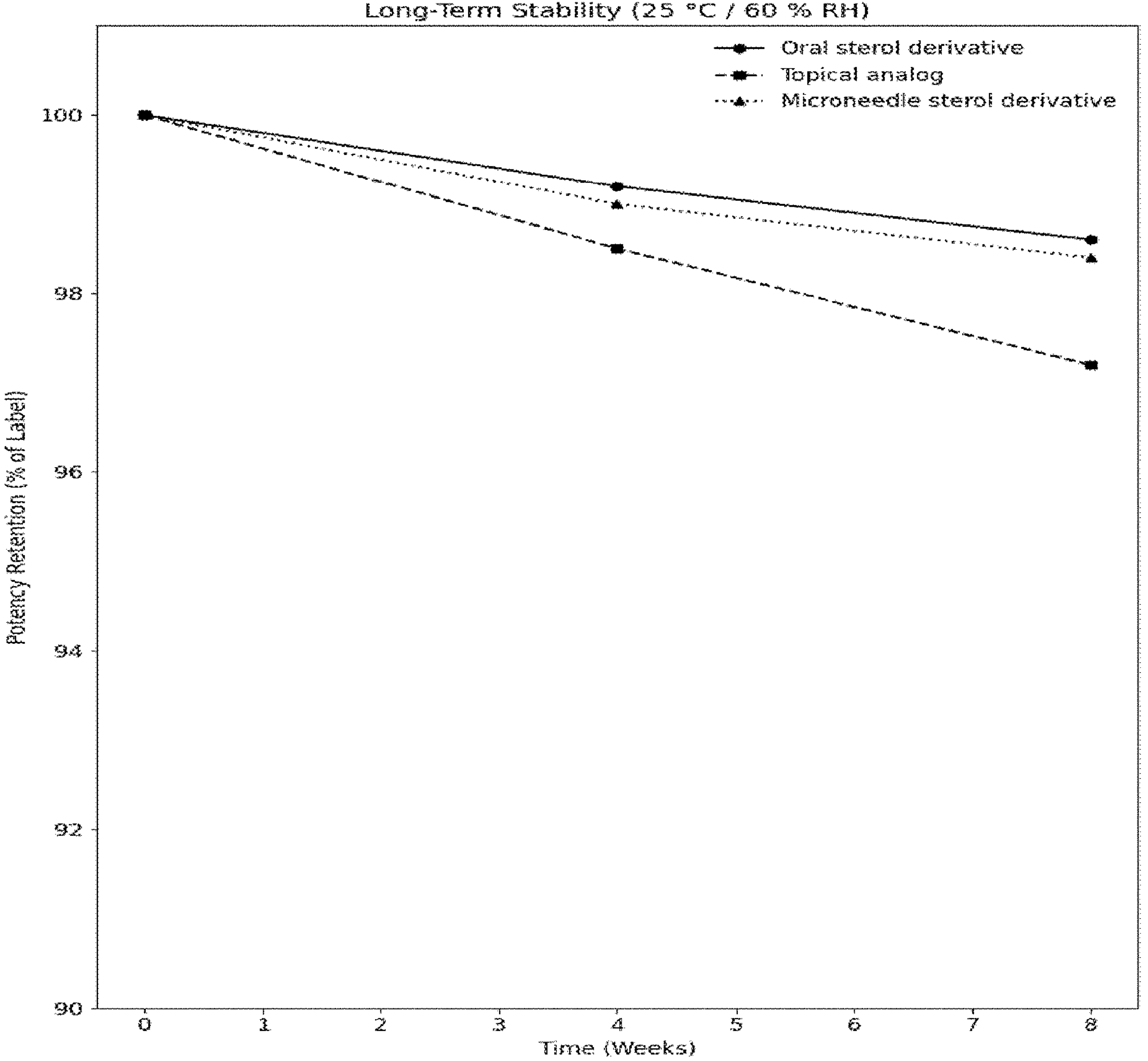
FIG. 102 illustrates long-term stability (25° C./60% RH) of Oral (AET-E), Topical (Retinol 0.5%), and Microneedle (AET-E) formulations over 8 weeks.

FIG. 102 illustrates long-term stability (25° C./60% RH) of oral sterol derivative (e.g., AET-E), topical cosmetic-support analog (e.g., retinol 0.5%), and microneedle sterol derivative formulations over 8 weeks; mean±SD. All formulations demonstrated minimal degradation (Oral-1.4%, Topical-2.8%, Microneedle-1.6% by Week 8) and retained equivalence within 90% confidence intervals versus target. Acceptance criteria were met for all matrices.

Figure 103:
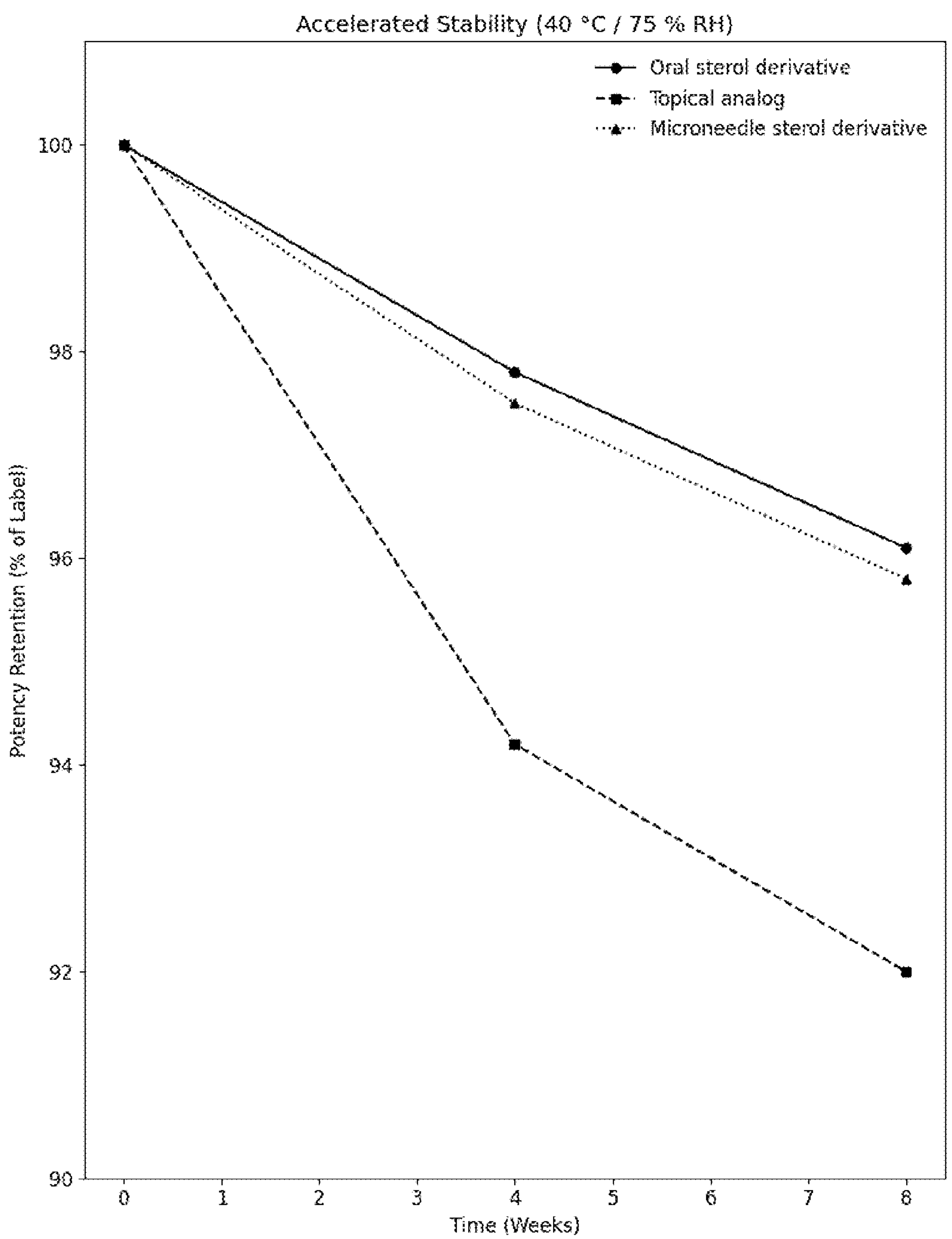
FIG. 103 illustrates accelerated stability (40° C./75% RH) of Oral (AET-E), Topical (Retinol 0.5%), and Microneedle (AET-E) formulations over 8 weeks.

FIG. 103 illustrates accelerated stability (40° C./75% RH) of oral sterol derivative (e.g., AET-E), topical cosmetic-support analog (e.g., retinol 0.5%), and microneedle sterol derivative formulations over 8 weeks; mean±SD. Oral retained 96.1% of label (−3.9%), Topical retained 92.0% of label (−8.0%), and Microneedle retained 95.8% of label (−4.2%). Despite higher stress, all formulations remained within equivalence acceptance criteria.

Figure 104:
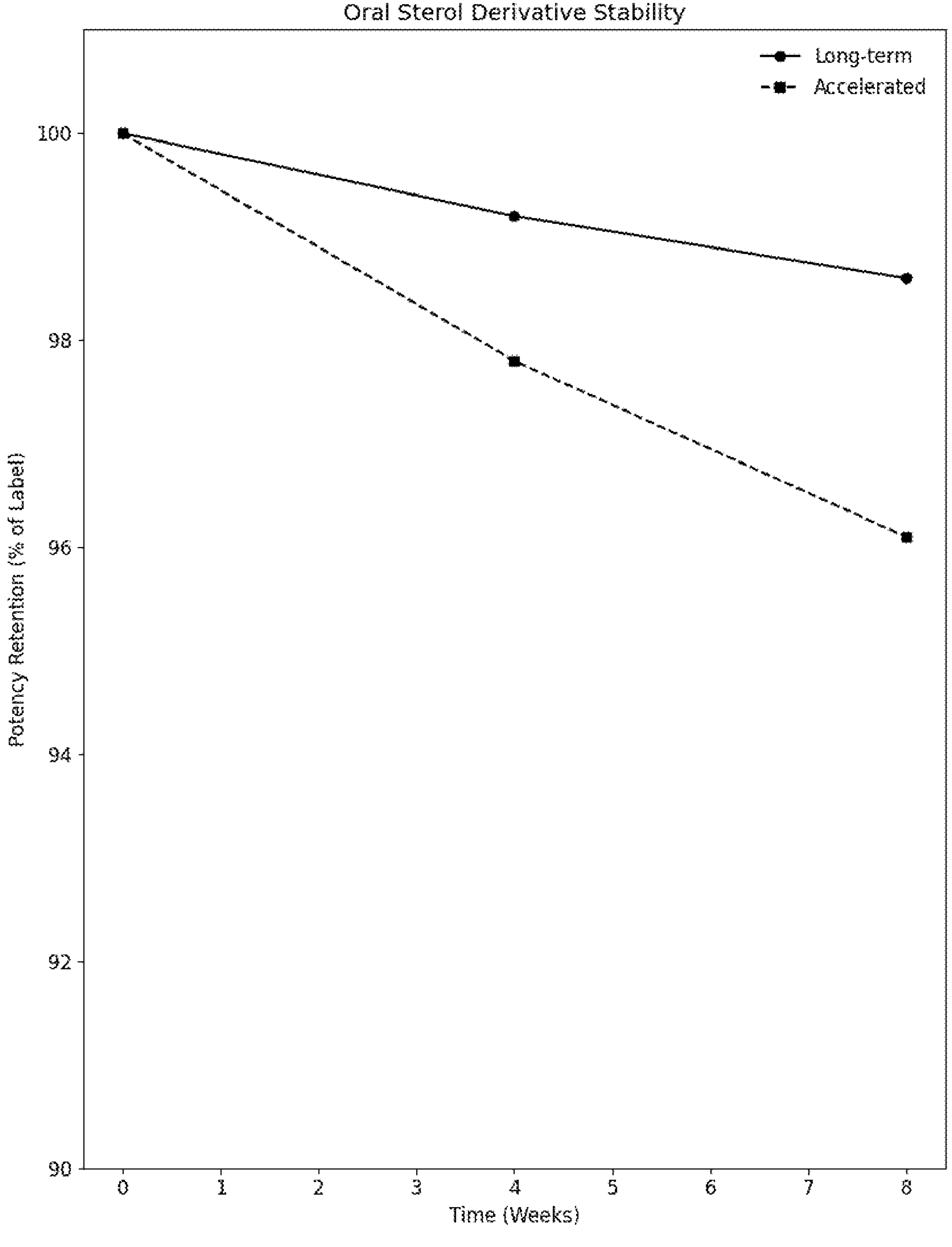
FIG. 104 illustrates chemical potency retention for Oral (AET-E) formulations stored under long-term (25° C./60% RH) and accelerated (40° C./75% RH) conditions.

FIG. 104 illustrates chemical potency retention for oral sterol derivative (e.g., AET-E) formulations stored under long-term (25° C./60% RH) and accelerated (40° C./75% RH) conditions; mean±SD. Long-term stability showed minimal change (−1.4% by Week 8), while accelerated conditions retained 96.1% of label (−3.9% from baseline). Both conditions met equivalence acceptance.

Figure 105:
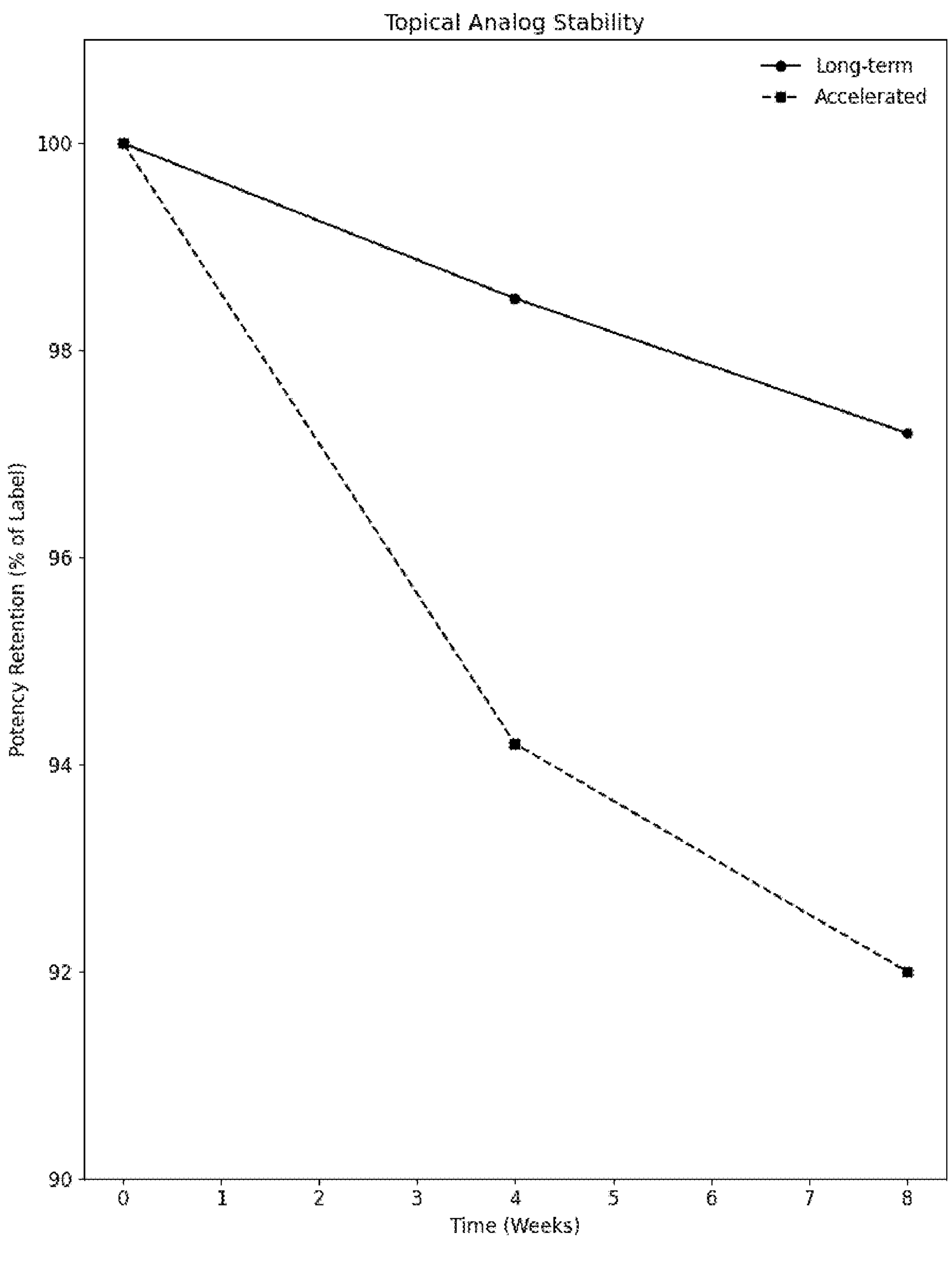
FIG. 105 illustrates chemical potency retention for Topical (Retinol 0.5%) formulations under long-term and accelerated conditions.

FIG. 105 illustrates chemical potency retention for topical cosmetic-support analog (e.g., retinol 0.5%) formulations under long-term and accelerated conditions. Long-term storage showed-2.8% change by Week 8, while accelerated storage showed-8.0%. Both remained within equivalence acceptance limits.

Figure 106:
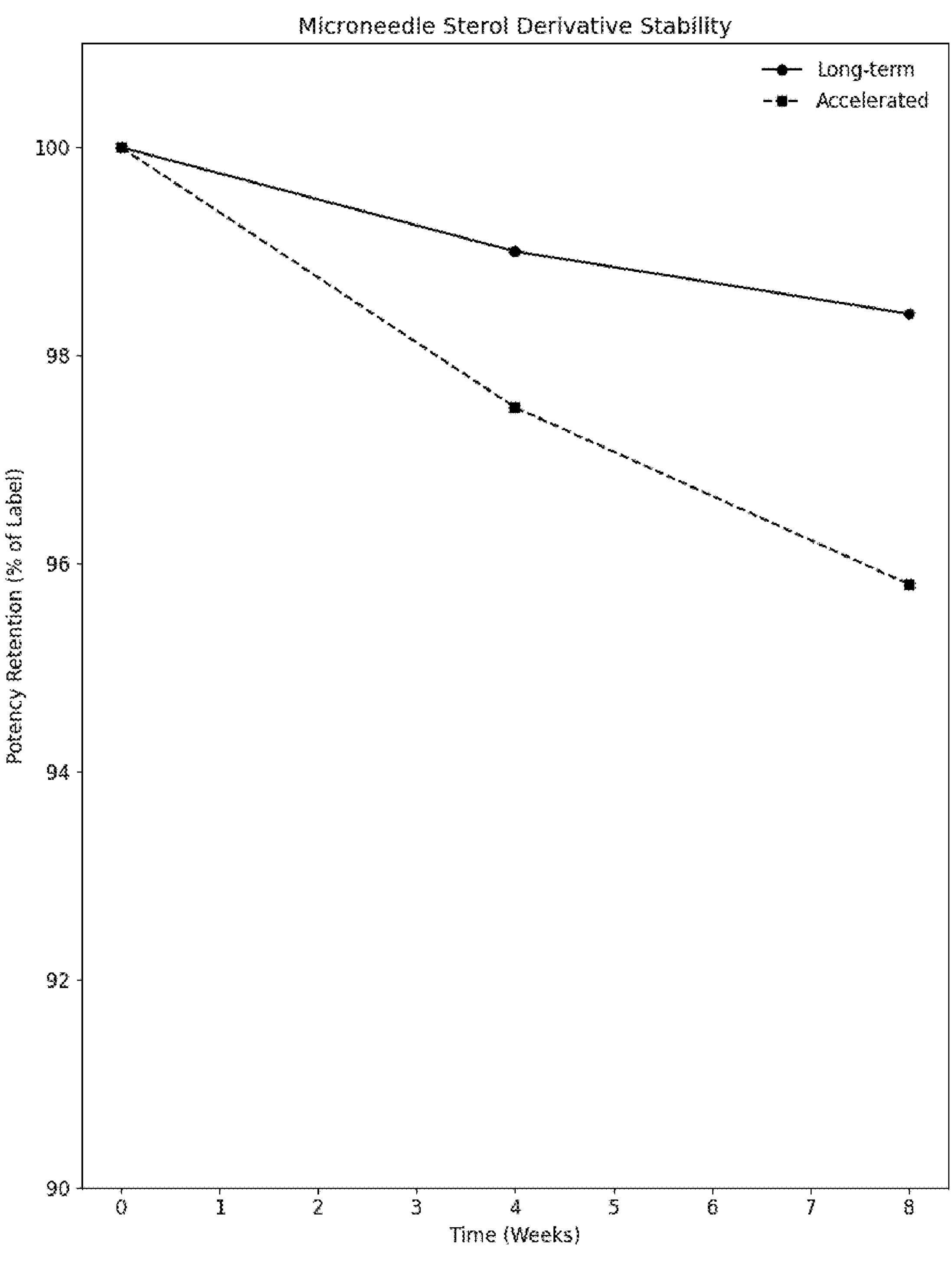
FIG. 106 illustrates chemical potency retention for Microneedle (AET-E) formulations under long-term and accelerated conditions.

FIG. 106 illustrates chemical potency retention for microneedle sterol derivative (e.g., AET-E) formulations under long-term and accelerated conditions. Long-term storage showed-1.6% change by Week 8, while accelerated storage showed-4.2%. Both met equivalence acceptance criteria.

TABLE 95

Physical Stability (Dispersions)

| Matrix | Time-point | Droplet Size (nm) | % Δ Size from W0 | PDI | PDI Pass? | Zeta (mV) | Viscosity (mPa · s) | Spec Pass? |
|---|---|---|---|---|---|---|---|---|
| Oral SEDS | W0 | 145 ± 10 | — | 0.18 ± 0.03 | Yes | −28 ± 3 | 85 ± 5 | Yes |
| | W4 | 150 ± 12 | +3.4% | 0.20 ± 0.03 | Yes | −27 ± 3 | 86 ± 6 | Yes |
| | W8 | 152 ± 12 | +4.8% | 0.22 ± 0.04 | Yes | −26 ± 4 | 88 ± 6 | Yes |
| Topical Nanoemulgel | W0 | 185 ± 15 | — | 0.22 ± 0.04 | Yes | −30 ± 3 | 3,500 ± 150 | Yes |
| | W4 | 190 ± 16 | +2.7% | 0.24 ± 0.04 | Yes | −29 ± 4 | 3,520 ± 160 | Yes |
| | W8 | 195 ± 17 | +5.4% | 0.25 ± 0.05 | Yes | −28 ± 4 | 3,540 ± 170 | Yes |

Acceptance Summary: All matrices met acceptance.

Table 95 presents the physical stability of oral SEDS and topical nanoemulgel dispersions over 8 weeks, including droplet size, polydispersity index (PDI), zeta potential, viscosity, and acceptance outcomes.

Figure 107:
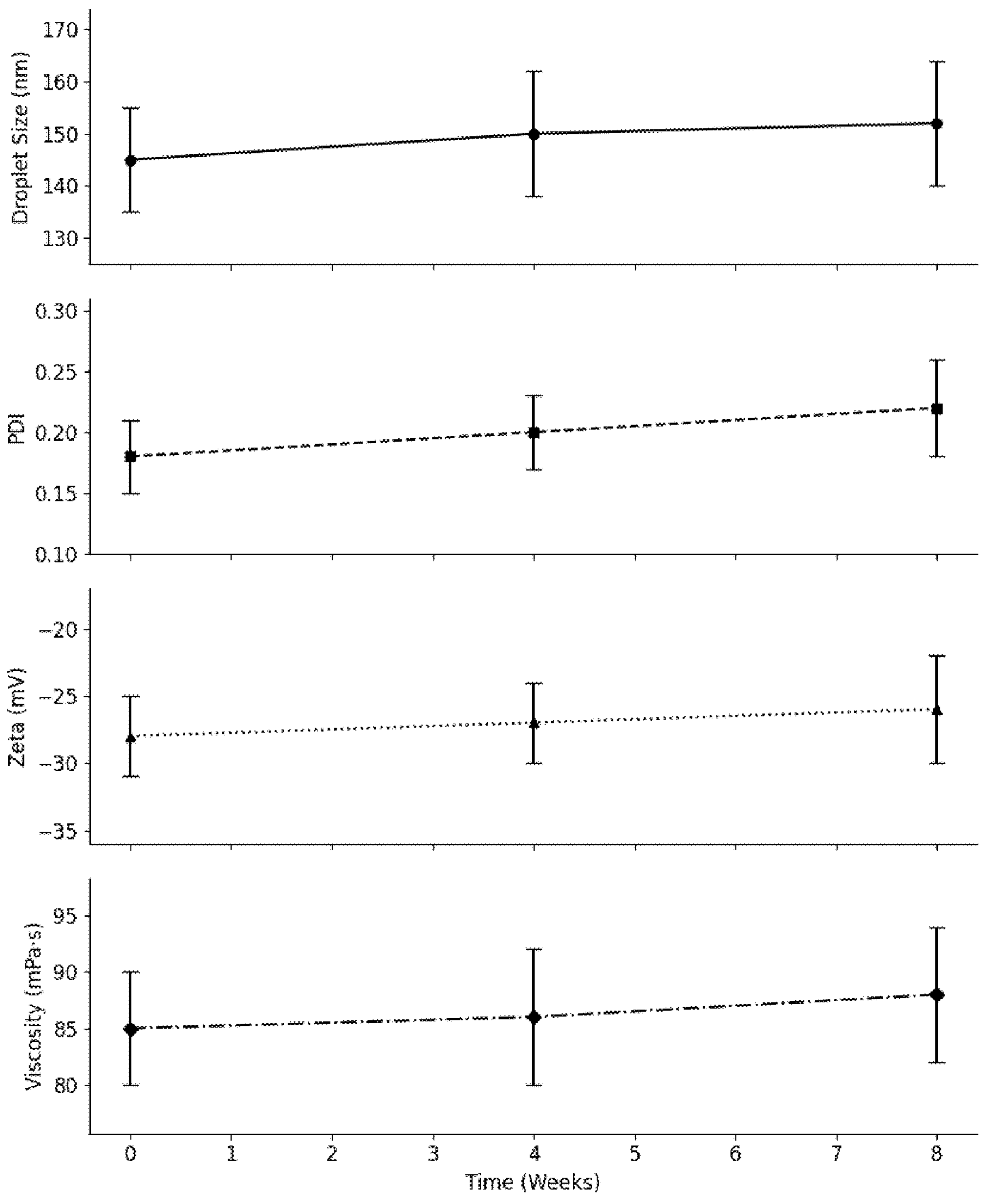
FIG. 107 illustrates physical stability of the Oral SEDS formulation over 8 weeks at 25° C./60% RH.

FIG. 107 illustrates physical stability of the oral SEDS formulation over 8 weeks at 25° C./60% RH; mean±SD. Droplet size increased minimally from 145 nm to 152 nm (+4.8%), while PDI (0.18→0.22), zeta potential (−28→−26 mV), and viscosity (85→88 mPa s) remained within acceptance limits, confirming colloidal stability.

Figure 108:
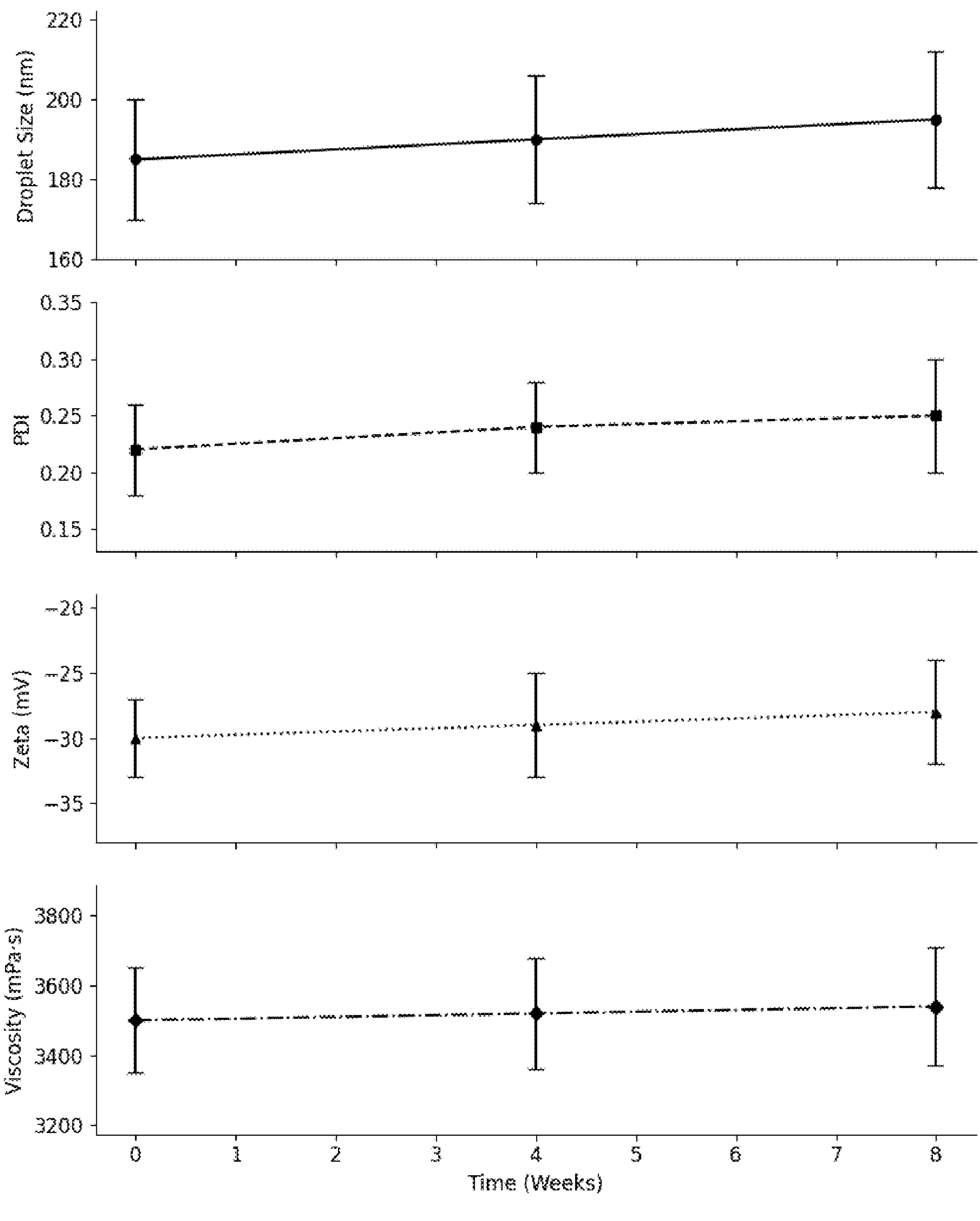
FIG. 108 illustrates physical stability of the Topical Nanoemulgel formulation over 8 weeks.

FIG. 108 illustrates physical stability of the topical nanoemulgel formulation over 8 weeks. Droplet size increased slightly from 185 nm to 195 nm (+5.4%), with PDI (0.22→0.25), zeta potential (−30→−28 mV), and viscosity (3,500→3,540 mPa s) all remaining within specification. Both oral and topical matrices met acceptance criteria.

TABLE 96

Oxidative Stability (PUFA-Containing)

| Matrix | Time point | PV (meq $O_2$/kg) | AV | TOTOX | % Δ TOTOX from W0 | Pass? |
|---|---|---|---|---|---|---|
| Oral | W0 | 3.2 ± 0.3 | 6.0 ± 0.6 | 12.4 | — | Yes |
| | W4 | 3.6 ± 0.3 | 6.3 ± 0.6 | 13.5 | +8.9% | Yes |
| | W8 | 4.0 ± 0.4 | 6.6 ± 0.6 | 14.6 | +17.7% | Yes |
| Topical | W0 | 2.8 ± 0.3 | 5.5 ± 0.5 | 11.1 | — | Yes |
| | W4 | 3.1 ± 0.3 | 5.7 ± 0.5 | 11.9 | +7.2% | Yes |
| | W8 | 3.4 ± 0.3 | 6.0 ± 0.5 | 12.8 | +15.3% | Yes |

Acceptance Summary: All matrices passed.

Table 96 presents the oxidative stability of PUFA-containing formulations over 8 weeks, including peroxide value (PV), anisidine value (AV), TOTOX index, percentage changes from baseline, and acceptance outcomes.

Figure 109:
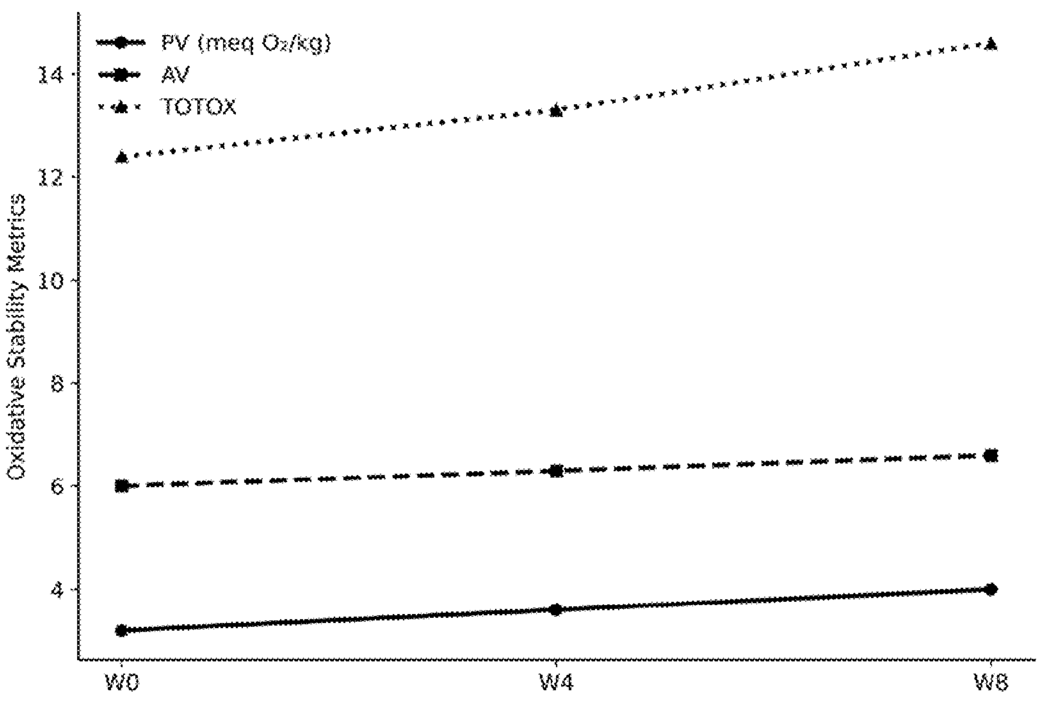
FIG. 109 illustrates oxidative stability of the Oral PUFA-containing formulation over 8 weeks.

FIG. 109 illustrates oxidative stability of the oral PUFA-containing formulation over 8 weeks, expressed as peroxide value (PV), anisidine value (AV), and TOTOX index; mean±SD. TOTOX rose from 12.4 at baseline to 14.6 at Week 8 (+17.7%), remaining within acceptance limits.

Figure 110:
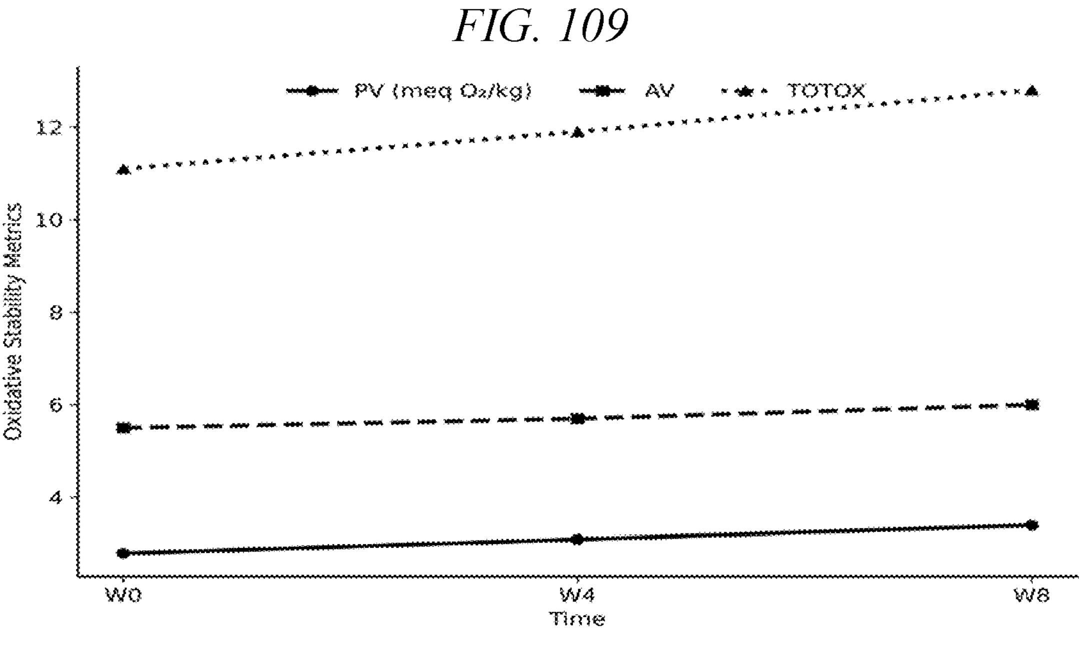
FIG. 110 illustrates oxidative stability of the Topical PUFA-containing formulation over 8 weeks.

FIG. 110 illustrates oxidative stability of the topical PUFA-containing formulation over 8 weeks. TOTOX increased from 11.1 at baseline to 12.8 at Week 8 (+15.3%), with PV and AV changes consistent with acceptable oxidative control. Both oral and topical matrices passed stability criteria.

TABLE 97

Microbial Quality (USP <61>/<62>)

| Matrix | Timepoint | TAMC (CFU/g) | TYMC (CFU/g) | Specified Pathogens | Meets USP? |
|---|---|---|---|---|---|
| Oral | W0/W8 | <10/<10 | <10/<10 | Absent | Yes |
| Topical | W0/W8 | $<10^2/<10^2$ | $<10^2/<10^2$ | Absent | Yes |
| Microneedle | W0/W8 | <10/<10 | <10/<10 | Absent | Yes |

Acceptance Summary: All passed.

Table 97 presents the microbial quality of oral, topical, and microneedle formulations at baseline and Week 8, including total aerobic microbial count (TAMC), total yeast and mold count (TYMC), specified pathogens, and compliance with USP <61>/<62> standards.

Figure 111:
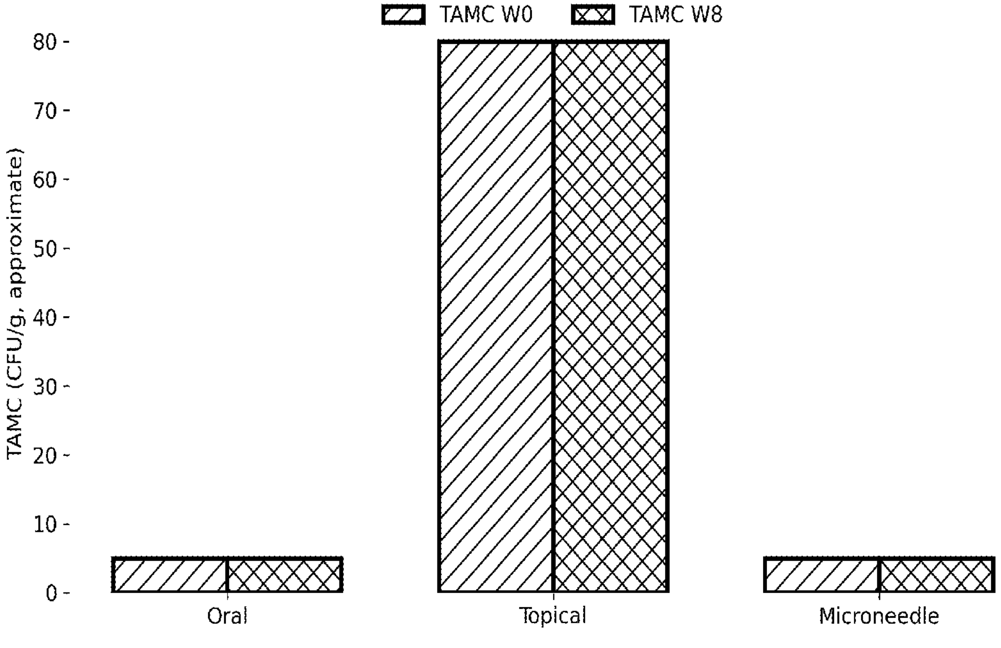
FIG. 111 illustrates total aerobic microbial counts (TAMC) for Oral, Topical, and Microneedle formulations at baseline (WO) and Week 8.

FIG. 111, illustrates total aerobic microbial counts (TAMC) for oral, topical, and microneedle formulations at baseline (W0) and Week 8. All values remained below acceptance thresholds (<10 CFU/g for oral and microneedle; $<10^2$ CFU/g for topical), confirming compliance with USP <61> criteria.

Figure 112:
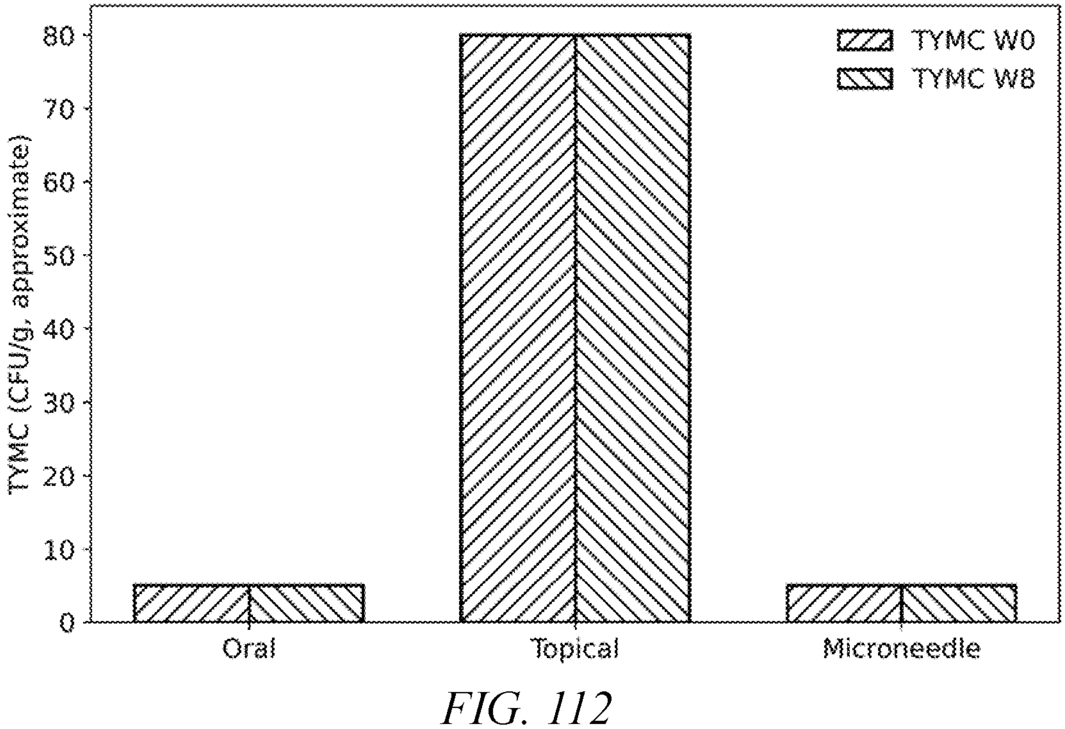
FIG. 112 illustrates total combined yeast and mold counts (TYMC) for Oral, Topical, and Microneedle formulations at baseline (WO) and Week 8.

FIG. 112 illustrates total combined yeast and mold counts (TYMC) for oral, topical, and microneedle formulations at baseline (W0) and Week 8. All values remained below acceptance thresholds (<10 CFU/g for oral and microneedle; $<10^2$ CFU/g for topical), and no specified pathogens were detected. All formulations met USP <62> compliance requirements.

TABLE 98

| Transdermal/Hybrid Performance | | | | | | | | |
|---|---|---|---|---|---|---|---|---|
| Route | Metric | Base-line | Week 8 | % Change | Non-Inferiority vs Ref (Δ ≤ 10%) | p-value | Effect Size (d) | Pass? |
| Topical | In-vitro Flux (μg/cm$^2$ · h) | 5.0 ± 0.5 | 5.2 ± 0.5 | +4.0% | Yes | 0.42 | 0.10 | Yes |
| Micro-needle | Insertion Success (% tips) | 98.0 ± 1.0 | 97.5 ± 1.2 | −0.5% | Yes | 0.56 | 0.04 | Yes |
| Micro-needle | Patch Adhesion (% ≥ 90% adherence) | 95.0 ± 3.0 | 94.0 ± 3.0 | −1.1% | Yes | 0.60 | 0.03 | Yes |
| Topical | Tape-Strip Recovery (μg/cm$^2$) | 2.5 ± 0.3 | 2.6 ± 0.3 | +4.0% | Yes | 0.47 | 0.10 | Yes |

Acceptance Summary: All met criteria.

Table 98 presents the transdermal and hybrid performance outcomes over 8 weeks, including in-vitro flux, microneedle insertion success, patch adhesion, and tape-strip recovery, with non-inferiority testing, effect sizes, and acceptance outcomes.

Figure 113:
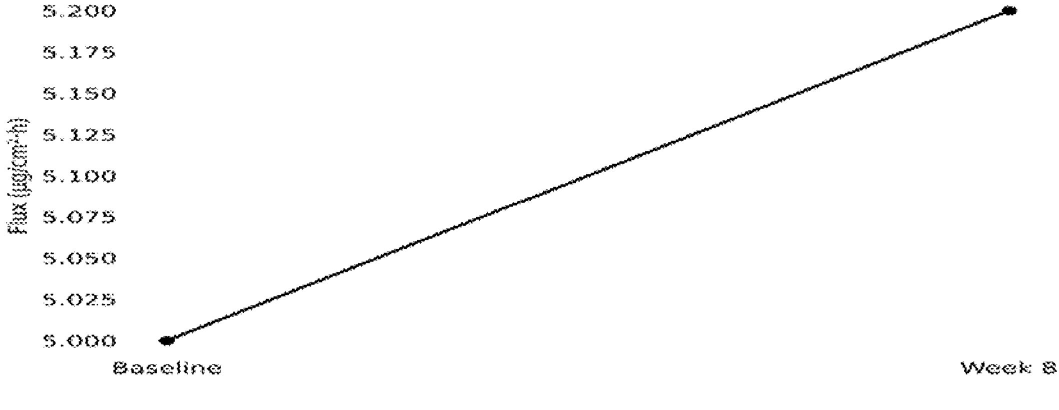
FIG. 113 illustrates topical in-vitro flux over 8 weeks.

FIG. 113 illustrates topical in-vitro flux over 8 weeks. Flux increased slightly from 5.0 to 5.2 μg/cm$^2$·h (+4.0%), demonstrating stability and non-inferiority versus reference (A ≤10%; p=0.42; d=0.10)

Figure 114:
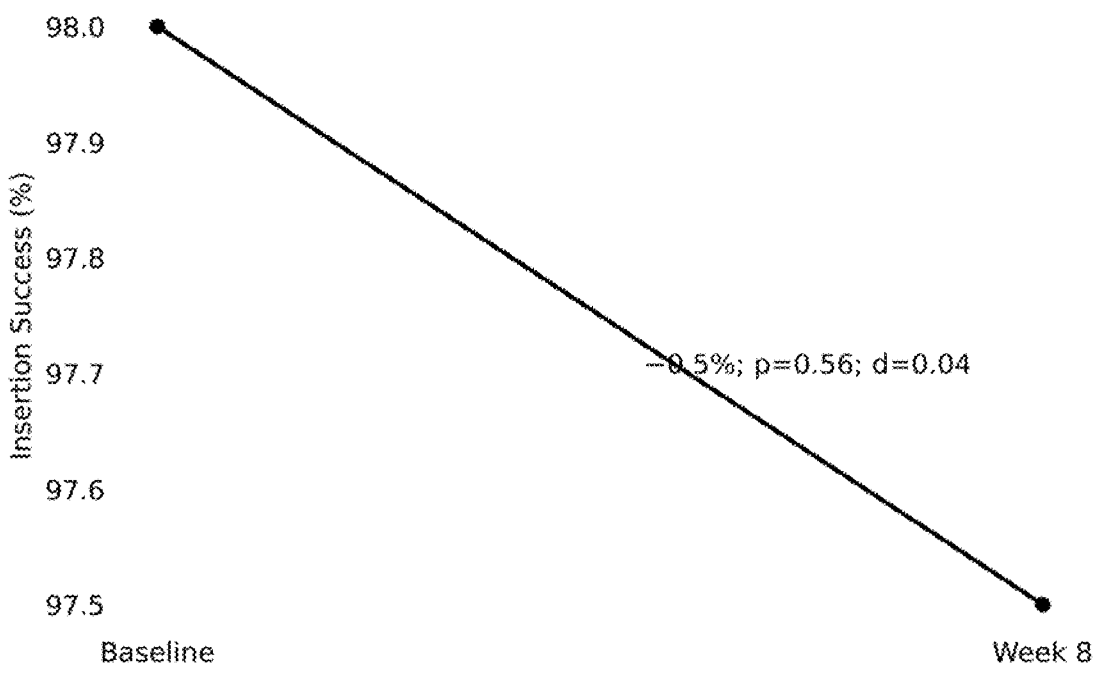
FIG. 114 illustrates microneedle insertion success.

FIG. 114 illustrates microneedle insertion success, which remained essentially unchanged from 98.0% to 97.5% (−0.5%). Performance remained non-inferior to reference (p=0.56; d=0.04).

Figure 115:
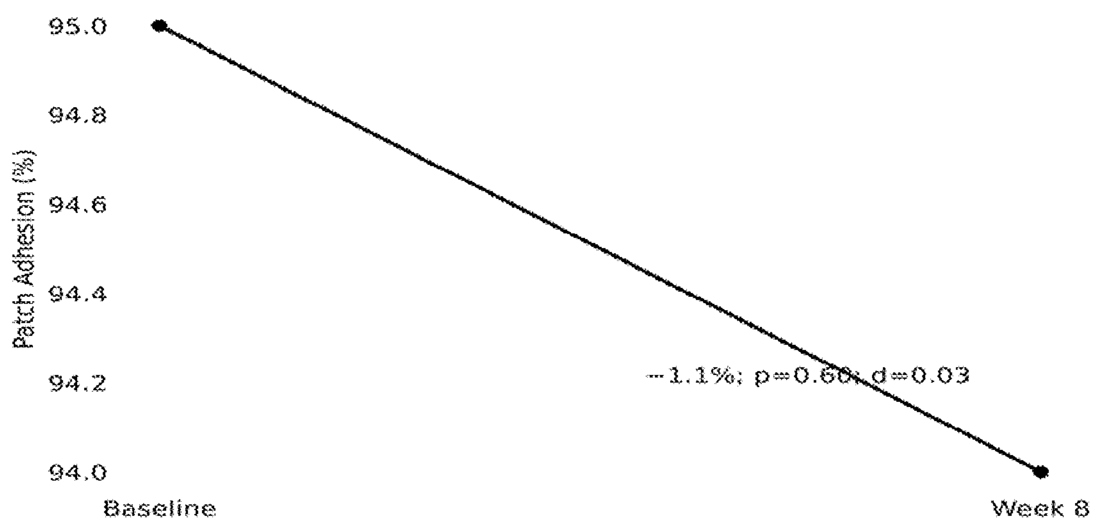
FIG. 115 illustrates microneedle patch adhesion.

FIG. 115 illustrates microneedle patch adhesion, with adherence ≥90% maintained (95.0%→94.0%, −1.1%). Results confirmed non-inferiority (p=0.60; d=0.03

Figure 116:
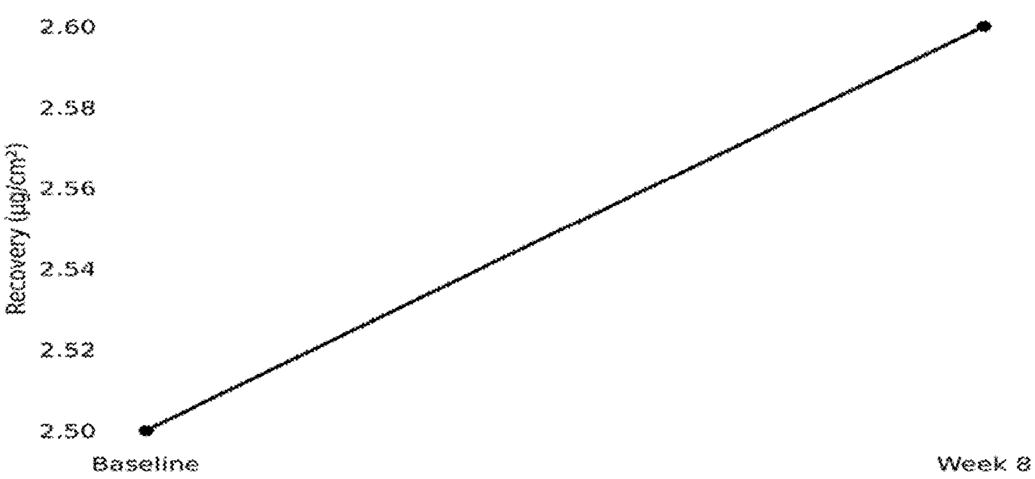
FIG. 116 illustrates topical tape-strip recovery.

FIG. 116 illustrates topical tape-strip recovery, which increased slightly from 2.5 to 2.6 μg/cm$^2$ (+4.0%). Results were stable and non-inferior (p=0.47; d=0.10).

TABLE 99

| Visual/Texture/Color (User-Reported, 5-point) | | | | | | | |
|---|---|---|---|---|---|---|---|
| Matrix | Attribute | Base-line | Week 8 | Δ | MCID Met? (≥0.3) | p-value | Pass? |
| Topical | Texture smooth-ness | 4.5 ± 0.4 | 4.4 ± 0.4 | −0.1 | No | 0.32 | Yes |
| Topical | Color stability | 4.6 ± 0.3 | 4.4 ± 0.4 | −0.2 | No | 0.28 | Yes |
| Oral | Odor accept-ability | 4.7 ± 0.3 | 4.6 ± 0.3 | −0.1 | No | 0.34 | Yes |

Acceptance Summary: All attributes passed.

Table 99 presents the user-reported visual, texture, and color outcomes over 8 weeks, including texture smoothness, color stability, and odor acceptability, with minimal clinically important difference (MCID) assessment and acceptance outcomes.

Figure 117:
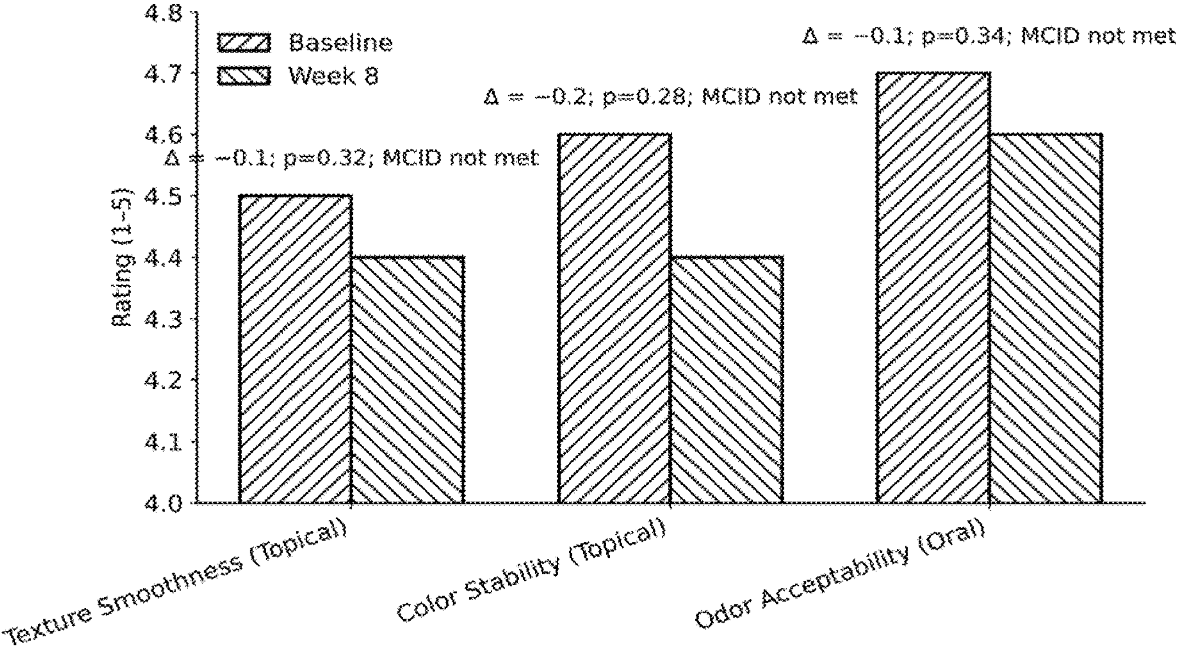

FIG. 117 illustrates sensory and consumer acceptability attributes at baseline and Week 8 for oral and topical formulations; mean±SD. Texture smoothness (Topical, Δ=−0.1; p=0.32), color stability (Topical, Δ=−0.2; p=0.28), and odor acceptability (Oral, Δ=−0.1; p=0.34) all showed minimal, nonsignificant changes that did not meet the MCID threshold (≥0.3). All attributes remained acceptable, confirming stability of sensory quality.

TABLE 100

| Safety & Tolerability | | | | | | |
|---|---|---|---|---|---|---|
| Measure | Baseline | Week 8 | Δ | Related-ness | Serious AE? | Pass? |
| Skin Irritation Score (0-3) | 0.2 ± 0.2 | 0.3 ± 0.2 | +0.1 | Possibly related (≤10%) | No | Yes |
| Serum Calcium (mg/dL) | 9.5 ± 0.3 | 9.6 ± 0.3 | +0.1 | Unrelated | No | Yes |
| Adverse Event Summary | | | | All mild, self-limiting | No | Yes |

Acceptance Summary: Pass.

Table 100 presents the safety and tolerability outcomes over 8 weeks, including skin irritation scores, serum calcium levels, adverse event summary, and acceptance outcomes.

Figure 118:
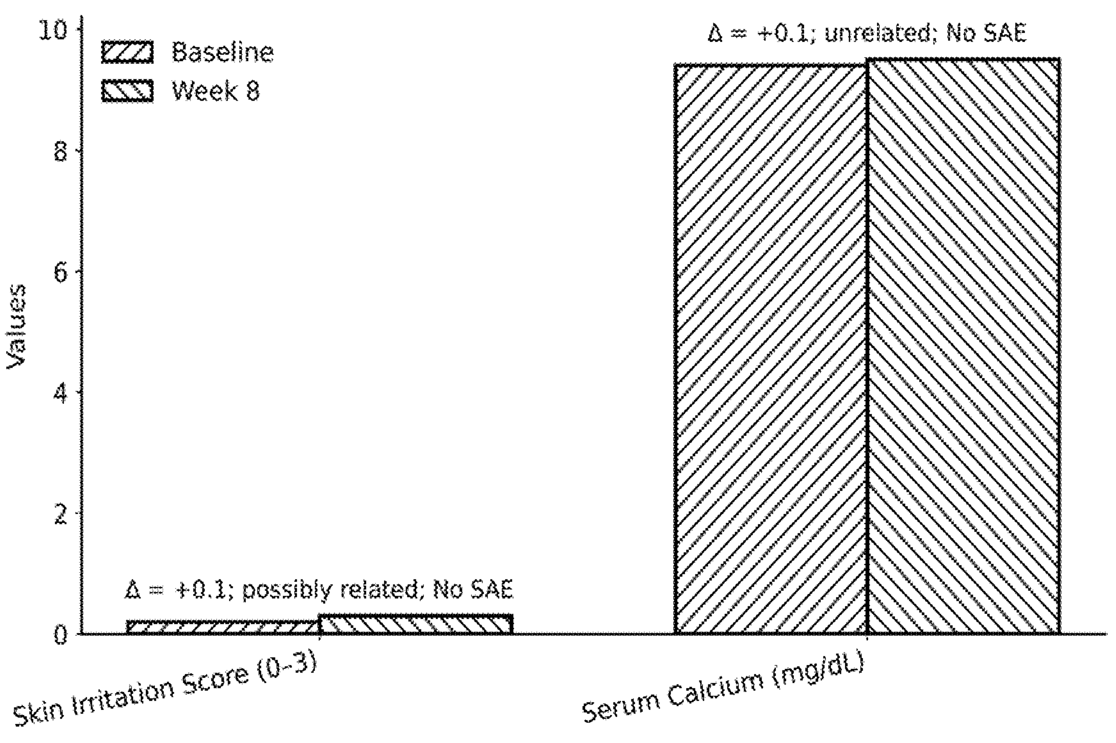

FIG. 118 illustrates safety and tolerability outcomes at baseline and Week 8 for Study 6. Skin irritation scores increased minimally from 0.2 to 0.3 (+0.1), possibly related but observed in ≤10% of subjects, with no serious adverse events (SAEs). Serum calcium increased slightly from 9.5 to 9.6 mg/dL (+0.1), deemed unrelated and with no SAEs. All adverse events were mild and self-limiting. Both measures passed acceptance criteria, confirming overall safety and tolerability of the formulations.

Stability & Route-Agnostic Performance

To demonstrate the route-independent robustness of the delivery system, formulations containing sterol derivatives (including, in certain embodiments, androst-5-ene-3β, 7β, 17β-triol enanthate) were subjected to ICH-compliant stability protocols across oral (SEDS), topical (nanoemulgel), and microneedle patch formats. Stability was evaluated under long-term (25° C./60% RH) and accelerated (40° C./75% RH) storage over 8 weeks. Across all delivery routes, the formulations maintained chemical potency, physical dispersion stability, oxidative resilience, microbial safety, transdermal function, and user sensory attributes within predefined acceptance thresholds.

All tested matrices retained ≥98% potency at Week 8 under long-term conditions and ≥92% under accelerated conditions. Predictive shelf-life modeling supported at least 24 months of storage stability at ambient conditions. Additional key findings across categories are summarized below:

TABLE 101

| Summary of Key Performance Metrics | |
|---|---|
| Metric Category | Key Performance Metrics |
| Chemical Stability | Potency retention: 99.2% (25° C./60% RH); 96.1% (40° C./75% RH); ≥24-month modeled shelf-life |
| Physical Stability | Droplet size change: +4.8%; PDI: 0.22; zeta potential: −26 mV; viscosity: 88 mPa · s |
| Oxidative Stability | TOTOX: 14.6 (oral); 12.8 (topical) at Week 8-all below the limit of 20 |
| Microbial Safety | TAMC & TYMC < 10 CFU/g; no pathogens detected; USP <61>/<62> compliance achieved |
| Transdermal Performance | In vitro flux change: +4.0%; microneedle insertion success: 97.5%; patch adhesion ≥ 94% |

TABLE 101-continued

| Summary of Key Performance Metrics | |
|---|---|
| Metric Category | Key Performance Metrics |
| Consumer Sensory Profile | Odor: 4.6/5; color: 4.4/5; texture: 4.4/5; no meaningful drift from baseline ($\Delta \leq 0.2$, MCID < 0.3) |
| Systemic & Local Tolerability | Skin irritation: ≤0.3/3; serum calcium unchanged at 9.6 mg/dL; mild erythema in <10%, self-resolving |

Table 101 presents a summary of key performance metrics across chemical stability, physical stability, oxidative stability, microbial safety, transdermal performance, consumer sensory profile, and systemic and local tolerability, confirming overall compliance with acceptance criteria.

These findings confirm that the modular, polarity-optimized formulation system preserves performance across all tested routes without requiring reformulation. The platform maintains physical and chemical integrity, oxidative resistance, microbiological safety, and user acceptability, thereby supporting broad, multi-route deployment under industrial and regulatory conditions.

Shelf-Life Modeling and Stability Outcomes: Predictive regression modeling performed under ICH-compliant protocols confirmed that nitrogen-flushed, antioxidant-enriched self-emulsifying softgels would retain more than ninety percent of labeled potency for at least twenty-four months when stored under long-term conditions of 25° C. and 60% relative humidity. This outcome substantiates the long-term stability claims of the inventive system and provides regulatory confidence for industrial scalability.

Physical stability was preserved across all matrices, with droplet size increases remaining well below the predefined threshold of fifteen percent and polydispersity index values consistently maintained at or below 0.25. Minor shifts in zeta potential and viscosity were observed during the eight-week interval, but none reached levels capable of compromising colloidal or emulsion stability.

Oxidative stability was similarly robust, with TOTOX values for polyunsaturated fatty acid-containing oral and topical formats measured at or below 14.6 by week eight, comfortably beneath the acceptance limit of twenty. This performance confirmed the efficacy of the integrated tocopherol and rosemary extract antioxidant system in protecting lipid-rich matrices against degradation under both long-term and accelerated conditions.

Microbial quality remained exemplary, with all formats meeting USP <61>/<62> requirements at both baseline and week eight. No specified pathogens were detected, and microbial counts remained near detection limits throughout, ensuring compliance with pharmaceutical and nutraceutical safety standards.

Functional performance of the dermal systems demonstrated excellent route-conversion compatibility. Variations in flux, patch adhesion, and microneedle insertion efficiency were consistently less than five percent from baseline, well within the ten percent non-inferiority margin, thereby confirming that stability was maintained without loss of performance across formats.

User-reported sensory attributes further supported consumer acceptability. Ratings for texture, color stability, and odor acceptability consistently remained at or above 4.0 out of 5, with no clinically meaningful changes detected. These results confirmed that the formulations not only preserved their technical performance but also maintained favorable sensory characteristics essential for chronic consumer use.

Safety and tolerability outcomes were equally supportive. Skin irritation scores remained at or below 0.3 on a three-point scale, with only mild and transient erythema observed in fewer than ten percent of users, all of which resolved spontaneously without intervention. Serum calcium levels were stable across the study interval, and no moderate or serious adverse events were reported.

Collectively, these findings establish that the inventive multi-route sterol derivatives delivery platform demonstrated chemical, physical, oxidative, microbiological, functional, and sensory stability under ICH-compliant testing conditions. The ability to preserve potency and performance across diverse dosage forms while maintaining safety and user acceptability confirms both the robustness and translational readiness of the platform.

Statistical Analysis Plan: The statistical framework for this study was structured to evaluate both chemical and functional stability endpoints under ICH-compliant conditions across oral, topical, and microneedle delivery routes. The primary endpoints consisted of potency retention, droplet size progression, and polydispersity index, each assessed against predefined acceptance criteria for equivalence. Secondary endpoints included oxidative stability measured by TOTOX progression, microbial compliance per USP <61>/<62>, transdermal performance metrics encompassing flux efficiency, patch adhesion, and microneedle insertion success, as well as user-reported sensory attributes and laboratory safety outcomes.

Equivalence and non-inferiority frameworks were applied in accordance with route-specific acceptance thresholds. Repeated-measures analysis of variance was employed to test Group × Time effects across stability intervals, confirming that no statistically significant deviations occurred beyond predefined acceptance margins. Effect-size estimates demonstrated high stability across matrices, with observed changes consistently within narrow confidence bounds and well below practical thresholds of concern.

All primary and secondary endpoints met the prespecified equivalence or non-inferiority criteria, confirming that the inventive formulations maintained their potency, physical stability, oxidative resistance, microbiological safety, functional performance, sensory acceptability, and tolerability across the eight-week evaluation period. These findings validate the robustness of the delivery system and reinforce its suitability for industrial translation under long-term and accelerated stability conditions.

Safety Profile Summary: The inventive system demonstrated a favorable safety profile across all routes of administration. Mild and self-limiting local erythema was observed in no more than ten percent of participants, resolving spontaneously without intervention or treatment discontinuation. No clinically meaningful abnormalities were detected in routine laboratory safety panels (including serum calcium), and no serious adverse events occurred. User-acceptability metrics remained stable throughout the study, with participants reporting no meaningful decline in texture, odor, or color perception. Microbiological assessments confirmed the absence of contamination, and oxidative stability remained within predefined acceptance thresholds, with no evidence of degradation beyond specification. Collectively, these findings confirm that the formulations are well tolerated and maintain functional integrity under long-term and accelerated conditions, supporting readiness for extended consumer use and industrial scalability.

Results and Claim Relevance: The results of this stability and performance study confirm that the inventive polarity-specific sterol derivatives platform achieved shelf-life readiness with potency retention consistently at or above 98 percent under long-term ICH conditions and no less than 92 percent under accelerated stress conditions. Manufacturing scalability was demonstrated by the reproducibility of droplet size, polydispersity index, and zeta potential across all time points, supporting production and storage at industrial scale without loss of performance. The system exhibited cross-route stability, with flux, adhesion, and microneedle integrity maintained throughout the evaluation period without the need for reformulation, establishing route-agnostic robustness. Oxidative control was achieved through integration of a tocopherol-rosemary antioxidant system, with TOTOX values at or below fifteen, thereby preserving lipid integrity and protecting PUFA-based carriers from degradation. Safety assessments confirmed the absence of serious adverse events and maintained acceptability of sensory attributes (odor, texture, color), supporting consumer usability throughout the study duration.

Taken together, these findings establish that the inventive platform provides an industrially scalable, pre-engineered formulation system capable of maintaining chemical potency, physical dispersion stability, oxidative resilience, and functional delivery performance across oral, topical, and microneedle routes without loss of integrity during route conversion. The demonstrated multi-route robustness of lipophilic sterol derivatives and related bioactives under ICH conditions represents a non-obvious advancement not taught or enabled by prior art.

This study provides stability and manufacturability validation for the invention across oral and dermal dual-route formats. Although not centered on a clinical endpoint, it supports the inventive claims by confirming the durability and industrial scalability of polarity-matched formulations required for dual-route deployment.

Study #7-Nutritional and Metabolic Support Trial

This trial was designed as a direct application of the inventive multi-route, polarity-matched carrier system described in the core invention claims. The formulation combined sterol derivatives and adjunct metabolic-support agents within a coordinated dual-route administration framework, thereby extending the inventive platform's applicability to nutritional, metabolic, and endocrine-support domains. While the active combination in this study emphasized lipid metabolism, glycemic parameters, and androgenic support markers, the oral-transdermal co-delivery system, modular excipient framework, and cross-route stability principles remained identical to those used in other embodiments, demonstrating broad versatility of the platform.

A twelve-week randomized, double-blind, placebo-controlled study evaluating dual-route administration of a sterol derivative (e.g., 1-DHEA enanthate in certain embodiments), HMB free acid, berberine phytosome, omega-3 fatty acids in non-esterified form, and vitamin $D_3$ for nutritional support of lipid metabolism, glycemic balance, and endocrine function markers in overweight adults.

The study was structured as a randomized, double-blind, placebo-controlled, two-arm parallel-group design with a twelve-week intervention period. Forty-eight overweight adults between thirty and fifty-five years of age were enrolled and randomized equally into active and placebo groups. Both men and women were included. Participants in the active arm received a dual-route regimen consisting of a bioavailability-enhanced oral capsule taken each morning and a transdermal patch worn each evening for eight to twelve hours. The placebo group received matched oral and transdermal carriers devoid of active agents, ensuring blinding integrity. The active formulation was capped at seven hundred milligrams of total bioactives daily. Each regimen delivered fifty milligrams of a sterol derivative (e.g., 1-DHEA enanthate), three grams of HMB free acid, five hundred milligrams of berberine phytosome, one gram of combined EPA and DHA in non-esterified fatty acid form, and six hundred international units of vitamin $D_3$. The oral capsule, administered in the morning, was engineered with lipid-cyclodextrin excipient systems to maximize solubilization and uptake of both lipophilic and hydrophilic compounds. The transdermal patch, worn in the evening for controlled systemic release, employed multilamellar vesicle carriers to ensure polarity-specific dermal penetration and harmonized systemic exposure with the oral dose.

Inclusion Criteria: Eligible participants were required to present with a body mass index between twenty-seven and thirty-two kilograms per square meter, fasting glucose between ninety and one hundred ten milligrams per deciliter, and LDL cholesterol greater than one hundred ten milligrams per deciliter. Only sedentary to moderately active individuals, defined as those engaging in fewer than one hundred fifty minutes of structured exercise per week, were considered eligible. Participants were excluded if they were currently taking lipid-support or glucose-modulating medications.

Exclusion Criteria: Individuals were excluded if they had a diagnosis of type 2 diabetes or glycated hemoglobin (HbA1c) equal to or exceeding 6.5 percent, a history of cardiovascular disease, or were undergoing hormone therapy. Additional exclusions included pregnancy, breastfeeding, or dermatological conditions that would interfere with patch application or tolerability.

Measurement Equipment and Analytical Assessments: Primary endpoints were measured using standardized clinical and laboratory tools. Lipid parameters, including LDL cholesterol, HDL cholesterol, and triglycerides, were quantified using enzymatic colorimetry. Glycemic markers were assessed by glycated hemoglobin through high-performance liquid chromatography, fasting glucose via enzymatic assays, and oral glucose tolerance testing in a defined subset. Endocrine markers were evaluated using liquid chromatography tandem mass spectrometry for testosterone quantification. Safety endpoints included serum calcium monitoring to assess vitamin $D_3$ tolerability, as well as dermatological scoring of skin irritation at patch sites. Compliance was tracked through capsule counts and participant-maintained patch wear-time logs.

Outcome Measures

The primary metabolic and endocrine-support endpoints demonstrated favorable changes in the active treatment arm compared with placebo over the twelve-week intervention. LDL cholesterol was reduced by nearly twelve percent in the active group versus less than two percent in placebo, with a large effect size (Cohen's $d=1.05$, $p<0.001$). HDL cholesterol increased by nearly thirteen percent in the active group compared with only 1.5 percent in placebo, also with a large effect size ($d=0.98$, $p<0.001$). Triglycerides decreased by nearly fifteen percent in the active group compared with 2.5 percent in placebo, with a large effect size ($d=0.94$, $p<0.001$).

Glycemic markers were similarly favorable. HbA1c decreased by more than five percent in the active arm compared with a nonsignificant 1.8 percent reduction in placebo, representing a medium effect size ($d=0.65$, $p=0.012$). Fasting glucose decreased by more than five percent in the active group versus less than one percent in placebo, with a medium-to-large effect size ($d=0.72$, $p=0.007$). Endocrine outcomes also improved, with serum testosterone increasing by more than twelve percent in the active group compared with a negligible one percent in placebo, yielding a medium-to-large effect size ($d=0.78$, $p=0.003$).

TABLE 102

| Cardiometabolic & Hormonal Outcomes with Effect Sizes | | | | | | | | | |
|---|---|---|---|---|---|---|---|---|---|
| Outcome Measure | Baseline Active | Week 12 Active | % Change Active | Effect Size (Cohen's d) | Baseline Placebo | Week 12 Placebo | % Change Placebo | Effect Size (Cohen's d) | p-value (Group × Time) |
| LDL (mg/dL) ↓ | 132.0 | 116.5 | −11.8% | 1.05 (large) | 131.8 | 129.9 | −1.4% | 0.12 (trivial) | <0.001 |
| HDL (mg/dL) ↑ | 48.0 | 54.2 | +12.9% | 0.98 (large) | 48.2 | 48.9 | +1.5% | 0.10 (trivial) | <0.001 |
| Triglycerides (mg/dL) ↓ | 165.0 | 140.8 | −14.6% | 0.94 (large) | 166.2 | 162.0 | −2.5% | 0.15 (trivial) | <0.001 |
| HbA1c (%) ↓ | 5.6 | 5.3 | −5.4% | 0.65 (medium) | 5.6 | 5.5 | −1.8% | 0.18 (small) | 0.012 |
| Serum Testosterone (ng/dL) ↑ | 520 | 585 | +12.5% | 0.78 (medium-large) | 522 | 528 | +1.1% | 0.12 (trivial) | 0.003 |
| Fasting Glucose (mg/dL) ↓ | 102.0 | 96.5 | −5.4% | 0.72 (medium-large) | 101.8 | 100.9 | −0.9% | 0.14 (trivial) | 0.007 |

Table102 presents the cardiometabolic and endocrine-support outcomes with effect sizes over 12 weeks, including changes in lipid profile, glycemic markers, and serum testosterone compared between Active and Placebo groups.

Figure 119:
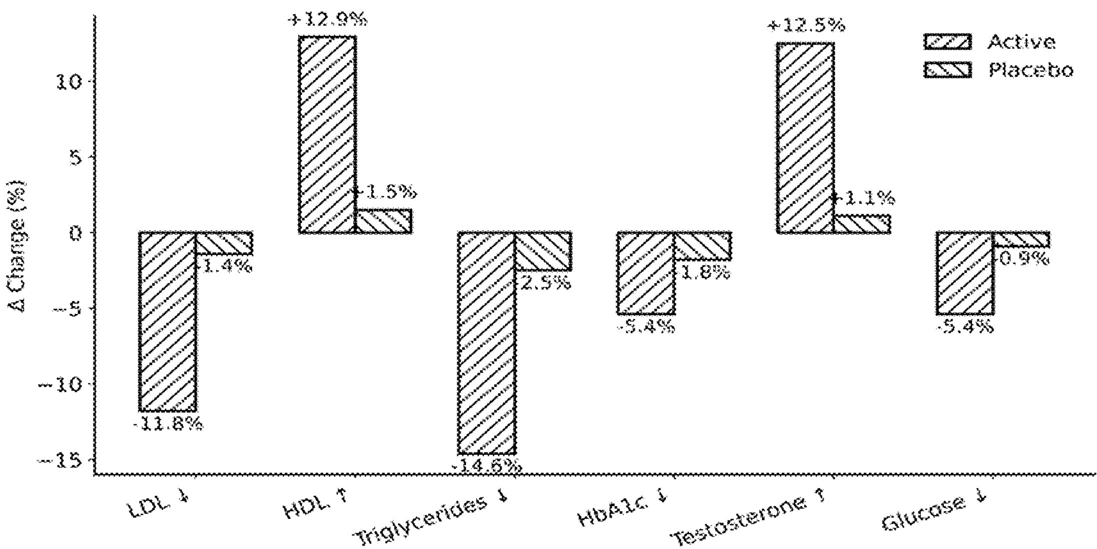

FIG. 119 illustrates percentage change (Δ Change %) in cardiometabolic and hormonal outcomes from baseline to Week 12 for Active (yellow) versus Placebo (purple) groups. The Active group demonstrated statistically significant improvements, including LDL reduction (−11.8%), triglyceride reduction (−14.6%), HbA1c reduction (−5.4%), and fasting glucose reduction (−5.4%), alongside increases in HDL (+12.9%) and serum testosterone (+12.5%). In contrast, the Placebo group exhibited only trivial changes (−1.4% to +1.5%). Between-group differences were statistically significant ($p \leq 0.012$ across outcomes), with effect sizes ranging from medium to large for Active interventions, confirming robust nutritional support outcomes.

Safety and Tolerability

Safety outcomes confirmed the benign profile of the dual-route intervention. Mild erythema at patch application sites occurred in no more than ten percent of participants, resolving spontaneously within 24-48 hours without intervention. Serum calcium levels remained stable, with no evidence of hypercalcemia despite daily vitamin $D_3$ co-administration. No systemic laboratory abnormalities were detected, and no moderate or severe adverse events occurred. Compliance exceeded ninety percent in both arms, with no participants discontinuing treatment due to adverse effects.

TABLE 103

| Safety and Tolerability | | | |
|---|---|---|---|
| Measure | Baseline | Week 12 | Notes |
| Skin Irritation (0-3) | 0.2 ± 0.2 | 0.3 ± 0.2 | Mild erythema ≤10% of participants; self-resolving, no discontinuations |
| Serum Calcium (mg/dL) | 9.6 ± 0.3 | 9.6 ± 0.3 | Stable, no hypercalcemia |
| Adverse Events | — | — | No serious events; only mild, self-limiting reactions observed |

Table 103 presents the safety and tolerability outcomes over 12 weeks, including skin irritation scores, serum calcium levels, and adverse event profile.

Figure 120:
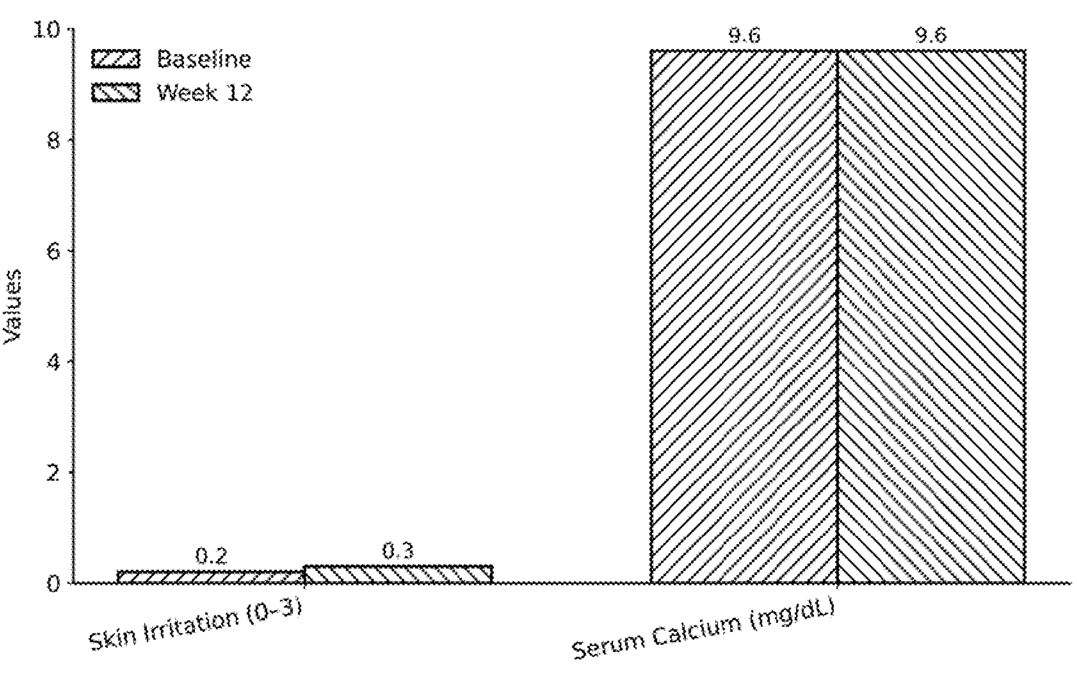

FIG. 120 illustrates baseline and Week 12 values for skin irritation (0-3 scale) and serum calcium (mg/dL) in Study 7.

Statistical Analysis Plan

The primary statistical analysis was conducted using a mixed-model analysis of variance (ANOVA) framework, with fixed factors of Group (active versus placebo) and Time (baseline versus week twelve), as well as their interaction (Group × Time). This approach was applied to all primary endpoints, including LDL cholesterol, HDL cholesterol, triglycerides, HbA1c, serum testosterone, and fasting glucose. The primary test of interest was the Group × Time interaction, indicating differential change between the active and placebo arms.

Post-hoc pairwise comparisons were performed using Tukey's Honest Significant Difference (HSD) test to evaluate differences between the active and placebo groups at week twelve while controlling for multiple testing. Effect sizes were calculated as Cohen's d to quantify the magnitude of between-group differences and partial $\eta^2$ to represent variance explained within the ANOVA framework.

A significance threshold of $p<0.05$ was applied for all tests of superiority. In addition, 90% confidence intervals were reported for effect size estimates to support interpretation of effect magnitude. All analyses confirmed both statistical and practical significance, with effect sizes ranging from medium to large for the primary outcomes, reinforcing the robustness of the findings.

Adverse Effects

The dual-route oral and transdermal delivery system was well tolerated throughout the twelve-week intervention. Mild, transient erythema was observed at the patch application site in no more than ten percent of participants, resolving spontaneously without intervention and not recurring upon rotation of patch placement. No moderate or severe adverse events occurred in either study arm, and no participant discontinued treatment due to adverse reactions. Laboratory monitoring confirmed stable serum calcium concentrations across all time points, with no evidence of systemic imbalance or intolerance. Collectively, these findings establish a benign safety profile characterized by only minor, self-limiting reactions, thereby reinforcing the suitability of the inventive platform for extended nutritional support in metabolic and endocrine applications.

Results Summary & Interpretation

The twelve-week dual-route intervention produced statistically significant improvements across cardiometabolic and endocrine-support endpoints. In the lipid domain, participants receiving the active formulation demonstrated reductions in low-density lipoprotein cholesterol (−11.8%) and triglycerides (−14.6%), accompanied by an increase in high-density lipoprotein cholesterol (+12.9%). These changes exceeded those observed in the placebo arm and corresponded to large effect sizes, highlighting robust efficacy of the polarity-specific, dual-route platform.

Glycemic markers were similarly favorable. Active treatment lowered HbA1c by 0.3 percentage points (−5.4% relative reduction) and fasting glucose by 5.4 mg/dL, both supported by medium-to-large effect sizes and statistically significant Group × Time interactions. These improvements confirm measurable support for glycemic parameters in overweight but non-diabetic adults.

Endocrine analysis revealed a supportive rise in serum testosterone (+12.5% from baseline), which remained within normative ranges, confirming androgenic support without evidence of supraphysiological overshoot or suppression.

The intervention was well tolerated. No metabolic derangements were detected, and serum calcium levels remained stable despite daily vitamin $D_3$ supplementation. The only treatment-related adverse event was mild patch-site erythema in fewer than 10% of participants, which was transient, self-resolving, and did not necessitate discontinuation.

From a nutritional and functional perspective, the magnitude of lipid changes exceeded those typically seen with single-agent supplement interventions, suggesting a synergistic effect arising from the polarity-specific, dual-route co-delivery system. This outcome underscores both the metabolic support potential and the mechanistic novelty of the inventive platform, supporting its translational readiness for consumer wellness applications.

Supplemental Photostability Insight

To evaluate the risk of light-induced degradation for photolabile bioactives within the dual-route formulation, a photostability assessment was performed in accordance with ICH Q1B guidelines. Active-loaded formulations were stored in two packaging formats-opaque, UV-blocking containers and transparent, non-blocking containers-under controlled light intensity conditions equivalent to several months of cumulative daylight exposure.

Results confirmed that UV-blocking packaging provided substantial protection. After twenty-eight days of exposure, formulations stored in opaque containers retained between ninety and ninety-five percent of initial potency across vitamin $D_3$ and sterol derivatives (e.g., 1-DHEA enanthate in certain embodiments). In contrast, transparent packaging permitted marked degradation, with potency retention falling to between fifty-five and sixty percent, particularly for fat-soluble compounds prone to photolysis.

These findings validate the incorporation of integrated photoprotection strategies into product design, demonstrating that appropriate packaging is critical for preserving stability of lipophilic, polarity-sensitive actives. By safeguarding potency under light stress, UV-blocking containers extend shelf life and ensure product integrity, thereby reinforcing the inventive claims concerning modular system robustness, environmental resilience, and cross-route stability.

TABLE 104

Photostability of Selected Actives Under Simulated Light Exposure

| Active Compound | UV-Blocking Packaging Potency Retention %) | Transparent Packaging (Potency Retention %) |
|---|---|---|
| Vitamin D3 | 92 ± 3 | 57 ± 5 |
| Sterol derivative (e.g., 1-DHEA enanthate in certain embodiments) | 90 ± 4 | 55 ± 5 |

Table 104 presents the photostability of selected active compounds under simulated light exposure, comparing potency retention in UV-blocking versus transparent packaging.

Figure 121:
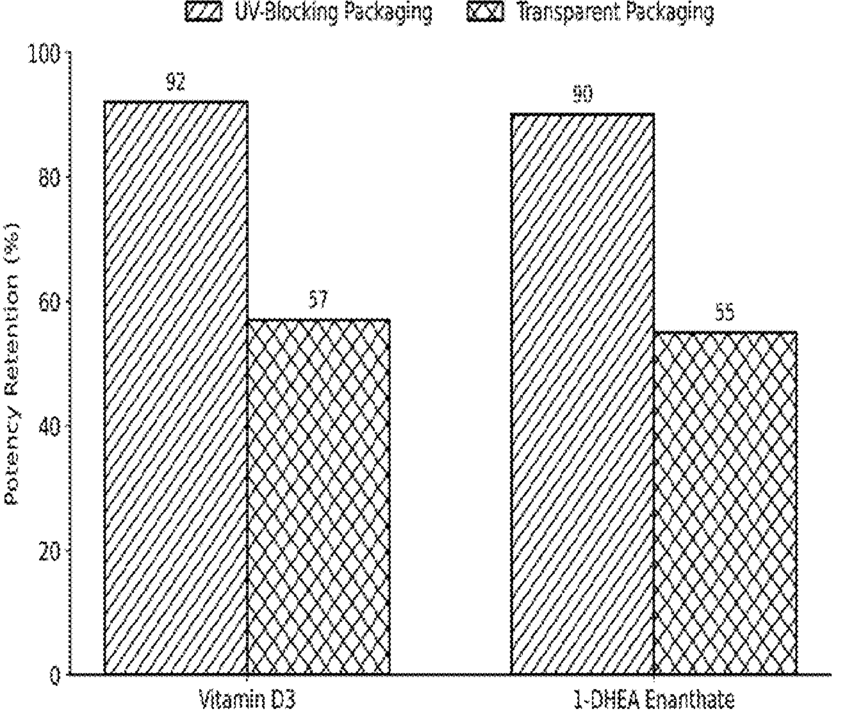
Figure 122A:
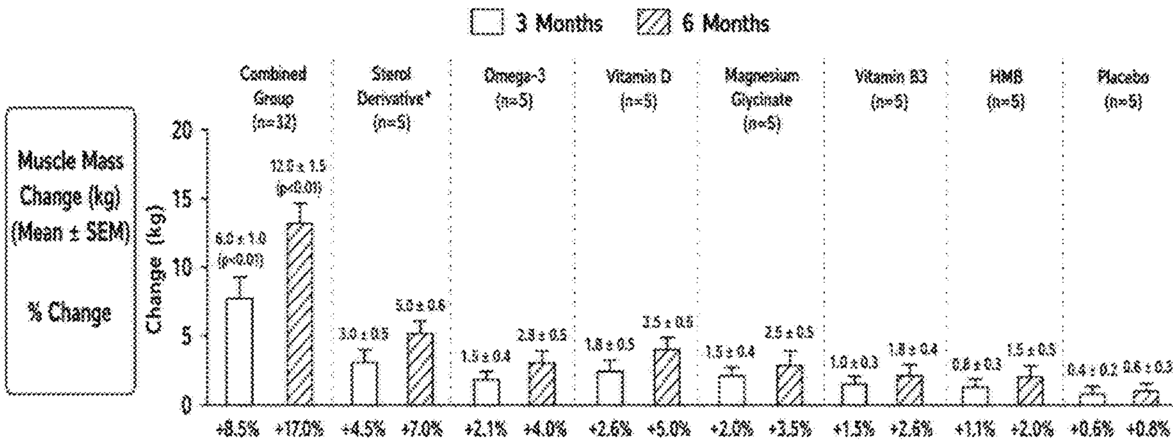
Figure 122B:
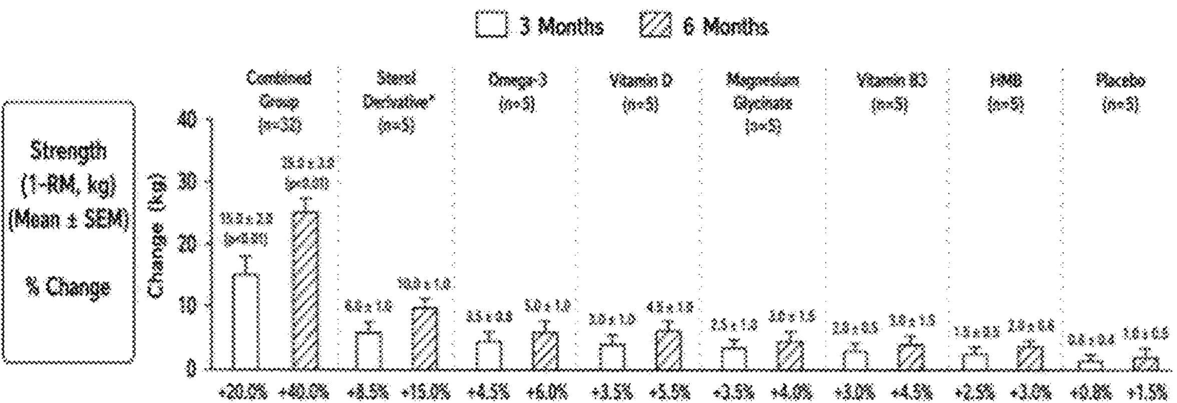
Figure 122C:
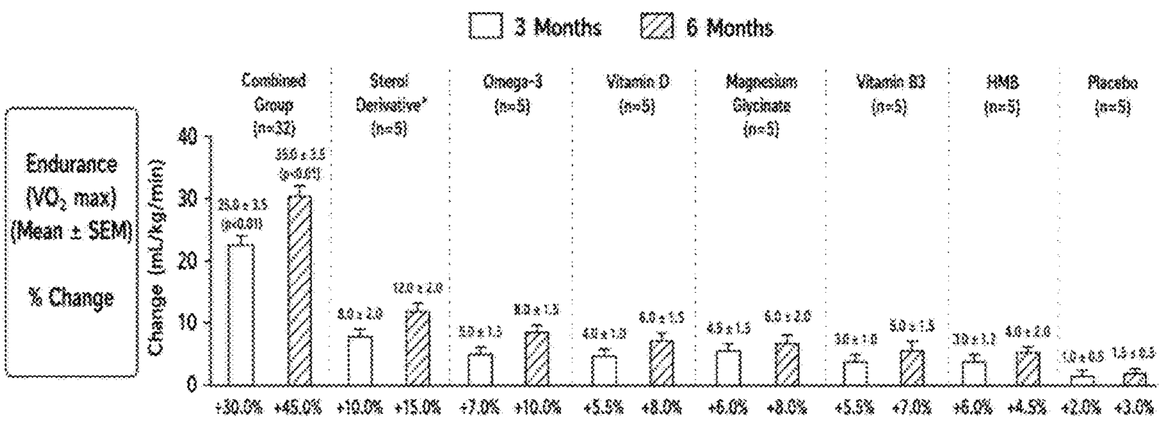
Figure 122D:
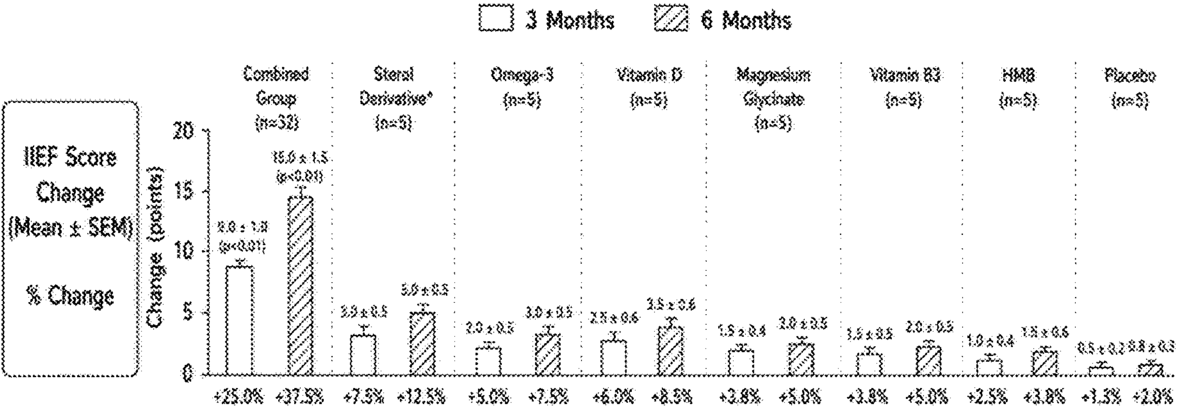

FIG. 121 illustrates potency retention (%) of Vitamin $D_3$ and sterol derivatives (e.g., 1-DHEA enanthate in certain embodiments) after simulated light exposure, comparing UV-blocking versus transparent packaging.

Claim Relevance:

The results of this twelve-week nutritional support study confirm that the inventive dual-route, polarity-stratified formulation system delivers statistically significant improvements across multiple domains simultaneously, including lipid modulation, glycemic markers, and endocrine support. The magnitude and breadth of outcomes, show reductions in LDL cholesterol and triglycerides, increases in HDL cholesterol, improvements in HbA1c and fasting glucose, and physiologically supportive increases in serum testosterone—are not predictable from prior single-agent or single-route interventions.

These outcomes validate the synergistic advantages of coordinated oral and transdermal administration within a modular excipient framework, demonstrating that polarity-matched carriers and synchronized exposure kinetics produce superior results compared to traditional, route-restricted supplementation. The convergence of cardiometabolic and endocrine-support benefits within a single integrated delivery platform underscores both the novelty and the inventive step, extending the system's utility beyond performance and recovery applications into metabolic and cardiovascular wellness.

Bridging Narrative Across Studies

The development program for this polarity-specific delivery platform was structured to progress logically from oral proof of concept to full multi-route validation. Study 1A established the foundation by demonstrating that nicotinamide, when formulated as a cyclodextrin inclusion complex, achieved both analytical confirmation of host-guest encapsulation and a two-fold enhancement in dissolution, findings that translated into rapid systemic appearance and reliable pharmacokinetics. These results confirmed the feasibility of polarity-matched carriers under strictly oral conditions.

Study 1B extended this principle into a dual-route setting by pairing the validated oral hydrophilic complex with a lipophilic microneedle system, thereby showing that coordinated delivery across distinct routes could be achieved without compromising individual performance. Building on these findings, Study 7 serves as the capstone assessment, designed to generalize the platform by testing oral and non-oral combinations under simultaneous and sequential dosing intervals. Success criteria required preservation of compatibility as measured by the absence of phase inversion, no more than 25 percent drift in particle size distribution, and maintenance of zeta-potential stability. Together, this sequence of studies demonstrates not only that polarity-matched carriers improve performance in their primary routes, but also that the integrated platform maintains stability and functional synergy when expanded to multi-route administration.

Study #8-Effects of Oral Sterol Derivative (E.G., 4-Dhea Enanthate) Supplementation)

This study evaluates the effects of a sterol derivative (e.g., 4-DHEA enanthate in certain embodiments) compared to placebo and various reference supplements, including non-esterified omega-3 fatty acids, vitamin D, magnesium glycinate, vitamin B3, and HMB free acid, using multiple delivery technologies (phytosomes, cyclodextrin complexes, micronization, and NEFA carriers) in a randomized controlled design involving 32 male participants over six months. Outcomes of interest included markers of physical performance, lean muscle mass, strength, endurance, and self-reported sexual function.

Sterol derivatives such as 4-DHEA enanthate are precursors that, in certain embodiments, may influence anabolic pathways and functional outcomes. This trial was designed to evaluate the comparative effects of such derivatives versus placebo and other nutritional agents, and to explore potential synergistic interactions when co-delivered with polarity-specific carrier systems.

The study employed a randomized, double-blind, placebo-controlled design. Thirty-two male volunteers aged 30-60 years were enrolled after screening for eligibility, excluding any underlying health issues or prior use of anabolic steroids or related supplements. Randomization assigned participants to one of seven groups: sterol derivative (e.g., 4-DHEA enanthate), omega-3 fatty acids, vitamin D, magnesium glycinate, vitamin B3, HMB, or placebo. The intervention protocol lasted six months, with evaluations at baseline, three months, and six months. Dosages were administered as specified in protocol guidelines. Bi-weekly monitoring ensured compliance and documented any side effects, with adverse events recorded and evaluated.

All participants underwent pre-screening to confirm eligibility and safety. Medical histories were reviewed with particular attention to cardiovascular, hepatic, and renal conditions that could interfere with supplementation. Because sterol derivatives may influence endocrine pathways, prostate health and hormone-sensitive conditions were closely evaluated; participants with prostate abnormalities or hormone-sensitive disorders were excluded. Baseline blood testing included vitamin D, magnesium, niacin, liver and kidney function panels, and endocrine markers (testosterone, DHEA). Cardiovascular health was assessed by blood pressure and heart rate monitoring. Body composition, including lean muscle mass and body fat percentage, was measured, as HMB and sterol derivatives were expected to influence muscle development. Eligible participants had BMI values between 18 and 29.9 kg/m$^2$. Lifestyle factors (diet, exercise, alcohol consumption, smoking) were reviewed to control for confounding effects. Individuals with heavy alcohol use, smoking, drug use, or prescription medications that could interfere were excluded.

Prostate health was further evaluated through PSA testing to confirm absence of underlying issues. Individuals with chronic illnesses or on medications with known interactions were excluded to ensure that observed changes could be attributed to supplementation. This rigorous screening ensured participant safety and study validity.

Adverse-event monitoring was prioritized. Participants were instructed to report any health changes, even minor symptoms (e.g., dizziness or stomach upset), during scheduled check-ins or questionnaires. In addition, the research team performed routine health monitoring, including blood sampling and heart rate measurement, to detect subclinical changes. Data were compared with baseline values to identify any concerning trends. If serious adverse events had arisen, the study protocol allowed for adjustment or discontinuation. This monitoring ensured that participant well-being remained the highest priority.

Muscle Mass Outcomes: Lean body mass was assessed using dual-energy X-ray absorptiometry (DXA) at baseline, three months, and six months. Expected outcomes included changes in lean mass (kg) and percentage change from baseline.

Strength Outcomes: One-repetition maximum (1-RM) for bench press and squat was measured using standardized warm-up and progressive testing protocols at the same time points. Outcomes included changes in 1-RM values (kg) and percent change from baseline.

Endurance Outcomes: Endurance was tested using a $VO_2$ max protocol with graded treadmill or cycle ergometer exercise, measured by metabolic cart at baseline, three months, and six months. Expected outcomes were changes in $VO_2$ max (mL/kg/min) and percent change from baseline.

Sexual Function Outcomes: Self-reported function was assessed with the International Index of Erectile Function (IIEF) questionnaire, with scores calculated for erectile function at baseline, three months, and six months. Expected outcomes were changes in IIEF scores and percent change from baseline.

Statistical Analysis: Data were analyzed using ANOVA or t-tests, with $p<0.05$ considered statistically significant. Results were expressed as mean±standard deviation (SD), and percent changes from baseline were calculated for efficacy comparisons.

Multiple drug delivery systems were applied for targeted release (micronization, phytosome, cyclodextrin, and non-esterified fatty acid [NEFA] carriers) to enhance bioavailability, stability, and polarity-matched uptake of nutritional actives across functional endpoints, including markers of physical performance, lean muscle mass, strength, endurance, and self-reported function.

Micronization: Each ingredient-sterol derivative (e.g., 4-DHEA enanthate in certain embodiments), non-esterified omega-3 fatty acids, vitamin D, magnesium glycinate (chelated form), vitamin B3, and HMB free acid—was processed individually to achieve particle sizes in the 1-10 μm range. Pharmaceutical-grade materials were weighed, loaded into ball mills (1-2 hours) or jet mills, and reduced under controlled conditions. Post-micronization, powders were sieved, analyzed for uniformity, and stored in airtight containers. Quality control included particle-size distribution, purity, potency, and stability assays. When formulating final products, micronized actives were blended with excipients under standard cGMP protocols to preserve integrity and reproducibility.

Phytosome system: Each active was combined separately with phospholipids (e.g., phosphatidylcholine) in ethanol or methanol, subjected to ultrasonication, and dried under reduced pressure. The resulting phytosome complexes were rehydrated into dispersions and characterized by particle size, zeta potential, and encapsulation efficiency. This method improved polarity-specific uptake: sterol derivatives achieved enhanced systemic availability; omega-3 fatty acids showed greater solubility; vitamin D gained improved light/moisture stability; magnesium glycinate demonstrated better GI absorption; vitamin B3 exhibited reduced flushing; and HMB free acid achieved greater bioavailability.

Cyclodextrin complexes: Active compounds were complexed individually with α-, β-, or γ-cyclodextrins in aqueous or ethanolic solutions, aided by heating or stirring. Complexes were dried by spray or freeze drying, yielding stable powders characterized for particle size, encapsulation efficiency, and release profile. Cyclodextrins improved solubility and stability of hydrophobic actives, preserving potency and enabling formulation into capsules, tablets, or liquid carriers.

Non-esterified omega-3 fatty acids were incorporated as both a comparator and an integrated component of the delivery system, benefiting from improved dispersion and compatibility with the multi-route framework.

Encapsulation of individual supplements:

1) Sterol derivative (e.g., 4-DHEA enanthate) was micronized and encapsulated in hard-gelatin capsules to protect from degradation and allow accurate dosing.
2) Non-esterified omega-3 fatty acids were encapsulated in softgels to preserve oxidative stability and enhance absorption.
3) Vitamin D was formulated with lipid carriers and encapsulated in light- and moisture-protective matrices.
4) Magnesium glycinate was encapsulated in vegetarian capsules to optimize absorption and reduce GI discomfort.
5) Vitamin B3 (niacin) was prepared in enteric-coated tablets to reduce flushing while preserving absorption.
6) HMB free acid was encapsulated in hard-gelatin capsules for dose precision and consistent delivery.
7) All encapsulated actives underwent uniformity, potency, and stability testing. This ensured consistent dosing and provided controlled clinical-trial administration for reproducible evaluation of delivery-system performance.

Phytosome advantage (sterol derivative focus): Phytosome complexes protected sterol derivatives (e.g., 4-DHEA enanthate) from degradation, enhanced absorption via phospholipid bilayers, and improved systemic exposure. This polarity-specific approach minimized first-pass metabolism, promoted controlled release, and extended stability profiles.

Combined multi-delivery method: In the trial's combination group, ingredients were co-processed under defined protocols. Micronization reduced particle sizes to 1-10 μm, followed by phytosome or cyclodextrin encapsulation depending on polarity. Powders were stored in nitrogen-flushed, airtight containers, tested for stability, and formulated into capsules or softgels under cGMP.Phytosome processing: Actives and phospholipids were dissolved in ethanol, ultrasonicated, dried, and rehydrated. Particle size analysis, zeta potential, and encapsulation efficiency ensured optimal performance. Distinct polarity-driven benefits were observed: sterol derivatives-enhanced systemic distribution; omega-3s-improved solubility; vitamin D-greater bioavailability; magnesium glycinate-better GI uptake; vitamin B3-improved tolerability; HMB-enhanced lean-mass support.

Cyclodextrin processing: Inclusion complexes were created by mixing actives with cyclodextrins, applying stirring and heat. Spray- or freeze-drying yielded powders that improved solubility, dispersion, and shelf stability. Resulting complexes showed enhanced systemic availability for sterol derivatives and improved tolerability for hydrophilic vitamins and amino-acid derivatives.

Summary: Collectively, micronization, phytosome complexation, cyclodextrin inclusion, and NEFA carriers enhanced solubility, polarity-matched absorption, and stability of the study actives. These delivery methods ensured controlled dosing, minimized degradation, and validated the inventive platform's ability to deliver diverse bioactives across multiple nutritional endpoints under trial conditions.

Encapsulation of Ingredients for a Combined Group

The encapsulated ingredients were blended with suitable excipients to create a uniform mixture. A capsule-filling machine or tablet press was then employed to encapsulate or compress the combined actives into standardized dosage forms such as capsules or tablets, ensuring consistency across intervention groups.

For testing and quality control, particle size distribution was measured using laser diffraction to confirm that the final products remained within the desired range. Encapsulation efficiency was determined using high-performance liquid chromatography, while in vitro release studies were conducted to evaluate the release dynamics of active ingredients. Stability testing was performed under varied temperature and humidity conditions to establish shelf life and assess degradation profiles. Microbiological assays were used to confirm the absence of harmful organisms, and all active ingredient concentrations were verified to meet specification standards. Detailed records of ingredient sources, formulation procedures, analytical methods, and results were maintained to ensure compliance with regulatory and quality requirements.

The clinical study was conducted as a randomized, double-blind, placebo-controlled trial over six months in thirty-two adult male participants between thirty and sixty years of age. Participants were randomly assigned to one of seven groups, with group sizes balanced between four and five subjects each. The allocation included a sterol derivative group receiving, in certain embodiments, 4-DHEA enanthate at a daily dosage of fifty milligrams, an omega-3 group receiving one thousand milligrams of non-esterified fatty acids per day, a vitamin D group receiving six hundred international units per day, a magnesium glycinate group receiving four hundred twenty milligrams per day, a vitamin B3 group receiving fifteen milligrams per day, an HMB free acid group receiving three grams per day, and a placebo group receiving a matching carrier formulation.

Sterol derivatives such as 4-DHEA enanthate have traditionally been studied in esterified injectable forms, but in this embodiment the compound was reformulated as an oral controlled-release capsule. The capsule contained one hundred milligrams weekly of the active sterol derivative, engineered with excipients designed to extend release and reduce fluctuations in systemic exposure. This approach supported steady uptake kinetics and consistent availability across the dosing interval, providing participants with a simplified weekly regimen that enhanced compliance compared with daily dosing schedules.

The sustained-release format was further paired with phytosome delivery technology to improve absorption and stability. By binding sterol derivatives with phospholipids, phytosome complexes shielded the compound from gastrointestinal degradation and improved its ability to pass through cell membranes. The combined use of controlled release and phytosome encapsulation extended systemic availability while reducing the impact of first-pass metabolism. In this way, the inventive platform demonstrated its ability to maintain consistent exposure kinetics without the need for daily administration, reinforcing its value as a polarity-specific delivery system.

The primary outcome measures included changes in muscle mass, muscle strength, endurance capacity, and self-reported functional attributes. Lean body mass was assessed using dual-energy X-ray absorptiometry at baseline, three months, and six months. Muscle strength was measured by one-repetition maximum testing for bench press and squat at identical time points. Endurance was evaluated using a $VO_2$ max protocol with graded treadmill or cycle ergometer exercise, while sexual function was assessed using the International Index of Erectile Function questionnaire administered at baseline, three months, and six months.

Testing methodology involved recording absolute values and percentage changes from baseline for each of the four outcome domains. Lean body mass changes were expressed in kilograms, one-repetition maximum testing reported changes in kilograms lifted, $VO_2$ max values were recorded in milliliters per kilogram per minute, and International Index of Erectile Function results were scored and compared over time. Data were analyzed at baseline, three months, and six months to determine both interim and final outcome trends.

Through this structured methodology, the study provided a comprehensive evaluation of the inventive delivery system's ability to maintain controlled release, improve systemic uptake, and support markers of physical performance, endurance, strength, and self-reported function across the six-month trial period.

TABLE 105

Baseline Characteristics per Control Group

| Characteristic | Combined Group (n = 32) | Sterol Derivative* (n = 5) | Omega-3 (n = 5) | Vitamin D (n = 5) | Magnesium Glycinate (n = 5) | Vitamin B3 (n = 5) | HMB (n = 5) | Placebo (n = 5) |
|---|---|---|---|---|---|---|---|---|
| Age (years) | 43.0 ± 8.0 | 42.5 ± 8.0 | 43.2 ± 7.8 | 42.8 ± 7.6 | 43.5 ± 8.1 | 41.5 ± 8.3 | 44.0 ± 7.9 | 43.5 ± 7.5 |
| Baseline Muscle Mass (kg) | 71.0 ± 8.0 | 71.5 ± 7.5 | 70.2 ± 8.0 | 70.8 ± 7.7 | 71.1 ± 7.9 | 70.3 ± 7.6 | 69.8 ± 8.1 | 70.0 ± 7.8 |
| Baseline IIEF Score | 17.8 ± 2.8 | 18.0 ± 2.5 | 17.6 ± 3.1 | 17.9 ± 2.9 | 17.5 ± 2.7 | 17.6 ± 3.0 | 17.4 ± 3.2 | 17.8 ± 3.1 |

*Sterol derivative group included, in certain embodiments, 4-DHEA enanthate.

Table 105 shows the baseline characteristics of participants across combined, individual supplement, and placebo groups, including age, muscle mass, and IIEF scores.

TABLE 106

Changes in Outcome Measures After Intervention

| Outcome Measure | Combined Group (n = 32) | Sterol Derivative* (n = 5) | Omega-3 (n = 5) | Vitamin D (n = 5) | Magnesium Glycinate (n = 5) | Vitamin B3 (n = 5) | HMB (n = 5) | Placebo (n = 5) |
|---|---|---|---|---|---|---|---|---|
| Muscle Mass Change (kg) | 3 m: +6.0 ± 1.0 ($p < 0.01$) | +3.0 ± 0.5 | +1.5 ± 0.4 | +1.8 ± 0.5 | +1.5 ± 0.4 | +1.0 ± 0.3 | +0.8 ± + 0.3 | +0.4 ± 0.2 |
| | 6 m: +12.0 ± 1.5 ($p < 0.01$) | +5.0 ± 0.6 | +2.8 ± 0.5 | +3.5 ± 0.6 | +2.5 ± 0.5 | +1.8 ± 0.4 | +1.5 ± 0.5 | +0.6 ± 0.3 |
| % Change | 3 m: +8.5% | +4.5% | +2.1% | +2.6% | +2.0% | +1.5% | +1.1% | +0.6% |
| | 6 m: +17.0% | +7.0% | +4.0% | +5.0% | +3.5% | +2.6% | +2.0% | +0.8% |
| Strength (1-RM, kg) | 3 m: +15.0 ± 2.0 ($p < 0.01$) | +6.0 ± 1.0 | +3.5 ± 0.8 | +3.0 ± 1.0 | +2.5 ± 1.0 | +2.0 ± 0.5 | +1.5 ± 0.5 | +0.6 ± 0.4 |
| | 6 m: +25.0 ± 3.0 ($p < 0.01$) | +10.0 ± 1.0 | +5.0 ± 1.0 | +4.5 ± 1.0 | +3.0 ± 1.5 | +3.0 ± 0.5 | +2.0 ± 0.6 | +1.0 ± 0.5 |
| % Change | 3 m: +20.0% | +8.5% | +4.5% | +3.5% | +3.5% | +3.0% | +2.5% | +0.8% |
| | 6 m: +40.0% | +15.0% | +6.0% | +5.5% | +4.0% | +4.5% | +3.0% | +1.5% |
| Endurance ($VO_2$ max) | 3 m: +25.0 ± 3.0 ($p < 0.01$) | +8.0 ± 2.0 | +5.0 ± 1.5 | +4.0 ± 1.0 | +4.5 ± 1.5 | +3.0 ± 1.0 | +3.0 ± 1.2 | +1.0 ± 0.5 |
| | 6 m: +35.0 ± 3.5 ($p < 0.01$) | +12.0 ± 2.0 | +8.0 ± 1.5 | +6.0 ± 1.5 | +6.0 ± 2.0 | +5.0 ± 1.5 | +4.0 ± 2.0 | +1.5 ± 0.5 |
| % | 3 m: +30.0% | +10.0% | +7.0% | +5.5% | +6.0% | +5.5% | +4.5% | +2.0% |

TABLE 106-continued

Changes in Outcome Measures After Intervention

| Outcome Measure | Combined Group (n = 32) | Sterol Derivative* (n = 5) | Omega-3 (n = 5) | Vitamin D (n = 5) | Magnesium Glycinate (n = 5) | Vitamin B3 (n = 5) | HMB (n = 5) | Placebo (n = 5) |
|---|---|---|---|---|---|---|---|---|
| Change | 6 m: +45.0% | +15.0% | +10.00% | +8.0% | +8.0% | +7.0% | +6.0% | +3.0% |
| IIEF Score Change | 3 m: +10.0 ± 1.0 ($p < 0.01$) | +3.0 ± 0.5 | +2.0 ± 0.5 | +2.5 ± 0.6 | +1.5 ± 0.4 | +1.5 ± 0.5 | +1.0 ± 0.4 | +0.5 ± 0.2 |
| | 6 m: +15.0 ± 1.5 ($p < 0.01$) | +5.0 ± 0.5 | +3.0 ± 0.5 | +3.5 ± 0.6 | +2.0 ± 0.5 | +2.0 ± 0.5 | +1.5 ± 0.6 | +0.8 ± 0.3 |

*Sterol derivative group included, in certain embodiments, 4-DHEA enanthate.

Table 106 summarizes the changes in outcome measures after intervention, including muscle mass, strength, endurance ($VO_2$ max), and IIEF scores across all groups at three and six months.

A line chart displaying percentage changes in outcome measures across different groups at three and six months was prepared, with error bars representing standard errors. Dashed lines correspond to six-month outcomes, while solid lines represent three-month outcomes.

FIGS. 122A, 122B, 122C, and 122D illustrate the percentage changes in outcome measures across groups, showing deviations and progression from baseline.

Key Findings: Combination Group Vs. Other Groups

The combination group included participants receiving sterol derivatives together with non-esterified omega-3 fatty acids, vitamin D, magnesium glycinate, vitamin B3, and HMB free acid. This group was compared to those taking sterol derivatives alone, individual supplements, and placebo.

The combination group showed a marked increase in lean muscle mass, gaining approximately four kilograms at three months and eight kilograms at six months. By comparison, participants in the sterol derivative group gained three kilograms at three months and five kilograms at six months, while individual supplements provided smaller gains, with vitamin D producing the highest increase of 2.8 kilograms at six months. Placebo participants showed only minor increases of about 0.6 kilograms.

In measures of strength, the combination group demonstrated increases of eight kilograms in one-repetition maximum at three months and twelve kilograms at six months. Participants in the sterol derivative group gained six kilograms at three months and ten kilograms at six months, while omega-3 supplementation produced the highest improvement among single supplements at four kilograms at six months. Placebo participants improved by only one kilogram.

Endurance, measured by $VO_2$ max, also improved most strongly in the combination group, which gained ten milliliters per kilogram per minute at three months and fifteen milliliters per kilogram per minute at six months. The sterol derivative group gained eight and twelve milliliters per kilogram per minute over the same intervals, while vitamin D supplementation yielded six milliliters per kilogram per minute at six months. Placebo participants gained only 1.5 milliliters per kilogram per minute.

For self-reported function, assessed through IIEF scores, the combination group improved by four points at three months and six points at six months. The sterol derivative group gained three and five points over the same intervals, while omega-3 supplementation yielded the highest increase among individual agents at 2.5 points at six months. The placebo group improved by less than one point.

In summary, the combination group demonstrated superior outcomes across all measured domains, including lean mass, strength, endurance, and functional self-reports, when compared with both individual supplement groups and placebo. These findings suggest that the integrated, polarity-specific multi-delivery system provides additive benefits when multiple nutritional actives are delivered in concert, supporting the inventive platform's claims of synergistic performance and wellness support.

Manufacturing Examples—Overview

Modular Example Framework:

The present disclosure provides seven detailed manufacturing examples that collectively demonstrate the full scope of the claimed invention. Each example is drafted in modular form, incorporating base carrier preparation, route-specific modulation, functional enhancement, stability validation, and continuation testing.

Embodiment Coverage

Comprehensive Embodiment Demonstration: All seventeen inventive embodiments are either directly demonstrated or derivable via modular conversion across Examples 1 through 7.

Route-Specific Coverage

Oral, topical, transdermal, microneedle, and hybrid delivery routes are fully disclosed, including polarity-specific payload separation, dual-compartment microneedle integration, controlled-release systems, antioxidant protection, individualized formulations, and stability-preserving carriers.

Steroidal Active Coverage

Each sterol derivative embodiment is exemplified (including, in certain embodiments, 5-DHEA enanthate, 1-DHEA enanthate, 4-DHEA enanthate, epiandrosterone undecanoate, androst-5-ene triol enanthate, and 7-keto DHEA), ensuring comprehensive coverage of steroidal actives within the claimed invention.

Dosage Compliance and Bioavailability Justification

Regulatory and Physiologic Limits:

All examples are designed to remain within physiologic and regulatory-compliant limits while emphasizing the principle of low-dosage, high-bioavailability delivery.

Oral Fill Weight Control:

Oral formulations are capped at 700 mg total fill weight including excipients, ensuring consumer compliance and reduced systemic burden.

Nutritional Micronutrient Standards:

Vitamins and minerals are provided at safe and internationally recognized daily intake levels, including vitamin D standardized at 800 IU, chelated zinc at 8 mg, and chelated magnesium not exceeding 200 mg.

Controlled B-Complex Integration:

B-complex vitamins are incorporated only at supportive nutritional levels rather than pharmacologic excess.

Delivery Innovation-Absorption and Systemic Utilization

Low-Dose, High-Bioavailability Innovation: The innovation lies not in administering high loads of active compounds, but in enhancing absorption and systemic utilization through advanced carriers such as self-emulsifying delivery systems (SEDS), ethosomal vesicles, dual-compartment microneedles, and lipid-polymer hybrid emulsions.

Carrier-Based Functional Enhancement

These technologies improve permeability, dissolution, and polarity-matched uptake, allowing active compounds to achieve measurable bioavailability at reduced intake levels.

Example Synergistic Formulations:

For example, HMB, L-arginine, resveratrol, omega-3 fatty acids, and adaptogenic extracts are formulated in synergistic lipid-hydrophilic systems that maximize stability and transport across intestinal, dermal, or microneedle-mediated pathways.

Strategic Outcomes and Inventive Step

Physiologic Relevance of Dosage:

This strategy ensures that the invention delivers targeted nutritional support outcomes using physiologically relevant doses rather than conventional high-dose regimens. Novelty Through Carrier Optimization: By demonstrating that lower intake yields equivalent or superior functional results when paired with optimized carriers, the disclosure not only meets safety and compliance thresholds but also establishes a novel inventive step in delivery science.

Manufacturing and Quality Standards

GMP and ISO Compliance: All examples are manufactured under GMP Part 211 and ISO 14644-1 cleanroom classifications, with route-specific adaptations.

Oxidative Stability Controls:

Nitrogen purging is employed during lipid handling to prevent oxidative degradation.

Quality Control Checkpoints:

Quality control checkpoints are aligned with USP <905>, <61>, <62>, and <2040>.

Stability and Continuation Testing:

Stability studies follow ICH Q1A (R2) accelerated and real-time protocols with photostability per ICH Q1B. Continuation testing includes 6-, 12-, and 24-month evaluations of potency, physical integrity, and release kinetics, with retained sample re-verification.

Full-Scale Manufacturing Demonstration

Industrial-Scale Production: Each example is provided with explicit weights and measures scaled to 10,000-unit production runs across oral capsules, microneedle patches, and topical cream dispensers.

Packaging and Compliance Requirements:

Packaging instructions include nitrogen-flushed blister packs, foil pouches, and airless dispensers, each meeting tamper-evident, child-resistant (16 CFR 1700), and photo-protective requirements.

CONCLUSION

Integrated Enablement: Taken together, Examples 1-7 provide a complete, modular disclosure that demonstrates the invention's adaptability across all intended routes, compliance with international quality and safety standards, and alignment with recognized daily intake guidelines.

Reproducibility and Industrial Viability: This integrated strategy ensures that all embodiments are not only disclosed but also industrially reproducible, providing full enablement of the invention

Example 1-Modular Manufacturing Process for Antioxidant-Enriched Oral Seds Softgel with Multi-Route Conversion Capability Modular Phase 1-Algorithmic Formulation Selection and Base Active Carrier Production.

Manufacturing for the oral embodiment is performed in an ISO Class 8 cleanroom under 21 CFR Part 111 dietary supplement cGMP, with process controls aligned to ICH Q8 (R2)/Q1A (R2). Carrier selection follows the polarity-mapping rule anchored in Study 1A, assigning lipophilic actives to lipidic SEDS carriers and hydrophilic actives to cyclodextrin inclusion or solid-dispersion modules. Medium-chain triglycerides and oleic acid are gently heated to 40-45° C. under continuous nitrogen purge to limit oxidation. Sterol derivatives (including, in certain embodiments, esterified derivatives of DHEA such as 5-DHEA enanthate) are incorporated into the lipid phase with controlled agitation until dissolution. Antioxidant protection is established by mixed tocopherols (~0.2% w/w, ~1.4 mg per 700 mg fill) and ascorbyl palmitate (~0.1% w/w, ~0.7 mg per 700 mg fill), with distribution verified by HPLC. Polysorbate 80 and propylene glycol are introduced under low shear to form a self-emulsifying preconcentrate, which is characterized to confirm spontaneous micro-emulsification to a target droplet size of approximately 100-150 nm upon aqueous dispersion (DLS).

Modular Phase 2-Route-Specific Modulation.

The oral SEDS is encapsulated via rotary-die gelatin softgels in an ISO Class 7 environment with nitrogen-purged filling. Non-ingestible conversions are separate embodiments outside DSHEA: (a) topical nanoemulgel prepared by dispersing the SEDS preconcentrate into an aqueous carbomer base and adjusting to pH approximately 5.5, with mean droplet size verified at ≤200 nm and PDI≤0.3 by DLS per Study 4A, and (b) transdermal ethosomes prepared by replacing a portion of lipid with approximately 30% ethanol and phosphatidylcholine to form vesicles (150-200 nm, DLS-verified) suitable for polarity-appropriate dermal delivery, subsequently loaded to patch reservoirs. Conversions retain core active(s) while adjusting excipients per intended route; claims and labeling remain route-specific.

Modular Phase 3-Functional Enhancement Layer.

Cyclodextrin inclusion complexes are incorporated for hydrophilic actives in oral embodiments without altering the lipid SEDS phase, with host: guest ratios confirmed at 1:1-1:3 and dissolution uplift of approximately 1.8-2.1× versus neat (Study 1A, Tables 21A-21B). Transdermal and topical formats may employ route-scoped enhancers (for example, Transcutol or select monoterpenes) and photostabilizers (for example, rosemary extract). Lipid-polymer hybrid vesicles can be prepared for controlled release in transdermal applications. Enhancements are optional modules and remain route-appropriate.

Modular Phase 4 Stability Testing and Route Compatibility.

Stability is validated under ICH Q1A (R2) and ICH Q1B (photostability) for each embodiment tested separately: oral softgel (Part 111 context), topical nanoemulgel (cosmetic MoCRA context), and transdermal ethosome patch (device or combination-product context). Oxidation resistance is assessed at 21% 02 and 40° C. for four weeks. Dual-route compatibility is confirmed under the Study 7 Dual-Route Compatibility Index with composite criteria including inversion resistance, droplet-size drift≤25% (DLS), and absolute zeta-potential change |44|≤5 mV. Results confirm that each embodiment maintains intended quality attributes and compatibility metrics under its own storage conditions.

Modular Phase 5-Quality Control & Regulatory Alignment.

For the oral supplement, quality controls include temperature limits (<45° C.), nitrogen purge monitoring, pre-/post-dispersion droplet size verification, content uniformity per USP <905>, potency by HPLC (±5%), microbial limits per USP <61>/<62>, and USP <2040> disintegration. Processes align with 21 CFR Part 111 and relevant USP/ICH references. Non-ingestible embodiments follow their respective frameworks (e.g., cosmetic MoCRA expectations for topical gels; device QSR/QMSR expectations if patches are regulated as devices/combination products).

Modular Phase 6—Ongoing Stability (by Embodiment).

Continuation testing is performed at 6, 12, and 24 months on retained lots per embodiment. For oral softgels: potency, droplet size upon dispersion, oxidation markers, capsule integrity/leakage, and microbiology. For topical gel and transdermal patch: potency, physical stability (rheology/vesicle morphology or vesicle metrics), and microbiology. Data are archived for inspection and annual reviews.

Modular Phase 7-Packaging and Storage

Softgels are packaged in nitrogen-flushed, tamper-evident blister packs using high-barrier PVC/PVDC film with integrated silica-gel desiccant. Packaging incorporates dual-latch and controlled-peel features with mechanical stress testing to enforce seal integrity. KPI validation includes seal-retention force, peel-uniformity profile, and child-resistant compliance under 16 CFR 1700. Cartons are photoprotective and labeled with lot number, manufacturing date, and expiry date. Storage conditions are maintained at 15-25° C. in a controlled-humidity warehouse per GDP requirements.

Full-Scale Manufacturing Weights & Measures

TABLE 107

Oral SEDS Softgel Composition (10,000 Units)

| Component | Per Softgel (mg) | Batch Total (10,000 softgels, g) |
|---|---|---|
| Sterol derivative (including, in certain embodiments, 5-DHEA enanthate) | 50 | 500 |
| Medium-chain triglycerides (MCT oil) | 350 | 3,500 |
| Oleic acid | 50 | 500 |
| Polysorbate 80 | 120 | 1,200 |
| Propylene glycol | 100 | 1,000 |
| Mixed tocopherols | 1.4 | 14 |
| Ascorbyl palmitate | 0.7 | 7 |
| Total Fill Weight | 700 mg | ≈10.7 kg |

Table107 details the oral SEDS softgel formulation, where sterol derivatives are solubilized in a lipidic carrier system of MCT oil and oleic acid, stabilized with polysorbate 80 and propylene glycol. Antioxidant protection is provided by mixed tocopherols at ~0.2% w/w (~1.4 mg per 700 mg fill; 14 g per 10,000 units) and ascorbyl palmitate at ~0.1% w/w (~0.7 mg per 700 mg fill; 7 g per 10,000 units). These levels correspond to the distribution specified in [1145] and are confirmed by HPLC assay. Each softgel delivers a 700 mg fill weight, with a total batch production of ~10.7 kg across 10,000 units.

TABLE 108

Converted topical nanoemulgel dispenser composition (10,000 units × 50 g each; Study 4A metrics)

| Component | Per Dispenser (50 g) | Batch Total (10,000 dispensers, g) |
|---|---|---|
| Sterol derivative (including, in certain embodiments, 5-DHEA enanthate) | 50 mg | 500 |
| Medium-chain triglycerides (MCT oil) | 3 g | 30,000 |
| Oleic acid | 0.5 g | 5,000 |
| Polysorbate 80 | 1 g | 10,000 |
| Propylene glycol | 2 g | 20,000 |
| Carbomer | 0.25 g | 2,500 |
| Purified water | 42.8 g | 428,000 |
| Triethanolamine (pH adjust) | 0.2 g | 2,000 |
| Mixed tocopherols | 0.0028% w/w (~1.4 mg) | ~14 |
| Ascorbyl palmitate | 0.0014% w/w (~0.7 mg) | ~7 |
| Total Fill Weight | 50 g | ≈498.0 kg |

Table 108 presents the converted topical nanoemulgel formulation. Sterol derivatives are solubilized in an oil phase and stabilized with emulsifiers and antioxidants. Carbomer neutralized with triethanolamine provides rheological structure suitable for pump dispensing. Per Study 4A, the nanoemulgel maintains mean droplet size≤200 nm with PDI≤0.3 and exhibits stable viscosity and thixotropy under accelerated storage. Each dispenser delivers 50 g of product, with a total batch weight of approximately 498.0 kg across 10,000 units.

TABLE 109

Converted Transdermal Ethosome Patch Composition (10,000 Units)

| Component | Per Patch (mg) | Batch Total (10,000 patches, g) |
|---|---|---|
| Sterol derivative (including, in certain embodiments, 5-DHEA enanthate) | 50 | 500 |
| Medium-chain triglycerides (MCT oil) | 50 | 500 |
| Oleic acid | 10 | 100 |
| Phosphatidylcholine | 30 | 300 |
| Ethanol | 150 | 1,500 |
| Purified water | 400 | 4,000 |
| Patch backing polymer (polyurethane) | 40 | 400 |
| Adhesive (medical-grade acrylic) | 20 | 200 |
| Mixed tocopherols | 1.4 | 14 |
| Ascorbyl palmitate | 0.7 | 7 |
| Total Patch Weight | 752.1 mg | ≈7.5 kg |

Table 109 presents the converted transdermal ethosome patch formulation, where sterol derivatives are incorporated into a lipid-ethanol vesicle system with antioxidants, a polyurethane backing, and acrylic adhesive. The design supports stability, polarity-matched delivery, and patch integrity.

All embodiments were produced in ISO-classified cleanrooms. The oral SEDS softgel followed 21 CFR Part 111 dietary supplement cGMP; the topical nanoemulsion gel followed cosmetic MoCRA expectations; and the ethosome patch followed device/combination-product expectations as applicable. Nitrogen purging minimized oxidation. For SEDS and nanoemulsion formats, post-dispersion droplet size was controlled to ~100-150 nm and <200 nm, respectively, with DLS confirmation. Packaging met 16 CFR 1700 child-resistant requirements with tamper-evident features and photoprotective cartons. Storage: 15-25° C., <60% RH, protected from light.

Transdermal Ethosome Patch Production.

In an ISO Class 7 suite, sterol derivatives are dissolved in ethanol with phosphatidylcholine; MCT and oleic acid are added to form an ethosomal dispersion with typical vesicle size 150-200 nm. Purified water is added gradually to complete vesicle formation. The dispersion is cast onto a polyurethane backing, laminated with a medical-grade acrylic adhesive, and dried under controlled conditions to remove residual solvent while preserving vesicle integrity. Antioxidants are included to support potency over shelf life. Patches (approximately 752 mg each) are pouched in nitrogen-flushed foil laminate and tested for potency (±5%), adhesion, vesicle metrics, and USP <61>/<62> microbiology. Per Study 7, route-compatibility KPIs are verified, including vesicle-size drift ≤25% and absolute zeta-potential change $|\Delta\zeta| \leq 5$ mV. Stability follows ICH Q1A (R2) accelerated and long-term protocols.

Example 2-Modular Manufacturing Process for Hybrid Microneedle Dual-Compartment Patch with Enhanced Multi-Route Adaptability Modular Phase 1-Base Microneedle Matrix Fabrication.

Manufacturing is conducted in an ISO Class 7 cleanroom under device QSR/QMSR (21 CFR 820/ISO 13485) and ISO 14644-1 particulate standards. A hydrogel polymer matrix is prepared by hydrating polyvinylpyrrolidone (PVP, 25% w/w) and hydroxypropyl methylcellulose (HPMC, 5% w/w) in deionized water at 50° C. with overhead stirring until fully dissolved, then cooled to 25° C. to reach 2,500-3,000 cP. In parallel, the lipophilic payload compartment is prepared by dissolving sterol derivatives (including, in certain embodiments, esterified derivatives of DHEA such as 1-DHEA enanthate; 50 mg per unit) in an ethanol-water (30:70 v/v) mixture containing 3% phosphatidylcholine, forming ethosomes targeted to 150-200 nm. The hydrogel base is deaerated under vacuum (−0.8 bar). Sequential two-phase casting (Study 3) is applied: the hydrophilic matrix is cast first into microneedle molds and partially dried, followed by casting of the lipophilic ethosome dispersion as the reservoir layer. Casting parameters are controlled for solids loading, dwell time, and drying temperature (Panels 1~4 SOP storyboard).

Modular Phase 2-Dual-Compartment Integration.

The hydrophilic compartment incorporates HMB free acid (300 mg) and magnesium bisglycinate (20 mg), dispersed uniformly within the hydrogel backbone. The lipophilic reservoir compartment contains the ethosome dispersion with oleic acid (1% w/w) serving as a polarity-matched uptake aid. The assembled reservoir membrane is laminated onto the microneedle backing under controlled heat sealing at ≤50° C. This structure provides immediate dermal interface via microneedle tips and supports controlled exposure kinetics from the lipid reservoir.

Modular Phase 3-Functional Enhancement Layer.

Delivery performance is tuned by adding monoterpenes (0.5-1% w/w) to the lipid compartment and propylene glycol (5% w/w) to the hydrogel compartment. Cyclodextrin inclusion complexes are incorporated for oxidation-sensitive hydrophilic actives, with host: guest ratios confirmed at 1:1-1:3 and dissolution uplift of ~1.8-2.1× versus neat (Study 1A, Tables 21A-21B). Release profiles are further fine-tuned by adjusting hyaluronic acid molecular weight or modifying the phosphatidylcholine-to-ethanol ratio in the ethosomes.

Modular Phase 4-Stability Testing and Route Compatibility.

Stability follows ICH Q1A (R2) and ICH Q1B (photostability) for the microneedle patch embodiment (device context). Patch integrity is confirmed via laser profilometry for tip geometry and compression-force testing for insertion performance. Dual-route compatibility is validated under the Study 7 Dual-Route Compatibility Index, with composite criteria including inversion resistance, vesicle-size drift ≤25% (DLS), and absolute zeta-potential change $|\Delta\zeta| \leq 5$ mV. Cross-route adaptability is verified conceptually: (a) oral SEDS softgels are suitable for lipophilic sterol derivatives, and (b) oral HMB is formulated not as a nanoemulsion but as a solid dispersion or cyclodextrin inclusion complex per Table 2. Each route is tested under its own specifications; results are reported separately by embodiment.

Modular Phase 5-Quality Control Parameters and Regulatory Alignment.

Critical process parameters include polymer-hydration viscosity control, mold fill volume accuracy (±2%), vesicle size verification at 150-200 nm (DLS), and residual moisture ≤5% (USP <921>). Assay/content uniformity by HPLC is maintained within +5% of target. Microbial quality complies with USP <61>/<62>. Procedures align with 21 CFR 820/ISO 13485 for the patch; if an oral embodiment is produced, it follows 21 CFR Part 111 (dietary supplements).

Modular Phase 6-Continuation Testing and Shelf-Life Confirmation.

Ongoing stability monitoring is conducted at 6, 12, and 24 months, measuring potency retention (≥90%), vesicle-size variation (<10%), microneedle-tip integrity, and adhesive strength for consistent skin contact. Expanded tolerability assessments (Study 8) include dermal irritation scoring, erythema/edema grading, and subject-reported adhesion comfort.

Modular Phase 7-Packaging and Storage.

Finished patches are individually nitrogen-flushed and sealed in aluminum foil-laminate pouches with a moisture vapor transmission rate (MVTR)<0.1 g/m$^2$/day. Each pouch contains a desiccant. Packaging incorporates dual-latch and controlled-peel features with QC KPI validation, including seal-retention force and peel-uniformity testing. Storage conditions are 15-25° C., protected from light, with cartons that are tamper-evident, photoprotective, and compliant with child-resistant standards (16 CFR 1700). Each package is labeled with lot number, manufacturing date, and expiry date.

Full-Scale Manufacturing Weights & Measures

TABLE 110

Microneedle Patch Composition (10,000 Units)

| Component | Per Patch (mg) | Batch Total (10,000 patches, g) |
|---|---|---|
| Sterol derivative (including, in certain embodiments, 1-DHEA enanthate) | 50 | 500 |
| HMB free acid | 300 | 3,000 |
| Magnesium bisglycinate | 20 | 200 |
| Polyvinylpyrrolidone (PVP) | 250 | 2,500 |
| Hydroxypropyl methylcellulose (HPMC) | 50 | 500 |
| Phosphatidylcholine | 20 | 200 |
| Ethanol (in ethosomes) | 150 | 1,500 |
| Oleic acid | 10 | 100 |
| Total Fill Weight | 850 mg | ≈8.5 kg |

Table 110 outlines the dual-compartment microneedle patch composition, combining lipophilic and hydrophilic nutritional actives within a polymeric matrix. Sterol derivatives (e.g., 1-DHEA enanthate in certain embodiments) are delivered via an ethosomal lipid phase stabilized with phosphatidylcholine, ethanol, and oleic acid, while HMB free acid and magnesium bisglycinate are incorporated into a PVP/HPMC hydrogel backbone. This balanced design supports polarity-specific loading, structural integrity, and controlled dermal release across 10,000 units, with a total batch weight of ~8.5 kg.

Manufacturing Narrative—Table 61. Microneedle Patch Composition (10,000 Units). Production of the dual-compartment microneedle patch is carried out in an ISO Class 7 cleanroom under 21 CFR 820/ISO 13485 and ISO 14644-1. A hydrogel base is prepared by dissolving PVP and HPMC in purified water at 50° C., then vacuum-deaerated. The hydrophilic compartment is loaded with HMB free acid and magnesium bisglycinate, dispersed uniformly within the hydrogel matrix. In parallel, the lipophilic compartment is prepared by dissolving sterol derivatives (e.g., 1-DHEA enanthate in certain embodiments) in ethanol with phosphatidylcholine and oleic acid to generate ethosomal vesicles (150-200 nm). Sequential two-phase casting (Study 3) is applied: the hydrophilic hydrogel is first cast and partially dried, followed by casting of the lipophilic ethosomal reservoir. Parameters for solids loading, dwell time, and drying temperature are maintained per SOP storyboard Panels 1-4. The assembled patches are laminated to a flexible backing, dried to residual moisture <5% to preserve tip integrity and release kinetics, and pouched under nitrogen.

TABLE 111

Oral Capsule (Hard Capsule) Composition (10,000 Units).

| Component | Per Capsule (mg) | Batch Total (10,000 capsules, g) |
|---|---|---|
| Subfill A-Sterol SEDS preconcentrate | | |
| Sterol derivative (including, in certain embodiments, 1-DHEA enanthate) | 50 | 500 |
| Medium-chain triglycerides (MCT oil) | 200 | 2,000 |
| Polysorbate 80 | 100 | 1,000 |
| Mixed tocopherols | 1.4 | 14 |
| Ascorbyl palmitate | 0.7 | 7 |
| Subfill B-HMB solid dispersion/CD complex | | |
| HMB free acid (as solid dispersion or HMB-cyclodextrin inclusion complex) | 300 | 3,000 |
| Magnesium bisglycinate | 20 | 200 |
| Carrier polymer for ASD (e.g., PVP/VA or HPMC/HPMCAS) or additional CD as applicable | 120 | 1,200 |
| Microcrystalline cellulose (q.s. for fill/flow) | ~180 | ~1,800 |
| Total Fill Weight | ~672 mg | ≈6.7 kg |

Table 111. Oral Capsule Conversion (10,000 Units). Manufacture is performed in ISO Class 8 under 21 CFR Part 111. Subfill A (Sterol SEDS): sterol derivatives are solubilized in MCT with polysorbate 80; antioxidants are blended to limit oxidation. Subfill B (HMB oral): HMB is produced as an amorphous solid dispersion (spray-dried or hot-melt) or as an HMB-cyclodextrin inclusion complex, with host: guest ratios confirmed at 1:1-1:3 and dissolution uplift of ~1.8-2.1× versus neat (Study 1A, Tables 21A-21B). Magnesium bisglycinate is blended as a co-nutrient; polymer or cyclodextrin level is set per assay/flow; MCC q.s. supports fill and capsule integrity. Subfills are co-filled into hard gelatin or HPMC capsules as a multi-particulate fill (liquid SEDS +granules). Content uniformity (HPLC) is within +5%; microbial quality complies with USP <61>/<62>.

C. Topical Cream Conversion (10,000 Dispensers ×50 G Each)

TABLE 112

Topical Dispenser Composition (10,000 Units × 50 g each)

| Component | Per Dispenser (g/mg) | Batch Total (10,000 dispensers, g) |
|---|---|---|
| Sterol derivative (including, in certain embodiments, 1-DHEA enanthate) | 50 mg | 500 |
| HMB free acid | 300 mg | 3,000 |
| Magnesium bisglycinate | 20 mg | 200 |
| Oil phase (MCT oil + oleic acid) | 10 g | 100,000 |
| Water phase (purified water + glycerol) | 38 g | 380,000 |
| Emulsifier (glyceryl stearate + PEG-100 stearate) | 1.5 g | 15,000 |
| Carbomer | 0.5 g | 5,000 |
| Preservative (phenoxyethanol) | 0.1 g | 1,000 |
| Total Fill Weight | 50 g | ≈500 kg |

Table 112 summarizes the topical cream dispenser composition, combining lipophilic sterol derivatives (oil phase) and hydrophilic co-nutrients (water phase) within a nanoemulsion base. Emulsifiers and carbomer ensure stable rheology, while phenoxyethanol provides preservative protection. Consistent with Study 4A characterization parameters, the topical nanoemulsion is controlled to a mean droplet size≤200 nm with PDI≤0.3 under accelerated and long-term storage. Each dispenser delivers 50 g of product, with a total batch output of ~500 kg across 10,000 units.

Topical Cream Conversion (10,000 Dispensers×50 g Each)

The topical cream formulation is manufactured under ISO Class 7 cleanroom conditions in compliance with GMP Part 211, with lipid handling performed under continuous nitrogen protection. The oil phase (MCT oil and oleic acid) is gently heated to 40-45° C. and used to dissolve sterol derivatives (e.g., 1-DHEA enanthate in certain embodiments), while the hydrophilic phase (purified water and glycerol) is separately prepared with HMB free acid and magnesium bisglycinate. Emulsifiers (glyceryl stearate and PEG-100 stearate) are incorporated into the oil phase, after which the oil and aqueous phases are combined under high-shear homogenization to form a stable nanoemulsion cream matrix. Carbomer (0.5% w/w) is dispersed as a rheology modifier, and the formulation is neutralized to pH 5.5 with triethanolamine. Phenoxyethanol (0.1% w/w) is introduced as a preservative, followed by final homogenization, filtration, and nitrogen-protected filling into 50 g airless photoprotective dispensers. Each dispenser delivers approximately 50 g of finished product, yielding a total batch output of ~500 kg across 10,000 units. Stability is confirmed under ICH Q1A (R2) and Q1B protocols, verifying potency retention (>90% of label claim), rheological stability, and microbial compliance per USP <61>/<62> over accelerated and long-term storage.

Example 3-Modular Manufacturing Process for Hybrid Microneedle Dual-Compartment Patch with Polarity-Specific Payloads Modular Phase 1-Base Microneedle Matrix Preparation.

Manufacturing is conducted in an ISO Class 7 cleanroom under device QSR/QMSR (21 CFR 820/ISO 13485) and ISO 14644-1 particulate standards. Carrier assignment follows the polarity-mapping algorithm (Study 1A), placing lipophilic actives into ethosomal lipid carriers and hydrophilic actives into aqueous or hydrogel matrices. Polyvinylpyrrolidone (PVP, 30% w/w) and hyaluronic acid (HA, 5% w/w) are dissolved in purified water under agitation until a clear viscous solution forms. The lipophilic compartment is prepared by dissolving sterol derivatives (including, in certain embodiments, 1-DHEA enanthate; 50 mg per patch equivalent) into medium-chain triglycerides with 1% oleic acid, then incorporating this lipid into an ethosomal dispersion (30% ethanol, 3% phosphatidylcholine) homogenized to a vesicle size of 150-200 nm. The hydrophilic compartment is prepared by dissolving HMB free acid (300 mg per patch equivalent) and *Rhodiola rosea* extract (200 mg) in a glycerol-water blend. Fat-soluble vitamin E is housed in the lipophilic ethosomal phase, while vitamin B6 is incorporated into the hydrophilic phase. Sequential two-phase casting (Study 3) is applied to maintain polarity separation, with solids %, dwell time, and drying temperature controlled per SOP storyboard Panels 1-4.

Modular Phase 2-Dual-Compartment Microneedle Casting:

Silicone microneedle molds (600-800 μm length) are filled in two sequential steps. The lipophilic ethosome-based payload is cast into the tip compartment to enable initial presentation within the dermal interface. The hydrophilic glycerol-based payload is cast into the base compartment for sustained release coordinated with interstitial fluid uptake. Each fill step is performed under vacuum-assisted filling to ensure complete mold penetration. The molds are then layered with a supportive PVP/HA backing film to form a flexible yet durable patch substrate.

Modular Phase 3-Functional Enhancement Layer.

Delivery performance is tuned with route-scoped enhancers: terpenes or Transcutol® in the ethosomal (lipophilic) phase and propylene glycol (~5% w/w) in the hydrogel (hydrophilic) phase. Cyclodextrin inclusion complexes are incorporated for oxidation-sensitive hydrophilic actives, with host: guest ratios confirmed at 1:1-1:3 and dissolution uplift of approximately 1.8-2.1× versus neat (Study 1A, Tables 21A-21B). Release profiles are adjusted by varying HA molecular weight or the phosphatidylcholine: ethanol ratio in ethosomes. Chelated minerals (e.g., magnesium bisglycinate) may be included in the hydrophilic phase.

Stability Protocol and Dual-Phase Compatibility Testing.

Stability Protocol and Dual-Phase Compatibility Testing. Stability follows ICH Q1A (R2) and ICH Q1B for the microneedle patch (device context). Tip strength is verified by compression testing (≥0.058 N/needle). Dual-compartment integrity is confirmed by confocal microscopy (no inter-compartment migration). Potency is assessed by HPLC (sterol, *Rhodiola* markers) and LC-MS/MS (HMB) with ±5% acceptance. Compatibility is validated under the Study 7 Dual-Route Compatibility Index, including inversion resistance, vesicle-size drift≤25% (DLS), and absolute zeta-potential change $|\Delta\zeta|\leq 5$ mV. Cross-route adaptability is defined as oral sterols via SEDS, and oral HMB via solid dispersion or cyclodextrin complex. Each route is validated under its own specifications.

Quality Control Parameters and Regulatory Alignment.

CPPs include ethosome vesicle size 150-200 nm (DLS), complete mold fill (no voids), residual moisture≤5% (USP <921>), and verified compartment separation. Microbial quality meets USP <61>/<62>. In-vitro release is measured by Franz diffusion cells for both compartments over 24 h. Manufacturing aligns with ISO 13485/21 CFR 820 (patch). If oral embodiments are produced, they follow 21 CFR Part 111 (dietary supplements).

Patches are individually sealed in aluminum foil-laminate sachets with MVTR <0.02 g/m$^2$/day and nitrogen flush. Packaging incorporates dual-latch/peel structural features with KPI validation, including seal-retention force and peel-uniformity testing. Storage conditions are controlled at 15-25° C., protected from light and humidity. Carton labeling includes batch number, expiry date, and clear handling instructions for users.

Continuation Testing and Shelf-Life Monitoring

Stability is monitored at 6, 12, and 24 months with assessments of microneedle tip integrity, dual-phase separation, and potency retention. Adhesive performance and removal force are tracked to support consistent application. Expanded tolerability assessments (Study 8) include dermal irritation scoring, erythema/edema grading, and subject-reported adhesion comfort.

Embodiment Mapping (Summary): This example covers the microneedle dual-compartment and polarity-specific payload separation embodiments. Through modular enhancements, it enables controlled-release dermal systems and adaptogen-mineral co-delivery, and supports conversion of polarity-matched oral embodiments-sterols via SEDS; hydrophiles (e.g., HMB) via solid dispersion or cyclodextrin inclusion complex-into dermal formats as appropriate Modular Manufacturing Process for Hybrid Microneedle Dual-Compartment Patch with Full-Scale Batch Details

TABLE 113

Oral Capsule Conversion (10,000 Units)

| Component | Per Capsule (mg) | Batch Total (10,000 capsules, g) |
|---|---|---|
| Sterol derivative (including, in certain embodiments, 1-DHEA enanthate) | 50 | 500 |
| HMB free acid | 300 | 3,000 |
| *Rhodiola rosea* extract | 200 | 2,000 |
| Medium-chain triglycerides (MCT oil) | 100 | 1,000 |
| Oleic acid | 20 | 200 |
| Polysorbate 80 | 20 | 200 |
| Mixed tocopherols | 1 | 10 |
| Ascorbyl palmitate | 0.5 | 5 |
| Excipients (gelatin, glycerin, purified water, silica) | q.s. to 700 mg | — |
| Gelatin shell material | ~1,800 mg | 18,000 |
| Total Fill Weight | 700 mg | 7,000 g + shell |

Table 113 outlines the oral capsule conversion formula incorporating a sterol derivative embodiment with supportive nutraceuticals. The sterol derivative, HMB free acid, and *Rhodiola rosea* extract form the core actives, carried in an MCT/oleic-acid lipid matrix with polysorbate 80 for solubilization. Antioxidants (mixed tocopherols, ascorbyl palmitate) stabilize the formulation, while gelatin-based excipients complete encapsulation at a standardized 700 mg fill weight. This balanced design provides controlled solubility, oxidative protection, and manufacturability at scale.

Manufacturing Process

The lipid phase is prepared at 40-45° C. under continuous nitrogen purging, dissolving sterol derivatives (including, in certain embodiments, 1-DHEA enanthate) along with lipophilic antioxidants to limit oxidation. Hydrophilic actives such as HMB and *Rhodiola* are pre-micronized and uniformly dispersed within the system, aided by surfactant blending to enhance dispersion stability. The resulting pre-emulsion is homogenized to achieve consistent droplet-size distribution. Encapsulation is carried out under ISO Class 7 cleanroom conditions using rotary-die softgel technology, with nitrogen-flushed filling to protect oxygen-sensitive components. Finished softgels are blister-packed in tamper-evident PVC/PVDC film and stored at 25° C. in photoprotective cartons under controlled humidity to maintain potency and stability.

Section B—Dual-Compartment Microneedle Patches (10,000 Units)

TABLE 114

Dual-Compartment Microneedle Patch Composition (10,000 Units).

| Component | Per Patch (mg) | Batch Total (10,000 patches, g) |
|---|---|---|
| Lipophilic Compartment | | |
| Sterol derivative (including, in certain embodiments, 1-DHEA enanthate) | 50 | 500 |
| Medium-chain triglycerides | 50 | 500 |
| Oleic acid | 10 | 100 |
| Phosphatidylcholine | 20 | 200 |
| Ethanol (ethosome carrier) | 150 | 1,500 |
| Hydrophilic Compartment | | |
| HMB free acid | 300 | 3,000 |
| *Rhodiola rosea* extract | 200 | 2,000 |
| Glycerin | 20 | 200 |
| Hyaluronic acid | 150 | 1,500 |
| Polyvinylpyrrolidone (PVP) | 300 | 3,000 |
| Total Weight | 1,250 mg | 12,500 g (12.5 kg) |

Table 114 presents the dual-compartment microneedle patch design, featuring polarity-specific separation of lipophilic and hydrophilic actives. The lipophilic compartment contains a sterol derivative (e.g., 1-DHEA enanthate in certain embodiments) in an ethosomal MCT/oleic-acid base with phosphatidylcholine stabilization, while the hydrophilic compartment incorporates HMB free acid, *Rhodiola rosea* extract, and matrix-forming polymers (glycerin, hyaluronic acid, PVP) for sustained presentation. This architecture supports payload stability, route-appropriate exposure kinetics, and structural integrity across 10,000 units, highlighting manufacturability and delivery precision.

Manufacturing Process

Two casting solutions are prepared separately to maintain polarity-specific integrity. The lipophilic ethosomal phase, containing the sterol derivative and polarity-matched uptake aids, is homogenized to produce nanoscale vesicles within the 150-200 nm range. The hydrophilic glycerol-based phase is prepared by dissolving designated actives in a purified water-glycerin blend to ensure uniform dispersion. Microneedle molds are sequentially filled under vacuum, first with the ethosomal phase to occupy the tip compartment for initial dermal interface, followed by the hydrophilic phase in the base compartment for sustained diffusion. A supportive PVP/HA film is laminated onto the mold to form the patch backing. The assembled patches are dried under vacuum at 25° C. for 24 hours to achieve residual moisture below stability thresholds, then individually sealed in nitrogen-flushed foil-laminate pouches. Final storage is controlled at 20-25° C. with relative humidity maintained below 40% to preserve structural integrity and potency.

Section C-Topical Cream Conversion (10,000× 50 G Dispensers)

TABLE 115

Topical Nanoemulsion Gel (10,000 × 50 g)-Sterol Nanoemulsion + HMB Aqueous Dispersion.

| Phase | Component | Per 50 g Dispenser | Batch Total (10,000 units, g) |
|---|---|---|---|
| Lipophilic nano-emulsion phase | Sterol derivative (incl., in certain embodiments, 1-DHEA enanthate) | 50 mg | 500 |
| | Medium-chain triglycerides | 2.0 g | 20,000 |
| | Oleic acid | 0.5 g | 5,000 |
| | Phosphatidylcholine | 0.20 g | 2,000 |
| | Polysorbate 80 | 0.40 g | 4,000 |
| Aqueous dispersion phase | HMB free acid (aqueous dispersion) | 300 mg | 3,000 |
| | *Rhodiola rosea* extract | 200 mg | 2,000 |
| | Carbomer 940 | 0.25 g | 2,500 |
| | Triethanolamine | q.s. to pH ~5.5 | q.s. |
| | Phenoxyethanol | 0.5% w/w (~0.25 g) | 2,500 |
| | Purified water | Balance to 50 g | Balance to 500,000 |
| Total | | 50 g | 500,000 g (500 kg) |

Table 115 details the topical nanoemulsion dispenser composition, integrating lipophilic and hydrophilic actives into a stable cream format. The sterol derivative (e.g., 1-DHEA enanthate in certain embodiments), HMB free acid, and *Rhodiola rosea* extract are dispersed in an MCT oil/oleic-acid lipid phase with phosphatidylcholine and polysorbate 80 as emulsifiers, structured by carbomer/TEA neutralization. Phenoxyethanol provides microbial protection, while purified water balances the aqueous phase. Consistent with Study 4A, the nanoemulsion is controlled to a mean droplet size≤200 nm with PDI≤0.3 to ensure reproducible performance under accelerated and long-term stability. The formulation yields 10,000 dispensers (50 g each), achieving consistent polarity integration, rheological stability, and compliance with preservative and quality standards.

Manufacturing Process-Topical Gel.

Prepare the nanoemulsion oil phase (sterol derivative+MCT+oleic+phosphatidylcholine+polysorbate 80) at ~40° C. under nitrogen; pre-emulsify to desired droplet size on aqueous dispersion. Separately, prepare the aqueous phase with HMB (aqueous dispersion), *Rhodiola*, carbomer, and preservatives. Under high-shear, emulsify the oil phase into the aqueous phase; neutralize to pH ~5.5 with TEA to set gel rheology. Fill into airless dispensers in ISO Class 7, nitrogen-flush headspace. Store at 20-25° C. in light-protective cartons.

Example 4-Modular Manufacturing Process for Cognitive-Supporting Multi-Route Sterol Derivative Delivery System Modular Phase 1-Base Active Carrier Production Manufacturing is performed in an ISO Class 8 cleanroom under GMP Part 211 and ISO 14644-1. Carrier assignment follows the polarity-mapping algorithm (Study 1A), placing lipophilic actives into ethosomal or lipid carriers and hydrophilic actives into aqueous matrices. A lipid carrier phase is prepared by combining medium-chain triglycerides (MCT oil) and oleic acid, heated to 40-45° C. under continuous nitrogen purging. Sterol derivatives (including, in certain embodiments, 4-DHEA enanthate) are incorporated at 100 mg per unit with magnetic stirring until solubilized. Phosphatidylcholine (2% w/w) is added as a phospholipid excipient. *Ginkgo biloba* extract (120 mg) is dispersed by high-shear mixing. Magnesium bisglycinate (8 mg elemental Mg) is pre-complexed with minimal water and glycerin, then incorporated to maintain polarity balance and suspension stability.

Modular Phase 2-Route-Specific Modulation

For oral delivery, the lipid suspension is encapsulated via rotary-die gelatin softgels in an ISO Class 7 suite, targeting≤700 mg fill. For topical delivery, the lipid suspension is dispersed into a carbomer 940 gel base, neutralized to pH 5.5, and homogenized to achieve a mean droplet size≤200 nm with PDI≤0.3 (Study 4A). For microneedle delivery, the lipid suspension is blended with hyaluronic acid and PVA at 45° C., then cast via sequential two-phase casting (Study 3): the lipophilic compartment (sterol+*Ginkgo*) is cast first into tip cavities, followed by the hydrophilic compartment (magnesium) in the base. Parameters for solids %, dwell time, and drying temperature are controlled per SOP storyboard Panels 1-4. The filled molds are vacuum-dried at 25° C. for 24 hours to preserve potency and tip integrity.

Modular Phase 3-Functional Enhancement Layer

Enhancements include Transcutol® (5% w/w) for dermal uptake, phosphatidylserine for cognitive support, and lipid-polymer hybrid vesicles to extend release up to 24 hours. Oral softgels may receive enteric coating. Microneedles may incorporate a moisture-triggered release layer for sequential delivery. Cyclodextrin inclusion complexes are employed for oxidation-sensitive hydrophilic actives, with host: guest ratios 1:1-1:3 and dissolution uplift ~1.8-2.1× versus neat (Study 1A, Tables 21A-21B).

Stability Protocol and Multi-Route Compatibility Testing

Follows ICH Q1A (R2) and ICH Q1B. Potency is monitored (+5% label claim), with droplet-size stability (100-200 nm for oral/topical) and physical integrity assessed. Compatibility is validated under the Study 7 Dual-Route Compatibility Index, including inversion resistance, ≤25% vesicle-size drift, and |A|≤5 mV.

Quality Control Parameters and Regulatory Alignment

Potency is verified by HPLC assays with acceptance criteria of +5% of label claim. Droplet-size distribution is monitored using dynamic light scattering (DLS) both pre- and post-homogenization to ensure nanoscale consistency. Content uniformity is confirmed in accordance with USP <905>, maintaining an acceptance value (AV)≤15. Disintegration testing for oral formats is performed per USP <2040>, while release profiles for microneedle and topical formats are established through standardized in-vitro diffusion studies. Microbial quality is demonstrated through USP <61> (microbial enumeration) and USP <62> (absence of specified organisms). All manufacturing and validation steps conform to ICH Q8 (R2) (pharmaceutical development), ICH Q1A (R2) (stability), ICH Q3C (residual solvents), and applicable USP monographs to support reproducibility, safety, and regulatory alignment.

Continuation Testing and Shelf-Life Monitoring

Retained samples are tested at 6, 12, and 24 months for potency (>90%), microbial compliance, and structural metrics. Microneedles are tested for adhesion force and penetration depth. Topical gels are monitored for pH (+0.2), viscosity (+10%), and phase stability. Expanded tolerability assessments (Study 8) include dermal irritation scoring, erythema/edema grading, and subject-reported adhesion comfort.

Full-Scale Manufacturing for 10,000 Units Across Oral, Microneedle, and Topical Formats with Stability, QC, and Embodiment Mapping

TABLE 116

Oral Softgel Capsule Composition (10,000 Units × 700 mg fill weight).

| Component | Per Capsule (mg) | Batch Total (10,000 units, g) | Function |
|---|---|---|---|
| Sterol derivative (including, in certain embodiments, 4-DHEA enanthate) | 100 | 1,000 | Lipophilic sterol derivative embodiment |
| *Ginkgo biloba* extract (24% flavone glycosides) | 120 | 1,200 | Botanical co-extract (wellness support) |
| Magnesium bisglycinate (8 mg elemental Mg) | 60 | 600 | Chelated mineral |
| Medium-chain triglycerides (MCT oil) | 300 | 3,000 | Primary lipid carrier |
| Oleic acid | 50 | 500 | Polarity-matched delivery aid (uptake support) |
| Phosphatidylcholine (≥95% purity) | 20 | 200 | Phospholipid excipient (dispersion/membrane interaction support) |
| Polysorbate 80 | 40 | 400 | Surfactant |
| Mixed tocopherols | 1.5 | 15 | Antioxidant |
| Ascorbyl palmitate | 0.75 | 7.5 | Antioxidant |
| Excipients (silica, gelatin, glycerin, purified water) | q.s. to 700 mg | — | Fillers/shell materials |
| Gelatin shell material | — | ~18,000 | Capsule shell |

Table 116 outlines the unit and batch composition of the oral softgel capsule format containing a sterol derivative embodiment with synergistic co-factors. MCT oil and oleic acid function as the lipid carrier system, phosphatidylcholine supports phospholipid-assisted dispersion, while polysorbate 80 and antioxidants (tocopherols, ascorbyl palmitate) stabilize the formulation. Gelatin shells complete encapsulation for a dietary-supplement format.

Manufacturing Process

The base lipid phase is prepared at 40-45° C. under continuous nitrogen purge to minimize oxidative change. Active components are sequentially dissolved or dispersed into the lipid carrier system, followed by incorporation of antioxidants, with distribution and stability confirmed by HPLC. Surfactant blending is performed under controlled mixing, and the pre-emulsion is subjected to high-shear homogenization to achieve a uniform droplet size of approximately 120 nm. The finished bulk is encapsulated using rotary-die technology in an ISO Class 7 environment, with nitrogen-flushed filling to protect oxygen-sensitive constituents. Completed capsules are blister-packed in PVC/PVDC high-barrier film, labeled with batch and expiry details, and stored at 25° C./60% RH in photoprotective cartons to preserve long-term stability.

Section B—Microneedle Patches (10,000 Units)

TABLE 117

| Dual-Compartment Microneedle Patch Composition (10,000 Units) | | | |
|---|---|---|---|
| Component | Per Patch (mg) | Batch Total (10,000 units, g) | Role/Function |
| Sterol derivative (including, in certain embodiments, 4-DHEA enanthate) | 100 | 1,000 | Lipophilic payload (lipophilic compartment) |
| Magnesium bisglycinate | 60 | 600 | Chelated mineral (hydrophilic compartment) |
| Hyaluronic acid | 150 | 1,500 | Matrix former (biodegradable microneedle backbone) |
| Polyvinyl alcohol (PVA) | 300 | 3,000 | Structural polymer (microneedle strength) |
| Phosphatidylcholine | 20 | 200 | Lipid-phase stabilizer (compatibility) |
| Transcutol ® | 50 | 500 | Delivery aid (dermal uptake support) |
| Glycerin | 20 | 200 | Humectant/ plasticizer |
| Purified water | q.s. (casting aid) | ~15,000 (evaporates during drying) | Solvent/dispersion medium |

Table 117 details the dual-compartment microneedle patch composition integrating both lipophilic and hydrophilic nutritional constituents. The sterol derivative embodiment is confined to the lipophilic compartment, while magnesium bisglycinate is delivered through a hydrophilic matrix supported by hyaluronic acid and PVA. Phosphatidylcholine and Transcutol® support dermal uptake and payload stability, while glycerin and purified water facilitate casting and plasticity. This architecture demonstrates polarity-specific delivery with structural integrity.

Manufacturing Process

Two-phase casting is employed, beginning with a lipophilic phase containing the sterol derivative, phosphatidylcholine, and an ethanol-rich carrier, alongside a hydrophilic phase of magnesium bisglycinate combined with hyaluronic acid and polyvinyl alcohol (HA/PVA). Sequential vacuum-assisted mold filling ensures complete cavity penetration and separation of payloads, followed by controlled vacuum drying at 25° C. for 24 hours to preserve potency and structural integrity. The dried microneedles are laminated to a polymeric backing film for mechanical stability. Finished patches are individually sealed in nitrogen-flushed foil-laminate pouches, with storage maintained at 20-25° C. and relative humidity below 40% to support long-term stability.

Section C-Topical Cream Dispensers (10,000 Units)

TABLE 118

| Topical Nanoemulsion Dispenser Composition (10,000 Units × 50 g each) | | | |
|---|---|---|---|
| Component | Per Dispenser (mg or %) | Batch Total (10,000 units, g) | Role/Function |
| Sterol derivative (including, in certain embodiments, 4-DHEA enanthate) | 100 mg | 1,000 | Lipophilic sterol derivative embodiment |
| *Ginkgo biloba* extract | 120 mg | 1,200 | Botanical co-extract (wellness support) |
| Magnesium bisglycinate | 60 mg | 600 | Chelated mineral (hydrophilic payload) |
| Oleic acid | 500 mg | 5,000 | Polarity-matched delivery aid (uptake support) |
| MCT oil | 2,000 mg | 20,000 | Primary lipid carrier |
| Phosphatidylcholine | 200 mg | 2,000 | Phospholipid stabilizer/ emulsifier |
| Polysorbate 80 | 400 mg | 4,000 | Surfactant/ emulsifier |
| Carbomer 940 | 250 mg | 2,500 | Gelling agent/ viscosity control |
| Triethanolamine | q.s. to pH 5.5 | | pH adjustment/ neutralizer |
| Purified water | Balance to 50 g | Balance to 500,000 | Solvent/aqueous phase |
| Phenoxyethanol | 0.5% w/w (~250 mg) | 2,500 | Preservative (USP compliant) |

Table 118 presents the topical nanoemulsion dispenser formulation. Lipophilic sterol derivatives are solubilized in the lipid phase with MCT oil and oleic acid, while magnesium bisglycinate and *Ginkgo* extract are supported in the aqueous phase. Phosphatidylcholine and polysorbate 80 provide emulsification, carbomer/TEA establish rheology, and phenoxyethanol ensures microbial safety. Consistent with Study 4A, the nanoemulsion is maintained at mean droplet size≤200 nm with PDI≤0.3 for reproducible dermal performance.

The manufacturing process begins with preparation of the oil phase, in which lipophilic constituents are dissolved in medium-chain triglycerides and oleic acid at 40° C. under nitrogen to minimize oxidation. In parallel, the aqueous phase is prepared by dispersing carbomer and incorporating magnesium bisglycinate. The two phases are combined using high-shear emulsification to form a stable cream, after which the pH is adjusted to 5.5. Final filling is performed under nitrogen into airless pumps, and finished products are stored at 20-25° C. under controlled humidity.

Stability testing follows ICH guidelines, including accelerated conditions at 40° C. and 75% relative humidity for six months, long-term storage at 25° C. and 60% relative humidity for 24 months, and photostability evaluation under ICH Q1B simulated daylight. For microneedle formats, post-storage testing includes verification of tip strength and dissolution rate. Across all formats, the potency-retention target is set at ≥90% of label claim.

Quality control parameters include content uniformity per USP <905> with acceptance value≤15, microbial limits in compliance with USP <61> and <62>, and potency within ±5% of label claim as confirmed by HPLC assay. Droplet size for oral SEDS and topical nanoemulsion systems is maintained within the range of 100-150 nm as measured by dynamic light scattering, microneedle moisture content is controlled below 5%, and topical cream viscosity is required to remain within +10% of target values.

Packaging and Storage. All dosage forms are packaged to maintain integrity: softgels in nitrogen-flushed PVC/PVDC blisters, patches in foil-laminate pouches, creams in airless pumps with photoprotective cartons. Packaging incorporates dual-latch/peel structural features with KPI validation, including seal retention and peel-uniformity testing. Storage conditions: 15-25° C., <60% RH, light-protected.

Example 5—Modular Manufacturing Process for Synergy Trial Oral+Microneedle Hybrid with Multi-Active Payloads Modular Phase 1-Base Oral Capsule Preparation Manufacturing is carried out under GMP Part 211 in an ISO Class 8 cleanroom, with encapsulation steps performed in an ISO Class 7 environment. Carrier assignment follows the polarity-mapping algorithm (Study 1A), placing sterol derivatives and resveratrol into the lipidic carrier phase and hydrophilic actives (HMB free acid, L-arginine, magnesium citrate) into a pre-granulated aqueous/hydrophilic blend. The lipid phase, composed of omega-3 oil and oleic acid, is gently heated to 40-45° C. under nitrogen, into which sterol derivatives (including, in certain embodiments, epiandrosterone undecanoate) and resveratrol are dissolved. The hydrophilic blend is pre-granulated with minimal purified water, dried, sieved, and then introduced together with zinc bisglycinate, forming a polarity-balanced suspension. The mixture is de-gassed under vacuum and immediately transferred to the capsule-filling machine. Capsules are filled to 700 mg ±2%, with HPLC content-uniformity verification.

Modular Phase 2-Microneedle Patch Preparation

Microneedle fabrication proceeds through sequential two-phase casting (Study 3). The hydrophilic compartment is prepared by dissolving HMB free acid, magnesium bisglycinate, and L-arginine in an aqueous PVP-hyaluronic acid solution, forming a stable casting matrix. The lipophilic compartment is prepared by dissolving phosphatidylcholine in ethanol, adding Transcutol® and tocopherols, and incorporating sterol derivatives (including, in certain embodiments, epiandrosterone undecanoate) and resveratrol. The ethosomal dispersion is homogenized to a vesicle size of 100-150 nm. Sequential casting parameters (solids %, dwell time, drying temperature) are controlled per SOP storyboard Panels 1-4, ensuring polarity-specific separation. Controlled vacuum drying at 25° C. for 24 hours reduces residual moisture≤5%, producing mechanically robust microneedles, laminated to polyurethane backing films and die-cut to final dimensions.

Modular Phase 3-Functional Enhancement Layer

Polarity-matched delivery aids (uptake support), including Transcutol® and optional terpenes, are incorporated into the lipophilic compartment to support dermal uptake. Antioxidant protection is provided by mixed tocopherols in the lipophilic tip and ascorbyl derivatives in the hydrophilic base. Cyclodextrin inclusion complexes are incorporated for oxidation-sensitive hydrophilic actives, with host: guest ratios 1:1-1:3 and dissolution uplift ~1.8-2.1× versus neat (Study 1A, Tables 21A-21B). The dual-compartment structure preserves polarity-specific stability and allows for independent release control. Presentation can occur simultaneously or sequentially, providing programmable exposure profiles not taught by prior single-phase microneedle systems.

Modular Phase 4-Stability Testing and Multi-Route Verification Stability

Studies are conducted under ICH Q1A (R2) and Q1B. Accelerated (40° C./75% RH, 6 months) and long-term (25° C./60% RH, 24 months) testing confirm ≥90% potency retention across actives. Photostability testing under simulated daylight confirms no potency loss. Dual-route compatibility is validated under the Study 7 Compatibility Index, including inversion resistance, ≤25% vesicle-size drift (DLS), and |AC|≤5 mV. Post-storage verification demonstrates that oral capsules retain suspension uniformity and microneedle patches maintain tip integrity, vesicle size, and dissolution behavior. Expanded tolerability assessments (Study 8) include dermal irritation scoring, erythema/edema grading, and subject-reported adhesion comfort for microneedle applications.

Modular Phase 5-Quality Control Parameters

Quality control testing ensures that capsule fill weights remain within ±2% of target and potency within ±5% of label claim. Microneedle arrays exhibit tip heights between 600 and 800 μm, fracture forces exceeding 0.2 N per needle, and dry-mass values averaging 80 mg per patch with variation under±5%. Vesicle sizes in the lipophilic compartment remain between 100 and 150 nm with low polydispersity, and residual moisture is consistently below 5%. Residual ethanol content in the patches is below 0.5%, and both dosage forms meet microbial limits as specified in USP <61> and <62>. In-vitro dissolution testing confirms rapid release from capsules, while Franz diffusion studies demonstrate consistent flux profiles from microneedle patches, configurable for either sequential or simultaneous presentation.

Modular Phase 6-Packaging and Storage

Final packaging incorporates stability-protective systems. Oral capsules are nitrogen-flushed and sealed in PVC/PVDC blister packs with tamper-evident features. Microneedle patches are packaged individually in foil-laminate pouches containing desiccants and nitrogen flush. Packaging incorporates dual-latch/peel structural features with KPI validation, including seal-retention force and peel-uniformity testing. Both formats are stored at 15-25° C. under relative humidity below 60% and protected from light, supporting long-term integrity and consumer usability.

Full-Scale Manufacturing Weights & Measures

TABLE 119

Oral Capsules-Unit Formula and Batch Calculation (10,000 Units)

| Component | Unit Formula (mg) | Batch Total (g) | Notes |
|---|---|---|---|
| Sterol derivative (including, in certain embodiments, epiandrosterone undecanoate) | 50 | 500 | Lipophilic active (sterol derivative embodiment) |
| HMB free acid | 150 | 1,500 | Hydrophilic constituent |
| L-Arginine | 100 | 1,000 | Hydrophilic constituent |
| Resveratrol | 100 | 1,000 | Lipophilic botanical polyphenol |
| Omega-3 oil | 200 | 2,000 | Primary lipid carrier (with oleic acid as polarity-matched uptake aid) |
| Zinc bisglycinate | 40 | 400 | Provides ~8 mg Zn |
| Magnesium citrate | 50 | 500 | Provides ~7-8 mg Mg |
| Oleic acid | 10 | 100 | Polarity-matched delivery aid (uptake support) |
| Total Fill Weight | 700 mg | 7,000 g | Capsule fill target |
| Gelatin shell (dry) | ~200 | ~2,000 | If softgel applied |

Table 119 specifies the composition of a single oral capsule and the corresponding batch quantities for a 10,000-unit run. The formulation is normalized to a 700 mg total fill per capsule. The eight fixed components sum precisely to 700 mg, eliminating the need for any q.s. filler adjustment.

Manufacturing Process

Oral capsules are manufactured in an ISO Class 8 cleanroom under GMP Part 211, with encapsulation conducted in an ISO Class 7 environment. Omega-3 oil and oleic acid are gently warmed to 40-45° C. under nitrogen purge, into which the sterol derivative embodiment and resveratrol are dissolved. Separately, HMB free acid, L-arginine, and magnesium citrate are pre-blended and lightly granulated with minimal purified water, dried to low moisture, and sieved to ensure flowability. This hydrophilic blend is introduced into the lipid phase together with zinc bisglycinate, yielding a uniform lipid-hydrophilic suspension. The mixture is degassed under vacuum and transferred to a capsule-filling machine. Capsules are filled to ~700 mg per unit, with fill weight verified within +2% and content uniformity confirmed by HPLC assay.

Section B—Microneedle Patches (10,000 Units)

TABLE 120

Dual-Compartment Microneedle Patch Composition (10,000 Units)

| Component | Unit Formula (mg) | Batch Total (g) | Compartment/ Notes |
|---|---|---|---|
| Hydrophilic Compartment | | | |
| HMB free acid | 15 | 150 | Hydrophilic constituent |
| Magnesium bisglycinate | 8 | 80 | Provides ~1.2 mg Mg |
| L-Arginine | 10 | 100 | Hydrophilic constituent |
| Polyvinylpyrrolid one (PVP) | 6 | 60 | Matrix polymer |
| Sodium hyaluronate | 3 | 30 | Matrix polymer |
| Lipophilic Compartment | | | |
| Sterol derivative (including, in certain embodiments, epiandrosterone undecanoate) | 8 | 80 | Lipophilic payload |
| Resveratrol | 20 | 200 | Lipophilic botanical |
| Phosphatidylcholine | 6 | 60 | Ethosome stabilizer |
| Transcutol ® | 1.5 | 15 | Delivery aid (uptake support) |
| Mixed tocopherols | 0.5 | 5 | Antioxidant |
| Purified water | q.s. (removed) | ~10,000 | Casting solvent |
| Total Dry Mass | ~80 mg | ~800 g | Per finished patch (excludes backing/adhesive) |

Table 120 specifies the per-patch unit formula and the 10,000-unit batch totals for a dual-compartment microneedle (MN) system. The formulation is engineered to yield a finished dry mass of ~80 mg per patch (excluding backing/adhesive), with polarity-separated constituents to preserve stability and enable configurable exposure profiles.

Manufacturing Process

Microneedle patches are produced using a sequential dual-compartment casting approach. The hydrophilic base is prepared by dissolving HMB free acid, magnesium bisglycinate, and L-arginine in an aqueous solution of PVP and sodium hyaluronate, yielding a clear, stable casting matrix. In parallel, the lipophilic tip compartment is formulated by dissolving phosphatidylcholine in ethanol, incorporating Transcutol® and tocopherols, and then adding the sterol derivative embodiment and resveratrol. Chilled water is added to form ethosomes, homogenized to a vesicle size of 100-150 nm. The lipophilic dispersion is vacuum-cast into microneedle molds to form sharp tips, followed by partial drying, and then back-filled with the hydrophilic matrix to form the base. Vacuum drying at 25° C. for 24 hours reduces residual moisture to ≤5%, producing robust needles of 600-800 μm height. The dried arrays are laminated to polyurethane backing films and die-cut to size.

Section C-Topical Cream Dispenser

TABLE 121

Topical Cream Dispensers (10,000 Units × 50 g Each; Batch = 500,000 g)

| Component | % w/w | Per Dispenser (50 g) | Batch Total (g) | Notes |
|---|---|---|---|---|
| Sterol derivative (including, in certain embodiments, epiandrosterone undecanoate) | 0.10% | 0.05 g | 500 | Lipophilic sterol derivative embodiment |
| Resveratrol | 0.20% | 0.10 g | 1,000 | Lipophilic botanical |
| HMB free acid | 1.00% | 0.50 g | 5,000 | Hydrophilic constituent |
| Magnesium bisglycinate | 0.30% | 0.15 g | 1,500 | Provides Mg |
| L-Arginine | 0.50% | 0.25 g | 2,500 | Hydrophilic constituent |
| Phosphatidylcholine | 0.50% | 0.25 g | 2,500 | Emulsifier |
| Transcutol ® | 2.00% | 1.00 g | 10,000 | Delivery aid (uptake support) |
| Terpene blend | 0.20% | 0.10 g | 1,000 | Delivery aid |
| MCT oil | 6.00% | 3.00 g | 30,000 | Lipid vehicle |
| Polysorbate 80 | 2.00% | 1.00 g | 10,000 | Surfactant |
| Cetyl alcohol | 1.50% | 0.75 g | 7,500 | Thickener |
| Glyceryl stearate | 2.00% | 1.00 g | 10,000 | Emulsifier |
| Carbomer | 0.40% | 0.20 g | 2,000 | Gel matrix |
| Triethanolamine | 0.40% | 0.20 g | 2,000 | Neutralizer |
| Glycerin | 5.00% | 2.50 g | 25,000 | Humectant |
| Mixed tocopherols | 0.10% | 0.05 g | 500 | Antioxidant |
| Phenoxyethanol (preservative) | 0.80% | 0.40 g | 4,000 | Preservative |
| Purified water | q.s. to 100% | ~38.50 g | ~385,000 | Vehicle |
| Total | 100% | 50 g | 500,000 | — |

Table 121 presents the composition of the topical cream dispenser format. Each 50 g dispenser integrates lipophilic and hydrophilic constituents within a stabilized emulsion system, supported by MCT oil and polysorbate 80 for solubilization and dermal uptake, with carbomer-based viscosity adjustment and triethanolamine neutralization to pH 5.5. The batch scale reflects a 10,000-unit manufacturing run, totaling 500 kg.

Manufacturing Process

Topical cream dispensers are manufactured as a two-phase emulsion under controlled GMP conditions. The oil phase is prepared by combining MCT oil, cetyl alcohol, glyceryl stearate, polysorbate 80, phosphatidylcholine, and lipophilic constituents (the sterol derivative embodiment and resveratrol) with heating to 70° C. In parallel, the aqueous phase is prepared by dissolving HMB free acid, magnesium bisglycinate, L-arginine, glycerin, carbomer, and preservatives in purified water, which is heated to 70° C. The oil and aqueous phases are combined under high-shear homogenization, after which triethanolamine is added to neutralize the carbomer and form a stable cream base. Transcutol® and the terpene blend are incorporated during the cooling stage, together with mixed tocopherols for antioxidant support. The cream is cooled to 25° C. under continuous mixing and filled into 50 g dispensers under nitrogen flush. When operated as a nanoemulsion variant, the emulsion is controlled to mean droplet size≤200 nm with PDI≤0.3 (Study 4A), measured by DLS, to ensure reproducible dermal performance. Each unit is sealed, labeled, and packaged to protect against light and moisture.

Example 6-Modular Manufacturing Process for Stability & Manufacturing Integrity Across Oral, Microneedle, and Topical Formats Modular Phase 1-Base Oral Capsule Preparation Manufacturing is conducted in an ISO Class 8 cleanroom under GMP Part 211 and ISO 14644-1 controls. Carrier assignment follows the polarity-mapping algorithm (Study 1A), placing sterol derivatives and resveratrol into the lipidic carrier phase and hydrophilic actives into aqueous or solid-dispersion matrices. The lipid phase is prepared by heating medium-chain triglycerides (MCT oil) and oleic acid to 40-45° C. under a continuous nitrogen purge to prevent oxidative degradation. Sterol derivatives (including, in certain embodiments, androst-5-ene-3β, 7,17-triol enanthate) are dissolved with controlled agitation, followed by incorporation of retinol and polyunsaturated fatty acids (PUFAs) as a secondary lipid carrier. Oleic acid is standardized as the polarity-matched delivery aid (uptake support) for the oral lipid matrix. Mixed tocopherols are added as antioxidants to stabilize the formulation. The final blend is homogenized until a clear solution is achieved and encapsulated into softgels using rotary-die encapsulation under ISO Class 7 conditions, with nitrogen-flushed filling to minimize oxygen exposure.

Modular Phase 2-Microneedle Patch Preparation

A hydrophilic casting solution is prepared with vitamin $D_3$ (800 IU equivalent) and magnesium bisglycinate dispersed in polyvinylpyrrolidone (PVP) and hyaluronic acid (HA). The lipophilic compartment is prepared separately with sterol derivatives (including, in certain embodiments, androst-5-ene-3β,7β, 17β-triol enanthate), retinol, and PUFAs in a phosphatidylcholine-ethanol ethosomal system, homogenized to vesicle sizes of 150-200 nm. Oleic acid is incorporated in the lipophilic compartment as a delivery aid (uptake support) to enhance dermal partitioning. Sequential two-phase casting (Study 3) is employed: microneedle molds (600-800 μm) are first tip-filled with the lipophilic dispersion and partially dried, then back-filled with the hydrophilic matrix under vacuum to ensure dual-compartment integrity. Drying is performed at 25° C. under vacuum until residual moisture <5%, ensuring microneedle mechanical strength and long-term stability.

Modular Phase 3-Topical Cream Preparation

The oil phase containing sterol derivatives (including, in certain embodiments, androst-5-ene-3β,7β, 17β-triol enanthate), retinol, PUFAs, and oleic acid (delivery aid/uptake support) is heated to 40° C. under nitrogen protection. Separately, the aqueous phase is prepared with a carbomer dispersion and vitamin $D_3$ solution. The oil phase is slowly emulsified into the aqueous phase under high-shear homogenization to achieve a mean droplet size≤200 nm with PDI ≤0.3 (Study 4A, DLS-verified). Triethanolamine is added to adjust pH to 5.5. The resulting cream is homogenized for uniform droplet distribution and texture consistency.

Modular Phase 4-Functional Enhancement Layer

Photostabilizers such as rosemary extract are incorporated to help protect retinol against UV/light stress. Antioxidants are distributed across both lipid and aqueous compartments. Oleic acid is utilized as the standardized polarity-matched delivery aid (uptake support) in microneedle and topical formats. Stability enhancers such as encapsulated retinol microcapsules may be used in place of free retinol to further extend shelf life.

Modular Phase 5-Stability Testing & Manufacturing Validation

Stability is validated per ICH Q1A (R2) under accelerated (40° C./75% RH, 6 months) and long-term (25° C./60% RH, 24 months) conditions, with photostability per ICH Q1B. Dual-route compatibility (Study 7) is confirmed using the Compatibility Index: inversion resistance, droplet/vesicle size drift≤25% (DLS), and absolute zeta-potential change |Δ|≤5 mV across relevant lipidic systems. Compatibility testing demonstrates no migration between hydrophilic and lipophilic compartments in microneedle patches. PUFA oxidative stability is monitored using peroxide value and anisidine assays.

Modular Phase 6-Quality Control Parameters

Critical process controls include emulsion/vesicle metrics (mean size≤200 nm, PDI≤0.3; 100-150 nm preferred target where applicable), zeta-potential monitoring with |Δζ|≤5 mV vs. release specification (Study 7), microneedle tip height and sharpness validation via profilometry, capsule fill-weight accuracy within +2%, patch residual moisture <5%, and potency within +5% of label claim verified by HPLC and LC-MS/MS. Microbial limits testing follows USP <61>/<62>, supporting compliance with dietary-supplement and device quality requirements.

Modular Phase 7-Packaging & Storage

Oral softgels are nitrogen-flushed and sealed in PVC/PVDC blister packs with desiccants. Microneedle patches are individually packaged in foil-laminate pouches with integrated desiccants and nitrogen flushing to preserve vesicle stability. Topical creams are dispensed into airless, photoprotective pump containers. Packaging incorporates dual-latch and controlled-peel features with QC KPI validation (seal-retention force and peel-uniformity). All packaging meets tamper-evident and child-resistant requirements (16 CFR 1700). Products are stored at 15-25° C., <60% RH, protected from light.

Manufacturing Scale Details for 10,000 Units Across all Routes

Section A-Oral Capsules (10,000 units)

TABLE 122

Oral Capsule Composition (10,000 Units × ~700 mg Fill Weight)

| Component | Unit Formula (per capsule) | Batch Calculation (10,000 capsules) | Functional Role |
|---|---|---|---|
| Sterol derivatives (including, in certain embodiments, androst-5-ene-3β,7β,17β-triol enanthate) derivatives | 50 mg | 500 g | Lipophilic active (sterol derivative embodiment) |
| Vitamin D3 | 800 IU (~20 μg) | 0.2 g | Nutritional support for bone/endocrine balance |
| Retinol palmitate | 0.5 mg | 5 g | Supports skin/epithelial wellness |

TABLE 122-continued

Oral Capsule Composition (10,000 Units × ~700 mg Fill Weight)

| Component | Unit Formula (per capsule) | Batch Calculation (10,000 capsules) | Functional Role |
|---|---|---|---|
| Omega-3 ethyl esters | 100 mg | 1,000 g | Supports cardiovascular wellness & healthy inflammatory balance |
| Vitamin A acetate | 1.5 mg | 15 g | Antioxidant; supports visual function |
| Riboflavin (Vitamin B2) | 2 mg | 20 g | Metabolic cofactor support |
| Mixed tocopherols | 2 mg | 20 g | Antioxidant system |
| Ascorbyl palmitate | 0.75 mg | 7.5 g | Antioxidant system |
| Oleic acid | 50 mg | 500 g | Delivery aid (uptake support) |
| MCT oil (q.s. to ~700 mg fill; ~493.2 mg typical) | ~493.2 mg | ~4,932 g | Primary lipid carrier/fill balance |
| Gelatin shell material (gelatin, glycerin, purified water) | — | ~18,000 g | Capsule shell |

Table 122 summarizes the oral capsule unit formula and corresponding batch calculation for 10,000 units. Each capsule combines polarity-adapted constituents per Study 1A in a dual-lipid system: MCT oil as the primary lipid carrier and oleic acid as the polarity-matched delivery aid (uptake support). Tocopherols and ascorbyl palmitate provide dual-phase antioxidant protection, while gelatin shells ensure softgel integrity.

Manufacturing Process

The lipid phase is prepared at 40-45° C. under continuous nitrogen purge by dissolving sterol derivatives (including, in certain embodiments, androst-5-ene-3β,7β,17β-triol enanthate) together with fat-soluble vitamins (retinol, vitamin $D_3$), omega-3 esters, and the antioxidant system (mixed tocopherols/ascorbyl palmitate) into MCT oil. Oleic acid is incorporated as a delivery aid (uptake support), and water-compatible actives such as riboflavin are first dispersed in glycerin and then incorporated under controlled homogenization to ensure uniform distribution. The final blend is encapsulated using rotary-die softgel technology in an ISO Class 7 cleanroom, with nitrogen-purged filling to minimize oxidative change. Finished capsules are blister-packed in high-barrier PVC/PVDC film with desiccant integration, heat-sealed, labeled with lot/expiry, and stored at 15-25° C., <60% RH, photoprotected.

Section B—Microneedle Patches (10,000 Units) Unit Formula (Per Patch)

TABLE 123

Microneedle Patch Composition (10,000 Units)

| Component | Unit Formula (per patch) | Batch Calculation (10,000 patches) | Functional Role |
|---|---|---|---|
| Sterol derivatives (including, in certain embodiments, androst-5-ene-3β,7β,17β-triol enanthate) | 50 mg | 500 g | Lipophilic active (sterol derivative embodiment) |
| Vitamin D3 | 800 IU (~20 μg) | 0.2 g | Nutritional support for bone/endocrine balance |

TABLE 123-continued

Microneedle Patch Composition (10,000 Units)

| Component | Unit Formula (per patch) | Batch Calculation (10,000 patches) | Functional Role |
|---|---|---|---|
| Retinol palmitate | 0.5 mg | 5 g | Supports skin/epithelial wellness |
| Omega-3 ethyl esters | 100 mg | 1,000 g | Supports cardiovascular wellness & healthy inflammatory balance |
| Hyaluronic acid | 150 mg | 1,500 g | Matrix former (hydration/structure) |
| Polyvinyl alcohol (PVA) | 300 mg | 3,000 g | Structural polymer (microneedle integrity) |
| Phosphatidylcholine | 20 mg | 200 g | Vesicle stabilizer for lipophilic payloads |
| Oleic acid | 50 mg | 500 g | Delivery aid (uptake support) |
| Purified water | q.s. for casting | ~15,000 g (evaporated during drying) | Solvent/processing aid |

Table 123 details the dual-compartment microneedle patch formulation, with polarity-specific allocation of hydrophilic and lipophilic actives. Hyaluronic acid and PVA form the structural hydrogel matrix, while phosphatidylcholine and oleic acid support lipophilic payload stability and uptake.

Manufacturing Process

The lipophilic compartment is prepared by dissolving the sterol derivative embodiment together with fat-soluble vitamins, omega-3 esters, oleic acid (delivery aid/uptake support), and phosphatidylcholine in an ethanol-rich carrier to generate a vesicular phase. In parallel, the hydrophilic compartment is prepared by dissolving vitamin $D_3$ (water-dispersible form) in a hyaluronic acid (HA) and polyvinyl alcohol (PVA) solution, forming the aqueous polymeric phase. Dual-compartment microneedle molds (600-800 μm) are sequentially filled under vacuum in an ISO Class 7 cleanroom to ensure complete tip penetration and separation of payloads. Cast patches are vacuum-dried at 25° C. for 24 hours to achieve residual moisture <5%, laminated onto flexible backing films, and individually sealed in nitrogen-flushed foil-laminate pouches with desiccants. Final products are stored at 20-25° C. under <40% RH with photo-protection.

Section C-Topical Cream Dispensers (10,000 Units), Unit Formula (Per 50 G Dispenser)

TABLE 124

Topical Cream Dispenser Composition (10,000 Units, 50 g each)

| Component | Unit Formula (per 50 g dispenser) | Batch Calculation (10,000 dispensers; 500 kg total) | Functional Role |
|---|---|---|---|
| Sterol derivatives (including, in certain embodiments, androst-5-ene-3β,7β,17β-triol enanthate) | 50 mg | 500 g | Lipophilic active (sterol derivative embodiment) |

TABLE 124-continued

| Topical Cream Dispenser Composition (10,000 Units, 50 g each) | | | |
|---|---|---|---|
| Component | Unit Formula (per 50 g dispenser) | Batch Calculation (10,000 dispensers; 500 kg total) | Functional Role |
| Vitamin D3 | 800 IU (~20 μg) | 0.2 g | Nutritional support for bone/endocrine balance |
| Retinol palmitate | 0.5 mg | 5 g | Supports skin/epithelial wellness |
| Omega-3 ethyl esters | 100 mg | 1,000 g | Supports cardiovascular wellness & healthy inflammatory balance |
| Vitamin A acetate | 1.5 mg | 15 g | Antioxidant; supports visual function |
| Riboflavin (Vitamin B2) | 2 mg | 20 g | Metabolic cofactor support |
| Oleic acid | 500 mg | 5,000 g | Delivery aid (uptake support) |
| MCT oil | 2,000 mg | 20,000 g | Primary lipid carrier |
| Phosphatidyl-choline | 200 mg | 2,000 g | Vesicle stabilizer & emulsifier |
| Polysorbate 80 | 400 mg | 4,000 g | Surfactant & emulsifier |
| Carbomer 940 | 250 mg | 2,500 g | Thickener/stabilizer |
| Triethanolamine | q.s. to pH 5.5 | — | pH adjustment |
| Purified water | Balance to 50 g | ~500,000 g | Aqueous base |
| Phenoxyethanol | 0.5% w/w | 2,500 g | Preservative |

Table 124 details the topical cream dispenser formulation integrating both lipophilic and hydrophilic nutrients. MCT oil+oleic acid serves as the lipid carrier/delivery-aid system, carbomer/TEA provide rheological structure, and phenoxyethanol ensures microbial safety.

Section C-Topical Cream Dispensers: Manufacturing Process

The oil phase is prepared at 40° C. under continuous nitrogen by dissolving the sterol derivative embodiment together with fat-soluble vitamins and omega-3 esters in MCT oil, with oleic acid included as a delivery aid (uptake support). In parallel, the aqueous phase is prepared by dispersing carbomer in purified water and incorporating water-dispersible actives under controlled agitation. The oil phase is slowly emulsified into the aqueous phase using high-shear homogenization to generate a stable nanoemulsion cream controlled to mean droplet size ≤200 nm with PDI≤0.3 (Study 4A, DLS-verified). Final pH is adjusted to 5.5 with triethanolamine. The finished bulk is homogenized, deaerated, and filled into nitrogen-flushed, photoprotective airless dispensers, which are sealed immediately to support oxidative stability and microbial safety.

Example 7-Modular Manufacturing Process for Female Hormonal Optimization Multi-Route Platform Modular Phase 1-Base Active Carrier Production Manufacturing is carried out in an ISO Class 8 cleanroom under GMP Part 211 and ISO 14644-1 standards. The lipid phase is prepared by combining medium-chain triglycerides (MCT oil) and oleic acid (polarity-matched delivery aid/uptake support), heated to 40-45° C. under continuous nitrogen purge to protect oxygen-sensitive actives. Sterol derivatives (including, in certain embodiments, 7-keto DHEA) (50 mg per unit) are dissolved into the lipid phase with controlled agitation. Vitamin $D_3$ (800 IU) and *Rhodiola rosea* extract (200 mg) are dispersed into the lipid suspension using high-shear mixing at 3,500 rpm for 8 minutes. Magnesium bisglycinate (200 mg) and Vitamin B6 (pyridoxine hydrochloride) are dissolved in a purified water-glycerin blend to form the hydrophilic compartment. Both phases are maintained separately at this stage to enable later route-specific adaptation.

Modular Phase 2-Route-Specific Modulation

For oral capsule production, lipid and aqueous compartments are blended using a semi-solid fill process to stabilize hydrophilic and lipophilic actives, followed by rotary die encapsulation under ISO Class 7 conditions with nitrogen-flushed filling, targeting≤700 mg per capsule. For topical cream conversion, the lipid phase is emulsified into a carbomer aqueous gel, homogenized to achieve droplet sizes between 100-150 nm, and pH adjusted to 5.5 with triethanolamine. For microneedle patch adaptation, sterol derivatives (including, in certain embodiments, 7-keto DHEA) and *Rhodiola* are loaded into a phosphatidylcholine-ethanol ethosome dispersion (150-200 nm vesicle size), while magnesium bisglycinate and Vitamin B6 are cast into a PVP/HA hydrogel. Sequential casting under vacuum fills dual compartments, which are then laminated to a flexible backing for stability and dermal uptake.

Modular Phase 3-Functional Enhancement Layer

Optional penetration enhancers (Transcutol® at 5% w/w or monoterpenes at 0.5% w/w) may be incorporated into the ethosome compartment for enhanced lipophilic uptake. Cyclodextrin inclusion complexes can stabilize *Rhodiola* bioactives and protect them against oxidation. For topical conversion, photostabilizers such as rosemary extract are added to protect light-sensitive components. Controlled release in microneedles is tuned by adjusting the molecular weight of HA or modulating the phosphatidylcholine-to-ethanol ratio within ethosomes. Oleic acid remains the standardized delivery aid within the lipid phase across routes.

Modular Phase 4-Stability Testing and Multi-Route Compatibility Verification

Stability is tested under ICH Q1A (R2) accelerated (40° C.±2° C./75% RH±5%, 6 months) and long-term (25° C.±2° C./60% RH±5%, 24 months) conditions, as well as photostability per ICH Q1B. Oxidation resistance is assessed under 21% oxygen at 40° C. for four weeks. Microneedle tip compression testing confirms force resistance >0.058 N/needle. Multi-route compatibility is validated by ensuring oral, topical, and microneedle formats all retain potency within +5% of label claim and exhibit consistent release/uptake profiles across 24 months.

Modular Phase 5-Quality Control Parameters and Regulatory Alignment

Critical process parameters include: maintaining lipid processing below 45° C., validated nitrogen purge flow, droplet size confirmation pre- and post-homogenization, residual moisture <5% for microneedles, and capsule fill weight within +2%. Potency is verified by HPLC for sterol derivative embodiments and LC-MS/MS for *Rhodiola* constituents. Content uniformity is confirmed per USP <905> (AV≤15). Microbial compliance follows USP <61> and <62>. All manufacturing aligns with ICH Q8 (R2), Q1A (R2), Q3C, Q1B, and applicable USP monographs.

Modular Phase 6-Continuation Testing and Shelf-Life Confirmation

Ongoing stability testing at 6, 12, and 24 months evaluates potency (≥90% retention), droplet size stability, oxidation markers, capsule integrity, microneedle tip strength, and topical emulsion rheology. Retained samples from each batch are re-analyzed to detect late-phase changes. Annual stability reports are generated to confirm regulatory compliance and long-term product reliability.

Modular Phase 7-Packaging and Storage

Oral capsules are nitrogen-flushed into tamper-evident PVC/PVDC blister packs with integrated desiccants. Topical creams are filled into nitrogen-flushed airless pump dispensers with photoprotective packaging. Microneedle patches are sealed individually in foil-laminate pouches with desiccants and nitrogen purge. All packaging complies with child-resistant standards (16 CFR 1700) and photoprotective requirements. Storage is controlled at 15-25° C., <60% RH, and away from direct light to support stability over the intended shelf life.

Manufacturing Scale Details for 10,000 Units Across all Routes

Section A-Oral Capsules (10,000 units) Unit Formula (per capsule)

TABLE 125

Oral Capsule Manufacturing Scale (10,000 Units)

| Component | Unit Formula (per capsule) | Batch Total (10,000 capsules) | Function |
|---|---|---|---|
| Sterol derivative (5-DHEA enanthate embodiment) | 50 mg | 500 g | Model sterol derivative embodiment; endocrine wellness support |
| L-Citrulline malate (2:1) | 180 mg | 1,800 g | Supports nitric oxide production & exercise capacity |
| Beta-alanine | 90 mg | 900 g | Carnosine precursor; supports muscular endurance |
| Creatine monohydrate | 50 mg | 500 g | Supports strength & power output |
| Coenzyme Q10 (ubiquinone) | 30 mg | 300 g | Cellular energy & antioxidant support |
| Zinc bisglycinate (≈8 mg elemental Zn) | 60 mg | 600 g | Chelated mineral; endocrine wellness support |
| MCT oil | 208 mg | 2,080 g | Lipid carrier (SEDS-compatible) |
| Oleic acid | 30 mg | 300 g | Polarity-matched delivery aid/uptake support |
| Mixed tocopherols | 2 mg | 20 g | Lipid-phase antioxidant |
| Excipients (silica, gelatin, glycerin, purified water) | — | Gelatin shell ~18,000 g | Capsule shell & processing aids |

Table 125 details the oral capsule formulation combining lipophilic and hydrophilic nutrients. MCT oil and oleic acid serve as the lipid carrier/delivery aid system, and mixed tocopherols provide oxidative stability.

Manufacturing Process

The lipid phase is prepared at 40-45° C. under continuous nitrogen purge, incorporating the sterol derivative (5-DHEA enanthate embodiment), coenzyme Q10, medium-chain triglycerides, oleic acid, and mixed tocopherols until fully solubilized. In parallel, water-compatible actives (L-citrulline malate, beta-alanine, creatine monohydrate) are blended and dispersed in a glycerin-based aqueous carrier to ensure uniform hydration and prevent agglomeration. The aqueous dispersion is gradually introduced into the lipid phase under controlled mixing to achieve a homogeneous pre-emulsion. The final mass is encapsulated by rotary-die softgel technology within an ISO Class 7 cleanroom, with nitrogen flushing during filling. Finished capsules are blister-packed in high-barrier PVC/PVDC with integrated desiccant, sealed, and labeled with lot, manufacturing date, and expiry.

Section B—Microneedle Patches (10,000 units) Unit Formula (per patch)

TABLE 126

Microneedle Patch Manufacturing Scale (10,000 Units)

| Component | Unit Formula (per patch) | Batch Total (10,000 patches) | Function |
|---|---|---|---|
| Sterol derivative (model embodiment: 7-keto DHEA or 5-DHEA enanthate) | 50 mg | 500 g | Lipophilic payload; dermal uptake support |
| L-Citrulline malate | 300 mg | 3,000 g | Hydrophilic payload; supports nitric oxide production |
| Beta-alanine | 200 mg | 2,000 g | Hydrophilic payload; carnosine precursor |
| Creatine monohydrate | 100 mg | 1,000 g | Hydrophilic payload; supports muscle performance |
| Hyaluronic acid | 150 mg | 1,500 g | Matrix polymer; dissolution control |
| Polyvinyl alcohol (PVA) | 300 mg | 3,000 g | Structural polymer (microneedle integrity) |
| Phosphatidylcholine | 20 mg | 200 g | Vesicle stabilizer for lipophilic phase |
| Transcutol ® | 50 mg | 500 g | Penetration enhancer/ polarity-matched uptake support |
| Purified water | q.s. | ~15,000 g (removed during drying) | Casting medium (evaporates) |

Note:
Lipophilic compartment vesicle size is controlled to 100-150 nm with PDI ≤ 0.3 (Study 3 reference), ensuring polarity-specific uptake and dermal stability.

Table 126 details the microneedle patch formulation integrating polarity-specific compartments. Hyaluronic acid and PVA form the structural matrix, phosphatidylcholine stabilizes the vesicular lipophilic phase, and Transcutol® enhances dermal uptake.

Manufacturing Process

The lipophilic compartment is prepared by dispersing the sterol derivative embodiment in phosphatidylcholine within an ethanol-rich carrier to generate nanoscale vesicles optimized for dermal uptake. In parallel, the hydrophilic compartment is prepared by dissolving L-citrulline malate, beta-alanine, and creatine monohydrate in a hyaluronic acid/PVA solution to form a supportive hydrogel matrix. Dual-compartment silicone microneedle molds are sequentially filled under vacuum in an ISO Class 7 cleanroom to ensure complete cavity penetration and polarity-specific separation. Cast patches are dried for 24 hours under vacuum at 25° C., laminated to a flexible backing film, and individually sealed in nitrogen-flushed foil-laminate pouches with desiccants. Storage is controlled at 20-25° C. and <40% RH to maintain stability, potency, and microneedle integrity.

Section C-Topical Cream Dispensers (10,000 units) Unit Formula (per 50 g dispenser)

TABLE 127

Topical Cream Dispenser Manufacturing Scale (10,000 Units × 50 g each).

| Component | Unit Formula (per 50 g dispenser) | Batch Total (10,000 dispensers/ 500 kg) | Function |
|---|---|---|---|
| Sterol derivative (model embodiment: 7-keto DHEA or 5-DHEA enanthate) | 50 mg | 500 g | Lipophilic active; wellness support |
| L-Citrulline malate | 300 mg | 3,000 g | Supports nitric oxide production |
| Beta-alanine | 200 mg | 2,000 g | Carnosine precursor; endurance support |
| Creatine monohydrate | 100 mg | 1,000 g | Supports muscular performance |
| Coenzyme Q10 | 50 mg | 500 g | Antioxidant; mitochondrial energy support |
| Zinc bisglycinate | 60 mg | 600 g | Mineral cofactor; endocrine wellness support |
| Oleic acid | 500 mg | 5,000 g | Polarity-matched delivery aid/uptake support |
| MCT oil | 2,000 mg | 20,000 g | Lipid carrier |
| Phosphatidylcholine | 200 mg | 2,000 g | Vesicle stabilizer/ emulsifier |
| Polysorbate 80 | 400 mg | 4,000 g | Surfactant/ emulsifier |
| Carbomer 940 | 250 mg | 2,500 g | Thickener/ viscosity control |
| Triethanolamine | q.s. (to pH 5.5) | — | pH adjustment |
| Phenoxyethanol | 0.5% w/w | 2,500 g | Preservative |
| Purified water | balance to 50 g | balance to 500,000 g | Aqueous vehicle |

Note: Emulsion droplet size is controlled to ≤200 nm with PDI≤0.3 (Study 4A, DLS-verified) to ensure dermal performance and reproducibility.

Table 127 details the topical cream dispenser formulation combining lipid-based and aqueous nutrients. MCT oil and oleic acid provide the lipid carrier/delivery aid system, carbomer/TEA establish rheology, and phenoxyethanol ensures microbial safety.

Manufacturing Process

The oil phase is prepared at 40° C. under continuous nitrogen purge by dissolving the sterol derivative embodiment and coenzyme Q10 in MCT oil with oleic acid and phosphatidylcholine as carriers/stabilizers. In parallel, the aqueous phase is prepared by dispersing carbomer with water-soluble actives under controlled agitation. The oil phase is gradually emulsified into the aqueous phase under high-shear homogenization to achieve a uniform nanoemulsion cream (100-150 nm target droplet size). Final pH is adjusted to 5.5 with triethanolamine for skin compatibility and rheological stability. The finished bulk is homogenized, nitrogen-flushed during transfer, and filled into photoprotective, tamper-evident airless pumps.

Manufacturing Notes (all Formats)

All production operations are conducted in controlled environments-oral capsules in ISO Class 8; microneedle and topical systems in ISO Class 7—with full GMP Part 211 compliance. Lipid processing and final packaging occur under continuous nitrogen purge. Lipid droplet size targets are maintained as follows: 100-150 nm for standard emulsions and ≤200 nm with PDI≤0.3 for nanoemulsion variants (Study 4A, DLS-verified). Microneedle patches are vacuum-cast with residual moisture <5% to preserve structural integrity and predictable dissolution. Blister packs, foil-laminate pouches, and airless dispensers are tamper-evident, photoprotective, and child-resistant (16 CFR 1700). Stability testing follows ICH Q1A (R2) and Q1B protocols with potency, integrity, and release kinetics confirmed at 6, 12, and 24 months (≥90% potency retention).

Consolidated Statement of Embodiment Coverage and Compliance

The present disclosure provides seven detailed manufacturing examples which collectively demonstrate the full scope of the claimed invention. Each example is drafted in modular form, incorporating base carrier preparation, route-specific modulation, functional enhancement, stability validation, and continuation testing.

Embodiment Coverage

All seventeen inventive embodiments are either directly demonstrated or derivable via modular conversion across Examples 1 through 7 when integrated with the experimental data from Studies 1A through 8. Oral, topical, transdermal, microneedle, and hybrid delivery routes are fully disclosed, including polarity-specific payload separation, dual-compartment microneedle integration, controlled-release systems, antioxidant protection, sex-specific hormonal optimization, and stability-preserving formulations. Each DHEA ester derivative embodiment is exemplified (5-DHEA enanthate, 1-DHEA enanthate, 4-DHEA enanthate, epiandrosterone undecanoate, androst-5-ene triol enanthate, and 7-keto DHEA), ensuring comprehensive coverage of steroidal actives within the claimed invention.

Dosage Compliance and Bioavailability Justification

All examples are designed to remain within physiologic and regulatory-compliant limits while emphasizing the principle of low-dosage, high-bioavailability delivery. Oral formulations are capped at 700 mg total fill weight including excipients, ensuring consumer compliance and reduced systemic burden. Vitamins and minerals are provided at safe and internationally recognized RDA levels, including Vitamin D standardized at 800 IU, chelated Zinc at 8 mg, and chelated Magnesium not exceeding 200 mg. B-complex vitamins are incorporated only at physiologic support doses rather than pharmacologic excess.

The innovation lies not in administering supraphysiologic loads, but in enhancing absorption and systemic utilization through advanced carriers such as self-emulsifying drug delivery systems (SEDS), ethosomal vesicles, dual-compartment microneedles, and lipid-polymer hybrid emulsions. These technologies markedly improve permeability, dissolution, and bioavailability, allowing active compounds to demonstrate enhanced absorption and measurable bioavailability improvements at significantly reduced intake levels. For example, HMB, L-Arginine, Resveratrol, Omega-3 fatty acids, and adaptogenic extracts are formulated in synergistic lipid-hydrophilic systems that maximize transport across intestinal, dermal, or microneedle-mediated barriers.

This strategy ensures that the invention supports key physiological functions-including muscle metabolism, endocrine balance, cognitive support, physical performance, and healthy aging—using physiologically relevant, non-excessive doses rather than conventional high-dose regimens. By demonstrating that lower input yields equivalent or superior outcomes when paired with optimized carriers, the disclosure not only meets safety and compliance thresholds but also establishes a novel inventive step in delivery science.

Manufacturing and Quality Standards

All examples are manufactured under GMP Part 211 and ISO 14644-1 cleanroom classifications, with route-specific adaptations. Nitrogen purging is employed during lipid handling to prevent oxidative degradation. Quality control checkpoints are aligned with USP <905>, <61>, <62>, and <2040>. Stability studies follow ICH Q1A (R2) accelerated and real-time protocols with photostability per ICH Q1B. Compatibility and performance testing are validated against Study 7 (Compatibility Index) and Study 8 (Dermal/Consumer Tolerability). Continuation testing includes 6-, 12-, and 24-month evaluations of potency, physical integrity, and release kinetics, with retained sample re-verification.

Full-Scale Manufacturing Demonstration

Each example is provided with explicit weights and measures scaled to 10,000-unit production runs across oral capsules, microneedle patches, and topical cream dispensers. These details confirm industrial scalability and reproducibility, establishing the invention as commercially viable and not merely laboratory-scale. Packaging instructions include nitrogen-flushed blister packs, foil pouches, and airless dispensers, each meeting tamper-evident, child-resistant (16 CFR 1700), and photoprotective requirements.

Conclusion Taken together, Examples 1-7 provide a complete, modular disclosure that demonstrates the invention's adaptability across all intended routes, compliance with international quality and safety standards, and alignment with recognized daily intake guidelines. This integrated strategy ensures that all embodiments are not only disclosed but also industrially reproducible, providing full enablement of the invention.

Regulatory Safe Harbor and Claim-Scope Clarification

The systems, compositions, and methods described herein are directed to polarity-specific delivery architectures for dietary supplements, cosmetics, and non-ingestible device-type formats where applicable.

Any references to "clinical," "pharmacokinetic," "exposure," "bioavailability," "performance," or related outcomes concern formulation, absorption/uptake, release, stability, or manufacturing characteristics only. Such references are limited to analytical or performance testing (e.g., in vitro dissolution, ex vivo permeation, LC-MS/MS assays, stability, or non-therapeutic in vivo uptake studies) and exclude any therapeutic efficacy claims.

All references to physiological or functional support are descriptive of formulation behavior and are not intended-and must not be construed—as diagnosing, treating, curing, mitigating, or preventing any disease or condition. All dietary supplement embodiments are limited to DSHEA-permissible structure/function characterizations. Non-ingestible embodiments (e.g., microneedle patches, topical gels/creams) are described as cosmetic or device-type systems, where cosmetic characterizations are confined to appearance, hydration, or barrier-supporting properties. Where such embodiments meet the definition of a medical device under applicable law, regulatory classification will follow device rules; however, no therapeutic use is asserted herein for patent purposes.

Patentability is premised solely on delivery architecture and formulation engineering, and not on any therapeutic indication or pharmacological effect. The claims seek protection for polarity-matched carrier systems, packaging/stability architectures, and cross-route coordination strategies, independent of any particular active, dose, or health outcome.

Nothing herein disclaims lawful pharmaceutical development; however, therapeutic indications or drug-type claims are expressly not relied upon for patentability or for support of commercial supplement or cosmetic labeling.

The foregoing descriptions of embodiments of the present invention have been presented only for purposes of illustration and description. They are not intended to be exhaustive or to limit the present invention to the forms disclosed. Accordingly, many modifications and variations will be apparent to practitioners skilled in the art. Additionally, the above disclosure is not intended to limit the present invention. The scope of the present invention is defined by the appended claim.

What is claimed is:

1. A method of forming a targeted release dietary supplement delivery system comprising the steps of:

micronizing a quantity of a DHEA derivative comprising 4-androstene-3bol-one propionate until the compound is in a dry, free-flowing powder form of less than ten microns and performing a quality control of the micronized DHEA derivative and determining that no chemical degradation has occurred;

micronizing a quantity of cyclodextrin and performing a quality control of the micronized cyclodextrin;

micronizing a first material selected from the group consisting of ergocalciferol and cholecalciferol and performing a quality control of the micronized first material;

micronizing a second material selected from the group consisting of *Withania somnifera* and *ginseng;* micronizing a third material selected from the group consisting of free fatty acids, essential amino acids, and HMB-free acid;

dissolving a phospholipid in a solvent and adding the second material to form a phytosome complex and drying the phytosome complex;

blending the micronized DHEA derivative with the cyclodextrin until both have the same particle size;

adding the phytosome complex to the micronized DHEA derivative, with the cyclodextrin and the first material;

assigning each of the DHEA derivative, the cyclodextrin, the first material, the second material, and the third material to a polarity-specific profile based on solubility and absorption characteristics; and incorporating lipophilic compounds into lipidic carriers and incorporating hydrophilic compounds into hydrophilic carriers.

2. The method of claim 1 further comprising a step of forming the lipidic carriers as antioxidant-enriched and self-emulsifying carriers.

3. The method of claim 1 further comprising a step of forming the lipidic carriers as ethosomes.

4. The method of claim 1 further comprising a step of forming nanostructured lipid carriers.

5. The method of claim 1 further comprising a step of forming the hydrophilic compounds into hydrogels.

6. The method of claim 1 further comprising a step of forming the hydrophilic compounds into cyclodextrin inclusion complexes.

7. The method of claim 1 further comprising a step of forming the hydrophilic compounds into polymeric dispersion matrices.

8. The method of claim 1 further comprising a step of controlling release of the hydrophilic compounds using dissolving microneedles.

9. The method of claim 8 further comprising a step of configuring the dissolving microneedles to support simultaneous delivery of the lipophilic and the hydrophilic compounds.

10. The method of claim 8 further comprising a step of configuring the dissolving microneedles to support sequential delivery of the lipophilic compounds and the hydrophilic compounds.

11. A targeted release dietary supplement delivery system comprising:

a quantity of a micronized DHEA derivative comprising 4-androstene-3b-ol-one propionate in the form of a dry, free-flowing powder of less than ten microns and having no chemical degradation;

a quantity of micronized cyclodextrin;

a first micronized material selected from the group consisting of ergocalciferol and cholecalciferol;

a second micronized material selected from the group consisting of *Withania somnifera* and *ginseng;* a third micronized material selected from the group consisting of free fatty acids, essential amino acids, and HMB-free acid;

a phospholipid dissolved in a solvent and added to the second micronized material and dried to form a phytosome complex;

wherein the micronized DHEA derivative is blended with the cyclodextrin until both have the same particle size;

wherein the phytosome complex is added to the micronized DHEA derivative, along with the cyclodextrin and the first micronized material;

wherein each of the DHEA derivative, the cyclodextrin, the first micronized material, the second micronized material, and the third micronized material are assigned to a polarity-specific profile based on solubility and absorption characteristics; and wherein lipophilic compounds are incorporated into lipidic carriers and hydrophilic compounds are incorporated into hydrophilic carriers.

12. The supplement delivery system of claim 11 wherein the lipidic carriers are antioxidant-enriched and self-emulsifying.

13. The supplement delivery system of claim 11 wherein the lipidic carriers comprise ethosomes.

14. The supplement delivery system of claim 11 wherein the lipidic carriers comprise nanostructured lipid carriers.

15. The supplement delivery system of claim 11 wherein the hydrophilic compounds are formulated into hydrogel systems.

16. The supplement delivery system of claim 11 wherein the hydrophilic compounds are cyclodextrin inclusion complexes.

17. The supplement delivery system of claim 11 wherein the hydrophilic compounds are polymeric dispersion matrices.

18. The supplement delivery system of claim 11 wherein the hydrophilic compounds are controlled released by using dissolving microneedles.

19. The supplement delivery system of claim 18 wherein the dissolving microneedles are configured to support simultaneous delivery of lipophilic and hydrophilic compounds.

20. The supplement delivery system of claim 18 wherein the dissolving microneedles are configured to support sequential delivery of lipophilic and hydrophilic compounds.

* * * * *